US012286421B2

(12) United States Patent
Hooker

(10) Patent No.: US 12,286,421 B2
(45) Date of Patent: Apr. 29, 2025

(54) INHIBITING MONOACYLGLYCEROL LIPASE (MAGL)

(71) Applicant: Psy Therapeutics, Inc., Boston, MA (US)

(72) Inventor: Jacob Matthew Hooker, Winchester, MA (US)

(73) Assignee: Psy Therapeutics, Inc., Boston, MA (US)

( * ) Notice: Subject to any disclaimer, the term of this patent is extended or adjusted under 35 U.S.C. 154(b) by 0 days.

(21) Appl. No.: 18/663,460

(22) Filed: May 14, 2024

(65) Prior Publication Data

US 2024/0308985 A1 Sep. 19, 2024

Related U.S. Application Data

(63) Continuation of application No. PCT/US2022/082554, filed on Dec. 29, 2022.

(60) Provisional application No. 63/294,747, filed on Dec. 29, 2021.

(51) Int. Cl.
C07D 403/04 (2006.01)
A61K 31/397 (2006.01)
A61K 31/4155 (2006.01)
C07D 205/12 (2006.01)

(52) U.S. Cl.
CPC .......... C07D 403/04 (2013.01); A61K 31/397 (2013.01); A61K 31/4155 (2013.01); C07D 205/12 (2013.01)

(58) Field of Classification Search
CPC .............. A61K 31/397; A61K 31/4155; C07D 403/04; C07D 205/12
See application file for complete search history.

(56) References Cited

U.S. PATENT DOCUMENTS

| 9,133,148 | B2 | 9/2015 | Cisar |
| 9,828,379 | B2 | 11/2017 | Jones |
| 9,957,242 | B2 | 5/2018 | Cisar |
| 9,981,930 | B1 | 5/2018 | Grice |
| 10,093,635 | B2 | 10/2018 | Grice |
| 10,266,497 | B2 | 4/2019 | Grice |
| 10,350,205 | B2 | 7/2019 | Grice |
| 10,450,302 | B2 | 10/2019 | Blankman |
| 10,570,106 | B2 | 2/2020 | Grice |
| 10,781,211 | B2 | 9/2020 | Buzard |
| 10,899,737 | B2 | 1/2021 | Grice |
| 11,021,453 | B2 | 6/2021 | Cisar |
| 11,034,674 | B2 | 6/2021 | Blankman |
| 11,059,822 | B2 | 7/2021 | Grice |
| 11,129,827 | B2 | 9/2021 | Grice |
| 11,142,517 | B2 | 10/2021 | Grice |
| 11,149,037 | B2 | 10/2021 | Grice |
| 11,401,273 | B2 | 8/2022 | Leleti et al. |
| 2002/0039768 | A1 | 4/2002 | Hopmann |
| 2008/0176963 | A1 | 7/2008 | Malenka |
| 2009/0082435 | A1 | 3/2009 | Piomelli |
| 2010/0035893 | A1 | 2/2010 | Hoornaert |
| 2010/0324011 | A1 | 12/2010 | Bian |
| 2010/0324014 | A1 | 12/2010 | Bian |
| 2010/0324016 | A1 | 12/2010 | Flores |
| 2011/0039874 | A1 | 2/2011 | Makriyannis |
| 2011/0071178 | A1 | 3/2011 | Makriyannis |
| 2011/0166138 | A1 | 7/2011 | Makriyannis |
| 2011/0275650 | A1 | 11/2011 | Cravatt |
| 2012/0058986 | A1 | 3/2012 | Connolly |
| 2012/0077797 | A1 | 3/2012 | Connolly |
| 2012/0101081 | A1 | 4/2012 | Zhang |
| 2012/0157432 | A1 | 6/2012 | Edmondson |
| 2013/0085130 | A1 | 4/2013 | Connelly |
| 2013/0102584 | A1 | 4/2013 | Connolly |
| 2013/0244998 | A1 | 9/2013 | Connolly |
| 2014/0235580 | A1 | 8/2014 | Castro |
| 2016/0318864 | A1 | 11/2016 | Koike |
| 2017/0029390 | A1 | 2/2017 | Butler |
| 2017/0137401 | A1 | 5/2017 | Cox |
| 2017/0239242 | A1 | 8/2017 | Lotersztajn |
| 2017/0247387 | A1 | 8/2017 | Makriyannis |
| 2017/0283406 | A1 | 10/2017 | Ikeda |
| 2018/0079756 | A1 | 3/2018 | Ikeda |
| 2018/0099951 | A1 | 4/2018 | Blankman |
| 2018/0134674 | A1 | 5/2018 | Grice |
| 2018/0134675 | A1 | 5/2018 | Grice |
| 2018/0208608 | A1 | 7/2018 | Brodney |
| 2018/0256566 | A1 | 9/2018 | Grice |
| 2018/0339970 | A1 | 11/2018 | Grice |
| 2019/0125728 | A1 | 5/2019 | Ikeda |
| 2019/0152917 | A1 | 5/2019 | Malamas |
| 2020/0102303 | A1 | 4/2020 | Ameriks |
| 2020/0188393 | A1 | 6/2020 | Grice |

(Continued)

FOREIGN PATENT DOCUMENTS

EP 3279191 A1 2/2018
EP 3438109 A1 2/2019

(Continued)

OTHER PUBLICATIONS

U.S. Appl. No. 18/724,744, filed Jun. 27, 2024, Hooker.*
U.S. Appl. No. 18/724,766, filed Jun. 27, 2024, Hooker.*
U.S. Appl. No. 18/724,771, filed Jun. 27, 2024, Hooker et al.*
Patani et al. Chem. Rev. 1996, 96, pp. 3147-3176. (Year: 1996).*
Nocentini et al. Bioorganic Chemistry, 77, 2018, pp. 633-639. (Year: 2018).*
WO 2012/126275 Description Machine English Translation (Year: 2012).*
WO 2012/126275 Claims Machine English Translation (Year: 2012).*
Wager et al., Central Nervous System Multiparameter Optimization Desirability: Application in Drug Discovery, ACS Chem. Neurosci., 2016, 7(6),, pp. 767-775.

(Continued)

Primary Examiner — Kara R. McMillian
(74) Attorney, Agent, or Firm — Nixon Peabody LLP

(57) ABSTRACT

Provided herein are compounds for inhibiting monoacylglycerol lipase (MAGL), and related methods of making and using the compounds.

14 Claims, No Drawings

(56) References Cited

U.S. PATENT DOCUMENTS

| | | |
|---|---|---|
| 2020/0190063 A1 | 6/2020 | Grice |
| 2020/0291023 A1 | 9/2020 | Grice |
| 2020/0299277 A1 | 9/2020 | Benz |
| 2020/0308158 A1 | 10/2020 | Bell |
| 2020/0308190 A1 | 10/2020 | Bell |
| 2021/0024546 A1 | 1/2021 | Petersen |
| 2021/0107920 A1 | 4/2021 | Bell |
| 2021/0267959 A1 | 9/2021 | Moradi |
| 2021/0277020 A1 | 9/2021 | Anselm |
| 2021/0309669 A1 | 10/2021 | Brodney |
| 2021/0317094 A1 | 10/2021 | Ameriks |
| 2021/0387999 A1 | 12/2021 | Kuhn |
| 2022/0031676 A1 | 2/2022 | Beals |
| 2022/0089538 A1 | 3/2022 | Alcazar |
| 2022/0110933 A1 | 4/2022 | Lundbeck |
| 2022/0135591 A1 | 5/2022 | Benz |
| 2022/0213093 A1 | 7/2022 | Benz |
| 2022/0332713 A1 | 10/2022 | Ameriks |
| 2022/0363679 A1 | 11/2022 | Ameriks |
| 2023/0090255 A1 | 3/2023 | Zhang |

FOREIGN PATENT DOCUMENTS

| | | | |
|---|---|---|---|
| EP | 3889132 A1 | 10/2021 | |
| WO | WO 2001/077094 A1 | 10/2001 | |
| WO | WO 2006/116703 A2 | 11/2006 | |
| WO | WO 2008/145842 A2 | 12/2008 | |
| WO | WO 2009/052319 A1 | 4/2009 | |
| WO | WO 2009/117444 A1 | 9/2009 | |
| WO | WO 2010/056309 A2 | 5/2010 | |
| WO | WO 2010/124114 A1 | 10/2010 | |
| WO | WO 2010/124121 A1 | 10/2010 | |
| WO | WO 2012/030907 A1 | 3/2012 | |
| WO | WO 2012/044613 A1 | 4/2012 | |
| WO | WO 2012/054721 A1 | 4/2012 | |
| WO | WO-2012126275 A1 * | 9/2012 | .......... C07D 401/14 |
| WO | WO 2013/049289 A1 | 4/2013 | |
| WO | WO 2013/049332 A1 | 4/2013 | |
| WO | WO 2013/103973 A1 | 7/2013 | |
| WO | WO 2015/003002 A1 | 1/2015 | |
| WO | WO 2015/099196 A1 | 7/2015 | |
| WO | WO 2015/179559 A1 | 11/2015 | |
| WO | WO 2016/014975 A2 | 1/2016 | |
| WO | WO 2016/046130 A1 | 3/2016 | |
| WO | WO 2016/149401 A1 | 9/2016 | |
| WO | WO 2016/158956 A1 | 10/2016 | |
| WO | WO 2016/173097 A1 | 11/2016 | |
| WO | WO 2017/021805 A1 | 2/2017 | |
| WO | WO 2017/087854 A1 | 5/2017 | |
| WO | WO 2017/087858 A1 | 5/2017 | |
| WO | WO 2017/087863 A1 | 5/2017 | |
| WO | WO 2017/170830 A1 | 10/2017 | |
| WO | WO 2017/171100 A1 | 10/2017 | |
| WO | WO 2017/197192 A1 | 11/2017 | |
| WO | WO 2018/053447 A1 | 3/2018 | |
| WO | WO 2018/093946 A1 | 5/2018 | |
| WO | WO 2018/093947 A1 | 5/2018 | |
| WO | WO 2018/093949 A1 | 5/2018 | |
| WO | WO 2018/093950 A1 | 5/2018 | |
| WO | WO 2018/093953 A1 | 5/2018 | |
| WO | WO 2018/134695 A1 | 7/2018 | |
| WO | WO 2018/134698 A1 | 7/2018 | |
| WO | WO 2018/169880 A1 | 9/2018 | |
| WO | WO 2018/183112 A1 | 10/2018 | |
| WO | WO 2018/217805 A1 | 11/2018 | |
| WO | WO 2018/217809 A1 | 11/2018 | |
| WO | WO 2019/046318 A1 | 3/2019 | |
| WO | WO 2019/046330 A1 | 3/2019 | |
| WO | WO 2019/050988 A1 | 3/2019 | |
| WO | WO 2019/065791 A1 | 4/2019 | |
| WO | WO 2019/072785 A1 | 4/2019 | |
| WO | WO 2019/105915 A1 | 6/2019 | |
| WO | WO 2019/115660 A1 | 6/2019 | |
| WO | WO 2019/134985 A1 | 7/2019 | |
| WO | WO 2019/173394 A1 | 9/2019 | |
| WO | WO 2019/180185 A1 | 9/2019 | |
| WO | WO 2019/222266 A1 | 11/2019 | |
| WO | WO 2020/016710 A1 | 1/2020 | |
| WO | WO 2020/018554 A1 | 1/2020 | |
| WO | WO 2020/035424 A1 | 2/2020 | |
| WO | WO 2020/035425 A1 | 2/2020 | |
| WO | WO 2020/065613 A1 | 4/2020 | |
| WO | WO 2020/065614 A1 | 4/2020 | |
| WO | WO 2020/104930 A1 | 5/2020 | |
| WO | WO 2020/112905 A1 | 6/2020 | |
| WO | WO 2020/154683 A1 | 7/2020 | |
| WO | WO 2020/207941 A1 | 10/2020 | |
| WO | WO 2021/001330 A1 | 1/2021 | |
| WO | WO 2021/042911 A1 | 3/2021 | |
| WO | WO 2021/048036 A1 | 3/2021 | |
| WO | WO 2021/048241 A1 | 3/2021 | |
| WO | WO 2021/048242 A1 | 3/2021 | |
| WO | WO 2021/058443 A1 | 4/2021 | |
| WO | WO 2021/058445 A1 | 4/2021 | |
| WO | WO 2021/062232 A1 | 4/2021 | |
| WO | WO 2021/097107 A1 | 5/2021 | |
| WO | 2021/124222 A1 | 6/2021 | |
| WO | WO 2021/160602 A1 | 8/2021 | |
| WO | WO 2021/175913 A1 | 9/2021 | |
| WO | WO 2021/191359 A1 | 9/2021 | |
| WO | WO 2021/191384 A1 | 9/2021 | |
| WO | WO 2021/191390 A1 | 9/2021 | |
| WO | WO 2021/191391 A1 | 9/2021 | |
| WO | WO 2021/214550 A1 | 10/2021 | |
| WO | WO 2022/049134 A1 | 3/2022 | |
| WO | WO 2022/063784 A1 | 3/2022 | |
| WO | WO 2022/101412 A1 | 5/2022 | |
| WO | WO 2022/135461 A1 | 6/2022 | |
| WO | WO 2022/135462 A1 | 6/2022 | |
| WO | WO 2022/223750 A1 | 10/2022 | |
| WO | 2022/272248 A1 | 12/2022 | |
| WO | WO 2023031311 A1 | 3/2023 | |
| WO | WO 2023/062049 A1 | 4/2023 | |
| WO | WO 2023/078868 A1 | 5/2023 | |
| WO | WO 2023/110958 A1 | 6/2023 | |
| WO | WO 2023/130023 A1 | 7/2023 | |
| WO | WO 2023/130043 A1 | 7/2023 | |
| WO | WO 2023/130050 A1 | 7/2023 | |
| WO | WO 2023/213854 A1 | 11/2023 | |
| WO | WO 2024/073734 A1 | 4/2024 | |
| WO | 2024/215863 A2 | 10/2024 | |
| WO | 2025010392 A2 | 1/2025 | |
| WO | 2025010394 A2 | 1/2025 | |

OTHER PUBLICATIONS

Dalvie et al.; "Biotransformation Reactions of Five-Membered Aromatic Heterocyclic Rings"; Chem. Res. Toxicol., vol. 15, No. 3, pp. 269-299; Mar. 2002 (31 pages).

Bedse, G. et al.; "Therapeutic endocannabinoid augmentation for mood and anxiety disorders: comparative profiling of FAAH, MAGL and dual inhibitors"; Translational Psychiatry, vol. 8, No. 92, pp. 1-14; Apr. 26, 2018; DOI: 10.1038/s41398-018-0141-7 (14 pages).

Bedse, G. et al.; "Functional Redundancy Between Canonical Endocannabinoid Signaling Systems in the Modulation of Anxiety"; Biol. Psychiatry, vol. 82, No. 7, pp. 488-499; Oct. 1, 2017; DOI: 10.1016/j.biopsych.2017.03.002 (19 pages).

Bedse, G. et al.; "2-Arachidonoylglycerol Modulation of Anxiety and Stress Adaptation: from grass roots to novel therapeutics"; Biol. Psychiatry, vol. 88, No. 7, pp. 520-530; Oct. 1, 2020; DOI: 10.1016/j.biopsych.2020.01.015 (23 pages).

Long, J. et al.; "Dual blockade of FAAH and MAGL identifies behavioral processes regulated by endocannabinoid crosstalk in vivo"; PNAS, vol. 106, No. 48, pp. 20270-20275; Dec. 1, 2009; DOI: 10.1073/pnas.0909411106 (6 pages).

Tabrizi et al.; "Discovery of 1,5-Diphenylpyrazole-3-Carboxamide Derivatives as Potent, Reversible, and Selective Monoacylglycerol Lipase (MAGL) Inhibitors: Supplementary Materials"; J. Med. Chem., vol. 61, S1-S26; Jan. 8, 2018 (26 pages).

Tabrizi, M. et al.; "Discovery of 1,5-Diphenylpyrazole-3-Carboxamide Derivatives as Potent, Reversible, and Selective Monoacylglycerol Lipase (MAGL) Inhibitors"; J. Med. Chem., vol. 61, pp. 1340-1354; Jan. 8, 2018; DOI: 10.1021/acs.jmedchem.7b01845 (15 pages).

(56) References Cited

OTHER PUBLICATIONS

Aida, J. et al.; "Design, synthesis, and evaluation of piperazinyl pyrolidin-2-ones as a novel series of reversible monoacylglycerol lipase inhibitors"; J. Med. Chem., Sep. 25, 2018, pp. 1-56; DOI: 10.1021/acs.jmedchem.8b00824 (57 pages).

Aljoundi, A. et al.; "Covalent Versus Non-covalent Enzyme Inhibition: Which Route Should We Take? A Justification of the Good and Bad from Molecular Modelling Perspective"; The Protein Journal, pp. 1-9; Feb. 18, 2020; DOI: 10.1007/s10930-020-09884-2 (9 pages).

Barth, M. et al.; "Hexafluoroisopropyl carbamates as selective MAGL and dual MAGL/FAAH inhibitors: biochemical and physicochemical properties"; ChemMedChem, 2022, e202100757 (14 pages).

Martz, L.; "Lundbeck pivot emphasizes first in class in revamped pipeline"; Biocentury, Oct. 18, 2022, pp. 1-4 (4 pages).

Bononi, G et al.; "Discovery of long-chain salicylketoxime derivatives as monoacylglycerol lipase (MAGL) inhibitors"; European Journal of Medicinal Chemistry, Accepted Manuscript, pp. 1-62; Aug. 2018, DOI: 10.1016/j.ejmech.2018.08.038 (62 pages).

Bononi, G. et al.; "An updated patent review of monoacylglycerol lipase (MAGL) inhibitors (2018-present): Expert Opinion on Therapeutic Patents"; pp. 1-49; 2020; DOI: 10.1080/13543776.2021.1841166 (49 pages).

Bononi, G. et al.; "Monoacylglycerol lipase (MAGL) inhibitors based on a diphenylsulfide-bezoylpiperidine scaffold"; European Journal of Medicinal Chemistry, vol. 223, pp. 1-16 (2021) 113679; Jun. 29, 2021 (16 pages).

Bononi, G. et al.; "Reversible Monoacylglycerol Lipase Inhibitors: Discovery of a New Class of Benzylpiperidine Derivatives"; J. Med. Chem., 2022, vol. 65, pp. 7118-7140; May 26, 2022 (23 pages).

Chanda, P. et al.; "Monoacylglycerol Lipase Activity Is a Critical Modulator of the Tone and Integrity of the Endocannabinoid System"; Mol. Pharmacol, vol. 78, No. 6, pp. 996-1003; Sep. 14, 2010 (8 pages).

Chen, R. et al.; "Monoacylglycerol lipase is a new therapeutic target for Alzheimer's disease"; Cell Rep., vol. 2, No. 5, pp. 1329-1339; Nov. 29, 2012; DOI: 10.1016/j.celrep.2012.09.030 (22 pages).

Cisar, J. et al.; "Identification of ABX-1431, a Selective Inhibitor of Monoacylglycerol Lipase and Clinical Candidate for Treatment of Neurological Disorders"; J. Med. Chem., 2018, vol. 61, pp. 9062-9084; Aug. 1, 2018 (23 pages).

Clapper, J. et al.; "Monoacylglycerol Lipase Inhibition in Human and Rodent Systems Supports Clinical Evaluation of Endocannabinoid Modulators"; J. Pharmacol. Exp. Ther., vol. 367, pp. 494-508; Dec. 2018; DOI: 10.1124/jpet.118.252296 (15 pages).

Curry, Z. et al.; "Monoacylglycerol Lipase Inhibitors Reverse Paclitaxel-Induced Nociceptive Behavior and Proinflammatory Markers in a Mouse Model of Chemotherapy-Induced Neuropathy"; J. Pharmacol. Exp. Ther., vol. 366, pp. 169-183; Jul. 2018; DOI: 10.1124/jpet.117.245705 (15 pages).

Deng et al.; "Monoacylglycerol lipase inhibitors: modulators for lipid metabolism in cancer malignancy, neurological and metabolic disorders"; Acta Pharmaceutica Sinica B, 2020, vol. 10, No. 4, pp. 582-602; copyright 2020 (21 pages).

Dinos, G. et al.; "Kinetic study of irreversible inhibition of an enzyme consumed in the reaction it catalyses. Application to the inhibition of the puromycin reaction by spiramycin and hydroxylamine"; Journal of Enzyme Inhibition, 1997, vol. 12, No. 2, pp. 79-99; DOI: 10.3109/14756369709035811 (22 pages).

Di Stefano, M. et al.; "Design, synthesis and biological evaluation of benzylpiperidine and benzylpiperidine derivatives as novel reversible monoacylglycerol lipase (MAGL) inhibitors"; European Journal of Medicinal Chemistry, vol. 263, (2024) 115916; published online Nov. 2, 2023 (20 pages).

Galvani et al.; "Mechanistic Modeling of Monoglyceride Lipase Covalent Modification Elucidates the Role of Leaving Group Expulsion and Discriminates Inhibitors with High and Low Potency"; J. Chem. Inf. Model., 2022, 62, pp. 2771-2787 (17 pages).

Gil-Ordonez et al.; "Monoacylglycerol lipase (MAGL) as a promising therapeutic target"; Biochemical Pharmacology (2018), Accepted Manuscript, pp. 1-65; Jul. 25, 2018; DOI: 10.1016/j.bcp.2018.07.036 (66 pages).

Gonzalez-Bello et al.; "Designing Irreversible Inhibitors—Worth the Effort?"; ChemMedChem, 2016, vol. 11, pp. 22-30 (9 pages).

Granchi et al., "4-Aryliden-2-methyloxazol-5(4H)-one as a new scaffold for selectdive reversible MAGL inhibitors"; J. Enzyme Inhib. Med. Chem., 2015, pp. 1-10; Feb. 11, 2015 (11 pages).

Granchi et al.; "Structural Optimization of 4-Chlorobenzoylpiperidine Derivatives for the Development of Potent, Reversible, and Selective Monoacylglycerol Lipase (MAGL) Inhibitors"; J. Med. Chem., 2016, vol. 59, pp. 10299-10314; Nov. 3, 2016 (16 pages).

Granchi et al.; "Development of terphenyl-2-methyloxazol-5(4H)-one derivatives as selective reversible MAGL inhibitors"; Journal of Enzyme Inhibition and Medicinal Chemistry, 2017, vol. 32, No. 1, pp. 1240-1252; DOI: 10.1080/14756366.2017.1375484 (13 pages).

Granchi et al.; "A patent review of Monoacylglycerolerol Lipase (MAGL) inhibitors (2013-2017)"; Expert Opinion on Therapeutic Patents, DOI: 10.1080/13543776.2018.1389899 (12 pages).

Granchi et al., "Rational Development of MAGL Inhibitors, Chapter 20, Rational Drug Design: Methods and Protocols"; Methods in Molecular Biology, vol. 1824, Springer Science+Business Media, 2018, pp. 335-346 (12 pages).

Granchi et al., "Optimization of a Benzoylpiperidine Class Identifies a Highly Potent and Selective Reversible Monoacylglycerol Lipase (MAGL) Inhibitor" J. Med. Chem., 2019, vol. 62, pp. 1932-1958; Feb. 4, 2019; DOI: 10.1021/acs.jmedchem.8b01483 (27 pages).

Granchi et al., "Design, synthesis and biological evaluation of second-generation benzoylpiperidine derivatives as reversible monoacylglycerol lipase (MAGL) inhibitors"; European Journal of Medicinal Chemistry, 2021, vol. 209, 112857, pp. 1-30 (30 pages).

Griebel et al., "Selective blockade of the hydrolysis of the endocannabinoid 2-arachidonoylglycerol impairs learning and memory performance while producing antinociceptive activity in rodents"; Scientific Reports, 2015, vol. 5, 7642, pp. 1-16; Jan. 6, 2015; DOI: 10.1038/srep07642 (16 pages).

Yingfang He et al.; "Discovery, synthesis and evaluation of novel reversible Monoacylglycerolerol lipase radioligands bearing a morpholine-3-one scaffold"; Nuclear Medicine and Biology, vol. 108-109 (2022) pp. 24-32; Feb. 14, 2022 (9 pages).

Hernandez-Torres et al., "A Reversible and Selective Inhibitor of Monoacylglycerol Lipase Ameliorates Multiple Sclerosis" Supporting Information; Angew. Chem. Int. Ed., 2014, vol. 53, pp. S1-S65 (66 pages).

Hernandez-Torres et al., "A Reversible and Selective Inhibitor of Monoacylglycerol Lipase Ameliorates Multiple Sclerosis"; Angew. Chem. Int. Ed., 2014, vol. 53, pp. 13765-13770; Oct. 8, 2014; DOI: 10.1002/anie.201407807 (6 pages).

Hirsh, V., "Next-Generation Covalent Irreversible Kinase Inhibitors in NSCLC: Focus on Afatinib"; BioDrugs (2015) 29, pp. 167-183; Jun. 30, 2015; DOI: 10.1007/s40259-015-0130-9 (17 pages).

Ikeda et al.; "Design and Synthesis of Novel Spiro Derivatives as Potent and Reversible Monoacylglycerol Lipase (MAGL) Inhibitors: Bioisosteric Transformation from 3-Oxo-3,4-dihydro-2H-benzo[b][1,4]oxazin-6-yl Moiety"; J. Med. Chem., 2021, vol. 64, No. 15, pp. 11014-11044; Mar. 10, 2021; DOI: 10.1021/acs.jmedchem.1c00432 (31 pages).

Jha, V. et al.; "Discovery of Monoacylglycerol Lipase (MAGL) Inhibitors Based on a Pharmacophore-Guided Virtual Screening Study"; Molecules, 2021, vol. 26, No. 78, pp. 1-13; Dec. 26, 2020; DOI: 10.3390/molecules26010078 (13 pages).

Jiang et al., "Activity-Based Protein Profiling Delivers Selective Drug Candidate ABX-1431, a Monoacylglycerol Lipase Inhibitor, to Control Lipid Metabolism in Neurological Disorders"; J. Med. Chem., 2018, vol. 61, pp. 9059-9061; Oct. 11, 2018 (3 pages).

Jiang, M. et al.; "A Monoacylglycerolerol lipase inhibitor showing therapeutic efficacy in mice without central side effects or dependence"; Nature Communications, vol. 14:8039, pp. 1-19; Dec. 5, 2023; DOI: 10.1038/s41467-023-43606-3 (19 pages).

(56) References Cited

OTHER PUBLICATIONS

Johnson, D. et al., "Strategies for discovering and derisking covalent, irreversible enzyme inhibitors"; Future Med. Chem., 2010, vol. 2, No. 6, pp. 949-964; Jun. 1, 2010 (25 pages).
Kemble et al.; "A potent and selective inhibitor for the modulation of MAGL activity in the neurovasculature"; PLOS ONE, 17(9), pp. 1-24; Sep. 9, 2022 (24 pages).
Kemble et al.; "A potent and selective inhibitor for the modulation of MAGL activity in the neurovasculature"; bioRxiv preprint, May 4, 2022; pp. 1-31; DOI: https://doi.org/10.1101/2022.05.04.490688 (31 pages).
King et al., "Discovery of Potent and Reversible Monoacylglycerol Lipase Inhibitors"; Chem. Biol., 2009, vol. 16, No. 10, pp. 1045-1052; Oct. 30, 2009; DOI: 10.1016/j.chembiol.2009.09.012 (16 pages).
Kinsey, S. et al., "Repeated Low-Dose Administration of the Monoacylglycerol Lipase Inhibitor JZL184 Retains Cannabinoid Receptor Type 1-Mediated Antinociceptive and Gastroprotective Effects"; J. Pharmacol. Exp. Ther., 2013, 345, pp. 492-501; Jun. 2013; DOI: 10.1124/jpet.112.201426 (10 pages).
Labar, G. et al., "A Review on the Monoacylglycerol Lipase: At the Interface Between Fat and Endocannabinoid Signalling"; Current Medicinal Chemistry, 2010, vol. 17, pp. 2588-2607 (20 pages).
Li, R. et al., "Elevation of endocannabinoids in the brain by synthetic cannabinoid JWH-018: mechanism and effect on learning and memory"; Scientific Reports, 2019, vol. 9, 9621, pp. 1-11; Jul. 3, 2019; DOI: 10.1038/s41598-019-45969-4 (11 pages).
Long, J. et al., "Selective blockade of 2-arachidonoylglycerol hydrolysis produces cannabinoid behavioral effects"; Nat. Chem. Biol., 2009, vol. 5, No. 1, pp. 37-44; Jan. 2009; DOI: 10.1038/nchembio.129 (20 pages).
Lundbeck; "9M Financial results and business update"; pp. 1-56; Nov. 9, 2022 (56 pages).
McAllister et al.; "Discovery of Trifluoromethyl Glycol Carbamates as Potent and Selective Covalent Monoacylglycerol Lipase (MAGL) Inhibitors for Treatment of Neuroinflammation"; J. Med. Chem., 2018, 61, 3008-3026; Mar. 2, 2018 (19 pages).
Montesdeoca, N. et al.; "Inhibitors of lipogenic enzymes as a potential therapy against cancer"; The FASEB Journal, Jul. 18, 2020, 34, pp. 11355-11381; DOI: 10.1096/fj.202000705R (27 pages).
Mullard, A.; "Genetic biomarker trumps tissue type in landmark oncology approval"; Nature Reviews; Drug Discovery, Jul. 2017, vol. 16, p. 447 (1 page).
Mulvihill et al. "Therapeutic Potential of Monoacylglycerol Lipase Inhibitors"; Life Sci., Mar. 1, 20139, 92(8-9), 492-497; DOI: 10.1016/j.lfs.2012.10.25 (14 pages).
Muller-Vahl et al.; "Endocannabinoid Modulation Using Monoacylglycerol Lipase Inhibition in Tourette Syndrome: A Phase 1 Randomized, Placebo-Controlled Study"; Pharmacopsychiatry, Nov. 30, 2021, pp. 1-9; DOI:10.1055/a-1675-3494 (9 pages).
Pacher, P. et al.; "Modulating the endocannabinoid system in human health and disease: successes and failures"; FEBS J., vol. 280, No. 9, pp. 1918-1943; May 2013; DOI:10.1111/febs.12260 (35 pages).
Parker, L. et al.; "A comparison of novel, selective fatty acid amide hydrolase (FAAH), monoacylglycerol lipase (MAGL) and dual FAAH/MAGL inhibitors to suppress acute and anticipatory nausea in rat models"; Psychopharmacology (Berl), vol. 233, No. 12, pp. 2265-2275; Jun. 2016; DOI:10.1007/s00213-016-4277-y (20 pages).
Patel, J. et al.; "Loratadine analogues as MAGL inhibitors"; Bioorganic & Medicinal Chemistry Letters, vol. 25, pp. 1436-1442; Feb. 24, 2015 (7 pages).
Pertwee, R. G.; "Cannabinoid Receptor Ligands"; Tocris Bioscience Scientific Review Series; Tocris Reviews No. 27, pp. 1-16; 2010 (16 pages).
Poli, G. et al.; "Computationally driven discovery of phenyl(piperazin-1-yl)methanone derivatives as reversible monoacylglycerol lipase (MAGL) inhibitors"; Journal of Enzyme Inhibition and Medicinal Chemistry, vol. 34, No. 1, pp. 589-596; 2019; DOI: 10.1080/14756366.2019.1571271 (8 pages).
Roques, B. et al.; "Inhibiting the breakdown of endogenous opioids and cannabinoids to alleviate pain"; Nature Reviews, vol. 11, pp. 292-310; Apr. 2012 (19 pages).
Sabnis, R. et al.; "Novel Oxazine Monoacylglycerol Lipase (MAGL) Inhibitors"; ACS Med. Chem. Lett. vol. 12, pp. 312-313; 2021; DOI: 10.1021/acsmedchemlett.1c00055 (2 pages).
Schalk-Hihi, C. et al.; "Crystal structure of a soluble form of human monoglyceride lipase in complex with an inhibitor at 1.35 A resolution"; Protein Science, vol. 20, pp. 670-683; Feb. 3, 2011; DOI: 10.1002/pro.596 (14 pages).
Schlosburg, J. et al.; "Chronic monoacylglycerol lipase blockade causes functional antagonism of the endocannabinoid system"; Nature Neuroscience, vol. 13, No. 9, pp. 1113-1121; Sep. 2010; DOI: 10.1038/nn.2616 (9 pages).
Schlosburg, J. et al.; "Chronic monoacylglycerol lipase blockade causes functional antagonism of the endocannabinoid system: Supplementary Information"; Nature Neuroscience, vol. 13, No. 9, pp. 1-9; DOI: 10.1038/nn.2616 (19 pages).
Sumislawski, J. et al.; "Reversible Gating of Endocannabinoid Plasticity in the Amygdala by Chronic Stress: A Potential Role for Monoacylglycerolerol Lipase Inhibition in the Prevention of Stress-Induced Behavioral Adaptation"; Neuropsychopharmacology (2011) vol. 36, pp. 2750-2761; Jul. 22, 2011 (12 pages).
Chen, Z. et al.; "Design, Synthesis, and Evaluation of Reversible and Irreversible Monoacylglycerolerol Lipase Positron Emission Tomography (PET) Tracers Using a 'Tail Switching' Strategy on a Piperazinyl Azetidine Skeleton"; J. Med. Chem. 2019, vol. 62, pp. 3336-3353; DOI: 10.1021/acs.jmedchem.8b01778 (18 pages).
Cisneros, J. et al.; "Structure-Activity Relationship of a New Series of Reversible Dual Monoacylglycerolerol Lipase/Fatty Acid Amide Hydrolase Inhibitors": J. Med. Chem. 2012, vol. 55, pp. 824-836; Dec. 21, 2011 (13 pages).
Arimura et al., Compound 4f, a novel brain-penetrant reversible monoacylglycerol inhibitor, ameliorates neuroinflammation, neuronal cell loss and cognitive impairment in mice with kainic acid-induced neurodegeneration, Neuroscience 2022, Session 622—Neuroprotection III, Abstract, Nov. 16, 2022, Poster 622.22/L16 (2 pages).
Tuccinardi, T. et al.; "Identification and characterization of a new reversible MAGL inhibitor"; Bioorganic & Medicinal Chemistry, vol. 22, No. 13, pp. 3285-3291; Apr. 28, 2014; DOI: 10.1016/j.bmc.2014.04.057 (7 pages).
Van Esbroeck, A. et al.; Activity-based protein profiling reveals off-target proteins of the FAAH inhibitor BIA 10-2474; Science, vol. 356, pp. 1084-1087; Jun. 9, 2017 (5 pages).
Wilkerson, J. et al.; "Untapped endocannabinoid pharmacological targets: Pipe dream or pipeline?"; Pharmacology, Biochemistry and Behavior, vol. 206 (2021) 173192, pp. 1-18; Apr. 29, 2021; DOI: 10.1016/j.pbb.2021.173192 (18 pages).
International Search Report and Written Opinion for PCT/EP2021/074150, mailed Dec. 8, 2021 (11 pages).
Wyatt, R. et al.; "Pharmacologic Characterization of JNJ-42226314, [1-(4-Fluorophenyl)indol-5-yl]-[3-[4-(thiazole-2-carbonyl)piperazin-1-yl]azetidin-1-yl]methanone, a Reversible, Selective, and Potent Monoacylglycerol Lipase Inhibitor"; J. Pharmacol. Exp. Ther., 372:339-353; Mar. 2020 (22 pages).
Xiong et al.; "Discovery of novel reversible monoacylglycerol lipase inhibitors via docking-based virtual screening"; Bioorg. Med. Chem. Lett., 2021, 41, 127986, pp. 1-6; Mar. 22, 2021 (6 pages).
Zanfirescu et al.; "Targeting Monoacylglycerol Lipase in Pursuit of Therapies for Neurological and Neurodegenerative Diseases"; Molecules, 2021, 26, 5668, pp. 1-37; Sep. 18, 2021 (37 pages).
Zhi et al.; "Discovery of Aryl Formyl Piperidine Derivatives as Potent, Reversible, and Selective Monoacylglycerol Lipase Inhibitors"; J. Med. Chem., pp. 1-64; May 20, 2020; DOI: 10.1021/acs.jmedchem.9b021137 (65 pages).
Zhu et al.; "The discovery of diazetidinyl diamides as potent and reversible inhibitors of monoacylglycerol lipase (MAGL)"; Bioorganic & Medicinal Chemistry Letters, vol. 30, pp. 1-4; Apr. 18, 2020; 127198 (4 pages).
Zhu et al.; "The discovery of azetidine-piperazine di-amides as potent, selective and reversible monoacylglycerol lipase (MAGL)

(56) References Cited

OTHER PUBLICATIONS inhibitors"; Bioorganic & Medicinal Chemistry Letters, vol. 30, pp. 1-5; May 7, 2020; 127243 (5 pages).
Lundbeck, "H1 Financial results and business update", pp. 1-64; Aug. 17, 2022 (64 pages).
Press Release, "Lundbeck announces phase IIa study results of Lu Ag06466 in adults with Tourette Syndrome"; pp. 1-2; Mar. 27, 2020 (2 pages).
Abide Therapeutics; Press Release, "Abide and Celgene Enter Worldwide License Agreement for ABX-1772", pp. 1-2; Mar. 28, 2018 (2 pages).
Bristol Myers Squibb; "Investor Event—Nov. 16, 2021" presentation (140 pages).
International Search Report and Written Opinion for PCT/US2022/082554, mailed May 23, 2023, 14 pages.
International Search Report and Written Opinion for PCT/US2022/082585, mailed Apr. 27, 2023 (9 pages).
International Search Report and Written Opinion for PCT/US2022/082596, mailed Mar. 22, 2023 (9 pages).
National Center for Biotechnology Information; "Azetidin-1-yl(2-fluoro-3-hydroxyphenyl)methanone": Pubchem CID 155289023; Dec. 29, 2020; retrieved from: https://pubchem.ncbi.nlm.nih.gov/compound/155289023 (11 pages).
Qingjing Hao et al.; "Discovery of a novel class of reversible monoacylglycerol lipase inhibitors for potential treatment of depression"; European Journal of Medicinal Chemistry, vol. 268 (2024) 116285; Feb. 26, 2024 (18 pages).
National Center for Biotechnology Information; 2-Azaspiro[3.3]heptane-2-carbaldehyde: Pubchem CID 142487030; URL: https://pubchem.ncbi.nlm.nih.gov/compound/142487030; (8 pages).
National Center for Biotechnology Information; 2-Azaspiro[3.3]heptan-6-amine: Pubchem CID 56962140; URL: https://pubchem.ncbi.nlm.nih.gov/compound/56962140; (13 pages).
Feldman, H. et al.; "Development of a chemical toolset for studying the paralog-specific function of IRE1"; Acs Chem. Biol., vol. 14, No. 12, pp. 2595-2605; Dec. 20, 2019; DOI: 10.1021/acschembio.9b00482 (27 pages).
International Preliminary Report on Patentability for PCT/US2022/082554 dated Jun. 20, 2024, 10 pages.
International Preliminary Report on Patentability for PCT/US2022/082585 dated Jun. 20, 2024, 7 pages.
International Preliminary Report on Patentability for PCT/US2022/082596 dated Jun. 20, 2024, 6 pages.
Invitation to Pay Additional Fees for PCT/US2024/024039 dated Jun. 6, 2024, 11 pages.
National Center for Biotechnology Information; 6-[5-(Cyanomethyl)-4-iodo-3-pyridin-3-ylpyrazol-1-yl]-2-azaspiro[3.3] heptane-2-carboxylic acid: Pubchem Cid 156501386; URL: https://pubchem.ncbi.nlm.nih.gov/compound/156501386; 9 pages.
International Search Report and Written Opinion for PCT/US2024/024039 dated Aug. 27, 2024, 16 pages.
International Search Report and Written Opinion for PCT/US2024/036852 dated Sep. 18, 2024, 11 pages.
International Search Report and Written Opinion for PCT/US2024/036856 dated Sep. 18, 2024, 22 pages.

* cited by examiner

INHIBITING MONOACYLGLYCEROL LIPASE (MAGL)

CROSS-REFERENCE TO RELATED APPLICATIONS

This application is a continuation application under 35 U.S.C. § 120 and 35 U.S.C. § 365(c) of copending International Application No. PCT/US2022/082554 filed Dec. 29, 2022, which designates the U.S. and claims benefit under 35 U.S.C. § 119(e) of U.S. Provisional Patent Application No. 63/294,747 filed Dec. 29, 2021. The contents of all of which are incorporated herein by reference in their entireties.

TECHNICAL FIELD

The present disclosure relates to compounds and methods for inhibiting monoacylglycerol lipase (MAGL), including compounds and methods for reversible inhibition of MAGL.

BACKGROUND

MAGL is the principal enzyme responsible for the in vivo degradation of 2-arachidonoyl glycerol (2-AG), an endogenous ligand of the cannabindid receptors (e.g., CB1 and CB2). MAGL inhibition increases accumulation of the CB1/2 receptor agonist 2-arachidonoyl glycerol (2-AG), and reduces arachidonic acid (AA) and prostaglandin levels in the brain and peripheral tissues. Irreversible MAGL inhibitor compounds, such as JZL-184, increase brain and peripheral 2-AG and reduce brain AA, however tolerance can develop with chronic irreversible MAGL inhibition. Covalent interactions with MAGL could lead to irreversible enzymatic inhibition, with potential for immune-mediated toxicity.

There remains a need for reversible MAGL inhibitors useful for the treatment of MAGL-mediated diseases or disorders, including the development of therapeutic compounds with improved control of dose and exposure. Such compounds can be developed through clinical trials as analgesic compounds for the treatment of pain management and/or treatment of various MAGL-mediated conditions.

Thus, there is a need in the art for compounds that can potently, selectively and reversibly inhibit MAGL and for means for treating conditions or disorders that are associated with or linked to endocannabinoid signaling activities. The present disclosure addresses these and other unfulfilled needs in the art.

SUMMARY

The inventors have discovered inter alia compounds to inhibit monoacylglycerol lipase (MAGL), including compounds that reversibly inhibit MAGL. Accordingly, in another aspect, the disclosure provides compounds and methods for inhibiting monoacylglycerol lipase (MAGL).

In some embodiments, the disclosure provides a compound of Formula (I) or a pharmaceutically acceptable salt thereof:

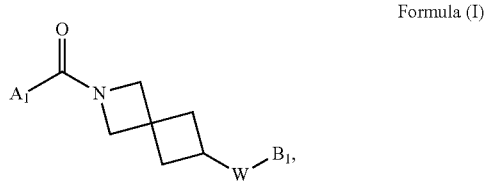

Formula (I)

wherein
$A_1$ is

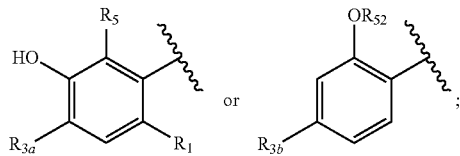

$R_1$ is hydrogen, halogen, or cyano;
$R_{3a}$ and $R_5$ are each independently hydrogen, halogen, or lower alkyl;
$R_{52}$ is lower alkyl, lower cycloalkyl or lower haloalkyl;
$R_{3b}$ is halogen;
W is a diazole optionally substituted with lower alkyl, lower cycloalkyl, or lower haloalkyl;
$B_1$ is

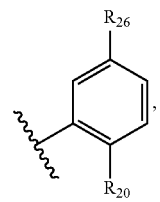

$R_{20}$ is hydrogen, halogen, lower alkyl, or lower haloalkyl; and
$R_{26}$ is hydrogen, or halogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (I) or a pharmaceutically acceptable salt thereof, wherein $R_1$ is hydrogen, fluoro, or cyano; and $R_{3a}$ and $R_5$ are each independently hydrogen, fluoro, or methyl. In some embodiments, the disclosure provides a compound of Formula (I) or a pharmaceutically acceptable salt thereof, wherein $R_1$ is fluoro; and $R_{3a}$ and $R_5$ are each independently hydrogen. In some embodiments, the disclosure provides a compound of Formula (I) or a pharmaceutically acceptable salt thereof, wherein $R_1$ is hydrogen, fluoro, or cyano; $R_{3a}$ is hydrogen, fluoro, or methyl; and $R_5$ is hydrogen. In some embodiments, the disclosure provides a compound of Formula (I) or a pharmaceutically acceptable salt thereof, wherein $R_1$ is hydrogen or fluoro; $R_{3a}$ is hydrogen, fluoro, or methyl; and $R_5$ is hydrogen.

In some embodiments, the disclosure provides a compound of Formula (I) or a pharmaceutically acceptable salt thereof, wherein $R_{52}$ is lower alkyl, cyclopropyl or lower haloalkyl; and $R_{3b}$ is fluoro. In some embodiments, the disclosure provides a compound of Formula (I) or a pharmaceutically acceptable salt thereof, wherein $R_{52}$ is lower alkyl and $R_{3b}$ is fluoro. In some embodiments, the disclosure provides a compound of Formula (I) or a pharmaceutically acceptable salt thereof, wherein $R_{52}$ is lower haloalkyl and $R_{3b}$ is fluoro. In some embodiments, the disclosure provides a compound of Formula (I) or a pharmaceutically acceptable salt thereof, wherein $R_{52}$ is lower alkyl optionally substituted with one or more fluoro and $R_{3b}$ is fluoro. In some embodiments, the disclosure provides a compound of Formula (I) or a pharmaceutically acceptable salt thereof, wherein $R_{52}$ is cyclopropyl, and $R_{3b}$ is fluoro.

In some embodiments, the disclosure provides a compound of Formula (I) or a pharmaceutically acceptable salt thereof, wherein W is selected from the group consisting of:

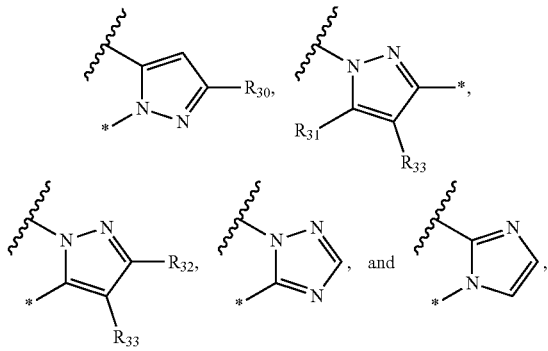

wherein * indicates a covalent bond to $B_1$; and $R_{30}$, $R_{31}$, $R_{32}$ and $R_{33}$ are each independently hydrogen, lower alkyl, lower haloalkyl, or lower cycloalkyl, provided that at least one of $R_{31}$ and $R_{33}$ and at least one of $R_{32}$ and $R_{33}$ is not hydrogen.

In some embodiments, the disclosure provides a compound of Formula (I) or a pharmaceutically acceptable salt thereof, wherein W is selected from the group consisting of:

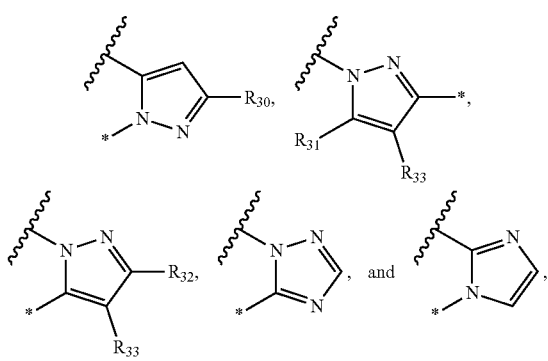

wherein * indicates a covalent bond to $B_1$; and $R_{30}$, $R_{31}$, $R_{32}$ and $R_{33}$ are each independently hydrogen, lower alkyl, lower haloalkyl, or lower cycloalkyl, provided that at least one of $R_{31}$ and $R_{33}$ and at least one of $R_{32}$ and $R_{33}$ is not hydrogen.

In some embodiments, the disclosure provides a compound of Formula (I) or a pharmaceutically acceptable salt thereof, wherein $R_{30}$, $R_{31}$, $R_{32}$ and $R_{33}$ are each independently hydrogen, methyl, $CF_3$, or cyclopropyl, provided that at least one of $R_{31}$ and $R_{33}$ and at least one of $R_{32}$ and $R_{33}$ is not hydrogen. In some embodiments, the disclosure provides a compound of Formula (I) or a pharmaceutically acceptable salt thereof, wherein $R_{30}$ is methyl. In some embodiments, the disclosure provides a compound of Formula (I) or a pharmaceutically acceptable salt thereof, wherein $R_{33}$ is hydrogen, methyl, $CF_3$, or cyclopropyl, provided that at least one of $R_{31}$ and $R_{33}$ and at least one of $R_{32}$ and $R_{33}$ is not hydrogen. In some embodiments, the disclosure provides a compound of Formula (I) or a pharmaceutically acceptable salt thereof, wherein $R_{32}$ is hydrogen and $R_{33}$ is methyl, $CF_3$ or cyclopropyl; or $R_{32}$ is methyl, $CF_3$ or cyclopropyl, and $R_3$ is hydrogen. In some embodiments, the disclosure provides a compound of Formula (I) or a pharmaceutically acceptable salt thereof, wherein $R_{31}$ is hydrogen and $R_{33}$ is methyl, $CF_3$ or cyclopropyl; or $R_{31}$ is methyl, $CF_3$ or cyclopropyl, and $R_{33}$ is hydrogen.

In some embodiments, the disclosure provides a compound of Formula (I) or a pharmaceutically acceptable salt thereof, wherein $R_{20}$ is hydrogen, fluoro, chloro, methyl, or $CF_3$; and $R_{26}$ is hydrogen, or fluoro. In some embodiments, the disclosure provides a compound of Formula (I) or a pharmaceutically acceptable salt thereof, wherein $R_{20}$ is fluoro, chloro, methyl, or $CF_3$; and $R_{26}$ is hydrogen, or fluoro. In some embodiments, the disclosure provides a compound of Formula (I) or a pharmaceutically acceptable salt thereof, wherein $R_{20}$ is methyl, or $CF_3$; and $R_{26}$ is hydrogen, or fluoro. In some embodiments, the disclosure provides a compound of Formula (I) or a pharmaceutically acceptable salt thereof, wherein $R_{20}$ is fluoro or chloro, or $CF_3$; and $R_{26}$ is hydrogen, or fluoro.

In some embodiments, the disclosure provides a compound of Formula (I) a pharmaceutically acceptable salt thereof, wherein the compound is not (2-fluoro-5-hydroxyphenyl){6-[3-methyl-1-(o-tolyl)-5-pyrazolyl]-2-aza-2-spiro[3.3]heptyl}methanone.

In some embodiments, the disclosure provides a compound of Formula (I) a pharmaceutically acceptable salt thereof, wherein the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (I) or a pharmaceutically acceptable salt thereof, wherein $A_1$ is

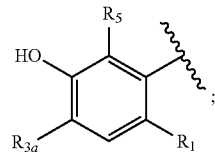

$R_1$ is hydrogen, F, or cyano; $R_{3a}$ and $R_5$ are each independently hydrogen, F, or methyl; W is

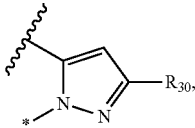

wherein * indicates a covalent bond to $B_1$; $R_{30}$ is hydrogen, methyl, $CF_3$, or cyclopropyl; and $R_{20}$ is hydrogen, F, Cl, methyl, or $CF_3$; and $R_{26}$ is hydrogen, or F; provided that the compound is not (2-fluoro-5-hydroxyphenyl)(6-(3-methyl-1-(o-tolyl)-1H-pyrazol-5-yl)-2-azaspiro[3.3]heptan-2-yl) methanone.

In some embodiments, the disclosure provides a compound of Formula (I) or a pharmaceutically acceptable salt thereof, wherein $A_1$ is

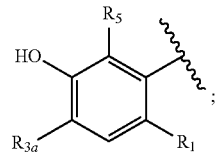

$R_1$ is hydrogen, F, or cyano; $R_{3a}$ and $R_5$ are each independently hydrogen, F, or methyl; W is

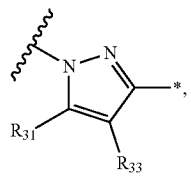

wherein * indicates a covalent bond to $B_1$; $R_{31}$ and $R_{33}$ are each independently hydrogen, methyl, $CF_3$, or cyclopropyl, provided that at least one of $R_{31}$ and $R_{33}$ is hydrogen; $R_{20}$ is hydrogen, F, Cl, methyl, or $CF_3$; and $R_{26}$ is hydrogen, or F.

In some embodiments, the disclosure provides a compound of Formula (I) or a pharmaceutically acceptable salt thereof, wherein $A_1$ is

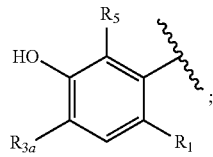

$R_1$ is hydrogen, F, or cyano; $R_{3a}$ and $R_5$ are each independently hydrogen, F, or methyl; W is

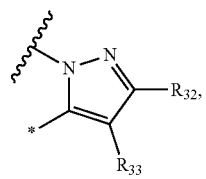

wherein * indicates a covalent bond to $B_1$; $R_{32}$ and $R_{33}$ are each independently hydrogen, methyl, $CF_3$, or cyclopropyl, provided that at least one of $R_{32}$ and $R_{33}$ is hydrogen; $R_{20}$ is hydrogen, F, Cl, methyl, or $CF_3$; and $R_{26}$ is hydrogen, or F.

In some embodiments, the disclosure provides a compound of Formula (I) or a pharmaceutically acceptable salt thereof, wherein $A_1$ is

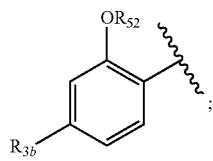

$R_{3b}$ is F; $R_{52}$ is lower alkyl optionally substituted with one or more F, or cyclopropyl; W is

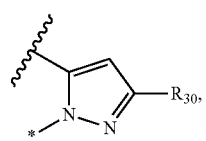

wherein * indicates a covalent bond to $B_1$; $R_{30}$ is hydrogen, methyl, $CF_3$, or cyclopropyl; $R_{20}$ is hydrogen, F, Cl, methyl, or $CF_3$; and $R_{26}$ is hydrogen, or F.

In some embodiments, the disclosure provides a compound of Formula (I) or a pharmaceutically acceptable salt thereof, wherein $A_1$ is

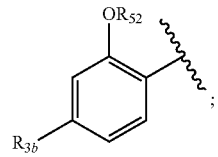

$R_{3b}$ is F; $R_{52}$ is lower alkyl optionally substituted with one or more F, or cyclopropyl; W is

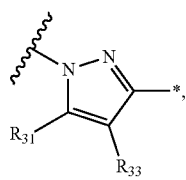

wherein * indicates a covalent bond to $B_1$; $R_{31}$ and $R_{33}$ are each independently hydrogen, methyl, $CF_3$, or cyclopropyl, provided that at least one of $R_{31}$ and $R_{33}$ is hydrogen; $R_{20}$ is hydrogen, F, Cl, methyl, or $CF_3$; and $R_{26}$ is hydrogen, or F.

In some embodiments, the disclosure provides a compound of Formula (I) or a pharmaceutically acceptable salt thereof, wherein $A_1$ is

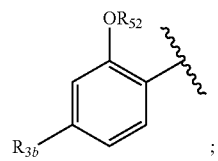

$R_{3b}$ is F; $R_{52}$ is lower alkyl optionally substituted with one or more F, or cyclopropyl; W is

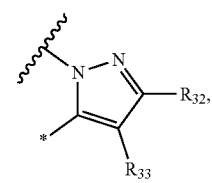

wherein * indicates a covalent bond to $B_1$; $R_{32}$ and $R_{33}$ are each independently hydrogen, methyl, $CF_3$, or cyclopropyl, provided that at least one of $R_{32}$ and $R_{33}$ is hydrogen; $R_{20}$ is hydrogen, F, Cl, methyl, or $CF_3$; and $R_{26}$ is hydrogen, or F.

Generally, methods disclosed herein include administering a compound described by a chemical formula disclosed herein to inhibit MAGL. In some embodiments, the compounds described by the chemical formulae disclosed herein can be used by contacting a compound with a cell (e.g., a cell expressing MAGL) to reversibly inhibit MAGL in the cell. In still another aspect, the disclosure provides a method for treating a monoglycerol lipase mediated disease or disorder. Without limitations, administering to the cell can be in vitro or in vivo. In some embodiments, the method comprises administering to a subject in need thereof a therapeutically effective amount of a compound described by a chemical formula disclosed herein. For example, an effective amount of a compound disclosed herein can be administered to a subject to treat a condition responsive to the reversible inhibition of MAGL.

In some embodiments, the disclosure provides a compound of Formula (I) or a pharmaceutically acceptable salt thereof,

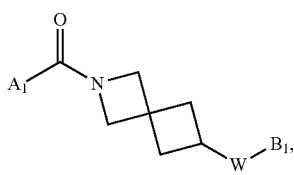

Formula (I)

wherein:
$A_1$ is

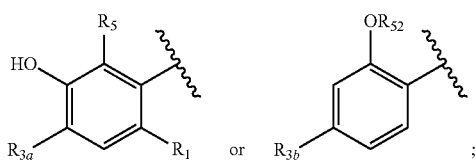

$R_1$ is halogen, hydrogen, or cyano;
$R_3$, and $R_5$ are each independently hydrogen, halogen, or lower alkyl;
$R_{52}$ is lower alkyl, lower cycloalkyl or lower haloalkyl;
$R_{3b}$ is halogen;
W is a diazole optionally substituted with lower alkyl, lower cycloalkyl, or lower haloalkyl;
$B_1$ is

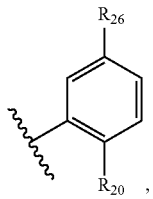

$R_{20}$ is halogen, hydrogen, lower alkyl, or lower haloalkyl; and
$R_{26}$ is hydrogen, or halogen;
provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (I) or a pharmaceutically acceptable salt thereof, wherein
$R_1$ is hydrogen, fluoro, or cyano;
$R_{3a}$ and $R_5$ are each independently hydrogen, halogen, or methyl;
$R_{52}$ is lower alkyl, cyclopropyl or lower haloalkyl;
$R_3$, is fluoro;

W is a diazole optionally substituted with one of methyl, cyclopropyl, or $CF_3$;
$R_{20}$ is fluoro or chloro, methyl, or $CF_3$; and
$R_{26}$ is hydrogen, fluoro or chloro.

In some embodiments, the disclosure provides a compound of Formula (I) or a pharmaceutically acceptable salt thereof, wherein W is selected from the group consisting of:

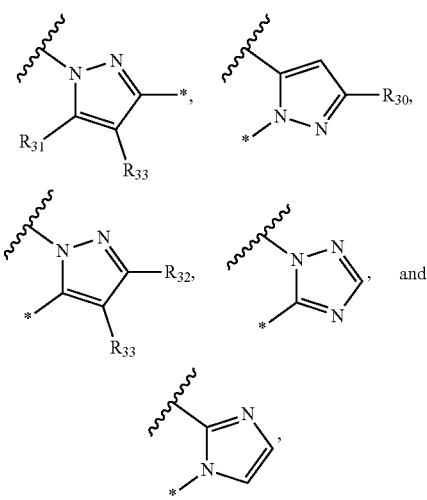

wherein * indicates a covalent bond to $B_1$; and
$R_{30}$, $R_{31}$, $R_{32}$ and $R_{33}$ are each independently hydrogen, lower alkyl, lower haloalkyl, or lower cycloalkyl, provided that at least one of $R_{31}$ and $R_{33}$ and at least one of $R_{32}$ and $R_{33}$ is not hydrogen.

In some embodiments, the disclosure provides a compound of Formula (I) or a pharmaceutically acceptable salt thereof, wherein $R_{30}$, $R_{31}$, $R_{32}$ and $R_{33}$ are each independently hydrogen, methyl, $CF_3$, or cyclopropyl, provided that at least one of $R_{31}$ and $R_{33}$ and at least one of $R_{32}$ and $R_{33}$ is not hydrogen.

In some embodiments, the disclosure provides a compound of Formula (I) or a pharmaceutically acceptable salt thereof, wherein W is selected from the group consisting of:

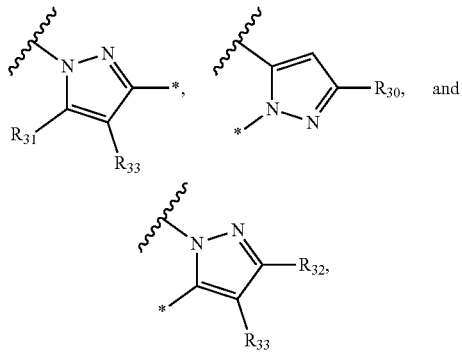

wherein * indicates a covalent bond to $B_1$.

In some embodiments, the disclosure provides a compound of Formula (I) or a pharmaceutically acceptable salt thereof, wherein W is

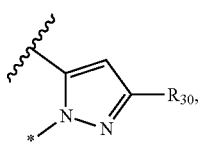

wherein * indicates a covalent bond to $B_1$, and $R_{30}$ is methyl.

In some embodiments, the disclosure provides a compound of Formula (I) or a pharmaceutically acceptable salt thereof, wherein W is

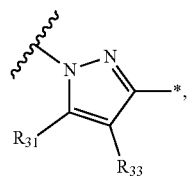

wherein * indicates a covalent bond to $B_1$, and $R_{31}$ and $R_{33}$ are each independently hydrogen, methyl, $CF_3$, or cyclopropyl, provided that one of $R_{31}$ and $R_{33}$ is hydrogen.

In some embodiments, the disclosure provides a compound of Formula (I) or a pharmaceutically acceptable salt thereof, wherein W is

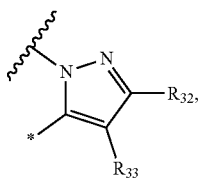

wherein * indicates a covalent bond to $B_1$, and $R_{32}$ and $R_{33}$ are each independently hydrogen, methyl, $CF_3$, or cyclopropyl, provided that one of $R_{32}$ and $R_{33}$ is hydrogen.

In some embodiments, the disclosure provides a compound of Formula (I) or a pharmaceutically acceptable salt thereof, wherein $A_1$ is

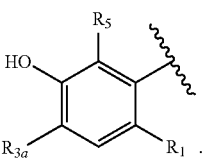

In some embodiments, the disclosure provides a compound of Formula (I) or a pharmaceutically acceptable salt thereof, wherein $R_5$ is hydrogen.

In some embodiments, the disclosure provides a compound of Formula (I) or a pharmaceutically acceptable salt thereof, wherein $R_1$ is fluoro.

In some embodiments, the disclosure provides a compound of Formula (I) or a pharmaceutically acceptable salt thereof, wherein $R_{3a}$ is hydrogen, fluoro, or methyl.

In some embodiments, the disclosure provides a compound of Formula (I) or a pharmaceutically acceptable salt thereof, wherein $R_{3a}$ is hydrogen.

In some embodiments, the disclosure provides a compound of Formula (I) or a pharmaceutically acceptable salt thereof, wherein $R_{20}$ is methyl, and $R_{26}$ is hydrogen or fluoro; or $R_{20}$ is chloro, fluoro or $CF_3$, and $R_2$ is hydrogen.

In some embodiments, the disclosure provides a compound of Formula (I) or a pharmaceutically acceptable salt thereof, wherein $A_1$ is

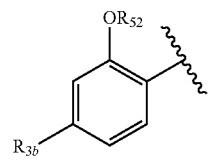

In some embodiments, the disclosure provides a compound of Formula (I) or a pharmaceutically acceptable salt thereof, wherein $R_{52}$ is lower alkyl optionally substituted with one or more fluoro and cyclopropyl.

In some embodiments, the disclosure provides a compound of Formula (I) or a pharmaceutically acceptable salt thereof, wherein $R_{3b}$ is fluoro.

In some embodiments, the disclosure provides a compound of Formula (I) or a pharmaceutically acceptable salt thereof, wherein
  $R_{20}$ is methyl, and $R_{26}$ is hydrogen or fluoro; or
  $R_{20}$ is fluoro or $CF_3$, and $R_{26}$ is hydrogen.

In some embodiments, the disclosure provides a compound of Formula (II-B) or a pharmaceutically acceptable salt thereof:

Formula (II-B)

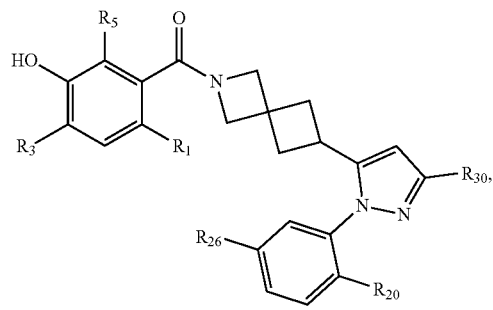

wherein
  $R_1$ is halogen or cyano;
  $R_3$ is hydrogen, lower alkyl, or halogen;
  $R_5$ is hydrogen, halogen or lower alkyl;
  $R_{20}$ is halogen or lower alkyl optionally substituted with one or more halogen;
  $R_{26}$ is halogen or hydrogen; and
  $R_{30}$ is hydrogen or lower alkyl optionally substituted with one or more halogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (II-B) or a pharmaceutically acceptable salt thereof, wherein
  $R_1$ is F or cyano;
  $R_3$ is hydrogen, methyl, or F;
  $R_5$ is hydrogen, F or methyl;
  $R_{20}$ is F, methyl, or $CF_3$;
  $R_{26}$ is hydrogen or F; and $R_{30}$ is hydrogen, methyl or $CF_3$, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (II-C) or a pharmaceutically acceptable salt thereof:

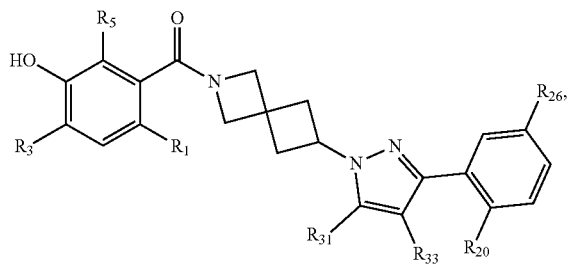

Formula (II-C)

wherein
$R_1$ is halogen or cyano;
$R_3$ is hydrogen, lower alkyl, or halogen;
$R_5$ is hydrogen, halogen or lower alkyl;
$R_{20}$ is halogen or lower alkyl optionally substituted with one or more halogen;
$R_{26}$ is hydrogen or halogen; and
$R_{31}$ and $R_{33}$ are each independently hydrogen or lower alkyl optionally substituted with one or more halogen, provided that one of $R_{31}$ and $R_{33}$ is hydrogen.

In some embodiments, the disclosure provides a compound of Formula (II-C) or a pharmaceutically acceptable salt thereof, wherein
$R_1$ is F or cyano;
$R_3$ is hydrogen, methyl, or F;
$R_5$ is hydrogen, F or methyl;
$R_{20}$ is F, methyl, or $CF_3$;
$R_{26}$ is hydrogen or F; and
$R_{31}$ and $R_{33}$ are each independently hydrogen, methyl or $CF_3$.

In some embodiments, the disclosure provides a compound of Formula (II-D) or a pharmaceutically acceptable salt thereof:

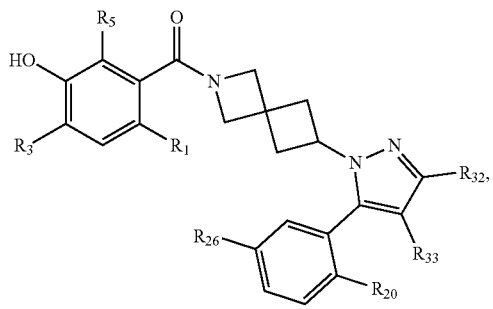

wherein
$R_1$ is halogen or cyano;
$R_3$ is hydrogen, lower alkyl, or halogen;
$R_5$ is hydrogen, halogen or lower alkyl;
$R_6$ is hydrogen;
$R_{20}$ is halogen or lower alkyl optionally substituted with one or more halogen;
$R_{26}$ is halogen or hydrogen; and
$R_{32}$ and $R_{33}$ are each independently hydrogen or lower alkyl optionally substituted with one or more halogen, provided that one of $R_{32}$ and $R_{33}$ is hydrogen.

In some embodiments, the disclosure provides a compound of Formula (II-D) or a pharmaceutically acceptable salt thereof, wherein
$R_1$ is F or cyano;
$R_3$ is hydrogen, F or methyl;
$R_5$ is hydrogen, F or methyl;
$R_{20}$ is F or methyl, or $CF_3$;
$R_{26}$ is hydrogen or F; and
$R_{32}$ and $R_{33}$ are each independently hydrogen, methyl or, $CF_3$ provided that one of $R_{32}$ and $R_{33}$ is hydrogen.

In some embodiments, the disclosure provides a compound of Formula (III-B) or a pharmaceutically acceptable salt thereof:

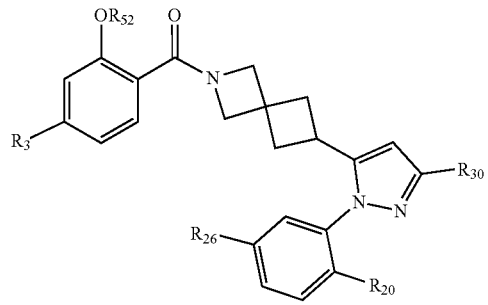

Formula (III-B)

wherein
$R_3$ is halogen;
$R_{52}$ is lower alkyl or lower cycloalkyl, each optionally substituted with halogen,
$R_{30}$ is lower alkyl;
$R_{20}$ is lower alkyl; and
$R_{26}$ is hydrogen or halogen.

In some embodiments, the disclosure provides a compound of Formula (III-B) or a pharmaceutically acceptable salt thereof, wherein
$R_3$ is F;
$R_{52}$ is lower alkyl optionally substituted with one or more F or cyclopropyl;
$R_{30}$ is methyl;
$R_{20}$ is methyl; and
$R_{26}$ is hydrogen or F.

In some embodiments, the disclosure provides a compound of Formula (III-C) or a pharmaceutically acceptable salt thereof:

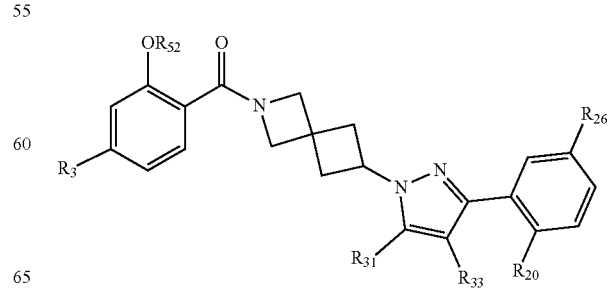

wherein

R$_3$ is halogen;

R$_{52}$ is lower alkyl or lower cycloalkyl, each optionally substituted with halogen, R$_{31}$ and R$_{33}$ are each independently hydrogen or lower alkyl optionally substituted with one or more halogen, provided that one of R$_{31}$ and R$_{33}$ is hydrogen.

R$_{20}$ is lower alkyl optionally substituted with halogen; and

R$_{26}$ is hydrogen or halogen.

In some embodiments, the disclosure provides a compound of Formula (III-C) or a pharmaceutically acceptable salt thereof, wherein R$_3$ is F;

R$_{52}$ is lower alkyl optionally substituted with one or more F; or cyclopropyl;

R$_{31}$ and R$_{33}$ are each independently hydrogen, methyl or CF$_3$, provided that one of R$_{31}$ and R$_{33}$ is hydrogen;

R$_{20}$ is methyl or CF$_3$; and

R$_{26}$ is hydrogen or F.

In some embodiments, the disclosure provides a compound of Formula (III-D) or a pharmaceutically acceptable salt thereof:

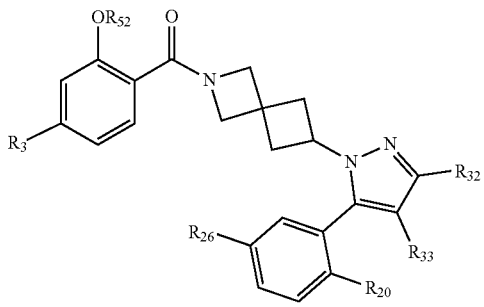

Formula (III-D)

wherein

R$_3$ is halogen;

R$_{52}$ is lower alkyl or lower cycloalkyl, each optionally substituted with halogen, R$_{32}$ and R$_{33}$ are each independently hydrogen or lower alkyl optionally substituted with one or more halogen, provided that one of R$_{32}$ and R$_{33}$ is hydrogen.

R$_{20}$ is lower alkyl optionally substituted with halogen; and

R$_{26}$ is hydrogen or halogen.

In some embodiments, the disclosure provides a compound of Formula (III-D) or a pharmaceutically acceptable salt thereof, wherein R$_3$ is F;

R$_{52}$ is lower alkyl optionally substituted with one or more F, or cyclopropyl;

R$_{32}$ and R$_{33}$ are each independently hydrogen, methyl or CF$_3$, provided that one of R$_{32}$ and R$_{33}$ is hydrogen;

R$_{20}$ is methyl or CF$_3$; and

R$_{26}$ is hydrogen or F.

In some embodiments, the disclosure provides a compound of Formula (II), or a pharmaceutically acceptable salt thereof,

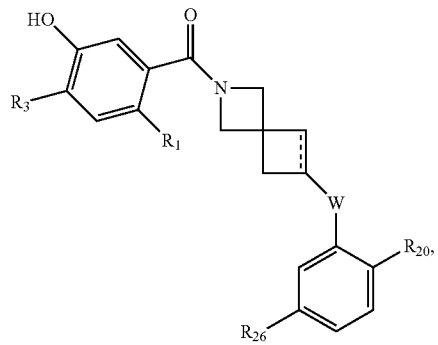

Formula (II)

wherein the dashed line represents an optional double bond;

R$_1$ is halogen;

R$_3$ is hydrogen;

W is A;

A is a 5-member heteroaryl ring optionally substituted with one or more R$_{30}$;

R$_{20}$ is halogen or lower alkyl optionally substituted with one or more halogen;

R$_{30}$ is lower alkyl optionally substituted with one or more halogen; and

R$_{26}$ is halogen or hydrogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (I) or a pharmaceutically acceptable salt thereof, wherein the compound is

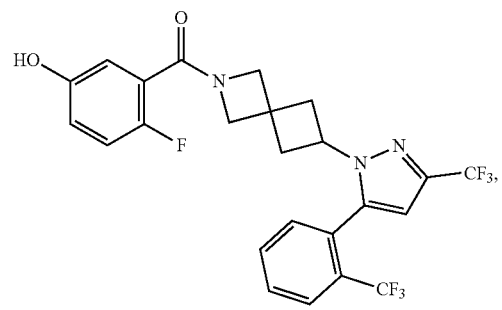 [SMILES: O=C(c1cc(O)ccc1F)N1CC2(CC(n3nc(C(F)(F)F)cc3-c3ccccc3C(F)(F)F)C2)C1]

or a pharmaceutically acceptable salt thereof.

In some embodiments, the disclosure provides a compound of Formula (I) or a pharmaceutically acceptable salt thereof, wherein the compound is

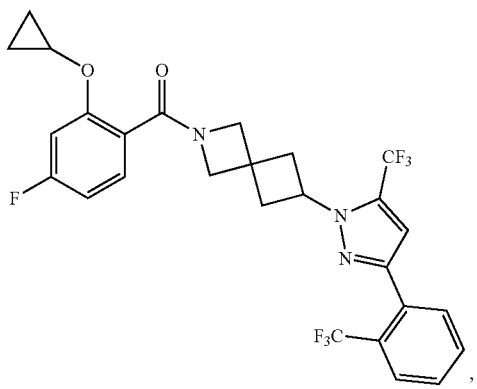 [SMILES: O=C(c1ccc(F)cc1OC1CC1)N1CC2(CC(n3nc(-c4ccccc4C(F)(F)F)cc3C(F)(F)F)C2)C1]

or a pharmaceutically acceptable salt thereof.

In some embodiments, the disclosure provides a compound of Formula (I) or a pharmaceutically acceptable salt thereof, wherein the compound is

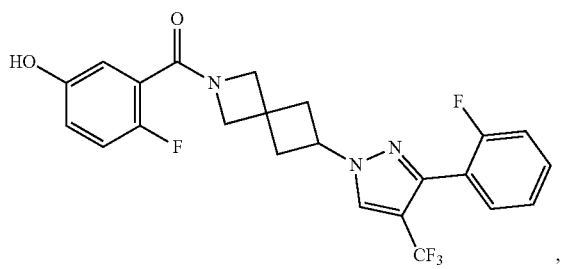

or a pharmaceutically acceptable salt thereof.

In some embodiments, the disclosure provides a compound of Formula (I) or a pharmaceutically acceptable salt thereof, wherein the compound is

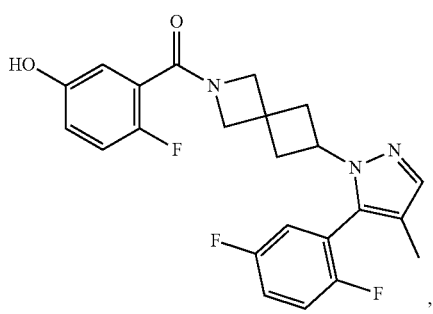 [SMILES: Cc1cnn(C2CC3(C2)CN(C(=O)c2cc(O)ccc2F)C3)c1-c1cc(F)ccc1F]

or a pharmaceutically acceptable salt thereof.

In some embodiments, the disclosure provides a compound of Formula (I) or a pharmaceutically acceptable salt thereof, wherein the compound is

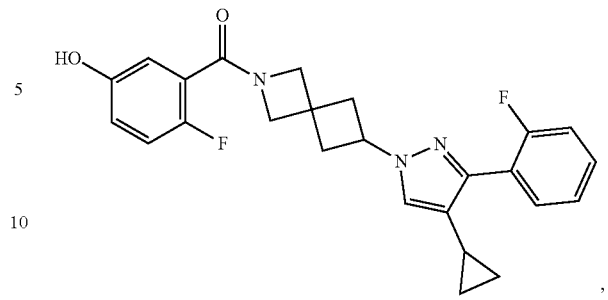

or a pharmaceutically acceptable salt thereof.

In some embodiments, the disclosure provides a compound of Formula (I) or a pharmaceutically acceptable salt thereof, wherein the compound is

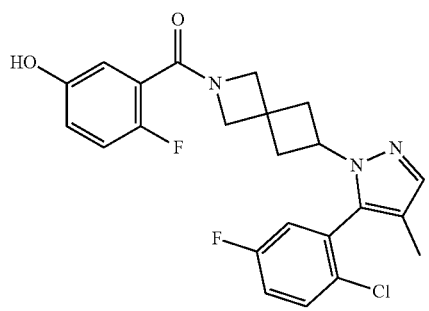

or a pharmaceutically acceptable salt thereof.

In some embodiments, the disclosure provides a compound of Formula (I) or a pharmaceutically acceptable salt thereof, wherein the compound is

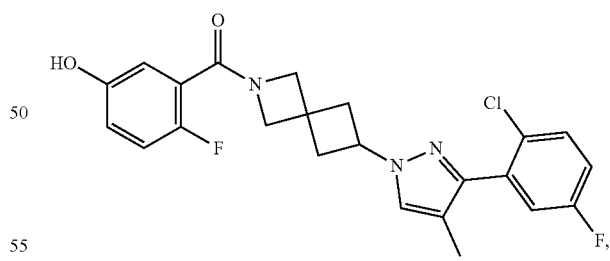

or a pharmaceutically acceptable salt thereof.

In some embodiments, the disclosure provides a compound of Formula (I) or a pharmaceutically acceptable salt thereof, wherein the compound is

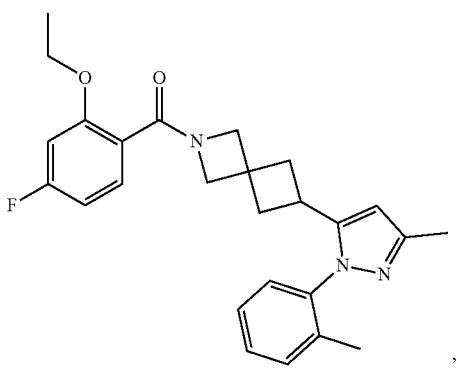 [SMILES: CCOc1cc(F)ccc1C(=O)N1CC2(CC(c3cc(C)nn3-c3ccccc3C)C2)C1]

or a pharmaceutically acceptable salt thereof.

In some embodiments, the disclosure provides a compound of Formula (I) or a pharmaceutically acceptable salt thereof, wherein the compound is

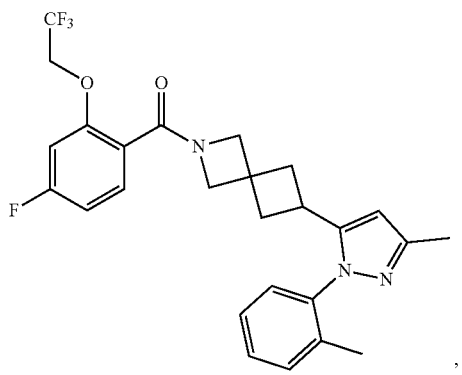 [SMILES: Cc1cc(C2CC3(C2)CN(C(=O)c2ccc(F)cc2OCC(F)(F)F)C3)n(-c2ccccc2C)n1]

or a pharmaceutically acceptable salt thereof.

In some embodiments, the disclosure provides a pharmaceutical composition comprising a compound defined herein, or a pharmaceutically acceptable salt thereof as the active pharmaceutical ingredient (API), provided the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a method of inhibiting monoacylglycerol lipase (MAGL) in a subject comprising the step of administering to a subject in need thereof a therapeutically effective amount of a compound defined herein.

In some embodiments, the disclosure provides a method of reversibly inhibiting monoacylglycerol lipase (MAGL) comprising the step of contacting a compound defined hereinwith a cell expressing MAGL.

The disclosure also provides a pharmaceutical composition comprising a compound defined herein as a Reversible MAGL Inhibitor Compound and/or Selective MAGL Inhibitor Compound disclosed herein, and a pharmaceutically acceptable carrier or excipient.

BRIEF DESCRIPTION OF THE FIGURES

No Figures are included in the disclosure.

DETAILED DESCRIPTION

Applicants have discovered chemical compounds that are Reversible MAGL Inhibitor Compounds and Selective MAGL Inhibitor Compounds. In some embodiments, the compound is a Reversible MAGL Inhibitor Compound. In some embodiments, the compound is a Selective MAGL Inhibitor Compound. In some embodiments, the compound is both a Reversible MAGL Inhibitor Compound and a Selective MAGL Inhibitor Compound.

In some embodiments, the compound is a reversible MAGL Inhibitor Compound that is not (2-fluoro-5-hydroxyphenyl)(6-(3-methyl-1-(o-tolyl)-1H-pyrazol-5-yl)-2-azaspiro[3.3]heptan-2-yl)methanone. In some embodiments, the compound is a Reversible MAGL Inhibitor Compound and a Selective MAGL Inhibitor Compound that is not (2-fluoro-5-hydroxyphenyl)(6-(3-methyl-1-(o-tolyl)-1H-pyrazol-5-yl)-2-azaspiro[3.3]heptan-2-yl)methanone.

Compounds

In some embodiments, the disclosure provides certain compounds that are both a Selective MAGL Inhibitor Compound and a Reversible MAGL Inhibitor Compound as defined herein, or a pharmaceutically acceptable salt thereof.

In some embodiments, the disclosure provides certain compounds of Formula (I-A) that are both a Selective MAGL Inhibitor Compound and a Reversible MAGL Inhibitor Compound as defined herein, or a pharmaceutically acceptable salt thereof.

Formula (I-A)

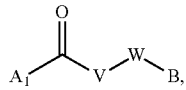

wherein $A_1$ is an aryl or heteroaryl optionally substituted with one or more Ra;

each Ra is independently halogen, cyano, lower alkyl optionally substituted with one or more halogen, cycloalkyl, aminoalkyl, carboxy, carboxamide, or —$OR_6$;

$R_6$ is hydrogen, lower alkyl or lower cycloalkyl optionally substituted with one or more halogen;

V is selected from

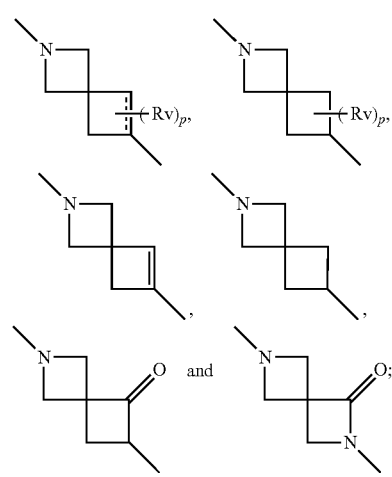

each p is independently 0, 1, 2, 3 or 4;

each Rv is independently hydrogen, halogen, or alkyl optionally substituted with one or more halogen;

W is -A$_2$-, —C(O)—, C(O)-A$_2$-, —C(O)N(R$_{10}$)— and —C(O)N(R$_{10}$)-A$_2$-;

A$_2$ is a 5-member heteroaryl ring optionally substituted with one or more R$_{30}$;

each R$_{10}$ is lower alkyl;

R$_{10}$ is hydrogen or lower alkyl;

B is 5- or 6-member aryl or heteroaryl optionally substituted with one or more R$_b$ or or —OR$_b$; and each R$_b$ is independently halogen, cyano, lower alkyl optionally substituted with one or more halogen, cycloalkyl, aminoalkyl, carboxy, or carboxamide; and provided that the compound of Formula (I-A) is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, a compound is both a Selective MAGL Inhibitor Compound and a Reversible MAGL Inhibitor Compound of Formula (I-A) that is not (2-fluoro-5-hydroxyphenyl)(6-(3-methyl-1-(o-tolyl)-1H-pyrazol-5-yl)-2-azaspiro[3.3]heptan-2-yl)methanone, wherein A$_1$ is a 6-member aryl or heteroaryl ring comprising at least one nitrogen; A$_2$ is a 5-member heteroaryl ring comprising at least one nitrogen heteroatom, and B is a 5- or 6-member aryl or B is a 5- or 6-member heteroaryl ring comprising at least one nitrogen atom, wherein each heteroaryl ring in A$_1$, A$_2$ and B comprises one or more heteroatoms selected from the group consisting of nitrogen, oxygen and sulfur.

In some embodiments, A$_1$ in Formula (I-A) is a 6-member aryl or heteroaryl optionally substituted with one or more R$_a$. In some embodiments, A$_1$ in Formula (I-A) is phenyl optionally substituted with one or more R$_a$. In some embodiments, A$_1$ in Formula (I-A) is pyridine optionally substituted with one or more R$_a$. In some embodiments, A$_1$ in Formula (I-A) is phenyl optionally substituted with one or more R$_a$.

Each R$_a$ substitution of A$_1$ of Formula (I-A) can be the same or different. Each R$_a$ in Formula (I-A) is independently halogen, cyano, lower alkyl optionally substituted with one or more halogen, cycloalkyl, aminoalkyl, carboxy, carboxamide, or —OR$_6$; and each R$_6$ in Formula (I-A) is independently hydrogen, lower alkyl or lower cycloalkyl optionally substituted with one or more halogen. In some embodiments, the halogen in Ra in Formula (I-A) is F or Cl. In some embodiments, the halogen in Ra in Formula (I-A) is F. In some embodiments, the halogen in Ra in Formula (I-A) is F or Cl. In some embodiments, the lower alkyl in Ra in Formula (I-A) is (C$_1$-C$_4$) alkyl. In some embodiments, the lower alkyl in Ra in Formula (I-A) is methyl optionally substituted with one or more F. In some embodiments, R$_a$ in Formula (I-A) is CHF$_2$, CH$_2$F, CF$_3$-cylopropyl, aminoalkyl (including azridinyl), carboxy, carboxamide, formamide, and amide. In some embodiments, cycloalkyl in R$_a$ in Formula (I-A) is cyclopropyl. In some embodiments, R$_a$ in Formula (I-A) is —NRxCORy or —CONRx or NRxCO, wherein Rx and Ry are each independently hydrogen or lower alkyl. In some embodiments, R$_a$ in Formula (I-A) is —NRxCORy or —CONRx or NRxCO, wherein Rx and Ry are each independently (C$_1$-C$_4$) alkyl or hydrogen. In some embodiments, R$_a$ in Formula (I-A) is —NRxCORy or —CONRx or NRxCO, wherein Rx and Ry are each independently methyl. In some embodiments, R$_a$ in Formula (I-A) is —NRxCORy or —CONRx or NRxCO, wherein Rx and Ry are each independently hydrogen.

In some embodiments, V in Formula (I-A) is

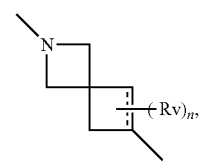

where n and each Rv is as defined above. In some embodiments, V in Formula (I-A) is

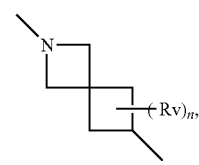

where n and each Rv is as defined above. In some embodiments, V in Formula (I-A) is

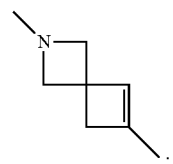

In some embodiments, V in Formula (I-A) is

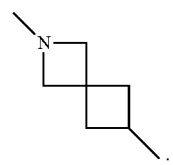

In some embodiments, V in Formula (I-A) is

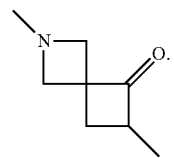

In some embodiments, V in Formula (I-A) is

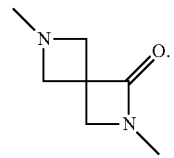

In some embodiments, V in Formula (I-A) is

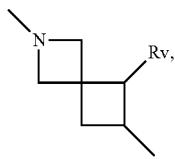

wherein Rv is as defined herein with respect to Formula (I-A).

In some embodiments, each Rv in Formula (I-A) is independently hydrogen, halogen, or alkyl optionally substituted with one or more halogen. In some embodiments, one or more Rv in Formula (I-A) is hydrogen. In some embodiments, one or more Rv in Formula (I-A) is F or Cl. In some embodiments, one or more Rv in Formula (I-A) is F. In some embodiments, one or more Rv in Formula (I-A) is alkyl optionally substituted with one or more F. In some embodiments, one or more Rv in Formula (I-A) is lower alkyl optionally substituted with one or more F. In some embodiments, one or more Rv in Formula (I-A) is $(C_1$-$C_4)$ alkyl optionally substituted with one or more F. In some embodiments, one or more Rv in Formula (I-A) is $CF_3$. In some embodiments, each Rv in Formula (I-A) is —O—$R_{v2}$ where $R_{v2}$ is hydrogen or alkyl optionally substituted with one or more halogen. In some embodiments, each Rv in Formula (I-A) is —O—$R_{v2}$ where $R_{v2}$ is hydrogen or lower alkyl optionally substituted with one or more halogen. In some embodiments, each Rv in Formula (I-A) is —O—$R_{v2}$ where $R_{v2}$ is hydrogen or lower alkyl optionally substituted with one or more F. In some embodiments, each Rv in Formula (I-A) is —O—$R_{v2}$ where $R_{v2}$ is hydrogen. In some embodiments, each Rv in Formula (I-A) is —O—$R_{v2}$ where $R_{v2}$ is lower alkyl optionally substituted with one or more halogen. In some embodiments, each Rv in Formula (I-A) is F. In some embodiments, each Rv in Formula (I-A) is methyl optionally substituted with one or more F. In some embodiments, each Rv in Formula (I-A) is methyl.

In some embodiments, each Rv in Formula (I-A) is —O—$R_{v2}$ where $R_{v2}$ is $(C_1$-$C_4)$ alkyl optionally substituted with one or more halogen. In some embodiments, each Rv in Formula (I-A) is —O—$R_{v2}$ where $R_{v2}$ is $(C_1$-$C_4)$ alkyl optionally substituted with one or more F. In some embodiments, each Rv in Formula (I-A) is —O—$R_{v2}$ where $R_2$ is methyl optionally substituted with one or more F.

In some embodiments, each n with respect to Rv in Formula (I-A) is 0, 1, 2, 3 or 4. In some embodiments, each n with respect to Rv in Formula (I-A) is 0. In some embodiments, each n with respect to Rv in Formula (I-A) is 1. In some embodiments, each n with respect to Rv in Formula (I-A) is 2. In some embodiments, each n with respect to Rv in Formula (I-A) is 3. In some embodiments, each n with respect to Rv in Formula (I-A) is 4.

In some embodiments, V in Formula (I-A) is

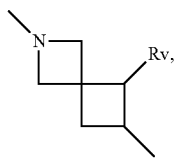

wherein Rv is halogen, lower alkyl optionally substituted with one or more halogen, or —O—$R_{v2}$ where $R_{v2}$ is $(C_1$-$C_4)$ alkyl optionally substituted with one or more halogen. In some embodiments, V in Formula (I-A) is

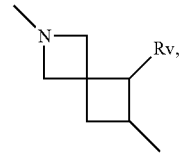

wherein Rv is F, $(C_1$-$C_4)$ alkyl optionally substituted with one or more F, or —O—$R_{v2}$ where $R_{v2}$ is methyl optionally substituted with one or more halogen. In some embodiments, V in Formula (I-A) is

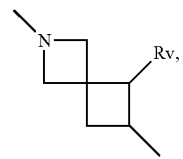

wherein Rv is F, methyl optionally substituted with one or more F, or —O—$R_{v2}$ where $R_{v2}$ is methyl optionally substituted with one or more halogen. In some embodiments, V in Formula (I-A) is

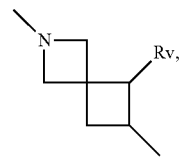

wherein Rv is F, methyl, ethyl, —$CF_3$, or —O—$R_{v2}$ where $R_{v2}$ is methyl optionally substituted with one or more halogen.

In some embodiments, W in Formula (I-A) is $A_2$, wherein $A_2$ is as defined above. In some embodiments, W in Formula (I-A) is —C(O)— or —C(O)N($R_{10}$)—, wherein $R_{10}$ is as defined above with respect to Formula (I-A). In some embodiments, W in Formula (I-A) is —C(O)—. In some embodiments, W in Formula (I-A) is —C(O)N($R_{10}$)—, wherein $R_{10}$ is as defined above with respect to Formula (I-A).

In some embodiments, W in Formula (I-A) is $A_2$, and W in Formula (I-B) is A, wherein A or $A_2$ is a 5-member heteroaryl comprising one or more heteroatoms selected from nitrogen, oxygen and sulfur, and optionally substituted with one or more $R_{30}$ as defined above. In some W in Formula (I-A) or Formula (I-B) is a 5-member heteroaryl comprising one or more nitrogen heteroatoms and optionally further comprising one or more additional heteroatoms selected from nitrogen, oxygen and sulfur, and optionally substituted with one or more $R_{30}$ as defined above. In some W in Formula (I-A) or Formula (I-B) is a 5-member heteroaryl comprising one or more nitrogen heteroatoms and optionally further comprising one or two additional heteroatoms selected from nitrogen, oxygen and sulfur, and optionally substituted with one or more $R_{30}$ as defined above. In some W in Formula (I-A) or Formula (I-B) is selected from the group consisting of:

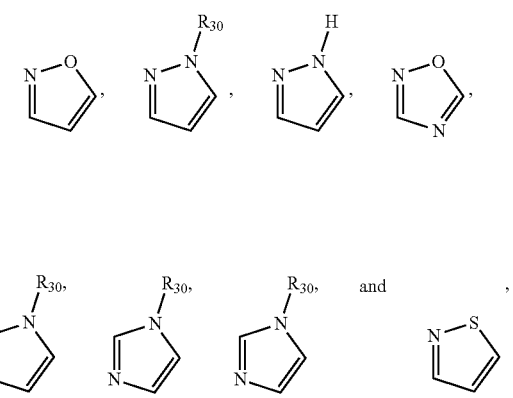

wherein $R_{30}$ is as defined herein.

In some embodiments, $A_2$ in Formula (I-A) is a 5-member heteroaryl ring optionally substituted with one or more $R_{30}$, wherein $R_{30}$ is $(C_1-C_4)$ alkyl. In some embodiments, $A_2$ in Formula (I-A) is a 5-member heteroaryl ring optionally substituted with one or more $R_{30}$, wherein $R_{30}$ is methyl.

In some embodiments, each $R_{10}$ in Formula (I-A) can be the same or different. In some embodiments, each $R_{10}$ in Formula I-A is hydrogen or $(C_1-C_4)$ alkyl. In some embodiments, one or more $R_{10}$ in Formula I-A is hydrogen. In some embodiments, one or more $R_{10}$ in Formula I-A is $(C_1-C_4)$ alkyl. In some embodiments, one or more $R_{10}$ in Formula I-A is methyl.

In some embodiments, B in Formula (I-A) is 5- or 6-member aryl or heteroaryl optionally substituted with one or more $R_b$; and each $R_b$ is independently halogen, cyano, lower alkyl optionally substituted with one or more halogen, cycloalkyl, aminoalkyl, carboxy, carboxamide, or —$OR_6$; and $R_6$ is hydrogen, lower alkyl or lower cycloalkyl optionally substituted with one or more halogen.

In some embodiments, B in Formula (I-A) is phenyl or 5- or 6-member heteroaryl comprising one or more heteroatoms selected from N, O and S, wherein the B group is optionally substituted with one or more $R_b$; and each $R_b$ is independently halogen, cyano, $(C_1-C_4)$ alkyl optionally substituted with one or more halogen, $(C_3-C_6)$cycloalkyl, 3-6 member heterocycloalkyl, aminoalkyl, carboxy, carboxamide, or —$OR_6$; and $R_6$ is hydrogen, $(C_1-C_4)$alkyl or $(C_3-C_6)$cycloalkyl optionally substituted with one or more halogen. In some embodiments, any one or more halogen within the B group in Formula (I-A) is F.

In some embodiments, B in Formula (I-A) is phenyl optionally substituted with one or more $R_b$; and each $R_b$ is independently F, Cl, cyano, $(C_1-C_4)$ alkyl optionally substituted with one or more F or Cl, $(C_3-C_6)$cycloalkyl, 3-6 member heterocycloalkyl, aminoalkyl, carboxy, carboxamide, or —$OR_6$; and $R_6$ is hydrogen, $(C_1-C_4)$alkyl or $(C_3-C_6)$cycloalkyl optionally substituted with one or more F or Cl.

In some embodiments, B in Formula (I-A) is 5-member heteroaryl comprising one or more heteroatoms selected from N, O and S, optionally substituted with one or more $R_b$; and each $R_b$ is independently F, Cl, cyano, $(C_1-C_4)$ alkyl optionally substituted with one or more F or Cl, $(C_3-C_6)$ cycloalkyl, 3-6 member heterocycloalkyl, aminoalkyl, carboxy, carboxamide, or —$OR_6$; and $R_6$ is hydrogen, $(C_1-C_4)$ alkyl or $(C_3-C_6)$cycloalkyl optionally substituted with one or more F or Cl. In some embodiments, B in Formula (I-A) is 5-member heteroaryl comprising nitrogen and 0, 1 or 2 additional heteroatoms selected from N, O and S, optionally substituted with one or more $R_b$; and each $R_b$ is independently F, Cl, cyano, $(C_1-C_4)$ alkyl optionally substituted with one or more F or Cl, $(C_3-C_6)$cycloalkyl, 3-6 member heterocycloalkyl, aminoalkyl, carboxy, carboxamide, or —$OR_6$; and $R_6$ is hydrogen, $(C_1-C_4)$alkyl or $(C_3-C_6)$cycloalkyl optionally substituted with one or more F or Cl.

In some embodiments, B in Formula (I-A) is 6-member heteroaryl comprising one or more heteroatoms selected from N, O and S, optionally substituted with one or more $R_b$; and each $R_b$ is independently F, Cl, cyano, $(C_1-C_4)$ alkyl optionally substituted with one or more F or Cl, $(C_3-C_6)$ cycloalkyl, 3-6 member heterocycloalkyl, aminoalkyl, carboxy, carboxamide, or —$OR_6$; and $R_6$ is hydrogen, $(C_1-C_4)$ alkyl or $(C_3-C_6)$cycloalkyl optionally substituted with one or more F or Cl. In some embodiments, B in Formula (I-A) is 6-member heteroaryl comprising nitrogen and 0, 1 or 2 additional heteroatoms selected from N, O and S, optionally substituted with one or more $R_b$; and each $R_b$ is independently F, Cl, cyano, $(C_1-C_4)$ alkyl optionally substituted with one or more F or Cl, $(C_3-C_6)$cycloalkyl, 3-6 member heterocycloalkyl, aminoalkyl, carboxy, carboxamide, or —$OR_6$; and $R_6$ is hydrogen, $(C_1-C_4)$alkyl or $(C_3-C_6)$cycloalkyl optionally substituted with one or more F or Cl.

In some embodiments, B in Formula (I-A) is substituted with 0, 1, 2, 3, 4 or 4 $R_b$ that are each the same or different from each other. In some embodiments, one or more $R_b$ in Formula (I-A) is F. In some embodiments, one or more $R_b$ in Formula (I-A) is Cl. In some embodiments, one or more $R_b$ in Formula (I-A) is —CN. In some embodiments, one or more $R_b$ in Formula (I-A) is $(C_1-C_4)$ alkyl optionally substituted with one or more F or Cl. In some embodiments, one or more $R_b$ in Formula (I-A) is $(C_1-C_4)$ alkyl optionally substituted with one or more F. In some embodiments, one or more $R_b$ in Formula (I-A) is methyl optionally substituted with one or more F or Cl. In some embodiments, one or more $R_b$ in Formula (I-A) is methyl optionally substituted with one or more F. In some embodiments, one or more $R_b$ in Formula (I-A) is $(C_3-C_6)$cycloalkyl. In some embodiments, one or more $R_b$ in Formula (I-A) is cyclopropyl. In some embodiments, one or more $R_b$ in Formula (I-A) is cyclobutyl. In some embodiments, one or more $R_b$ in Formula (I-A) is cyclohexyl. In some embodiments, one or more $R_b$ in Formula (I-A) is a 3-member heterocycloalkyl group comprising an O, N or S heteroatom. In some embodiments, one or more $R_b$ in Formula (I-A) is a 4-member heterocycloalkyl group comprising one or more O, N or S heteroatoms. In some embodiments, one or more $R_b$ in Formula (I-A) is a 5-member heterocycloalkyl group comprising one or more O, N or S heteroatoms. In some embodiments, one or more $R_b$ in Formula (I-A) is a 6-member heterocycloalkyl group comprising one or more O, N or S heteroatoms. In some embodiments, one or more $R_b$ in Formula (I-A) is an aminoalkyl. In some embodiments, one or more $R_b$ in Formula (I-A) is carboxy group. In some embodiments, one or more $R_b$ in Formula (I-A) is $OR_6$, and $R_6$ is hydrogen, $(C_1-C_4)$alkyl or $(C_3-C_6)$cycloalkyl optionally substituted with one or more F or Cl.

In some embodiments, the disclosure provides a compound of Formula (I-B) or a pharmaceutically acceptable salt thereof:

Formula (I-B)

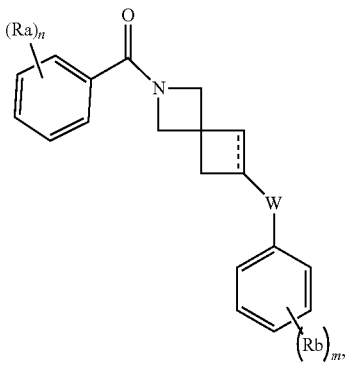

wherein
n is 1, 2, 3, 4 or 5;
each $R_a$ is independently halogen, cyano, lower alkyl optionally substituted with one or more halogen, —$OR_6$, amine, amide, or ester,
$R_6$ is hydrogen, lower alkyl or cycloalkyl optionally substituted with one or more halogen;
W is A, —C(O)—, or —C(O)N($R_{10}$)—;
A is aryl or heteroaryl each optionally substituted with one or more $R_{10}$;
each $R_{30}$ is independently lower alkyl optionally substituted with one or more halogen;
$R_{10}$ is hydrogen or lower alkyl;
m is 1, 2, 3, 4 or 5; and
each $R_b$ is independently halogen, or lower alkyl optionally substituted with one or more halogen.

In some embodiments, compounds can be a compound of Formula (I-B), wherein n is 1, 2 or 3 and each $R_a$ is independently halogen, cyano, lower alkyl optionally substituted with one or more halogen, or —$OR_6$; $R_6$ is hydrogen, lower alkyl or cycloalkyl optionally substituted with one or more halogen. In compounds of Formula (I-B), n is 1, 2 or 3 and each $R_a$ is independently F or Cl, cyano, ($C_1$-$C_4$)alkyl optionally substituted with one or more F, or —$OR_6$; $R_6$ is hydrogen, ($C_1$-$C_4$)alkyl or cyclopropyl optionally substituted with one or more F.

In some embodiments, the disclosure provides a compound of Formula (I-B) or a pharmaceutically acceptable salt thereof:

Formula (I-B)

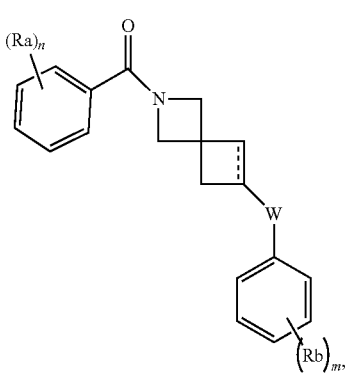

wherein
n is 1, 2, or 3;
each Ra is independently halogen, cyano, lower alkyl optionally substituted with one or more halogen, or —$OR_6$;
$R_6$ is hydrogen, lower alkyl or lower cycloalkyl optionally substituted with one or more halogen;
W is A, —C(O)—, —C(O)-A-, or —C(O)N($R_{10}$)—;
$R_{10}$ is hydrogen or lower alkyl;
A is a 5-member heteroaryl ring optionally substituted with one or more $R_{30}$;
$R_{30}$ is lower alkyl;
m is 1, or 2; and
each $R_b$ is independently halogen, or lower alkyl optionally substituted with one or more halogen;
provided that the compound of Formula (I-B) is not (2-fluoro-5-hydroxyphenyl)(6-(3-methyl-1-(o-tolyl)-1H-pyrazol-5-yl)-2-azaspiro[3.3]heptan-2-yl)methanone.

In compounds of Formula (I-B), W is a 5-member heteroaryl ring comprising at least one nitrogen, such as a triazole, imidazole, pyrazole, or an oxadiazole. In some embodiments, one or more of the lower alkyl groups in Ra, Rv, $R_6$, $R_{10}$, $R_{10}$, $R_{30}$ and $R_b$ can independently be methyl. In some embodiments, a compound is a compound of Formula (I-B), wherein each $R_a$ is independently Cl, F, CN, cyano, methyl, or —$OR_6$; $R_6$ is hydrogen, ($C_1$-$C_4$)alkyl optionally substituted with one or more F or cyclopropyl; W is -A-, —C(O)—, or —C(O)N($R_{10}$)—; $R_{10}$ is hydrogen or methyl; A is a 5-member heteroaryl ring optionally substituted with one or more $R_{30}$; $R_{30}$ is ($C_1$-$C_4$)alkyl; m is 1, or 2; and each $R_b$ is independently halogen, or ($C_1$-$C_4$)alkyl optionally substituted with one or more F. In some embodiments, a compound is a compound of Formula (I-B) wherein $R_{30}$ is methyl; and each $R_b$ is independently halogen, or methyl optionally substituted with one or more F. In some embodiments, a compound is a compound of Formula (I-B) wherein A is pyrazole, imidazole, or triazole, each optionally substituted with one methyl. In some embodiments, a compound is a compound of Formula (I-B) wherein A is oxadiazole. In some embodiments, a compound is a compound of Formula (I-B), wherein A is pyrazole substituted with one methyl. In some embodiments, a compound is a compound of Formula (I-B), wherein one Ra is —$OR_6$.

In some embodiments, compounds of Formula (I-A) of Formula (I-B) can be a compound of Formula (I-B-1), or pharmaceutically acceptable salt thereof:

Formula (I-B-1)

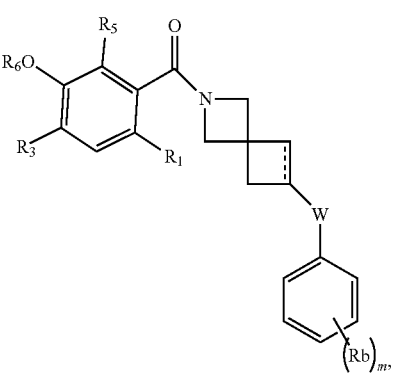

wherein
R$_1$ is hydrogen or halogen;
R$_3$ is hydrogen, halogen, or lower alkyl optionally substituted with one or more halogen;
R$_5$ is hydrogen, halogen, lower alkoxy or lower alkyl each optionally substituted with one or more halogen;
R$_6$ is hydrogen, lower alkyl or cycloalkyl optionally substituted with one or more halogen; and
W is A, —C(O)—, or —C(O)N(R$_{10}$)—;
A is aryl or heteroaryl each optionally substituted with one or more R$_{30}$;
each R$_{30}$ is independently lower alkyl optionally substituted with one or more halogen;
R$_{10}$ is hydrogen or lower alkyl; and
m is 1, 2, 3, 4 or 5; and
each R$_b$ is independently halogen, or lower alkyl optionally substituted with one or more halogen;
provided that the compound of Formula (I-B-1) is not (2-fluoro-5-hydroxyphenyl)(6-(3-methyl-1-(0-tolyl)-1H-pyrazol-5-yl)-2-azaspiro[3.3]heptan-2-yl)methanone.

In some embodiments, a compound is a compound of Formula (I-B-1) wherein R$_1$ is hydrogen, —CN, Cl or F. In some embodiments, R$_6$ is hydrogen, (C$_1$-C$_4$)alkyl or cyclopropyl optionally substituted with one or more F. In some embodiments, a compound is a compound of Formula (I-B-1) wherein R$_1$ is hydrogen, —CN, Cl or F and R$_6$ is hydrogen, (C$_1$-C$_4$)alkyl or cyclopropyl optionally substituted with one or more F. In some embodiments, R$_3$ is hydrogen, F, or methyl optionally substituted with one or more halogen. In some embodiments, a compound is a compound of Formula (I-B-1) wherein R$_1$ is hydrogen, —CN, Cl or F; R$_6$ is hydrogen, (C$_1$-C$_4$)alkyl or cyclopropyl optionally substituted with one or more F; and R$_3$ is hydrogen, F, or methyl optionally substituted with one or more halogen. In some embodiments, a compound is a compound of Formula (I-B-1) wherein R$_1$ is hydrogen, —CN, Cl or F; R$_b$ is hydrogen, (C$_1$-C$_4$)alkyl or cyclopropyl optionally substituted with one or more F; R$_3$ is hydrogen, F, or methyl optionally substituted with one or more halogen; and R$_5$ is hydrogen.

In some embodiments, a compound is a compound of Formula (I-B-1) wherein R$_1$ is Cl, F or —CN and R$_6$ is hydrogen. In some embodiments, a compound is a compound of Formula (I-B-1) wherein R$_1$ is F. In some embodiments, a compound is a compound of Formula (I-B-1) wherein R$_1$ is Cl, F or —CN and R$_3$, R$_5$ and R$_6$ are each hydrogen. In some embodiments, a compound is a compound of Formula (I-B-1) wherein R$_1$ is Cl, F or —CN; R$_3$ is hydrogen, methyl or F; R$_5$ is hydrogen, methyl or F; and R$_6$ is hydrogen. In some embodiments, a compound is a compound of Formula (I-B-1) wherein R$_1$ is F; R$_3$ is hydrogen, methyl or F; R$_5$ is hydrogen; and R$_6$ is hydrogen. In some embodiments, a compound is a compound of Formula (I-B-1) wherein R$_1$ is F; R$_3$ is hydrogen; R$_5$ is hydrogen or F; and R$_6$ is hydrogen. In some embodiments, a compound is a compound of Formula (I-B-1) wherein R$_1$ is hydrogen; R$_3$ is hydrogen or F; R$_5$ is hydrogen; and R$_6$ is hydrogen. In some embodiments, a compound is a compound of Formula (I-B-1) wherein R$_1$ is F or —CN; R$_3$ is hydrogen or F; R$_5$ is hydrogen; and R$_6$ is hydrogen. In some embodiments, a compound is a compound of Formula (I-B-1) wherein R$_1$ and R$_6$ are each hydrogen.

In some embodiments, a compound is a compound of Formula (I-B-1) wherein R$_1$ is F and R$_6$ is hydrogen. In some embodiments, a compound is a compound of Formula (I-B-1) wherein R$_j$ is F, R$_6$ is hydrogen and at least one of R$_3$ and R$_5$ is hydrogen. In some embodiments, a compound is a compound of Formula (I-B-1) wherein R$_1$ is F, R$_6$ is hydrogen, and R$_3$ and R$_5$ are each hydrogen. In some embodiments, a compound is a compound of Formula (I-B-1) wherein R$_1$ is F, R$_6$ is hydrogen and at least one of R$_3$ and R$_5$ is hydrogen and at least one of R$_3$ and R$_5$ is F or methyl.

In some embodiments, a compound is a compound of Formula (I-B-1) wherein W is A and A is 5-member aryl or 5-member heteroaryl wherein each A is optionally substituted with one or more R$_{30}$; and each R$_{30}$ is independently lower alkyl optionally substituted with one or more halogen. In some embodiments, a compound is a compound of Formula (I-B-1) wherein W is A and A is 5-member heteroaryl comprising at least one nitrogen heteroatom wherein each A is optionally substituted with one or more R$_{30}$; and each R$_{30}$ is independently (C$_1$-C$_4$) alkyl optionally substituted with one or more halogen. In some embodiments, a compound is a compound of Formula (I-B-1) wherein W is A and A is 5-member heteroaryl comprising at least one nitrogen heteroatom wherein each A is optionally substituted with one or more R$_{30}$; and each R$_{30}$ is independently F or methyl optionally substituted with one or more F.

In some embodiments, compounds of Formula (I-A) or Formula (I-B) can be a compound of Formula (I-B-2), or pharmaceutically acceptable salt thereof:

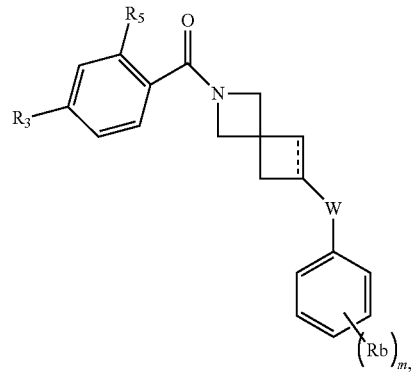

Formula (I-B-2)

wherein
R$_3$ is hydrogen or halogen;
R$_5$ is —O—R$_{52}$;
R$_{52}$ is lower alkyl or cycloalkyl, each optionally substituted with halogen,
W is A, —C(O)—, or —C(O)N(R$_{10}$)—;
A is aryl or heteroaryl each optionally substituted with one or more R$_{30}$;
each R$_{30}$ is independently lower alkyl optionally substituted with one or more halogen;
R$_{10}$ is hydrogen or lower alkyl; and
m is 1, 2, 3, 4 or 5; and
each R$_b$ is independently halogen, or lower alkyl optionally substituted with one or more halogen.

In some embodiments, a compound is a compound of Formula (I-B-2) wherein R$_3$ is hydrogen, Cl or F. In some embodiments, a compound is a compound of Formula (I-B-2) wherein R$_3$ is F. In some embodiments, a compound is a compound of Formula (I-B-2) wherein R$_{52}$ is (C$_1$-C$_4$) alkyl optionally substituted with one or more halogen, or cyclopropyl. In some embodiments, a compound is a compound of Formula (I-B-2) wherein $R_3$ is F and $R_{52}$ is $(C_1-C_4)$alkyl optionally substituted with one or more halogen, or cyclopropyl. In some embodiments, a compound is a compound of Formula (I-B-2) wherein $R_{52}$ is $(C_1-C_4)$alkyl optionally substituted with one or more F, or cyclopropyl. In some embodiments, a compound is a compound of Formula (I-B-2) wherein $R_3$ is F and $R_{52}$ is $(C_1-C_4)$alkyl optionally substituted with one or more F, or cyclopropyl.

In some embodiments, a compound is a compound of Formula (I-B-2) wherein $R_{52}$ is selected from the group consisting of: methyl, ethyl, propyl optionally substituted with one or more F. In some embodiments, a compound is a compound of Formula (I-B-2) wherein $R_3$ is F and $R_{52}$ is selected from the group consisting of: methyl, ethyl, propyl optionally substituted with one or more F. In some embodiments, a compound is a compound of Formula (I-B-2) wherein $R_{52}$ is selected from the group consisting of: methyl, ethyl, isopropyl, —$CH_2$—$CF_3$ and cyclopropyl. In some embodiments, a compound is a compound of Formula (I-B-2) wherein R; is F and $R_{52}$ is selected from the group consisting of: methyl, ethyl, isopropyl, —$CH_2$—$CF_3$ and cyclopropyl.

In some embodiments, a compound is a compound of Formula (I-B-2) wherein W is A and A is 5-member aryl or 5-member heteroaryl wherein each A is optionally substituted with one or more $R_{30}$; and each $R_{30}$ is independently lower alkyl optionally substituted with one or more halogen. In some embodiments, a compound is a compound of Formula (I-B-2) wherein W is A and A is 5-member heteroaryl comprising at least one nitrogen heteroatom wherein each A is optionally substituted with one or more $R_{30}$; and each $R_{30}$ is independently $(C_1-C_4)$ alkyl optionally substituted with one or more halogen. In some embodiments, a compound is a compound of Formula (I-B-2) wherein W is A and A is 5-member heteroaryl comprising at least one nitrogen heteroatom wherein each A is optionally substituted with one or more $R_{30}$; and each $R_{30}$ is independently F or methyl optionally substituted with one or more F.

In some embodiments, a compound is a compound of Formula (I-A), Formula (I-B), Formula (I-B-1) or Formula (I-B-2), wherein W is A, and A is an aryl or heteroaryl optionally substituted with one or more $R_{30}$, and $R_{10}$ is $(C_1-C_4)$alkyl optionally substituted with one or more halogen. In some embodiments, a compound is a compound of Formula (I-A), Formula (I-B), Formula (I-B-1) or Formula (I-B-2), wherein A is a 5-member heteroaryl optionally substituted with one or more $(C_1-C_4)$alkyl optionally substituted with one or more halogen. In some embodiments, a compound is a compound of Formula (I-A), Formula (I-B), Formula (I-B-1) or Formula (I-B-2), wherein A is a 5-member heteroaryl comprising one or more nitrogen heteroatoms and optionally substituted with one or more methyl.

In some embodiments, a compound is a compound of Formula (I-A), Formula (I-B), Formula (I-B-1) or Formula (I-B-2), wherein W is selected from the group consisting of: imidazole, pyrazole, triazole and oxadiazole each optionally substituted with one or more lower alkyl. In some embodiments, a compound is a compound of Formula (I-A), Formula (I-B), Formula (I-B-1) or Formula (I-B-2), wherein W is selected from the group consisting of: imidazole, pyrazole, triazole and oxadiazole each optionally substituted with one or more methyl. In some embodiments, a compound is a compound of Formula (I-A), Formula (I-B), Formula (I-B-1) or Formula (I-B-2), wherein W is selected from the group consisting of A1, A2, A3, A4, A5, A6 and A7 as shown below, wherein $R_{30}$, $R_{32}$, $R_{33}$, $R_{34}$, $R_{36}$, $R_{37}$, $R_{38}$ and $R_{39}$ are each independently hydrogen or lower alkyl:

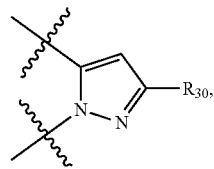
A1

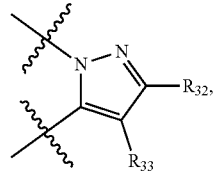
A2

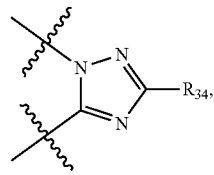
A3

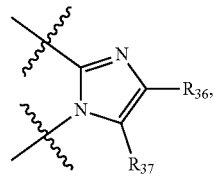
A4

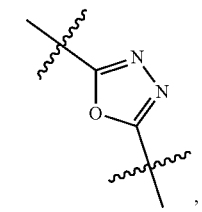
A5

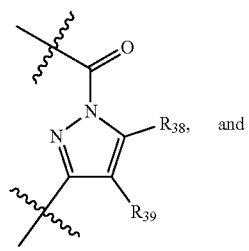
A6

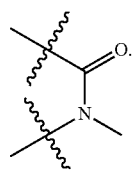
A7

In some embodiments, a compound is a compound of Formula (I-A), Formula (I-B), Formula (I-B-1) or Formula (I-B-2), wherein W is selected from the group consisting of A1, A2, A3, A4, A5, and A6 as shown above, wherein $R_{30}$, $R_{32}$, $R_{33}$, $R_{34}$, $R_{36}$, $R_{37}$, $R_{38}$ and $R_{39}$ are each independently hydrogen or methyl. In some embodiments, a compound is a compound of Formula (I-A), Formula (I-B), Formula (I-B-1) or Formula (I-B-2), wherein W is selected from the group consisting of A1, A2, A3, A4, A5, and A6 as shown above, wherein $R_{30}$, $R_{32}$, $R_{33}$, $R_{34}$, $R_{36}$, $R_{37}$, $R_{38}$ and $R_{39}$ are each independently hydrogen or methyl.

In some embodiments, a compound is a compound of Formula (I-A), Formula (I-B), Formula (I-B-1) or Formula (I-B-2), wherein W is A1 and $R_{30}$ is hydrogen or methyl. In some embodiments, a compound is a compound of Formula (I-A), Formula (I-B), Formula (I-B-1) or Formula (I-B-2), wherein W is A1 and $R_{30}$ is hydrogen. In some embodiments, a compound is a compound of Formula (I-A), Formula (I-B), Formula (I-B-1) or Formula (I-B-2), wherein W is A1 and $R_{30}$ is methyl. In some embodiments, a compound is a compound of Formula (I-A), Formula (I-B), Formula (I-B-1) or Formula (I-B-2), wherein W is A2 and $R_{32}$ and $R_{33}$ is hydrogen or methyl.

In some embodiments, a compound is a compound of Formula (I-A), Formula (I-B), Formula (I-B-1) or Formula (I-B-2), wherein W is A2 and one of $R_{32}$ and $R_{33}$ is hydrogen and one of $R_{32}$ and $R_{33}$ is methyl. In some embodiments, a compound is a compound of Formula (I-A), Formula (I-B), Formula (I-B-1) or Formula (I-B-2), wherein W is A2 and $R_{32}$ is methyl and $R_{33}$ is hydrogen. In some embodiments, a compound is a compound of Formula (I-A), Formula (I-B), Formula (I-B-1) or Formula (I-B-2), wherein W is A2 and $R_{32}$ is hydrogen and $R_{33}$ is methyl. In some embodiments, a compound is a compound of Formula (I-A), Formula (I-B), Formula (I-B-1) or Formula (I-B-2), wherein W is A2 and $R_{32}$ is hydrogen and $R_{33}$ is hydrogen.

In some embodiments, a compound is a compound of Formula (I-A), Formula (I-B), Formula (I-B-1) or Formula (I-B-2), wherein W is A3 and $R_{34}$ is hydrogen or methyl. In some embodiments, a compound is a compound of Formula (I-A), Formula (I-B), Formula (I-B-1) or Formula (I-B-2), wherein W is A3 and $R_{34}$ is hydrogen. In some embodiments, a compound is a compound of Formula (I-A), Formula (I-B), Formula (I-B-1) or Formula (I-B-2), wherein W is A1 and $R_{34}$ is methyl.

In some embodiments, a compound is a compound of Formula (I-A), Formula (I-B), Formula (I-B-1) or Formula (I-B-2), wherein W is A4 and one of $R_{36}$ and $R_{37}$ is hydrogen and one of $R_{36}$ and $R_{37}$ is methyl. In some embodiments, a compound is a compound of Formula (I-A), Formula (I-B), Formula (I-B-1) or Formula (I-B-2), wherein W is A4 and $R_{36}$ is methyl and $R_{37}$ is hydrogen. In some embodiments, a compound is a compound of Formula (I-A), Formula (I-B), Formula (I-B-1) or Formula (I-B-2), wherein W is A4 and $R_{36}$ is hydrogen and $R_{37}$ is methyl. In some embodiments, a compound is a compound of Formula (I-A), Formula (I-B), Formula (I-B-1) or Formula (I-B-2), wherein W is A4 and $R_{36}$ is hydrogen and $R_{37}$ is hydrogen.

In some embodiments, a compound is a compound of Formula (I-A), Formula (I-B), Formula (I-B-1) or Formula (I-B-2), wherein W is A5.

In some embodiments, a compound is a compound of Formula (I-A), Formula (I-B), Formula (I-B-1) or Formula (I-B-2), wherein W is A6 and one of $R_{38}$ and $R_{39}$ is hydrogen and one of $R_{38}$ and $R_{39}$ is methyl. In some embodiments, a compound is a compound of Formula (I-A), Formula (I-B), Formula (I-B-1) or Formula (I-B-2), wherein W is A6 and $R_{38}$ is methyl and $R_{39}$ is hydrogen. In some embodiments, a compound is a compound of Formula (I-A), Formula (I-B), Formula (I-B-1) or Formula (I-B-2), wherein W is A6 and $R_{38}$ is hydrogen and $R_{39}$ is methyl. In some embodiments, a compound is a compound of Formula (I-A), Formula (I-B), Formula (I-B-1) or Formula (I-B-2), wherein W is A6 and $R_{38}$ is hydrogen and $R_{39}$ is hydrogen.

In some embodiments, a compound is a compound of Formula (I-A), Formula (I-B), Formula (I-B-1) or Formula (I-B-2), wherein at least one of Ra is hydroxyl or $(C_1-C_4)$ alkoxy optionally substituted with one or more halogen, and n is 1, 2 or 3. In some embodiments, a compound is a compound of Formula (I-A), Formula (I-B), Formula (I-B-1) or Formula (I-B-2), wherein at least one of Ra is hydroxyl or $(C_1-C_4)$alkoxy optionally substituted with one or more F, and n is 1, 2 or 3. In some embodiments, a compound is a compound of Formula (I-A), Formula (I-B), Formula (I-B-1) or Formula (I-B-2), wherein at least one of Ra is hydroxyl, $(C_1-C_4)$alkoxy or —O—$(C_1-C_6)$cycloalkyl each optionally substituted with one or more F, with the remaining Ra selected from the group consisting of halogen, methyl, and cyano; and n is 1, 2 or 3. In some embodiments, a compound is a compound of Formula (I-A), Formula (I-B), Formula (I-B-1) or Formula (I-B-2), wherein at least one of Ra is hydroxyl, $(C_1-C_4)$alkoxy or —O-(cyclopropyl) each optionally substituted with one or more F, with the remaining Ra selected from the group consisting of halogen, methyl, and cyano; and n is 1, 2 or 3. In some embodiments, a compound is a compound of Formula (I-A), Formula (I-B), Formula (I-B-1) or Formula (I-B-2), wherein at least one of Ra is hydroxyl, $(C_1-C_4)$alkoxy or —O-(cyclopropyl) each optionally substituted with one or more F, with the remaining $R_a$ selected from the group consisting of Cl, F, methyl, and cyano; and n is 1, 2 or 3.

In some embodiments, a compound is a compound of Formula (I-A), Formula (I-B), Formula (I-B-1) or Formula (I-B-2), wherein W is A7.

In some embodiments, a compound is a compound of Formula (I-A), Formula (I-B), Formula (I-B-1) or Formula (I-B-2), wherein W is —C(O)—.

In some embodiments, a compound is a compound of Formula (I-A), Formula (I-B), Formula (I-B-1) or Formula (I-B-2), wherein W is —C(O)N($R_{10}$)—, and —$R_{10}$ is hydrogen. In some embodiments, a compound is a compound of Formula (I-A), Formula (I-B), Formula (I-B-1) or Formula (I-B-2), wherein W is —C(O)N($R_{10}$)—, and —$R_{10}$ is methyl. In some embodiments, a compound is a compound of Formula (I-A), Formula (I-B), Formula (I-B-1) or Formula (I-B-2), wherein W is —C(O)N($R_{10}$)—, and —$R_{10}$ is $(C_1-C_4)$ alkyl optionally substituted with F. In some embodiments, a compound is a compound of Formula (I-A), Formula (I-B), Formula (I-B-1) or Formula (I-B-2), wherein W is —C(O)N($R_{10}$)—, and —$R_{10}$ is lower alkyl optionally substituted with halogen.

In some embodiments, compounds of Formula (I-A) or Formula (I-B) can be a compound of Formula (I-C), or pharmaceutically acceptable salt thereof:

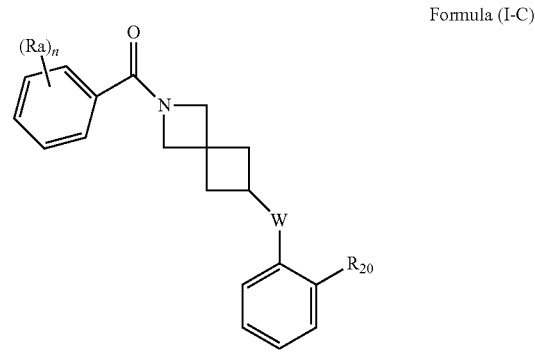

Formula (I-C)

wherein:
R$_{20}$ is lower alkyl;
n is 1, 2, or 3;
each R$_a$ is independently halogen, cyano, lower alkyl optionally substituted with one or more halogen, or —OR$_6$; and
R$_6$ is hydrogen, lower alkyl or lower cycloalkyl optionally substituted with one or more halogen; and
W is as defined above for Formula (I-A) or Formula (I-B).

In some embodiments, a compound is a compound of Formula (I-C), wherein R$_{20}$ is (C$_1$-C$_4$)alkyl. In some embodiments, a compound is a compound of Formula (I-C), wherein R$_{20}$ is methyl. In some embodiments, a compound is a compound of Formula (I-C), wherein W is A7

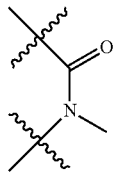

A7 and R$_{20}$ is methyl, each R$_a$ is independently F, Cl, —CN, (C$_1$-C$_4$)alkyl optionally substituted with one or more F or Cl, or —OR$_6$ and R$_6$ is hydrogen, (C$_1$-C$_4$)alkyl or cyclopropyl optionally substituted with one or more F or Cl. In some embodiments, a compound is a compound of Formula (I-C), wherein n is 1, 2 or 3, W is A7 and R$_{20}$ is methyl, each Ra is independently F, Cl, —CN, methyl, or —OH. In some embodiments, a compound is a compound of Formula (I-C), wherein n is 2, W is A7 and R$_{20}$ is methyl, each Ra is independently F or —OH.

In some embodiments, a compound is a compound of Formula (I-C), wherein at least one of Ra is hydroxyl or (C$_1$-C$_4$)alkoxy optionally substituted with one or more halogen, and n is 1, 2 or 3. In some embodiments, a compound is a compound of Formula (I-C), wherein at least one of Ra is hydroxyl or (C$_1$-C$_4$)alkoxy optionally substituted with one or more F, and n is 1, 2 or 3. In some embodiments, a compound is a compound of Formula (I-C), wherein at least one of Ra is hydroxyl, (C$_1$-C$_4$)alkoxy or —O—(C$_1$-C$_6$)cycloalkyl each optionally substituted with one or more F, with the remaining Ra selected from the group consisting of halogen, methyl, and cyano; and n is 1, 2 or 3. In some embodiments, a compound is a compound of Formula (I-C), wherein at least one of Ra is hydroxyl, (C$_1$-C$_4$)alkoxy or —O-(cyclopropyl) each optionally substituted with one or more F, with the remaining Ra selected from the group consisting of halogen, methyl, and cyano; and n is 1, 2 or 3. In some embodiments, a compound is a compound of Formula (I-C), wherein at least one of Ra is hydroxyl, (C$_1$-C$_4$)alkoxy or —O-(cyclopropyl) each optionally substituted with one or more F, with the remaining Ra selected from the group consisting of Cl, F, methyl, and cyano; and n is 2 or 3. In some embodiments, a compound is a compound of Formula (I-C), wherein at least one of Ra is hydroxyl, with the remaining Ra selected from the group consisting of F, methyl, and cyano; and n is 2 or 3.

In some embodiments, the disclosure provides a compound of Formula (I-A) or Formula (I-B) that are also compounds of Formula (II) or a pharmaceutically acceptable salt thereof:

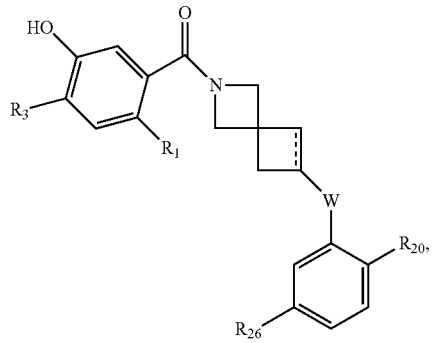

Formula (II)

wherein
R$_1$ is halogen or cyano;
R$_3$ is hydrogen, lower alkyl, or halogen;
W is —C(O)-A, —C(O)N(R$_{10}$)-A, and A;
R$_{10}$ is hydrogen or lower alkyl;
A is a 5-member heteroaryl ring optionally substituted with one or more R$_{30}$;
R$_{20}$ is halogen or lower alkyl optionally substituted with one or more halogen;
R$_{30}$ is lower alkyl optionally substituted with one or more halogen; and
R$_{26}$ is halogen or hydrogen.

In some embodiments, a compound of Formula (I-A) or Formula (I-B) can be a compound of Formula (II) wherein R$_1$ is Cl, F or cyano; R$_3$ is hydrogen, F or methyl; R$_{10}$ is hydrogen or methyl; R$_{20}$ and R$_{30}$ are each independently methyl; and R$_{26}$ is F or hydrogen. In some embodiments, a compound of Formula (I) can be a compound of Formula (II) wherein R$_1$ is Cl, F or cyano; R$_3$ is hydrogen, F or methyl; R$_{10}$ is hydrogen or methyl; R$_{20}$ and R$_{10}$ are each independently methyl; and R$_{26}$ is hydrogen. In some embodiments, a compound of Formula (I) can be a compound of Formula (II) wherein W is —C(O)N(R$_{10}$)-A, and A wherein R$_{10}$ is hydrogen or methyl and A is a 5-member heteroaryl ring comprising at least one nitrogen optionally substituted with one or more lower alkyl, the lower alkyl being optionally substituted with one or more halogen; and R$_{26}$ is hydrogen. In some embodiments, a compound of Formula (I) can be a compound of Formula (II) wherein R$_{20}$ and R$_{30}$ are each independently lower alkyl optionally substituted with one or more F and R$_{26}$ is hydrogen. In some embodiments, a compound of Formula (I) can be a compound of Formula (II) wherein R$_{20}$ is halogen or lower alkyl optionally substituted with one or more F; R$_{30}$ is lower alkyl optionally substituted with one or more F; and R$_{26}$ is hydrogen. In some embodiments, a compound of Formula (I) can be a compound of Formula (II) wherein R$_{20}$ is Cl, F or methyl optionally substituted with one or more F; R$_{30}$ is methyl optionally substituted with one or more F; and R$_{26}$ is hydrogen.

In some embodiments, a compound of Formula (I-A) or Formula (I-B) can be a compound of Formula (II) wherein W is an amide optionally substituted with lower alkyl, carboxyl or 5-member heteroaryl ring comprising at least one nitrogen, such as a pyrazole, imidazole, triazole or oxadiazole, each optionally substituted with lower alkyl. In some embodiments, R$_1$ is Cl, F or CN in Formula (II); and R$_{26}$ is hydrogen. In some embodiments, R$_3$ is methyl; and R$_{26}$ is hydrogen. In some embodiments, R$_3$ is hydrogen; and R$_{26}$ is hydrogen. In some embodiments, R$_3$ is F; and R$_{26}$ is hydrogen. In some embodiments, a compound can be a compound of Formula (II) wherein W is pyrazole, imidazole, triazole or oxadiazole, each optionally substituted with methyl; $R_1$ is Cl, F or CN; $R_3$ is hydrogen, methyl or F; and $R_{26}$ is hydrogen.

In some embodiments, a compound of Formula (I-A) or Formula (I-B) can be a compound of Formula (II) wherein the lower alkyl in $R_1$, $R_3$, and $R_{20}$ is methyl; and $R_{26}$ is hydrogen. In some embodiments, a compound of Formula (I) can be a compound of Formula (II) wherein $R_{10}$ is methyl; A is pyrazole, imidazole, triazole or oxadiazole each optionally substituted with methyl; and $R_{20}$ is methyl; and $R_{26}$ is hydrogen. In some embodiments, a compound of Formula (I) can be a compound of Formula (II) wherein W is pyrazole optionally substituted with one or more methyl; $R_1$ is the F; $R_3$ is H or F and $R_{20}$ is methyl; and $R_{26}$ is hydrogen. In some embodiments, a compound of Formula (I) can be a compound of Formula (II) wherein W is pyrazole optionally substituted with one or more methyl, $R_1$ is the F, Ra is H and $R_{20}$ is methyl and $R_{26}$ is hydrogen.

In some embodiments, a compound of Formula (I-A) or Formula (I-B) can be a compound of Formula (II) wherein the lower alkyl in $R_1$, $R_3$, and $R_{20}$ is methyl; and $R_{26}$ is F. In some embodiments, a compound of Formula (I) can be a compound of Formula (II) wherein $R_{10}$ is methyl; A is pyrazole, imidazole, triazole or oxadiazole each optionally substituted with methyl; and $R_{20}$ is methyl; and $R_{26}$ is F. In some embodiments, a compound of Formula (I) can be a compound of Formula (II) wherein W is pyrazole optionally substituted with one or more methyl; $R_1$ is the F; $R_3$ is H or F and $R_{20}$ is methyl; and $R_{26}$ is F. In some embodiments, a compound of Formula (I) can be a compound of Formula (II) wherein W is pyrazole optionally substituted with one or more methyl, $R_1$ is the F, $R_3$ is H and $R_{20}$ is methyl and $R_{26}$ is F.

In some embodiments, the disclosure provides a compound of Formula (I-A) or Formula (I-B) that are also compounds of Formula (II) or a pharmaceutically acceptable salt thereof:

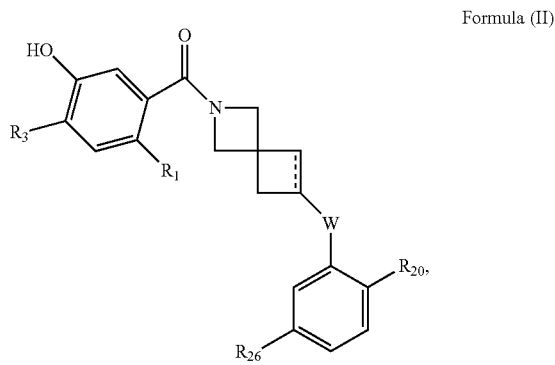

Formula (II)

wherein
  $R_1$ is halogen or cyano;
  $R_3$ is hydrogen or halogen;
  W is A, —C(O)—, or —C(O)N($R_{10}$)—;
  $R_{10}$ is hydrogen or lower alkyl;
  A is a 5-member heteroaryl ring optionally substituted with one or more $R_{10}$; and
  $R_{20}$ and $R_{30}$ are each independently lower alkyl; and
  $R_{26}$ is as defined herein for Formula (I-A) or Formula (I-B);

provided that the compound of Formula (II) is not (2-fluoro-5-hydroxyphenyl)(6-(3-methyl-1-(o-tolyl)-1H-pyrazol-5-yl)-2-azaspiro[3.3]heptan-2-yl)methanone.

In compounds of Formula (II), W is a 5-member heteroaryl ring comprising at least one nitrogen, such as a pyrazole. In some embodiments, $R_1$ is Cl, F or CN. In some embodiments, $R_3$ is H. In some embodiments, $R_3$ is F. In some embodiments, the lower alkyl in each of Ra, $R_6$, $R_{10}$, $R_{10}$ and $R_b$ can independently be methyl. In some embodiments, W is pyrazole optionally substituted with one or more methyl, $R_1$ is the F, $R_3$ is H or F and each of Ra, $R_6$, $R_{10}$, $R_{30}$ and Rb is methyl in a compound of Formula (II). In some embodiments, W is pyrazole optionally substituted with one or more methyl, $R_1$ is the F, $R_3$ is H and each of Ra, $R_6$, $R_{10}$, $R_{30}$ and Rb is methyl in a compound of Formula (II).

In some embodiments, the compound of Formula (II) is selected from the group consisting of:

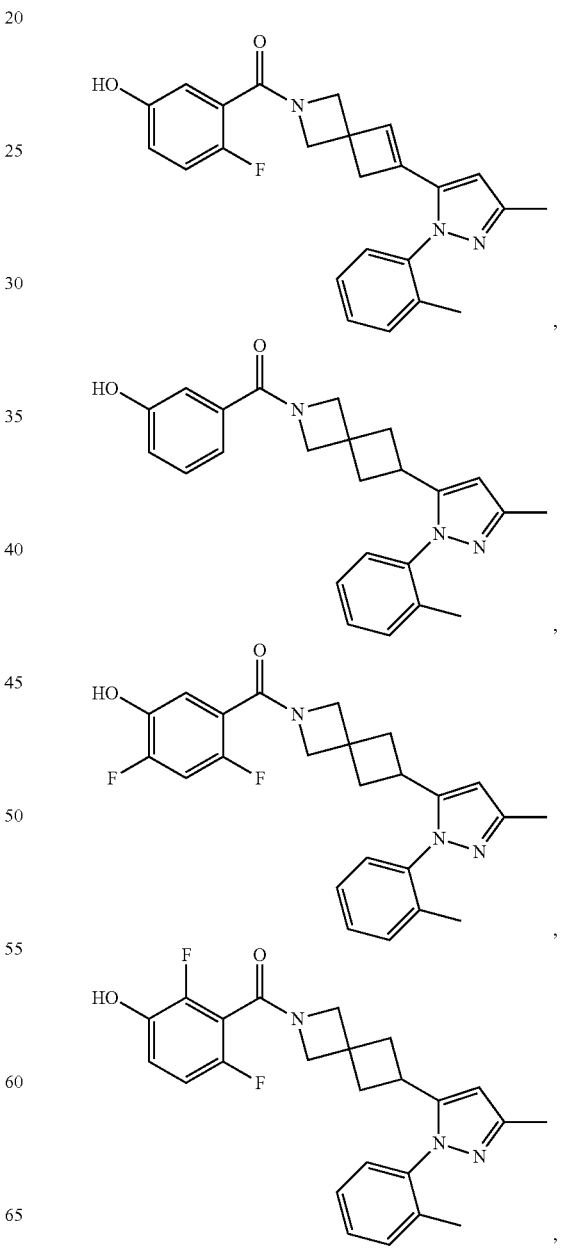

-continued
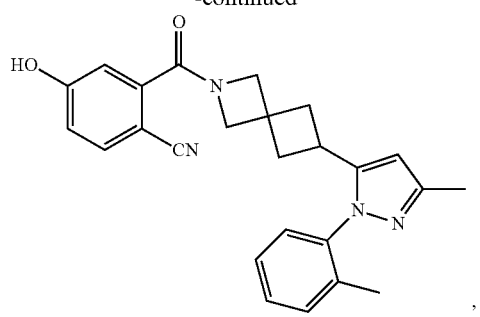
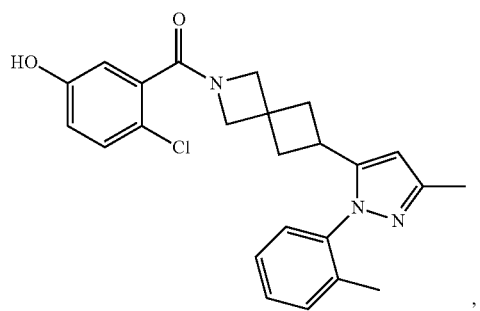
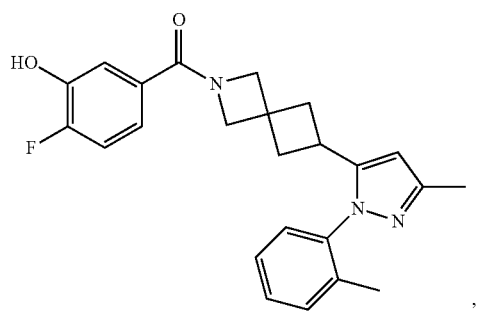
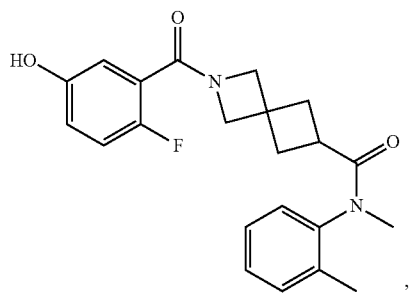
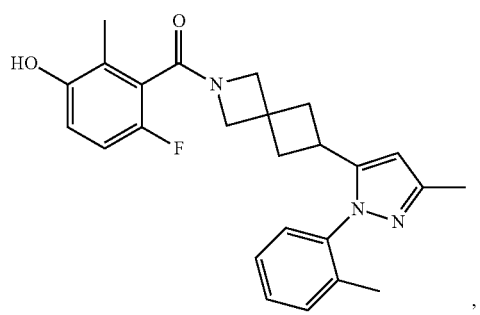
-continued
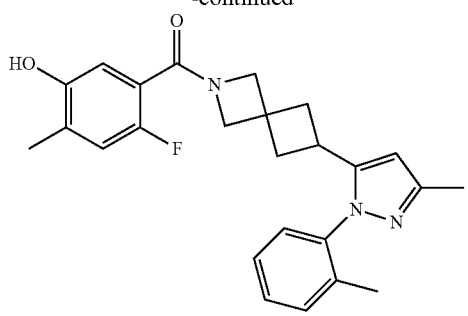
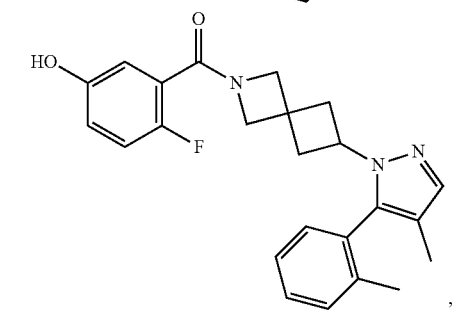
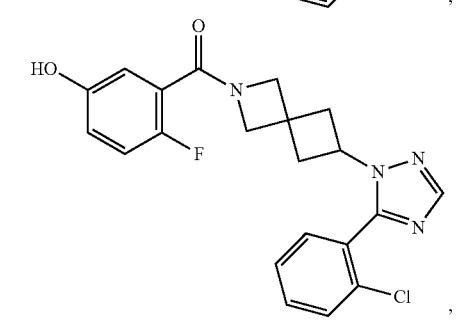
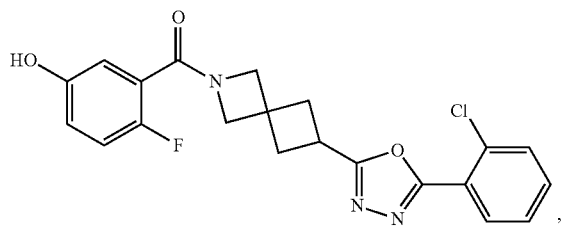
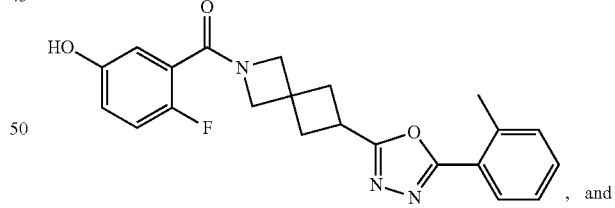, and
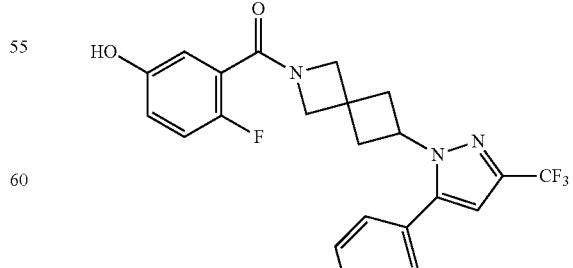
or a pharmaceutically acceptable salt thereof.

In some embodiments, the compound of Formula (II) is selected from the group consisting of:
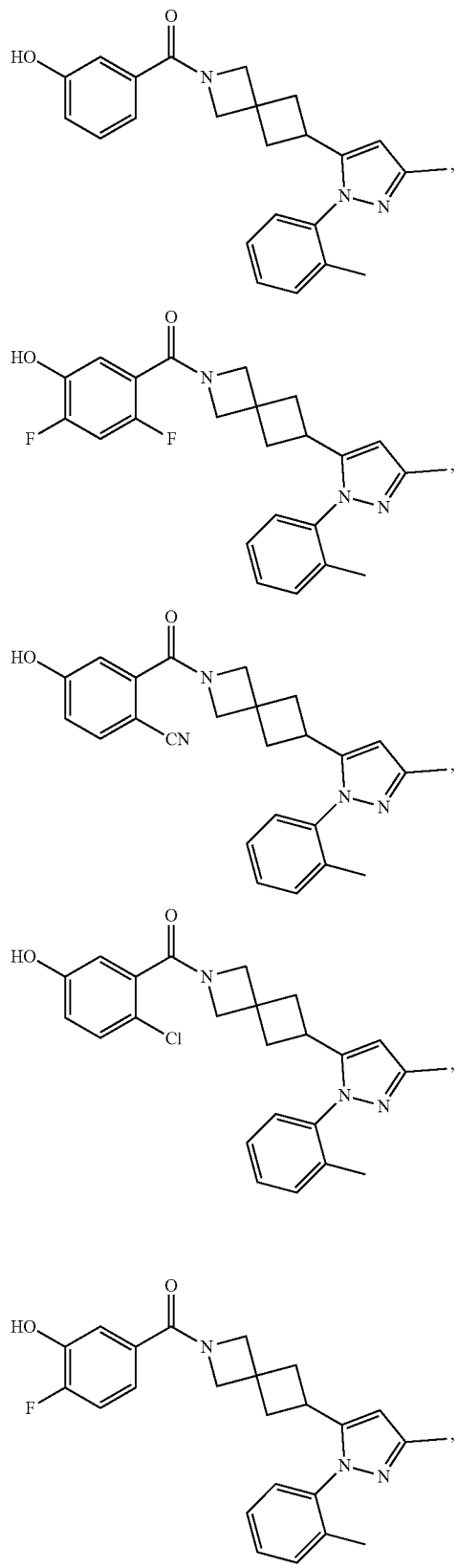
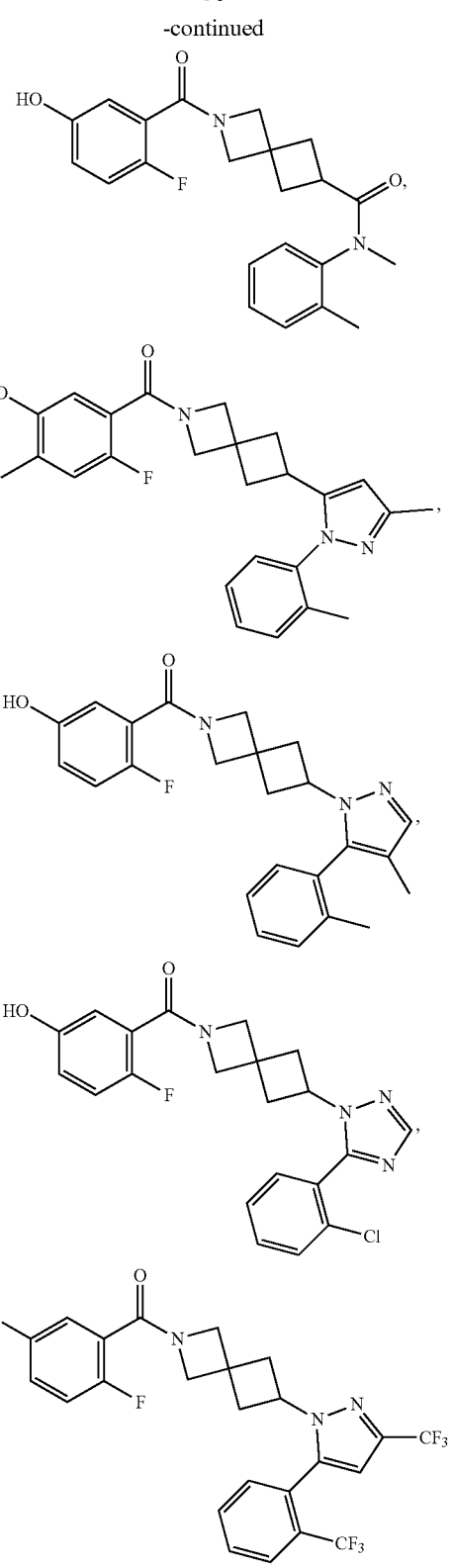
and or a pharmaceutically acceptable salt thereof.
In some embodiments, the disclosure provides a compound of Formula (II-B) or a pharmaceutically acceptable salt thereof:

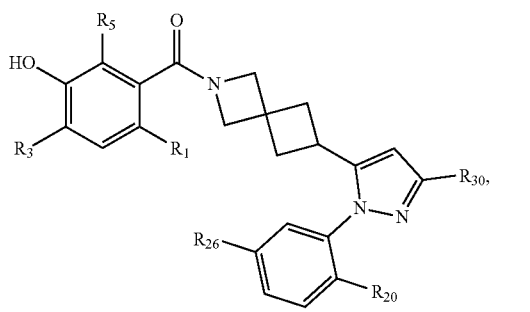

Formula (II-B)

wherein
- R₁ is halogen or cyano;
- R₃ is hydrogen, lower alkyl, or halogen;
- R₅ is hydrogen, halogen or lower alkyl;
- R₂₀ is halogen or lower alkyl optionally substituted with one or more halogen;
- R₂₆ is halogen or hydrogen; and
- R₃₀ is hydrogen or lower alkyl optionally substituted with one or more halogen.

In some embodiments, the disclosure provides a compound of Formula (II-B) or a pharmaceutically acceptable salt thereof, wherein the compound is not (2-fluoro-5-hydroxyphenyl)(6-[3-methyl-1-(o-tolyl)-5-pyrazolyl]-2-aza-2-spiro[3.3]heptyl methanone.

In some embodiments, the disclosure provides a compound of Formula (II-B) or a pharmaceutically acceptable salt thereof, wherein the compound is not (2-fluoro-5-hydroxyphenyl)(6-(3-methyl-1-(o-tolyl)-1H-pyrazol-5-yl)-2-azaspiro[3.3]heptan-2-yl)methanone.

In some embodiments, the disclosure provides a compound of Formula (II-B) or a pharmaceutically acceptable salt thereof, wherein when R₁ is fluoro, R₃ and R₅ are both hydrogen, and R₃₀ is methyl, then R₂₆ is not hydrogen.

General Procedure for Acid Amine Coupling for Preparing Compounds of Formula (II-B)

In general, analogs of formula of II-B can be made by following a modified version of synthetic scheme for PSY05-00367 (Compound 367). 2-(tert-butoxycarbonyl)-2-azaspiro[3.3]heptane-6-carboxylic acid, Int-1, is treated with methoxyamine hydrochloride to generate Weinreb amide, Int-2, which undergoes Grignard addition with methylmagnesium bromide (CH₃MgBr) to yield methyl ketone intermediate Int-3. Treating Int-3 with N,N-dimethylacetamide dimethyl acetal (DMA-DMA) yields spirocyclic-substituted 3-(dimethylamino)but-2-en-1-one intermediate, Int-4. 1,3-dipolarcycloaddition of Int-4 with various phenyl hydrazines yields desired variation of 3-methylpyrazole intermediate, Int-5. N-Boc deprotection of Int-5 with trifluoroacetic acid yields corresponding trifluoroacetate salt of Int-5, Int-6, which then couples with various substituted benzoic acids to yield final analog.

To a stirred solution of 6-(3-methyl-1-(o-tolyl)-1H-pyrazol-5-yl)-2-azaspiro[3.3]heptane 2,2,2-trifluoroacetate (1 eq.) and 2-fluoro-benzoic acid (1.5 eq.) in DMF (10 V) at 0° C., was added DIPEA (5 eq.) and stirred for 15 min. To this reaction mixture T₃P (50% solution in ethyl acetate) (1.5 eq.) was added. The resulting mixture was stirred at room temperature for 2 h. The reaction mixture was quenched by the addition of ice cold water (10 mL) and extracted by ethyl acetate (3×25 mL). The organic layer was dried over sodium sulphate and concentrated under reduced pressure. The crude material was purified by column chromatography using 5% MeOH in DCM.

TABLE 1

| Structure | Description |
|---|---|
| PSY-05-00122 | Compound 122 by followed the general procedure given above from 70 mg of 6-(3-methyl-1-(o-tolyl)-1H-pyrazol-5-yl)-2-azaspiro[3.3]heptane 2,2,2-trifluoroacetate (1 eq.) to obtain (2-fluorophenyl)(6-(3-methyl-1-(o-tolyl)-1H-pyrazol-5-yl)-2-azaspiro[3.3]heptan-2-yl)methanone (20 mg, 28%) as a white solid. Compound can be prepared by reacting Int-4 with o-tolylhydrazine hydrochloride, then reacting Int-6 with 2-fluorobenzoic acid. |
| PSY-05-00125 | Compound-125 was prepared by followed the general procedure given above from 70 mg of 6-(3-methyl-1-(o-tolyl)-1H-pyrazol-5-yl)-2-azaspiro[3.3]heptane 2,2,2-trifluoroacetate (1 eq.) to obtain (3-hydroxyphenyl)(6-(3-methyl-1-(o-tolyl)-1H-pyrazol-5-yl)-2-azaspiro[3.3]heptan-2-yl)methanone)(15 mg, 21%) as a white solid. Compound can be prepared by reacting Int-4 with o-tolylhydrazine hydrochloride, then reacting Int-6 with 3-(benzyloxy)benzoic acid, which then undergoes Pd/C hydrogenolysis to liberate free hydroxl group. |

TABLE 1-continued

| Structure | Description |
|---|---|
| 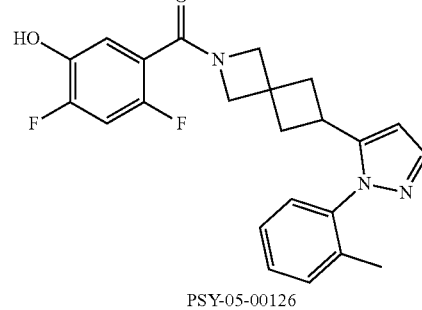

PSY-05-00126 | Compound-126 was prepared by followed the general procedure given above from 100 mg of 6-(3-methyl-1-(o-tolyl)-1H-pyrazol-5-yl)-2-azaspiro[3.3]heptane 2,2,2-trifluoroacetate (1 eq.) to obtain (2,4-difluoro-5-hydroxyphenyl)(6-(3-methyl-1-(o-tolyl)-1H-pyrazol-5-yl)-2-azaspiro[3.3]heptan-2-yl)methanone (50 mg, 21%) as a white solid. Compound can be prepared by reacting Int-4 with o-tolylhydrazine hydrochloride, then reacting Int-6 with 5-(benzyloxy)-2,4-difluorobenzoic acid, which then undergoes Pd/C hydrogenolysis to liberate free hydroxl group. 5-(benzyloxy)-2,4-difluorobenzoic acid is prepared by reacting 2,4-difluoro-5-hydroxybenzoic acid with benzyl bromide, then performing sodium hydroxide-catalyzed ester hydrolysis to liberate the free acid. |
| 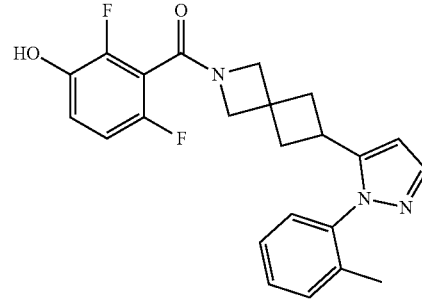

PSY-05-00127 | Compound-00127 was prepared by followed the general procedure given above from 100 mg of 6-(3-methyl-1-(o-tolyl)-1H-pyrazol-5-yl)-2-azaspiro[3.3]heptane 2,2,2-trifluoroacetate (1 eq.) to obtain (2,6-difluoro-3-hydroxyphenyl)(6-(3-methyl-1-(o-tolyl)-1H-pyrazol-5-yl)-2-azaspiro[3.3]heptan-2-yl)methanone) (20 mg, 18%) as a white solid. Compound can be prepared by reacting Int-4 with o-tolylhydrazine hydrochloride, then reacting Int-6 with 3-(benzyloxy)-2,6-difluorobenzoic acid, which then undergoes Pd/C hydrogenolysis to liberate free hydroxl group. 3-(benzyloxy)-2,6-difluorobenzoic acid is prepared by reacting 2,6-difluoro-3-hydroxybenzoic acid with benzyl bromide, then performing sodium hydroxide-catalyzed ester hydrolysis to liberate the free acid. |
| 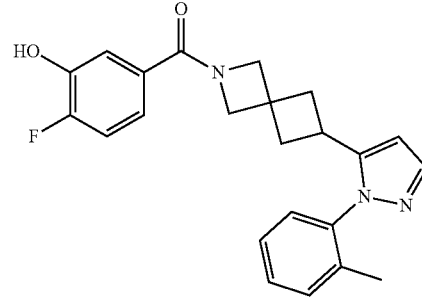

Compound 141 | Compound-00141-001 was prepared by followed the general procedure given above from 120 mg of 6-(3-methyl-1-(o-tolyl)-1H-pyrazol-5-yl)-2-azaspiro [3.3] heptane 2,2,2-trifluoroacetate (1 eq.) to obtain (4-fluoro-3-hydroxyphenyl)(6-(3-methyl-1-(o-tolyl)-1H-pyrazol-5-yl)-2-azaspiro[3.3]heptan-2-yl)methanone (19 mg, 100.49%) as a white solid. Compound can be prepared by reacting Int-4 with o-tolylhydrazine hydrochloride, then reacting Int-6 with 3-(benzyloxy)-4-fluorobenzoic acid, which then undergoes Pd/C hydrogenolysis to liberate free hydroxl group. 3-(benzyloxy)-4-fluorobenzoic acid is prepared by reacting 4-fluoro-3-hydroxybenzoic acid with benzyl bromide, then performing sodium hydroxide-catalyzed ester hydrolysis to liberate the free acid. |
| 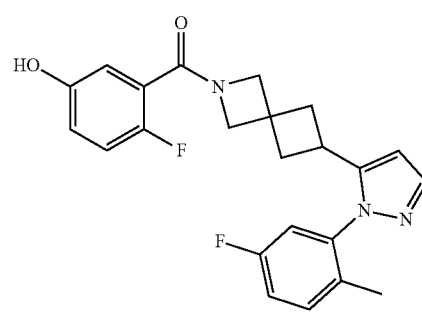

Compound 365 | Compound can be prepared by reacting Int-4 with (5-fluoro-2-methylphenyl)hydrazine hydrochloride, then reacting Int-6 with 5-(benzyloxy)-2-fluorobenzoic acid, which then undergoes Pd/C hydrogenolysis to liberate free hydroxl group. 5-(benzyloxy)-2-fluorobenzoic acid is prepared by reacting 2-fluoro-5-hydroxybenzoic acid with benzyl bromide, then performing sodium hydroxide-catalyzed ester hydrolysis to liberate the free acid. |

TABLE 1-continued

| Structure | Description |
|---|---|
| 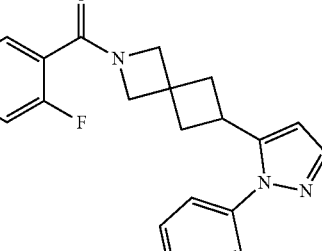
Compound 366 | Compound can be prepared by reacting Int-4 with (2-(trifluoromethyl)phenyl)hydrazine hydrochloride, then reacting Int-6 with 5-(benzyloxy)-2-fluorobenzoic acid, which then undergoes Pd/C hydrogenolysis to liberate free hydroxl group. 5-(benzyloxy)-2-fluorobenzoic acid is prepared by reacting 2-fluoro-5-hydroxybenzoic acid with benzyl bromide, then performing sodium hydroxide-catalyzed ester hydrolysis to liberate the free acid. |
| 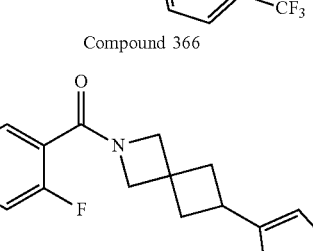
Compound 371 | Compound can be prepared by reacting Int-4 with o-tolylhydrazine hydrochloride, then reacting Int-6 with 5-(benzyloxy)-2-fluoro-4-methylbenzoic acid, which then undergoes Pd/C hydrogenolysis to liberate free hydroxl group. 5-(benzyloxy)-2-fluoro-4-methylbenzoic acid is prepared by reacting 2-fluoro-5-hydroxy-4-methylbenzoic acid with benzyl bromide, then performing sodium hydroxide-catalyzed ester hydrolysis to liberate the free acid. |

In some embodiments, the disclosure provides a compound of Formula (II-C) or a pharmaceutically acceptable salt thereof:

Formula (II-C)

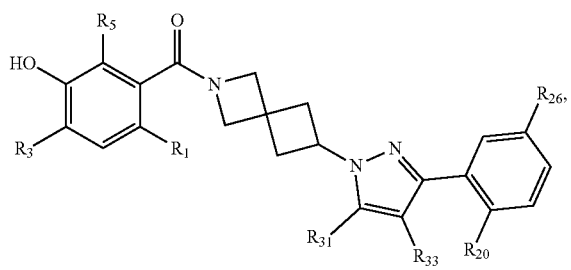

wherein
$R_1$ is halogen or cyano;
$R_3$ is hydrogen, lower alkyl, or halogen;
$R_5$ is hydrogen, halogen or lower alkyl;
$R_{20}$ is halogen or lower alkyl optionally substituted with one or more halogen;
$R_{26}$ is halogen or hydrogen; and
$R_{31}$ and $R_{33}$ are each independently hydrogen or lower-alkyl optionally substituted with one or more halogen, provided that one of $R_{31}$ and $R_{33}$ is hydrogen.

General Procedure for Preparing Compounds of Formula (II-C)

Analogs with a 1-(4-methyl)pyrazolyl warhead (W) can be made by following the synthetic scheme for PSY-05-00519-001 (Compound 519). Substituted propiophenone intermediate (Int-1) is treated with N,N-dimethylformamide dimethyl acetal (DMF-DMA) to yield phenyl-substituted 3-(dimethylamino)prop-2-en-1-one intermediate, Int-2, which subsequently undergoes 1,3-dipolar cycloaddition with hydrazine ($NH_2NH_2$) to yield 5-aryl-4-methylpyrrazole intermediate, Int-3. Simultaneous synthesis of tert-butyl 6-((methylsulfonyl)oxy)-2-azaspiro[3.3]heptane-2-carboxylate, Int-C, is performed by reacting tert-butyl 6-hydroxy-2-azaspiro[3.3]heptane-2-carboxylate with methanesulfonyl chloride. N-alkylation of Int-3 with Int-C yields a mixture of two regioisomers: 1,4,5-trisubstituted pyrazole product, Int-4, and 1,3,4-trisubstituted pyrazole product Int-4A. Both Int-4 and Int-4A are subjected to N-Boc-deprotection with trifluoroacetic acid to yield corresponding trifluoroacetate salts, Int-5 and Int-5A, respectively. Amidation of 2,fluoro-5-hydroxybenzoic acid with either Int-5 or Int-5A yields either 1-(5-aryl-4-methyl)pyrazolyl or 1-(3-aryl-4-methyl) pyrazolyl analogs, respectively.

Analogs with a 1-(4-trifluoromethyl)pyrazole warhead can be made by following the synthetic scheme for PSY-05-00475-001 (Compound 475). Substituted iodobenzene, Int-A, undergoes Sonogashira coupling with ethyl propiolate to generate phenyl-substituted propiolate intermediate, Int-B. Sodium hydroxide-catalyzed ester hydrolysis of Int-B yields the propiolic acid intermediate, Int-1, which then undergoes a unique copper-mediated decarboxylative trifluoromethylation with Togni's reagent to generate the α-trifluoromethyl ketone intermediate, Int-2. Treatment of Int-2 with N,N-dimethylformamide dimethyl acetal (DMF-DMA) affords the 3-(dimethylamino)-2-(trifluoromethyl)prop-2-en-1-one intermediate, Int-3, which undergoes 1,3-dipolar cycloaddition with hydrazine to yield 2-aryl-4-(trifluoromethyl)pyrazole intermediate, Int-4. Treatment of Int-4 with spirocyclic mesylate intermediate described previously, Int-C, yields a mixture of two regioisomers: 1,4,5-trisubstituted pyrazole product, Int-5, and 1,3,4-trisubstituted pyrazole product Int-5A. Both Int-5 and Int-5A are subjected to N-Boc-deprotection with trifluoroacetic acid to yield corresponding trifluoroacetate salts, Int-6 and Int-6A, respectively. Amidation of 2,fluoro-5-hydroxybenzoic acid with either Int-6 or Int-6A yields either 1-(5-aryl-4-trifluoromethyl)pyrazolyl or 1-(3-aryl-4-trifluoromethyl)pyrazolyl analogs, respectively.

Similar to the synthesis of Compound 525, the syntheses of 1-(4-cyclopropyl)pyrazole warhead analogs begins with treating substituted acetophenone, Int-1, with N,N-dimethylformamide dimethyl acetal (DMF-DMA) to form 3-(dimethylamino)prop-2-en-1-one intermediate, Int-2, which subsequently undergoes 1,3-dipolar cycloaddition with hydrazine to form 2-arylpyrazole intermediate, Int-3. 4-iodination of Int-3 forms Int-4 which subsequently undergoes N-PMB protection to form Int-5. Suzuki coupling of Int-5 with cyclopropylboronic acid affords the 2-aryl-4-cyclopropylpyrazole intermediate, Int-6, which undergoes PMB-deprotection to liberate the free N—H pyrazole intermediate, Int-7. Treatment of Int-7 with spirocyclic mesylate intermediate described previously, Int-C, yields a mixture of two regioisomers: 1,4,5-trisubstituted pyrazole product, Int-8, and 1,3,4-trisubstituted pyrazole product Int-8A. Both Int-8 and Int-8A are subjected to N-Boc-deprotection with trifluoroacetic acid to yield corresponding trifluoroacetate salts, Int-9 and Int-9A, respectively. Amidation of 2,fluoro-5-hydroxybenzoic acid with either Int-9 or Int-9A yields either 1-(5-aryl-4-cyclopropyl)pyrazolyl or 1-(3-aryl-4-cyclopropyl)pyrazolyl analogs, respectively.

For analogs with a 5-(1-aryl-3-methyl)pyrazolyl warhead, the first two steps are identical to the steps provided for the syntheses of analogs in Formula (II-B). Beginning with Int-3 from Formula (II-B), Claisen-type condensation is performed with ethyl acetate to yield the 1,3-dicarbonyl intermediate, Int-4.

For analogs with a 1-(5-aryl-3-cyclopropyl)pyrazolyl or 1-(3-aryl-5-cyclopropyl)pyrazolyl warhead, substituted acetophenone, Int-1, undergoes a Claisen-type condensation with ethyl cyclopropanecarboxylate to yield the 1,3-dicarbonyl intermediate, Int-2. Cyclization of Int-2 with substituted hydrazine hydrate affords the 5-aryl-3-cyclopropylpyrazole intermediate, Int-3, which undergoes N-alkylation with spirocyclic mesylate intermediate, Int-C, to form two trisubstituted regioisomers: 1-(5-aryl-3-cyclopropyl)pyrazolyl intermediate, Int-4, and 1-(3-aryl-5-cyclopropyl)pyrazolyl intermediate, Int-4a. Both Int-4 and Int-4A are subjected to N-Boc-deprotection with trifluoroacetic acid to yield corresponding trifluoroacetate salts, Int-5 and Int-5A, respectively. Amidation of 2,fluoro-5-hydroxybenzoic acid with either Int-5 or Int-5A yields either 1-(5-aryl-3-cyclopropyl)pyrazolyl or 1-(3-aryl-5-cyclopropyl)pyrazolyl analogs, respectively.

The synthesis of 1-(5-aryl-3-cyclopropyl)pyrazolyl and 1-(3-aryl-5-cyclopropyl)pyrazolyl warhead analogs pertains to the synthesis of the following analogs: 1-(5-aryl-3-methyl)pyrazolyl warhead analogs, and 1-(3-aryl-5-methyl)pyrazolyl warhead analogs. For these two types of analogs, replace ethyl cyclopropane carboxylate with ethyl acetate in step 1. For 1-(5-aryl-3-trifluoromethyl)pyrazolyl warhead analogs and -(3-aryl-5-trifluoromethyl)pyrazolyl warhead analogs, replace ethyl cyclopropanecarboxylate with ethyl 2,2,2-trifluoroacetate.

TABLE 2

| Structure | Description |
|---|---|
| 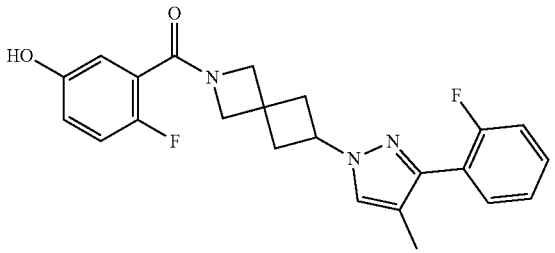<br>Compound 417 | Compound-## was prepared by followed the general procedure given above from 70 mg of 6-(3-methyl-1-(o-tolyl)-1H-pyrazol-5-yl)-2-azaspiro[3.3]heptane 2,2,2-trifluoroacetate (1 eq.) to obtain (2-fluoro-5-methoxyphenyl)(6-(3-methyl-1-(o-tolyl)-1H-pyrazol-5-yl)-2-azaspiro[3.3]heptan-2-yl)methanone (25 mg, 15%) as a white solid. LCMS: ## m/z [M + H]$^+$. $^1$H NMR (400 MHz, Methanol-d$_4$) δ ###<br>Analog is prepared by following method for preparation of 1-(4-methyl)pyrazolyl warhead (W) analogs. Compound can be prepared by reacting 1-(2-fluorophenyl)propan-1-one with DMF-DMA to form Int-1. Int-4A is selectively advanced for N-Boc-deprotection and subsequent amide coupling to yield final compound. |
| 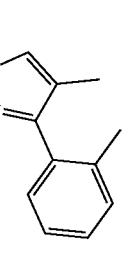<br>Compound 440 | Analog is prepared by following method for preparation of 1-(4-methyl)pyrazolyl warhead (W) analogs. Compound can be prepared by reacting 1-(o-tolyl)propan-1-one with DMF-DMA to form Int-1. Int-4A is selectively advanced for N-Boc-deprotection and subsequent amide coupling to yield final compound. |

TABLE 2-continued

| Structure | Description |
|---|---|
| 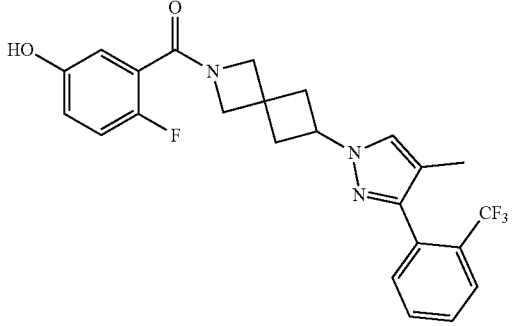 [SMILES: Cc1cn(C2CC3(C2)CN(C(=O)c2cc(O)ccc2F)C3)nc1-c1ccccc1C(F)(F)F]<br>Compound 444 | Analog is prepared by following method for preparation of 1-(4-methyl)pyrazolyl warhead (W) analogs. Compound can be prepared by reacting 1-(2-(trifluoromethyl)phenyl)propan-1-one with DMF-DMA to form Int-1. Int-4A is selectively advanced for N-Boc-deprotection and subsequent amide coupling to yield final compound. |
| 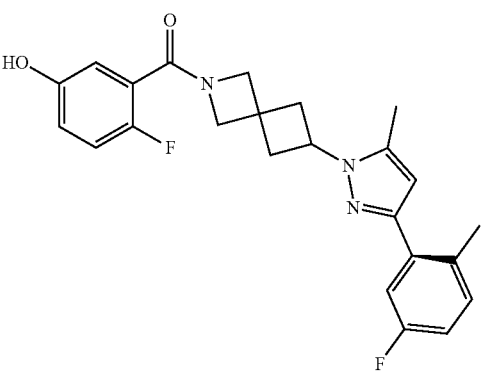<br>Compound 446 | Synthesis of compound follows synthesis for 1-(3-aryl-5-methyl)pyrazolyl warhead analogs. 1-(5-fluoro-2-methylphenyl)ethan-1-one is used as Int-1. Int-4A is selectively advanced for N-Boc-deprotection and subsequent amide coupling to yield final compound. |
| 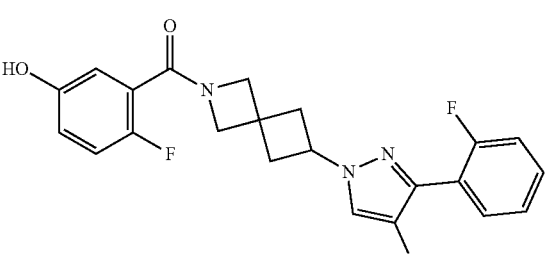<br>Compound 473 | Analog is prepared by following method for preparation of 1-(4-trifluoromethyl)pyrazolyl warhead (W) analogs. 1-fluoro-2-iodobenzene is used as Int-A for generating propiolic acid Int-1. Int-5A is selectively advanced for N-Boc-deprotection and subsequent amide coupling to yield final compound. |
| 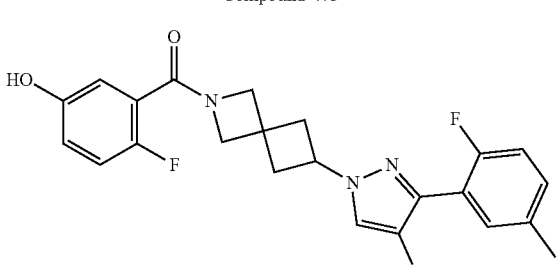<br>Compound 475 | Analog is prepared by following method for preparation of 1-(4-trifluoromethyl)pyrazolyl warhead (W) analogs. 1-fluoro-2-iodo-4-methylbenzene is used as Int-A for generating propiolic acid Int-1. Int-5A is selectively advanced for N-Boc-deprotection and subsequent amide coupling to yield final compound. |
| 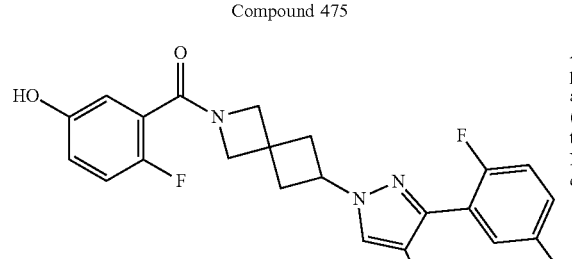<br>Compound 477 | Analog is prepared by following method for preparation of 1-(4-methyl)pyrazolyl warhead (W) analogs. Compound can be prepared by reacting 1-(2,5-difluorophenyl)propan-1-one with DMF-DMA to form Int-1. Int-4A is selectively advanced for N-Boc-deprotection and subsequent amide coupling to yield final compound. |

TABLE 2-continued

| Structure | Description |
| --- | --- |
| Compound 488 | Analog is prepared by following method for preparation of 1-(4-cyclopropyl)pyrazolyl warhead (W) analogs. Compound can be prepared by using 1-(2-(trifluoromethyl)phenyl)ethan-1-one as Int-1. Int-9A is selectively advanced for N-Boc-deprotection and subsequent amide coupling to yield final compound. |
| Compound 491 | Analog is prepared by following method describing synthesis for analogs with a 1-(3-aryl-5-cyclopropyl)pyrazolyl warhead. 1-(5-fluoro-2-methylphenyl)ethan-1-one is used as Int-1. Int-4A is selectively advanced for N-Boc-deprotection and subsequent amide coupling to yield final compound. |
| Compound 493 | Analog is prepared by following method for preparation of 1-(4-cyclopropyl)pyrazolyl warhead (W) analogs. Compound can be prepared by using 1-(2-fluorophenyl)ethan-1-one as Int-1. Int-9A is selectively advanced for N-Boc-deprotection and subsequent amide coupling to yield final compound. |
| Compound 520 | Analog is prepared by following method for preparation of 1-(4-methyl)pyrazolyl warhead (W) analogs. Compound can be prepared by reacting 1-(2-chloro-5-fluorophenyl)propan-1-one with DMF-DMA to form Int-1. Int-4A is selectively advanced for N-Boc-deprotection and subsequent amide coupling to yield final compound. |
| Compound 525 | Analog is prepared by following method for preparation of 1-(4-methyl)pyrazolyl warhead (W) analogs. Compound can be prepared by reacting 1-(2-(trifluoromethyl)phenyl)ethan-1-one with DMF-DMA to form Int-1. Int-4A is selectively advanced for N-Boc-deprotection and subsequent amide coupling to yield final compound. |

In some embodiments, the disclosure provides a compound of Formula (II-D) or a pharmaceutically acceptable salt thereof.

Formula (II-D)

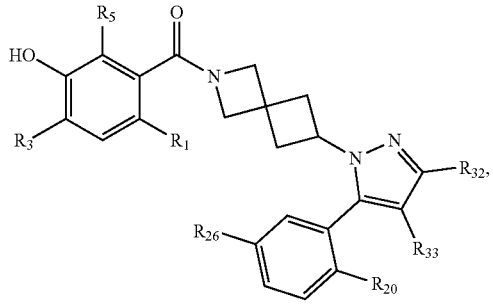

wherein $R_1$ is halogen or cyano;

$R_3$ is hydrogen, lower alkyl, or halogen;

$R_5$ is hydrogen, halogen or lower alkyl;

$R_6$ is hydrogen;

$R_{20}$ is halogen or lower alkyl optionally substituted with one or more halogen;

$R_{26}$ is halogen or hydrogen; and $R_{32}$ and $R_{33}$ are each independently hydrogen or lower alkyl optionally substituted with one or more halogen, provided that one of $R_{32}$ and $R_{33}$ is hydrogen.

General Procedure for Preparing Compounds of Formula (II-D)

Syntheses of analogs can be performed by following methods provided in Formula (II-C).

TABLE 3

| Structure | Description |
|---|---|
| PSY-05-407 | Compound-## was prepared by followed the general procedure given above from 70 mg of 6-(3-methyl-1-(o-tolyl)-1H-pyrazol-5-yl)-2-azaspiro[3.3]heptane 2,2,2-trifluoroacetate (1 eq.) to obtain (2-fluoro-5-methoxyphenyl)(6-(3-methyl-1-(o-tolyl)-1H-pyrazol-5-yl)-2-azaspiro[3.3]heptan-2-yl)methanone (25 mg, 15%) as a white solid. LCMS: ## m/z [M + H]$^+$. $^1$H NMR (400 MHz, Methanol-d$_4$) δ ###. |
| Compound 408 | Analog is prepared by following method for preparation of 1-(4-methyl)pyrazolyl warhead (W) analogs. Compound can be prepared by reacting 1-(2-fluorophenyl)propan-1-one with DMF-DMA to form Int-1. Int-4 is selectively advanced for N-Boc-deprotection and subsequent amide coupling to yield final compound. |
| Compound 410 | Analog is prepared by following method for preparation of 1-(4-methyl)pyrazolyl warhead (W) analogs. Compound can be prepared by reacting 1-(2-(trifluoromethyl)phenyl)propan-1-one with DMF-DMA to form Int-1. Int-4 is selectively advanced for N-Boc-deprotection and subsequent amide coupling to yield final compound. |

TABLE 3-continued

| Structure | Description |
|---|---|
| 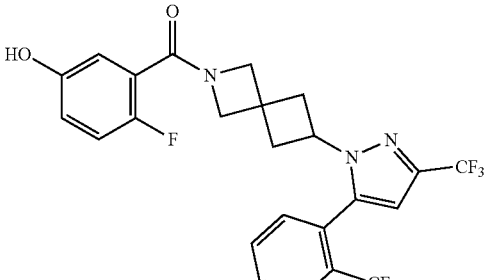
Compound 414 | Analog is prepared by following synthesis for 1-(5-aryl-3-trifluoromethyl)pyrazolyl warhead analogs. Compound can be synthesized by using 1-(2-(trifluoromethyl)phenyl)ethan-1-one as Int-1. Int-4 is selectively advanced for N-Boc-deprotection and subsequent amide coupling to yield final compound. |
| 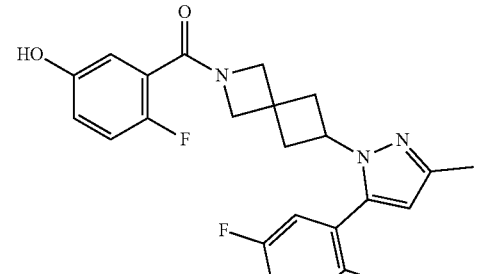
Compound 415 | Analog is prepared by following synthesis for 1-(5-aryl-3-methyl)pyrazolyl warhead analogs. Compound can be synthesized by using 1-(5-fluoro-2-methylphenyl)ethan-1-one is used as Int-1. Int-4 is selectively advanced for N-Boc-deprotection and subsequent amide coupling to yield final compound. |
| 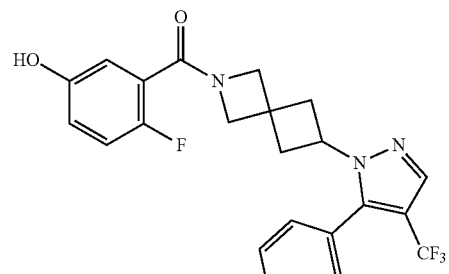
Compound 472 | Analog is prepared by following method for preparation of 1-(4-trifluoromethyl)pyrazolyl warhead (W) analogs. 1-fluoro-2-iodobenzene is used as Int-A for generating propiolic acid Int-1. Int-5 is selectively advanced for N-Boc-deprotection and subsequent amide coupling to yield final compound. |
| 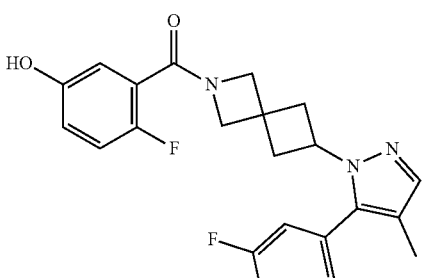
Compound 476 | Analog is prepared by following method for preparation of 1-(4-methyl)pyrazolyl warhead (W) analogs. Compound can be prepared by reacting 1-(2,5-difluorophenyl)propan-1-one with DMF-DMA to form Int-1. Int-4 is selectively advanced for N-Boc-deprotection and subsequent amide coupling to yield final compound. |

TABLE 3-continued

| Structure | Description |
|---|---|
| Compound 489 | Analog is prepared by following method for preparation of 1-(4-cyclopropyl)pyrazolyl warhead (W) analogs. Compound can be prepared by using 1-(2-(trifluoromethyl)phenyl)ethan-1-one as Int-1. Int-9 is selectively advanced for N-Boc-deprotection and subsequent amide coupling to yield final compound. |
| Compound 490 | Analog is prepared by following method for preparation of 1-(5-aryl-3-cyclopropyl)pyrazolyl analogs. Compound can be synthesized by using 1-(5-fluoro-2-methylphenyl)ethan-1-one as Int-1. Int-4 is selectively advanced for N-Boc-deprotection and subsequent amide coupling to yield final compound. |
| Compound 492 | Analog is prepared by following method for preparation of 1-(4-cyclopropyl)pyrazolyl warhead (W) analogs. Compound can be prepared by using 1-(2-fluorophenyl)ethan-1-one as Int-1. Int-9 is selectively advanced for N-Boc-deprotection and subsequent amide coupling to yield final compound. |
| Compound 519 | Analog is prepared by following method for preparation of 1-(4-methyl)pyrazolyl warhead (W) analogs. Compound can be prepared by reacting 1-(2-chloro-5-fluorophenyl)propan-1-one with DMF-DMA to form Int-1. Int-4 is selectively advanced for N-Boc-deprotection and subsequent amide coupling to yield final compound. |

TABLE 3-continued

| Structure | Description |
| --- | --- |
| 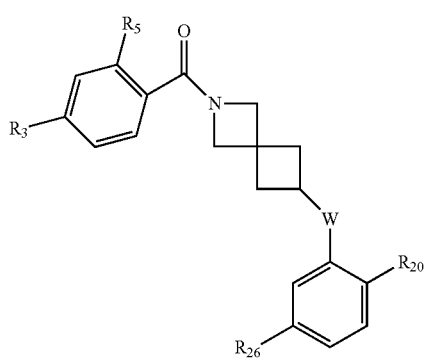 Compound 526 | Analog is prepared by following method for preparation of 1-(4-methyl)pyrazolyl warhead (W) analogs. Compound can be prepared by reacting 1-(2-(trifluoromethyl)phenyl)ethan-1-one with DMF-DMA to form Int-1. Int-4 is selectively advanced for N-Boc-deprotection and subsequent amide coupling to yield final compound. |

In some embodiments, the disclosure provides a compound of Formula (III) or a pharmaceutically acceptable salt thereof:

Formula (III)

wherein
$R_3$ is halogen;
$R_5$ is —O—$R_{52}$;
$R_{52}$ is lower alkyl or cycloalkyl, each optionally substituted with halogen,
W is a 5-member heteroaryl ring optionally substituted with one or more $R_{30}$;
$R_{30}$ is lower alkyl;
$R_{20}$ is lower alkyl; and
$R_{26}$ is hydrogen or halogen.

In some embodiments, $R_{20}$ is methyl and $R_{26}$ is hydrogen or F in compounds of Formula (III). In some embodiments, $R_{20}$ is methyl and $R_{26}$ is hydrogen in compounds of Formula (III). In some embodiments, $R_{20}$ is methyl and $R_{26}$ is F.

In compounds of Formula (III), W is a 5-member heteroaryl ring comprising at least one nitrogen, such as a pyrazole. In some embodiments, $R_3$ is F. In some embodiments, $R_{62}$ is lower alkyl or cycloalkyl. In some embodiments, the lower alkyl in $R_{20}$, $R_{30}$ and $R_{62}$ can be methyl. In some embodiments, W is pyrazole optionally substituted with one or more methyl, and $R_3$ is the F. In some embodiments, W is pyrazole optionally substituted with one or more methyl, and $R_3$ is the F, $R_{62}$ is methyl, ethyl, propyl or cyclopropyl each optionally substituted with one or more F, and $R_{20}$ is methyl in a compound of Formula (III).

In some embodiments, the compound of Formula (III) is selected from the group consisting of:

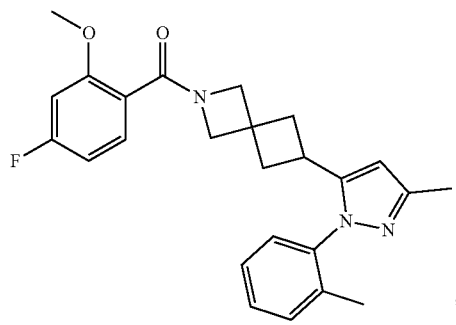 [SMILES: COc1cc(F)ccc1C(=O)N1CC2(CC(c3cc(C)nn3-c3ccccc3C)C2)C1]
,

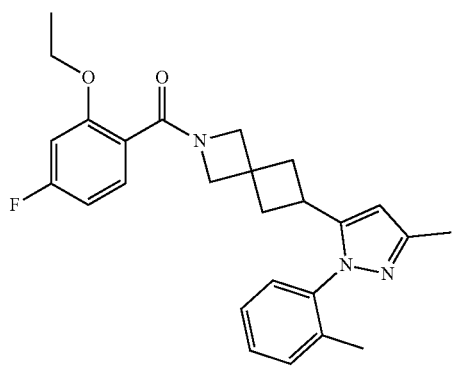
,

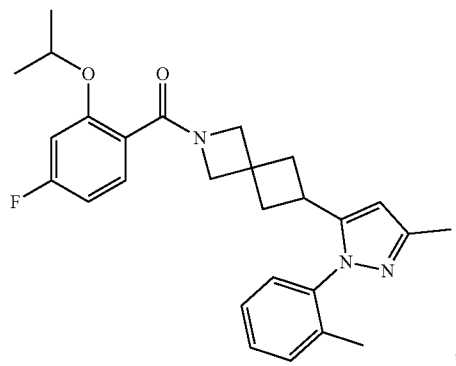
,

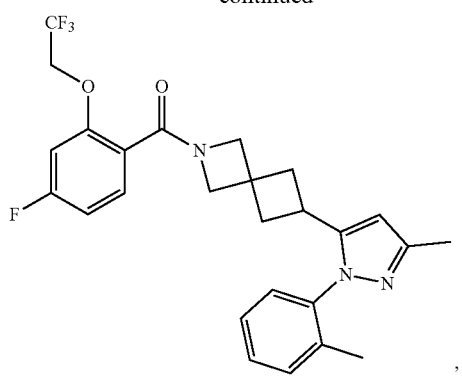
, and
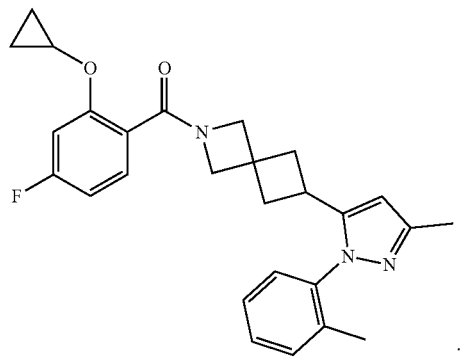
.
In some embodiments, the compound of Formula (III) is selected from the group consisting of:
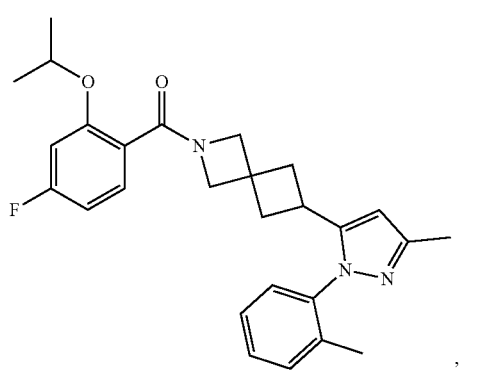
, and
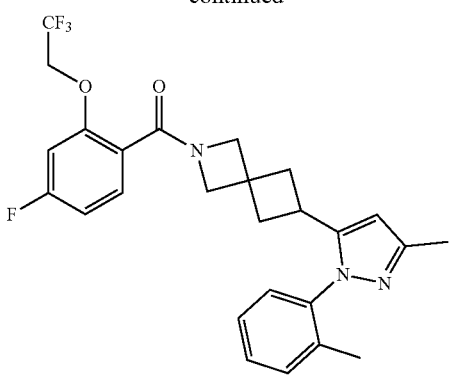
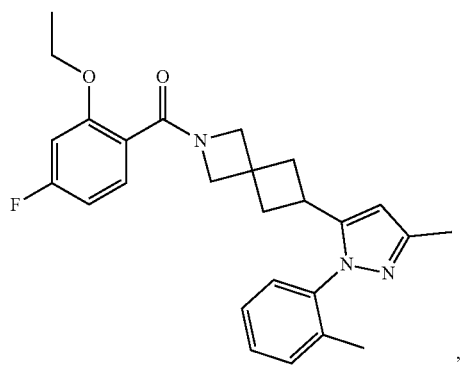
,
In some embodiments, the compound is selected from the group consisting of:
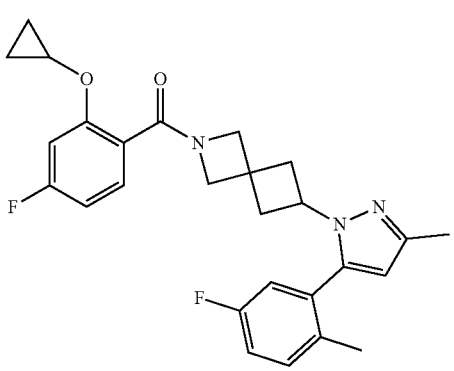
,
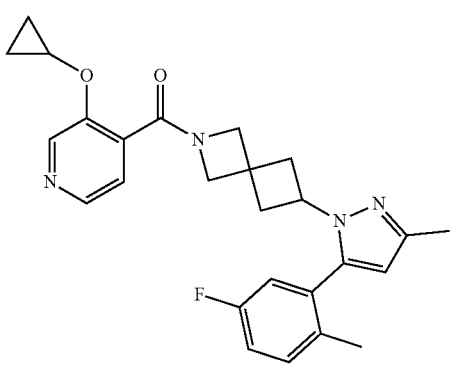
,
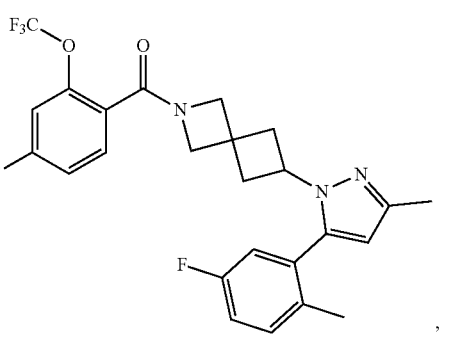
, and -continued

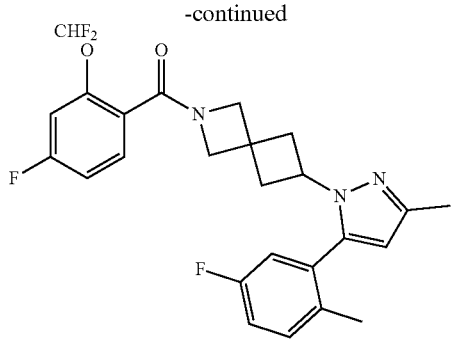

In some embodiments, the disclosure provides a compound of Formula (III) or a pharmaceutically acceptable salt thereof:

Formula (III-A)

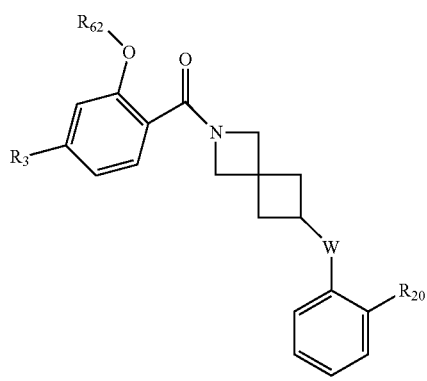

wherein
R$_3$ is halogen;
R$_{62}$ is lower alkyl or cycloalkyl, each optionally substituted with halogen,
W is a 5-member heteroaryl ring optionally substituted with one or more R$_{30}$;
R$_{30}$ is lower alkyl; and
R$_{20}$ is lower alkyl.

In compounds of Formula (III-A), W is a 5-member heteroaryl ring comprising at least one nitrogen, such as a pyrazole. In some embodiments, R$_3$ is F. In some embodiments, R$_{62}$ is lower alkyl or cycloalkyl. In some embodiments, the lower alkyl in R$_{20}$, R$_{30}$ and R$_{62}$ can be methyl. In some embodiments, W is pyrazole optionally substituted with one or more methyl, and R$_3$ is the F. In some embodiments, W is pyrazole optionally substituted with one or more methyl, and R$_3$ is the F, R$_{62}$ is methyl, ethyl, propyl or cyclopropyl each optionally substituted with one or more F, and R$_{20}$ is methyl in a compound of Formula (III-A).

In some embodiments, the disclosure provides a compound of Formula (III-B) or a pharmaceutically acceptable salt thereof.

Formula (III-B)

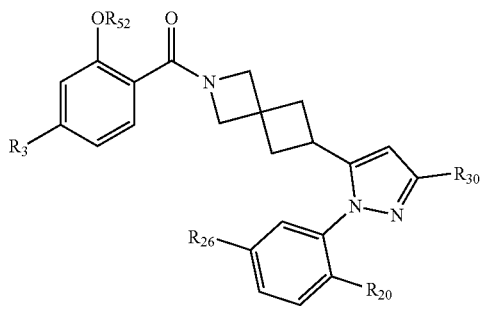

wherein
R$_3$ is halogen;
R$_{52}$ is lower alkyl or lower cycloalkyl, each optionally substituted with halogen,
R$_{30}$ is lower alkyl;
R$_{20}$ is lower alkyl; and
R$_{26}$ is hydrogen or halogen.

General Procedure for Preparing Compounds of Formula (III-B)

Syntheses of analogs is performed by following methods provided in Formulas (II-B) and (II-C).

TABLE 4

| Structure | Description |
|---|---|
| ![structure] PSY-05-00142-001 | Compound 00142-001 was prepared by followed the general procedure given above from 120 mg of 6-(3-methyl-1-(o-tolyl)-1H-pyrazol-5-yl)-2-azaspiro[3.3]heptane 2,2,2-trifluoroacetate (1 eq.) to obtain (4-fluoro-2-methoxyphenyl)(6-(3-methyl-1-(o-tolyl)-1H-pyrazol-5-yl)-2-azaspiro[3.3] heptan-2-yl)methanone (35 mg, 19.44%) as a white solid. Compound can be made by following synthetic methodology provided in Formula (II-B). Int-4 is reacted with o-tolylhydrazine hydrochloride, then Int-6 is reacted with 4-fluoro-2-methoxybenzoic acid to yield the final analog. |

TABLE 4-continued

| Structure | Description |
|---|---|
| 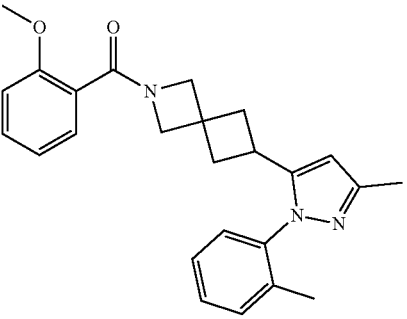 [SMILES: COc1ccccc1C(=O)N1CC2(CC(c3cc(C)nn3-c3ccccc3C)C2)C1]<br>PSY-05-00143-001 | Compound-00143-001 was prepared by followed the general procedure given above from 80 mg of 6-(3-methyl-1-(o-tolyl)-1H-pyrazol-5-yl)-2-azaspiro[3.3]heptane 2,2,2-trifluoroacetate (1 eq.) to obtain (2-methoxyphenyl)(6-(3-methyl-1-(o-tolyl)-1H-pyrazol-5-yl)-2-azaspiro[3.3] heptan-2-yl)methanone (25 mg, 20.83%) as a white solid.<br>Compound can be made by following synthetic methodology provided in Formula (II-B). Int-4 is reacted with o-tolylhydrazine hydrochloride, then Int-6 is reacted with 2-methoxybenzoic acid to yield the final analog. |
| 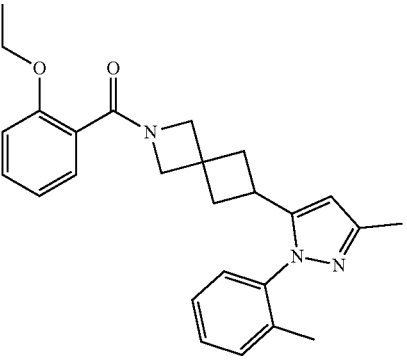 [SMILES: CCOc1ccccc1C(=O)N1CC2(CC(c3cc(C)nn3-c3ccccc3C)C2)C1]<br>PSY-05-00145-001 | Compound-00145-001 was prepared by followed the general procedure given above from 80 mg of 6-(3-methyl-1-(o-tolyl)-1H-pyrazol-5-yl)-2-azaspiro[3.3]heptane 2,2,2-trifluoroacetate (1 eq.) to obtain (2-ethoxyphenyl)(6-(3-methyl-1-(o-tolyl)-1H-pyrazol-5-yl)-2-azaspiro[3.3]heptan-2-yl)methanone (30 mg, 24.19%) as a white solid.<br>Compound can be made by following synthetic methodology provided in Formula (II-B). Int-4 is reacted with o-tolylhydrazine hydrochloride, then Int-6 is reacted with 2-ethoxybenzoic acid to yield the final analog. |
| 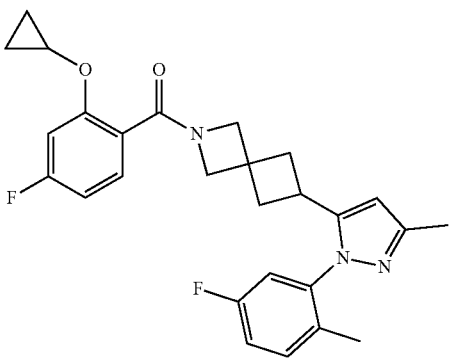 [SMILES: Cc1cc(C2CC3(C2)CN(C(=O)c2ccc(F)cc2OC2CC2)C3)n(-c2cc(F)ccc2C)n1]<br>PSY-05-418 | Compound can be made by following synthetic methodology provided in Formula (II-B). Int-4 is reacted with (5-fluoro-2-methylphenyl)hydrazine hydrochloride, then Int-6 is reacted with 2-cyclopropoxy-4-fluorobenzoic acid to yield the final analog. |

TABLE 4-continued

| Structure | Description |
|---|---|
| 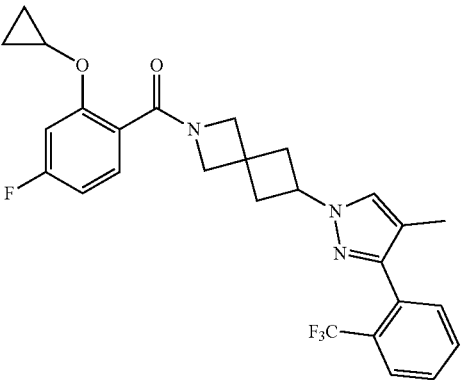 [SMILES: Cc1cn(C2CC3(C2)CN(C(=O)c2ccc(F)cc2OC2CC2)C3)nc1-c1ccccc1C(F)(F)F]<br>PSY-05-448 | Analog is prepared by following method for preparation of 1-(4-methyl)pyrazolyl warhead analogs. Compound can be prepared by reacting 1-(2-(trifluoromethyl)phenyl)propan-1-one with DMF-DMA to form Int-1. Int-4A is selectively advanced for N-Boc-deprotection and subsequent amide coupling with 2-cyclopropoxy-4-fluorobenzoic acid to yield final compound. |
| 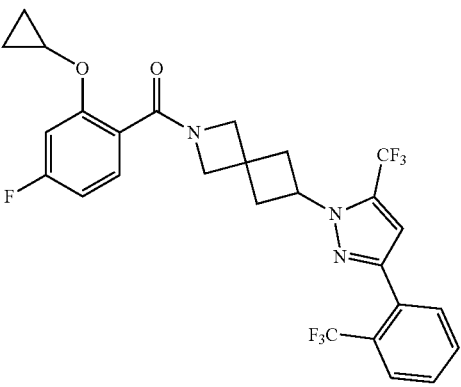 [SMILES: O=C(c1ccc(F)cc1OC1CC1)N1CC2(CC(n3nc(-c4ccccc4C(F)(F)F)cc3C(F)(F)F)C2)C1]<br>PSY-05-451 | Analog is prepared by following synthesis for 1-(3-aryl-5-trifluoromethyl)pyrazolyl warhead analogs. Compound can be synthesized by using 1-(2-(trifluoromethyl)phenyl)ethan-1-one as Int-1. Int-4A is selectively advanced for N-Boc-deprotection and subsequent amide coupling with 2-cyclopropoxy-4-fluorobenzoic acid to yield final compound. |

In some embodiments, the disclosure provides a compound of Formula (III-C) or a pharmaceutically acceptable salt thereof:

In some embodiments, the disclosure provides a compound of Formula (III-D) or a pharmaceutically acceptable salt thereof:

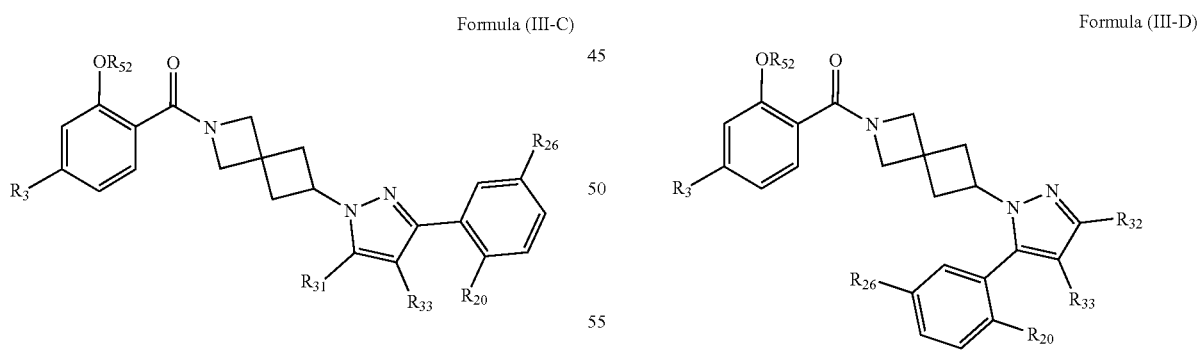

Formula (III-C)

Formula (III-D)

wherein $R_3$ is halogen;

$R_{52}$ is lower alkyl or lower cycloalkyl, each optionally substituted with halogen, $R_{31}$ and $R_{33}$ are each independently hydrogen or lower alkyl optionally substituted with one or more halogen, provided that one of $R_{31}$ and $R_{33}$ is hydrogen.

$R_{20}$ is lower alkyl optionally substituted with halogen; and $R_{26}$ is hydrogen or halogen.

wherein $R_3$ is halogen;

$R_{52}$ is lower alkyl or lower cycloalkyl, each optionally substituted with halogen, $R_{32}$ and $R_{33}$ are each independently hydrogen or lower-alkyl optionally substituted with one or more halogen, provided that one of $R_{32}$ and $R_{33}$ is hydrogen.

$R_{20}$ is lower alkyl optionally substituted with halogen; and $R_{26}$ is hydrogen or halogen.

General procedure for Preparing Compounds of Formula (III-D)

TABLE 5

| Structure | Description |
|---|---|
| 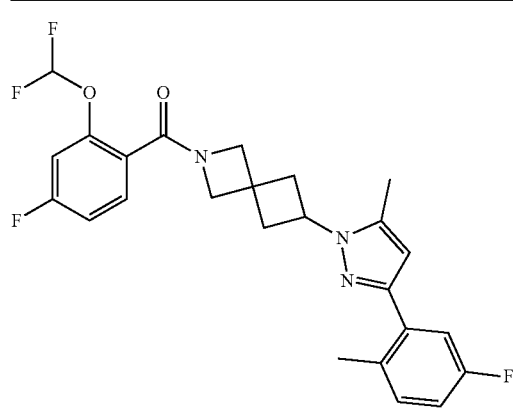 PSY-05-455 | Analog can be prepared by following synthesis for 1-(3-aryl-5-methyl)pyrazolyl warhead analogs. 1-(5-fluoro-2-methylphenyl)ethan-1-one is used as Int-1. Int-4A is selectively advanced for N-Boc-deprotection and subsequent amide coupling with 2-(difluoromethoxy)-4-fluorobenzoic acid to yield final compound. |
| 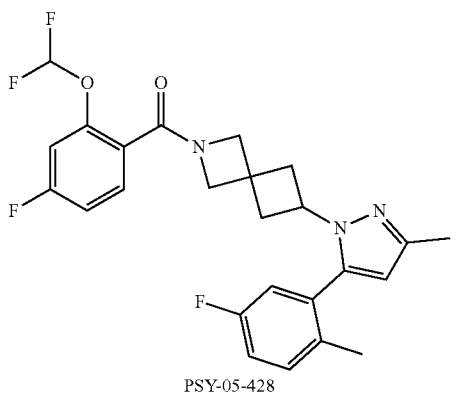 PSY-05-428 | Analog can be prepared by following synthesis for 1-(5-aryl-3-methyl)pyrazolyl warhead analogs. 1-(5-fluoro-2-methylphenyl)ethan-1-one is used as Int-1. Int-4 is selectively advanced for N-Boc-deprotection and subsequent amide coupling with 2-(difluoromethoxy)-4-fluorobenzoic acid to yield final compound. |
| 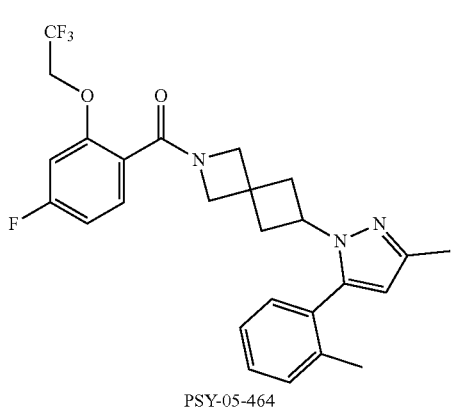 PSY-05-464 | Analog can be prepared by following synthesis for 1-(5-aryl-3-methyl)pyrazolyl warhead analogs. 1-(o-tolyl)ethan-1-one is used as Int-1. Int-4 is selectively advanced for N-Boc-deprotection and subsequent amide coupling with 4-fluoro-2-(2,2,2-trifluoroethoxy)benzoic acid to yield final compound. 4-fluoro-2-(2,2,2-trifluoroethoxy)benzoic acid is prepared by reacting methyl 2,4-difluorobenzoate with 2,2,2-trifluoroethanol, than performing sodium hydroxide-catalyzed ester hydrolysis to liberate the free acid. |

TABLE 5-continued

| Structure | Description |
| --- | --- |
| 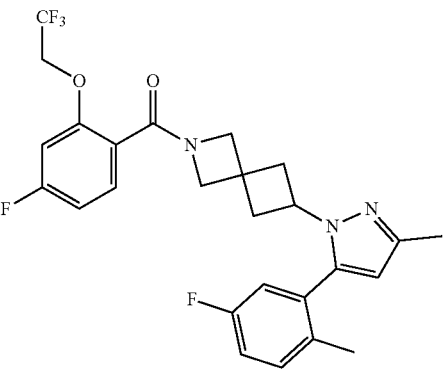 [SMILES: Cc1cc(-c2cc(F)ccc2C)n(C2CC3(C2)CN(C(=O)c2ccc(F)cc2OCC(F)(F)F)C3)n1] PSY-05-466 | Analog can be prepared by following synthesis for 1-(5-aryl-3-methyl)pyrazolyl warhead analogs. 1-(5-fluoro-2-methylphenyl)ethan-1-one is used as Int-1. Int-4 is selectively advanced for N-Boc-deprotection and subsequent amide coupling with 4-fluoro-2-(2,2,2-trifluoroethoxy)benzoic acid to yield final compound. 4-fluoro-2-(2,2,2-trifluoroethoxy)benzoic acid is prepared by reacting methyl 2,4-difluorobenzoate with 2,2,2-trifluoroethanol, than performing sodium hydroxide-catalyzed ester hydrolysis to liberate the free acid. |

In some embodiments, V in Formula (I-A) is

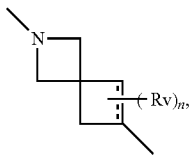

where n and each Rv is as defined above, and the dashed line represents an optional double bond. In some embodiments, in Formula (I-B) the dashed line represents an optional double bond. In some embodiments, in Formula (I-B-1) the dashed line represents an optional double bond. In some embodiments, in Formula (I-B-2) the dashed line represents an optional double bond. In some embodiments, in Formula (II) the dashed line represents an optional double bond.

The compounds described herein can exist as salts, such as with pharmaceutically acceptable acids. Accordingly, such salts of the compounds described herein are included. The term "pharmaceutically acceptable salt" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutical Compositions

In certain embodiments, the present application is directed to a pharmaceutical composition comprising an active pharmaceutical ingredient. In certain embodiments, the pharmaceutical composition comprises a compound as disclosed herein as the active pharmaceutical ingredient (API) and a pharmaceutically acceptable carrier comprising one or more excipients. In some embodiments, the pharmaceutical composition optionally further comprises an additional therapeutic compound (i.e., agent) with the pharmaceutically acceptable carrier. The pharmaceutical composition can be a medicament.

Pharmaceutically acceptable carriers include those known in the art. The choice of a pharmaceutically acceptable carrier can depend, for example, on the desired route of administration of the composition. A pharmaceutical composition (preparation) can be administered to a subject by any of a number of routes of administration including, for example, parenteral administration (e.g. intravenously, subcutaneously, or intramuscularly), oral administration (for example, tablets, and capsules); absorption through the oral mucosa (e.g., sublingually) or transdermally (for example as a patch applied to the skin) or topically (for example, as a cream, ointment or spray applied to the skin).

In some embodiments, pharmaceutical compositions comprising compounds of Formula (I) or pharmaceutically acceptable salts thereof can be formulated for oral administration. For example, a compound provided herein can be combined with suitable compendial excipients to form an oral unit dosage form, such as a capsule or tablet, containing a target dose of a compound of Formula (I). The drug product can be prepared by first manufacturing the compound of Formula (I) as an active pharmaceutical ingredient (API), followed by roller compaction/milling with intragranular excipients and blending with extra granular excipients. A Drug Product can contain the selected compound of Formula (I) as the API and excipient components in a tablet in a desired dosage strength of Compound 1. The blended material can be compressed to form tablets and then film coated. The excipients can be selected from materials appropriate for inclusion in a pharmaceutical composition for an intended purpose and route of delivery including providing a desired manufacturing and stability properties and/or desired in vivo characteristics or other properties to the pharmaceutical composition. In some embodiments, the pharmaceutical composition can include a compound of Formula (I) as the API in combination with a filler (e.g., a form of microcrystalline cellulose), a dry binder or disintegrant (e.g., a cross-linked polymer), a glidant (e.g., colloidal silicon dioxide) and/or a lubricant (e.g., magnesium stearate). In some embodiments, the pharmaceutical composition can comprise a material such as an extended release or disintegrant involved in carrying or transporting the API pharmaceutical agent from one organ, or portion of the body, to another organ, or portion of the body of a subject, including materials to desirable control the absorption of the API in the intestine.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

To prepare solid dosage forms for oral administration, the active ingredient is mixed with one or more pharmaceutically acceptable carriers, such as sodium citrate or dicalcium phosphate, and/or any of the following: (1) fillers or extenders, (2) binders, (3) humectants, (4) disintegrating agents, (5) solution retarding agents, (6) absorption accelerators, (7) wetting agents, (8) absorbents, (9) lubricants, (10) complexing agents, and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using suitable excipients. The pharmaceutical compositions according to the present invention may contain conventional pharmaceutical carriers and/or auxiliary agents. In some embodiments, the pharmaceutical compositions according to the present invention may contain conventional carrier agents including a binder, a lubricant and/or a glidant selected from those products and materials generally used in pharmaceutical industry for preparation of pharmaceutical compositions for an intended route of administration.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Liquid dosage forms useful for oral administration include pharmaceutically acceptable carriers and the active ingredient provided as a solid form for reconstitution prior to administration or as a liquid (e.g., solutions, suspensions, or emulsions). In addition to the active ingredient, a liquid dosage forms may contain inert diluents commonly used in the art. For example, formulations of pharmaceutically acceptable compositions for injection can include aqueous solutions such as water or physiologically buffered saline or other solvents or vehicles suitable for the intended route of administration. In some embodiments, the pharmaceutical composition is formulated for parenteral administration.

The therapeutically effective amount of a pharmaceutical composition can be determined by human clinical trials to determine the safe and effective dose for a patient with a relevant diagnosis. It is generally understood that the effective amount of the compound may vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the pharmaceutical composition at a dose and dose interval determined to be safe and effective for the patient.

The present disclosure includes the use of pharmaceutically acceptable salts of compounds of the invention in the compositions and methods of the present invention. Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt, in some embodiments, a pharmaceutically-acceptable salt is an ammonium salt. For example, a pharmaceutically acceptable acid addition salt can exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Methods of Use

The compounds described herein can modulate activity of monoacylglycerol lipase. For example, the compounds described herein can inhibit MAGL. Accordingly, in one aspect the disclosure provides a method for inhibiting MAGL, e.g., in a cell expressing MAGL. Generally, the method comprises administering to the cell a compound of Formula (I) described herein. It is noted that the inhibition can be reversible or irreversible. In some embodiments, the compounds are capable of reversibly inhibiting MAGL. As used herein, "reversible inhibition" means MAGL retains its activity once the compound is taken away or MAGL is no longer in contact with the compound. In other words, the activity of MAGL returns to the same level it was prior to use of the compound.

The compound can be administered to the cell, e.g. cell expressing MAGL in vitro or ex vivo. As used herein, administering the compound to the cell means contacting the cell with the compound so that the compound is taken up by the cell. Generally, the cell can be contacted with the compound in a cell culture e.g., in vitro or ex vivo, or the compound can be administered to a subject, e.g., in vivo. The term "contacting" or "contact" as used herein in connection with contacting a cell includes subjecting the cells to an appropriate culture media, which comprises a compound of Formula (I). Where the cell is in vivo, "contacting" or "contact" includes administering the compound, e.g., in a pharmaceutical composition to a subject via an appropriate administration route such that the compound contacts the cell in vivo.

As described herein, the compound of Formula (I) can be administered to a cell in vivo for modulating MAGL, e.g., inhibiting MAGL. Accordingly, in some embodiments, a therapeutically effective amount of a compound of Formula (I) can be administered to a subject for inhibiting monoacylglycerol lipase. For example, a therapeutically effective amount of a compound of Formula (I) can be administrated to a subject for treating a monoglycerol lipase mediated disease or disorder.

By a MAGL-mediated disease or disorder is meant a disease or disorder wherein activity of MAGL is a cause of the disease or disorder. Non-limiting example, of MAGL-mediated diseases or disorders include neurodegenerative diseases, neuropsychiatric disorders, pain and chronic inflammatory diseases, cancer and other conditions that can be treated with a reversible MAGL inhibitor of Formula (I).

In some embodiments, a compound of Formula (I) is useful for evaluation as a drug candidate for the treatment of neurodegenerative diseases such as Parkinson's disease, amyotrophic internal sclerosis, Alzheimer's disease or Huntington's disease. In some embodiments, a compound of Formula (I) is useful for evaluation as a drug candidate for the treatment of neuropsychiatric disorders such as head injury, epilepsy, cerebral ischemia and anxiety and/or depression. In some embodiments, a compound of Formula (I) is useful for evaluation as a drug candidate for the treatment of pain and inflammatory diseases or conditions. In some embodiments, a compound of Formula (I) is useful for evaluation as a drug candidate for the treatment of forms of cancer treatable by increasing 2-AG. In some embodiments, a compound of Formula (I) is useful for evaluation as a drug candidate for the treatment of obesity, fibrosis, emesis, asthma, fever and osteoporosis. In some embodiments, a compound of Formula (I) is useful for evaluation as a drug candidate for increasing levels of 2-AG in a subject in need thereof.

A subject can be one who has been previously diagnosed with or identified as suffering from or having a condition in need of treatment a MAGL-mediated disease or disorder or one or more complications related to such a condition, and optionally, have already undergone treatment for such a disease or disorder. Alternatively, a subject can also be one who has not been previously diagnosed as having a MAGL-mediated disease or disorder or one or more complications related to such a disease or disorder. A "subject in need" of treatment for a particular condition can be a subject having that condition, diagnosed as having that condition, or at risk of developing that condition.

In one embodiment, the subject is human. In another embodiment, the subject is an experimental animal or animal substitute as a disease model.

It is noted that the terms "administered" and "subjected" are used interchangeably in the context of treatment of a disease or disorder. In jurisdictions that forbid the patenting of methods that are practiced on the human body, the meaning of "administering" of a composition to a human subject shall be restricted to prescribing a controlled substance that a human subject will be administer to the subject by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration will generally be local rather than systemic.

In preferred embodiments, the compositions are orally administered. Without limitations, oral administration can be in the form of solutions, suspensions, tablets, pills, capsules, sustained-release formulations, oral rinses, powders and the like.

The phrase "therapeutically-effective amount" as used herein means that amount of a compound, material, or composition comprising a compound described herein which is effective for producing some desired therapeutic effect in at least a sub-population of cells, e.g., modulate or inhibit activity of MAGL in a subject at a reasonable benefit/risk ratio applicable to any medical treatment. Thus, "therapeutically effective amount" means that amount which, when administered to a subject for treating a disease, is sufficient to affect such treatment for the disease.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively, or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

The data obtained from the cell culture assays and animal studies can be used in formulating a range of dosage for use in humans. The dosage of such compounds lies preferably within a range of circulating concentrations that include the $IC_{50}$ with little or no toxicity. The dosage may vary within this range depending upon the dosage form employed and the route of use or administration utilized. The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

It will be appreciated that methods of treatment of the present invention can be employed in combination with additional therapies. For example, a treatment according to the present disclosure can be co-administered with one or more desired therapeutics or medical procedures for treating a MAGL-mediated disease or disorder.

Definitions

Unless otherwise defined herein, scientific and technical terms used in this application shall have the meanings that are commonly understood by those of ordinary skill in the art.

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein, the term "Selective MAGL Inhibitor Compound" refers to a compound that selectively inhibits MAGL with an $IC_{50}$ that is at least 10 times the $IC_{50}$ for its inhibition of fatty acid amide hydrolase (FAAH), and that has an $IC_{50}$ of 100 nM or less for MAGL inhibition (according to the MAGL Potency assay of Example 22 and the FAAH potency assay of Example 15).

As used herein, the term "Reversible MAGL Inhibitor Compound" the percent inhibition after dilution to the $IC_{50}$ concentration is 50+15% in the assay described for "determining MAGL reversible inhibition" section of Example 16 below.

As used herein, the term "Reversible Selective MAGL Inhibitor Compound" refers to a compound that is both a Selective MAGL Inhibitor Compound and a Reversible MAGL Inhibitor Compound, or a pharmaceutically acceptable salt thereof.

As used herein, the term "alkyl" refers to an aliphatic hydrocarbon group which can be straight or branched having 1 to about 10 carbon atoms in the chain, and which preferably have about 1 to about 6 carbons in the chain. "Lower alkyl" refers to an alkyl group having 1 to about 4 carbon atoms. "Higher alkyl" refers to an alkyl group having about 5 to about 10 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

As used herein, the term "cycloalkyl" refers to a non-aromatic mono- or multicyclic ring system of about 3 to about 12 carbon atoms. Representative monocyclic cycloalkyl rings include cyclopropyl, cyclobutyl, and cyclohexyl. Useful multicyclic cycloalkyl rings include adamantyl. "Lower cycloalkyl" refers to an alkyl group having 3 to about 6 carbon atoms in the cycloalkyl ring, optionally substituted with halogen, alkyl, alkoxy or other substituents disclosed herein. "Higher alkyl" refers to an alkyl group having about 5 to about 10 carbon atoms.

"Aryl" refers to an aromatic carbocyclic radical containing about 3 to about 10 carbon atoms. The aryl group can be optionally substituted with one or more substituents, which can be the same or different, where "aryl group substituent" includes alkyl, alkenyl, alkynyl, hydroxy, alkoxy, carboxy, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, and alkylene. Exemplary aryl groups include substituted or unsubstituted phenyl.

"Heterocyclyl" refers to a nonaromatic 3-8 membered monocyclic, or 8-12 membered bicyclic ring systems having 1-3 heteroatoms if monocyclic, or 1-6 heteroatoms if bicyclic, said heteroatoms selected from O, N, or S (e.g., carbon atoms and 1-3, or 1-6 heteroatoms of N, O, or S if monocyclic, or bicyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Heteroaryl" refers to an aromatic 3-8 membered monocyclic, or 8-12 membered fused bicyclic ring system having 1-3 heteroatoms if monocyclic, or 1-6 heteroatoms if bicyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryls and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl or xanthenyl, each of which can be optionally substituted.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to an alkyl structure with at least one substituent of fluorine, chorine, bromine or iodine, or with combinations thereof. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$ or —$NH_3^+$ where one or more hydrogens are optionally substituted with alkyl, and the alkyl is optionally further substituted with one or more halogen or other substituents disclosed herein. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkylxalkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like. Exemplary alkylamino includes, but is not limited to, NH($C_1$-$C_{10}$alkyl), such as —$NHCH_3$, —$NHCH_2CH_3$, —$NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N($CH(CH_3)_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxy" and "hydroxyl" mean the radical —OH.

The terms "alkoxyl" or "alkoxy" as used herein refers to an alkyl group, as defined above, having an oxygen radical attached thereto, and can be represented by one of —O-alkyl, —O— alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. As used herein, a carboxy group includes —COOH, i.e., carboxyl group.

The term "cyano" means the radical —CN.

The term "nitro" means the radical —$NO_2$.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N═, —NR$^N$—, —N$^+$(O$^-$)═, —O—, —S— or —S(O)$_2$—, —OS(O)$_2$—, and —SS—, wherein R$^N$ is H or a further substituent.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Carbamoyl" refers to an $H_2N$—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, amikylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, 3, 4 or 5 groups selected from OH, CN, SH, $SO_2NH_2$, $SO_2(C_1-C_4)$ alkyl, $SO_2NH(C_1-C_4)$alkyl, halogen, carbonyl, thiol, cyano, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)— alkyl, C(O)— alkyl, alkylcarbonylaminyl, $CH_2$—[CH(OH)]$_m$—(CH$_2$)$_p$—OH, $CH_2$—[CH(OH)]$_m$—(CH$_2$)$_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

In some embodiments, an optionally substituted group is substituted with 1 substituent. In some other embodiments, an optionally substituted group is substituted with 2 independently selected substituents, which can be same or different. In some other embodiments, an optionally substituted group is substituted with 3 independently selected substituents, which can be same, different or any combination of same and different. In still some other embodiments, an optionally substituted group is substituted with 4 independently selected substituents, which can be same, different or any combination of same and different. In yet some other embodiments, an optionally substituted group is substituted with 5 independently selected substituents, which can be same, different or any combination of same and different.

As used herein, the compound designation terms "Compound #", "PSY-#" and "PSY-05-4" (where # indicates any number having one or more digits) are synonymous with each other, unless otherwise indicated (e.g., "Compound 1" refers to a compound alternatively designated as "PSY-05-0001" or "PSY-1").

As used herein, Compound (PSY-05-00074) (alternatively designated as Compound 74) is:

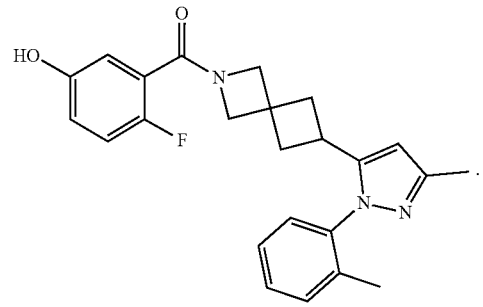 [SMILES: Cc1cc(C2CC3(C2)CN(C(=O)c2cc(O)ccc2F)C3)n(-c2ccccc2C)n1]

Compound (PSY-05-00074) is referred to by name as (2-fluoro-5-hydroxyphenyl)(6-(3-methyl-1-(o-tolyl)-1H-pyrazol-5-yl)-2-azaspiro[3.3]heptan-2-yl)methanone, or (2-fluoro-5-hydroxyphenyl){6-[3-methyl-1-(o-tolyl)-5-pyrazolyl]-2-aza-2-spiro[3.3]heptyl}methanone. Either name may be used interchangeably herein to refer to Compound (PSY-05-00074).

In some embodiments, the compound is selected from the group consisting of:

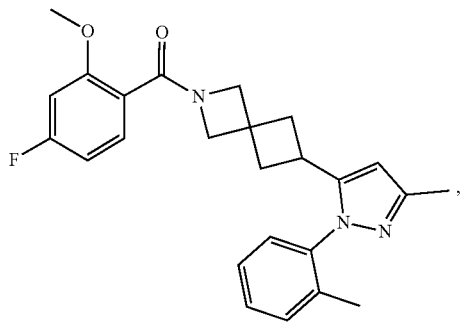

,

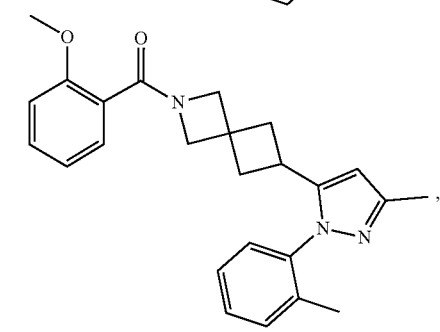

,

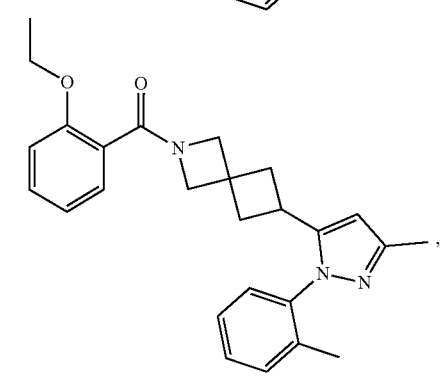

,

-continued
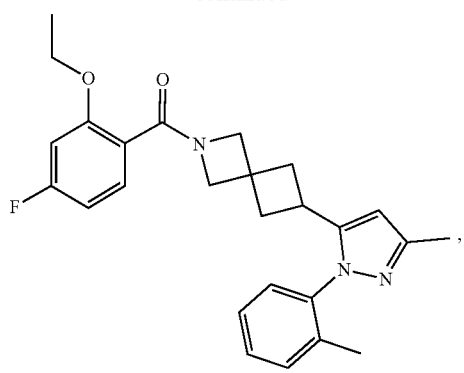
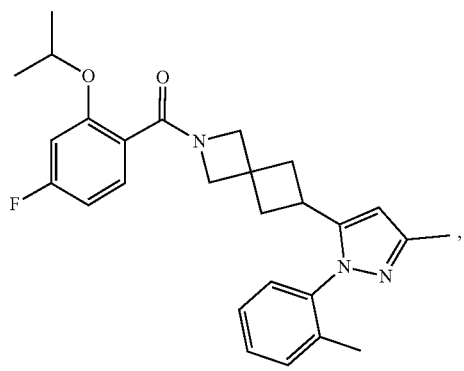
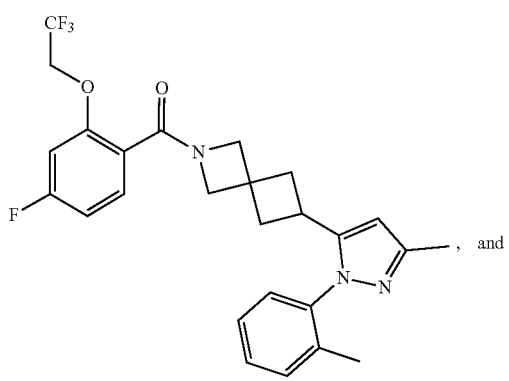
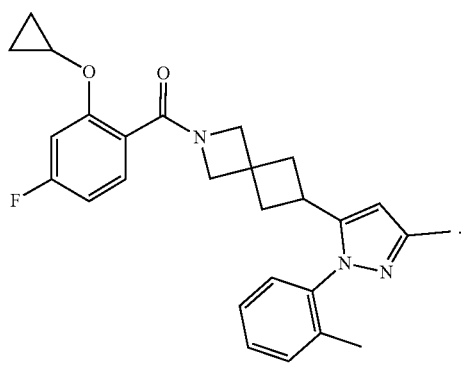
In some embodiments, the compound is selected from the group consisting of:
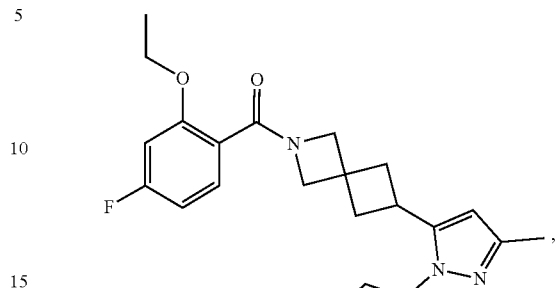
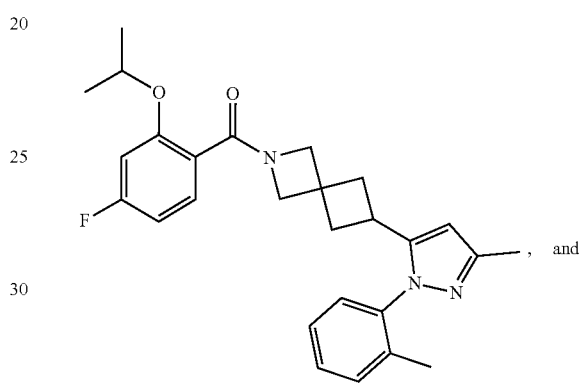
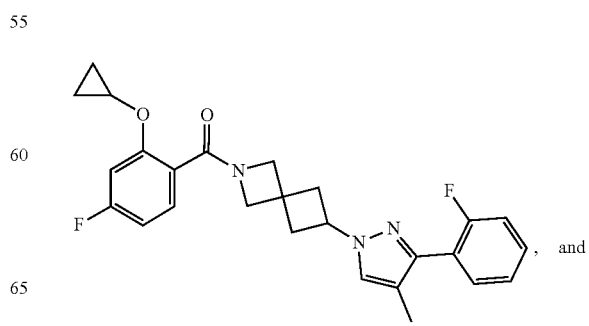
In some embodiments, the compound is selected from the group consisting of:

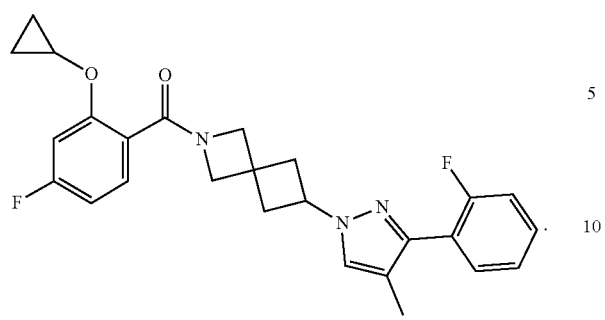
Other compounds include the compounds shown below that are Selective MAGL Inhibitors and Reversible MAGL Inhibitors:
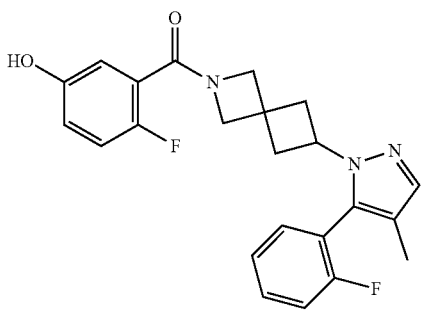
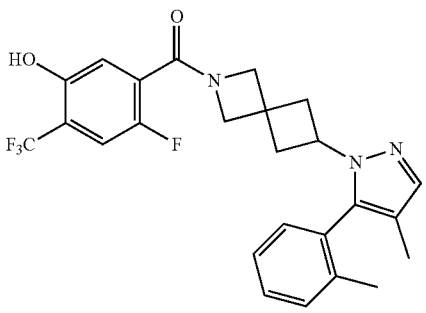
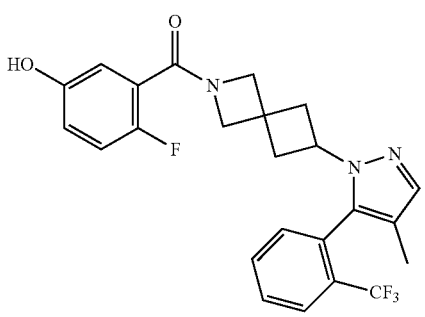
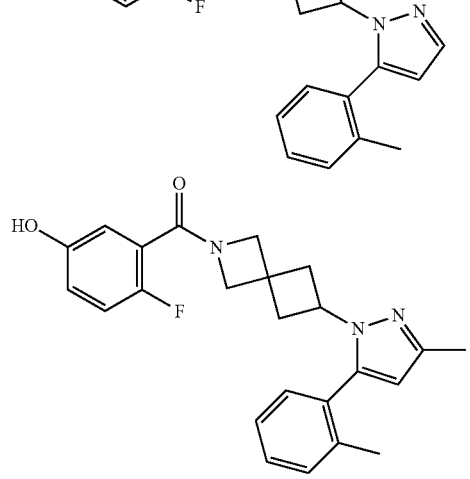
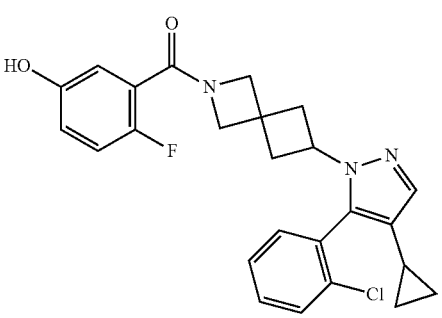
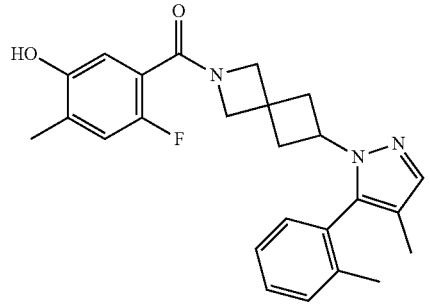
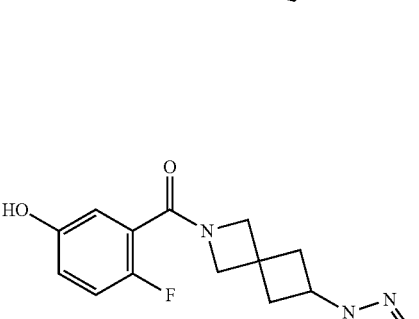
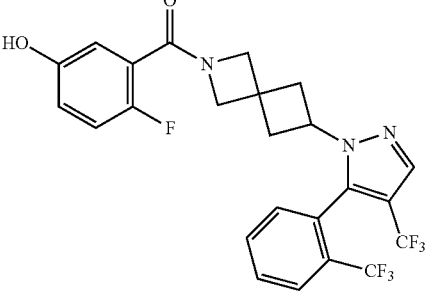

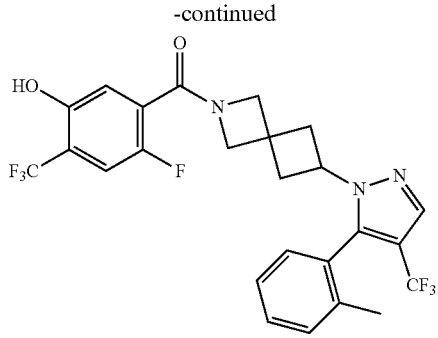
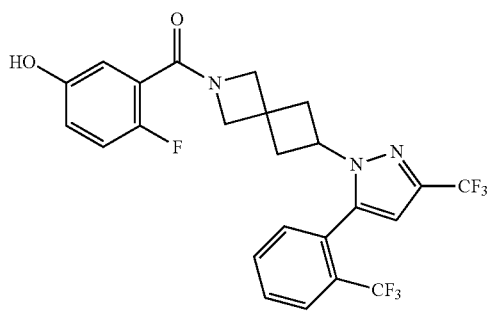
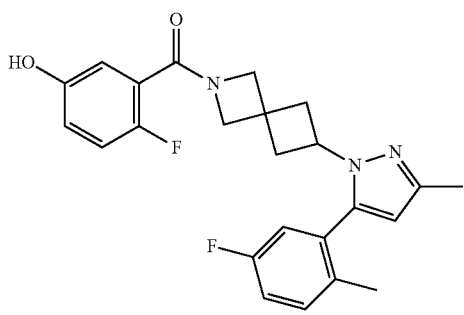
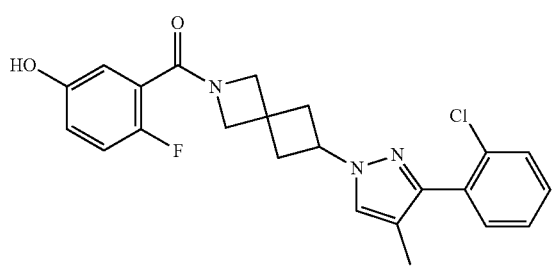
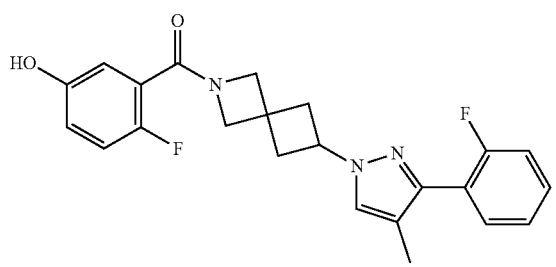
Other compounds include compounds shown below:
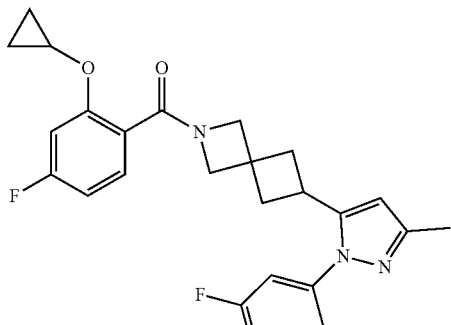
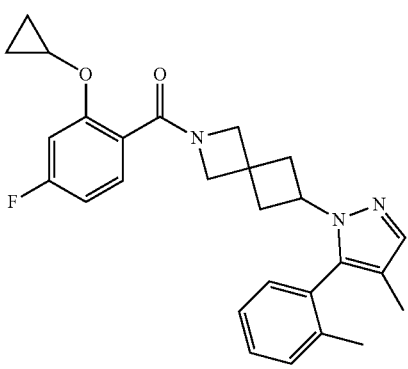
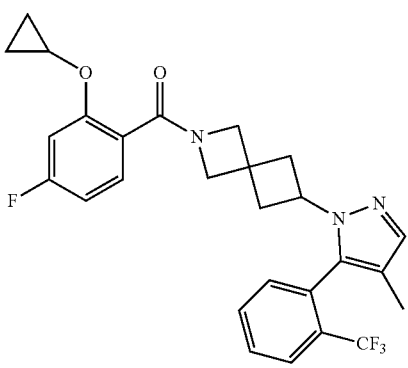
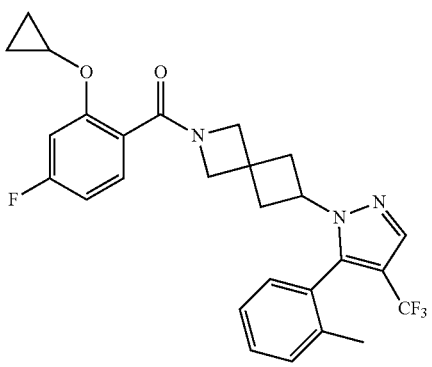

89
-continued

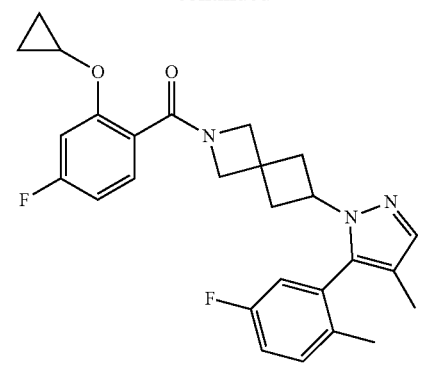

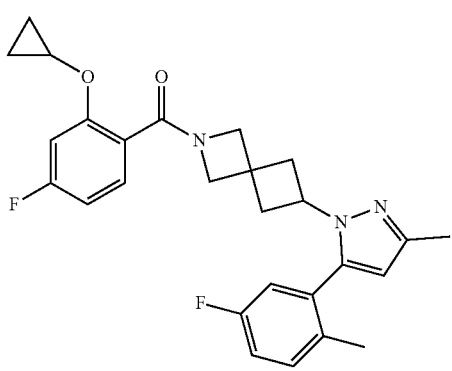

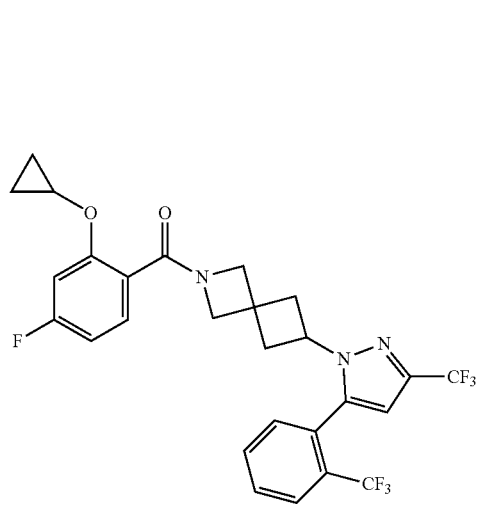

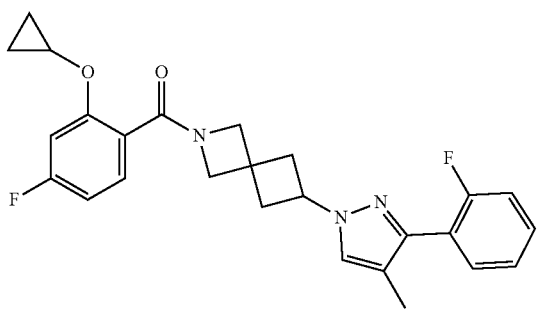

90
-continued

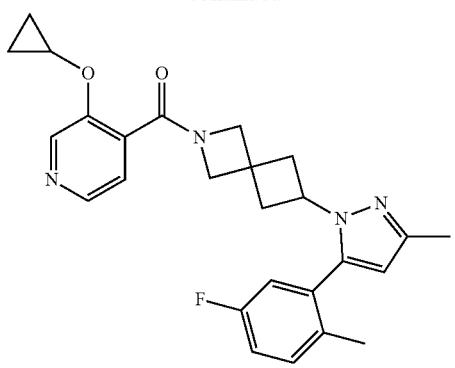

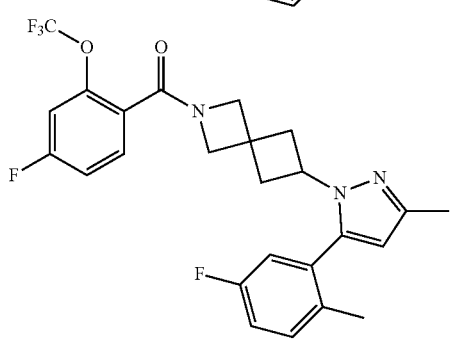

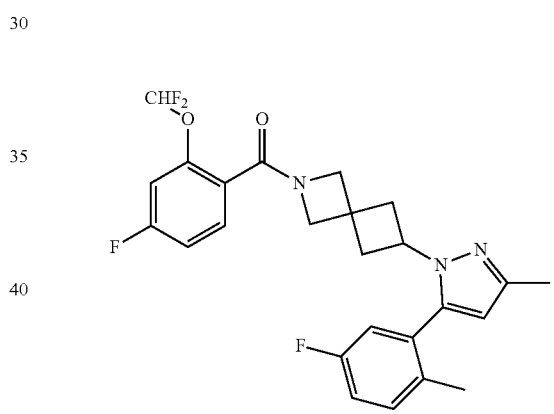

Additional Embodiments

Further, although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The Additional Embodiments include those listed below:

1. A Reversible and Selective MAGL Inhibitor Compound of Formula (I) or a pharmaceutically acceptable salt thereof,

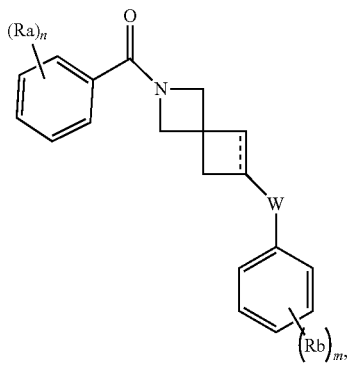

Formula (I-B)

wherein
  n is 1, 2, or 3;
  each Ra is independently halogen, cyano, lower alkyl optionally substituted with one or more halogen, or —$OR_6$;
  $R_6$ is hydrogen, lower alkyl or lower cycloalkyl optionally substituted with one or more halogen;
  W is A, —C(O)—, or —C(O)N($R_{10}$)—;
  $R_{10}$ is hydrogen or lower alkyl;
  A is a 5-member heteroaryl ring optionally substituted with one or more $R_{30}$;
  $R_{10}$ is lower alkyl;
  m is 1, or 2; and
  each $R_b$ is independently halogen, or lower alkyl optionally substituted with one or more halogen,
  provided that the compound is not (2-fluoro-5-hydroxyphenyl)(6-(3-methyl-1-(o-tolyl)-1H-pyrazol-5-yl)-2-azaspiro[3.3]heptan-2-yl)methanone.

2. The compound of embodiment 1, wherein
  a. each Ra is independently Cl, F, CN, cyano, methyl, or —$OR_6$;
  b. $R_6$ is hydrogen, ($C_1$-$C_4$)alkyl optionally substituted with one or more F or cyclopropyl;
  c. W is A;
  d. $R_{10}$ is hydrogen or methyl;
  e. A is a 5-member heteroaryl ring optionally substituted with one or more $R_{30}$;
  f. $R_{30}$ is ($C_1$-$C_4$)alkyl;
  g. m is 1, or 2; and
  h. each $R_b$ is independently halogen, or ($C_1$-$C_4$)alkyl optionally substituted with one or more F.

3. The compound of embodiment 2, wherein $R_3$ is methyl; and each $R_b$ is independently halogen, or methyl optionally substituted with one or more F.

4. The compound of embodiment 3, wherein A is selected from the group consisting of
  a. pyrazole, imidazole, or triazole, each optionally substituted with one methyl; and
  b. oxadiazole.

5. The compound of embodiment 4, wherein A is pyrazole substituted with one methyl.

6. The compound of any one of embodiments 1-5, wherein one Ra is —$OR_6$.

7. The compound of embodiment 6, wherein one Rb is methyl.

8. The compound of embodiment 1, of Formula (I-B-1):

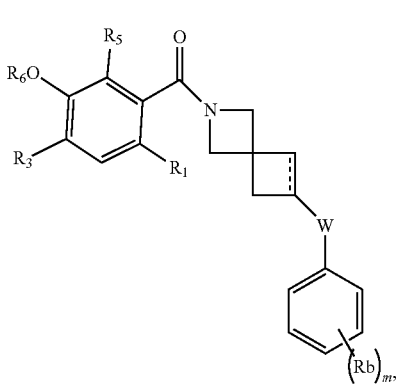

Formula (I-B-1)

wherein
  $R_1$ is hydrogen or halogen;
  $R_3$ is hydrogen, halogen, or lower alkyl optionally substituted with one or more halogen;
  $R_5$ is hydrogen, halogen, lower alkoxy or lower alkyl each optionally substituted with one or more halogen; and
  $R_6$ is hydrogen, lower alkyl or cycloalkyl optionally substituted with one or more halogen.

9. The compound of embodiment 1, of Formula (I-B-2),

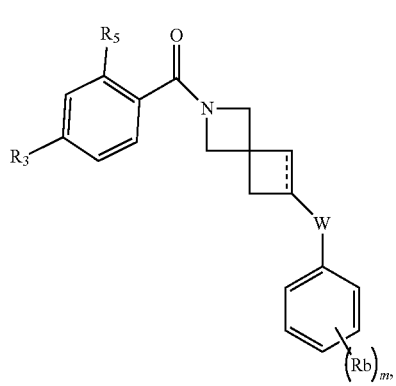

Formula (I-B-2)

wherein
  $R_3$ is hydrogen or halogen;
  $R_5$ is —O—$R_{52}$; and
  $R_{52}$ is lower alkyl or cycloalkyl, each optionally substituted with halogen 10. The compound of any one of embodiments 1, 8 or 9, wherein W is selected from the group consisting of A1, A2, A3, A4, A5, A6 and A7,

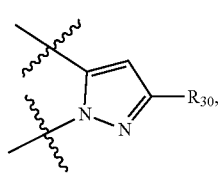

A1

A2 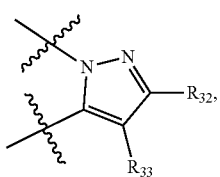

A3 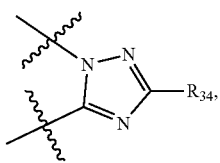

A4 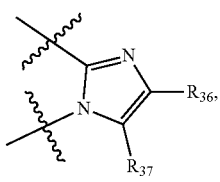

A5 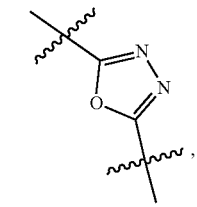

A6 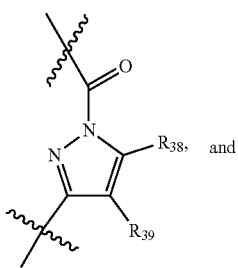

A7 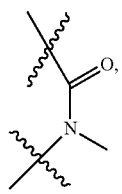

and $R_{30}$, $R_{32}$, $R_{33}$, $R_{34}$, $R_{36}$, $R_{37}$, $R_{38}$ and $R_{39}$ are each independently hydrogen or lower alkyl.

11. The compound of embodiment 10, wherein $R_{30}$, $R_{32}$, $R_{33}$, $R_{34}$, $R_{36}$, $R_{37}$, $R_{38}$ and $R_{39}$ are each independently hydrogen or methyl.

12. The compound of embodiment 10, wherein W is A1 and $R_{30}$ is methyl.

13. The compound of embodiment 10, wherein W is A2 and $R_{32}$ is hydrogen and $R_{33}$ is methyl.

14. The compound of embodiment 10, wherein W is A7 and Rb is methyl.

15. The compound of embodiment 1, of Formula (I-C),

Formula (I-C)

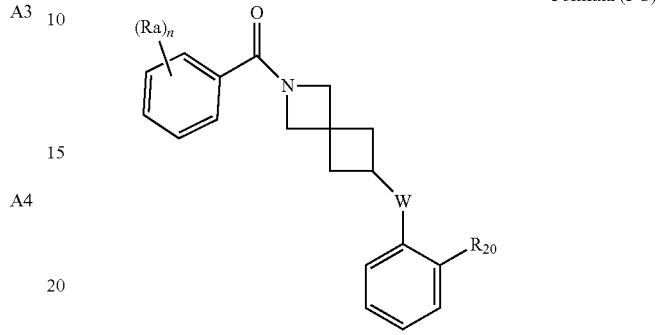

wherein $R_{20}$ is lower alkyl; and Ra, n, and W are as defined above with respect to Formula (I).

16. The compound of embodiment 15, wherein $R_{20}$ is methyl optionally substituted with one or more F.

17. A Reversible and Selective MAGL Inhibitor Compound of Formula (II), or a pharmaceutically acceptable salt thereof, Formula (II)

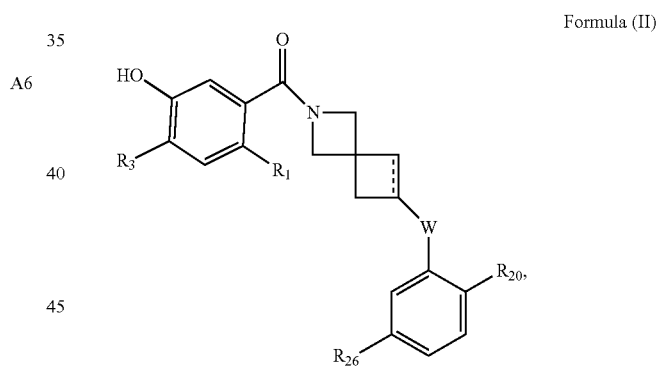

wherein $R_1$ is halogen or cyano;

$R_3$ is hydrogen or halogen;

W is A, —C(O)—, —C(O)N($R_{10}$)—;

$R_{10}$ is hydrogen or lower alkyl;

A is a 5-member heteroaryl ring optionally substituted with one or more $R_{30}$; and $R_{20}$ and $R_{30}$ are each independently lower alkyl, provided that the compound is not (2-fluoro-5-hydroxyphenyl)(6-(3-methyl-1-(o-tolyl)-1H-pyrazol-5-yl)-2-azaspiro[3.3]heptan-2-yl)methanone.

18. A Reversible and Selective MAGL Inhibitor Compound of Formula (III), or a pharmaceutically acceptable salt thereof,

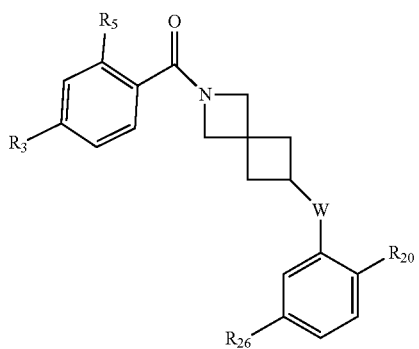

Formula (III)

wherein
- R₃ is halogen;
- R₅ is —O—R₅₂;
- R₅₂ is lower alkyl or cycloalkyl, each optionally substituted with halogen,
- W is a 5-member heteroaryl ring optionally substituted with one or more R₃₀;
- R₃₀ is lower alkyl;
- R₂₀ is lower alkyl; and
- R₂₆ is hydrogen or halogen.

19. The compound of embodiment 18, wherein
- R₃ is F;
- R₅₂ is methyl optionally substituted with halogen, or cyclopropyl;
- W is a 5-member heteroaryl ring comprising at least one nitrogen atom and optionally substituted with one or more R₃₀;
- R₃₀ is methyl;
- R₂₀ is methyl; and
- R₂₆ is hydrogen, or F.

20. A compound selected from the group consisting of:

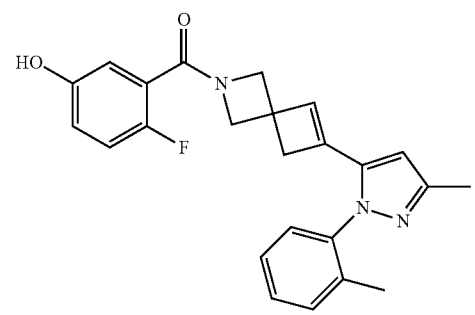

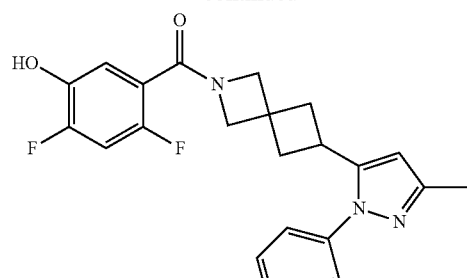

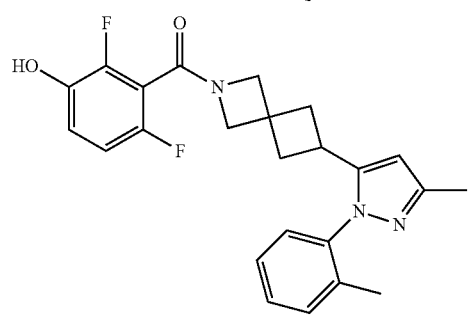

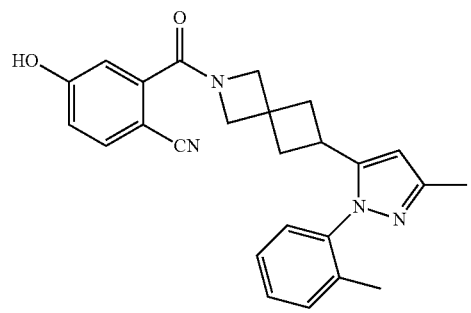

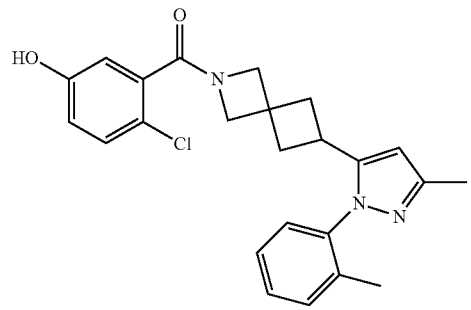

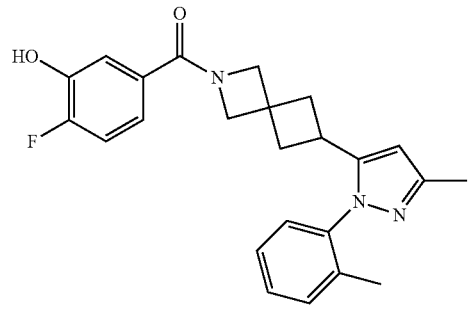

-continued
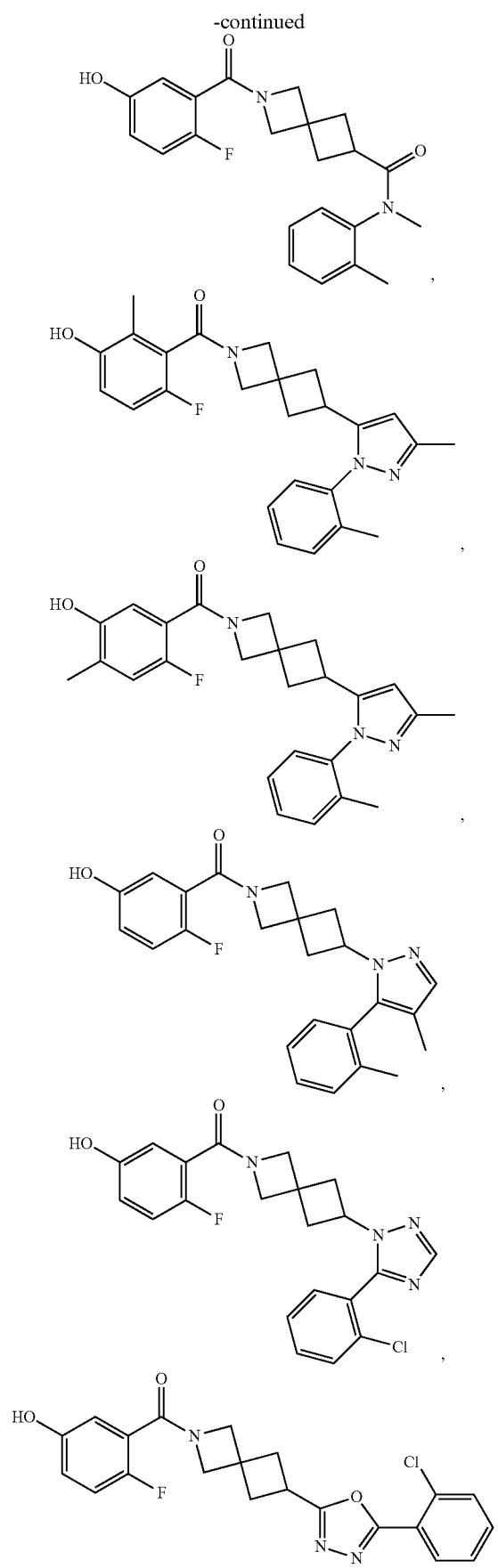
-continued
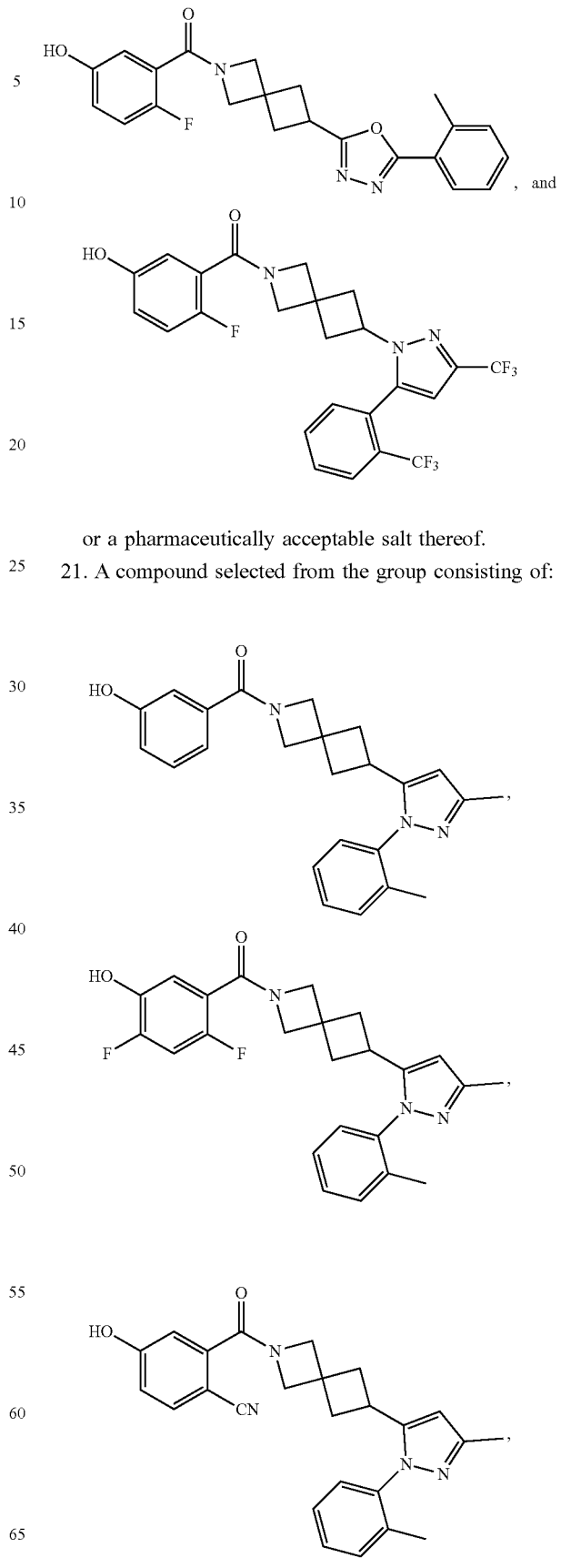
or a pharmaceutically acceptable salt thereof.
21. A compound selected from the group consisting of:

-continued
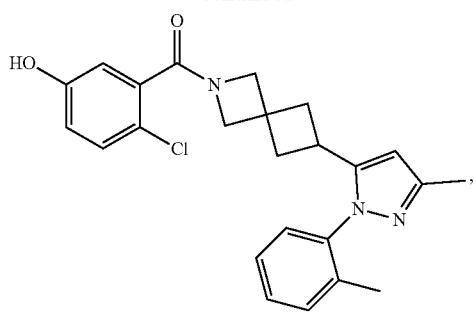
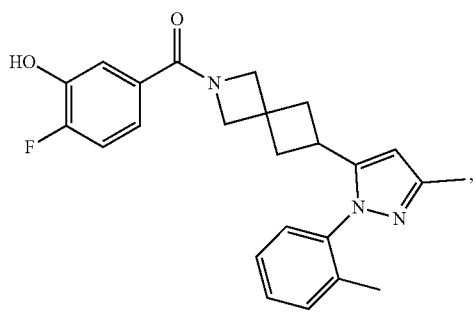
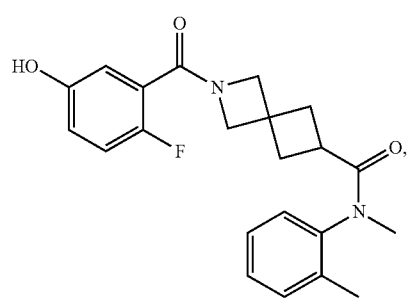
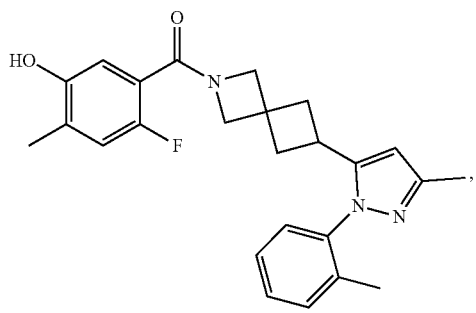
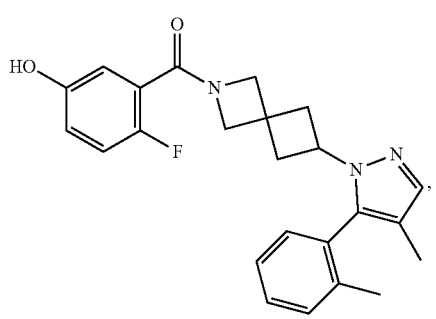
-continued
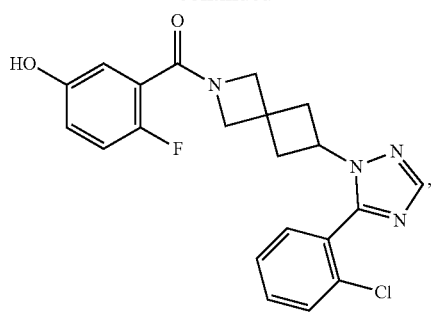
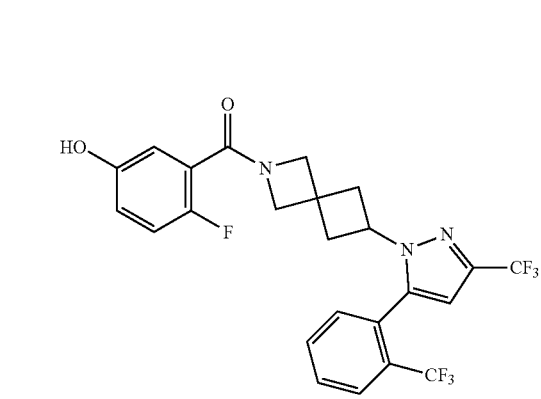
and or a pharmaceutically acceptable salt thereof.
22. A compound selected from the group consisting of:
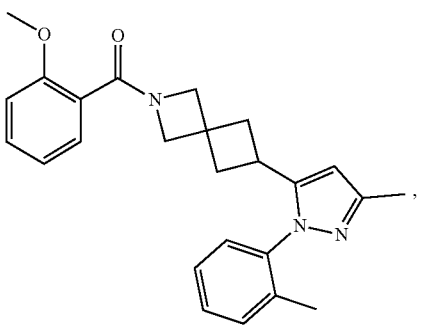
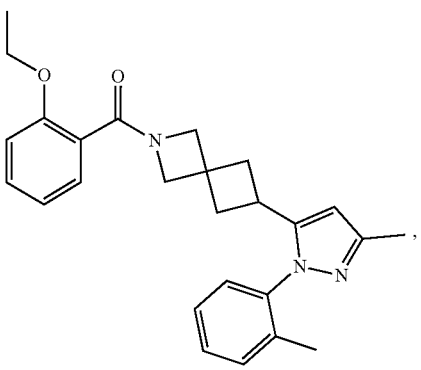

-continued
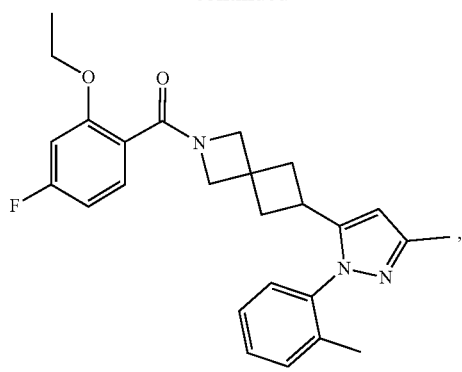
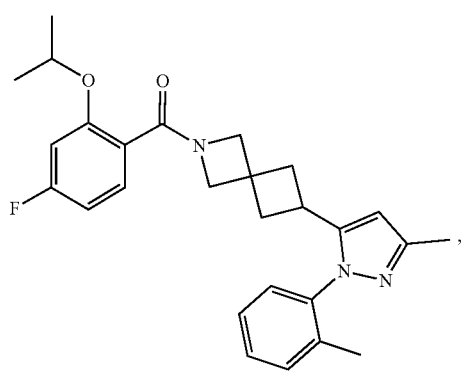
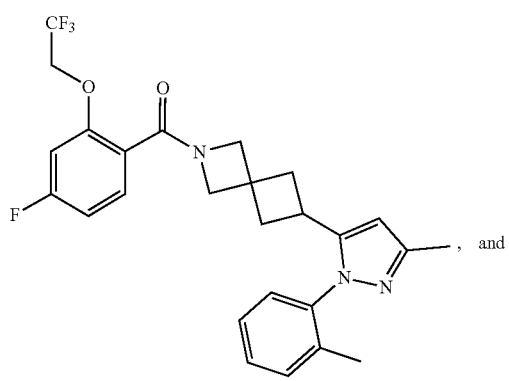
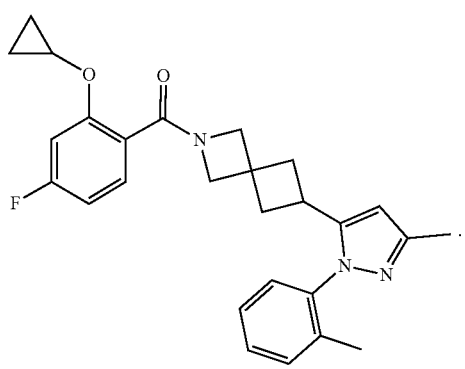
23. A compound selected from the group consisting of:
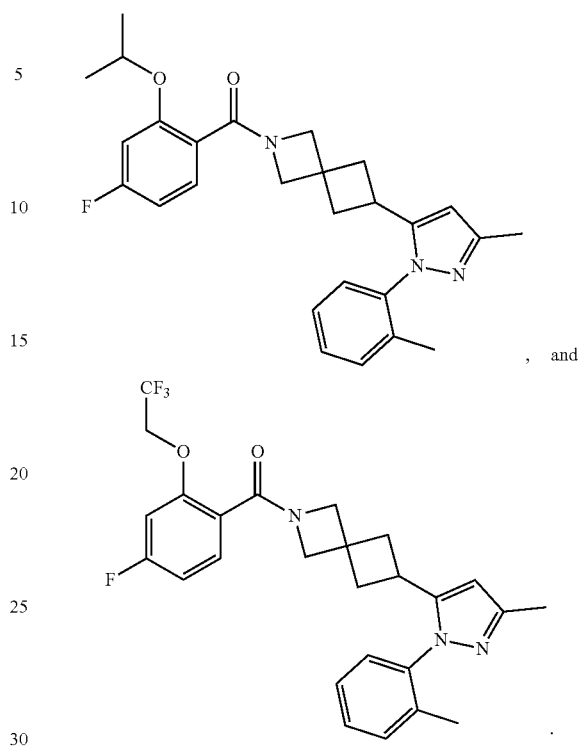
24. The compound
or a pharmaceutically acceptable salt thereof.
25. The compound
or a pharmaceutically acceptable salt thereof.

26. The compound

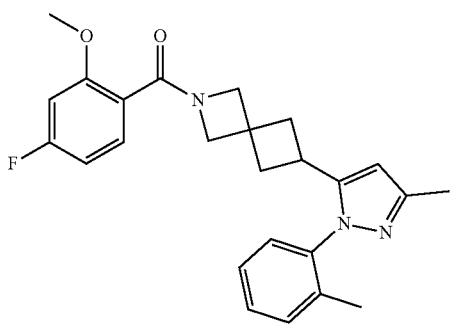 [SMILES: COc1cc(F)ccc1C(=O)N1CC2(CC(c3cc(C)nn3-c3ccccc3C)C2)C1]

or a pharmaceutically acceptable salt thereof.

27. The compound

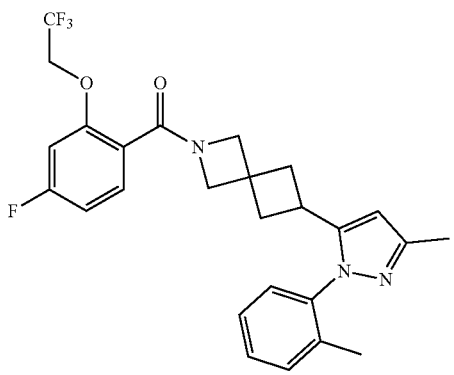 [SMILES: Cc1cc(C2CC3(C2)CN(C(=O)c2ccc(F)cc2OCC(F)(F)F)C3)n(-c2ccccc2C)n1]

or a pharmaceutically acceptable salt thereof.

28. The compound

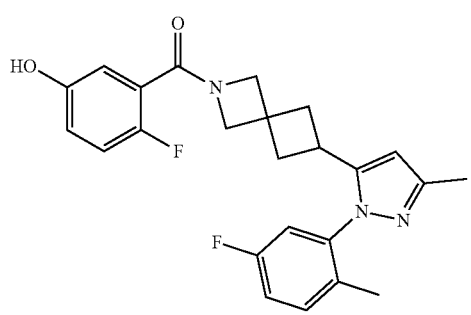 [SMILES: Cc1cc(C2CC3(C2)CN(C(=O)c2cc(O)ccc2F)C3)n(-c2cc(F)ccc2C)n1]

or a pharmaceutically acceptable salt thereof.

29. The compound

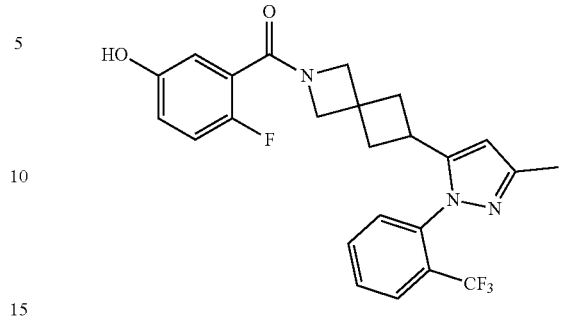

or a pharmaceutically acceptable salt thereof.

30. The compound

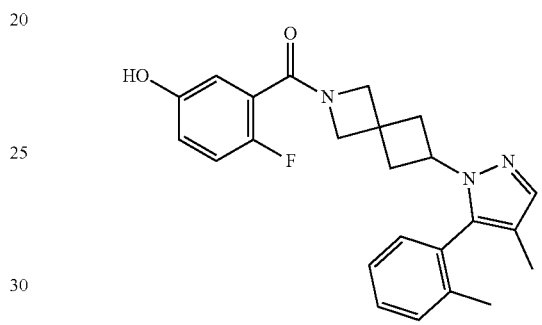

or a pharmaceutically acceptable salt thereof.

31. The compound

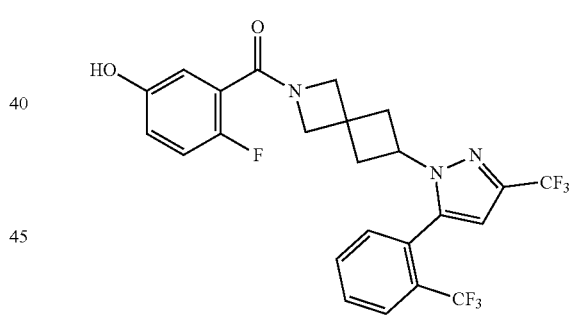

or a pharmaceutically acceptable salt thereof.

32. The compound of embodiment 17, wherein W is —C(O)N($R_{10}$)— and $R_{10}$ is methyl; and $R_{20}$ is methyl.

33. The compound of embodiment 32, wherein $R_{26}$ is hydrogen.

34. The compound of any one of embodiments 32-33, wherein $R_1$ is F.

35. The compound of embodiment 34, wherein $R_3$ is hydrogen.

36. The compound of embodiment 18, wherein W is —C(O)N($R_{10}$)— and $R_{10}$ is methyl; and $R_{20}$ is methyl.

37. The compound of embodiment 36, wherein $R_{26}$ is hydrogen.

38. The compound of any one of embodiments 36-37, wherein $R_5$ is —O—$R_{52}$; and $R_{52}$ is ($C_1$-$C_4$)alkyl.

39. The compound of embodiment 34, wherein $R_3$ is F.

40. The compound of any one of embodiments 1, 8, 9, 15, or 17, wherein W is A.

41. A compound of Formula (II-A), or a pharmaceutically acceptable salt thereof:

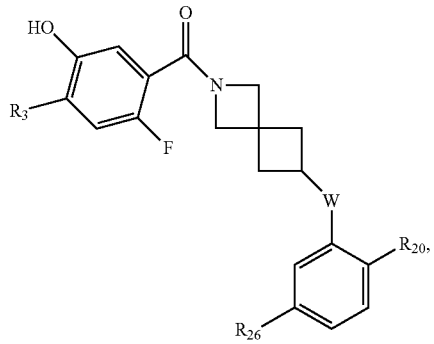

Formula (II-A)

wherein
  $R_3$ is hydrogen, methyl optionally substituted with one or more F, or F;
  W is a 5-member heteroaryl ring comprising at least one nitrogen heteroatom optionally substituted with one methyl optionally substituted with one or more F; or cyclopropyl;
  $R_{20}$ is methyl optionally substituted with one or more F, Cl or F;
  $R_{26}$ is hydrogen or F; and
  provided that the compound of Formula (II) is not (2-fluoro-5-hydroxyphenyl)(6-(3-methyl-1-(o-tolyl)-1H-pyrazol-5-yl)-2-azaspiro[3.3]heptan-2-yl)methanone.

42. A compound of Formula (III-A), or a pharmaceutically acceptable salt thereof,

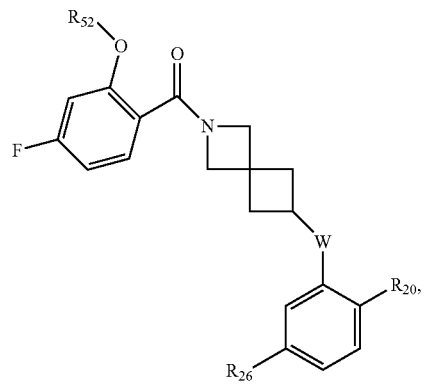

Formula (III-A)

wherein
  $R_{52}$ is cyclopropyl or ($C_1$-$C_4$) alkyl optionally substituted with one or more F;
  W is C(O)N($R_{10}$)— and $R_{10}$ is methyl; or W is a 5-member heteroaryl ring comprising at least one nitrogen heteroatom and optionally substituted with one methyl;
  $R_{20}$ is ($C_1$-$C_4$) alkyl; and
  $R_{26}$ is hydrogen or F.

43. The compound of embodiment 42, wherein $R_{52}$ is ethyl or methyl.

44. The compound of embodiment 42, wherein $R_{52}$ is cyclopropyl.

45. The compound of any one of embodiments 42-44, wherein $R_{20}$ is methyl.

46. The compound of any one of embodiments 42-44, wherein $R_{20}$ is —$CF_3$.

47. The compound of any one of embodiments 42-46, wherein $R_{26}$ is hydrogen.

48. The compound of any one of embodiments 1, 2, 3, 6-11, 15-19, or 41-47, wherein W is selected from the group consisting of A1, A2, A3, A4, A5, and A6,

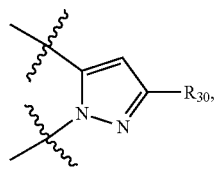

A1

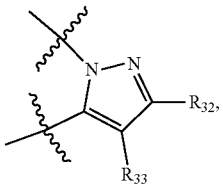

A2

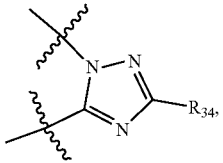

A3

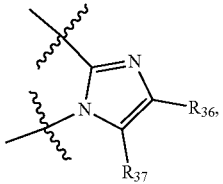

A4

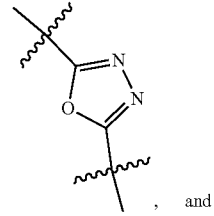

A5

, and

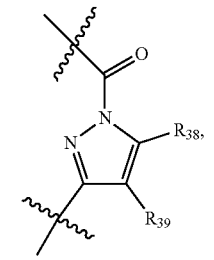

A6 and $R_{30}$, $R_{32}$, $R_{33}$, $R_{34}$, $R_{36}$, $R_{37}$, $R_{38}$ and $R_{39}$ are each independently hydrogen or methyl.

49. The compound of embodiment 48, wherein $R_{30}$, $R_{32}$, $R_{33}$, and $R_{34}$ are each independently methyl.

50. The compound of embodiment 49, wherein
   a. one of $R_3$ and $R_{37}$ is methyl and the other is hydrogen; and
   b. one of $R_{38}$ and $R_{39}$ is methyl and the other is hydrogen.

51. The compound of any one of embodiments 48-50, wherein W is selected from the group consisting of A1, A2, A3, A4, and A5.

52. The compound of any one of embodiments 1-19 or 32-52, wherein W is selected from the group consisting of:

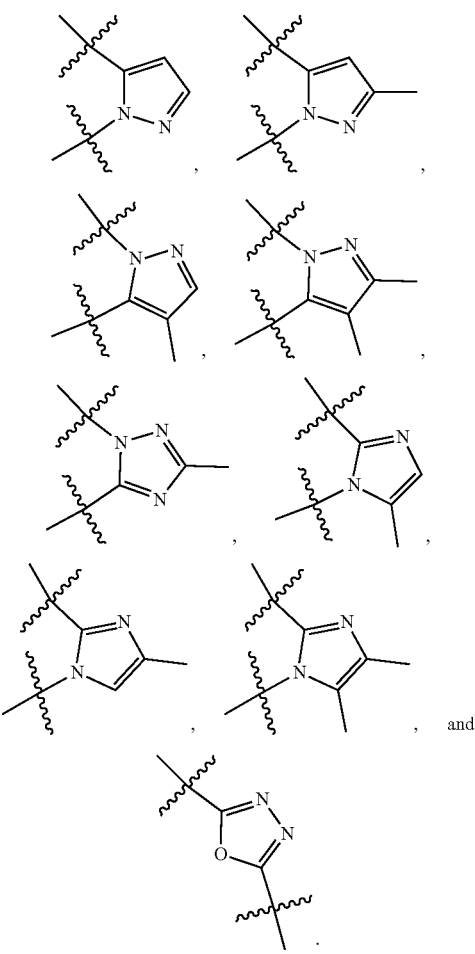

53. The compound of any one of embodiments 1-19 or 32-52, wherein W is selected group consisting of:

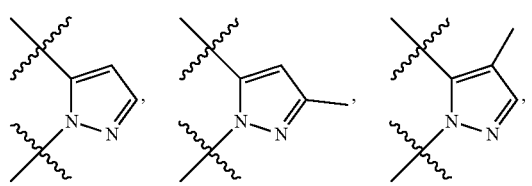

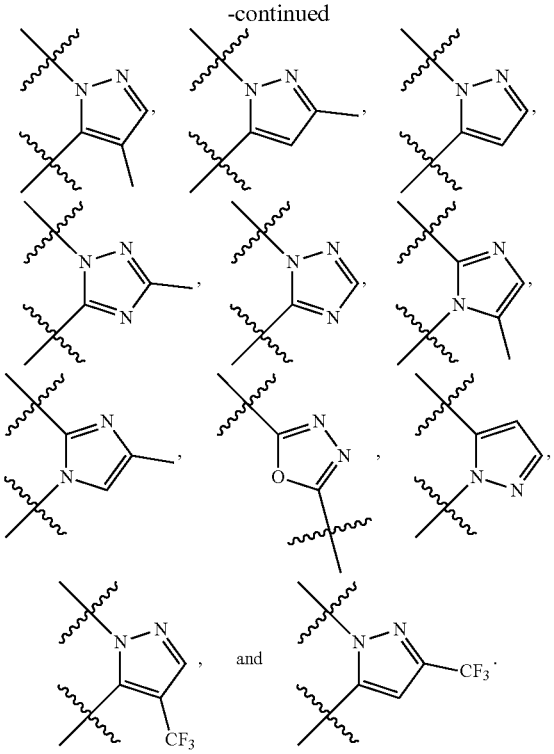

54. The compound of any one of embodiments 1-19 or 32-52, wherein W is

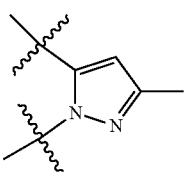

55. The compound of any one of embodiments 1-19 or 32-52, wherein W is

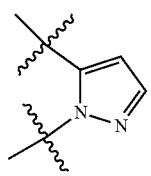

56. The compound of any one of embodiments 1-19 or 32-52, wherein W is

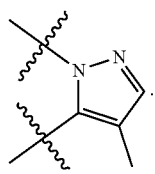

57. The compound of any one of embodiments 1-19 or 32-52, wherein W is

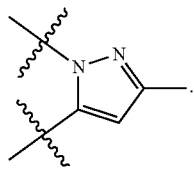 [SMILES: *c1cc(C)nn1*]

58. The compound of any one of embodiments 1-19 or 32-52, wherein W is

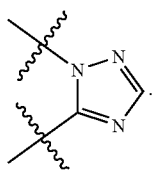 [SMILES: *c1ncnn1*]

59. The compound of any one of embodiments 1-19 or 32-52, wherein W is

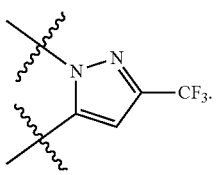 [SMILES: *c1cc(C(F)(F)F)nn1*]

60. The compound of any one of embodiments 1-19 or 32-52, wherein W is

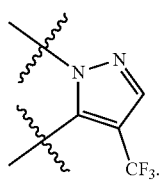

61. A Reversible Selective MAGL Inhibitor Compound that is not (2-fluoro-5-hydroxyphenyl)(6-(3-methyl-1-(o-tolyl)-1H-pyrazol-5-yl)-2-azaspiro[3.3]heptan-2-yl)methanone.

The Additional Embodiments include those listed below:

1. A compound selected from the group consisting of:
(2,4-difluoro-5-hydroxyphenyl){6-[3-methyl-1-(o-tolyl)-5-pyrazolyl]-2-aza-2-spiro[3.3]heptyl}methanone (Compound 126);
4-hydroxy-2-({6-[3-methyl-1-(o-tolyl)-5-pyrazolyl]-2-aza-2-spiro[3.3]heptyl}carbonyl)benzonitrile (Compound 128);
(2-fluoro-5-hydroxyphenyl)(6-[1-(5-fluoro-2-tolyl)-3-methyl-5-pyrazolyl]-2-aza-2-spiro[3.3]heptyl)methanone (Compound 365);
(2-fluoro-5-hydroxyphenyl)(6-(3-methyl-1-[o-(trifluoromethyl)phenyl]-5-pyrazolyl]-2-aza-2-spiro[3.3]heptyl)methanone (Compound 366);
(2-fluoro-5-hydroxyphenyl)(6-(5-(trifluoromethyl)-3-[o-(trifluoromethyl)phenyl]-1-pyrazolyl)-2-aza-2-spiro[3.3]heptyl)methanone (Compound 414);
(2-fluoro-5-hydroxyphenyl){6-[3-(o-fluorophenyl)-4-methyl-1-pyrazolyl]-2-aza-2-spiro[3.3]heptyl}methanone (Compound 417);
(2-fluoro-5-hydroxyphenyl){6-[4-methyl-3-(o-tolyl)-1-pyrazolyl]-2-aza-2-spiro[3.3]heptyl}methanone (Compound 440);
(2-fluoro-5-hydroxyphenyl)(6-{4-methyl-3-[o-(trifluoromethyl)phenyl]-1-pyrazolyl}-2-aza-2-spiro[3.3]heptyl)methanone (Compound 444);
(2-fluoro-5-hydroxyphenyl){6-[3-(5-fluoro-2-tolyl)-5-methyl-1-pyrazolyl]-2-aza-2-spiro[3.3]heptyl}methanone (Compound 446);
(2-fluoro-5-hydroxyphenyl){6-[3-(o-fluorophenyl)-4-(trifluoromethyl)-1-pyrazolyl]-2-aza-2-spiro[3.3]heptyl}methanone (Compound 473);
(2-fluoro-5-hydroxyphenyl){6-[3-(2-fluoro-5-tolyl)-4-(trifluoromethyl)-1-pyrazolyl]-2-aza-2-spiro[3.3]heptyl}methanone (Compound 475);
{6-[3-(2,5-difluorophenyl)-4-methyl-1-pyrazolyl]-2-aza-2-spiro[3.3]heptyl}(2-fluoro-5-hydroxyphenyl)methanone (Compound 477);
(6-{4-cyclopropyl-3-[o-(trifluoromethyl)phenyl]-1-pyrazolyl}-2-aza-2-spiro[3.3]heptyl)(2-fluoro-5-hydroxyphenyl)methanone (Compound 488);
{6-[5-cyclopropyl-3-(5-fluoro-2-tolyl)-1-pyrazolyl]-2-aza-2-spiro[3.3]heptyl}(2-fluoro-5-hydroxyphenyl)methanone (Compound 491);
{6-[4-cyclopropyl-3-(o-fluorophenyl)-1-pyrazolyl]-2-aza-2-spiro[3.3]heptyl}(2-fluoro-5-hydroxyphenyl)methanone (Compound 493);
(6-[3-(2-chloro-5-fluorophenyl)-4-methyl-1-pyrazoyl]-2-aza-2-spiro[3.3]heptyl}(2-fluoro-5-hydroxyphenyl)methanone (Compound 520);
(2-fluoro-5-hydroxyphenyl)(6-(3-[o-(trifluoromethyl)phenyl]-1-pyrazolyl)-2-aza-2-spiro[3.3]heptyl)methanone (Compound 525);
(2-ethoxy-4-fluorophenyl){6-[3-methyl-1-(o-tolyl)-5-pyrazolyl]-2-aza-2-spiro[3.3]heptyl}methanone (Compound 146); and
[4-fluoro-2-(2,2,2-trifluoroethoxy)phenyl]{6-[3-methyl-1-(o-tolyl)-5-pyrazolyl]-2-aza-2-spiro[3.3]heptyl}methanone (Compound 178), or a pharmaceutically acceptable salt thereof.

2. The compound of embodiment 1, wherein the compound is (2,4-difluoro-5-hydroxyphenyl){6-[3-methyl-1-(o-tolyl)-5-pyrazolyl]-2-aza-2-spiro[3.3]heptyl}methanone (Compound 126), or a pharmaceutically acceptable salt thereof.

3. The compound of embodiment 1, wherein the compound is 4-hydroxy-2-({6-[3-methyl-1-(o-tolyl)-5-pyrazolyl]-2-aza-2-spiro[3.3]heptyl}carbonyl)benzonitrile (Compound 128), or a pharmaceutically acceptable salt thereof.

4. The compound of embodiment 1, wherein the compound is (2-fluoro-5-hydroxyphenyl){6-[1-(5-fluoro-2-tolyl)-3-methyl-5-pyrazolyl]-2-aza-2-spiro[3.3]heptyl}methanone (Compound 365), or a pharmaceutically acceptable salt thereof.

5. The compound of embodiment 1, wherein the compound is (2-fluoro-5-hydroxyphenyl)(6-{3-methyl-1-[o-(trifluoromethyl)phenyl]-5-pyrazolyl}-2-aza-2-spiro[3.3]heptyl)methanone (Compound 366), or a pharmaceutically acceptable salt thereof.

6. The compound of embodiment 1, wherein the compound is (2-fluoro-5-hydroxyphenyl)(6-{5-(trifluoromethyl)-3-[o-(trifluoromethyl)phenyl]-1-pyrazolyl}-2-aza-2-spiro[3.3]heptyl)methanone (Compound 414), or a pharmaceutically acceptable salt thereof.
7. The compound of embodiment 1, wherein the compound is (2-fluoro-5-hydroxyphenyl){6-[3-(o-fluorophenyl)-4-methyl-1-pyrazolyl]-2-aza-2-spiro[3.3]heptyl}methanone (Compound 417), or a pharmaceutically acceptable salt thereof.
8. The compound of embodiment 1, wherein the compound is (2-fluoro-5-hydroxyphenyl){6-[4-methyl-3-(o-tolyl)-1-pyrazolyl]-2-aza-2-spiro[3.3]heptyl)methanone (Compound 440), or a pharmaceutically acceptable salt thereof.
9. The compound of embodiment 1, wherein the compound is (2-fluoro-5-hydroxyphenyl)(6-(4-methyl-3-[o-(trifluoromethyl)phenyl]-1-pyrazolyl-2-aza-2-spiro[3.3]heptyl)methanone (Compound 444), or a pharmaceutically acceptable salt thereof.
10. The compound of embodiment 1, wherein the compound is (2-fluoro-5-hydroxyphenyl)(6-[3-(5-fluoro-2-tolyl)-5-methyl-1-pyrazolyl]-2-aza-2-spiro[3.3]heptyl}methanone (Compound 446), or a pharmaceutically acceptable salt thereof.
11. The compound of embodiment 1, wherein the compound is (2-fluoro-5-hydroxyphenyl)(6-[3-(o-fluorophenyl)-4-(trifluoromethyl)-1-pyrazolyl]-2-aza-2-spiro[3.3]heptyl)methanone (Compound 473), or a pharmaceutically acceptable salt thereof.
12. The compound of embodiment 1, wherein the compound is (2-fluoro-5-hydroxyphenyl){6-[3-(2-fluoro-5-tolyl)-4-(trifluoromethyl)-1-pyrazolyl]-2-aza-2-spiro[3.3]heptyl}methanone (Compound 475), or a pharmaceutically acceptable salt thereof.
13. The compound of embodiment 1, wherein the compound is {6-[3-(2,5-difluorophenyl)-4-methyl-1-pyrazolyl]-2-aza-2-spiro[3.3]heptyl}(2-fluoro-5-hydroxyphenyl)methanone (Compound 477), or a pharmaceutically acceptable salt thereof.
14. The compound of embodiment 1, wherein the compound is (6-{4-cyclopropyl-3-[o-(trifluoromethyl)phenyl]-1-pyrazolyl}-2-aza-2-spiro[3.3]heptyl)(2-fluoro-5-hydroxyphenyl)methanone (Compound 488), or a pharmaceutically acceptable salt thereof.
15. The compound of embodiment 1, wherein the compound is {6-[5-cyclopropyl-3-(5-fluoro-2-tolyl)-1-pyrazolyl]-2-aza-2-spiro[3.3]heptyl}(2-fluoro-5-hydroxyphenyl)methanone (Compound 491), or a pharmaceutically acceptable salt thereof.
16. The compound of embodiment 1, wherein the compound is {6-[4-cyclopropyl-3-(o-fluorophenyl)-1-pyrazolyl]-2-aza-2-spiro[3.3]heptyl}(2-fluoro-5-hydroxyphenyl)methanone (Compound 493), or a pharmaceutically acceptable salt thereof.
17. The compound of embodiment 1, wherein the compound is {6-[3-(2-chloro-5-fluorophenyl)-4-methyl-1-pyrazolyl]-2-aza-2-spiro[3.3]heptyl}(2-fluoro-5-hydroxyphenyl)methanone (Compound 520), or a pharmaceutically acceptable salt thereof.
18. The compound of embodiment 1, wherein the compound is (2-fluoro-5-hydroxyphenyl)(6-{3-[o-(trifluoromethyl)phenyl]-1-pyrazolyl}-2-aza-2-spiro[3.3]heptyl)methanone (Compound 525), or a pharmaceutically acceptable salt thereof.
19. The compound of embodiment 1, wherein the compound is (2-ethoxy-4-fluorophenyl){6-[3-methyl-1-(o-tolyl)-5-pyrazolyl]-2-aza-2-spiro[3.3]heptyl}methanone (Compound 146), or a pharmaceutically acceptable salt thereof.
20. The compound of embodiment 1, wherein the compound is [4-fluoro-2-(2,2,2-trifluoroethoxy)phenyl]{6-[3-methyl-1-(o-tolyl)-5-pyrazolyl]-2-aza-2-spiro[3.3]heptyl}methanone (Compound 178), or a pharmaceutically acceptable salt thereof.

Additional Embodiments include those listed below:
1. A compound of Formula (I) or a pharmaceutically acceptable salt thereof, Formula (I)

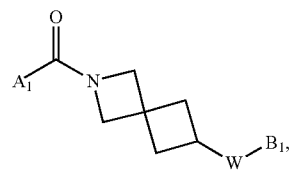

wherein:
$A_1$ is

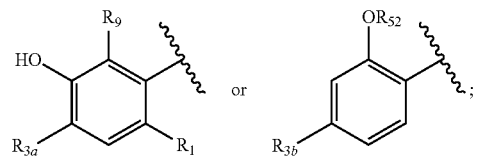

$R_1$ is hydrogen, halogen, or cyano;
$R_{3a}$ and $R_5$ are each independently hydrogen, halogen, or lower alkyl;
$R_{52}$ is lower alkyl, lower cycloalkyl or lower haloalkyl;
$R_{3b}$ is halogen;
W is a diazole optionally substituted with lower alkyl, lower cycloalkyl, or lower haloalkyl;
$B_1$ is

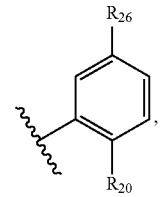

$R_{20}$ is hydrogen, halogen, lower alkyl, or lower haloalkyl; and
$R_{26}$ is hydrogen, or halogen;
provided the compound is not (2-fluoro-5-hydroxyphenyl)(6-(3-methyl-1-(o-tolyl)-1H-pyrazol-5-yl)-2-azaspiro[3.3]heptan-2-yl)methanone.

2. The compound of embodiment 1, wherein
$R_1$ is hydrogen, fluoro, or cyano;
$R_{3a}$ and $R_5$ are each independently hydrogen, halogen, or methyl;
$R_{52}$ is lower alkyl, cyclopropyl or lower haloalkyl;
$R_{3b}$ is fluoro;
W is a diazole optionally substituted with one of methyl, cyclopropyl, or $CF_3$;

$R_{20}$ is fluoro or chloro, methyl, or $CF_3$; and $R_{26}$ is hydrogen, fluoro or chloro.

3. The compound of embodiment 2, wherein W is selected from the group consisting of:

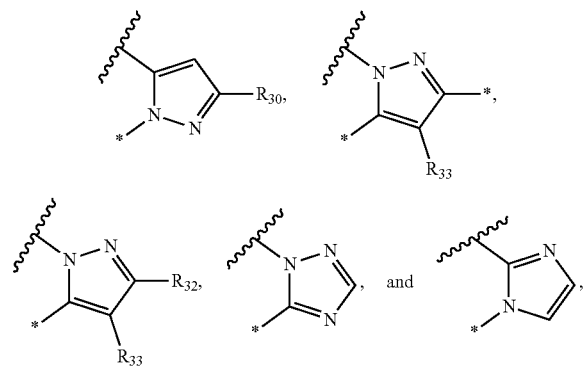

wherein * indicates a covalent bond to $B_1$; and $R_{30}$, $R_{31}$, $R_{32}$ and $R_{33}$ are each independently hydrogen, lower alkyl, lower haloalkyl, or lower cycloalkyl, provided that at least one of $R_{31}$ and $R_{33}$ and at least one of $R_{32}$ and $R_{33}$ is not hydrogen.

4. The compound of embodiment 3, wherein $R_{30}$, $R_{31}$, $R_{32}$ and $R_{33}$ are each independently hydrogen, methyl, $CF_3$, or cyclopropyl, provided that at least one of $R_{31}$ and $R_3$ and at least one of $R_{32}$ and $R_{33}$ is not hydrogen.

5. The compound of embodiment 4, wherein W is selected from the group consisting of:

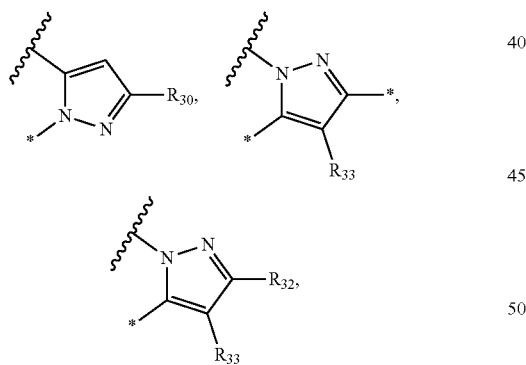

wherein * indicates a covalent bond to $B_1$.

6. The compound of embodiment 5, wherein W is

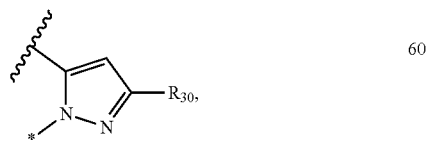

wherein * indicates a covalent bond to $B_1$, and $R_{30}$ is methyl.

7. The compound of embodiment 5, wherein W is

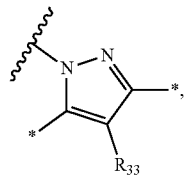

wherein * indicates a covalent bond to $B_1$, and $R_{31}$ and $R_{33}$ are each independently hydrogen, methyl, $CF_3$, or cyclopropyl, provided that one of $R_{31}$ and $R_{33}$ is hydrogen.

8. The compound of embodiment 5, wherein W is

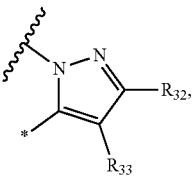

wherein * indicates a covalent bond to $B_1$, and $R_{32}$ and $R_{33}$ are each independently hydrogen, methyl, $CF_3$, or cyclopropyl, provided that one of $R_{32}$ and $R_{33}$ is hydrogen.

9. The compound of any one of embodiments 4-8, wherein $A_1$ is

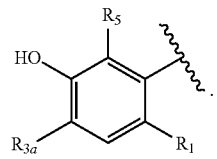

10. The compound of embodiment 9, wherein $R_5$ is hydrogen.

11. The compound of embodiment 10, wherein $R_1$ is fluoro.

12. The compound of embodiment 11, wherein $R_{3a}$ is hydrogen, fluoro, or methyl.

13. The compound of embodiment 12, wherein $R_{3a}$ is hydrogen.

14. The compound of embodiment 13, wherein $R_{20}$ is methyl, and $R_{26}$ is hydrogen or fluoro; or $R_{20}$ is chloro, fluoro or $CF_3$, and $R_{26}$ is hydrogen.

15. The compound of any one of embodiments 4-8, wherein $A_1$ is

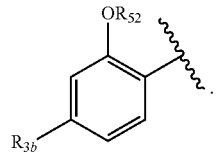

16. The compound of embodiment 15, wherein $R_{52}$ is lower alkyl optionally substituted with one or more fluoro and cyclopropyl.

17. The compound of embodiment 16, wherein $R_{3b}$ is fluoro.

18. The compound of embodiment 17, wherein

R$_{20}$ is methyl, and R$_{26}$ is hydrogen or fluoro; or

R$_{20}$ is fluoro or CF$_3$, and R$_{26}$ is hydrogen.

19. The compound of embodiment 1, wherein the compound is

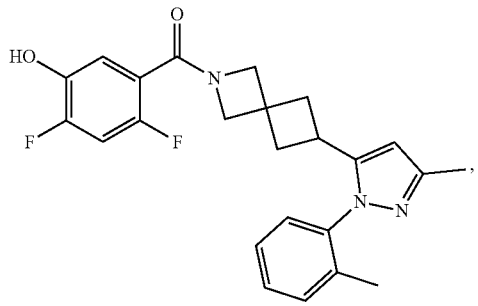 [SMILES: Cc1cc(C2CC3(C2)CN(C(=O)c2cc(O)c(F)cc2F)C3)n(-c2ccccc2C)n1]

or a pharmaceutically acceptable salt thereof.

20. The compound of embodiment 1, wherein the compound is

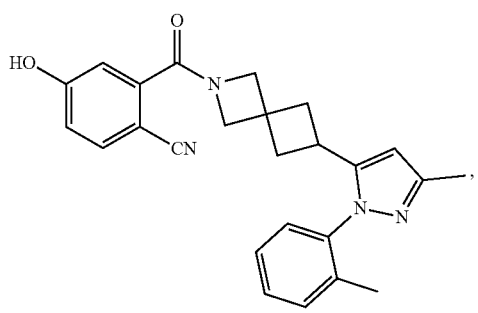 [SMILES: Cc1cc(C2CC3(C2)CN(C(=O)c2cc(O)ccc2C#N)C3)n(-c2ccccc2C)n1]

or a pharmaceutically acceptable salt thereof.

21. The compound of embodiment 1, wherein the compound is

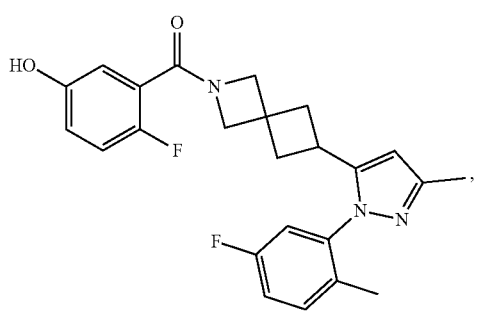 [SMILES: Cc1cc(C2CC3(C2)CN(C(=O)c2cc(O)ccc2F)C3)n(-c2cc(F)ccc2C)n1]

or a pharmaceutically acceptable salt thereof.

22. The compound of embodiment 1, wherein the compound is

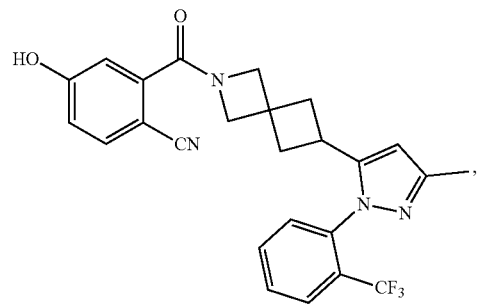 [SMILES: Cc1cc(C2CC3(C2)CN(C(=O)c2cc(O)ccc2C#N)C3)n(-c2ccccc2C(F)(F)F)n1]

or a pharmaceutically acceptable salt thereof.

23. The compound of embodiment 1, wherein the compound is

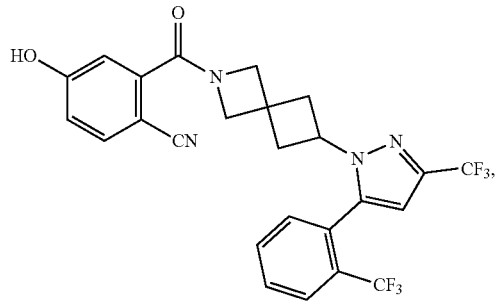 [SMILES: N#Cc1ccc(O)cc1C(=O)N1CC2(CC(n3nc(C(F)(F)F)cc3-c3ccccc3C(F)(F)F)C2)C1]

or a pharmaceutically acceptable salt thereof.

24. The compound of embodiment 1, wherein the compound is

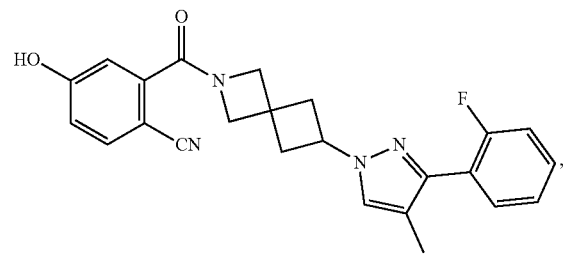 [SMILES: Cc1cn(C2CC3(C2)CN(C(=O)c2cc(O)ccc2C#N)C3)nc1-c1ccccc1F]

or a pharmaceutically acceptable salt thereof.

25. The compound of embodiment 1, wherein the compound is,

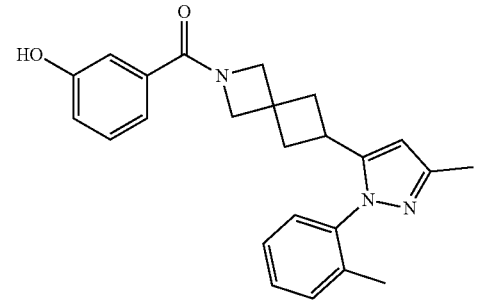 [SMILES: Cc1cc(C2CC3(C2)CN(C(=O)c2cccc(O)c2)C3)n(-c2ccccc2C)n1]

or a pharmaceutically acceptable salt thereof.

26. The compound of embodiment 1, wherein the compound is

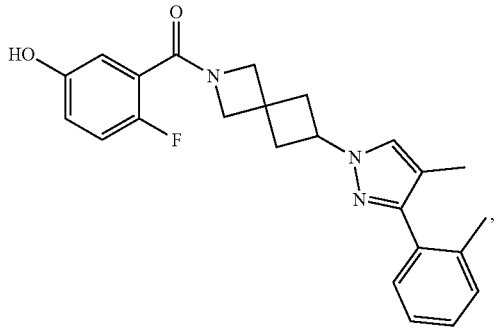 [SMILES: Cc1ccccc1-c1nn(C2CC3(C2)CN(C(=O)c2cc(O)ccc2F)C3)cc1C]

or a pharmaceutically acceptable salt thereof.

27. The compound of embodiment 1, wherein the compound is

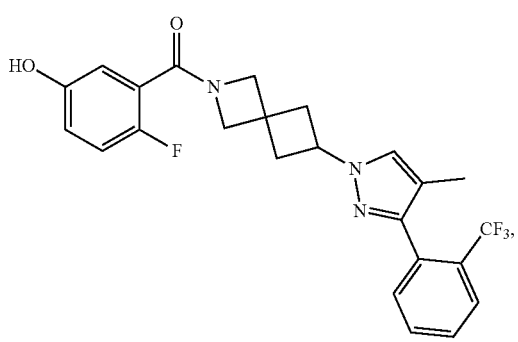 [SMILES: Cc1cn(C2CC3(C2)CN(C(=O)c2cc(O)ccc2F)C3)nc1-c1ccccc1C(F)(F)F]

or a pharmaceutically acceptable salt thereof.

28. The compound of embodiment 1, wherein the compound is

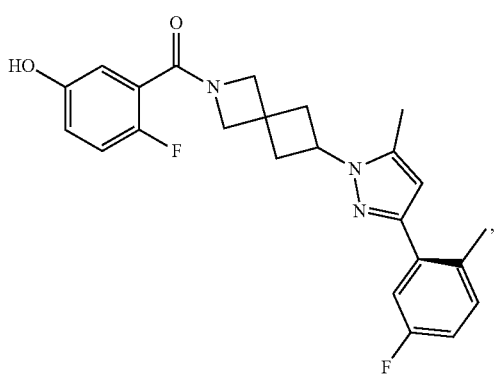

or a pharmaceutically acceptable salt thereof.

29. The compound of embodiment 1, wherein the compound is

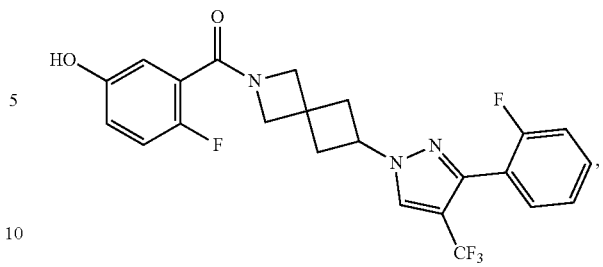

or a pharmaceutically acceptable salt thereof

30. The compound of embodiment 1, wherein the compound is

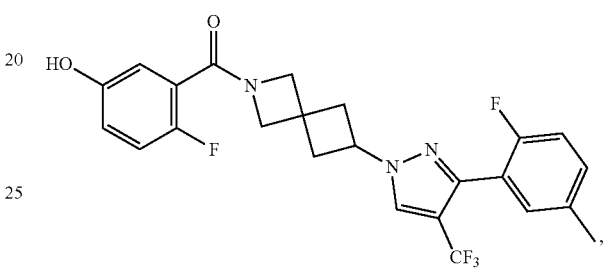

or a pharmaceutically acceptable salt thereof.

31. The compound of embodiment 1, wherein the compound is

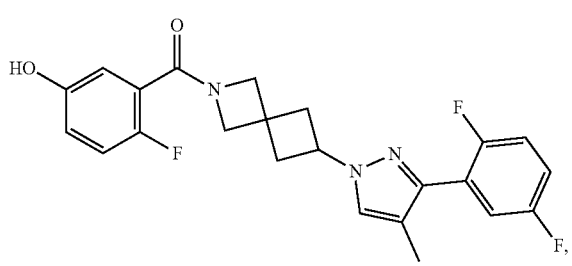 [SMILES: Cc1cn(C2CC3(C2)CN(C(=O)c2cc(O)ccc2F)C3)nc1-c1cc(F)ccc1F]

or a pharmaceutically acceptable salt thereof.

32. The compound of embodiment 1, wherein the compound is

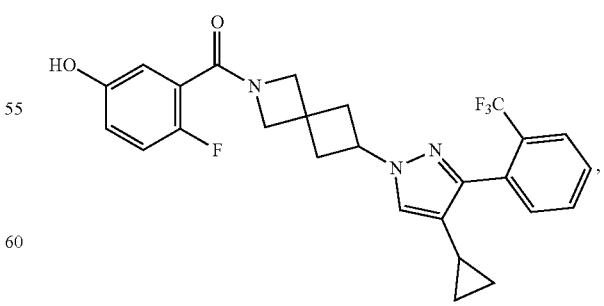

or a pharmaceutically acceptable salt thereof.

33. The compound of embodiment 1, wherein the compound is

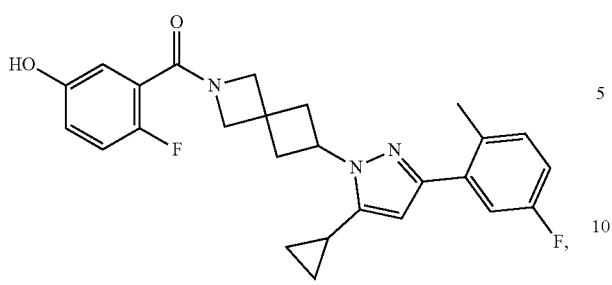

or a pharmaceutically acceptable salt thereof.

34. The compound of embodiment 1, wherein the compound is

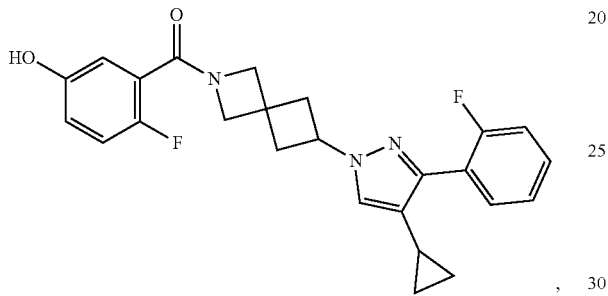

or a pharmaceutically acceptable salt thereof.

35. The compound of embodiment 1, wherein the compound is

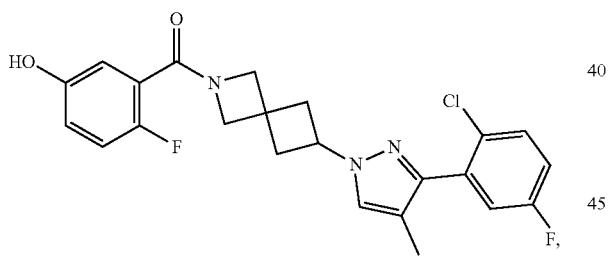

or a pharmaceutically acceptable salt thereof.

36. The compound of embodiment 1, wherein the compound is or a pharmaceutically acceptable salt thereof.

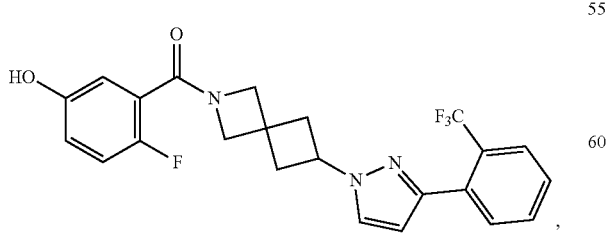

37. The compound of embodiment 1, wherein the compound is

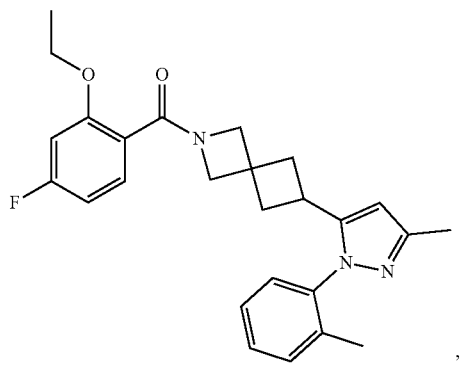 [SMILES: CCOc1cc(F)ccc1C(=O)N1CC2(CC(c3cc(C)nn3-c3ccccc3C)C2)C1]

or a pharmaceutically acceptable salt thereof.

38. The compound of embodiment 1, wherein the compound is

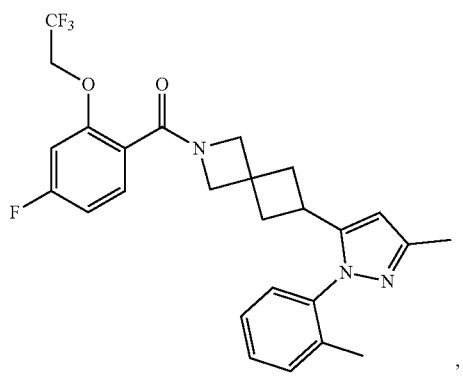 [SMILES: Cc1cc(C2CC3(C2)CN(C(=O)c2ccc(F)cc2OCC(F)(F)F)C3)n(-c2ccccc2C)n1]

or a pharmaceutically acceptable salt thereof

39. The compound of embodiment 1, wherein the compound is

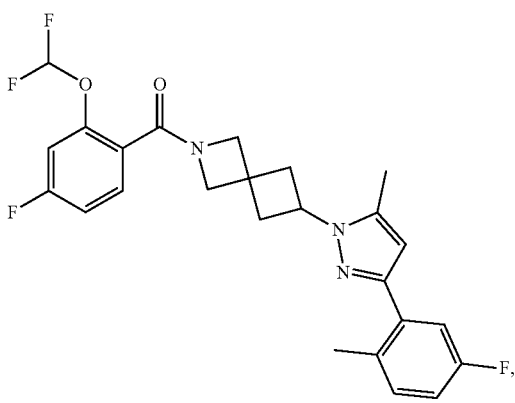 [SMILES: Cc1ccc(F)cc1-c1cc(C)n(C2CC3(C2)CN(C(=O)c2ccc(F)cc2OC(F)F)C3)n1]

or a pharmaceutically acceptable salt thereof.

40. The compound of embodiment 1, wherein the compound is

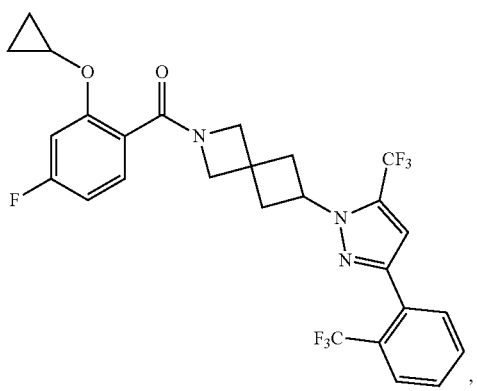 [SMILES: O=C(c1ccc(F)cc1OC1CC1)N1CC2(CC(n3nc(-c4ccccc4C(F)(F)F)cc3C(F)(F)F)C2)C1]

or a pharmaceutically acceptable salt thereof.

41. The compound of embodiment 1, wherein the compound is

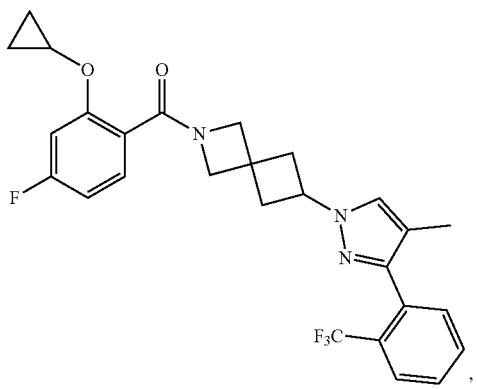 [SMILES: Cc1cn(C2CC3(C2)CN(C(=O)c2ccc(F)cc2OC2CC2)C3)nc1-c1ccccc1C(F)(F)F]

or a pharmaceutically acceptable salt thereof.

42. The compound of embodiment 1, wherein the compound is

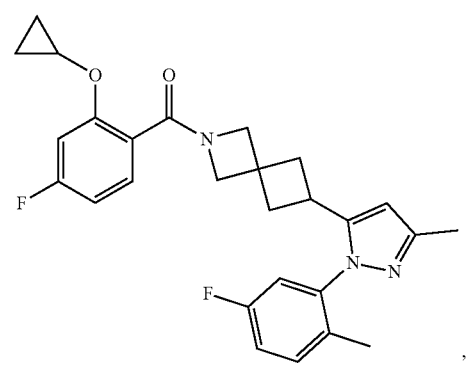 [SMILES: Cc1cc(C2CC3(C2)CN(C(=O)c2ccc(F)cc2OC2CC2)C3)n(-c2cc(F)ccc2C)n1]

or a pharmaceutically acceptable salt thereof.

43. The compound of embodiment 1, wherein the compound is

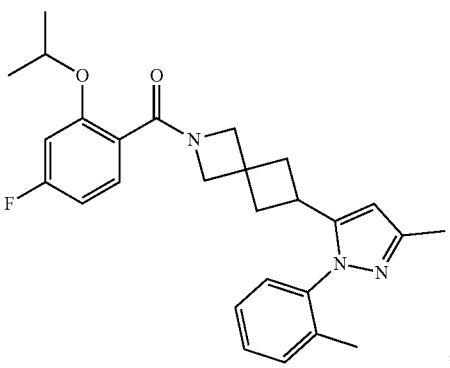

or a pharmaceutically acceptable salt thereof.

44. A compound of Formula (II-B) or a pharmaceutically acceptable salt thereof:

Formula (II-B)

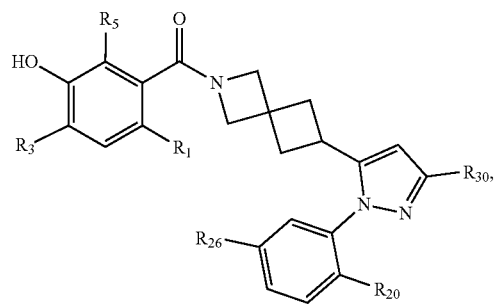

wherein $R_1$ is halogen or cyano;

$R_3$ is hydrogen, lower alkyl, or halogen;

$R_5$ is hydrogen, halogen or lower alkyl;

$R_{20}$ is halogen or lower alkyl optionally substituted with one or more halogen;

$R_{26}$ is halogen or hydrogen; and $R_{30}$ is hydrogen or lower alkyl optionally substituted with one or more halogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

45. The compound of embodiment 44, wherein $R_1$ is F or cyano;

$R_3$ is hydrogen, methyl, or F;

$R_5$ is hydrogen, F or methyl;

$R_{20}$ is F, methyl, or $CF_3$;

$R_{26}$ is hydrogen or F; and $R_{30}$ is hydrogen, methyl or $CF_3$, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

46. A compound of Formula (II-C) or a pharmaceutically acceptable salt thereof:

Formula (II-C)

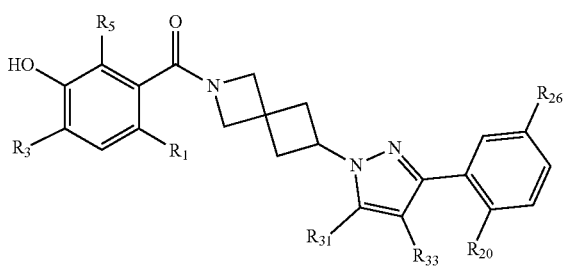

wherein
$R_1$ is halogen or cyano;
$R_3$ is hydrogen, lower alkyl, or halogen;
$R_5$ is hydrogen, halogen or lower alkyl;
$R_{20}$ is halogen or lower alkyl optionally substituted with one or more halogen;
$R_{26}$ is hydrogen or halogen; and
$R_{31}$ and $R_{33}$ are each independently hydrogen or lower alkyl optionally substituted with one or more halogen, provided that one of $R_3$ and $R_{33}$ is hydrogen.

47. The compound of embodiment 46, wherein
$R_1$ is F or cyano;
$R_3$ is hydrogen, methyl, or F;
$R_5$ is hydrogen, F or methyl;
$R_{20}$ is F, methyl, or $CF_3$;
$R_{26}$ is hydrogen or F; and
$R_{31}$ and $R_{33}$ are each independently hydrogen, methyl or $CF_3$.

48. A compound of Formula (II-D) or a pharmaceutically acceptable salt thereof:

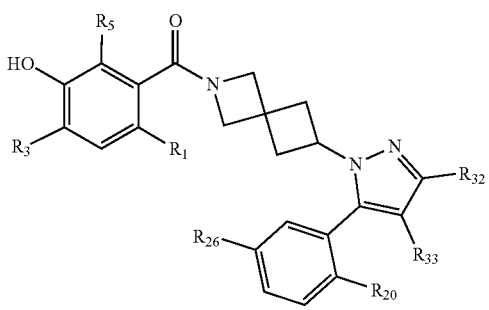

wherein
$R_1$ is halogen or cyano;
$R_3$ is hydrogen, lower alkyl, or halogen;
$R_5$ is hydrogen, halogen or lower alkyl;
$R_6$ is hydrogen;
$R_{20}$ is halogen or lower alkyl optionally substituted with one or more halogen;
$R_{26}$ is halogen or hydrogen; and
$R_{32}$ and $R_{33}$ are each independently hydrogen or lower alkyl optionally substituted with one or more halogen, provided that one of $R_{32}$ and $R_{33}$ is hydrogen.

49. The compound of embodiment 48, wherein
$R_1$ is F or cyano;
$R_3$ is hydrogen, F or methyl;
$R_5$ is hydrogen, F or methyl;
$R_{20}$ is F or methyl, or $CF_3$;
$R_{26}$ is hydrogen or F; and
$R_{32}$ and $R_{33}$ are each independently hydrogen, methyl or $CF_3$, provided that one of $R_{32}$ and $R_{33}$ is hydrogen.

50. A compound of Formula (III-B) or a pharmaceutically acceptable salt thereof:

Formula (III-B)

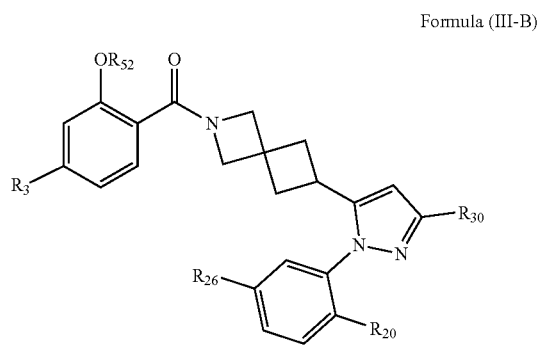

wherein
$R_3$ is halogen;
$R_{52}$ is lower alkyl or lower cycloalkyl, each optionally substituted with halogen,
$R_{30}$ is lower alkyl;
$R_{20}$ is lower alkyl; and
$R_{26}$ is hydrogen or halogen.

51. The compound of embodiment 50, wherein
$R_3$ is F;
$R_{32}$ is lower alkyl optionally substituted with one or more F or cyclopropyl;
$R_{30}$ is methyl;
$R_{20}$ is methyl; and
$R_{26}$ is hydrogen or F.

52. A compound of Formula (III-C) or a pharmaceutically acceptable salt thereof:

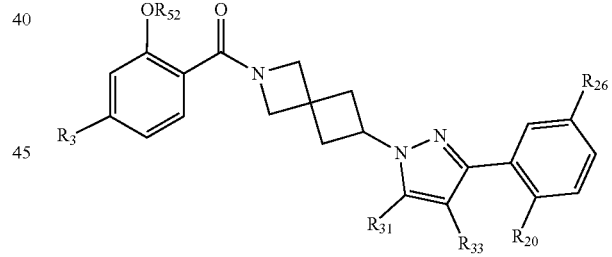

wherein
$R_3$ is halogen;
$R_{52}$ is lower alkyl or lower cycloalkyl, each optionally substituted with halogen,
$R_{31}$ and $R_{33}$ are each independently hydrogen or lower alkyl optionally substituted with one or more halogen, provided that one of $R_{31}$ and $R_{33}$ is hydrogen.
$R_{20}$ is lower alkyl optionally substituted with halogen; and
$R_{26}$ is hydrogen or halogen.

53. The compound of embodiment 52, wherein
$R_3$ is F;
$R_{52}$ is lower alkyl optionally substituted with one or more F; or cyclopropyl;
$R_{31}$ and $R_{33}$ are each independently hydrogen, methyl or $CF_3$, provided that one of $R_{31}$ and $R_{33}$ is hydrogen;
$R_{20}$ is methyl or $CF_3$; and
$R_{26}$ is hydrogen or F.

54. A compound of Formula (III-D) or a pharmaceutically acceptable salt thereof:

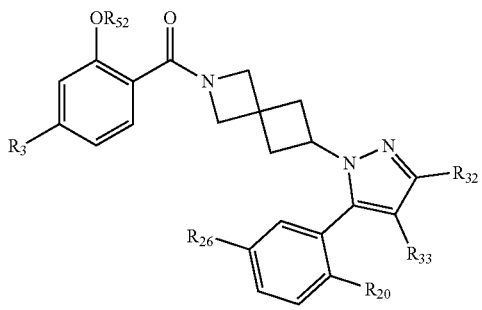

Formula (III-D)

wherein
$R_3$ is halogen;
$R_{52}$ is lower alkyl or lower cycloalkyl, each optionally substituted with halogen,
$R_{32}$ and $R_{33}$ are each independently hydrogen or lower alkyl optionally substituted with one or more halogen, provided that one of $R_{32}$ and $R_{33}$ is hydrogen.
$R_{20}$ is lower alkyl optionally substituted with halogen; and
$R_{26}$ is hydrogen or halogen.

55. The compound of embodiment 54, wherein
$R_3$ is F;
$R_{52}$ is lower alkyl optionally substituted with one or more F, or cyclopropyl;
$R_{32}$ and $R_{33}$ are each independently hydrogen, methyl or $CF_3$, provided that one of
$R_{32}$ and $R_{33}$ is hydrogen;
$R_{20}$ is methyl or $CF_3$; and
$R_{26}$ is hydrogen or F.

56. A compound of Formula (II), or a pharmaceutically acceptable salt thereof,

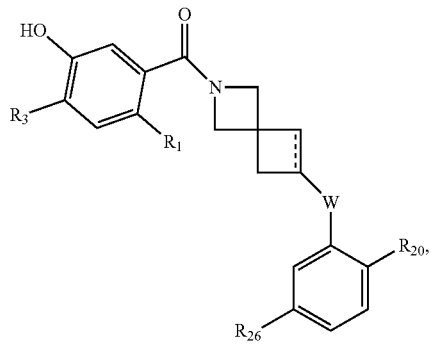

Formula (II)

wherein
the dashed line represents an optional double bond;
$R_1$ is halogen;
$R_3$ is hydrogen;
W is A;
A is a 5-member heteroaryl ring optionally substituted with one or more $R_{30}$;
$R_{20}$ is halogen or lower alkyl optionally substituted with one or more halogen;
$R_{30}$ is lower alkyl optionally substituted with one or more halogen; and
$R_{26}$ is halogen or hydrogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

57. A pharmaceutical composition comprising a compound of any one of embodiments 1-56, or a pharmaceutically acceptable salt thereof as the active pharmaceutical ingredient (API), provided the compound is not (2-fluoro-5-hydroxyphenyl)(6-(3-methyl-1-(o-tolyl)-1H-pyrazol-5-yl)-2-azaspiro[3.3]heptan-2-yl)methanone.

58. A method of inhibiting monoacylglycerol lipase (MAGL) in a subject comprising the step of administering to a subject in need thereof a therapeutically effective amount of a compound of any one of embodiments 1-56.

59. A method of reversibly inhibiting monoacylglycerol lipase (MAGL) comprising the step of contacting a compound of any one of embodiments 1-56 with a cell expressing MAGL.

Additional Embodiments include those listed below:

1. A compound of Formula (I) or a pharmaceutically acceptable salt thereof,

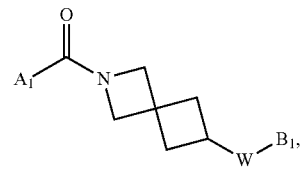

Formula (I)

wherein:
$A_1$ is

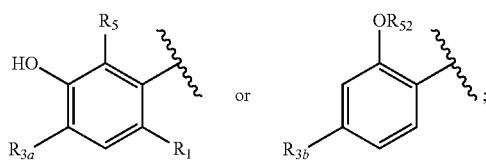

$R_1$ is halogen, hydrogen, or cyano;
$R_{3a}$ and $R_5$ are each independently hydrogen, halogen, or lower alkyl;
$R_{52}$ is lower alkyl, lower cycloalkyl or lower haloalkyl;
$R_{3b}$ is halogen;
W is a diazole optionally substituted with lower alkyl, lower cycloalkyl, or lower haloalkyl;

$B_1$ is

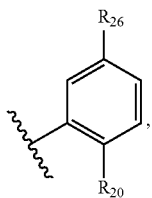

$R_{20}$ is halogen, hydrogen, lower alkyl, or lower haloalkyl; and
$R_{26}$ is hydrogen, or halogen;
provided the compound is not (2-fluoro-5-hydroxyphenyl)(6-(3-methyl-1-(o-tolyl)-1H-pyrazol-5-yl)-2-azaspiro[3.3]heptan-2-yl)methanone.

2. The compound of embodiment 1, wherein
$R_1$ is hydrogen, fluoro, or cyano;
$R_{3a}$ and $R_5$ are each independently hydrogen, halogen, or methyl;
$R_{52}$ is lower alkyl, cyclopropyl or lower haloalkyl;
$R_{3b}$ is fluoro;
W is a diazole optionally substituted with one of methyl, cyclopropyl, or $CF_3$;
$R_{20}$ is fluoro or chloro, methyl, or $CF_3$; and
$R_{26}$ is hydrogen, fluoro or chloro.

3. The compound of embodiment 2, wherein W is selected from the group consisting of:

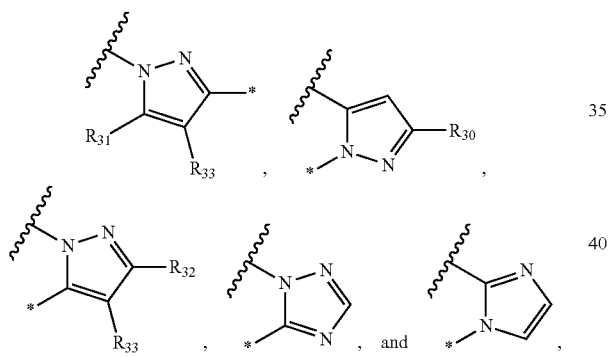

wherein * indicates a covalent bond to $B_1$; and
$R_{30}$, $R_{31}$, $R_{32}$ and $R_{33}$ are each independently hydrogen, lower alkyl, lower haloalkyl, or lower cycloalkyl, provided that at least one of $R_{31}$ and $R_{33}$ and at least one of $R_{32}$ and $R_{33}$ is not hydrogen.

4. The compound of embodiment 3, wherein $R_{30}$, $R_{31}$, $R_{32}$ and $R_{33}$ are each independently hydrogen, methyl, $CF_3$, or cyclopropyl, provided that at least one of $R_{31}$ and $R_{33}$ and at least one of $R_{32}$ and $R_{33}$ is not hydrogen.

5. The compound of embodiment 4, wherein W is selected from the group consisting of:

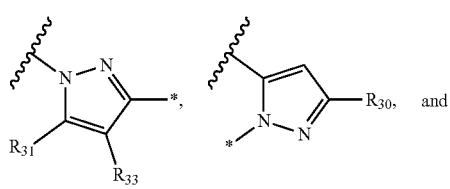

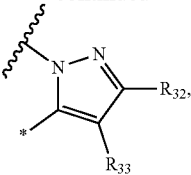

wherein * indicates a covalent bond to $B_1$.

6. The compound of embodiment 5, wherein W is

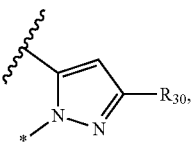

wherein * indicates a covalent bond to $B_1$, and $R_{30}$ is methyl.

7. The compound of embodiment 5, wherein W is

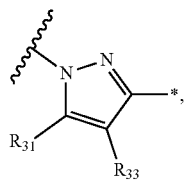

wherein * indicates a covalent bond to $B_1$, and $R_{31}$ and $R_{33}$ are each independently hydrogen, methyl, $CF_3$, or cyclopropyl, provided that one of $R_{31}$ and $R_{33}$ is hydrogen.

8. The compound of embodiment 5, wherein W is

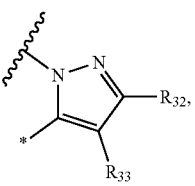

wherein * indicates a covalent bond to $B_1$, and $R_{32}$ and $R_{33}$ are each independently hydrogen, methyl, $CF_3$, or cyclopropyl, provided that one of $R_{32}$ and $R_{33}$ is hydrogen.

9. The compound of any one of embodiments 4-8, wherein $A_1$ is

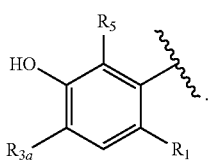

10. The compound of embodiment 9, wherein $R_5$ is hydrogen.
11. The compound of embodiment 10, wherein $R_1$ is fluoro.

12. The compound of embodiment 11, wherein $R_3$, is hydrogen, fluoro, or methyl.
13. The compound of embodiment 12, wherein $R_{3a}$ is hydrogen.
14. The compound of embodiment 13, wherein $R_{20}$ is methyl, and $R_{26}$ is hydrogen or fluoro; or $R_{20}$ is chloro, fluoro or $CF_3$, and $R_{26}$ is hydrogen.
15. The compound of any one of embodiments 4-8, wherein $A_1$ is

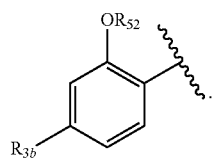

16. The compound of embodiment 15, wherein $R_{52}$ is lower alkyl optionally substituted with one or more fluoro and cyclopropyl.
17. The compound of embodiment 16, wherein $R_{3b}$ is fluoro.
18. The compound of embodiment 17, wherein
    $R_{20}$ is methyl, and $R_{26}$ is hydrogen or fluoro; or
    $R_{20}$ is fluoro or $CF_3$, and $R_{26}$ is hydrogen.
19. A compound of Formula (II-B) or a pharmaceutically acceptable salt thereof:

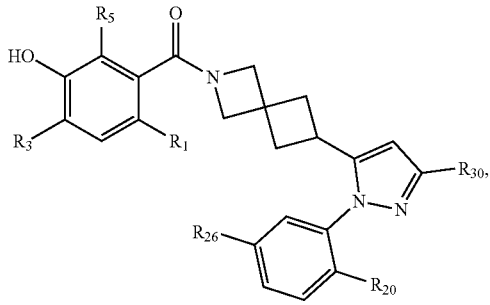

Formula (II-B)

wherein
  $R_1$ is halogen or cyano;
  $R_3$ is hydrogen, lower alkyl, or halogen;
  $R_5$ is hydrogen, halogen or lower alkyl;
  $R_{20}$ is halogen or lower alkyl optionally substituted with one or more halogen;
  $R_{26}$ is halogen or hydrogen; and
  $R_{30}$ is hydrogen or lower alkyl optionally substituted with one or more halogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.
20. The compound of embodiment 19, wherein
    $R_1$ is F or cyano;
    $R_3$ is hydrogen, methyl, or F;
    $R_5$ is hydrogen, F or methyl;
    $R_{20}$ is F, methyl, or $CF_3$;
    $R_{26}$ is hydrogen or F; and
    $R_{30}$ is hydrogen, methyl or $CF_3$, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

21. A compound of Formula (II-C) or a pharmaceutically acceptable salt thereof:

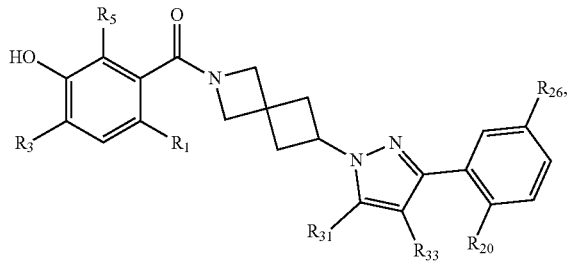

Formula (II-C)

wherein
  $R_1$ is halogen or cyano;
  $R_3$ is hydrogen, lower alkyl, or halogen;
  $R_5$ is hydrogen, halogen or lower alkyl;
  $R_{20}$ is halogen or lower alkyl optionally substituted with one or more halogen;
  $R_{26}$ is hydrogen or halogen; and
  $R_{31}$ and $R_{33}$ are each independently hydrogen or lower alkyl optionally substituted with one or more halogen, provided that one of $R_3$ and $R_1$; is hydrogen.
22. The compound of embodiment 21, wherein
    $R_1$ is F or cyano;
    $R_3$ is hydrogen, methyl, or F;
    $R_5$ is hydrogen, F or methyl;
    $R_{20}$ is F, methyl, or $CF_3$;
    $R_{26}$ is hydrogen or F; and
    $R_{31}$ and $R_{33}$ are each independently hydrogen, methyl or $CF_3$.
23. A compound of Formula (II-D) or a pharmaceutically acceptable salt thereof:

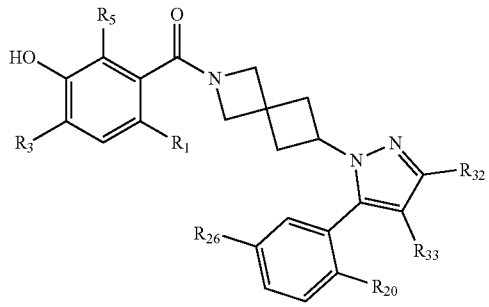

wherein
  $R_1$ is halogen or cyano;
  $R_3$ is hydrogen, lower alkyl, or halogen;
  $R_5$ is hydrogen, halogen or lower alkyl;
  $R_6$ is hydrogen;
  $R_{20}$ is halogen or lower alkyl optionally substituted with one or more halogen;
  $R_{26}$ is halogen or hydrogen; and
  $R_{32}$ and $R_{33}$ are each independently hydrogen or lower alkyl optionally substituted with one or more halogen, provided that one of $R_{32}$ and $R_{33}$ is hydrogen.
24. The compound of embodiment 23, wherein
    $R_1$ is F or cyano;
    $R_3$ is hydrogen, F or methyl;

$R_5$ is hydrogen, F or methyl;
$R_{20}$ is F or methyl, or $CF_3$;
$R_{26}$ is hydrogen or F; and
$R_{32}$ and $R_{33}$ are each independently hydrogen, methyl or, $CF_3$ provided that one of $R_{32}$ and $R_{33}$ is hydrogen.

25. A compound of Formula (III-B) or a pharmaceutically acceptable salt thereof:

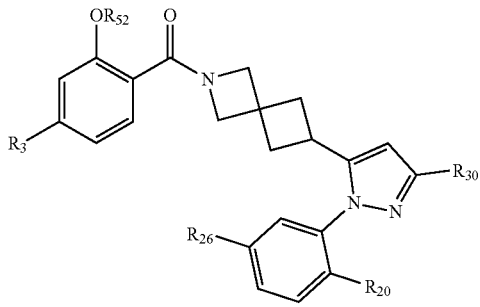

Formula (III-B)

wherein
$R_3$ is halogen;
$R_{52}$ is lower alkyl or lower cycloalkyl, each optionally substituted with halogen,
$R_{30}$ is lower alkyl;
$R_{20}$ is lower alkyl; and
$R_{26}$ is hydrogen or halogen.

26. The compound of embodiment 25, wherein
$R_3$ is F;
$R_{52}$ is lower alkyl optionally substituted with one or more F or cyclopropyl;
$R_{30}$ is methyl;
$R_{20}$ is methyl; and
$R_{26}$ is hydrogen or F.

27. A compound of Formula (III-C) or a pharmaceutically acceptable salt thereof:

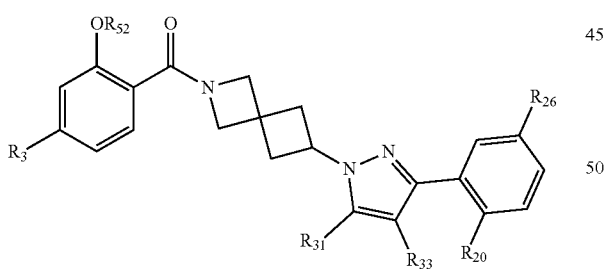

wherein
$R_3$ is halogen;
$R_{52}$ is lower alkyl or lower cycloalkyl, each optionally substituted with halogen,
$R_{31}$ and $R_{33}$ are each independently hydrogen or lower alkyl optionally substituted with one or more halogen, provided that one of $R_{31}$ and $R_{33}$ is hydrogen.
$R_{20}$ is lower alkyl optionally substituted with halogen; and
$R_{26}$ is hydrogen or halogen.

28. The compound of embodiment 27, wherein
$R_3$ is F;
$R_{52}$ is lower alkyl optionally substituted with one or more F; or cyclopropyl;
$R_{31}$ and $R_{33}$ are each independently hydrogen, methyl or $CF_3$, provided that one of
$R_{31}$ and $R_{33}$ is hydrogen;
$R_{20}$ is methyl or $CF_3$; and
$R_{26}$ is hydrogen or F.

29. A compound of Formula (III-D) or a pharmaceutically acceptable salt thereof:

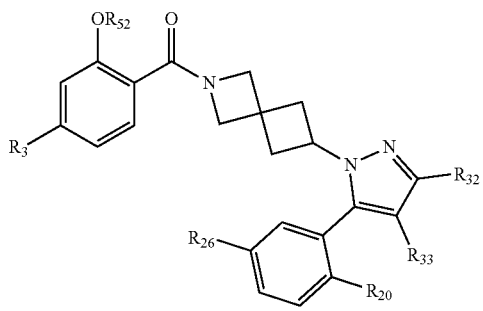

Formula (III-D)

wherein
$R_3$ is halogen;
$R_{52}$ is lower alkyl or lower cycloalkyl, each optionally substituted with halogen,
$R_{32}$ and $R_{33}$ are each independently hydrogen or lower alkyl optionally substituted with one or more halogen, provided that one of $R_{32}$ and $R_{33}$ is hydrogen.
$R_{20}$ is lower alkyl optionally substituted with halogen; and
$R_{26}$ is hydrogen or halogen.

30. The compound of embodiment 29, wherein
$R_3$ is F;
$R_{52}$ is lower alkyl optionally substituted with one or more F, or cyclopropyl;
$R_{32}$ and $R_{33}$ are each independently hydrogen, methyl or $CF_3$, provided that one of
$R_{32}$ and $R_{33}$ is hydrogen;
$R_{20}$ is methyl or $CF_3$; and
$R_{26}$ is hydrogen or F.

31. A compound of Formula (II), or a pharmaceutically acceptable salt thereof,

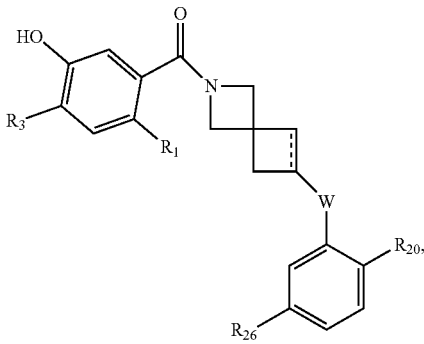

Formula (II)

wherein
the dashed line represents an optional double bond;
$R_1$ is halogen;
$R_3$ is hydrogen;
W is A;
A is a 5-member heteroaryl ring optionally substituted with one or more $R_{30}$;
$R_{20}$ is halogen or lower alkyl optionally substituted with one or more halogen;
$R_{30}$ is lower alkyl optionally substituted with one or more halogen; and
$R_{26}$ is halogen or hydrogen, provided the compound is not (2-fluoro-5-hydroxyphenyl)(6-(3-methyl-1-(o-tolyl)-1H-pyrazol-5-yl)-2-azaspiro[3.3]heptan-2-yl)methanone.

32. The compound of embodiment 1, wherein the compound is

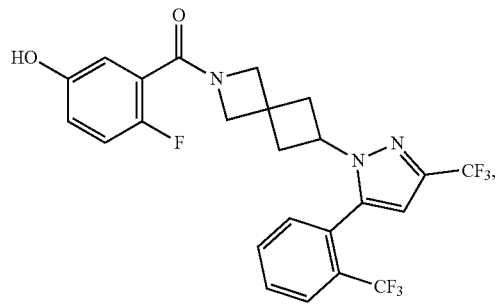 [SMILES: O=C(c1cc(O)ccc1F)N1CC2(CC(n3nc(C(F)(F)F)cc3-c3ccccc3C(F)(F)F)C2)C1]

or a pharmaceutically acceptable salt thereof.

33. The compound of embodiment 1, wherein the compound is

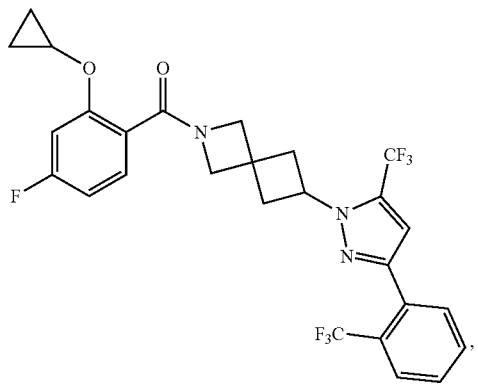 [SMILES: O=C(c1ccc(F)cc1OC1CC1)N1CC2(CC(n3nc(-c4ccccc4C(F)(F)F)cc3C(F)(F)F)C2)C1]

or a pharmaceutically acceptable salt thereof.

34. The compound of embodiment 1, wherein the compound is

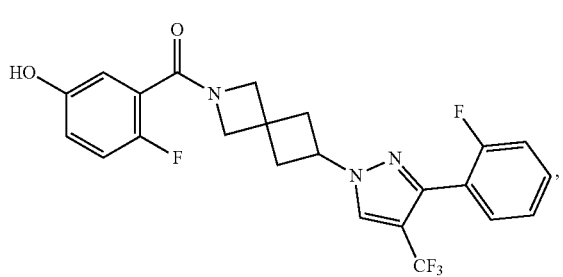

or a pharmaceutically acceptable salt thereof.

35. The compound of embodiment 1, wherein the compound is

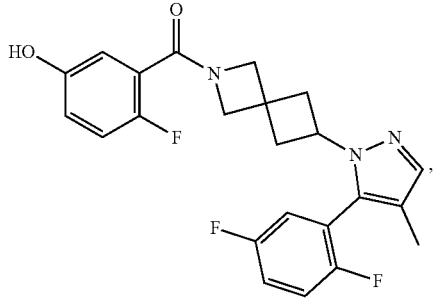 [SMILES: Cc1cnn(C2CC3(C2)CN(C(=O)c2cc(O)ccc2F)C3)c1-c1cc(F)ccc1F]

or a pharmaceutically acceptable salt thereof.

36. The compound of embodiment 1, wherein the compound is

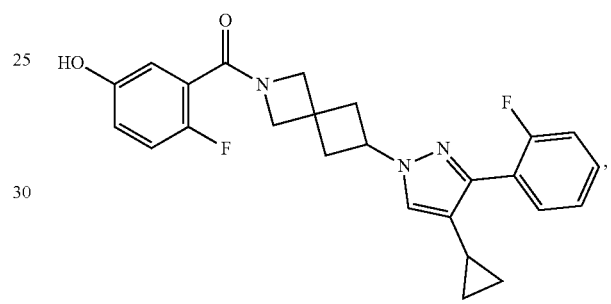

or a pharmaceutically acceptable salt thereof.

37. The compound of embodiment 1, wherein the compound is

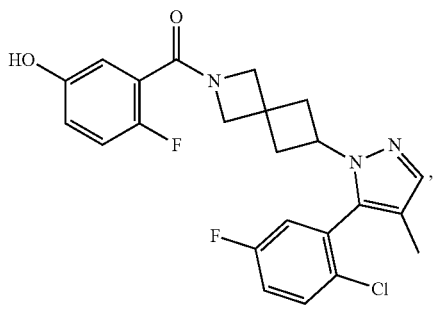 [SMILES: Cc1cnn(C2CC3(C2)CN(C(=O)c2cc(O)ccc2F)C3)c1-c1cc(F)ccc1Cl]

or a pharmaceutically acceptable salt thereof.

38. The compound of embodiment 1, wherein the compound is

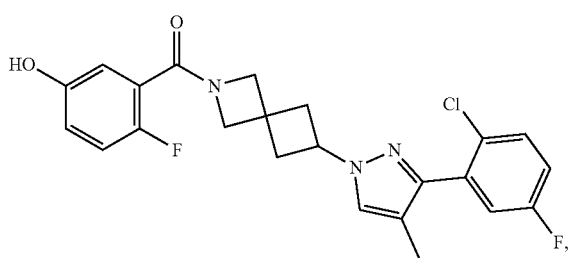 [SMILES: Cc1cn(C2CC3(C2)CN(C(=O)c2cc(O)ccc2F)C3)nc1-c1cc(F)ccc1Cl]

or a pharmaceutically acceptable salt thereof.

39. The compound of embodiment 1, wherein the compound is

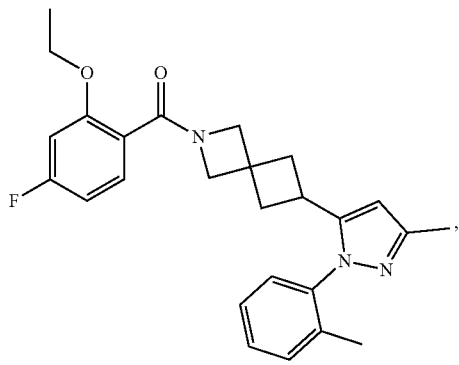 [SMILES: CCOc1cc(F)ccc1C(=O)N1CC2(CC(c3cc(C)nn3-c3ccccc3C)C2)C1]

or a pharmaceutically acceptable salt thereof.

40. The compound of embodiment 1, wherein the compound is

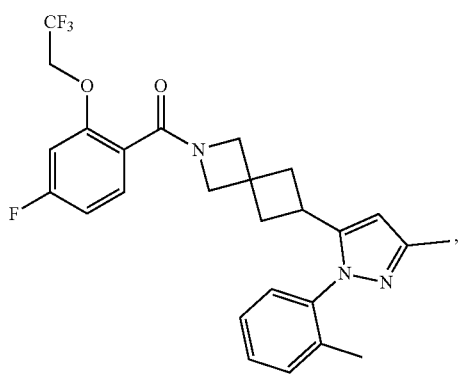 [SMILES: Cc1cc(C2CC3(C2)CN(C(=O)c2ccc(F)cc2OCC(F)(F)F)C3)n(-c2ccccc2C)n1]

or a pharmaceutically acceptable salt thereof.

41. A pharmaceutical composition comprising a compound of any one of embodiments 1-40, or a pharmaceutically acceptable salt thereof as the active pharmaceutical ingredient (API), provided the compound is not (2-fluoro-5-hydroxyphenyl)(6-(3-methyl-1-(o-tolyl)-1H-pyrazol-5-yl)-2-azaspiro[3.3]heptan-2-yl)methanone.

42. A method of inhibiting monoacylglycerol lipase (MAGL) in a subject comprising the step of administering to a subject in need thereof a therapeutically effective amount of a compound of any one of embodiments 1-40.

43. A method of reversibly inhibiting monoacylglycerol lipase (MAGL) comprising the step of contacting a compound of any one of embodiments 1-40 with a cell expressing MAGL.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

LC/MS . . .

Table of Abbreviations

Example 1: Preparation of Synthetic Intermediates

Intermediate-5: 2-(2-ethoxy-4-fluorobenzoyl)-2-azaspiro [3.3]heptane-6-carboxylic acid

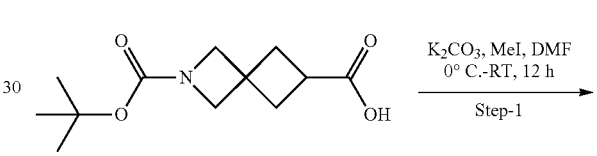

Int-1

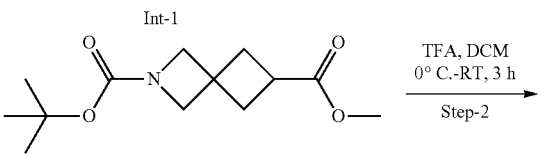

Int-2

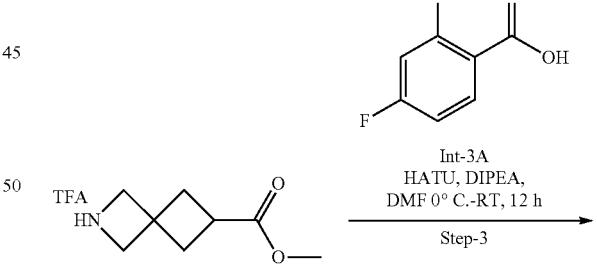

Int-3

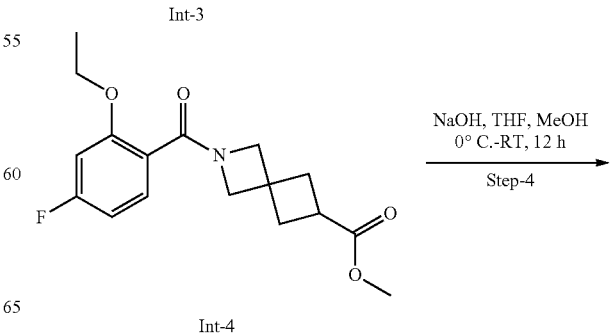

Int-4

-continued

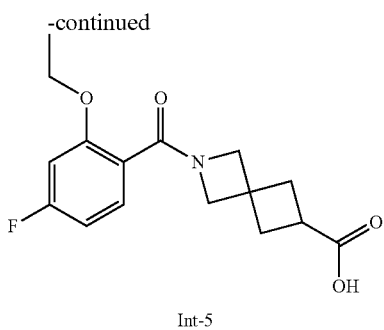

Int-5

Step-1: Synthesis of 2-(tert-butyl) 6-methyl 2-azaspiro [3.3] heptane-2,6-dicarboxylate (Int-2)

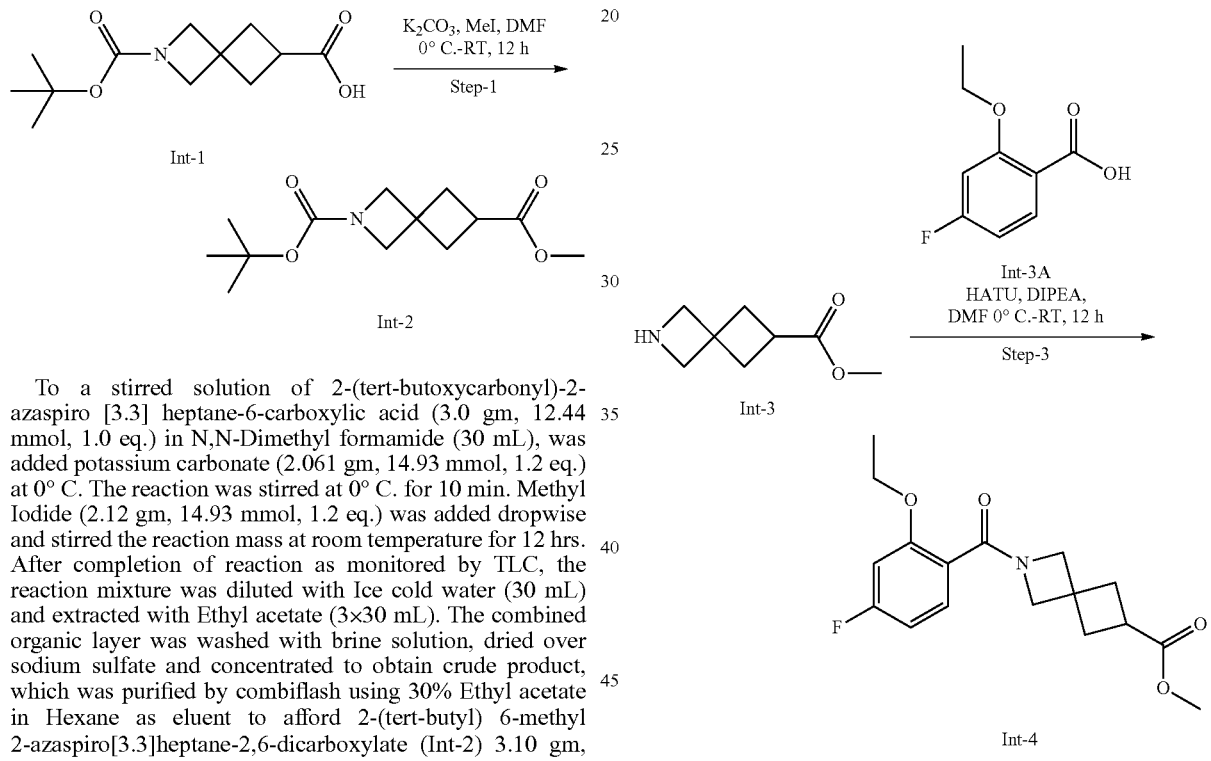

To a stirred solution of 2-(tert-butoxycarbonyl)-2-azaspiro [3.3] heptane-6-carboxylic acid (3.0 gm, 12.44 mmol, 1.0 eq.) in N,N-Dimethyl formamide (30 mL), was added potassium carbonate (2.061 gm, 14.93 mmol, 1.2 eq.) at 0° C. The reaction was stirred at 0° C. for 10 min. Methyl Iodide (2.12 gm, 14.93 mmol, 1.2 eq.) was added dropwise and stirred the reaction mass at room temperature for 12 hrs. After completion of reaction as monitored by TLC, the reaction mixture was diluted with Ice cold water (30 mL) and extracted with Ethyl acetate (3×30 mL). The combined organic layer was washed with brine solution, dried over sodium sulfate and concentrated to obtain crude product, which was purified by combiflash using 30% Ethyl acetate in Hexane as eluent to afford 2-(tert-butyl) 6-methyl 2-azaspiro[3.3]heptane-2,6-dicarboxylate (Int-2) 3.10 gm, (Yield—97.79%). LCMS: 200.2/z: [M−56]$^+$

Step-2: Synthesis of methyl 2-azaspiro [3.3] heptane-6-carboxylate (Int-3)

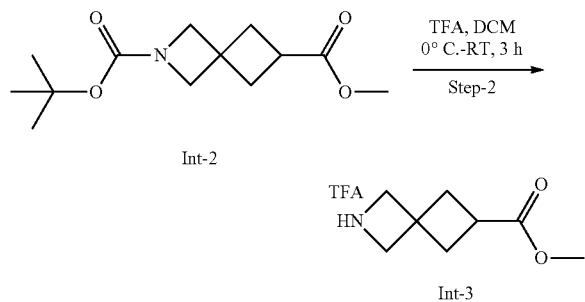

To a stirred solution of 2-(tert-butyl) 6-methyl 2-azaspiro [3.3]heptane-2,6-dicarboxylate (Int-2) (3.0 gm, 8.0 mmol, 1.0 eq.) in Dichloromethane (30 mL) was added Trifluoroacetic acid (3.0 mL) at 0° C. and allowed to stirred the reaction at Room temperature for 3 hr; the progress of the reaction of the was monitored by TLC. After completion of reaction, the reaction mixture was evaporated under vacuum and basified with bicarbonate solution (15 mL) extracted with Ethyl acetate (3*30 mL) Ethyl acetate layer separated dried over sodium sulfate and concentrated to obtain crude product methyl 2-azaspiro[3.3]heptane-6-carboxylate (Int-3) 2.50 gm (Yield: quantitative); LCMS: 155.90/z [M+1]$^+$

Step-3: Synthesis of methyl 2-(2-ethoxy-4-fluorobenzoyl)-2-azaspiro [3.3] heptane-6-carboxylate (Int-4)

To a stirred solution of 2-ethoxy-4-fluorobenzoic acid (2.0 gm, 10.86 mmol, 1 eq.) in N,N-Dimethyl formamide (20 mL) were added HATU (6.19 gm, 16.30 mmol, 1.5 eq.) DIPEA (4.20 gm, 32.6 mmol, 3.0 eq.) followed by methyl 2-azaspiro [3.3] heptane-6-carboxylate (Int-3) (1.33 gm, 10.86 mmol, 1.0 eq.) at 0° C. and allowed to stirred the reaction at room temperature for 12 hr; the progress of the reaction of was monitored by TLC. After completion of reaction, the reaction mixture was diluted with water (20 mL) and extracted with ethyl acetate (3×30 mL), washed with brine. The organic layer was dried over sodium sulphate and concentrated under vacuum to get crude material; which was purified by Combi-flash by using 70% Ethyl acetate in n Hexane as mobile phase to give desired product 2-(2-ethoxy-4-fluorobenzoyl)-2-azaspiro[3.3]heptane-6-carboxylic acid (Int-4) 2.4 gm (Yield: 73.52%); LCMS: 322.3 m/z [M+1]$^+$

Step-4: Synthesis of 2-(2-ethoxy-4-fluorobenzoyl)-2-azaspiro [3.3] heptane-6-carboxylic acid (Int-5)

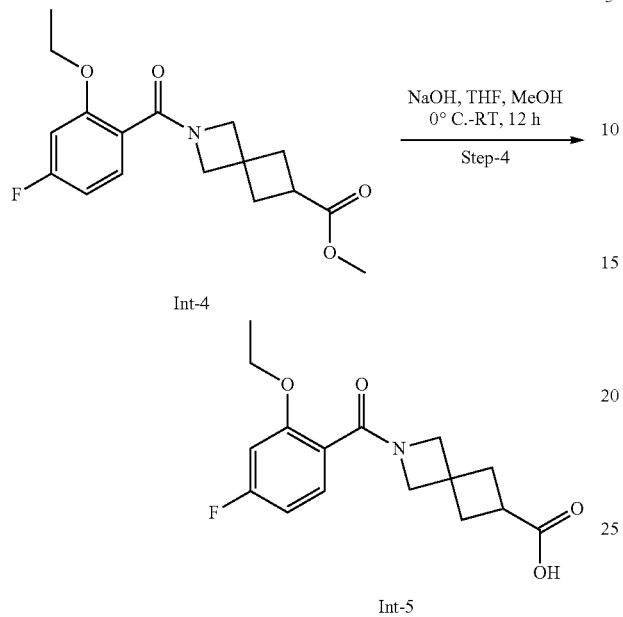

To a stirred solution of methyl 2-(2-ethoxy-4-fluorobenzoyl)-2-azaspiro [3.3] heptane-6-carboxylate (Int-4) (1.0 gm, 3.11 mmol, 1.0 eq.) in Tetrahydrofuran (10 mL), Methanol (5 mL), Water (10 mL) was added Sodium Hydroxide [NaOH] (0.13 gm, 6.23 mmol, 2.0 eq.) at 0° C. The reaction mixture was stirred at Room temperature for next 12 hr. The progress of the reaction was monitored by TLC; after completion of reaction, the reaction mixture was evaporated under vacuum. The crude product was acidified with 2N HCL (PH-4) The white solid was precipitated out which was filtered through Buchner funnel and dried under vacuum to give 2-(2-ethoxy-4-fluorobenzoyl)-2-azaspiro[3.3]heptane-6-carboxylic acid (Int-5), 0.75 gm (Yield: 72.11%); LCMS: 308.3 m/z [M+1]$^+$

Example 2: Synthesis of (2-fluoro-5-hydroxyphenyl)(6-(3-methyl-1-(o-tolyl)-1H-pyrazol-5-yl)-2-azaspiro[3.3]hept-5-en-2-yl)methanone. [Compound 120]

Synthetic Scheme:

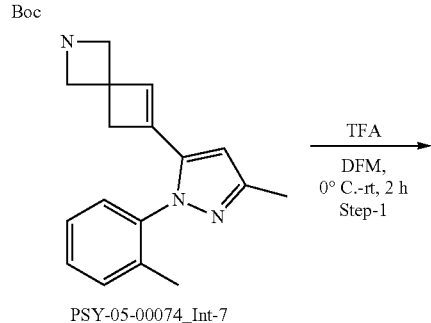

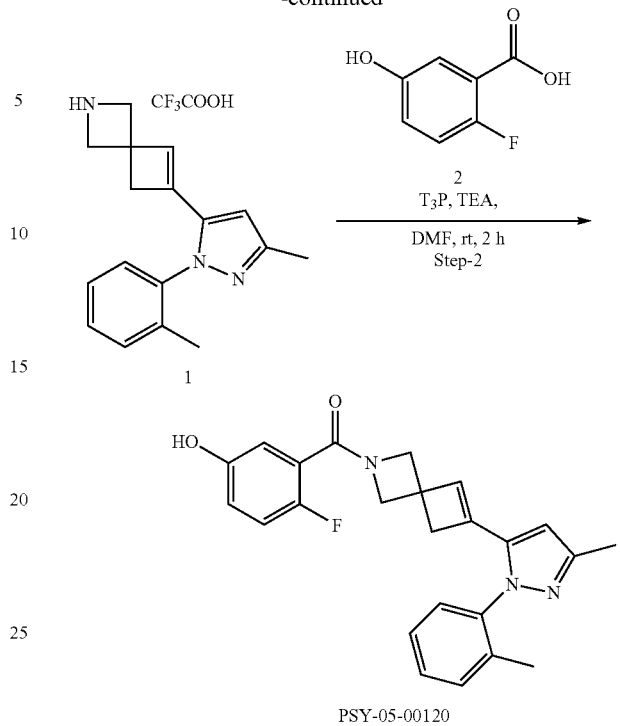

Step-1: 6-(3-methyl-1-(o-tolyl)-1H-pyrazol-5-yl)-2-azaspiro[3.3]hept-5-ene 2,2,2-trifluoroacetate To a stirred solution of tert-butyl 6-(3-methyl-1-(o-tolyl)-1H-pyrazol-5-yl)-2-azaspiro[3.3]hept-5-ene-2-carboxylate (100 mg) in DCM (0.5 ml) was added trifluroacetic acid (0.5 ml) at 0° C. The reaction was stirred at room temperature for 1 h. After completion of reaction as monitored by TLC, the reaction mixture was concentrated to get crude material. The crude material was triturated with mixture of diethyl ether and hexane (1:1, 10 mL*3) to get pure desire compound (0.11 g, quantitative) as a white solid. LCMS: 266.3 m/z [M+H]+; $^1$H NMR (400 MHz, Methanol-d4) δ: 7.51-7.47 (m, 1H), 7.44-7.36 (m, 2H), 7.28 (d, J=7.6 Hz, 1H), 6.38 (s, 1H), 5.36 (s, 1H), 4.19-4.13 (m, 4H), 2.88-2.86 (m, 2H), 2.31 (s, 3H), 2.01 (s, 3H).

Step-2: (2-fluoro-5-hydroxyphenyl)(6-(3-methyl-1-(o-tolyl)-H-pyrazol-5-yl)-2-azaspiro[3.3]hept-5-en-2-yl)methanone To a stirred solution of 6-(3-methyl-1-(o-tolyl)-1H-pyrazol-5-yl)-2-azaspiro[3.3]hept-5-ene 2,2,2-trifluoroacetate (0.11 g, 0.421 mmol) in DMF (1 mL) were added 2-fluoro-5-hydroxybenzoic acid (0.054 g, 0.506 mmol), TEA (0.088 g, 1.26 mmol) and T3P (0.111 g, 0.506 mmol) at 0° C. The resulting reaction mixture was stirred at room temperature for 2 h. After completion of reaction as monitored by TLC, the reaction mixture was diluted with water (50 mL) and extracted with ethyl acetate (3*50 mL). The organic layer was washed with brine (3*25 mL), dried over sodium sulphate and concentrated under vacuum to get crude material which was purified by combiflash using 3% MeOH in DCM as eluent to get ((2-fluoro-5-hydroxyphenyl)(6-(3-methyl-1-(o-tolyl)-1H-pyrazol-5-yl)-2-azaspiro[3.3]hept-5-en-2-yl)methanone) PSY-05-00120 (0.03 g, 27%) as white solid. LCMS: 473.7 m/z [M+H]+, ¹H NMR (400 MHz, Methanol-d₄) δ 7.51-7.33 (m, 3H), 7.28 (d, J=7.9 Hz, 1H), 7.00 (t, J=9.2 Hz, 1H), 6.92-6.78 (m, 2H), 6.35 (s, 1H), 5.39 (s, 1H), 4.29-4.09 (m, 4H), 2.78 (d, J=5.6 Hz, 2H), 2.30 (s, 3H), 2.00 (s, 3H).

Example 3: Synthesis of (4-fluoro-2-isopropoxyphenyl) (6-(3-methyl-1-(o-tolyl)-1H-pyrazol-5-yl)-2-azaspiro [3.3] heptan-2-yl) methanone. [Compound 177]

Synthetic Scheme:

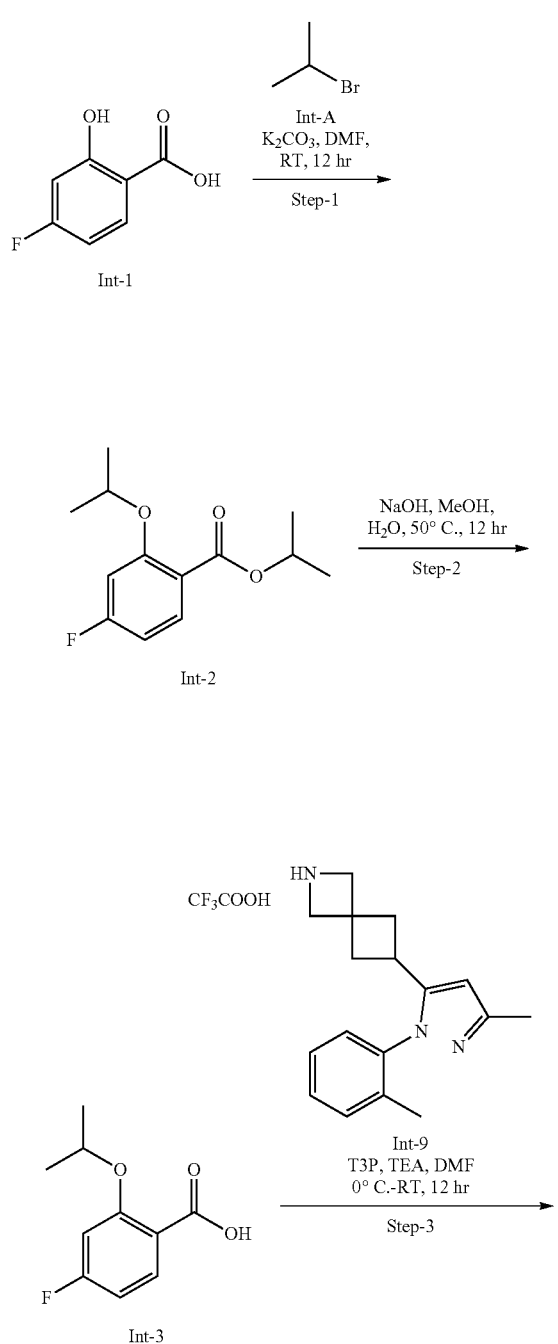

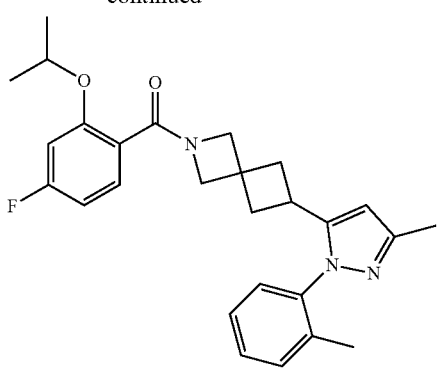

PSY-05-00177

Step-1: Synthesis of isopropyl 4-fluoro-2-isopropoxybenzoate (Int-2)

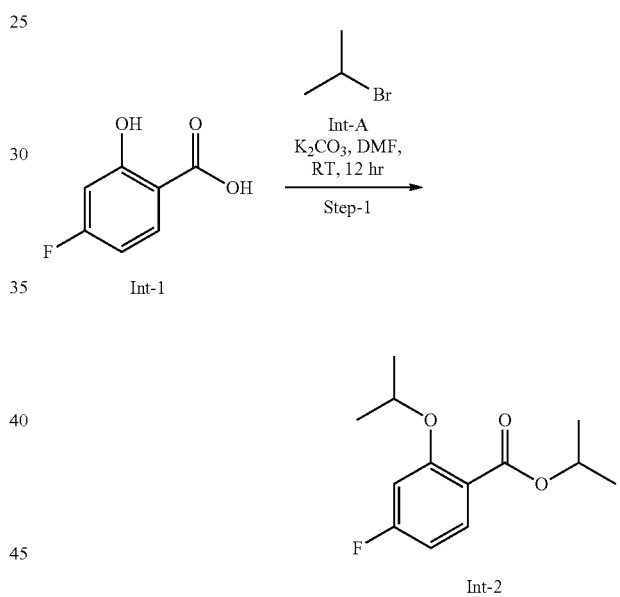

To a stirred solution of 4-fluoro-2-hydroxybenzoic acid (2.0 gm, 12.820 mmol, 1 eq.) in N,N-Dimethyl formamide (20 mL) were added Potassium carbonate (17.07 gm, 51.282 mmol, 4.0 eq.) followed by dropwise addition of Isopropyl iodide (8.88 gm, 51.282 mmol, 4.0 eq.) at 0° C. and allowed to stirred the reaction at room temperature for 12 hr; the progress of the reaction of the was monitored by TLC. After completion of reaction, the reaction mixture was diluted with water (30 mL) and extracted with ethyl acetate (3×50 mL), washed with brine. The organic layer was dried over sodium sulphate and concentrated under vacuum to get crude material; which was purified by combi-flash by using 20% Ethyl acetate in hexane as mobile phase to give desired product 4-fluoro-2-isopropoxybenzoic acid 2.0 gm (Yield: 65.14%); ¹H NMR (400 MHz, DMSO-d₆) δ 7.65 (dd, J=8.7, 7.0 Hz, 1H), 7.08 (dd, J=11.8, 2.4 Hz, 1H), 6.82 (td, J=8.4, 2.4 Hz, 1H), 5.09 (hept, J=6.2 Hz, 1H), 4.72 (p, J=6.0 Hz, 1H), 3.18 (d, J=5.2 Hz, 1H), 1.29 (dd, J=6.1, 2.7 Hz, 12H).

Step-2: Synthesis of 4-fluoro-2-isopropoxybenzoic acid carbonate (Int-3)

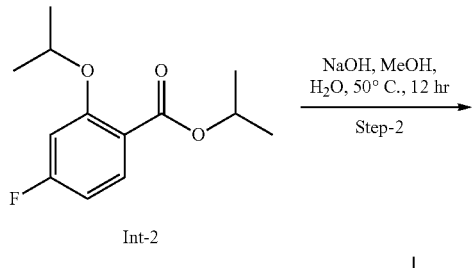

To a stirred solution of isopropyl 4-fluoro-2-isopropoxybenzoate (Int-2) (1.60 gm, 6.66 mmol, 1.0 eq.) in Tetrahydrofuran (10 mL), Methanol (10 mL), Water (10 mL) was added Sodium Hydroxide [NaOH] (0.53 gm, 13.33 mmol, 2.0 eq.) at 0° C. The reaction mixture was stirred at 50° C. for next 12 hr. The progress of the reaction was monitored by TLC; after completion of reaction, the reaction mixture was evaporated under vacuum. The crude product was acidified with 2N HCL (PH~4) The white solid was precipitated out which was filtered through Buchner funnel and dried under vacuum to give isopropyl 4-fluoro-2-isopropoxybenzoic acid (Int-3) 1.20 gm (Yield: 91%); $^1$H NMR (400 MHz, DMSO-$d_6$) δ 12.53 (s, 1H), 7.69 (t, J=7.9 Hz, 1H), 7.05 (dd, J=11.9, 2.5 Hz, 1H), 6.80 (td, J=8.4, 2.5 Hz, 1H), 4.69 (hept, =6.0 Hz, 1H), 1.27 (d, J=6.0 Hz, 6H).

Step-3: Synthesis of (4-fluoro-2-isopropoxyphenyl) (6-(3-methyl-1-(o-tolyl)-1H-pyrazol-5-yl)-2-azaspiro [3.3]heptan-2-yl)methanone (Compound-00177)

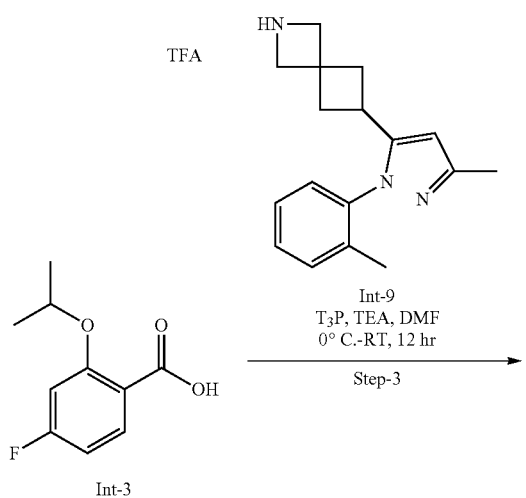

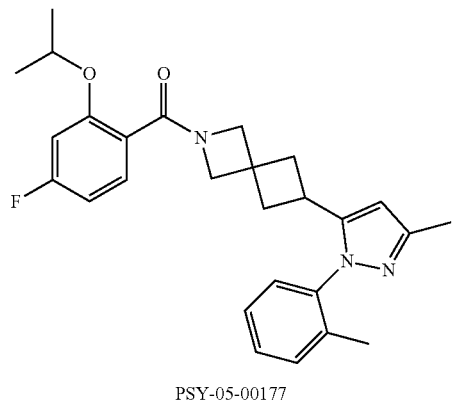

To a stirred solution of 6-(3-methyl-1-(o-tolyl)-1H-pyrazol-5-yl)-2-azaspiro [3.3] heptane 2,2,2-trifluoroacetate (0.150 gm, 0.56 mmol 1.0 eq.) in N,N-Dimethyl formamide (3 mL) were added 4-fluoro-2-isopropoxybenzoic acid (0.133 gm, 0.674 mmol, 1.2 eq.), TEA (0.170 gm, 1.68 mmol, 3.0 eq.) and T$_3$P (50% in ethyl acetate) (0.214 gm, 0.674 mmol, 1.2 eq.) at 0° C. The resulting reaction mixture was stirred at room temperature for 12 h. After completion of reaction as monitored by TLC, the reaction mixture was diluted with water (10 ml) and extracted with ethyl acetate (3*20 ml). The organic layer was washed with brine (10 ml), dried over sodium sulphate and concentrated under vacuum to get crude material which was purified by combiflash using 50% Ethyl acetate in hexane as eluent to get PSY-05-00177 as white solid (0.040. (Yield: 16%); LCMS: 448.5 m/z [M+H]$^+$. HPLC: 98.35%; $^1$H NMR (400 MHz, DMSO-$d_6$) δ 7.38 (t, J=8.3 Hz, 2H), 7.33-7.22 (m, 2H), 7.15 (dd, J=7.9, 4.2 Hz, 1H), 6.97 (dd, J=11.6, 8.5 Hz, 1H), 6.75 (q, J=7.6 Hz, 1H), 6.13 (d, J=17.6 Hz, 1H), 4.70-4.60 (m, 1H), 3.93 (s, 1H), 3.85 (d, J=15.1 Hz, 2H), 3.78 (s, 1H), 3.00 (dt, J=18.8, 8.5 Hz, 1H), 2.34-2.16 (m, 4H), 2.16 (s, 3H), 1.93 (s, 3H), 1.24 (dd, J=11.5, 6.1 Hz, 6H).

Example 4: Synthesis of (2,4-difluoro-5-hydroxyphenyl)(6-(3-methyl-1-(o-tolyl)-1H-pyrazol-5-yl)-2-azaspiro[3.3]heptan-2-yl)methanone. [Compound 126]

Synthetic Scheme:

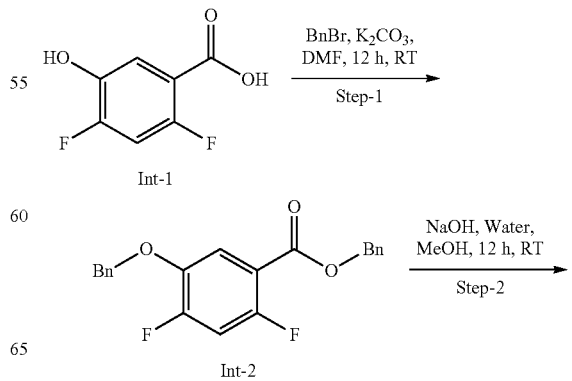

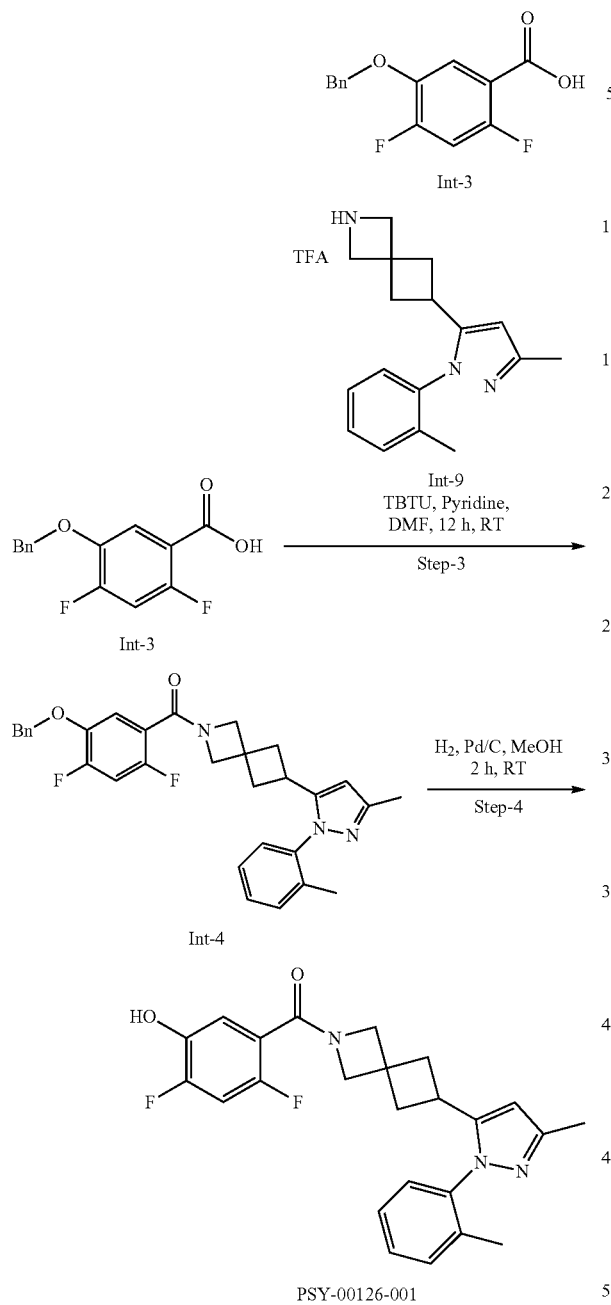

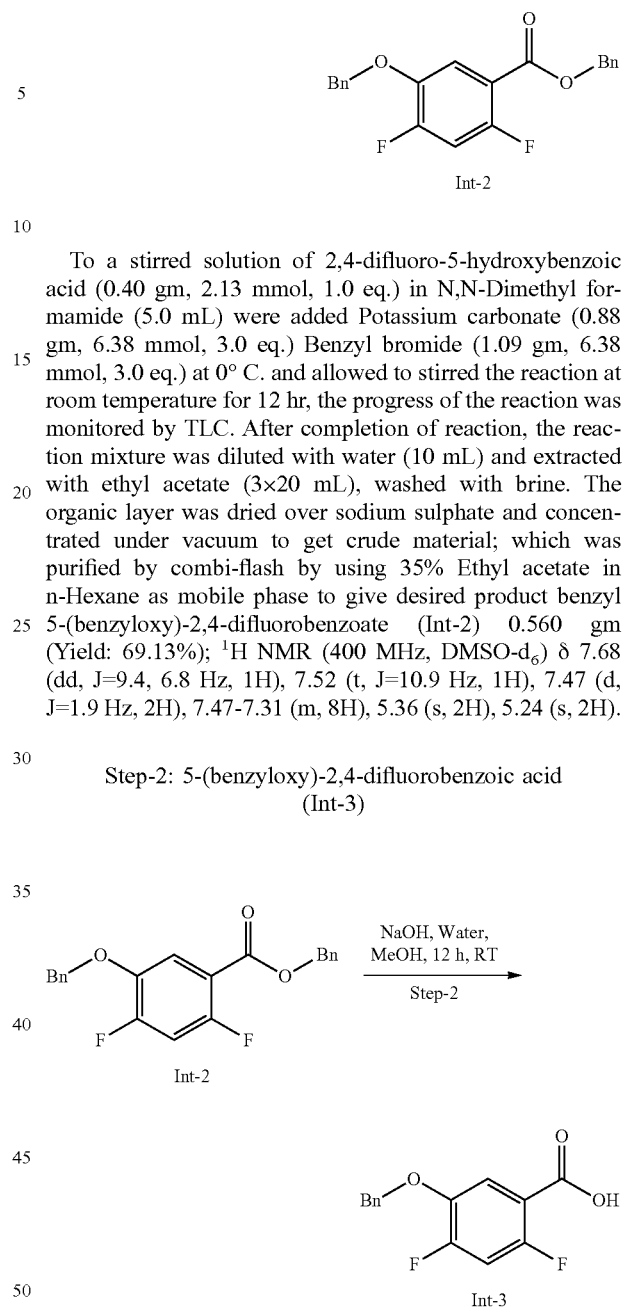

To a stirred solution of 2,4-difluoro-5-hydroxybenzoic acid (0.40 gm, 2.13 mmol, 1.0 eq.) in N,N-Dimethyl formamide (5.0 mL) were added Potassium carbonate (0.88 gm, 6.38 mmol, 3.0 eq.) Benzyl bromide (1.09 gm, 6.38 mmol, 3.0 eq.) at 0° C. and allowed to stirred the reaction at room temperature for 12 hr, the progress of the reaction was monitored by TLC. After completion of reaction, the reaction mixture was diluted with water (10 mL) and extracted with ethyl acetate (3×20 mL), washed with brine. The organic layer was dried over sodium sulphate and concentrated under vacuum to get crude material; which was purified by combi-flash by using 35% Ethyl acetate in n-Hexane as mobile phase to give desired product benzyl 5-(benzyloxy)-2,4-difluorobenzoate (Int-2) 0.560 gm (Yield: 69.13%); $^1$H NMR (400 MHz, DMSO-$d_6$) δ 7.68 (dd, J=9.4, 6.8 Hz, 1H), 7.52 (t, J=10.9 Hz, 1H), 7.47 (d, J=1.9 Hz, 2H), 7.47-7.31 (m, 8H), 5.36 (s, 2H), 5.24 (s, 2H).

Step-2: 5-(benzyloxy)-2,4-difluorobenzoic acid (Int-3)

To a stirred solution of benzyl 5-(benzyloxy)-2,4-difluorobenzoate (Int-2) (0.50 gm, 1.44 mmol, 1.0 eq.) in Tetrahydrofuran (5.0 mL), Methanol (5.0 mL), Water (5.0 mL) was added Sodium Hydroxide [NaOH](0.11 gm, 2.89 mmol, 2.0 eq.) at 0° C. The reaction mixture was stirred at Room temperature for next 12 hr. The progress of the reaction was monitored by TLC; after completion of reaction, the reaction mixture was evaporated under vacuum. The crude product was acidified with 2N HCL (PH-4) The white solid was precipitated out which was filtered through Buchner funnel and dried under vacuum to give 5-(benzyloxy)-2,4-difluorobenzoic acid (Int-3), 0.35 gm (Yield: 94.59%); $^1$H NMR (400 MHz, DMSO-$d_6$) δ 13.42 (s, 1H), 7.65 (dd, J=9.5, 6.9 Hz, 1H), 7.52-7.29 (m, 5H), 5.23 (s, 2H).

Step-1: Synthesis of benzyl 5-(benzyloxy)-2,4-difluorobenzoate (Int-2)

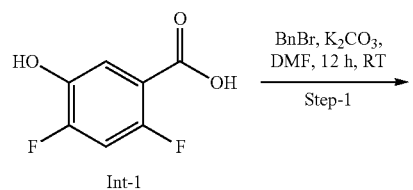

Step-3: Synthesis of (5-(benzyloxy)-2,4-difluorophenyl)(6-(3-methyl-1-(o-tolyl)-1H-pyrazol-5-yl)-2-azaspiro[3.3]heptan-2-yl)methanone (Int-4)

Step-4: Synthesis of (2,4-difluoro-5-hydroxyphenyl)(6-(3-methyl-1-(o-tolyl)-1H-pyrazol-5-yl)-2-azaspiro[3.3]heptan-2-yl) methanone (Compound-00126)

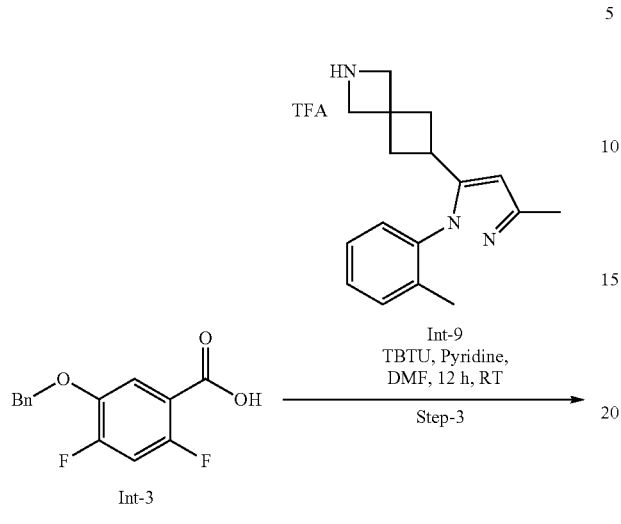

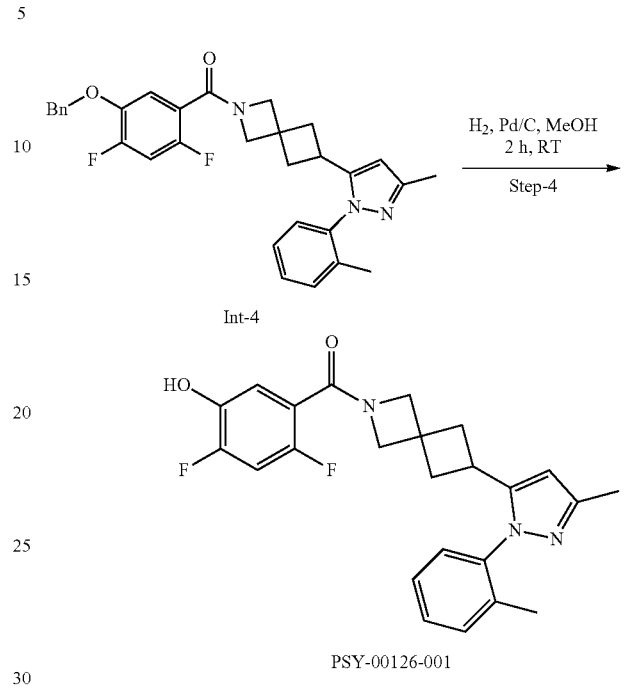

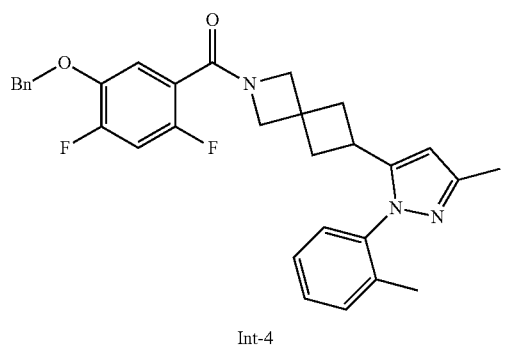

To a stirred solution of 2-(5-(benzyloxy)-2-fluorobenzoyl)-2-azaspiro[3.3]heptane-6-carboxylic acid (0.25 gm, 0.677 mmol, 1.0 eq.) in N,N-Dimethyl formamide (10.0 mL) were added TBTU (0.326 gm, 1.01 mmol, 1.5 eq.) Pyridine (0.15 gm, 2.03 mmol, 3.0 eq.) followed by addition of 5-(benzyloxy)-2,4-difluorobenzoic acid (Int-3) (0.16 gm, 0.677 mmol, 1.0 eq.) at 0° C. and allowed to stirred the reaction at room temperature for 12 hr; the progress of the reaction of the was monitored by TLC. After completion of reaction, the reaction mixture was diluted with water (10 mL) and extracted with ethyl acetate (3×20 mL), washed with brine. The organic layer was dried over sodium sulphate and concentrated under vacuum to get crude material; which was purified by combi-flash by using 80% Ethyl acetate in Hexane as mobile phase to give desired product (5-(benzyloxy)-2,4-difluorophenyl)(6-(3-methyl-1-(o-tolyl)-1H-pyrazol-5-yl)-2-azaspiro[3.3]heptan-2-yl)methanone (Int-4) 0.25 gm (Yield: 52.08%); LCMS: 514.05 m/z [M+].

To a stirred solution (5-(benzyloxy)-2,4-difluorophenyl)(6-(3-methyl-1-(o-tolyl)-1H-pyrazol-5-yl)-2-azaspiro[3.3]heptan-2-yl)methanone (Int-4) (0.20 gm, 0.400 mmol, 1.0 eq.) was dissolved in Methanol (10 mL). 10% Pd/C (with 50/6 moisture) 0.050 gm was added at Room Temperature and Reaction mixture was allowed to stir for 2 hr. under Hydrogen atmosphere. Reaction was monitored by TLC. After completion of the reaction, Reaction mixture was filtered through celite bed, washed with Methanol (50 mL) and concentrated to get crude compound, which was purified by column chromatography using 60-120 mesh size silica gel and 80% Ethyl acetate in Hexane as mobile phase to give the desired product (2,4-difluoro-5-hydroxyphenyl)(6-(3-methyl-1-(o-tolyl)-1H-pyrazol-5-yl)-2-azaspiro[3.3]heptan-2-yl) methanone (PSY-05-00126) as a white solid, 0.080 gm, (Yield: 48.78%); LCMS: 424.4 m/z [M+1] $^1$H NMR (400 MHz, DMSO-d$_6$) δ 10.30 (s, 1H), 7.38 (t, J=7.7 Hz, 3H), 7.33-7.23 (m, 1H), 7.15 (t, J=6.7 Hz, 11H), 7.02-6.93 (m, 1H), 6.14 (d, J=18.3 Hz, 1H), 3.97 (d, J=3.4 Hz, 2H), 3.91 (s, 2H), 2.98 (dt, J=18.5, 8.8 Hz, 1H), 2.45 (s, 1H), 2.34-2.22 (m, 1H), 2.19 (t, J=11.7 Hz, 3H), 1.93 (s, 3H).

Example 5: Synthesis of 4-hydroxy-2-(6-(3-methyl-1-(o-tolyl)-1H-pyrazol-5-yl)-2-azaspiro[3.3]heptane-2-carbonyl)benzonitrile [Compound 128]

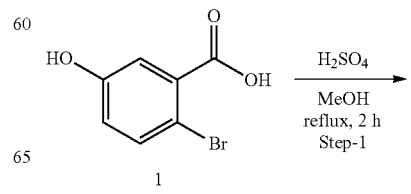

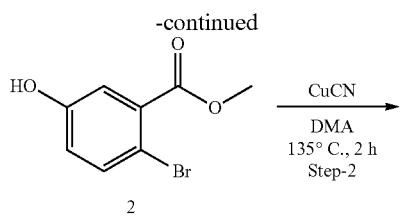

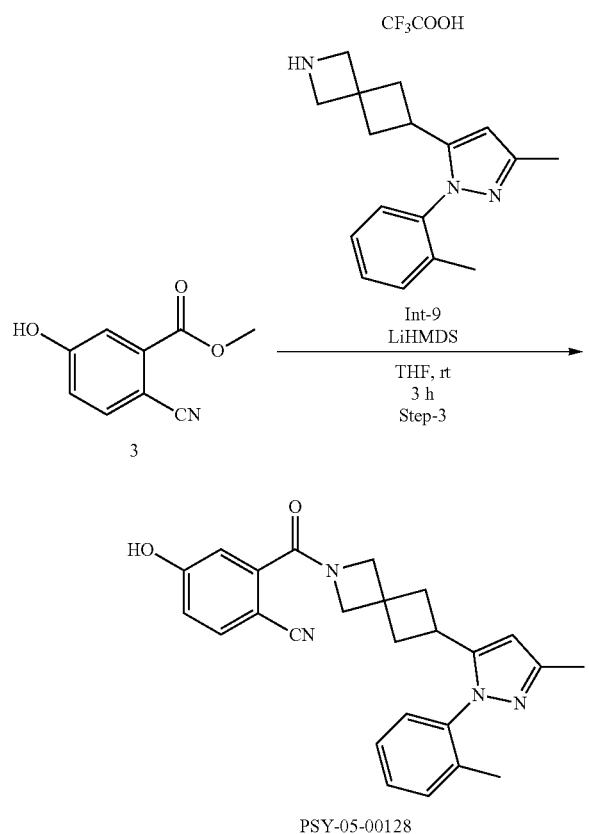

Step-1: Methyl 2-bromo-5-hydroxybenzoate (2)

To stirred solution of 2-bromo-5-hydroxybenzoic acid (0.5 g, 2.325 mmol), in MeOH, Con. $H_2SO_4$ (2 mL) was added dropwise. The reaction mixture was heated to 90° C. and stirred at same temperature for 2 h. After completed reaction RM was concentered, diluted with ethylacetate, washed with aq.$NaHCO_3$ solution (3×15 mL), dried over $Na_2SO_4$, and evaporated. The crude material was purified by combiflash using 30% ethylacetate in hexane to give methyl 2-bromo-5-hydroxybenzoate (300 mg, 56%) as colorless liquid. LCMS: 229.9 m/z $[M+H]^+$.

Step-2: Methyl 2-cyano-5-hydroxybenzoate (3)

To stirred solution of methyl 2-bromo-5-hydroxybenzoate (0.3 g, 1.31 mmol) in DMA, was added CuCN (0.174 g, 1.89 mmol) and stirred at 135° C. for 2 h. The reaction was quenched by the addition of cold water (50 mL) and extracted with ethyl acetate (3×25 mL). The organic layer was concentrated and purified by combiflash using 30% ethylacetate in hexane to give methyl 2-cyano-5-hydroxybenzoate (140 mg, 61%) as a white solid. $^1$H NMR (400 MHz, $CD_3Cl$) δ 7.71 (d, J=8.4 Hz, 1H), 7.60 (d, J=2 Hz, 1H), 7.13-7.10 (m, 1H), 6.31 (s, 1H), 4.01 (s, 3H).

Step-3: (4-hydroxy-2-(6-(3-methyl-1-(o-tolyl)-1H-pyrazol-5-yl)-2-azaspiro[3.3]heptane-2-carbonyl) benzonitrile) (Compound-00128)

To stirred solution of 6-(3-methyl-1-(o-tolyl)-1H-pyrazol-5-yl)-2-azaspiro[3.3]heptane 2,2,2-trifluoroacetate (0.120 g, 0.449 mmol) and methyl 2-cyano-5-hydroxybenzoate (0.0795 g, 0.449 mmol) in THF at −78° C., was added LiHMDS (1.35 mL, 1.347 mmol; 1 M solution in THF) for 15 min then it stirred at it for 3 h. The reaction mass was quenched by the addition of water (50 mL) and extracted by ethyl acetate (3×30 mL). The organic layer was concentrated under reduced pressure and purified by combiflash using 5% MeOH in DCM to give (4-hydroxy-2-(6-(3-methyl-1-(o-tolyl)-1H-pyrazol-5-yl)-2-azaspiro[3.3]heptane-2-carbonyl) benzonitrile) (60 mg 21%) as a white solid. LCMS: 413.4 m/z $[M+H]^+$; $^1$H NMR (400 MHz, DMSO-$d_6$) δ 7.68 (t, J=7.8 Hz, 1H), 7.43-7.26 (m, 3H), 7.15 (dd, J=7.8, 3.9 Hz, 1H), 6.98-6.85 (m, 2H), 6.13 (d, J=19.6 Hz, 1H), 3.99 (dd. J=24.0, 13.9 Hz, 4H), 2.99 (dt, J=22.2, 8.4 Hz, 1H), 2.39-2.28 (m, 2H), 2.23 (dd, J=12.7, 9.0 Hz, 2H), 2.17 (d, J=8.5 Hz, 3H), 1.92 (s, 3H).

Example 6: Synthesis of 2-(2-Fluoro-5-hydroxybenzoyl)-N-Methyl-N-(o-tolyl)-2-azaspiro [3.3]heptane-6-carboxamide [Compound 185] and 2-(2-Ethoxy-4-fluorobenzoyl)-N-Methyl-N-(o-tolyl)-2-azaspiro [3.3] heptane-6-carboxamide [Compound 187]

Reaction Scheme:

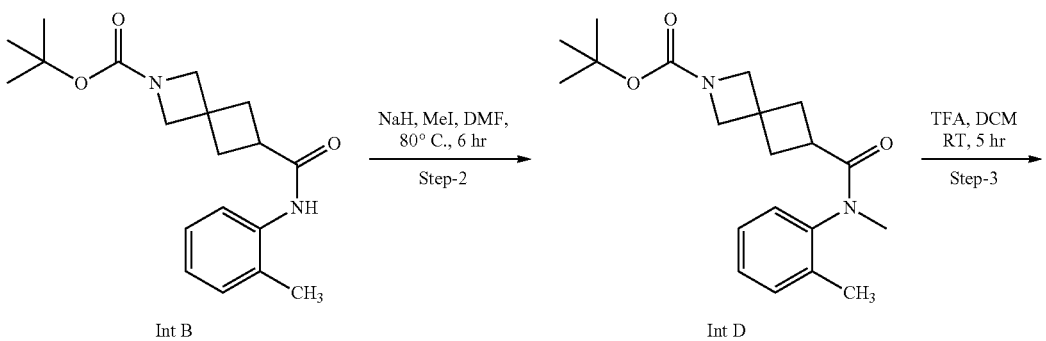

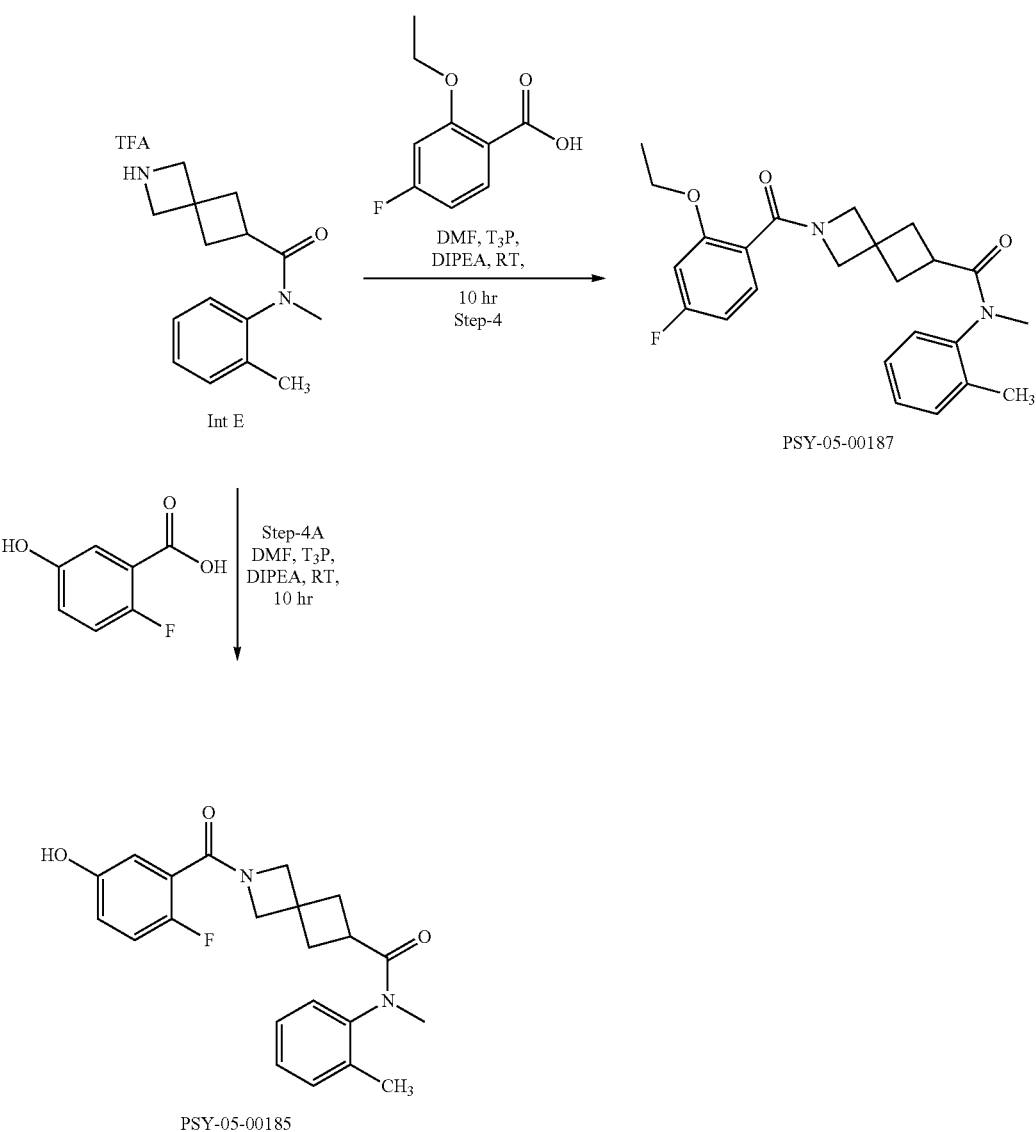
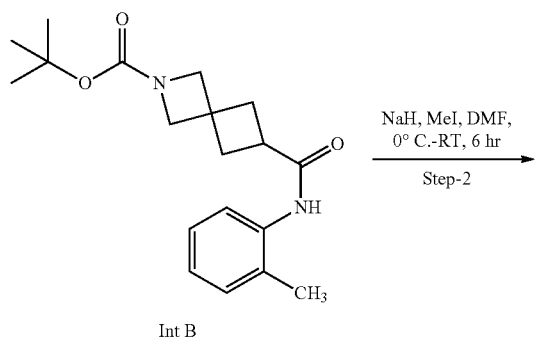
Step-1:—Synthesis of Tert-butyl 6-(methyl(o-tolyl) carbamoyl)-2-azaspiro [3.3] heptane-2-carboxylate (Int-D)
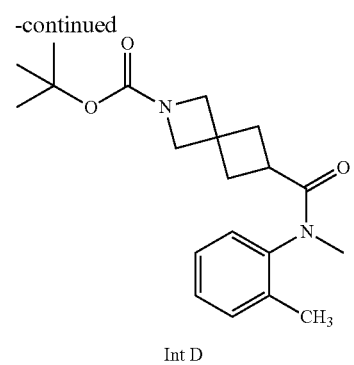
Tert-butyl 6-(o-tolylcarbamoyl)-2-azaspiro [3.3] heptane-2-carboxylate 0.5 g (1.5151 mmol, 1 eq.) dissolved in Dimethylformamide 5 mL Sodium hydride 0.08 g (1.9696 mml, 1.3 eq.) was added, stirred reaction mixture at room temperature for 15 min followed by Methyl Iodide 0.25 g (1.818 mmol, 1.2 eq.) added stirred reaction mixture at 60° C. for 6 hr. Reaction monitored on TLC. After completion of the reaction, the reaction mixture diluted with water. Product extracted with Ethyl Acetate (3*25 mL), combined organics concentrated to obtain crude product. Crude purified by column chromatography using Ethyl acetate:Hexanes as solvent system to get desired product. Tert-butyl 6-(methyl (o-tolyl) carbamoyl)-2-azaspiro [3.3] heptane-2-carboxylate. 0.51 g (Solid) (yield-98%) m/z 345.4 [M+1]+1H. NMR (400 MHz, Chloroform-d) δ 7.35-7.20 (m, 3H), 7.05 (d, J=7.6 Hz, 1H), 3.91-3.76 (m, 4H), 3.20 (s, 3H), 2.70 (q, J=8.3 Hz, 1H), 2.57-2.47 (in, 1H), 2.49-2.39 (m, 1H), 2.22 (s, 3H), 2.05-1.95 (m, 2H), 1.43 (s, 9H).

Step-2:—Synthesis of N-Methyl-N-(o-tolyl)-2-azaspiro [3.3] heptane-6-carboxamide (Int-E)

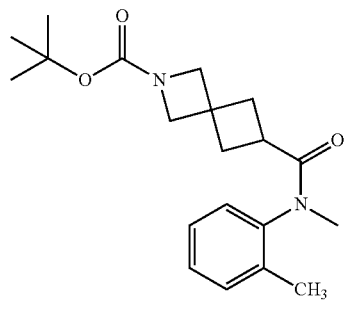

Int D

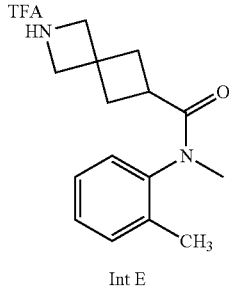

Int E

Tert-butyl 6-(methyl(o-tolyl) carbamoyl)-2-azaspiro [3.3] heptane-2-carboxylate 0.5 g was taken in Dichloromethane 50 mL, cooled it to 0° C., Trifluoroacetic acid 0.8 mL was added, stirred reaction mixture at room temperature for 5 hr. Reaction was monitored on TLC. After completion of the reaction it was concentrated completed was triturated with diethyl ether to get desired product as N-Methyl-N-(o-tolyl)-2-azaspiro [3.3] heptane-6-carboxamide 0.5 g (Solid) (yield-92%) m/z 245.4 [M+1]+.

Step-3: —Synthesis of 2-(2-Fluoro-5-hydroxybenzoyl)-N-Methyl-N-(o-tolyl)-2-azaspiro [3.3] heptane-6-carboxamide (Compound-00185)

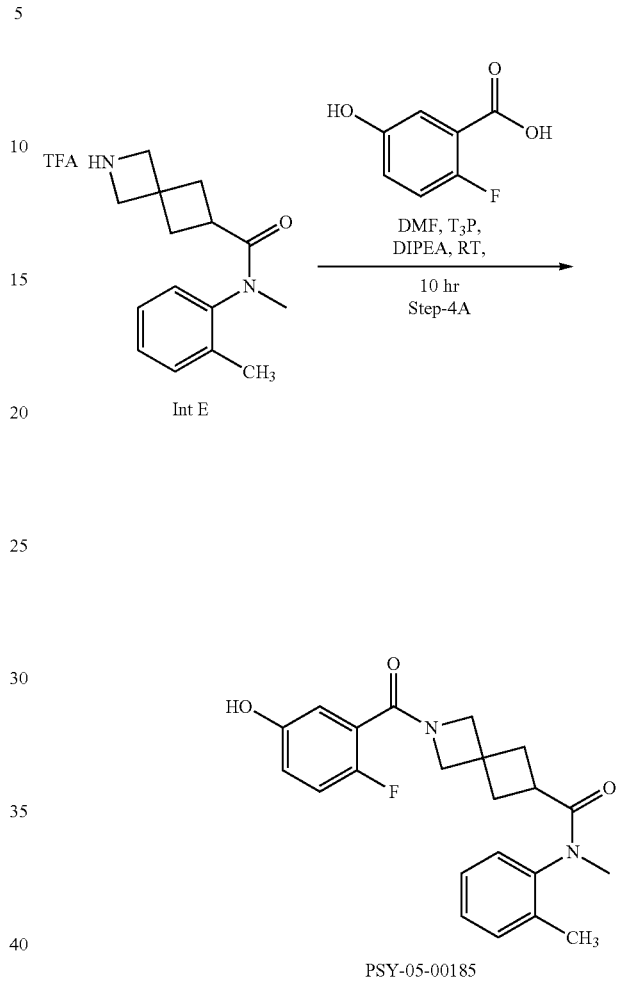

To a solution of 2-Fluoro-4-hydroxy benzoic acid 0.1 g (0.676 mmol, 1.1 eq.) in Dimethylformamide 2 mL. TFA salt of N-Methyl-N-(o-tolyl)-2-azaspiro [3.3] heptane-6-carboxamide 0.15 g (0.6147 mmol, 1 eq.) added and stir for 10 min. DIPEA 0.4 mL (2.459 mmol, 4 eq.), stirred reaction mixture for 10 min. T3P 0.4 mL (0.7377 mmol, 1.2 eq.) was added and stir, reaction mixture at room temperature for 10 hr. Reaction monitored on TLC. After completion of the reaction, it diluted with water. Product extracted with Ethyl acetate (3*15 mL), combined organics washed with water and dried over anhydrous Sodium sulphate. Organic layer concentrated to get crude compound. Crude gum, which purified by column chromatography using Ethyl acetate: Hexanes as solvent system. Desired product obtained as 2-(2-Fluoro-5-hydroxybenzoyl)-N-Methyl-N-(o-tolyl)-2-azaspiro [3.3] heptane-6-carboxamide 0.05 g (Solid). (yield-22.22%) m/z 383.35 [M+1]+1H NMR (400 MHz, DMSO-d6) δ 9.62 (d, J=13.5 Hz, 1H), 7.40-7.23 (m, 3H), 7.16 (s, 1H), 7.17-6.98 (m, 1H), 6.83 (ddt, J=12.9, 8.7, 3.7 Hz, 1H), 6.78-6.69 (m, 1H), 3.97-3.80 (m, 4H), 3.05 (d, J=6.1 Hz, 3H), 2.62 (td, J=15.6, 7.7 Hz, 1H), 2.39-2.23 (m, 2H), 2.22-2.05 (m, 3H), 2.00-1.90 (m, 2H).

Step-4:—Synthesis of 2-(2-Ethoxy-4-fluorobenzoyl)-N-Methyl-N-(o-tolyl)-2-azaspiro [3.3] heptane-6-carboxamide (Compound-00187)

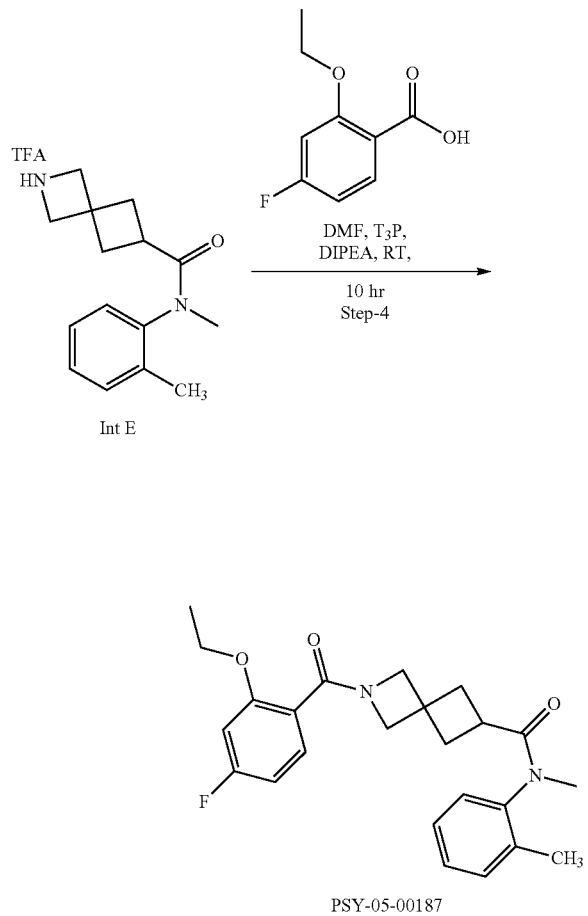

Example 7: Synthesis of (2-fluoro-5-hydroxyphenyl)(6-(1-(o-tolyl)-1H-pyrazol-5-yl)-2-azaspiro [3.3] heptan-2-yl) methanone [Compound 367]

Reaction Scheme:

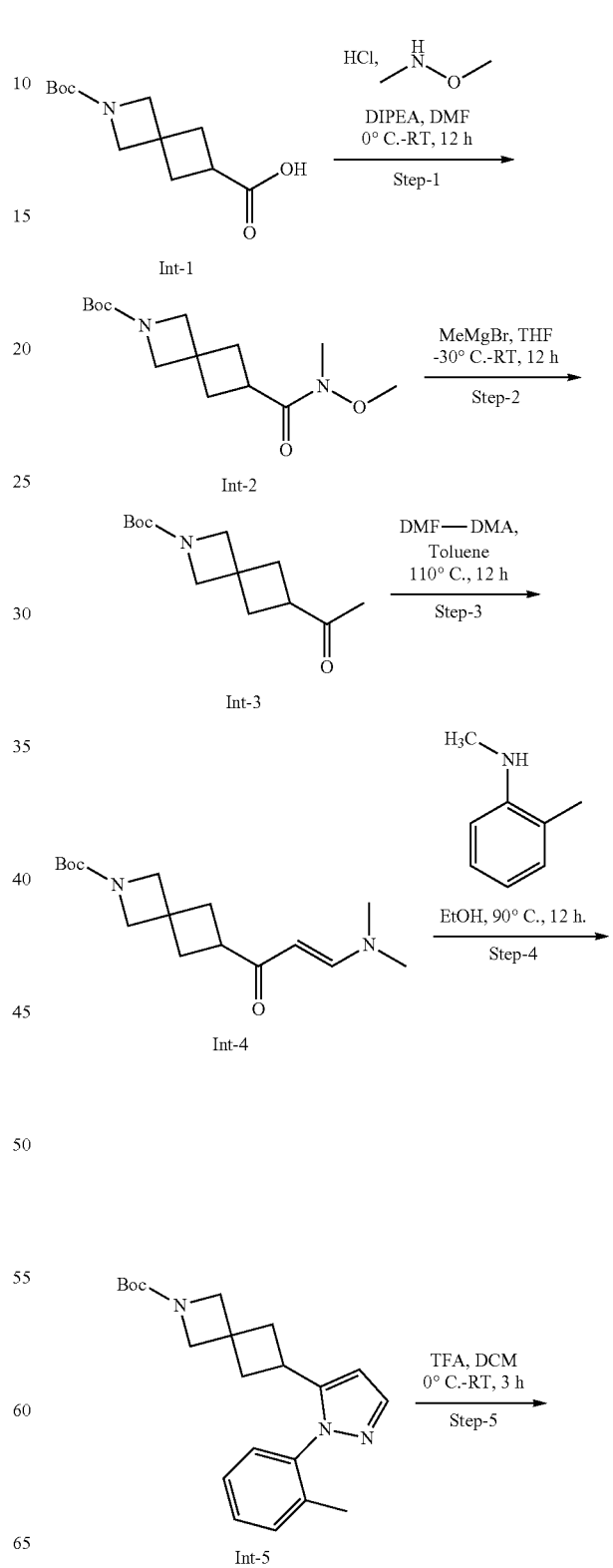

To a solution of 2-Ethoxy-4-fluorobenzoic acid 0.15 g (0.676 mmol, 1.1 eq.) in Dimethyl formamide 2 mL. TFA salt of N-Methyl-N-(o-tolyl)-2-azaspiro [3.3] heptane-6-carboxamide 0.15 g (0.6147 mmol, 1 eq.) was added followed by Di-isopropyl ethyl amine 0.4 mL (2.459 mmol, 4 eq.), stirred reaction mixture for 10 min. T3P 0.4 mL (0.7377 mmol, 1.2 eq.) was added, stirred reaction mixture at room temperature for 10 hr. Reaction was monitored on TLC. Reaction mixture diluted with water and extracted with Ethyl acetate (3*15 mL). Organic layer combined, concentrated to obtained crude. Crude compound as gum, which purified by column chromatography using EtOAC:Hexanes as solvent system to get desired product. 2-(2-Ethoxy-4-fluorobenzoyl)-N-Methyl-N-(o-tolyl)-2-azaspiro [3.3] heptane-6-carboxamide 0.05 g (Solid) (yield-21.22%) m/z 411.4 [M+1]+1H NMR (400 MHz, Methanol-d4) δ 7.42-7.22 (dq, J=27.9, 7.8 Hz, 4H), 7.14 (d, J=7.5 Hz, 1H), 6.91-6.66 (m, 2H), 4.18-3.89 (m, 5H), 3.87 (s, 1H), 3.17 (d, J=5.4 Hz, 3H), 2.79 (dp, J=24.3, 8.0 Hz, 1H), 2.43 (ddt, J=27.5, 19.5, 9.9 Hz, 2H), 2.20 (s, 3H), 2.17-1.98 (m, 2H), 1.41 (dt, J=18.6, 7.0 Hz, 3H).

157

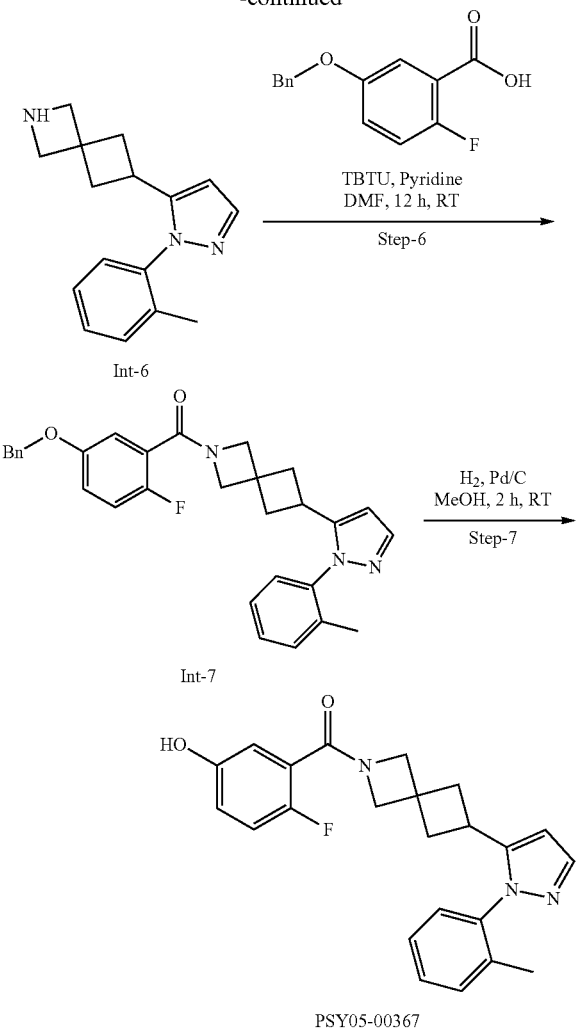

Step-1: Synthesis of tert-butyl 6-(methoxy (methyl) carbamoyl-2-azaspiro [3.4] heptane-2-carboxylate (Int-2)

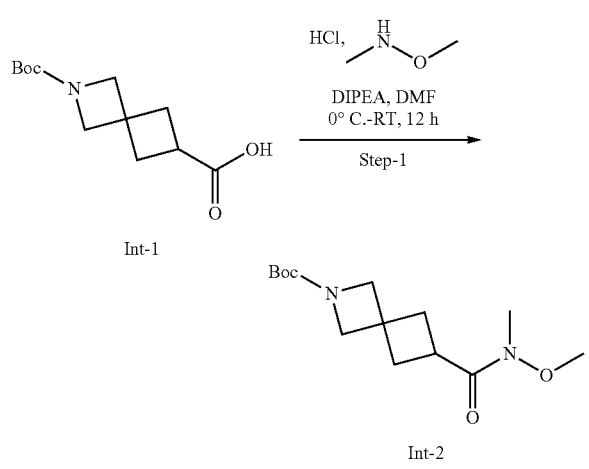

158

To a stirred solution of 2-(tert-butoxycarbonyl)-2-azaspiro[3.3]heptane-6-carboxylic acid (2.0 gm, 8.298 mmol, 1.0 eq.) in N,N-Dimethyl formamide (20 mL) were added HATU (3.15 gm, 8.29 mmol, 1.5 eq.), DIPEA (3.21 gm, 24.89 mmol, 3.0 eq.) followed by addition of N,O-Dimethylhydroxylamine Hydrochoride (1.00 gm, 10.37 mmol, 1.25 eq.) at 0° C. and allowed to stirred the reaction at room temperature for 12 hr; the progress of the reaction of the was monitored by TLC. After completion of reaction, the reaction mixture was diluted with water (25 mL) and extracted with ethyl acetate (3×30 mL), washed with brine. The organic layer was dried over sodium sulphate and concentrated under vacuum to get crude material; which was purified by comnbi-flash by using 100% Ethyl acetate as mobile phase to give desired product tert-butyl 6-(methoxy (methyl)carbamoyl)-2-azaspiro[3.3]heptane-2-carboxylate (Int-2) 1.50 gm (Yield: 63.82%), 1H NMR (400 MHz, DMSO-d6) δ 3.89 (s, 2H), 3.73 (s, 2H), 3.62 (s, 3H), 3.08 (s, 3H), 2.30 (dt, J=8.1, 2.1 Hz, 4H), 1.37 (s, 9H).

Step-2: Synthesis of tert-butyl 6-acetyl-2-azaspiro [3.3] heptane-2-carboxylate (Int-3)

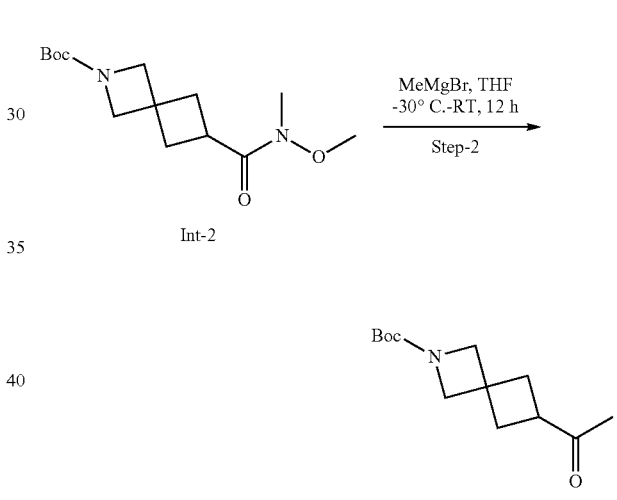

To a stirred solution of tert-butyl 6-(methoxy (methyl) carbamoyl)-2-azaspiro [3.3]heptane-2-carboxylate (Int-2) (1.7 gm, 5.98 mmol, 1.0 eq.) in THF was added Methyl magnesium bromide (3M in THF) (5.98 mL, 17.95 mmol, 3.0 eq.) under inert atmosphere at −30° C. The reaction mixture was stirred at Room temperature for next 12 hr. The progress of the reaction was monitored by TLC; after completion of reaction, the reaction mixture was cooled to 0° C. and quenched with saturated ammonium chloride solution (10 mL) further diluted with water (30 mL) and extracted with ethyl acetate (3×30 mL), washed with brine. The organic layer was dried over sodium sulphate and concentrated under vacuum to get crude material; which was purified by combi-flash by using 80% Ethyl acetate in Hexane as mobile phase to give desired product tert-butyl 6-acetyl-2-azaspiro [3.3] heptane-2-carboxylate (Int-3) 1.30 gm (Yield: 90.90%); 1H NMR (400 MHz, Chloroform-d) δ 3.98 (s, 2H), 3.85 (s, 2H), 3.16 (p, J=8.3 Hz, 1H), 2.46-2.32 (m, 4H), 2.14 (s, 3H), 1.47 (s, 9H).

Step-3: Synthesis of tert-butyl (E)-6-(3-(dimethylamino) acryloyl)-2-azaspiro [3.3] heptane-2-carboxylate (Int-4)

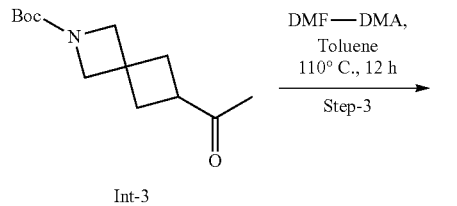

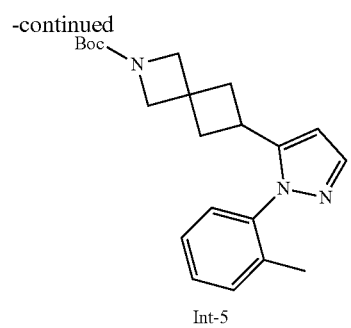

To a stirred solution of tert-butyl 6-acetyl-2-azaspiro[3.3] heptane-2-carboxylate (Int-3) (0.050 gm, 0.209 mmol, 1.0 eq.) in Toluene (1 mL) was added DMF-DMA (0.074 gm, 0.627 mmol, 3.0 eq.) and allowed to stirred the reaction at 100° C. for 12 hr, the progress of the reaction of the was monitored by TLC. After completion of reaction, the reaction mixture was diluted with water (3 mL) and extracted with ethyl acetate (3×5 mL), washed with brine. The organic layer was dried over sodium sulphate and concentrated under vacuum to get crude material; which was purified by combi-flash by using 90% Ethyl acetate in Hexane as mobile phase to give desired product tert-butyl (E)-6-(3 (dimethylamino) acryloyl)-2-azaspiro [3.3] heptane-2-carboxylate (Int-4) 0.040 gm (Yield: 65.04%); LCMS: 295.3 m/z [M+1]+

To a stirred solution of tert-butyl (E)-6-(3 (dimethylamino) acryloyl)-2-azaspiro [3.3]heptane-2-carboxylate (Int-4) (0.30 gm, 0.020 mmol, 1.0 eq.) in Ethanol (9 mL) was added o-tolylhydrazine (0.177 gm, 1.122 mmol, 1.1 eq.) and allowed to stirred the reaction at 90° C. for 12 hr; the progress of the reaction of the was monitored by TLC. After completion of reaction, the reaction mixture was evaporated under vacuum to get crude compound which was absorbed on silica gel and purified by combi-flash by using 100% Ethyl acetate as mobile phase to give desired product tert-butyl 6-(1-(o-tolyl)-1H-pyrazol-5-yl)-2-azaspiro[3.3] heptane-2-carboxylate (Int-5) 0.340 gm (Yield: 94.44%); LCMS: 354.3 m/z [M+1]+

Step-5: Synthesis of 6-(1-(o-tolyl)-1H-pyrazol-5-yl)-2-azaspiro [3.3] heptane (Int-6)

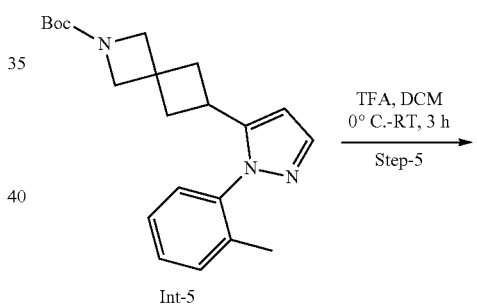

Step-4: Synthesis of tert-butyl 6-(1-(o-tolyl)-1H-pyrazol-5-yl)-2-azaspiro [3.3] heptane-2-carboxylate (Int-5)

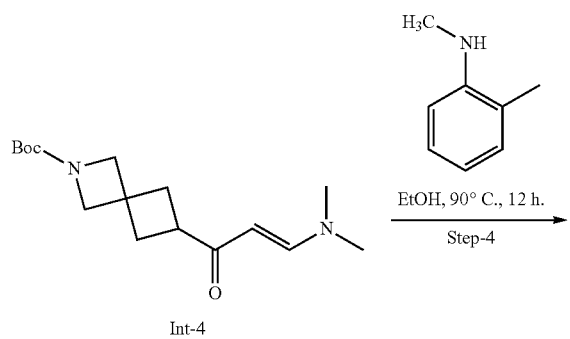

To a stirred solution of tert-butyl 6-(1-(o-tolyl)-1H-pyrazol-5-yl)-2-azaspiro [3.3]heptane-2-carboxylate (Int-5) (0.30 gm, 0.84 mmol, 1.0 eq.) in Dichloromethane (10 mL) was added Trifluoroacetic acid (1.0 mL) at 0° C. and allowed to stirred the reaction at Room temperature for 3 hr; the progress of the reaction of the was monitored by TLC. After completion of reaction, the reaction mixture was evaporated under vacuum and triturated with pentane to afford crude compound 6-(1-(o-tolyl)-1H-pyrazol-5-yl)-2-azaspiro[3.3] heptane (Int-6) 0.30 gm (Yield: quantitative); LCMS: 254.2 m/z [M+1]+

Step-6: Synthesis of (5-(benzyloxy)-2-fluorophenyl)(6-(1-(o-tolyl)-1H-pyrazol-5-yl)-2-azaspiro [3.3]heptan-2-yl) methanone (Int-7)

Step-7: Synthesis of (2-fluoro-5-hydroxyphenyl)(6-(1-(o-tolyl)-1H-pyrazol-5-yl)-2-azaspiro [3.3]heptan-2-yl) methanone (Compound-00367)

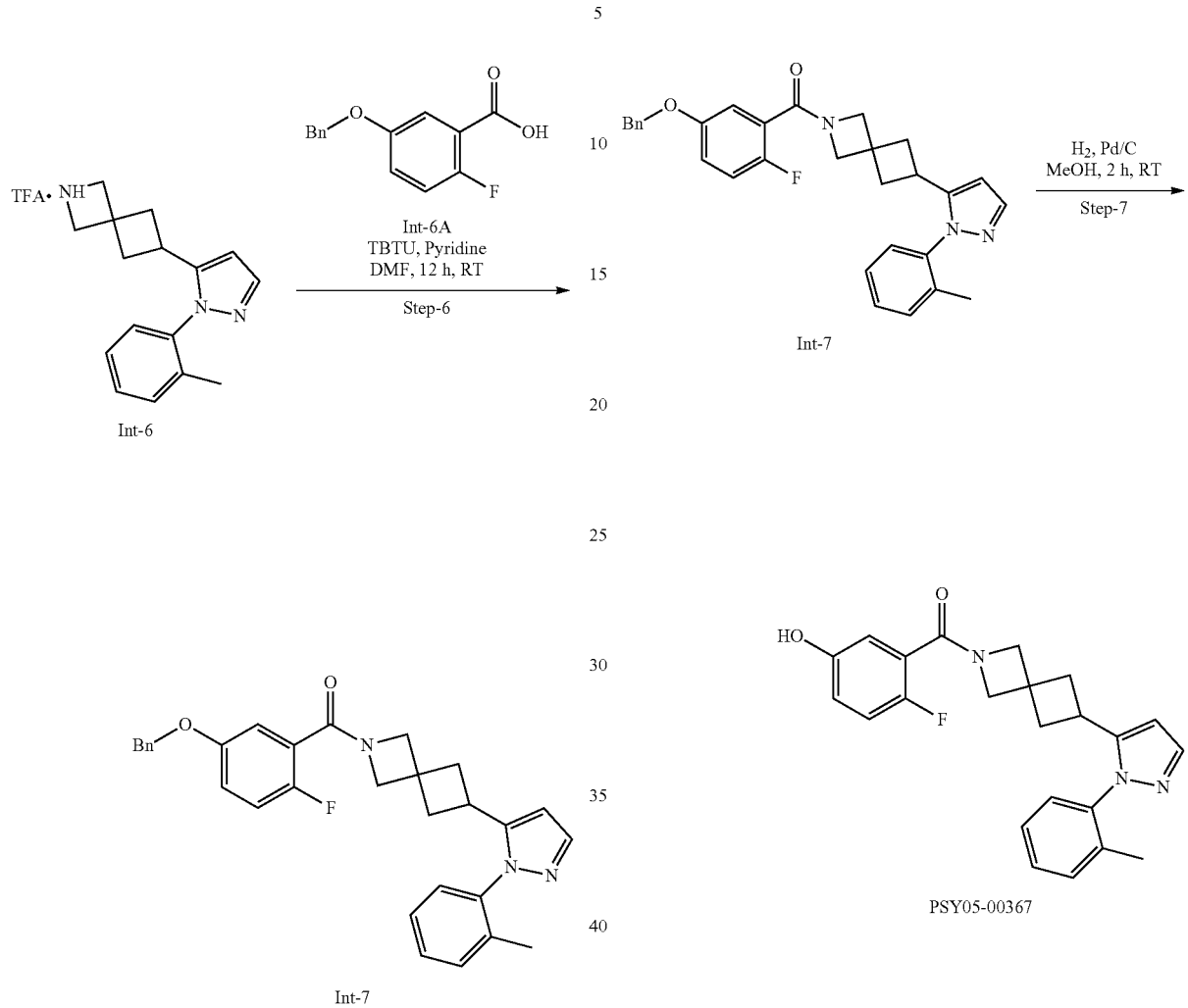

To a stirred solution of 5-(benzyloxy)-2-fluorobenzoic acid 6-(1-(o-tolyl)-1H-pyrazol-5-yl)-2-azaspiro [3.3] heptane (Int-6A) (0.25 gm, 1.016 mmol, 1.0 eq.) in N,N-Dimethyl formamide (10 mL) were added TBTU (0.58 gm, 1.52 mmol, 1.5 eq.) Pyridine (0.24 gm, 3.04 mmol, 3.0 eq.) followed by addition of 6-(1-(o-tolyl)-1H-pyrazol-5-yl)-2-azaspiro [3.3] heptane (Int-6) (0.30 gm, 1.21 mmol, 1.2 eq.) at 0° C. and allowed to stirred the reaction at room temperature for 12 hr; the progress of the reaction of the was monitored by TLC. After completion of reaction, the reaction mixture was diluted with water (15 mL) and extracted with ethyl acetate (3×20 mL), washed with brine. The organic layer was dried over sodium sulphate and concentrated under vacuum to get crude material; which was purified by combi-flash by using 90% Ethyl acetate in Hexane as mobile phase to give desired product (5-(benzyloxy)-2-fluorophenyl)(6-(1-(o-tolyl)-1H-pyrazol-5-yl)-2-azaspiro[3.3]heptan-2-yl)methanone (Int-7), 0.250 gm (Yield: 51.22%); LCMS: 482.3 m/z [M+1]+

To a stirred solution of (5-(benzyloxy)-2-fluorophenyl)(6-(1-(o-tolyl)-1H-pyrazol-5-yl)-2-azaspiro [3.3] heptan-2-yl) methanone (Int-7) (0.20 gm, 0.415 mmol, 1.0 eq.) was dissolved in Methanol (10 mL). 10% Pd/C (with 50% moisture) 0.050 gm was added at Room Temperature and Reaction mixture was allowed to stir for 2 hr. under Hydrogen atmosphere. Reaction was monitored by TLC. After completion of the reaction, Reaction mixture was filtered through celite bed, washed with Methanol (50 mL) and concentrated to get crude compound, which was purified by column chromatography using 60-120 mesh size silica gel and 80% Ethyl acetate in Hexane as mobile phase to give the desired product (2-fluoro-5-hydroxyphenyl)(6-(1-(o-tolyl)-1H-pyrazol-5-yl)-2-azaspiro[3.3]heptan-2-yl)methanone (PSY-05-00367) as a white solid, 0.120 gm, (Yield: 74.07%); LCMS: 392.1 m/z [M+] 1H NMR (400 MHz, DMSO-d6) δ 9.63 (dd, J=8.3, 2.5 Hz, 1H), 7.56 (d, J=9.5 Hz, 1H), 7.41 (t, J=8.5 Hz, 2H), 7.32 (d, J=8.7 Hz, 1H), 7.19 (t, J=7.4 Hz, 1H), 7.05 (tt, J=9.2, 5.3 Hz, 1H), 6.83 (s, 1H), 6.74 (dd, J=5.5, 2.7 Hz, 1H), 6.36 (d, J=18.6 Hz, 1H), 3.94 (dd, J=25.2, 10.5 Hz, 3H), 3.05 (dt, J=18.8, 8.4 Hz, 1H), 2.34 (q, J=12.2, 11.5 Hz, 2H), 2.24 (q, J=10.5, 9.9 Hz, 2H), 1.91 (d, J=2.4 Hz, 3H).

Example 8: Synthesis of [(2-chloro-5-hydroxyphenyl) (6-(3-methyl-1-(o-tolyl)-1H-pyrazol-5-yl)-2-azaspiro [3.3] heptan-2-yl) methanone] [Compound 140]

Synthetic Scheme:

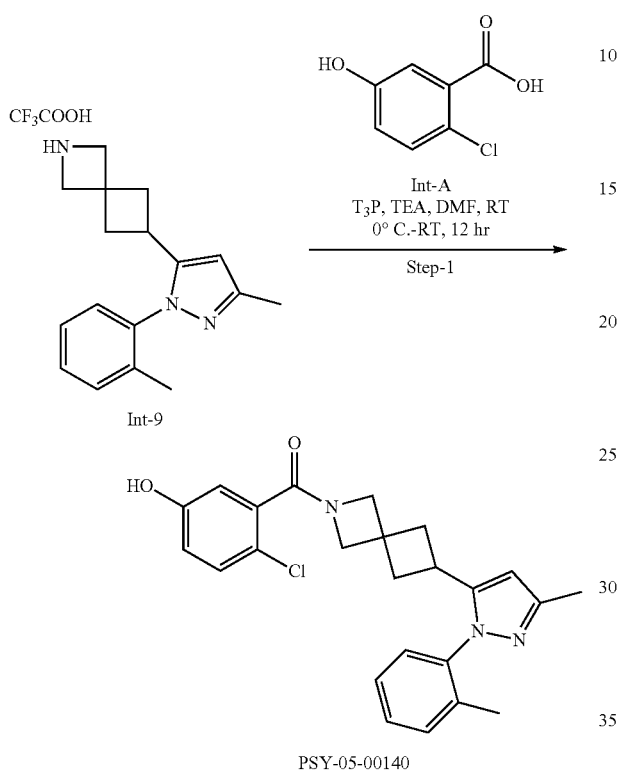

Step-1: Synthesis of [(2-chloro-5-hydroxyphenyl) (6-(3-methyl-1-(o-tolyl)-1H-pyrazol-5-yl)-2-azaspiro [3.3] heptan-2-yl) methanone] [Compound-00140]

To a stirred solution of 6-(3-methyl-1-(o-tolyl)-1H-pyrazol-5-yl)-2-azaspiro [3.3]hept-5-ene 2,2,2-trifluoroacetate (0.100 gm, 0.2624 mmol) in DMF (5.0 mL) were added 2-chloro-5-hydroxybenzoic acid (0.054 gm, 0.314 mmol), Triethylamine (0.106 gm, 1.049 mmol) and Propanephosphonic acid anhydride [T3P, 50 wt. % in ethyl acetate](0.125 gm, 0.393 mmol) at 0° C. The resulting reaction mixture was stirred at room temperature for next 12 hr. The progress of the reaction was monitored by TLC; After completion of reaction, the reaction mixture was diluted with water (10 mL) and extracted with Ethyl acetate (3*50 mL). The organic layer was washed with brine, dried over sodium sulphate and concentrated under vacuum to get crude material; which was purified by Prep HPLC using 0.1% Formic acid in water-100% Acetonitrile as mobile phase to give desired compound as [(2-chloro-5-hydroxyphenyl) (6-(3-methyl-1-(o-tolyl)-1H-pyrazol-5-yl)-2-azaspiro [3.3] heptan-2-yl) methanone] (PSY-05-0140) 0.028 gm (Yield: 26%) m/z 422.6 [M+1]$^+$; $^1$H NMR (400 MHz, DMSO-d$_6$) δ 9.95 (s, 1H), 7.43-7.1 (m, 4H), 7.15 (t, J=7.7 Hz, 1H), 6.80 (t, 1H), 6.67 (d, J=2.8 Hz, 1H), 6.16-6.10 (s, 1H), 3.98 (s, 1H), 3.92 (s, 1H), 3.82 (s, 1H), 3.76 (s, 1H), 2.99 (dt, J=20.8, 8.4 Hz, 1H), 2.32-2.19 (m, 2H), 2.17 (d, J=10.7 Hz, 2H), 2.09 (s, 3H), 1.93 (d, 1=2.2 Hz, 3H).

Example 9: Synthesis of (2-fluoro-5-hydroxyphenyl)(6-(S-(2-fluorophenyl)-4-(trifluoromethyl)-1H-pyrazol-1-yl)-2-azaspiro[3.3]heptan-2-yl)methanone [Compound 472] and (2-fluoro-5-hydroxyphenyl) (6-(3-(2-fluorophenyl)-4-(trifluoromethyl)-1H-pyrazol-1-yl)-2-azaspiro[3.3]heptan-2-yl)methanone [Compound 473]

Synthetic Scheme:

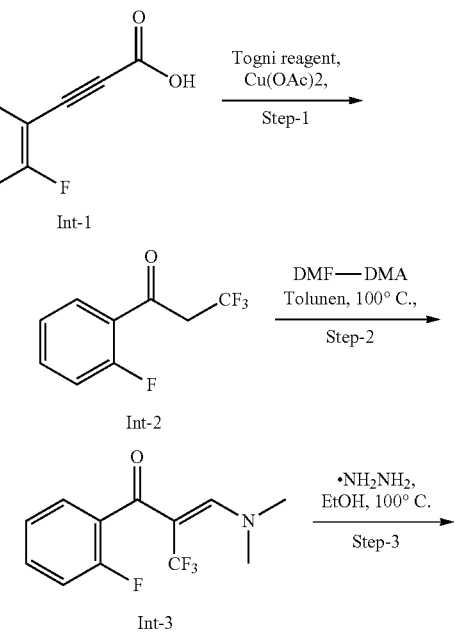

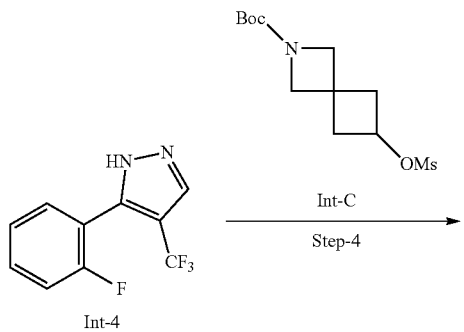

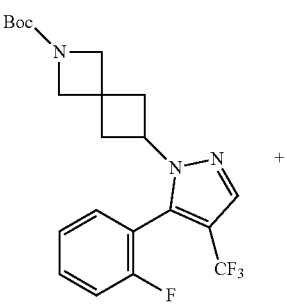

165
-continued

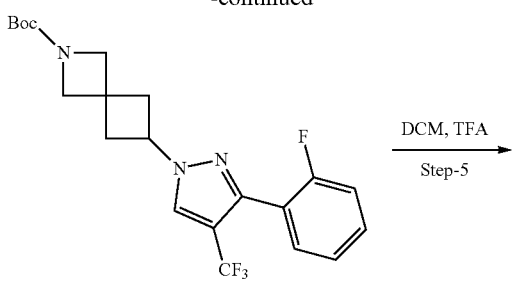

DCM, TFA
Step-5

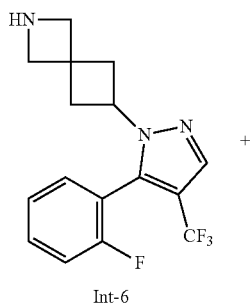

Int-6

+

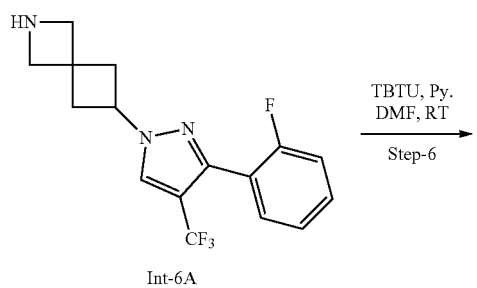

Int-6A

TBTU, Py.
DMF, RT
Step-6

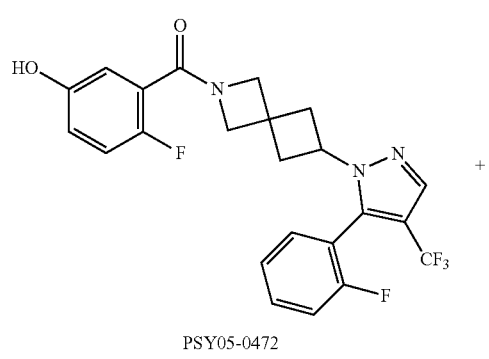

PSY05-0472

+

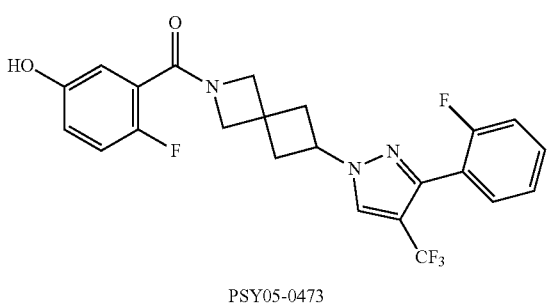

PSY05-0473

166
-continued

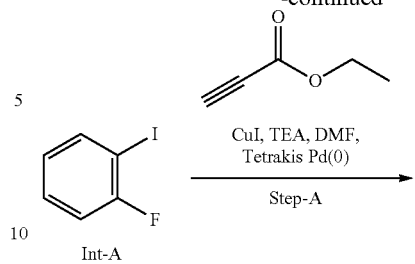

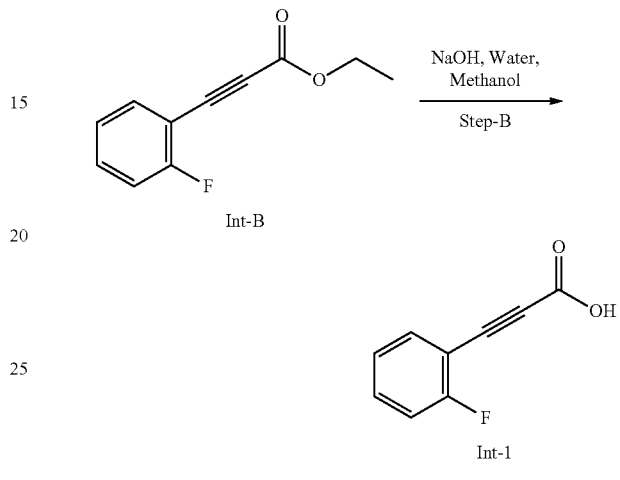

Step-A: ethyl 3-(2-fluoro-phenyl) propiolate (Int-B)

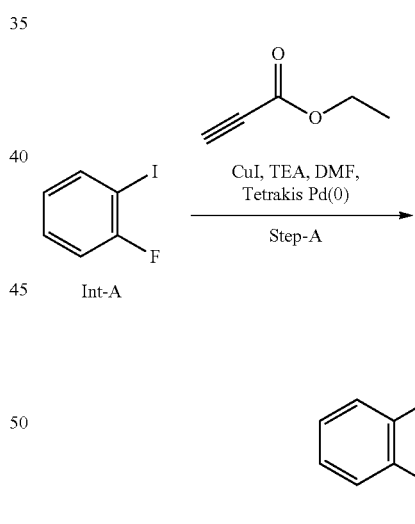

A mixture of the 1-fluoro-2-iodo-benzene (Int-A) (11.3 g, 56.06 mmol, 1.1 eq.). Tetrakis (Triphenyl phosphine) palladium (0) (5.8 g, 5.096 mmol, 0.1 eq.), and CuI (copper (1) iodide) (1.0 g, 5.096 mmol, 0.1 eq.) in Triethylamine (50 ml) was purged with nitrogen and treated with the ethyl propiolate (5.0 g, 50.96 mmol, 1.0 eq). The resultant mixture was stirred at room temperature overnight. The reaction mixture was poured into sat aq.NaHCO$_3$ Sol$^n$ and extracted with ethyl acetate. The organic layer was washed with brine, dried sodium sulphate, decanted, concentrated, and purified by flash chromatography (0-20% ethyl acetate in n-hexane)

to get desired product ethyl 3-(2-fluoro-phenyl)propiolate (Int-B) as a clear oil. (2.0 g, 20.44%).

Step-B: 3-(2-fluoro-phenyl) propiolic acid (Int-1)

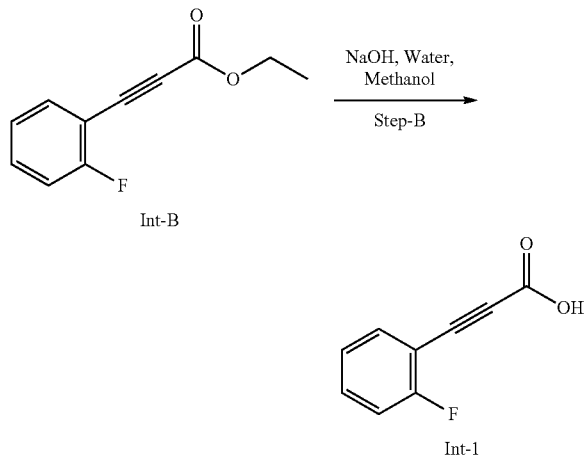

To a solution of the ethyl 3-(2-fluoro-phenyl) propiolate (Int-B) (2.0 g, 10.42 mmol, 1.0 eq.) in Methanol (5 mL) and H₂O (15 mL) was added NaOH (0.916 g, 22.91 mmol, 2.2 eq.). The mixture stirred at room temperature for 16 h, then concentrated in vacuum. The crude was diluted with water (100 mL) and acidified with an aq. solution of 2M HCl. This aq mixture was extracted with ethyl acetate (2×200 mL) and the combined organic extracts were washed with brine (400 mL), dried over sodium sulphate and concentrated in vacuum to provide to product of 3-(2-fluoro-phenyl) pro-piolic acid (Int-1) as solid. (1.6 g, 93.63%).

Step-1: 3,3,3-trifluoro-1-(2-fluoro-phenyl)propan-1-one (Int-2)

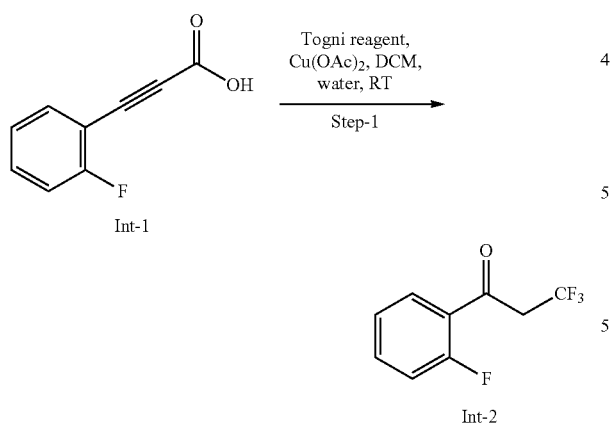

A Sealed test tube with a magnetic stirring bar was charged with 3-(2-fluoro-phenyl) propiolic acid (1.6 g, 9.816 mmol, 1.0 eq.) Togni-(II) (6.4 g, 19.632 mmol, 2.0 eq.) Cu(OAc)₂·H₂O (3.56 g, 19.632 mmol, 2.0 eq), TMEDA (3.6 mL, 24.54 mmol, 2.5 eq.), followed by dichloromethane (16 mL) and H₂O (24 mL). The reaction mixture was stirred at room temperature. After stirring for 24 h, the reaction mixture was extracted with dichloromethane (15 mL×3), dried over sodium sulphate, filtered and concentrated. The residue was purified with silica gel chromatography to provide pure product of 3,3,3-trifluoro-1-(2-fluoro-phenyl) propan-1-one (Int-2) as solid (0.200 g, 9.95%).

Step-2: (Z)-3-(dimethylamino)-1-(2-fluorophenyl)-2-(trifluoromethyl) prop-2-en-1-one (Int-3)

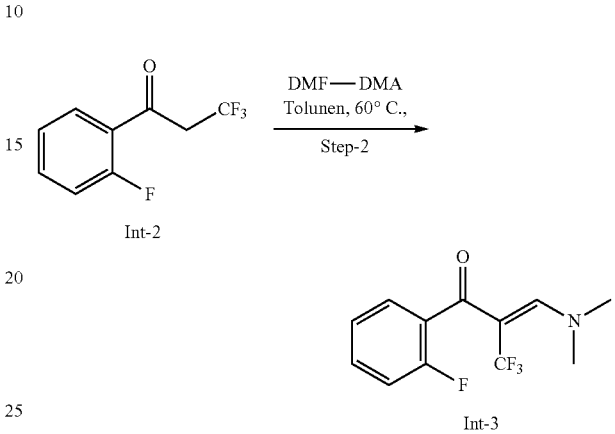

To a stirred solution of 3,3,3-trifluoro-1-(2-fluoro-phenyl) propan-1-one (Int-2) (1.5 g, 7.28 mmol, 1.0 eq.) in Toluene (10 mL) was added N,N-Dimethylformamide dimethyl-acetal (2.6 g, 21.84 mmol, 3.0 eq.) the reaction mass was heated at 60° C. for 16 h. After completion of reaction as monitored by TLC, the reaction mixture was poured in ice cold water (100 mL) and extracted with ethyl acetate (50 mL*3). The organic layer was washed with brine (100 mL), dried over sodium sulphate and concentrated under reduce pressure to get residue. The residue was purified by com-biflash using 15-20% ethyl acetate in n-hexane as eluent to get (Z)-3-(dimethylamino)-1-(2-fluorophenyl)-2-(trifluo-romethyl) prop-2-en-1-one (Int-3) (1.5 g, 78.91%).

Step-3: 5-(2-fluorophenyl)-4-(trifluoromethyl)-1H-pyrazole (Int-4)

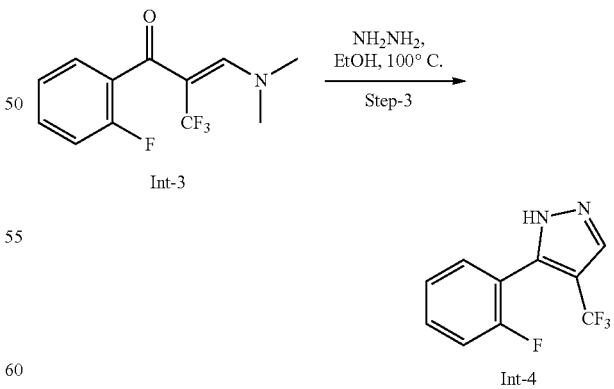

To a stirred solution of (Z)-3-(dimethylamino)-1-(2-fluo-rophenyl)-2-(trifluoromethyl)prop-2-en-1-one (1.5 g, 6.95 mmol, 1.0 eq.) in isopropyl alcohol (10 mL) was added hydrazine hydrate (0.38 g, 7.65 mmol, 1.1 eq.) the reaction mass was heated at 80° C. for 16 hr. After completion of reaction as monitored by TLC, the reaction mixture was concentrated to get residue. The residue was purified by combiflash using 15-20% ethyl acetate in n-hexane as eluent to get 5-(2-fluorophenyl)-4-(trifluoromethyl)-1H-pyrazole (Int-4) (0.90 g, 68.01%).

Step-4: Tert-butyl6-(5-(2-fluoro-phenyl)-4-(trifluoromethyl)-1H-pyrazol-1-yl)-2-azaspiro [3.3] heptane-2-carboxylate (Int-5) and tert-butyl6-(3-(2-fluoro-phenyl)-4-(trifluoromethyl)-1H-pyrazol-1-yl)-2-azaspiro [3.3] heptane-2-carboxylate (Int-5A)

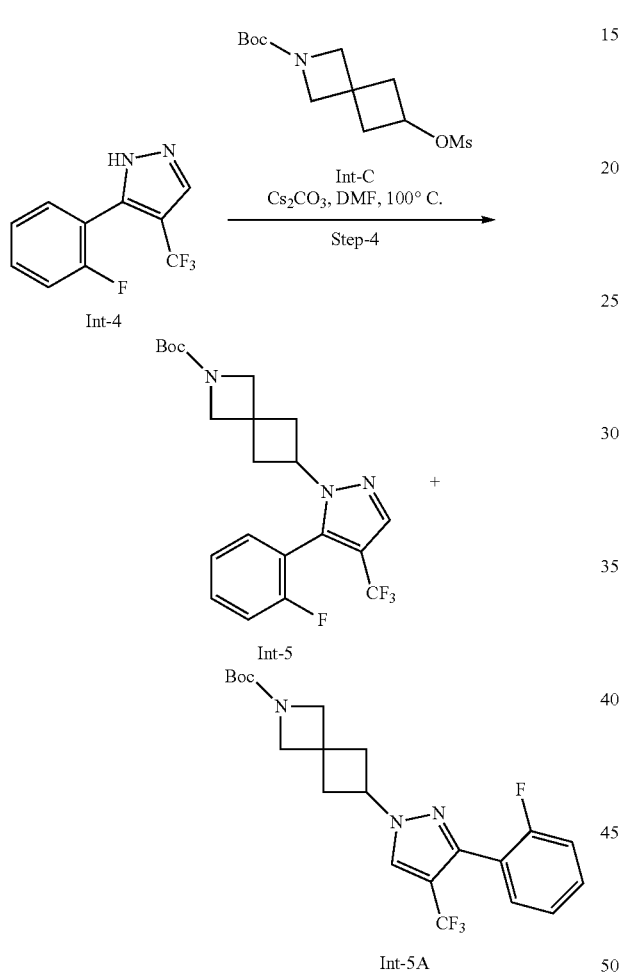

To a solution of 5-(2-fluoro-5-methylphenyl)-4-(trifluoromethyl)-1H-pyrazole (Int-4) (0.900 g, 3.9121 mmol, 1.0 eq.) in N,N-Dimethylformamide (10 mL), tert-butyl 6-((methyl sulfonyl) oxy)-2-azaspiro[3.3]heptane-2-carboxylate (Int-C) (1.37 g, 4.694 mmol, 1.2 eq.) and cesium carbonate (2.54 g, 7.824 mmol, 2.0 eq.) were added, and the reaction mixture was heated at 100° C. for 16 hr. After cooling to room temperature, the reaction mixture was poured into water (20 mL), and the solution was extracted with ethyl acetate (3×20 mL). The combined organic layers were washed with brine (20 mL), dried over sodium sulfate, filtered and concentrated under reduced pressure. The residue was purified by flash column chromatography on silica gel with ethyl acetate and n-hexane to get two region isomers of tert-butyl6-(5-(2-fluoro-phenyl)-4-(trifluorom-ethyl)-1H-pyrazol-1-yl)-2-azaspiro[3.3]heptane-2-carboxylate (Int-5) and tert-butyl6-(3-(2-fluoro-phenyl)-4-(trifluoromethyl)-1H-pyrazol-1-yl)-2-azaspiro[3.3]heptane-2-carboxylate (Int-5A) (1.0 g, 60.11%).

Step-5: 6-(5-(2-fluoro-phenyl)-4-(trifluoromethyl)-1H-pyrazol-1-yl)-2-azaspiro [3.3] heptane (Int-6) and 6-(3-(2-fluoro-5phenyl)-4-(trifluoromethyl)-1H-pyrazol-1-yl)-2-azaspiro [3.3] heptane (Int-6A)

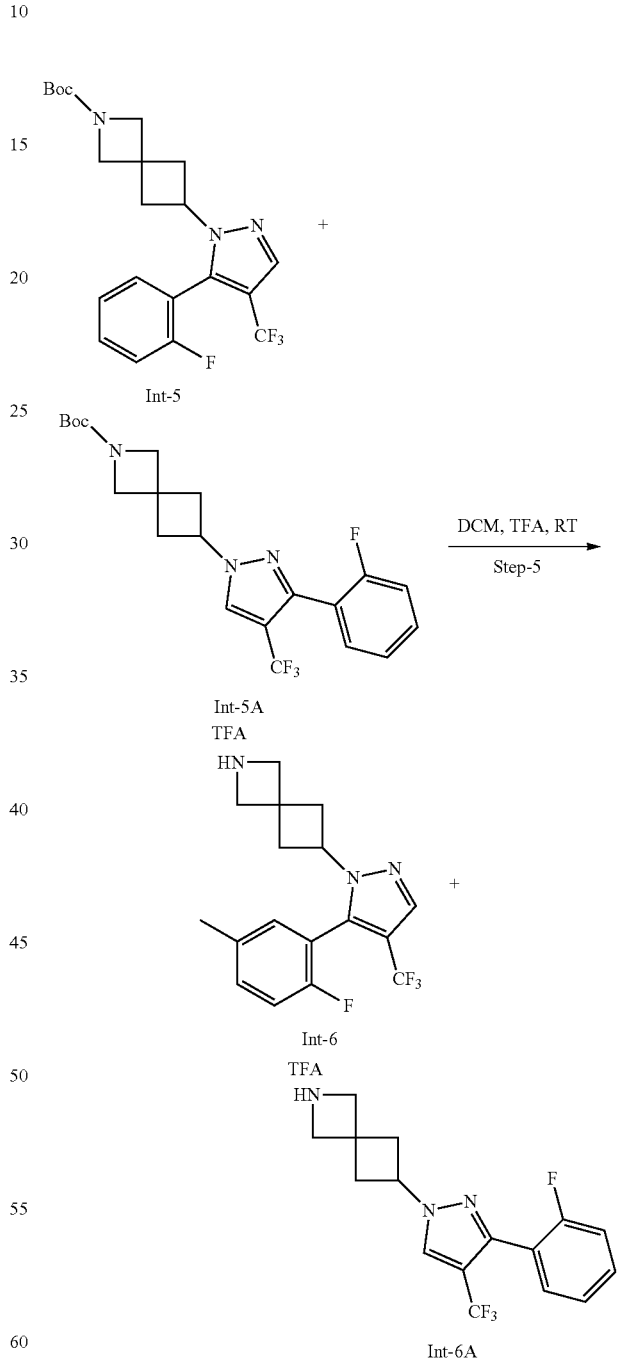

To a stirred solution of tert-butyl6-(5-(2-fluoro-phenyl)-4-(trifluoromethyl)-1H-pyrazol-1-yl)-2-azaspiro [3.3] heptane-2-carboxylate (Int-5) and tert-butyl6-(3-(2-fluoro-phenyl)-4-(trifluoromethyl)-1H-pyrazol-1-yl)-2-azaspiro[3.3] heptane-2-carboxylate (Int-5A) (1.0 g, 0.6605 mmol, 1.0 eq.) in dichloromethane (10 ml) was added Trifluroacetic acid (2.5 mL, 2.5 v) at 0° C. The reaction was stirred at room temperature for 16 hr. After completion of reaction as monitored by TLC, the reaction mixture was concentrated and triturated with mixture of diethyl ether and hexane (1:1, 10 ml*3) to get two regio-isomers. 6-(5-(5-fluoro-phenyl)-3-methyl-1H-pyrazol-1-yl)-2-azaspiro [3.3] heptane (Int-6) and 6-(3-(5-fluoro-phenyl)-5-methyl-1H-pyrazol-1-yl)-2-azaspiro [3.3] heptane) (Int-6A) (1.5 g (TFA salt).

Step-6: 2-fluoro-5-hydroxyphenyl)(6-(5-(2-fluoro-phenyl)-4-(trifluoromethyl)-1H-pyrazol-1-yl)-2-azaspiro[3.3]heptan-2-yl)methanone (PSY-05-00474-001) and 2-fluoro-5-hydroxyphenyl)(6-(3-(2-fluorophenyl)-4-(trifluoromethyl)-1H-pyrazol-1-yl)-2-azaspiro[3.3]heptan-2-yl)methanone (PSY-05-00475-001)

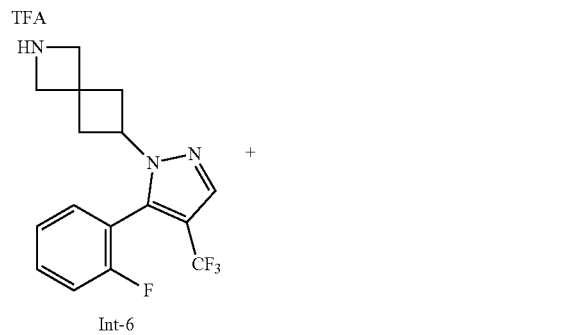

Int-6

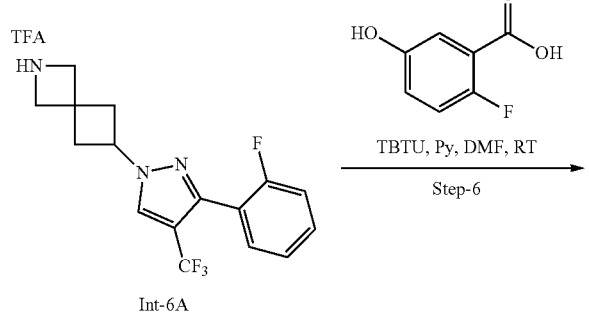

Int-6A

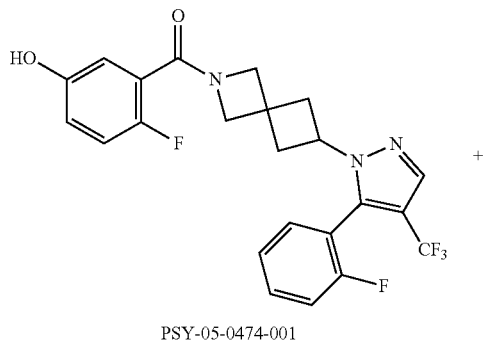

PSY-05-0474-001

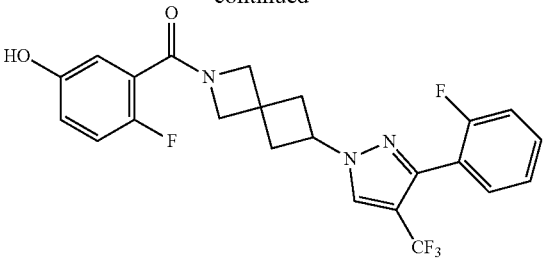

PSY-05-0475-001

To a stirred solution of 6-(5-(5-fluoro-phenyl)-3-methyl-1H-pyrazol-1-yl)-2-azaspiro[3.3]heptane(INT-5)&6-(3-(5-fluoro-phenyl)-5-methyl-1H-pyrazol-1-yl)-2-azaspiro[3.3] heptane) (Int-5A) (0.500 g, 1.537 mmol, 1.0 eq.) in N,N-Dimethylformamide (5.0 mL) were added, pyridine (1.07 g, 15.37 mmol, 10.0 eq.), TBTU (0.740 g, 0.2.306 mmol, 1.5 eq.) at 0° C. Reaction to stirred for 15 min. then to add a 2-fluoro-5-hydroxybenzoic acid (0.359 g, 2.306 mmol, 1.5 eq.) at 0° C. The resulting reaction mixture was stirred at room temperature for 16 hr. After completion of reaction as monitored by TLC, the reaction mixture was diluted with water (15 ml) and extracted with ethyl acetate (3*20 ml) and again washed with sat. NaHCO₃ solution. The organic layer was dried over sodium sulphate and concentrated under vacuum to get crude material which was purified by using reverse phase Prep-HPLC. To get two fraction.

Fraction-1: (2-fluoro-5-hydroxyphenyl)(6-(3-(2-fluoro-phenyl)-4-(trifluoromethyl)-1H-pyrazol-1-yl)-2-azaspiro [3.3]heptan-2-yl)methanone (PSY-05-00473-001) (0.012 g 1.68%). LCMS: m/z 464.01 [M+H]⁺. ¹H NMR (400 MHz, DMSO-di) δ 9.68 (s, 1H), 8.12 (d, J=9.7 Hz, 1H), 7.63-7.43 (dq, J=19.3, 9.9, 7.4 Hz, 4H), 7.08 (q, J=9.5 Hz, 1H), 6.85 (s, 1H), 6.77 (s, 1H), 4.50 (dt, J=14.3, 7.5 Hz, 1H), 4.03 (d, J=9.0 Hz, 4H), 2.79-2.63 (m, 4H).

Fraction-2: 2-fluoro-5-hydroxyphenyl)(6-(5-(2-fluoro-phenyl)-4-(trifluoromethyl)-1H-pyrazol-1-yl)-2-azaspiro [3.3]heptan-2-yl)methanone (PSY-05-00472-001) (0.031 g 4.35%). LCMS: m/z 464.41 [M+H]⁺. ¹H NMR (400 MHz, DMSO-d₆) δ 9.69 (d, J=5.5 Hz, 1H), 8.62 (d, J=9.6 Hz, 1H), 7.53 (s, 1H), 7.51-7.42 (m, 1H), 7.39-7.25 (m, 2H), 7.10 (q, J=9.0 Hz, 1H), 6.89-6.84 (m, 1H), 6.81 (s, 1H), 4.90 (dt, J=23.7, 7.9 Hz, 1H), 4.16 (d, J=10.3 Hz, 2H), 4.06 (d, J=8.1 Hz, 2H), 2.74 (dd, J=24.9, 10.1 Hz, 4H).

Example 10: Synthesis of (2-fluoro-5-hydroxyphenyl)(6-(3-(2-fluoro-5-methylphenyl)-4-(trifluoromethyl)-1H-pyrazol-1-yl)-2-azaspiro[3.3]heptan-2-yl) methanone [Compound 474]; and (2-fluoro-5-hydroxyphenyl)(6-(5-(2-fluoro-5-methylphenyl)-4-(trifluoromethyl)-1H-pyrazol-1-yl)-2-azaspiro [3.3] heptan-2-yl)methanone [Compound 475]

Synthetic Scheme:

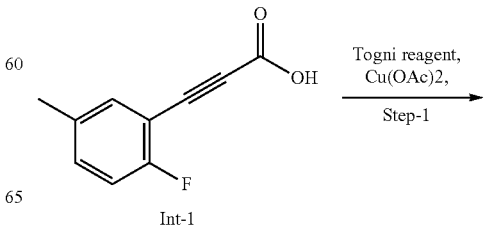

Int-1

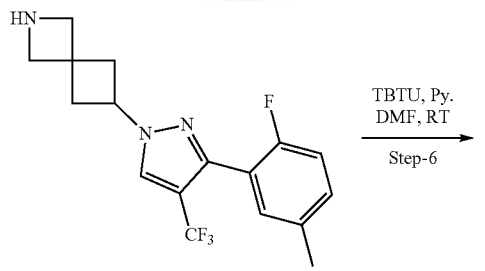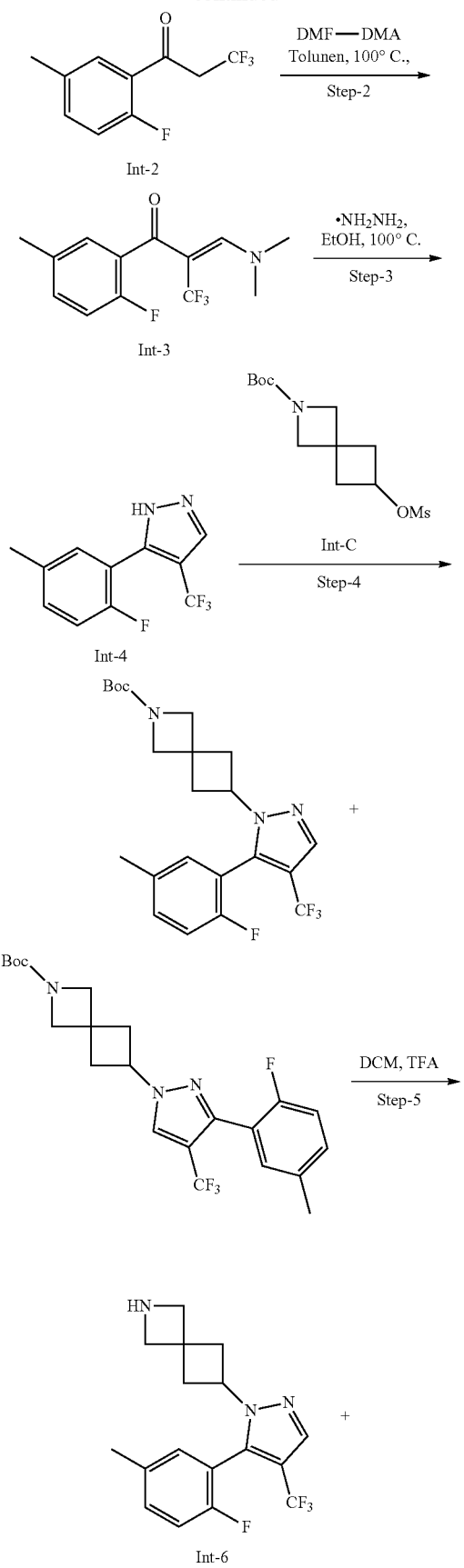

Step-A: ethyl 3-(2-fluoro-5-methylphenyl) propiolate (Int-A)

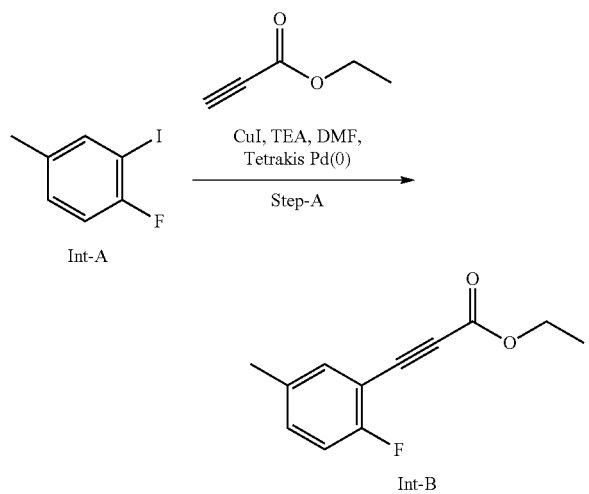

A mixture of the A1-fluoro-2-iodo-4-methylbenzene (Int-A) (5.0, 21.19 mmol, 1.0 eg.), Tetrakis (Triphenyl phosphine) palladium (0) (2.4 g, 2.119 mmol, 0.1 eq.) and CuI (0.403 g, 2.119 mmol, 0.1 eq.) in Triethylamine (30 mL) was purged with nitrogen and treated with the ethyl propiolate (2.28 g, 23.30 mmol, 1.1 eq.). The resultant mixture was stirred at room temperature overnight. The reaction mixture was poured into sat aq NaHCO3 (Sodium bicarbonate) and extracted with Ethyl acetate. The organic layer was washed with brine, dried over sodium sulfate, concentrated, and purified by flash chromatography (0-20% Ethyl acetate/hexane) to get desired product Ethyl 3-(2-fluoro-5-methylphenyl) propiolate (Int-B) as a clear oil. (1.0 g, 22.89%).

Step-B: 3-(2-fluoro-5-methylphenyl) propiolic acid (Int-1)

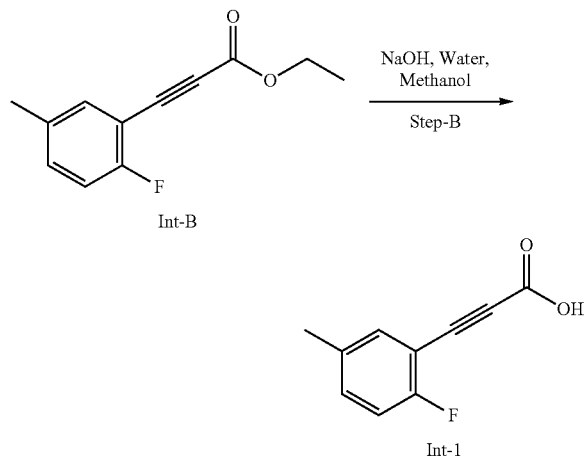

To a solution of the ethyl 3-(2-fluoro-5-methylphenyl) propiolate (1.0 g, 4.854 mmol, 1.0 eq.) in Methanol (5 mL) and H$_2$O (15 mL) was added NaOH (Sodium hydroxide) (0.388 g, 9.7086 mmol, 2.0 eq.). The mixture stirred at room temperature for 16 h, then concentrated in vacuum. The crude was diluted with H$_2$O (100 mL) and acidified with an aq solution of 2M HCl (Hydrochloric acid). This aq mixture was extracted with Ethyl acetate (2×200 mL) and the combined org extracts were washed with brine (400 mL), dried (MgSO4), and concentrated in vacuum to provide to product of 3-(2-fluoro-5-methylphenyl) propiolic acid (Int-1) as a solid. (0.500 g, 57.87%)

Step-1: 3,3,3-trifluoro-1-(2-fluoro-5-methylphenyl) propan-1-one (Int-2)

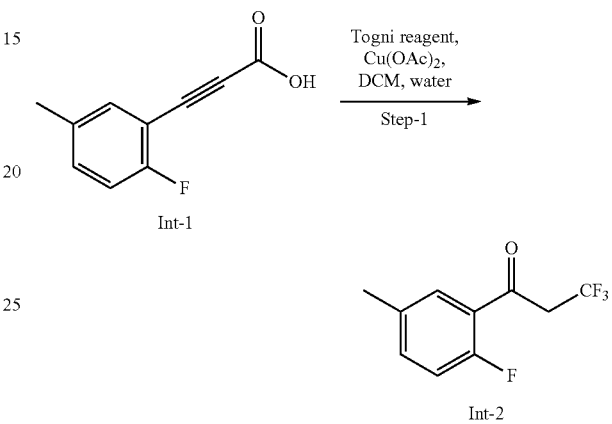

A Sealed test tube with a magnetic stirring bar was charged with 3-(2-fluoro-5-methylphenyl) propiolic acid (1.0 g, 5.6179 mmol, 1.0 eq.) Togni (II) (1.77 g, 5.6179 mmol, 1.0 eq.) Cu(OAc)$_2$H$_2$O (Cupric acetate hydrate) (2.04 g, 11.24 mmol, 2.0 eq.), TMEDA (1,2-Bis(dimethylamino)ethane) (1.306 g, 1.24 mmol, 2.0 eq.), followed by Dichloromethane (10 mL) and H$_2$O (10.5 mL). The reaction mixture was stirred at room temperature. After stirring for 24 hr., the reaction mixture was extracted with Dichloromethane (15 mL×3), dried over sodium sulphate and concentrated. The residue was purified with silica gel chromatography to provide pure product of 3,3,3-trifluoro-1-(2-fluoro-5-methylphenyl)propan-1-one (Int-2) as solid (0.350 g, 28.32%).

Step-2: (Z)-3-(dimethylamino)-1-(2-fluoro-5-methylphenyl)-2-(trifluoromethyl) prop-2-en-1-one (Int-3)

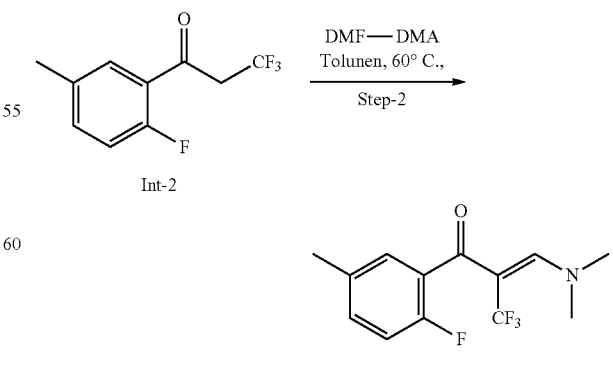

To a stirred solution of 3,3,3-trifluoro-1-(2-fluoro-5-methylphenyl)propan-1-one (0.90 g, 4.12 mmol, 1.0 eq.) in Toluene (10 mL) was added N,N-Dimethylformamide dimethylacetal (1.47 g, 12.38 mmol, 3.0 eq.) the reaction mass was heated at 60° C. for 16 h. After completion of reaction as monitored by TLC, the reaction mixture was poured in ice cold water (100 mL) and extracted with ethyl acetate (50 mL*3). The organic layer was washed with brine (100 mL), dried over Na₂SO₄ and concentrated under reduce pressure to get residue. The residue was purified by combiflash using 15-20% ethyl acetate in hexane as eluent to get (Z)-3-(dimethylamino)-1-(2-fluoro-5-methylphenyl)-2-(trifluoromethyl) prop-2-en-1-one (Int-3) (0.47 g, 41.77%).

Step-3: 5-(2-fluoro-5-methylphenyl)-4-(trifluoromethyl)-1H-pyrazole (Int-4)

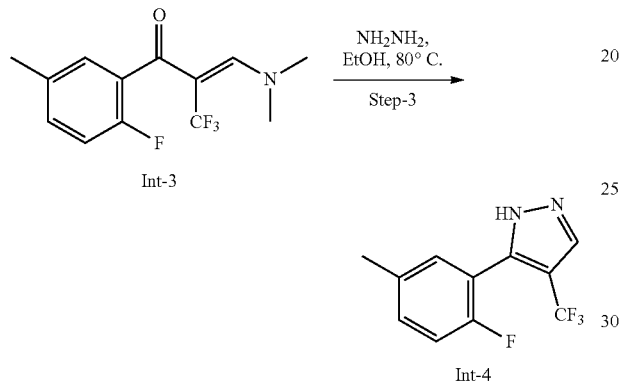

To a stirred solution of (Z)-3-(dimethylamino)-1-(2-fluoro-5-methylphenyl)-2-(trifluoromethyl)prop-2-en-1-one (0.47 g, 1.70 mmol, 1.0 eq.) in Isopropyl alcohol (5 mL) was added hydrazine hydrate (0.128 g, 2.56 mmol, 1.5 eq.) the reaction mass was heated at 80° C. for 16 hr. After completion of reaction as monitored by TLC, the reaction mixture was concentrated to get residue. The residue was purified by combiflash using 15-20% ethyl acetate in n-hexane as eluent to get 5-(2-fluoro-5-methylphenyl)-4-(trifluoromethyl)-1H-pyrazole (Int-4) (0.290 g, 69.55%).

Step-4: Tert-butyl6-(5-(2-fluoro-5-methylphenyl)-4-(trifluoromethyl)-1H-pyrazol-1-yl)-2-azaspiro [3.3] heptane-2-carboxylate (Int-5) and tert-butyl6-(3-(2-fluoro-5-methylphenyl)-4-(trifluoromethyl)-1H-pyrazol-1-yl)-2-azaspiro[3.3]heptane-2-carboxylate (Int-5A)

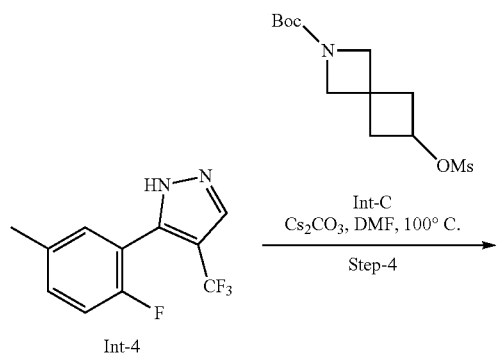

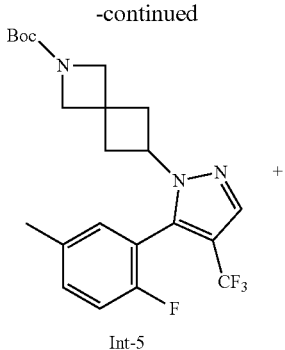

To a solution of 5-(2-fluoro-5-methylphenyl)-4-(trifluoromethyl)-1H-pyrazole (Int-4) (0.270 g, 1.1065 mmol, 1.0 eq.) in N,N-Dimethylformamide (4.8 mL), tert-butyl 6-((methyl sulfonyl)oxy)-2-azaspiro [3.3] heptane-2-carboxylate (Int-C) (0.386 g, 1.328 mmol, 1.2 eq.) and cesium carbonate (0.719 g, 2.213 mmol, 2.0 eq.) were added. The reaction mixture was heated at 100° C. for 16 h. After cooling to room temperature. The reaction mixture was poured into water (20 mL), and the solution was extracted with ethyl acetate (3×20 mL). The combined organic layers were washed with brine (20 mL), dried over sodium sulfate, concentrated under reduced pressure. The residue was purified by flash column chromatography on silica gel with n-hexane and ethyl acetate to get two region isomers of tert-butyl6-(5-(2-fluoro-5-methylphenyl)-4-(trifluoromethyl)-1H-pyrazol-1-yl)-2-azaspiro [3.3] heptane-2-carboxylate (Int-5) and tert-butyl6-(3-(2-fluoro-5-methylphenyl)-4-(trifluoromethyl)-1H-pyrazol-1-yl)-2-azaspiro[3.3] heptane-2-carboxylate (Int-5A) (0.450 g, 92.61%).

Step-5: 6-(5-(2-fluoro-5-methylphenyl)-4-(trifluoromethyl)-1H-pyrazol-1-yl)-2-azaspiro [3.3] heptane (Int-6) and 6-(3-(2-fluoro-5-methylphenyl)-4-(trifluoromethyl)-1H-pyrazol-1-yl)-2-azaspiro [3.3]heptane (Int-6A)

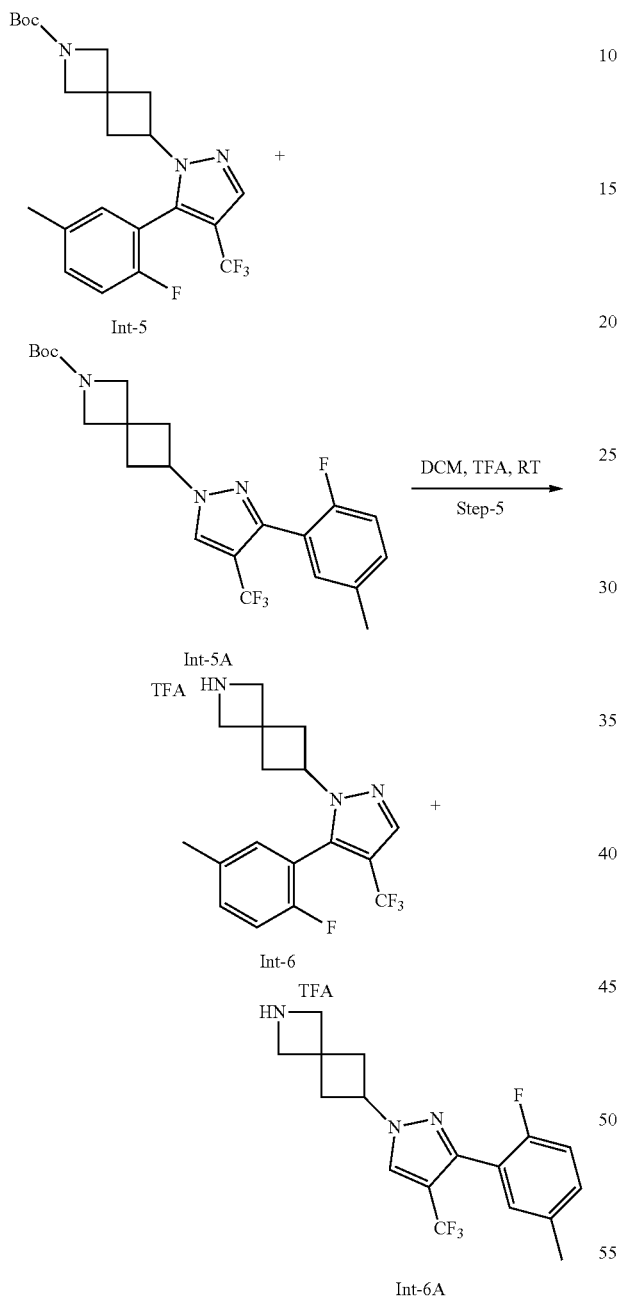

mixture was concentrated and triturated with mixture of diethyl ether and n-hexane (1:1, 10 mL*3) to get two regio-isomers. 6-(5-(5-fluoro-2-methylphenyl)-3-methyl-11H-pyrazol-1-yl)-2-azaspiro [3.3] heptane (Int-6) 6-(3-(5-fluoro-2-methylphenyl)-5-methyl-11H-pyrazol-1-yl)-2-azaspiro [3.3] heptane) (Int-6A) as a TFA salt (0.210 g, crude).

Step-6: 2-fluoro-5-hydroxyphenyl)(6-(5-(2-fluoro-5-methylphenyl)-4-(trifluoromethyl)-1H-pyrazol-1-yl)-2-azaspiro[3.3]heptan-2-yl)methanone (PSY-05-00474-001) & 2-fluoro-5-hydroxyphenyl)(6-(3-(2-fluoro-5-methylphenyl)-4-(trifluoromethyl)-1H-pyrazol-1-yl)-2-azaspiro[3.3]heptan-2-yl)methanone (PSY-05-00475-001)

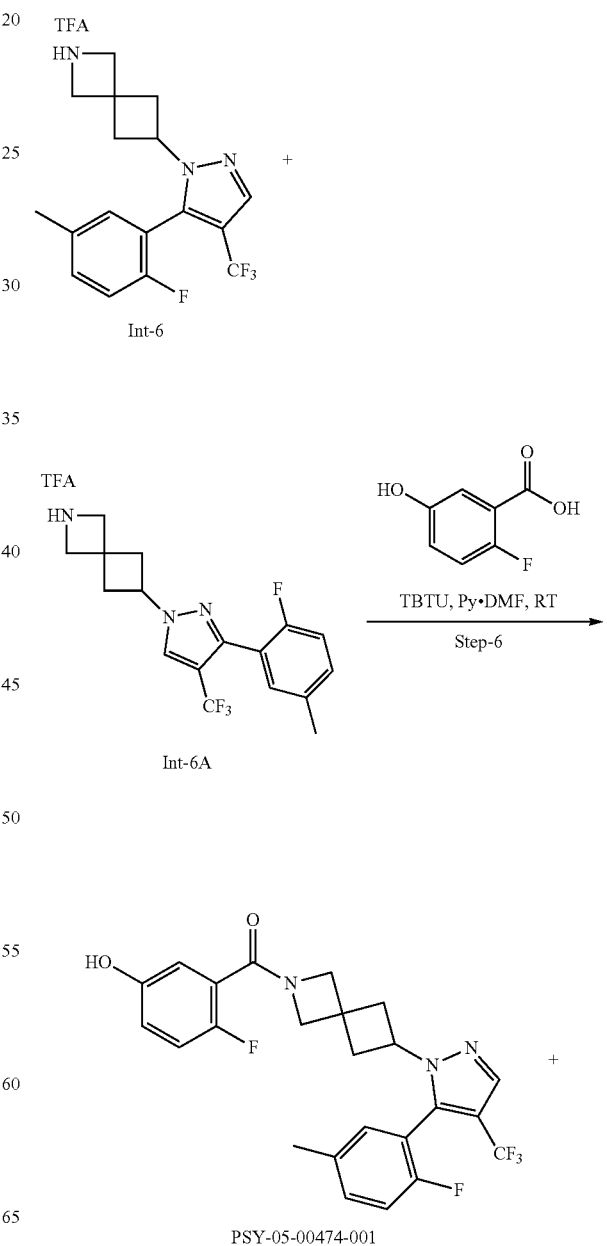

To a stirred solution of tert-butyl6-(5-(2-fluoro-5-methylphenyl)-4-(trifluoromethyl)-1H-pyrazol-1-yl)-2-azaspiro [3.3]heptane-2-carboxylate (Int-5) and tert-butyl6-(3-(2-fluoro-5-methylphenyl)-4-(trifluoromethyl)-1H-pyrazol-1-yl)-2-azaspiro[3.3]heptane-2-carboxylate (Int-5A) (0.290 g, 0.6605 mmol, 1.0 eq.) in dichloromethane (3.0 mL) was added Trifluroacetic acid (0.725 mL, 2.5 v) at 0° C. The reaction was stirred at room temperature for 16 hr. After completion of reaction as monitored by TLC, the reaction -continued

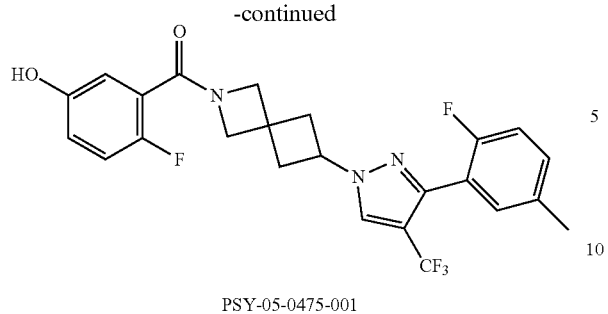

PSY-05-0475-001

To a stirred solution of 6-(5-(5-fluoro-2-methylphenyl)-3-methyl-1H-pyrazol-1-yl)-2-azaspiro[3.3]heptane (Int-6) 6-(3-(5-fluoro-2-methylphenyl)-5-methyl-1H-pyrazol-1-yl)-2-azaspiro[3.3]heptane)(Int-6A) (0.210 g, 0.6192 mmol, 1.0 eq.) in N,N-Dimethylformamide (2.0 mL) were added pyridine (0.247 g, 6.192 mmol, 10.0 eq.), 2-(1H-Benzotriazole-1-yl)-1,1,3,3-tetramethylaminium tetra fluoroborate (TBTU) (0.298 g, 0.9288 mmol, 1.5 eq.) at 0° C. and stirred for 15 mins. Then to added 2-fluoro-5-hydroxybenzoic acid (0.144 g, 0.9288 mmol, 1.5 eq.) at 0° C. The resulting reaction mixture was stirred at room temperature for 16 h. After completion of reaction as monitored by TLC, the reaction mixture was diluted with water (15 mL) and extracted with ethyl acetate (3*20 mL) and washed with sat. Sodium carbonate (NaHCO$_3$) solution. The organic layer was dried over sodium sulphate and concentrated under vacuum to get crude material which was purified by using Prep-HPLC using 1% formic acid in water:acetonitrile. To get two fractions.

Fraction-1: (2-fluoro-5-hydroxyphenyl)(6-(3-(2-fluoro-5-methylphenyl)-4-(trifluoromethyl)-1H-pyrazol-1-yl)-2-azaspiro[3.3]heptan-2-yl)methanone (PSY-05-00475-001) (0.023 g 8.2%). LCMS: 478.41 m/z [M+1]$^+$. $^1$H NMR (400 MHz, DMSO-d$_6$) δ 9.67 (s, 1H), 8.11 (d, J=9.9 Hz, 1H), 7.45 (s, 1H), 7.39-7.18 (m, 2H), 7.08 (q, J=9.6 Hz, 1H), 6.85 (s, 1H), 6.77 (s, 1H), 4.49 (dt, J=14.5, 7.7 Hz, 1H), 4.03 (d, J=8.7 Hz, 4H), 2.68 (ddt, J=51.2, 19.7, 8.6 Hz, 2H), 2.47 (m, 2H), 2.35 (d, J=9.5 Hz, 3H).

Fraction-2: (2-fluoro-5-hydroxyphenyl)(6-(5-(2-fluoro-5-methylphenyl)-4-(trifluoromethyl)-1H-pyrazol-1-yl)-2-azaspiro[3.3]heptan-2-yl)methanone (PSY-05-00474-001) (0.011 g 3.9%). LCMS: m/z 478.40 [M+1]$^+$ $^1$H NMR (400 MHz, DM SO-d$_6$) δ 9.67 (s, 1H), 8.1 (d, J=9.9 Hz, 1H), 7.29-7.20 (m, 3H), 7.09 (q, J=9.6 Hz, 1H), 6.84 (s, 1H), 6.79 (s, 1H), 4.88 (dt, J=14.5, 7.7 Hz, 1H), 4.03 (d, J=8.7 Hz, 4H), 2.74 (ddt, J=51.2, 19.7, 8.6 Hz, 4H), 2.35 (d, J=9.5 Hz, 3H).

Example 11: Synthesis of (6-(5-(2,5-Difluorophenyl)-4-methyl-1H-pyrazol-J-yl)-2-azaspiro [3.3] heptan-2-yl) (2-fluoro-5-hydroxyphenyl) methanone [Compound 476] and (6-(3-(2,5-Difluorophenyl)-4-methyl-1H-pyrazol-1-yl)-2-azaspiro [3.3] heptan-2-yl) (2-fluoro-S-hydroxyphenyl) methanone [Compound 477]

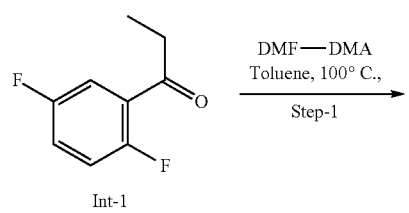

Int-1

-continued

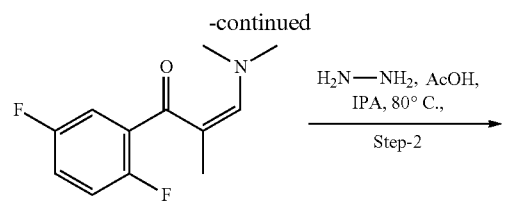

Int-2

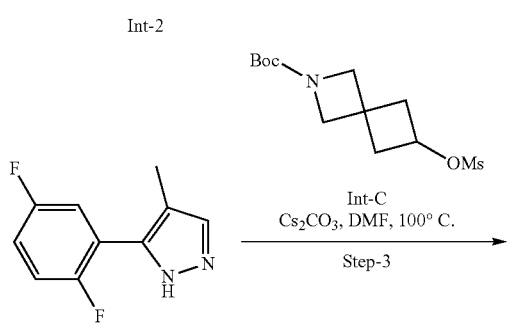

Int-3

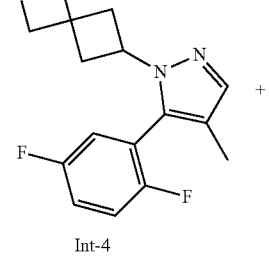

Int-4

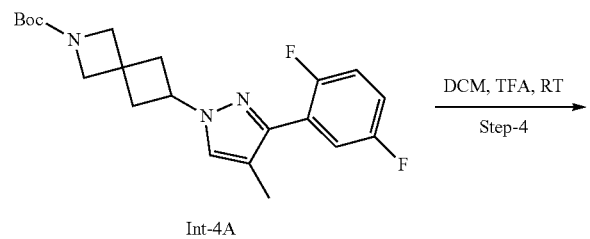

Int-4A

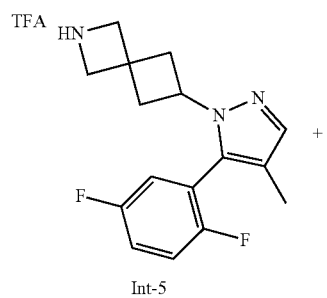

Int-5

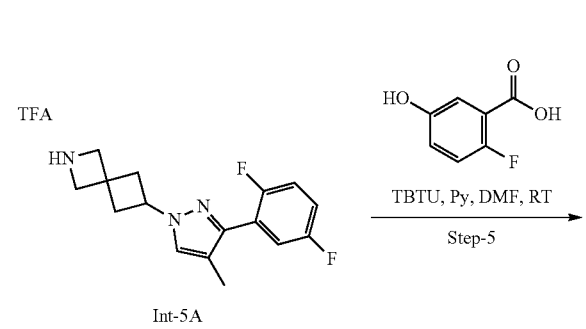

Int-5A

183

-continued

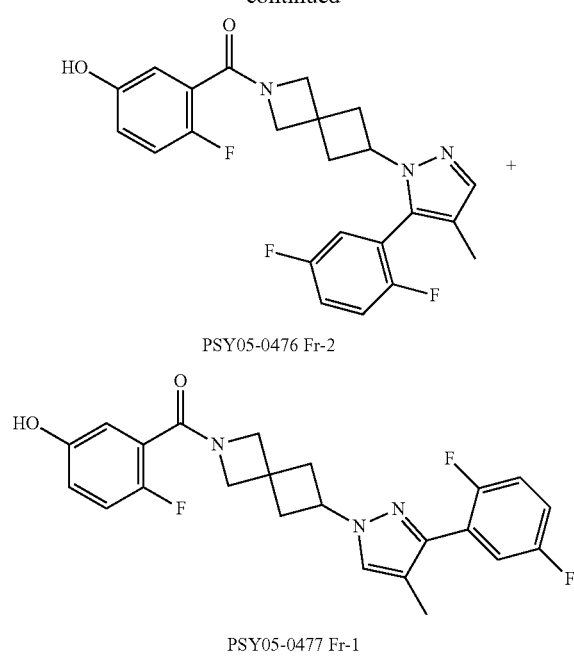

PSY05-0476 Fr-2

PSY05-0477 Fr-1

Step-1: Synthesis of (Z)-1-(2, 5-Difluorophenyl)-3-(dimethyl amino)-2-methylprop-2-en-1-one (Int-2)

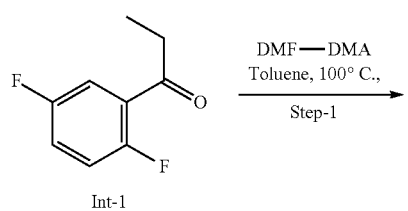

To a stirred solution of 1-(2,5-Difluorophenyl)propan-1-one (1.0 g, 5.8768 mmol, 1.0 eq.) in Toluene (10 mL) was added N,N-Dimethylformamide dimethylacetal (3.0 mL, 29,384 mmol, 5.0 eq.) the reaction mass was heated at 100° C. for 16 h. After completion of reaction as monitored by TLC and LCMS. After completion, reaction mixture was poured in ice cold water (50 mL) and extracted with ethyl acetate (20 mL*3). The organic layer was washed with brine (50 mL), dried over Sodium sulphate and concentrated under reduce pressure to get residue. The residue was purified by combi flash using 30-40% ethyl acetate in hexane as eluent to (Z)-1-(2, 5-Difluorophenyl)-3-(dimethyl amino)-2-methylprop-2-en-1-one (Int-2) (1.1 g, 84.61%).

184

Step-2: Synthesis of 5-(2,5-Difluorophenyl)-4-methyl-1H-pyrazole (Int-3)

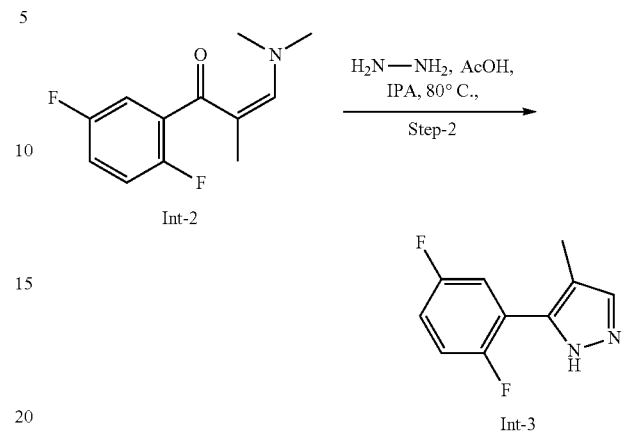

To a stirred solution of (Z)-1-(2,5-Difluorophenyl)-3-(dimethylamino)-2-methylprop-2-en-1-one (1.1 g, 4.88 mmol, 1.0 eq.) in Isopropyl alcohol (20 mL) was added hydrazine hydrate (0.36 mL, 7.33 mmol, 1.5 eq.) the reaction mass was heated at 80° C. for 16 h. After completion of reaction as monitored by TLC and LCMS, the reaction mixture was concentrated to get residue. The residue was purified by combi flash using 20-30% ethyl acetate in hexane as eluent to get 5-(2,5-Difluorophenyl)-4-methyl-1H-pyrazole (Int-3) (0.80 g, 84.38%).

Step-3: Synthesis of Tert-butyl 6-(5-(pyridin-3-yl)-3-(trifluoromethyl)-1H-pyrazol-1-yl)-2-azaspiro[3.3]heptane-2-carboxylate and Tert-butyl 6-(3-(pyridin-3-yl)-5-(trifluoromethyl)-1H-pyrazol-1-yl)-2-azaspiro[3.3]heptane-2-carboxylate (mix of Int-4 and Int-4A)

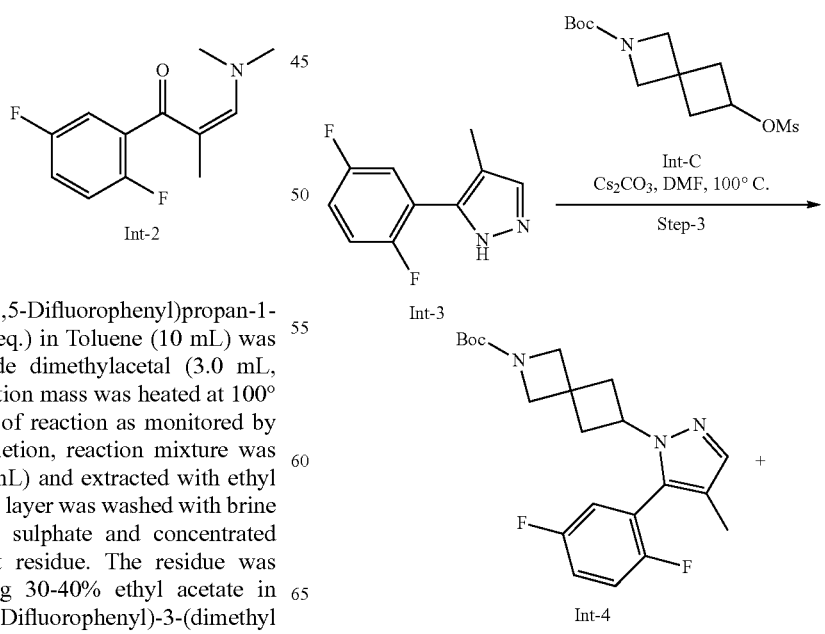

Int-4A

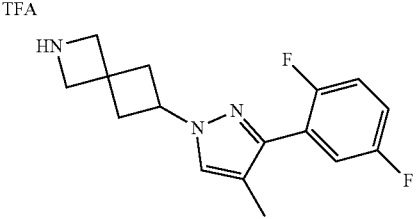

Int-5A

To a well stirred reaction mixture of 3-(3-(Trifluoromethyl)-1H-pyrazol-5-yl) pyridine (0.800 g, 4.12 mmol, 1.0 eq.), CS₂CO₃ (2.01 g, 6.18 mmol, 1.5 eq.) in N,N-di methyl formamide (10 mL) was added Tert-butyl 6-((methyl sulfonyl) oxy)-2-azaspiro [3.3] heptane-2-carboxylate (1.44 g, 4.94 mmol, 1.2 eq.). The reaction was heated at 100° C. for 12 h. After completion of reaction as monitored by TLC, the reaction mixture was poured in water (100 mL) and extracted with ethyl acetate (50 mL*3). The organic layer was washed with brine (100 mL), dried over Sodium sulphate and concentrated under reduce pressure to get residue. The residue was purified by combi flash using 30-50% ethyl acetate in hexane as eluent to get to mixture of Int-4 and Int-4A (1.0 g, 62.5%).

Step-4: Synthesis of 6-(5-(2,5-difluorophenyl)-4-methyl-1H-pyrazol-1-yl)-2-azaspiro[3.3]heptane TFA salt (Int-5) and 6-(3-(2,5-difluorophenyl)-4-methyl-1H-pyrazol-1-yl)-2-azaspiro[3.3]heptane TFA salt (Int-5A)

To a well stirred reaction mixture of Int-4 and Int-4A (1.0 g, 2.5706 mmol, 1.0 eq.) in dichloromethane (10 mL) was added TFA (2.0 mL) dropwise at 0° C. After completion of reaction as monitored by TLC and LCMS, the reaction mixture was concentrated to get TFA salt of Int-5 and Int-5A (1.1 g).

Step-5: Synthesis of (6-(5-(2,5-Difluorophenyl)-4-methyl-1H-pyrazol-1-yl)-2-azaspiro [3.3]heptan-2-yl) (2-fluoro-5-hydroxyphenyl) methanone and (6-(3-(2,5-Difluorophenyl)-4-methyl-1H-pyrazol-1-yl)-2-azaspiro [3.3] heptan-2-yl) (2-fluoro-5-hydroxyphenyl) methanone (PSY-05-00476-001 and PSY-05-00477-001)

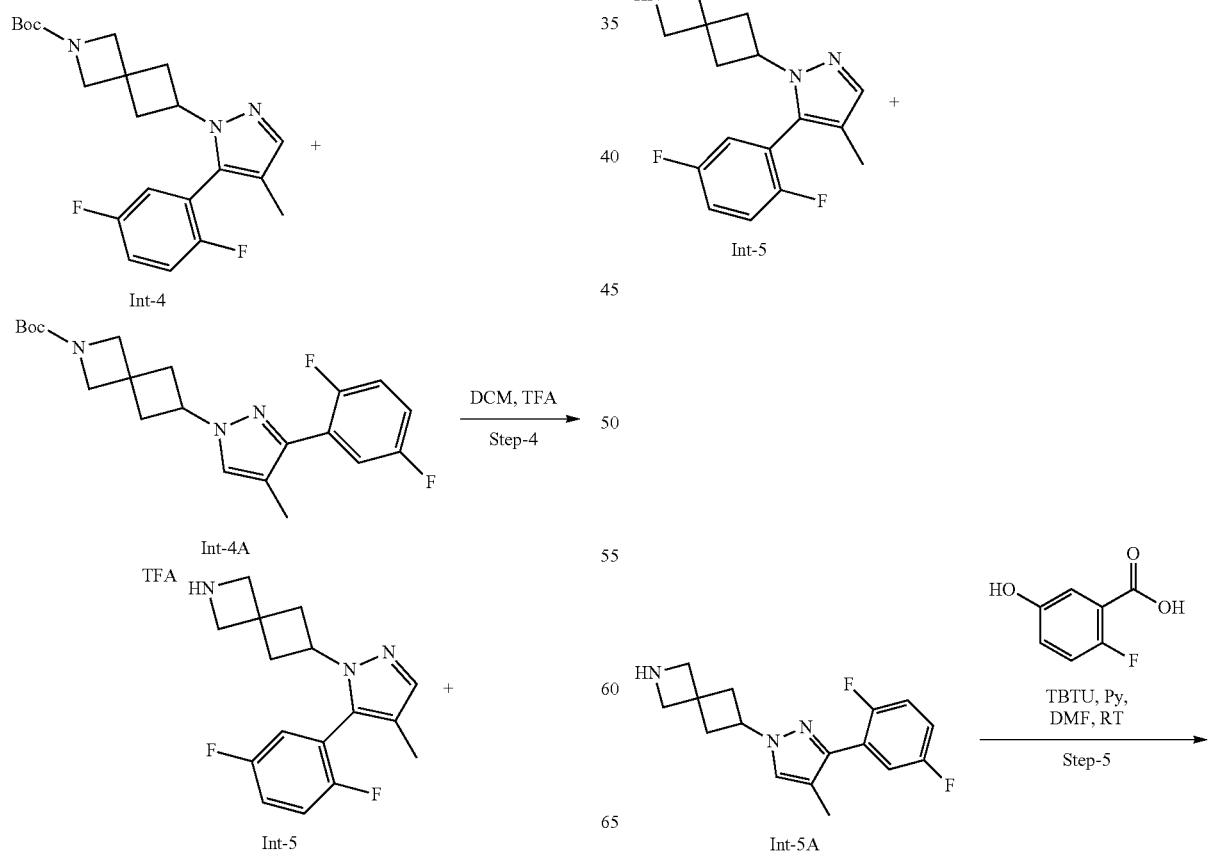

-continued

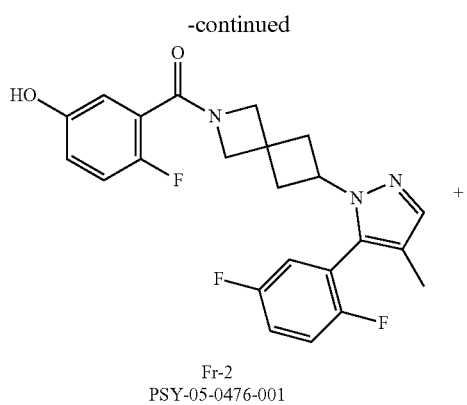

Fr-2
PSY-05-0476-001

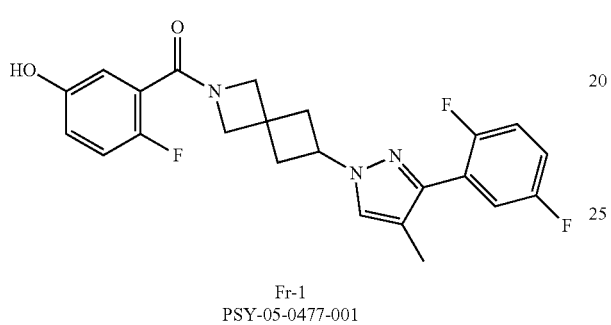

Fr-1
PSY-05-0477-001

To a well stirred reaction mixture of Int-5 and Int-5A (1.13 g, 2.9230 mmol, 1.2 eq.), Pyridine (0.98 mL, 12.1794 mmol, 5.0 eq.), 2-Fluoro-5-hydroxybenzoic acid (0.38 g, 2.4358 mmol, 1.0 eq.) in N,N-dimethyl formamide (5 mL) was added TBTU (0.321 g, 3.6538 mmol, 1.5 eq.) at 0° C. The reaction mass was stirred at room temperature for 3-4 hr. After completion of reaction as monitored by TLC and LCMS, the reaction mixture was poured in water (100 mL) and extracted with ethyl acetate (50 mL*3). The organic layer was washed with saturated solution of sodium carbonate (50 mL) and brine (100 mL), dried over sodium sulphate ($Na_2SO_4$) and concentrated under reduce pressure to get residue. The residue was purified by combi flash using 40-50% ethyl acetate in hexane as eluent. The crude was submitted to prep-HPLC for purification. (PSY-05-00476-001-FR-2: 0.308 g, 20.95%) (PSY-05-00477-001-FR-1: 0.096 g, 6.53%).

Fraction-1: (6-(3-(2,5-Difluorophenyl)-4-methyl-1H-pyrazol-1-yl)-2-azaspiro [3.3]heptan-2-yl) (2-fluoro-5-hydroxyphenyl) methanone (PSY-05-0477-001 Fr-1). LCMS: m/z 428.03 [M+1]$^+$. $^1$H NMR (400 MHz, DMSO-$d_6$) δ 7.52-7.40 (m, 3H), 7.30 (dd, J=5.4, 2.8 Hz, 1H), 7.08 (q, J=8.9 Hz, 1H), 6.85 (d, J=3.9 Hz, 1H), 6.81-6.75 (m, 1H), 4.47 (dt, J=15.6, 7.8 Hz, 1H), 4.07 (dd, J=24.5, 5.0 Hz, 4H), 2.60 (dd, J=20.2, 8.3 Hz, 4H), 1.90 (s, 3H).

Fraction-2: (6-(5-(2,5-Difluorophenyl)-4-methyl-1H-pyrazol-1-yl)-2-azaspiro [3.3]heptan-2-yl) (2-fluoro-5-hydroxyphenyl) methanone (PSY-05-00476-001 Fr-2). LCMS: m/z 428.3 [M+1]$^+$. $^1$H NMR (400 MHz, DMSO-$d_6$) δ 9.69 (s, 1H), 7.72 (d, J=5.9 Hz, 1H), 7.39-7.26 (m, 3H), 7.10 (q, J=9.1 Hz, 1H), 6.82-6.87 (q, J=9.1 Hz, 1H), 6.74-6.79 (q, J=9.1 Hz, 1H), 4.76 (dt, J=23.3, 7.9 Hz, 1H), 4.15 (d, J=11.2 Hz, 2H), 4.05 (d, J=8.7 Hz, 2H), 2.76-2.60 (m, 4H), 1.99 (s, 3H).

Example 12: Synthesis of (6-(4-Cyclopropyl-5-(2-(trifluoromethyl) phenyl)-1H-pyrazol-1-yl)-2-azaspiro [3.3] heptan-2-yl) (2-fluoro-5-hydroxyphenyl) methanone (PSY-05-00488-001); (6-(4-Cyclopropyl-3-(2-(trifluoromethyl) phenyl)-1H-pyrazol-1-yl)-2-azaspiro [3.3] heptan-2-yl) (2-fluoro-5-hydroxyphenyl) methanone (PSY-05-00489-001); (2-fluoro-5-hydroxyphenyl)(6-(3-(2-(trifluoro methyl) phenyl)-1H-pyrazol-1-yl)-2-azaspiro [3.3] heptan-2-yl)methanone (PSY-05-00525-001); and (2-fluoro-S-hydroxyphenyl)(6-(5-(2-(trifluoro methyl) phenyl)-1H-pyrazol-1-yl)-2-azaspiro [3.3] heptan-2-yl)methanone (PSY-05-00526-001)

Synthetic Scheme:

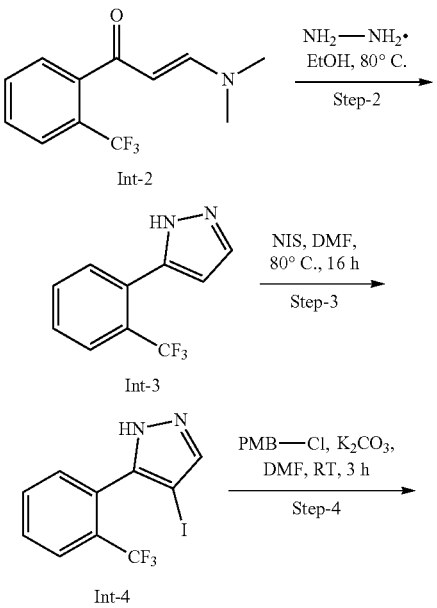

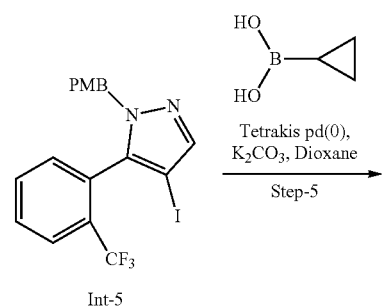

189
-continued
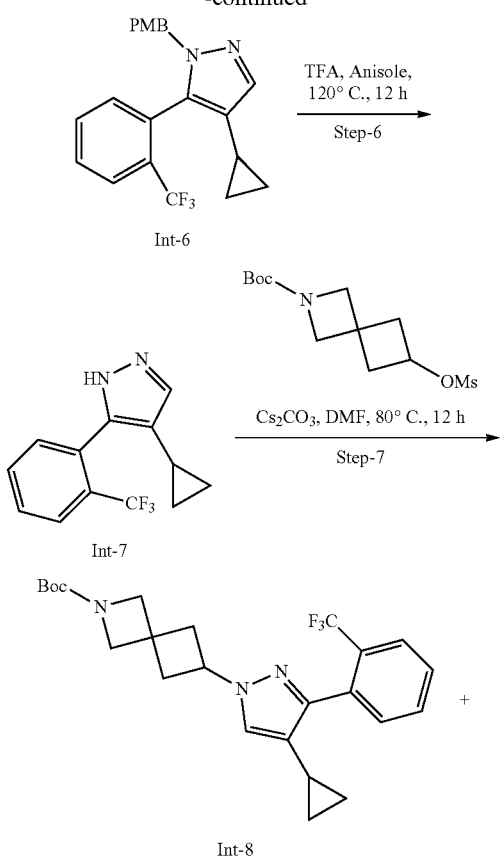
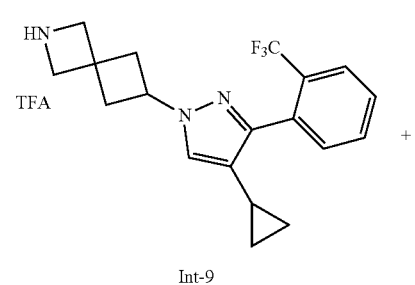
190
-continued
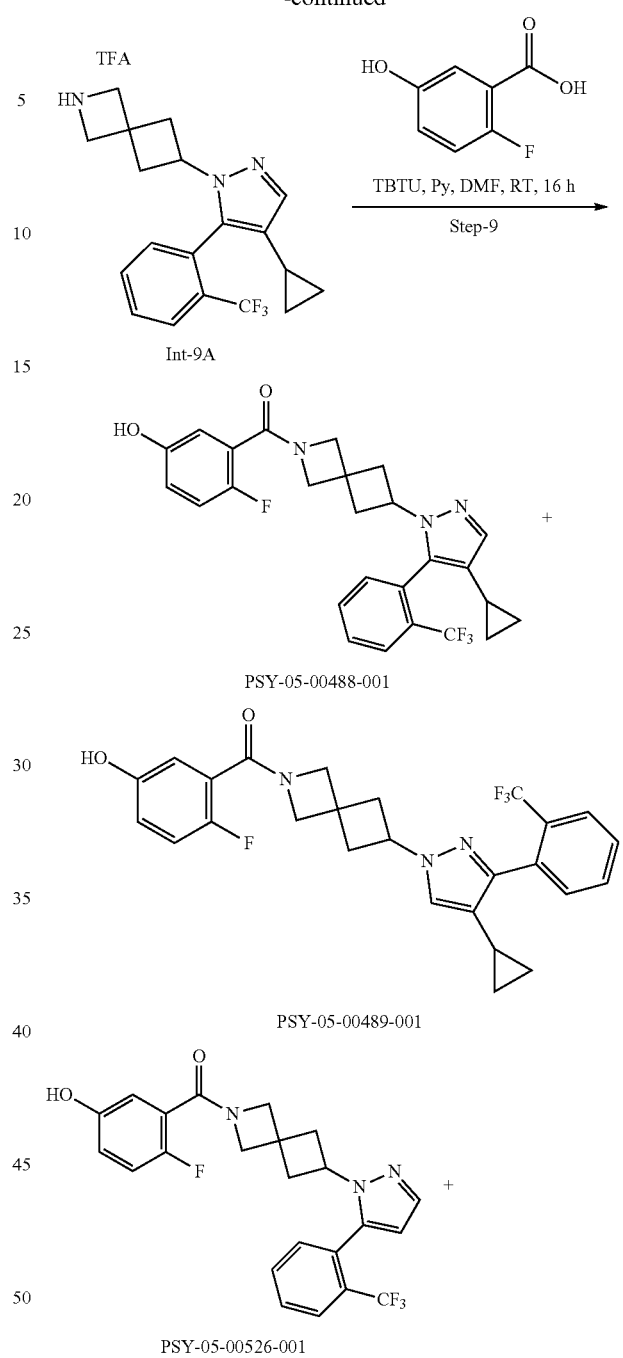
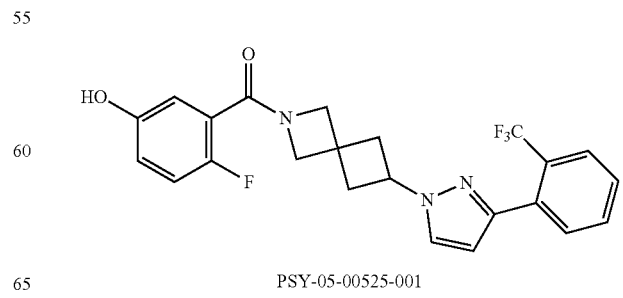

Step-1: Synthesis of (E)-3-(Dimethyl amino)-1-(2-(trifluoromethyl) phenyl) prop-2-en-1-one (Int-2)

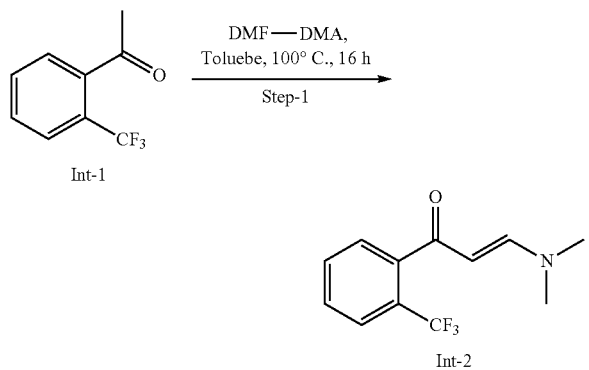

To a stirred solution of 1-(2-(Trifluoromethyl) phenyl) ethan-1 one (10.0 g, 53.19 mmol, 1.0 eq.) in Toluene (100 mL) was added N, N-Dimethylformamide dimethyl acetal (20.56 mL, 265.95 mmol, 5.0 eq.). The reaction mass was heated at 100° C. for 16 h. After completion of reaction as monitored by TLC and LCMS, reaction mixture was poured in ice cold water (50 mL) and extracted with ethyl acetate (75 ml*3). The organic layer was washed with brine (100 mL), dried over $Na_2SO_4$ and concentrated under reduce pressure to get residue. The residue was purified by combi flash using, 30-40% ethyl acetate in n-hexane as eluent to (E)-3-(Dimethyl amino)-1-(2-(trifluoromethyl) phenyl) prop-2-en-1-one (Int-2) (11.12 g, 86.06%).

Step-2: Synthesis of 5-(2-(Trifluoromethyl) phenyl)-1H-pyrazole (Int-3)

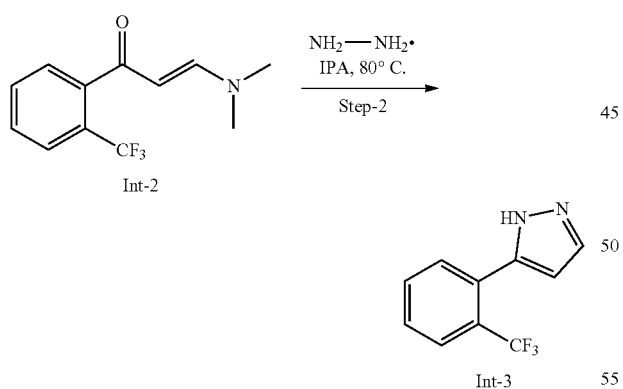

To a stirred solution of (E)-3-(Dimethyl amino)-1-(2-(trifluoromethyl) phenyl) prop-2-en-1-one (11.12 g, 45.7613 mmol, 1.0 eq.) in Isopropanol (100 mL) was added hydrazine hydrate (2.19 mL, 68.64 mmol, 1.5 eq.). The reaction mass was heated at 80° C. for 16 h. After completion of reaction as monitored by TLC and LCMS, the reaction mixture was concentrated to get residue. The residue was purified by combi flash using 20-30% ethyl acetate in n-hexane as eluent to get 5-(2-(Trifluoromethyl) phenyl)-1H-pyrazole (Int-3) (8.67 g, 89.38%).

Step-3: Synthesis of 4-Iodo-5-(2-(trifluoromethyl) phenyl)-1H-pyrazole (Int-4)

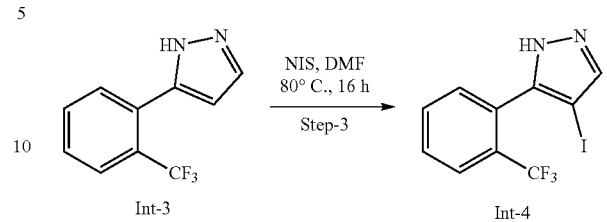

To a well stirred solution of 5-(2-(Trifluoromethyl) phenyl)-1H-pyrazole (8.67 g, 40.86 mmol, 1.0 eq.) in N,N-dimethyl formamide (90 mL) was added N-Iodo succinamide (10.11 g, 44.94 mmol, 1.1 eq.) in reaction mixture. The reaction was heated at 80° C. for 16 h. After completion of reaction as monitored by TLC, the reaction mixture was poured in ice water (100 mL) and extracted with ethyl acetate (100 mL*3). The organic layer was washed with brine (100 mL), dried over $Na_2SO_4$ and concentrated under reduce pressure to get residue. The residue was purified by combi flash using 30-50/o ethyl acetate in n-hexane as eluent to get to 4-Iodo-5-(2-(trifluoromethyl) phenyl)-1H-pyrazole (Int-4) (9.2 g, 66.6%).

Step-4: Synthesis of 4-Iodo-1-(4-methoxybenzyl)-5-(2-(trifluoromethyl) phenyl)-1H-pyrazole (Int-5)

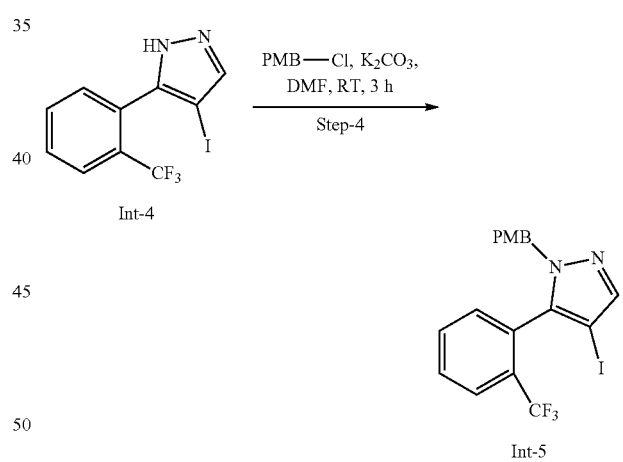

To a well stirred solution of 4-Iodo-5-(2-(trifluoromethyl) phenyl)-1H-pyrazole (9.2 g, 27.21 mmol, 1.0 eq.), $Cs_2CO_3$ (13.26 g, 40.82 mmol, 1.5 eq.) in N,N-dimethyl formamide (100 mL) was added 4-Methoxybenzyl chloride (4.44 mL, 32.66 mmol, 1.2 eq.). The reaction was stirred at room temperature for 2-3 h. After completion of reaction as monitored by TLC and LCMS, the reaction mixture was poured in ice water (100 mL) and extracted with ethyl acetate (100 mL*3). The organic layer was washed with brine (100 mL), dried over $Na_2SO_4$ and concentrated under reduce pressure to get residue. The residue was purified by combi flash using 30-50% ethyl acetate in n-hexane as eluent to get 4-Iodo-1-(4-methoxybenzyl)-5-(2-(trifluoromethyl) phenyl)-1H-pyrazole (Int-5) (10.10 g, 81.0%).

Step-5: Synthesis of 4-Cyclopropyl-1-(4-methoxybenzyl)-5-(2-(trifluoromethyl) phenyl)-1H-pyrazole (Int-6)

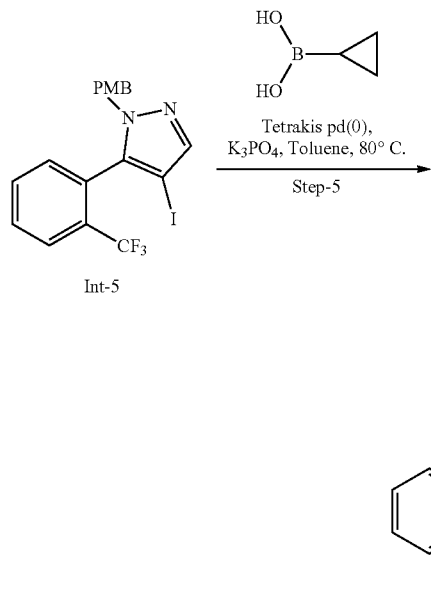

To a well stirred reaction mixture of 4-Iodo-1-(4-methoxybenzyl)-5-(2-(trifluoromethyl) phenyl)-1H-pyrazole (10.10 g, 22.05 mmol, 1.0 eq.), Cyclopropyl boronic acid (3.78 g, 44.10 mmol, 2.0 eq.), potassium phosphate (K₃PO₄) (14.04 g, 66.15 mmol, 3.0 eq.) in Toluene (100 mL). N$_{2(g)}$ was purged for 20 min, after that Tetrakis Pd(0) (1.27 g, 1.102 mmol, 1.2 eq.) was added and heated the reaction mixture for 80° C. for 48 h. After completion of reaction as monitored by TLC and LCMS, the reaction mixture was filtered through cellite bed, washed with ethyl acetate (3*15 mL). Filtrate was diluted in water (100 mL) and extracted with ethyl acetate (100 mL*3). The organic layer was washed with brine (100 mL), dried over Na₂SO₄ and concentrated under reduce pressure to get residue. The residue was purified by combi flash using 0-50% ethyl acetate in n-hexane as eluent to get to 4-Cyclopropyl-1-(4-methoxybenzyl)-5-(2-(trifluoromethyl) phenyl)-1H-pyrazole (Int-6) (4.5 g, 54.82%).

Step-6: Synthesis of 4-Cyclopropyl-5-(2-(trifluoromethyl) phenyl)-1H-pyrazole (Int-7)

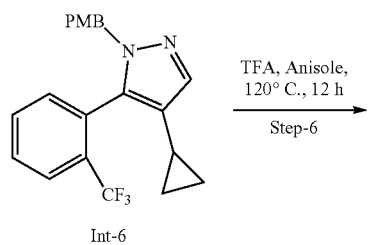

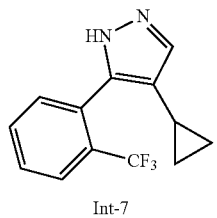

To a well stirred reaction mixture of 4-cyclopropyl-5-(2-fluorophenyl)-1-(4-methoxybenzyl)-1H-pyrazole (4.5 g, 12.06 mmol, 1.0 eq.) in 40 mL Anisole, was added 4.5 mL Trifluoro acetic acid (TFA). The reaction mixture was heated at 120° C. for 12 h. After completion of reaction as monitored by TLC and LCMS, the reaction mixture was poured in water (100 mL) and extracted with ethyl acetate (50 mL*3). The organic layer was washed with brine (100 mL), dried over Na₂SO₄ and concentrated under reduce pressure to get residue. The residue was purified by combi flash using 30-80% ethyl acetate in n-hexane as eluent to get to 4-Cyclopropyl-5-(2-(trifluoromethyl) phenyl)-1H-pyrazole (Int-7) (1.67 g, 54.79%).

Step-7: Synthesis of tert-butyl 6-(4-cyclopropyl-3-(2-(trifluoromethyl) phenyl)-1H-pyrazol-1-yl)-2-azaspiro [3.3] heptane-2-carboxylate (Int-8) and Tert-butyl 6-(4-cylopropyl-5-(2-(trifluoromethyl) phenyl)-1H-pyrazol-1-yl)-2-azaspiro [3.3]heptane-2-carboxylate (Int-8A)

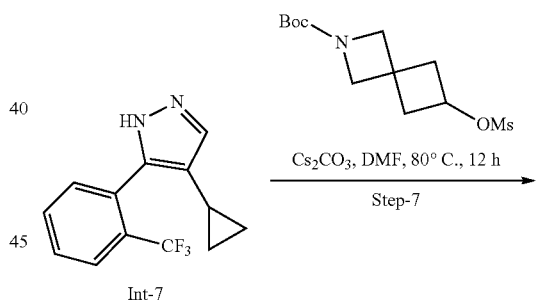

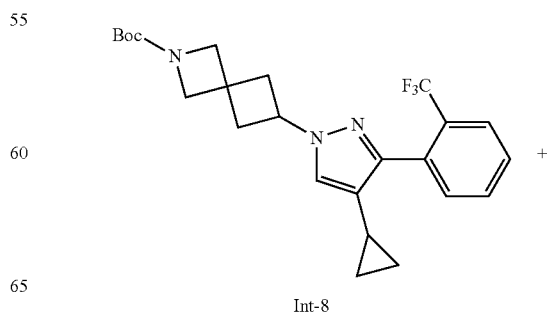

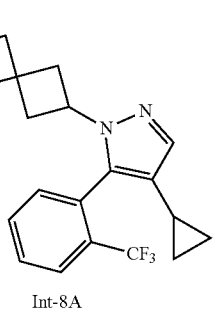

Int-8A

To a well stirred reaction mixture of 4-cyclopropyl-5-(2-fluorophenyl)-1H-pyrazole (1.67 g, 6.62 mmol, 1.0 eq.) Cs₂CO₃ (3.2 g, 9.94 mmol, 1.5 eq.) in N,N-dimethyl formamide (15 mL) was added Tert-butyl 6-((methyl sulfonyl)oxy)-2-azaspiro [3.3] heptane-2-carboxylate (1.92 g, 6.62 mmol, 1.0 eq.). The reaction was heated at 80° C. for 12 h. After completion of reaction as monitored by TLC and LCMS, the reaction mixture was poured in water (50 mL) and extracted with ethyl acetate (50 mL*3). The organic layer was washed with brine (50 mL), dried over Na₂SO₄ and concentrated under reduce pressure to get residue. The residue was purified by combi flash using 30-50% ethyl acetate in n-hexane as eluent to get to mixture of two regio isomer tert-butyl 6-(4-cyclopropyl-3-(2-(trifluoromethyl)phenyl)-1H-pyrazol-1-yl)-2-azaspiro[3.3]heptane-2-carboxylate (Int-8) and tert-butyl 6-(4-cyclopropyl-5-(2-(trifluoromethyl)phenyl)-1H-pyrazol-1-yl)-2-azaspiro[3.3]heptane-2-carboxylate (Int-8A) (1.5 g, 50.63%).

Step-8: Synthesis of 6-(4-cyclopropyl-3-(2-(trifluoromethyl)phenyl)-1H-pyrazol-1-yl)-2-azaspiro[3.3]heptane (Int-9) and 6-(4-cyclopropyl-5-(2-(trifluoromethyl)phenyl)-1H-pyrazol-1-yl)-2-azaspiro[3.3]heptane (Int-9A)

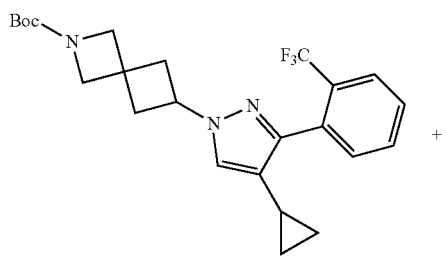

Int-8

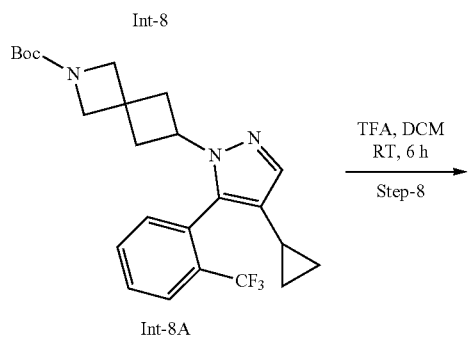

Int-8A

TFA, DCM
RT, 6 h
—————→
Step-8

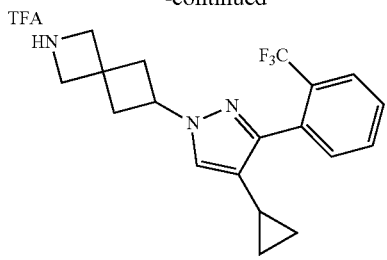

Int-9

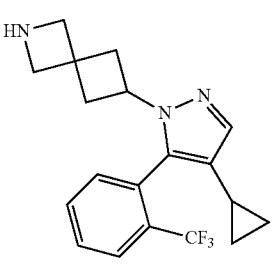

Int-9A

To a well stirred reaction mixture of tert-butyl 6-(4-cyclopropyl-3-(2-(trifluoromethyl)phenyl)-1H-pyrazol-1-yl)-2-azaspiro[3.3]heptane-2-carboxylate (Int-8) and tert-butyl 6-(4-cyclopropyl-5-(2-(trifluoromethyl)phenyl)-1H-pyrazol-1-yl)-2-azaspiro[3.3]heptane-2-carboxylate (Int-8A (1.5 g, 2.57 mmol, 1.0 eq.) in dichloromethane (10 mL) was added trifluoroacetic acid (TFA) (2.0 mL) dropwise at 0° C. and stirred for 2-3 h. After completion of reaction as monitored by TLC and LCMS, the reaction mixture was concentrated to get TFA salt of 6-(4-cyclopropyl-3-(2-(trifluoromethyl)phenyl)-1H-pyrazol-1-yl)-2-azaspiro[3.3]heptane (Int-9) and 6-(4-cyclopropyl-5-(2-(trifluoromethyl)phenyl)-1H-pyrazol-1-yl)-2-azaspiro[3.3]heptane (Int-9A) (1.7 g).

Step-9: Synthesis of (6-(4-Cyclopropyl-5-(2-(trifluoromethyl) phenyl)-1H-pyrazol-1-yl)-2-azaspiro [3.3] heptan-2-yl) (2-fluoro-5-hydroxyphenyl) methanone (PSY-05-00488-001) and (6-(4-Cyclopropyl-3-(2-(trifluoromethyl) phenyl)-1H-pyrazol-1-yl)-2-azaspiro [3.3] heptan-2-yl) (2-fluoro-5-hydroxyphenyl) methanone (PSY-05-00489-001)

(2-fluoro-5-hydroxyphenyl)(6-(3-(2-(trifluoromethyl)phenyl)-1H-pyrazol-1-yl)-2-azaspiro [3.3]heptan-2-yl)methanone (PSY-05-00525-001) and (2-fluoro-5-hydroxyphenyl)(6-(5-(2-(trifluoromethyl)phenyl)-1H-pyrazol-1-yl)-2-azaspiro[3.3]heptan-2-yl)methanone (PSY-05-00526-001)

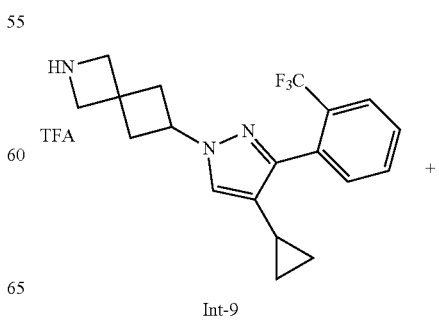

Int-9

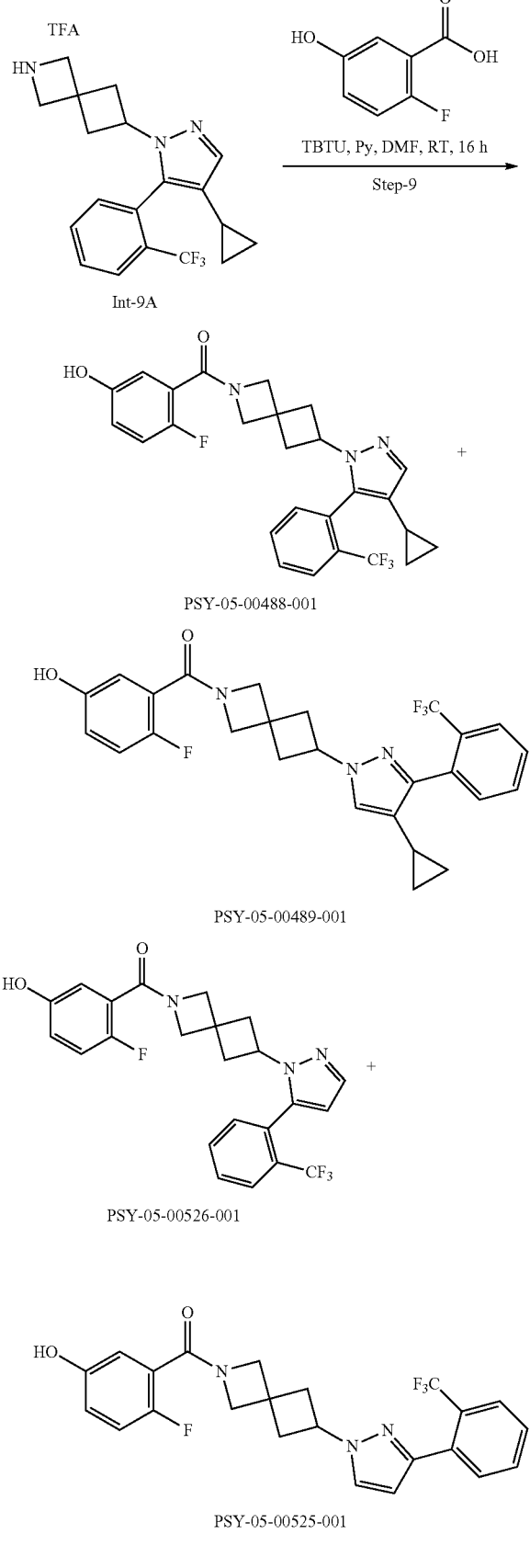

To a well stirred reaction mixture of TFA salt of 6-(4-cyclopropyl-3-(2-(trifluoromethyl)phenyl)-1H-pyrazol-1-yl)-2-azaspiro[3.3]heptane (Int-9) and 6-(4-cyclopropyl-5-(2-(trifluoromethyl)phenyl)-1H-pyrazol-1-yl)-2-azaspiro[3.3]heptane (Int-9A) (1.7 g, 4.92 mmol, 1.2 eq.), Pyridine (1.65 mL, 20.51 mmol, 5.0 eq.), 2-Fluoro-5-hydroxybenzoic acid (0.640 g, 4.10 mmol, 1.0 eq.) in N,N dimethyl formamide (5 mL) was added TBTU (1.97 g, 6.1538 mmol, 1.5 eq.) at 0° C. The reaction mass was stirred at room temperature for 16 h. After completion of reaction as monitored by TLC and LCMS, the reaction mixture was poured in water (50 mL) and extracted with ethyl acetate (50 mL*3). The organic layer was washed with saturated solution of sodium carbonate (50 mL) and brine (100 mL), dried over $Na_2SO_4$ and concentrated under reduce pressure to get residue. The residue was purified by combi flash using 0-100% ethyl acetate in n-hexane as eluent to get crude product. Which was purified by prep-HPLC to obtained two fractions.

Fraction-1: (6-(4-Cyclopropyl-5-(2-(trifluoromethyl)phenyl)-1H-pyrazol-1-yl)-2-azaspiro [3.3] heptan-2-yl) (2-fluoro-5-hydroxyphenyl) methanone (PSY-05-00488-001) (0.026 g, 1.11%). LCMS: m/z 486.33 [M+H]$^+$. NMR: $^1$H NMR (400 MHz, DMSO-d$_6$) δ 9.73 (s, 1H), 7.91 (dd, J=12.6, 8.1 Hz, 1H), 7.83-7.69 (m, 2H), 7.40 (t, J=8.0 Hz, 1H), 7.26 (d, J=10.1 Hz, 1H), 7.04 (dt, J=17.3, 9.2 Hz, 1H), 6.74 (s, 2H), 4.09 (dd, J=14.2, 6.8 Hz, 1H), 4.01-3.91 (m, 4H), 2.63 (s, 2H), 2.54 (s, 2H), 1.18 (m, 1H), 0.59 (s, 2H), 0.39 (d, J=15.1 Hz, 2H).

Fraction-2: (6-(4-Cyclopropyl-3-(2-(trifluoromethyl)phenyl)-1H-pyrazol-1-yl)-2-azaspiro [3.3] heptan-2-yl) (2-fluoro-5-hydroxyphenyl) methanone (PSY-05-00489-001) (0.07613 g, 3.20%). LCMS: m/z 486.33[M+H]$^+$. $^1$H NMR (400 MHz, DMSO-d$_6$) δ 9.67 (s, 1H), 7.83 (s, 1H), 7.72 (d, J=5.2 Hz, 1H), 7.63 (s, 1H), 7.53 (s, 2H), 7.09 (d, J=8.9 Hz, 1H), 6.85 (s, 2H), 4.70 (d, J=7.4 Hz, 1H), 4.12 (d, J=10.2 Hz, 2H), 4.00 (d, J=8.5 Hz, 2H), 2.65 (dd, J=19.9, 11.1 Hz, 4H), 1.29 (m, 1H), 0.67 (d, J=6.9 Hz, 2H), 0.41 (s, 2H).

(NOTE: In Suzuki coupling reaction, dess-iodo of Int-5 observe along with Int-6 product. There was no separation on TLC, LCMS. We used this mixture for next several steps. In Last Prep-HPLC purification, we had isolated Product as dess-CF$_3$ product of PSY-05-00488-001.)

Fraction-3: (2-fluoro-5-hydroxyphenyl)(6-(3-(2-(trifluoromethyl)phenyl)-1H-pyrazol-1-yl)-2-azaspiro [3.3] heptan-2-yl)methanone (PSY-05-00525-001) (0.028 g, 1.18%). LCMS: m/z 446.30 [M+H]$^+$. $^1$H NMR (400 MHz, DMSO-d$_6$) δ 9.64 (s, 1H), 7.89 (s, 1H), 7.78-7.71 (m, 2H), 7.58 (d, J=9.1 Hz, 1H), 7.42 (s, 1H), 7.03 (s, 1H), 6.82 (s, 1H), 6.75 (s, 1H), 6.28 (s, 1H), 4.26 (s, 1H), 3.99 (d, J=19.2 Hz, 4H), 2.78 (s, 4H).

Fraction-4: (2-fluoro-5-hydroxyphenyl)(6-(5-(2-(trifluoromethyl)phenyl)-1H-pyrazol-1-yl)-2-azaspiro [3.3] heptan-2-yl)methanone (PSY-05-00526-001) (0.19 g, 8.25%). LCMS: m/z 446.20 [M+H]$^+$. $^1$H NMR (400 MHz, DMSO-d$_6$) δ 9.66 (d, J=7.4 Hz, 1H), 7.82 (dd, J=16.3, 9.0 Hz, 2H), 7.73-7.54 (m, 3H), 7.08 (q, J=8.8 Hz, 1H), 6.88-6.82 (m, 1H), 6.79 (s, 1H), 6.42 (s, 1H), 4.82 (dt, J=23.6, 7.9 Hz, 1H), 4.14 (d, J=10.1 Hz, 2H), 4.04 (d, J=7.9 Hz, 2H), 2.71 (dt, J=17.5, 10.4 Hz, 4H).

Example 13: Synthesis of (6-(3-cyclopropyl-5-(5-fluoro-2-methylphenyl)-H-pyrazol-1-yl)-2-azaspiro[3.3] heptan-2-yl)(2-fluoro-5-hydroxyphenyl)methanone [Compound 490]; and (6-(5-cyclopropyl-3-(5-fluoro-2-methylphenyl)-1H-pyrazol-1-yl)-2-azaspiro[3.3] heptan-2-yl)(2-fluoro-5-hydroxyphenyl)methanone [Compound 491]
Reaction Scheme:
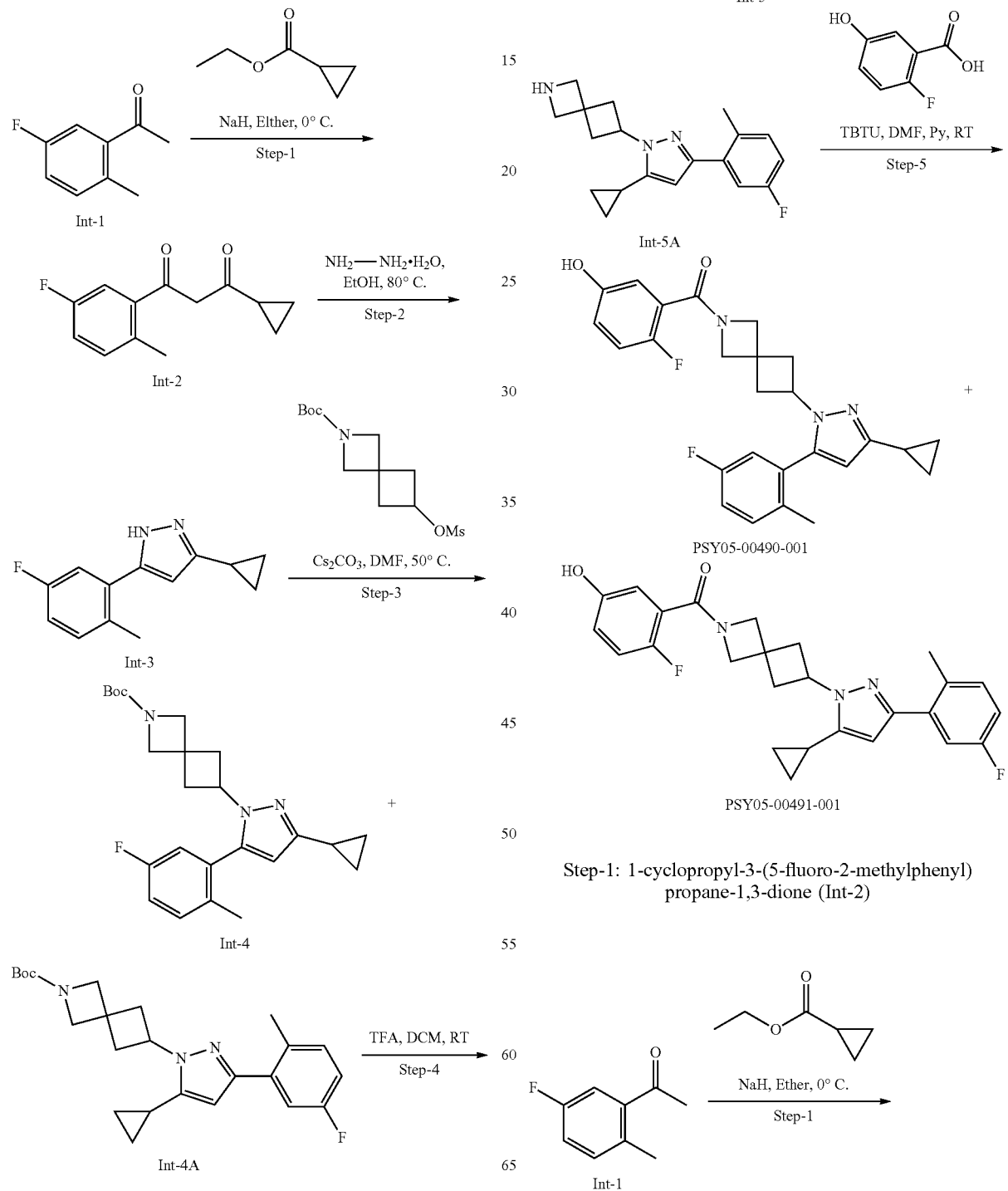
Step-1: 1-cyclopropyl-3-(5-fluoro-2-methylphenyl)propane-1,3-dione (Int-2)

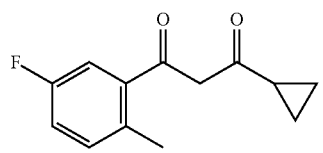

Int-2

To a stirred solution of 1-(5-fluoro-2-methylphenyl) ethan-1-one (2.0 g, 13.15 mmol, 1.0 eq.) in Diethyl ether (10 mL) was added NaH 60% (2.1 g, 52.63 mmol, 4.0 eq.) at 0° C., followed by the dropwise addition of ethyl cyclopropane carboxylate (7.5 g, 65.78 mmol, 5.0 eq.). The reaction mass was stirred at room temperature for 4-5 hr. After completion of reaction as monitored by TLC. The reaction mixture was poured in water (100 mL), acidified with 10% dilute HCl and extracted with ethyl acetate (50 mL*3). The organic layer was washed with brine (100 mL), dried over $Na_2SO_4$ and concentrated under reduce pressure to get residue. The residue was purified by combiflash using 2-5% ethyl acetate in n-hexane as eluent to obtain cyclopropyl-3-(5-fluoro-2-methylphenyl)propane-1,3-dione (Int-2) (2.7 g, 93.27%).

PSY-05-00490 Int-3 3-cyclopropyl-5-(5-fluoro-2-methylphen)-1H-pyrazole

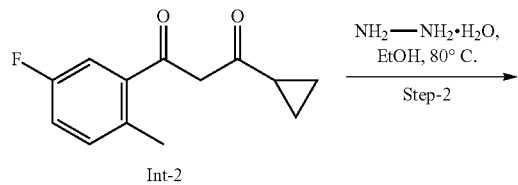

To a stirred solution of obtain 1-cyclopropyl-3-(5-fluoro-2-methylphenyl)propane-1,3-dione (Int-2) (2.7 g, 12.44 mmol, 1.0 eq.) in Isopropyl alcohol (30 mL) was added hydrazine hydrate (0.93 g, 18.66 mmol, 1.5 eq.) the reaction mass was heated at 80° C. for 16 hr. After completion of reaction as monitored by TLC, the reaction mixture was concentrated to get residue. The residue was purified by combiflash using 15-20% ethyl acetate in n-hexane as eluent to 3-cyclopropyl-5-(5-fluoro-2-methylphenyl)-1H-pyrazole (2.4 g, 90.53%).

Step-3: Tert-butyl 6-(3-cyclopropyl-5-(5-fluoro-2-methylphenyl)-1H-pyrazol-1-yl)-2-azaspiro [3.3] heptane-2-carboxylate (Int-4) and Tert-butyl 6-(5-cyclopropyl-3-(5-fluoro-2-methylphenyl)-1H-pyrazol-1-yl)-2-azaspiro [3.3] heptane-2-carboxylate (Int-4A)

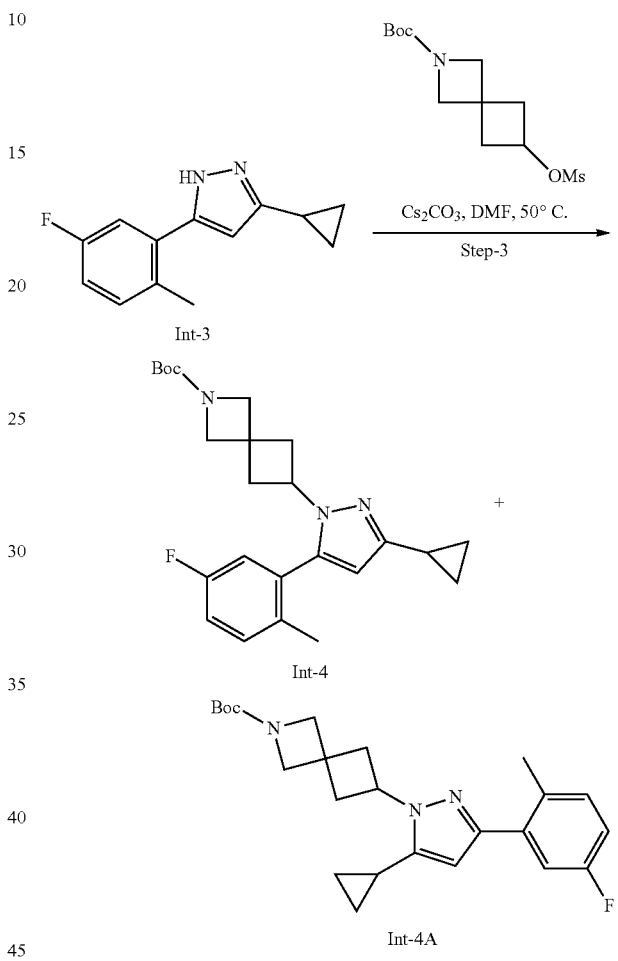

To a well stirred reaction mixture of 3-cyclopropyl-5-(5-fluoro-2-methylphenyl)-1H-pyrazole (Int-3) (1.3 g, 5.99 mmol, 1.0 eq.), $CS_2CO_3$ (2.9 g, 8.98 mmol, 1.5 eq.) in N,N-dimethyl formamide (10 mL) was added tert-butyl 6-((methyl sulfonyl)oxy)-2-azaspiro[3.3]heptane-2-carboxylate (1.74 g, 5.99 mmd, 1.0 eq.). The reaction was heated at 100° C. for 12 hr. After completion of reaction as monitored by TLC, the reaction mixture was poured in water (100 mL) and extracted with ethyl acetate (50 mL*3). The organic layer was washed with brine (100 mL), dried over $Na_2SO_4$ and concentrated under reduce pressure to get residue. The residue was purified by combiflash using 30-35% ethyl acetate in n-hexane as eluent to get the mixture of tert-butyl 6-(3-cyclopropyl-5-(5-fluoro-2-methylphenyl)-1H-pyrazol-1-yl)-2-azaspiro[3.3]heptane-2-carboxylate (int-4) and tert-butyl 6-(5-cyclopropyl-3-(5-fluoro-2-methylphenyl)-1H-pyrazol-1-yl)-2-azaspiro[3.3]heptane-2-carboxylate (int-4A) (0.80 g, 32.34%).

203

Step-4: 6-(3-cyclopropyl-5-(5-fluoro-2-methylphenyl)-1H-pyrazol-1-yl)-2-azaspiro 13.31 heptane (Int-5) and 6-(5-cyclopropyl-3-(5-fluoro-2-methylphenyl)-1H-pyrazol-1-yl)-2-azaspiro [3.3] heptane (Int-5A)

204

Step-5: (6-(3-cyclopropyl-5-(5-fluoro-2-methylphenyl)-1H-pyrazol-1-yl)-2-azaspiro 13.31 heptan-2-yl) (2-fluoro-5-hydroxyphenyl) methanone (PSY-05-00490-001 Fr-2) and (6-(5-cyclopropyl-3-(5-fluoro-2-methylphenyl)-1H-pyrazol-1-yl)-2-azaspiro [3.3] heptan-2-yl)(2-fluoro-5-hydroxyphenyl) methanone (PSY-05-00491-001 Fr-1)

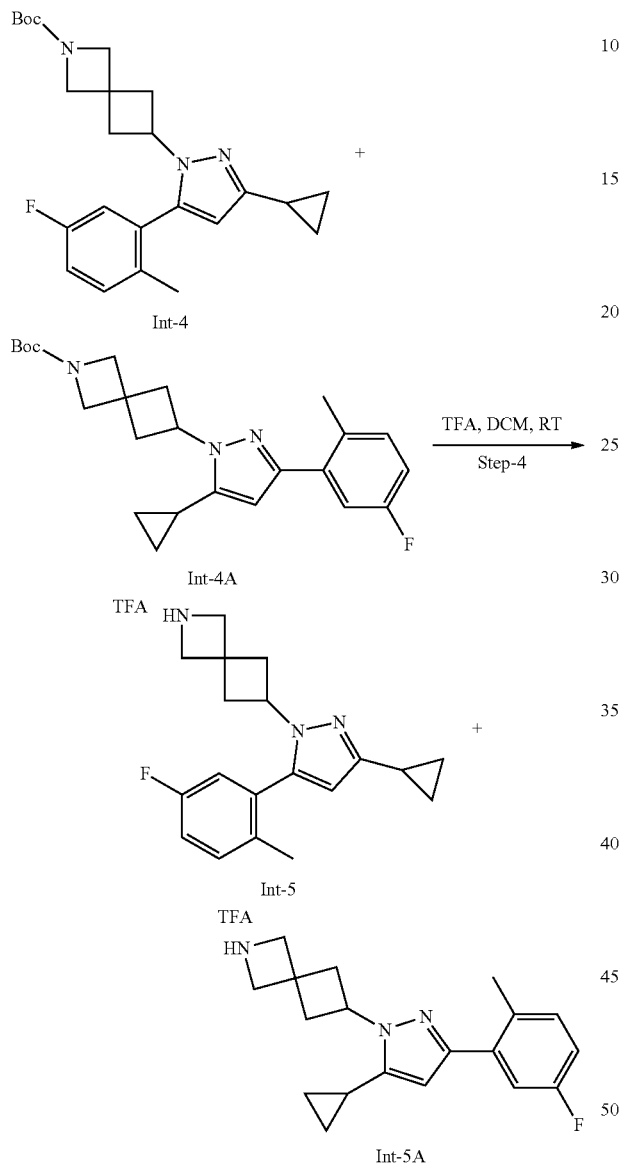

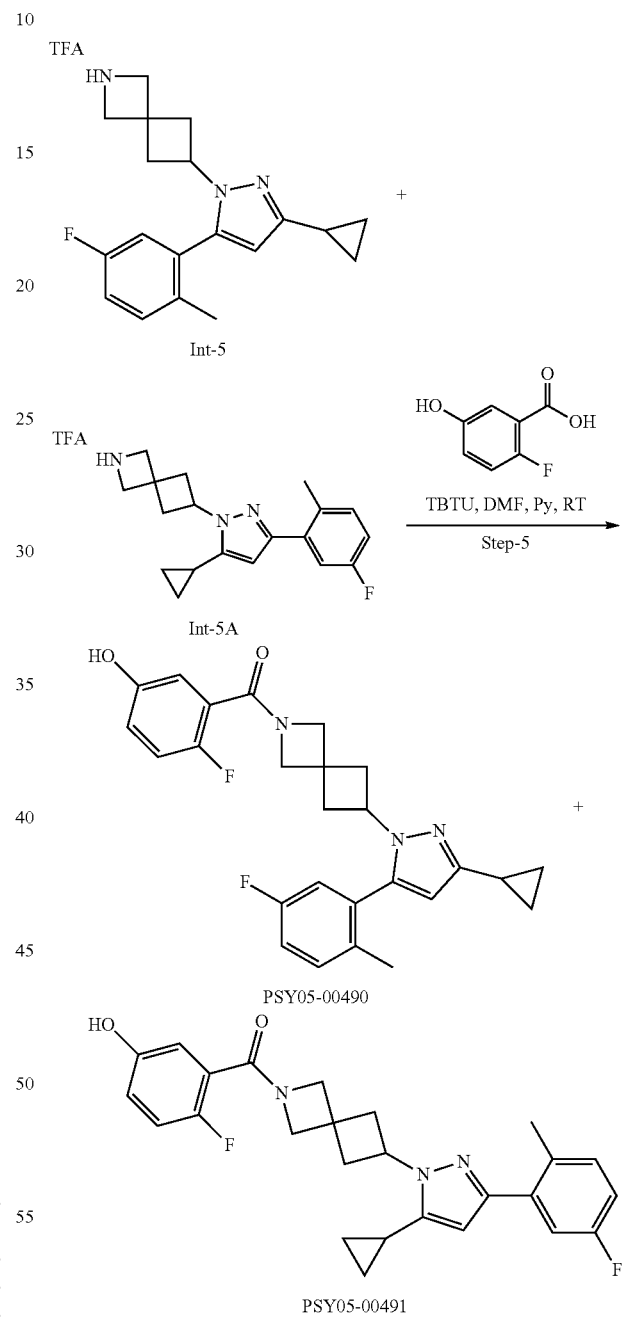

To a well stirred reaction mixture of tert-butyl 6-(3-cyclopropyl-5-(5-fluoro-2-methylphenyl)-1H-pyrazol-1-yl)-2-azaspiro[3.3]heptane-2-carboxylate (int-4) and tert-butyl 6-(5-cyclopropyl-3-(5-fluoro-2-methylphenyl)-1H-pyrazol-1-yl)-2-azaspiro[3.3]heptane-2-carboxylate (int-4A) (0.8 g, 1.94 mmol, 1.0 eq.) in dichloromethane (5 mL) was added Trifluoro acetic acid (1.2 mL) dropwise at 0° C. After completion of reaction as monitored by TLC, the reaction mixture was concentrated to get the mixture of 6-(3-cyclopropyl-5-(5-fluoro-2-methylphenyl)-1H-pyrazol-1-yl)-2-azaspiro[3.3]heptane (int-5) and 6-(5-cyclopropyl-3-(5-fluoro-2-methylphenyl)-1H-pyrazol-1-yl)-2-azaspiro [3.3]heptane (int-5A) (0.98 g, crude).

To a well stirred reaction mixture of 6-(3-cyclopropyl-5-(5-fluoro-2-methylphenyl)-1H-pyrazol-1-yl)-2-azaspiro [3.3] heptane (int-5) and 6-(5-cyclopropyl-3-(5-fluoro-2-methylphenyl)-1H-pyrazol-1-yl)-2-azaspiro[3.3]heptane (int-5A) (1.0 g, 3.52 mmol, 1.0 eq.), Pyridine (1.23 g, 17.62 mmd, 5.0 eq.), carboxylic acid (0.66 g, 4.23 mmol, 1.2 eq.) in N,N-dimethyl formamide (5 mL) was added TBTU (1.7 g, 5.28 mmd, 1.5 eq.) at 0° C. The reaction mass was stirred at room temperature for 3-4 hr. After completion of reaction as monitored by TLC, the reaction mixture was poured in water (100 mL) and extracted with ethyl acetate (50 mL*3). The organic layer was washed with saturated solution of sodium carbonate (50 mL) and brine (100 mL), dried over Na$_2$SO$_4$ and concentrated under reduce pressure to get residue. The residue was purified by combiflash using 30-35% ethyl acetate in n-hexane as eluent. The crude was submitted to prep HPLC for purification. Two Fraction was collected.

Fraction-1: (6-(5-cyclopropyl-3-(5-fluoro-2-methylphenyl)-1H-pyrazol-1-yl)-2-azaspiro [3.3] heptan-2-yl)(2-fluoro-5-hydroxyphenyl) methanone (PSY-05-00491-001 Fr-1) (0.075 g, 1.64%). LCMS: m/z 449.5 [M+1]+. NMR: $^1$H NMR (400 MHz, DMSO-d6) δ 9.65 (d, J=7.5 Hz, 1H), 7.36 (d, J=5.7 Hz, 1H), 7.21 (d, J=9.3 Hz, OH), 7.10-7.00 (m, 1H), 6.99 (d, J=9.0 Hz, 1H), 6.84 (s, 1H), 6.76 (s, 1H), 5.93 (s, 1H), 4.28-4.19 (m, 1H), 4.01 (d, J=9.4 Hz, 4H), 2.67 (s, 4H), 2.01 (s, 3H), 1.90 (s, 1H), 0.87 (s, 2H), 0.66 (d, J=14.9 Hz, 2H).

Fraction-2: (6-(3-cyclopropyl-5-(5-fluoro-2-methylphenyl)-1H-pyrazol-1-yl)-2-azaspiro [3.3] heptan-2-yl)(2-fluoro-5-hydroxyphenyl) methanone (PSY-05-00490-001 Fr-2) (0.041 g, 0.89%). LCMS: m/z 449.5 [M+1]+. NMR: $^1$H NMR (400 MHz, DMSO-d6) δ9.67 (d, J=8.4 Hz, 1H), 7.37-7.26 (m, 2H), 7.13-6.98 (m, 2H), 6.85 (s, 1H), 6.80 (s, 1H), 6.24 (s, 1H), 4.16 (d, J=9.1 Hz, 2H), 4.07 (s, 2H), 2.75 (s, 4H), 2.41 (d, J=17.2 Hz, 3H), 1.85 (s, 1H), 0.94 (s, 2H), 0.65 (s, 2H).

Example 14: Synthesis of (6-(4-Cyclopropyl-S-(2-fluorophenyl)-1H-pyrazol-1-yl)-2-azaspiro [3.3] heptan-2-yl) (2-fluoro-5-hydroxyphenyl) methanone [Compound 492]; and (6-(4-Cyclopropyl-3-(2-fluorophenyl)-H-pyrazol-1-yl)-2-azaspiro [3.3] heptan-2-yl) (2-fluoro-5-hydroxyphenyl) methanone [Compound 493]

Reaction Scheme:

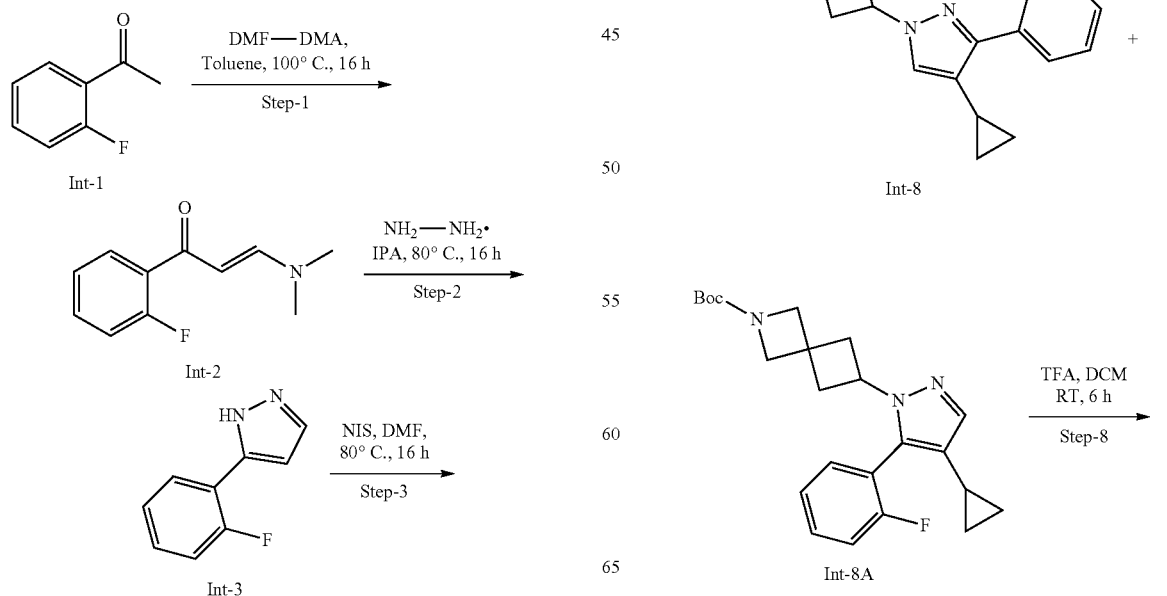

-continued

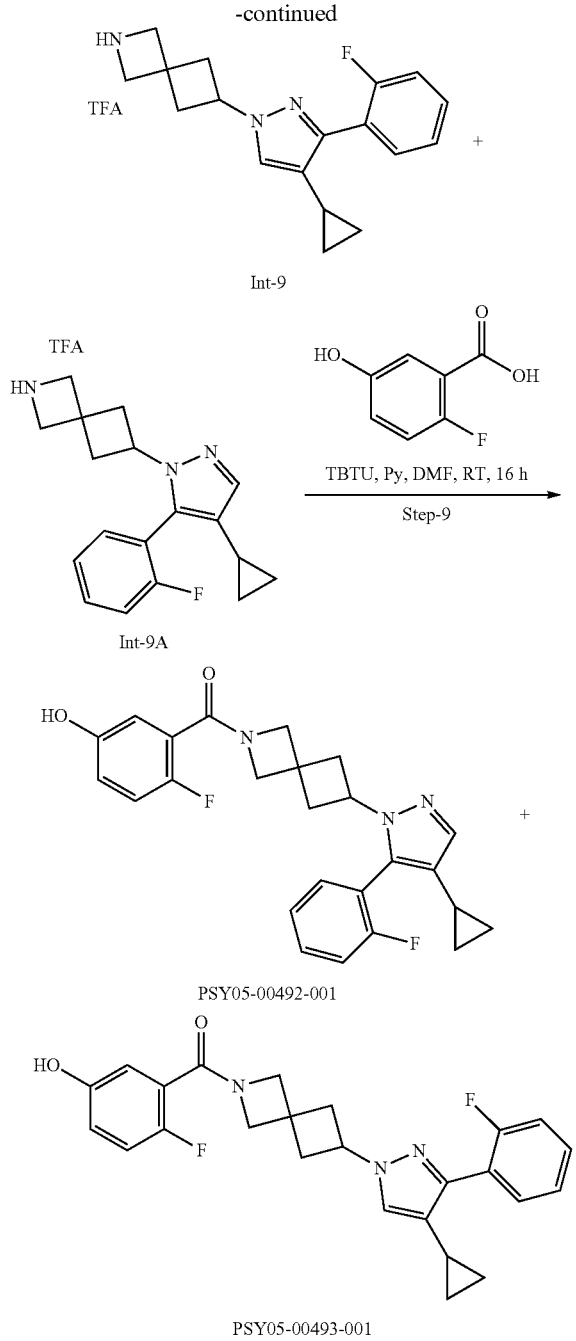

Step-1: Synthesis of (E)-3-(dimethyl amino)-1-(2-(fluorophenyl) prop-2-en-1-one (Int-2)

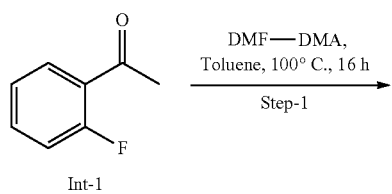

-continued

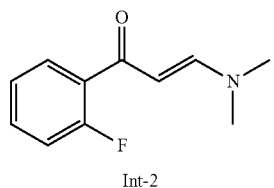

To a stirred solution of 1-(2-fluorophenyl) ethan-1-one (10.0 g, 5.8768 mmol, 1.0 eq) in Toluene (10 mL) was added N, Nd-Dimethylformamide dimethyl acetal (3.0 mL, 29.3841 mmol, 5.0 eq.). The reaction mass was heated at 100° C. for 16 h. After completion of reaction as monitored by TLC and LC MS. The reaction mixture was poured in ice cold water (50 mL) and extracted with ethyl acetate (20 mL*3). The organic layer was washed with brine (50 mL), dried over $Na_2SO_4$ and concentrated under reduce pressure to get residue. The residue was purified by combi flash using 30-40% ethyl acetate in n-hexane as eluent to (Z)-1-(2, 5-Difluorophenyl)-3-(dimethyl amino)-2-methylprop-2-en-1-one (Int-2) (105 g, 75.0%).

Step-2: Synthesis of 5-(2-Fluorophenyl)-11-pyrazole (Int-3)

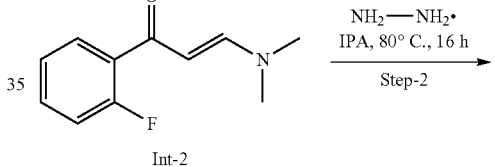

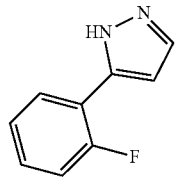

To a stirred solution of (E)-3-(dimethyl amino)-1-(2-fluorophenyl) prop-2-en-1-one (10.0 g, 51.81 mmol, 1.0 eq.) in Isopropyl alcohol (100 mL) was added hydrazine hydrate (2.49 mL, 77.72 mmol, 1.5 eq.). The reaction mass was heated at 80° C. for 16 h. After completion of reaction as monitored by TLC and LCMS, the reaction mixture was concentrated to get residue. The residue was purified by combi flash using 20-30% ethyl acetate in n-hexane as eluent to get 5-(2-Fluorophenyl)-1H-pyrazole (Int-3) (7.0 g, 83.40%).

Step-3: Synthesis of 5-(2-fluorophenyl)-4-iodo-1H-pyrazole (Int-4)

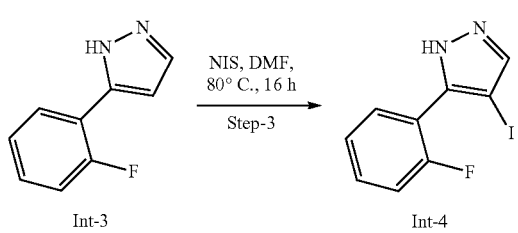 [SMILES: Fc1ccccc1-c1ccn[nH]1 ; Fc1ccccc1-c1[nH]ncc1I]

To a well stirred solution of 5-(2-fluorophenyl)-1H-pyrazole (7.0 g, 43.15 mmol, 1.0 eq.) in N,N-dimethyl formamide (10 mL) was added N-iodo succinamide (10.68 g, 47.4722 mmol, 1.1 eq.). The reaction was heated at 80° C. for 16 h. After completion of reaction as monitored by TLC, the reaction mixture was poured in ice water (100 mL) and extracted with ethyl acetate (50 mL*3). The organic layer was washed with brine (50 mL), dried over $Na_2SO_4$ and concentrated under reduce pressure to get residue. The residue was purified by combi flash using 30-50% ethyl acetate in n-hexane as eluent to get to 5-(2-Fluorophenyl)-4-iodo-1H-pyrazole (Int-4) (7.56 g, 60.80%).

Step-4: Synthesis of 5-(2-Fluorophenyl)-4-iodo-1-(4-methoxybenzyl)-1H-pyrazole (Int-5)

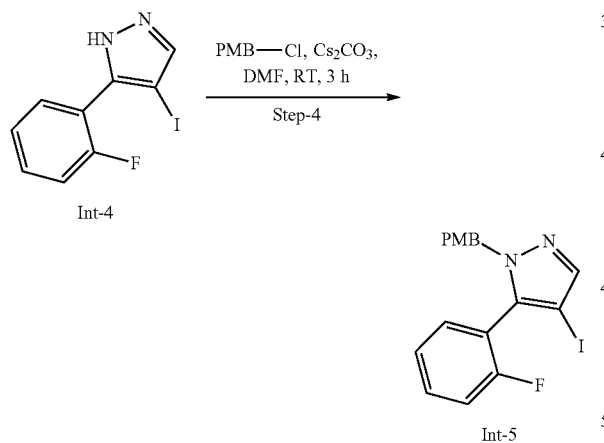

To a well stirred solution of 5-(2-fluorophenyl)-4-iodo-1H-pyrazole (7.56 g, 26.25 mmol, 1.0 eq.), $Cs_2CO_3$ (12.79 g, 39.37 mmol, 1.5 eq.) in N,N-dimethyl formamide (75 mL) was added 4-Methoxybenzyl chloride (4.28 mL, 31.500 mmol, 1.2 eq.). The reaction was stirred at room temperature for 2-3 h. After completion of reaction as monitored by TLC, the reaction mixture was poured in ice water (100 mL) and extracted with ethyl acetate (50 mL*3). The organic layer was washed with brine (50 mL), dried over $Na_2SO_4$ and concentrated under reduce pressure to get residue. The residue was purified by combi flash using 30-50% ethyl acetate in hexane as eluent to get 5-(2-Fluorophenyl)-4-iodo-1-(4-methoxybenzyl)-1H-pyrazole (Int-5) (8.25 g, 77.01%).

Step-5: Synthesis of 4-cyclopropyl-5-(2-fluorophenyl)-1-(4-methoxybenzyl)-1H-spyrazole (Int-6)

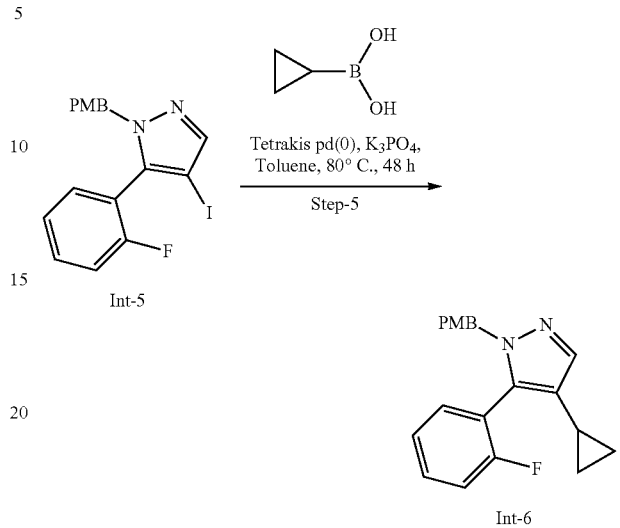

To a well stirred reaction mixture of 5-(2-fluorophenyl)-4-iodo-1-(4-methoxybenzyl)-1H-pyrazole (8.0 g, 19.60 mmol, 1.0 eq.), Cyclopropyl boronic acid (3.36 g, 39.21 mmol, 2.0 eq.), potassium phosphate (12.48 g, 58.80 mmd, 3.0 eq.) in Toluene (80 mL). $N_{2(g)}$ was purged for 20 min, after that Tetrakis (1.13 g, 0.98 mmol, 0.05 eq.) was added and heated the reaction mixture for 80° C. for 48 h. After completion of reaction as monitored by TLC, the reaction mixture was filtered through celite bed, celite bed was washed with ethyl acetate. Filtrate was diluted in water (100 mL) and extracted with ethyl acetate (50 mL*3). The organic layer was washed with brine (100 mL), dried over $Na_2SO_4$ and concentrated under reduce pressure to get residue. The residue was purified by combi flash using 0-50% ethyl acetate in n-hexane as eluent to get to 4-Cyclopropyl-5-(2-fluorophenyl)-1-(4-methoxybenzyl)-1H-pyrazole (Int-6) (1.2 g, 18.99%).

Step-6: Synthesis of 4-cyclopropyl-5-(2-fluorophenyl)-1H-pyrazole (Int-7)

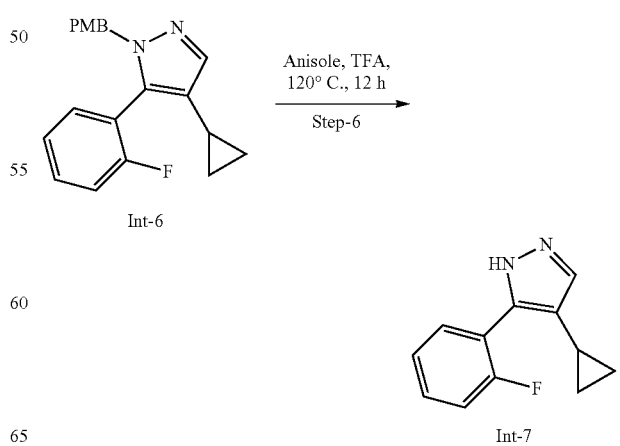

To a well stirred reaction mixture of 4-cyclopropyl-5-(2-fluorophenyl)-1-(4-methoxybenzyl)-1H-pyrazole (1.2 g, 3.7267 mmol, 1.0 eq.) in 10 mL Anisole, was added 1 mL trifluoro acetic acid. The reaction mixture was heated at 120° C. for 12 h. After completion of reaction as monitored by TLC, the reaction mixture was poured in water (100 mL) and extracted with ethyl acetate (50 mL*3). The organic layer was washed with brine (100 mL), dried over $Na_2SO_4$ and concentrated under reduce pressure to get residue. The residue was purified by combi flash using 30-50% ethyl acetate in n-hexane as eluent to get to 4-Cyclopropyl-5-(2-fluorophenyl)-1H-pyrazole (Int-7) (0.680 g, 90.33%).

Step-7: Synthesis of Tert-butyl 6-(4-cyclopropyl-3-(2-fluorophenyl)-1H-pyrazol-1-yl)-2-azaspiro [3.3] heptane-2-carboxylate (Int-8) and tert-butyl 6-(4-cyclopropyl-5-(2-fluorophenyl)-1H-pyrazol-1-yl)-2-azaspiro [3.3] heptane-2-carboxylate (Int-8A)

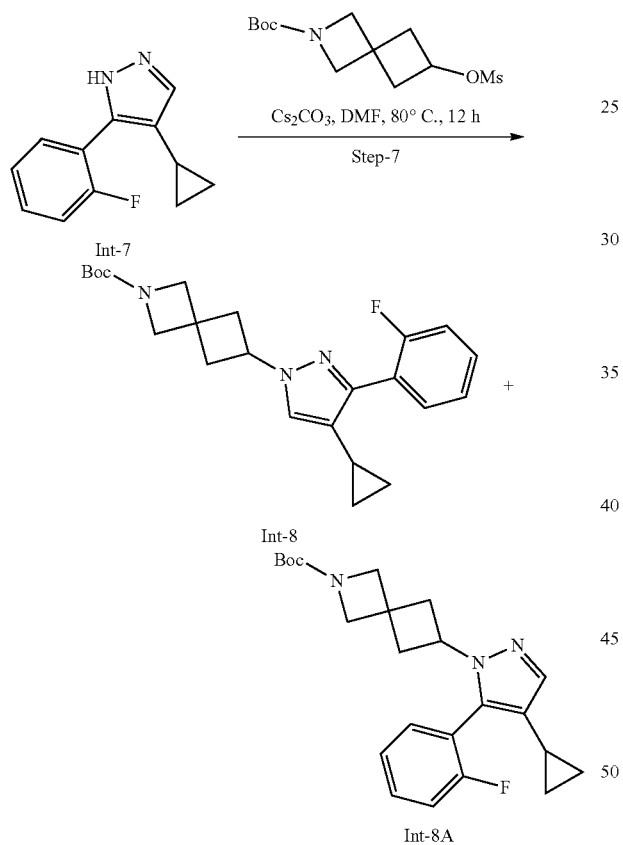

To a well stirred reaction mixture of 4-cyclopropyl-5-(2-fluorophenyl)-1H-pyrazole (0.80 g, 3.96 mmol, 1.0 eq.), $Cs_2CO_3$ (1.93 g, 5.94 mmol, 1.5 eq.) in N,N-dimethyl formamide (10 mL) was added Tert-butyl 6-((methyl sulfonyl)oxy)-2-azaspiro [3.3] heptane-2-carboxylate (1.15 g, 3.96 mmol, 1.0 eq.). The reaction was heated at 80° C. for 12 h. After completion of reaction as monitored by TLC and LCMS, the reaction mixture was poured in water (50 mL) and extracted with ethyl acetate (50 mL*3). The organic layer was washed with brine (50 mL), dried over $Na_2SO_4$ and concentrated under reduce pressure to get residue. The residue was purified by combi flash using 30-50% ethyl acetate in n-hexane as eluent to get to mixture of two regio isomer, tert-butyl 6-(4-cyclopropyl-3-(2-fluorophenyl)-1H-pyrazol-1-yl)-2-azaspiro[3.3]heptane-2-carboxylate (Int-8) and tert-butyl 6-(4-cyclopropyl-5-(2-fluorophenyl)-1H-pyrazol-1-yl)-2-azaspiro[3.3]heptane-2-carboxylate (Int-8A) (1.0 g, 63.60%).

Step-8: Synthesis of 6-(4-cyclopropyl-3-(2-fluorophenyl)-1H-pyrazol-1-yl)-2-azaspiro [3.3] heptane (Int-9) and 6-(4-cyclopropyl-5-(2-fluorophenyl)-1H-pyrazol-1-yl)-2-azaspiro [3.3] heptane (Int-9A)

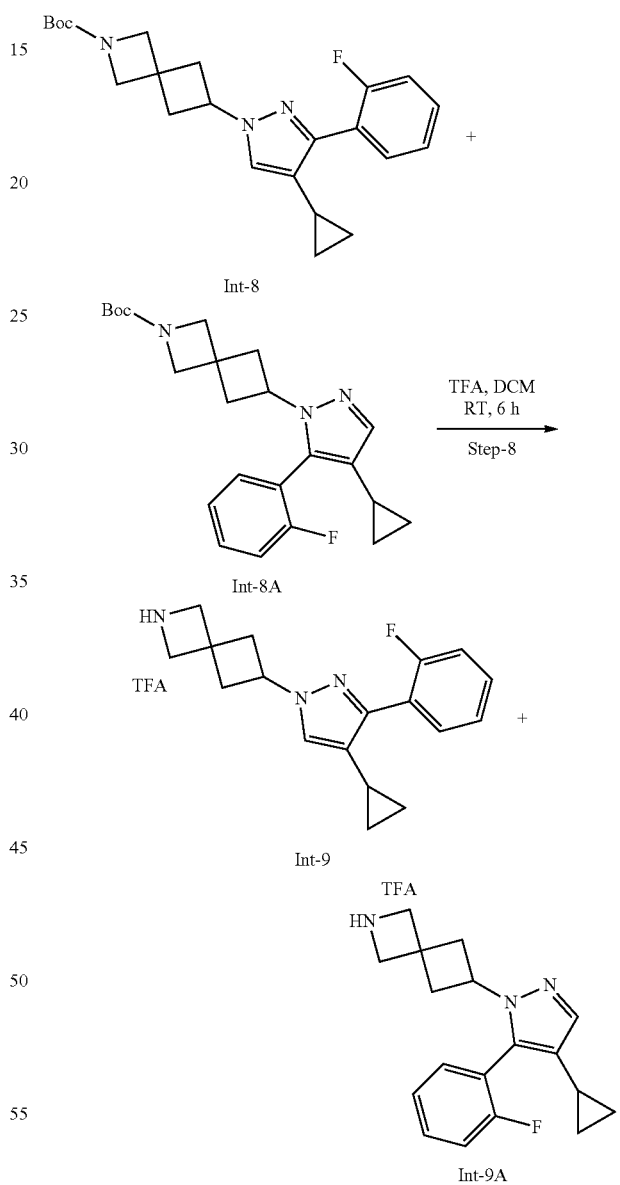

To a well stirred reaction mixture of tert-butyl 6-(4-cyclopropyl-3-(2-fluorophenyl)-1H-pyrazol-1-yl)-2-azaspiro[3.3]heptane-2-carboxylate (Int-8) and tert-butyl 6-(4-cyclopropyl-5-(2-fluorophenyl)-1H-pyrazol-1-yl)-2-azaspiro[3.3]heptane-2-carboxylate (Int-8A (1.0 g, 2.5706 mmol, 1.0 eq.) in dichloromethane (10 mL), was added trifluoro acetic acid (2.0 mL) dropwise at 0° C. for 6 h. After completion of reaction as monitored by TLC and LCMS, the reaction mixture was concentrated to get TFA salt of 6-(4-cyclopropyl-3-(2-fluorophenyl)-1H-pyrazol-1-yl)-2-azaspiro [3.3] heptane (Int-9) and 6-(4-cyclopropyl-5-(2-fluorophenyl)-1H-pyrazol-1-yl)-2-azaspiro [3.3] heptane (Int-9A) (1.13 g).

Step-9: Synthesis of (6-(4-Cyclopropyl-5-(2-fluorophenyl)-1H-pyrazol-1-yl)-2-azaspiro [3.3] heptan-2-yl) (2-fluoro-5-hydroxyphenyl) methanone (PSY-05-00492-001) and (6-(4-Cyclopropyl-3-(2-fluorophenyl)-1H-pyrazol-1-yl)-2-azaspiro [3.3] heptan-2-yl) (2-fluoro-5-hydroxyphenyl) methanone (PSY-05-00493-001)

To a well stirred reaction mixture of TFA salt of 6-(4-cyclopropyl-3-(2-fluorophenyl)-1H-pyrazol-1-yl)-2-azaspiro [3.3] heptane (Int-9) and 6-(4-cyclopropyl-5-(2-fluorophenyl)-1H-pyrazol-1-yl)-2-azaspiro [3.3] heptane (Int-9A) (0.868 g, 2.92 mmol, 1.2 eq.), Pyridine (0.98 mL, 12.17 mmol, 5.0 eq.), 2-Fluoro-5-hydroxybenzoic acid (0.38 g, 2.43 mmol, 1.0 eq.) in N,N-dimethyl formamide (5 mL) was added TBTU (1.17 g, 3.65 mmol, 1.5 eq.) at 0° C. The reaction mass was stirred at room temperature for 16 h. After completion of reaction as monitored by TLC and LCMS, the reaction mixture was poured in water (100 mL) and extracted with ethyl acetate (50 mL*3). The organic layer was washed with saturated solution of sodium carbonate (50 mL) and brine (100 mL), dried over $Na_2SO_4$ and concentrated under reduce pressure to get residue. The residue was purified by combi flash using 0-100% ethyl acetate in n-hexane as eluent to get mixture of two regio isomer. Which was purified by prep-HPLC purification to obtained two fractions.

Fraction-1: (6-(4-Cyclopropyl-3-(2-fluorophenyl)-1H-pyrazol-1-yl)-2-azaspiro [3.3] heptan-2-yl) (2-fluoro-5-hydroxyphenyl) methanone (PSY-05-00493-001) (0.027 g, 1.61%). LCMS: m/z: 436.22 [M+H]$^+$ $^1$H NMR (400 MHz, DMSO-d$_6$) δ 9.64 (s, 1H), 7.36 (dd, J=26.7, 8.4 Hz, 4H), 7.08 (d, J=9.0 Hz, 1H), 6.77 (s, 2H), 4.41 (s, 1H), 4.02 (s, 4H), 2.70 (s, 4H), 1.40 (s, 1H), 0.69 (s, 2H), 0.46 (s, 2H).

Fraction-2: (6-(4-Cyclopropyl-5-(2-fluorophenyl)-1H-pyrazol-1-yl)-2-azaspiro [3.3] heptan-2-yl) (2-fluoro-5-hydroxyphenyl) methanone (PSY-05-00492-001) (0.087 gm, 5.15%). LCMS: m/z 436.20 [M+H]$^+$. $^1$H NMR (400 MHz, DMSO-d$_6$) δ 9.69 (s, 1H), 7.56 (dd, J=20.5, 7.4 Hz, 3H), 7.33-7.24 (m, 2H), 6.81 (s, 2H), 4.76-4.66 (m, 1H), 4.15 (d, J=10.4 Hz, 2H), 4.04 (d, J=8.4 Hz, 2H), 2.72-2.62 (m, 4H), 1.56 (s, 1H), 0.76 (s, 2H), 0.44 (s, 2H).

Example 15: Synthesis of (6-(5-(2-chloro-5-fluorophenyl)-4-methyl-1H-pyrazol-1-yl)-2-azaspiro [3.3] heptan-2-yl) (2-fluoro-5-hydroxyphenyl) methanone [Compound 519], and (6-(3-(2-chloro-5-fluorophenyl)-4-methyl-1H-pyrazol-1-yl)-2-azaspiro [3.3] heptan-2-yl)(2-fluoro-S-hydroxyphenyl)methanone [Compound 520]

Synthetic Scheme:

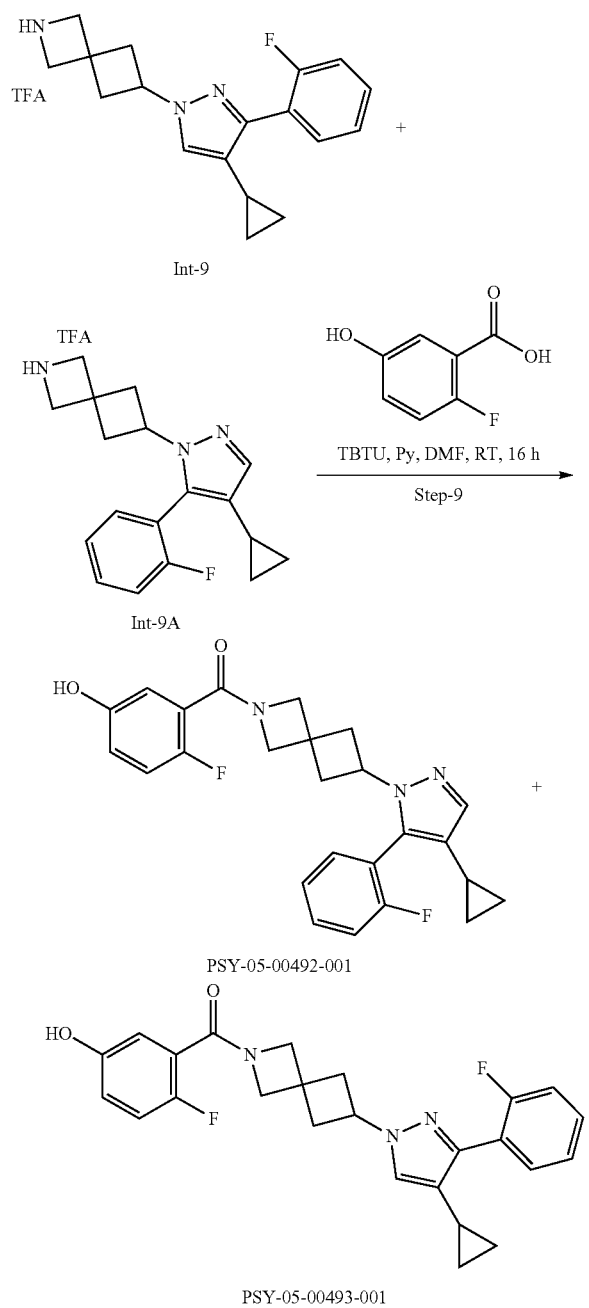

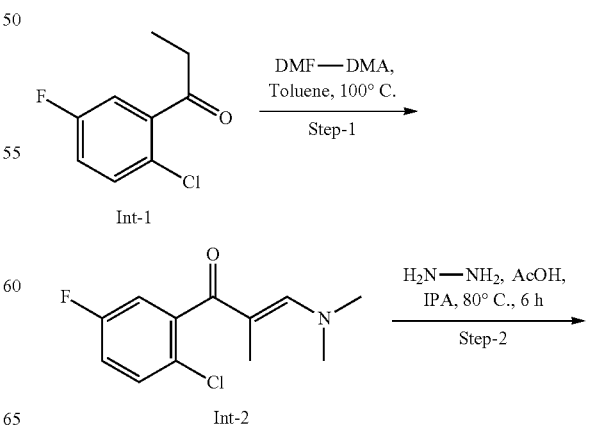

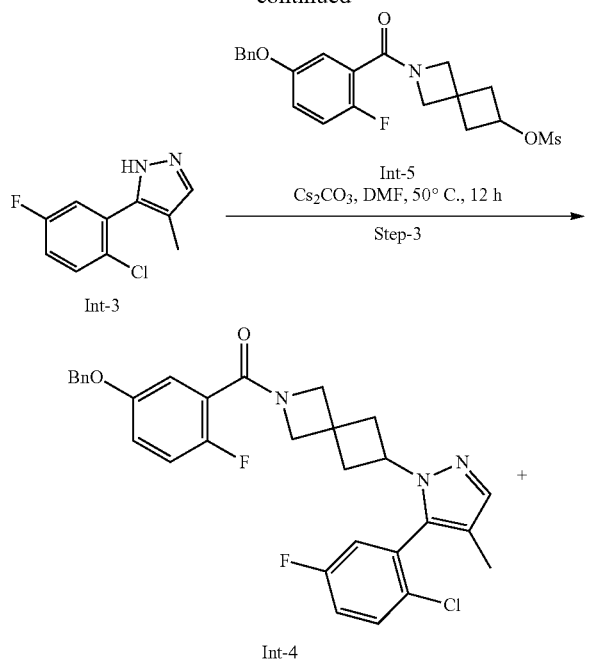

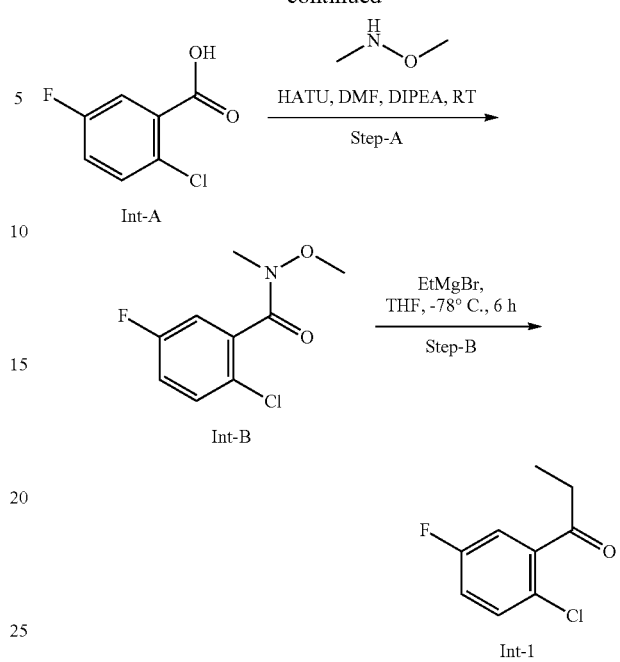

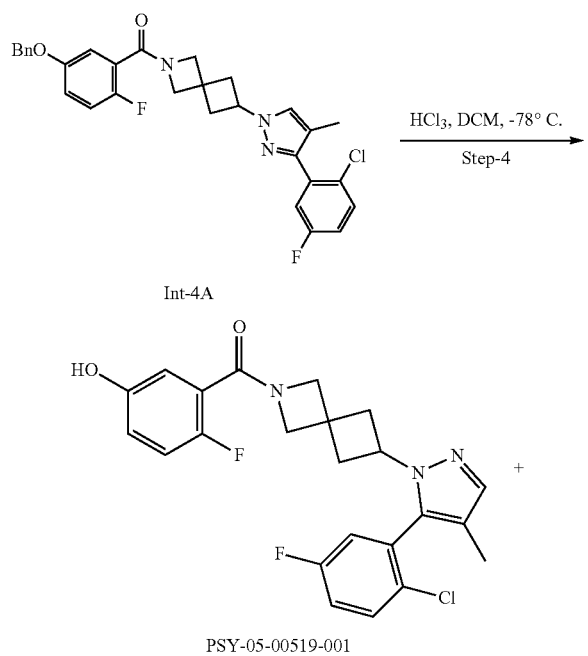

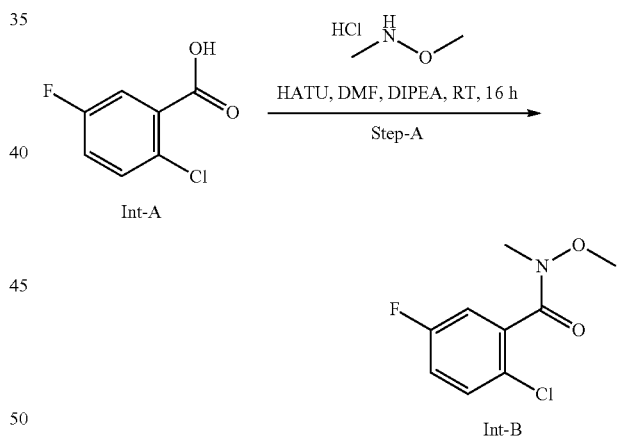

Step-A: 2-chloro-5-fluoro-N-methoxy-N-methylbenzamide (Int-B)

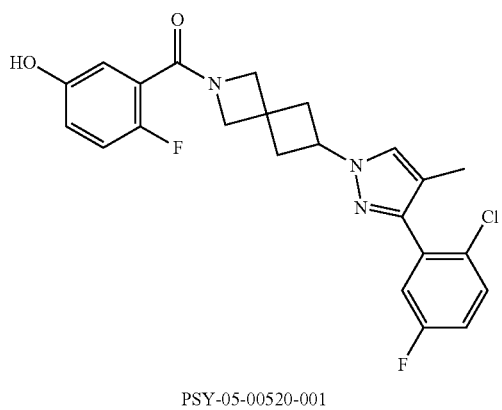

To a stirred solution of 2-chloro-5-fluorobenzoic acid (10.0 g, 57.27 mmol, 1.0 eq.), N,N-di-isopropyl ethylamine (29.4 mL, 171.82 mmol, 3.0 eq.), N,O-dimethyl hydroxylamine hydrochloride (6.142 g, 63.0 mmol, 1.1 eq.) in N,N-Dimethylformamide (50 mL) was added HATU (32.66 g, 85.91 mmol, 1.5 eq.) at 0° C. Stir the reaction at room temperature for 16 h. After completion of reaction as monitored by TLC, the reaction mixture was poured in ice cold water (100 mL) and extracted with ethyl acetate (50 mL*3). The organic layer was dried over Sodium sulfate and concentrated under reduce pressure to get residue. The residue was purified by combiflash using 25% Ethyl acetate in n-hexane as eluent to get 2-chloro-5-fluoro-N-methoxy-N-methylbenzamide (Int-B) (10.9 g, 87.3%).

Step-B: 1-(2-chloro-5-fluorophenyl) propan-1-one (Int-1)

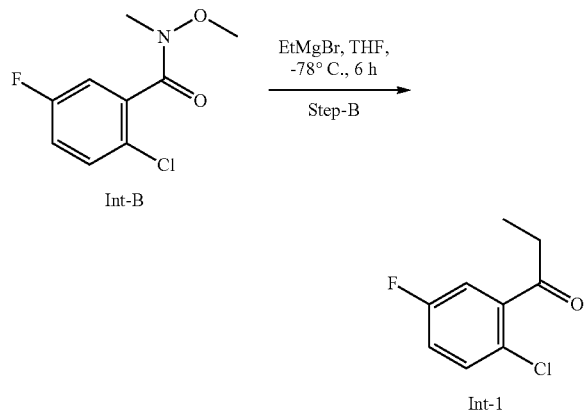

To a stirred solution of 2-chloro-5-fluoro-N-methoxy-N-methylbenzamide (10.9 g, 50.25 mmol, 1.0 eq.) in tetrahydrofuran (50 mL), was slowly added Ethyl magnesium bromide 3M sol$^n$ in Tetrahydrofuran (25.13 mL, 75.38 mmol, 1.5 eq.) at −78° C. Stir the reaction at room temperature for 6 h. After completion of reaction as monitored by TLC, the reaction mixture was poured in ice cold water (100 mL) and extracted with ethyl acetate (50 mL*3). The organic layer was dried over Sodium sulfate and concentrated under reduce pressure to get residue. The residue was purified by combiflash using 20-25% Ethyl acetate in n-hexane as eluent to get 1-(2-chloro-5-fluorophenyl) propan-1-one (Int-1) (5.28 g, 56.49%).

Step-1: (E)-1-(2-chloro-5-fluorophenyl)-3-(dimethylamino)-2-methylprop-2-en-1-one (Int-2)

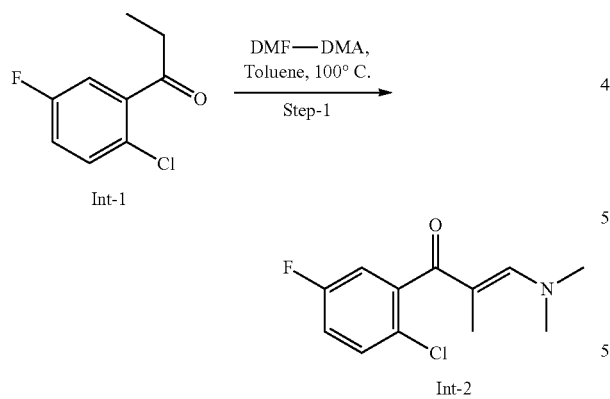

To a stirred solution of 1-(2-chloro-5-fluorophenyl)propan-1-one (5.28 g, 28.29 mmol, 1.0 eq.) in Toluene (15 mL) was added N,N-Dimethylformamide dimethyl acetal (23.60 g, 198.06 mmol, 7.0 eq.) the reaction mass was heated at 100° C. for 16 h. After completion of reaction as monitored by TLC, the reaction mixture was poured in ice cold water (100 mL) and extracted with ethyl acetate (50 mL*3). The organic layer was washed with brine (100 mL), dried over Sodium sulfate and concentrated under reduce pressure to get residue. The residue was purified by combiflash using 25-30/o ethyl acetate in hexane as eluent to get (E)-1-(2-chloro-5-fluorophenyl)-3-(dimethylamino)-2-methylprop-2-en-1-one (Int-2) (5.65 g, 82.62%).

Step-2: 5-(2-chloro-5-fluorophenyl)-4-methyl-1H-pyrazole (Int-3)

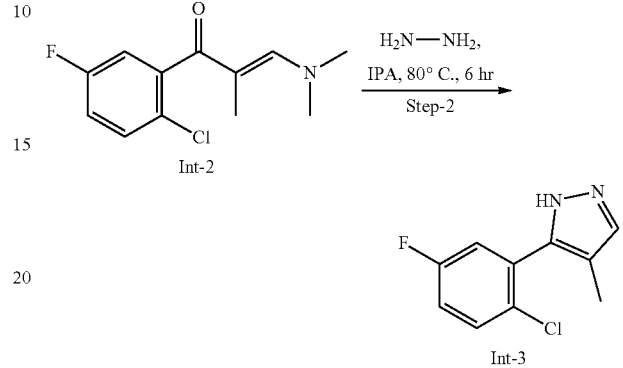

To a stirred solution of (E)-1-(2-chloro-5-fluorophenyl)-3-(dimethylamino)-2-methylprop-2-en-1-one (5.65 g, 23.44 mmol, 1.0 eq.) in Isopropyl alcohol (30 mL) was added hydrazine hydrate (2.0 g, 35.16 mmol, 1.5 eq.) the reaction mass was heated at 80° C. for 16 h. After completion of reaction as monitored by TLC, the reaction mixture was concentrated to get residue. The residue was purified by combiflash using 15-20% ethyl acetate in hexane as eluent to get 5-(2-chloro-5-fluorophenyl)-4-methyl-1H-pyrazole (Int-3) (4.3 g, 87.33%).

Step-3: (5-(benzyloxy)-2-fluorophenyl)(6-(5-(2-chloro-5-fluorophenyl)-4-methyl-1H-pyrazol-1-yl)-2-azaspiro [3.3] heptan-2-yl) methanone (Int-4) and (5-(benzyloxy)-2-fluorophenyl)(6-(3-(2-chloro-5-fluorophenyl)-4-methyl-1H-pyrazol-1-yl)-2-azaspiro [3.3] heptan-2-yl) methanone (Int-4A)

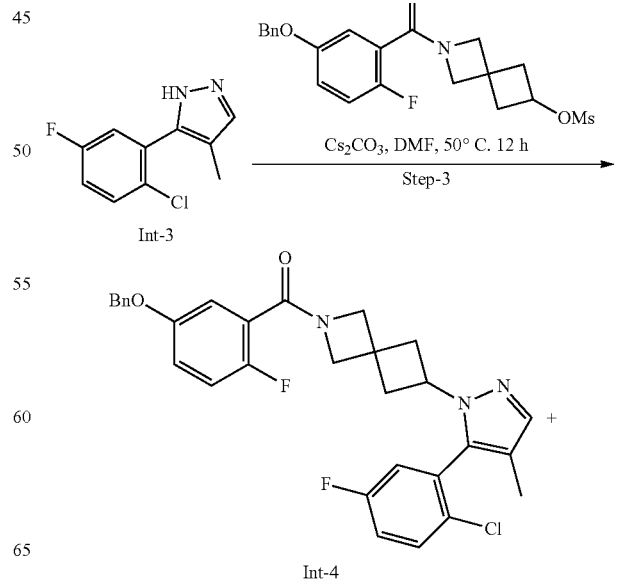

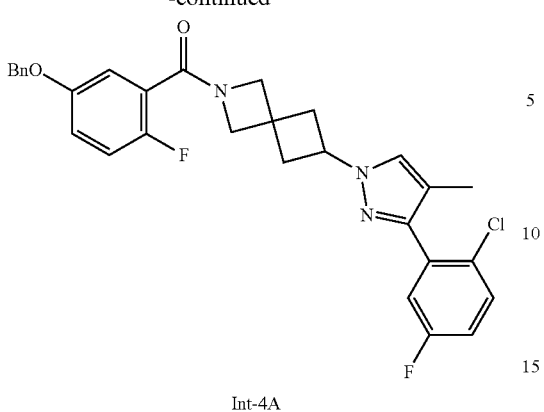

Int-4A

To a well stirred reaction mixture of 5-(2-chloro-5-fluorophenyl)-4-methyl-1H-pyrazole (0.2 g, 0.094 mmol, 1.0 eq.), Cesium carbonate (0.46 g, 1.42 mmol, 1.5 eq.) in N,N-Dimethylformamide (5 mL) was added 2-(5-(benzyloxy)-2-fluorobenzoyl)-2-azaspiro[3.3]heptan-6-yl methane sulfonate (0.43 g, 1.04 mmol, 1.3 eq.). The reaction was heated at 50° C. for 12 h. After completion of reaction as monitored by TLC, the reaction mixture was poured in water (30 mL) and extracted with ethyl acetate (50 mL). The organic layer was washed with brine (30 mL), dried over Sodium sulfate and concentrated under reduce pressure to get residue. The residue was purified by combiflash using 35-40/o ethyl acetate in n-hexane as eluent to get mixture of two regio isomers (5-(benzyloxy)-2-fluorophenyl)(6-(5-(2-chloro-5-fluorophenyl)-4-methyl-1H-pyrazol-1-yl)-2-azaspiro[3.3]heptan-2-yl)methanone (Int-4) and (5-(benzyloxy)-2-fluorophenyl)(6-(3-(2-chloro-5-fluorophenyl)-4-methyl-1H-pyrazol-1-yl)-2-azaspiro [3.3] heptan-2-yl) methanone (Int-4A) (0.9 g, 97.63%).

Step-4: (6-(5-(2-chloro-5-fluorophenyl)-4-methyl-1H-pyrazol-1-yl)-2-azaspiro [3.3]heptan-2-yl) (2-fluoro-5-hydroxyphenyl) methanone (PSY-05-00519-001) and (6-(3-(2-chloro-5-fluorophenyl)-4-methyl-1H-pyrazol-1-yl)-2-azaspiro [3.3] heptan-2-yl)(2-fluoro-5-hydroxyphenyl) methanone (PSY-05-00520-001)

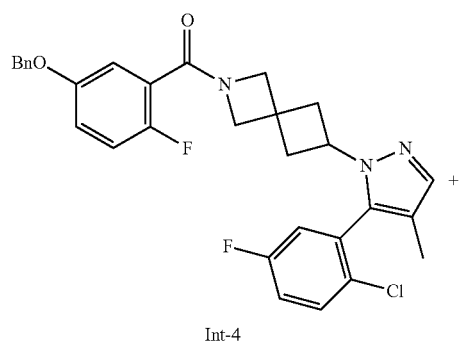

Int-4

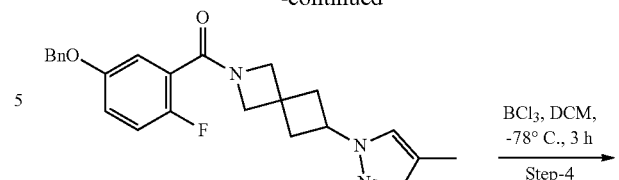

Int-4A

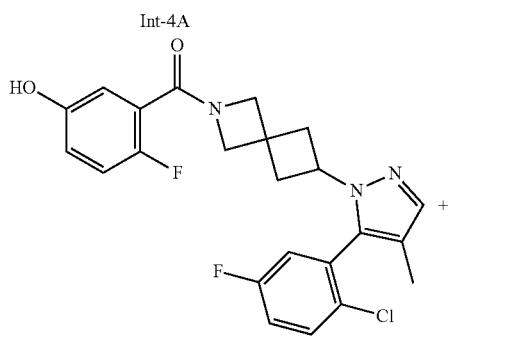

PSY-05-00519-001

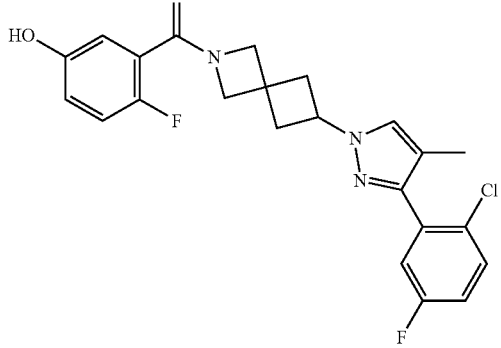

PSY-05-00520-001

To a stirred solution of (5-(benzyloxy)-2-fluorophenyl)(6-(5-(2-chloro-5-fluorophenyl)-4-methyl-1H-pyrazol-1-yl)-2-azaspiro [3.3] heptan-2-yl) methanone and (5-(benzyloxy)-2-fluorophenyl)(6-(3-(2-chloro-5-fluorophenyl)-4-methyl-1H-pyrazol-1-yl)-2-azaspiro [3.3] heptan-2-yl) methanone (0.5 g, 0.93 mmol, 1.0 eq.) in dichloromethane (5 mL) was cooled to −78° C., was added BCl$_3$ 1.0 M Sol″ in dichloromethane (2.8 mL, 2.80 mmol, 3.0 eq.), then the resulting reaction mixture was stirred at −78° C. for next 2-3 h. The progress of the reaction was monitored by TLC. After completion of reaction, the reaction mixture was quench with Triethylamine (2 mL) and concentrated under vacuum to get crude. The crude was purified by prep-HPLC to get two fractions.

Fraction-1: (6-(5-(2-chloro-5-fluorophenyl)-4-methyl-1H-pyrazol-1-yl)-2-azaspiro [3.3] heptan-2-yl) (2-fluoro-5-hydroxyphenyl) methanone (PSY-05-00519-001) (0.062 g, 15.01%). LCMS: m/z 444.40 [M+1]$^+$. NMR: $^1$H NMR (400 MHz, DMSO-d$_6$) δ 9.70 (s, 1H), 7.68 (d, J=5.0 Hz, 1H), 7.58 (dt, J=8.8, 5.6 Hz, 2H), 7.35-7.17 (m, 1H), 7.08 (q, J=9.1 Hz, 1H), 6.85-6.71 (m, 2H), 4.32 (dq, J=24.0, 7.9 Hz, 1H), 4.03 (d, J=10.7 Hz, 4H), 2.68 (q, J=15.2, 13.3 Hz, 4H), 1.81 (d, J=2.6 Hz, 3H).

Fraction-2: (6-(3-(2-chloro-5-fluorophenyl)-4-methyl-1H-pyrazol-1-yl)-2-azaspiro [3.3] heptan-2-yl) (2-fluoro-5-hydroxyphenyl) methanone (PSY-05-00520-001) (0.019 g, 4.76%). LCMS: m/z: 444.40 [M+1]. NMR: $^1$H NMR (400 MHz, DMSO-d$_6$) δ 9.80 (s, 1H), 7.68 (d, J=5.0 Hz, 11H), 7.58 (dt, J=8.8, 5.6 Hz, 1H), 7.35-7.17 (m, 2H), 7.08 (q, J=9.1 Hz, 1H), 6.87-6.74 (m, 2H), 4.72 (dq, J=24.0, 7.9 Hz, 1H), 4.13 (d, J=10.7 Hz, 2H), 4.02 (d, J=9.4 Hz, 2H), 2.68 (q, J=15.2, 13.3 Hz, 4H), 1.91 (d, J=2.6 Hz, 3H).

Example 16: Synthesis of 2-(2-ethoxy-4-fluorobenzoyl)-N-(2-isopropylphenyl)-N-methyl-2-azaspiro 13.3/heptane-6-carboxamide [Compound 205]

Synthetic Scheme:

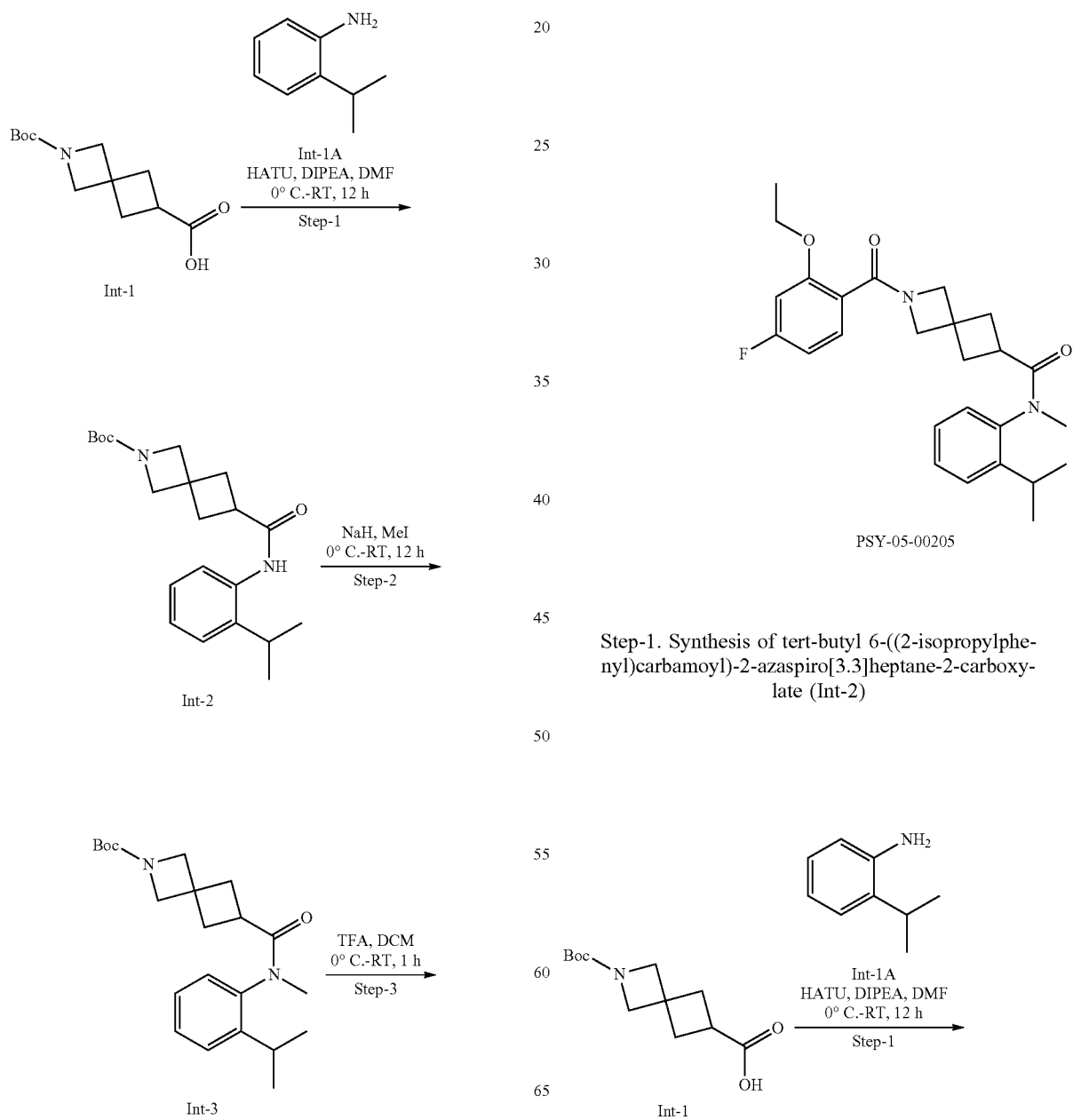

Step-1. Synthesis of tert-butyl 6-((2-isopropylphenyl)carbamoyl)-2-azaspiro[3.3]heptane-2-carboxylate (Int-2)

-continued

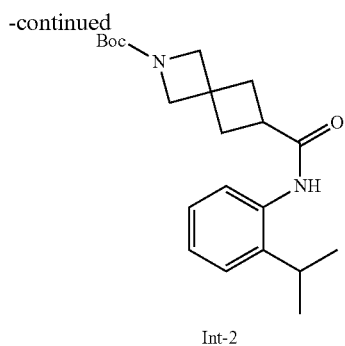

Int-2

To a stirred solution of 2-(tert-butoxycarbonyl)-2-azaspiro [3.3] heptane-6-carboxylic acid (0.30 gm, 1.24 mmol, 1 eq.) in N,N-Dimethyl formamide (5 mL) were added HATU (0.70 gm, 1.86 mmol, 1.5 eq.) DIPEA (0.802 gm, 6.22 mmol, 5.0 eq.) followed by addition of 2-isopropylaniline (Int-IA) (0.21 gm, 1.24 mmol, 1.0 eq.) at 0° C. and allowed to stirred the reaction at room temperature for 12 hr; the progress of the reaction of was monitored by TLC. After completion of reaction, the reaction mixture was diluted with water (10 mL) and extracted with ethyl acetate (3×20 mL), washed with brine. The organic layer was dried over sodium sulphate and concentrated under vacuum to get crude material; which was purified by combi-flash by using 30% Ethyl acetate in n Hexane as mobile phase to give desired product tert-butyl 6-((2-isopropylphenyl)carbamoyl)-2-azaspiro [3.3] heptane-2-carboxylate (Int-2) 0.280 gm (Yield: 63.63%); LCMS: 359.6 m/z [M+1]+

Step-2: Synthesis tert-butyl 6-((2-isopropylphenyl) (methyl)carbamoyl)-2-azaspiro [3.3] heptane-2-carboxylate acid (Int-3)

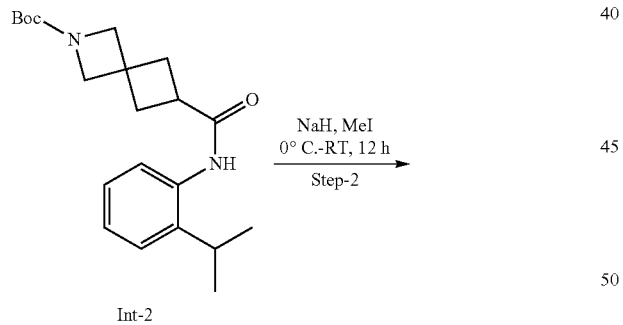

To a stirred solution of tert-butyl 6-((2-isopropylphenyl) carbamoyl)-2-azaspiro [3.3]heptane-2-carboxylate (0.4 gm, 1.11 mmol, 1.0 eq.) in N,N-Dimethyl formamide (5 mL), was added Sodium hydride (0.031 gm, 1.33 mmol, 1.2 eq.) at 0° C. The reaction was stirred at 0° C. for 10 min. Methyl Iodide (0.187 gm, 1.33 mmol, 1.2 eq.) was added dropwise and stirred the reaction mass at room temperature for 12 hrs. After completion of reaction as monitored by TLC, the reaction mixture was diluted with Ice cold water (10 mL) and extracted with Ethyl acetate (2×30 mL). The combined organic layer was washed with brine solution, dried over sodium sulfate and concentrated to obtain crude product, which was purified by combiflash using 30% Ethyl acetate in Hexane as eluent to afford tert-butyl 6-((2-isopropylphenyl)(methyl)carbamoyl)-2-azaspiro[3.3]heptane-2-carboxylate (Int-3) 0.31 gm, (Yield—75.60%). LCMS: 373.4 m/z [M⁺]

Step-3: Synthesis of N-(2-isopropylphenyl)-N-methyl-2-azaspiro [3.3] heptane-6-carboxamide (Int-4)

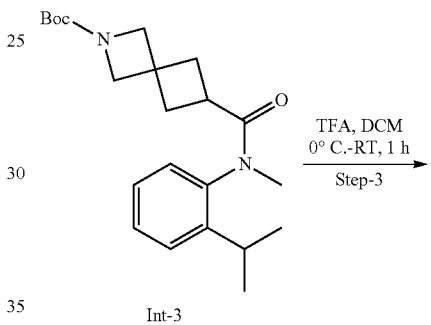

Int-3

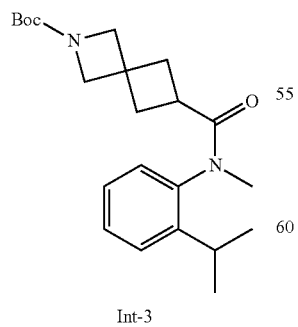

Int-4

To a stirred solution tert-butyl 6-((2-isopropylphenyl) (methyl)carbamoyl)-2-azaspiro [3.3] heptane-2-carboxylate (Int-3) (0.50 gm, 1.33 mmol, 1.0 eq.) in Dichloromethane (10 mL) was added Trifluoroacetic acid (1.0 mL) at 0° C. and allowed to stirred the reaction at Room temperature for 3 hr, the progress of the reaction of the was monitored by TLC. After completion of reaction, the reaction mixture was evaporated under vacuum and basified with bicarbonate solution (5 mL) extracted with Ethyl acetate. Ethyl acetate layer separated dried over sodium sulfate and concentrated to obtain crude product N-(2-isopropylphenyl)-N-methyl-2-azaspiro [3.3] heptane-6-carboxamide (Int-4) 0.350 gm (Yield: quantitative); LCMS: 273.4 m/z [M+1]+

Step-4: Synthesis of 2-(2-ethoxy-4-fluorobenzoyl)-N-(2-isopropylphenyl)-N-methyl-2-azaspiro[3.3]heptane-6-carboxamide (Compound-00205)

Example 17: Synthesis of 2-(2-ethoxy-4-fluorobenzoyl)-N-ethyl-N-(o-tolyl)-2-azaspiro [3.3]heptane-6-carboxamide [Compound 203]

Synthetic Scheme:

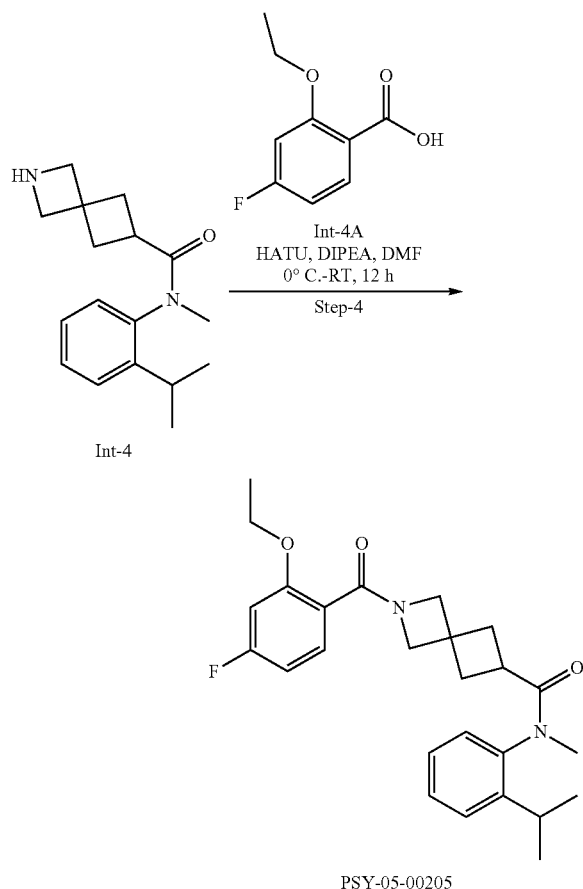

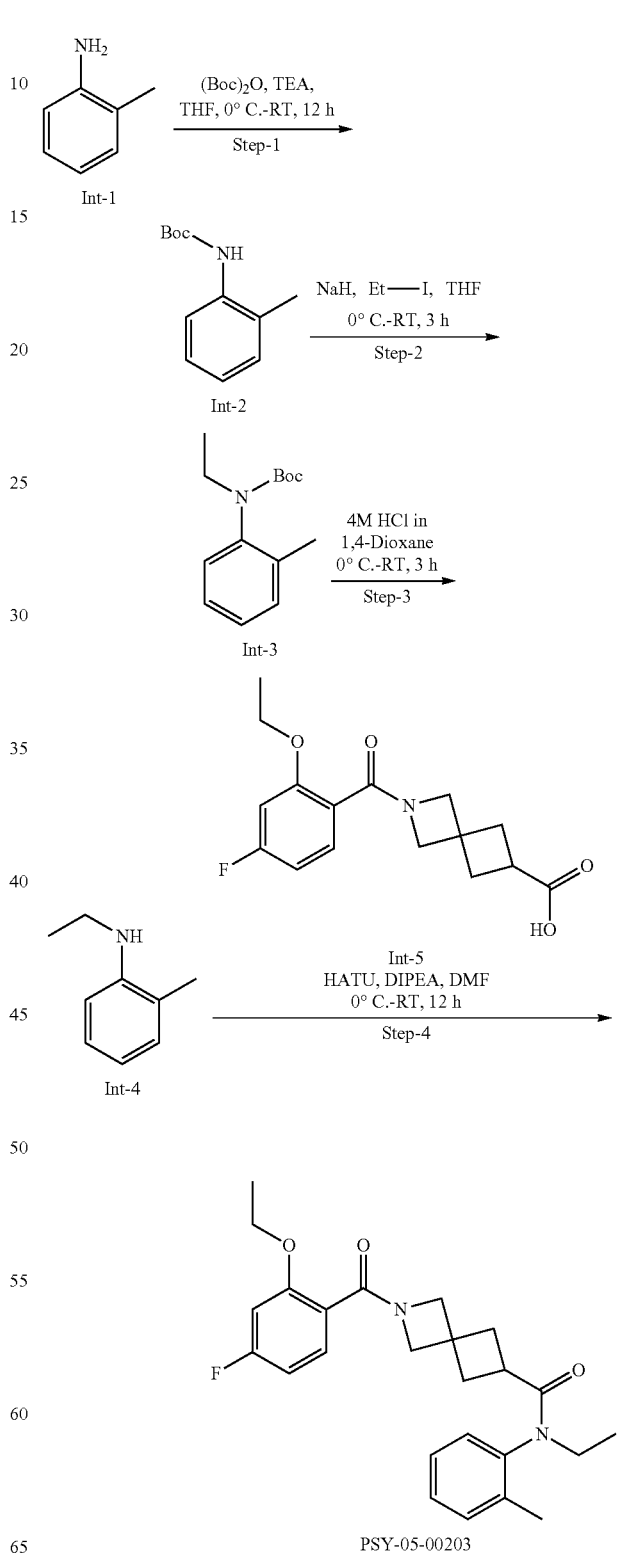

To a stirred solution of 2-ethoxy-4-fluorobenzoic acid (Int-4A), (0.150 gm, 0.815 mmol 1.0 eq.) in N,N-Dimethyl formamide (3 ml) were added N-(2-isopropylphenyl)-N-methyl-2-azaspiro [3.3] heptane-6-carboxamide (0.221 gm, 0.815 mmol, 1 eq.), DIPEA (0.31 gm, 2.445 mmol, 3.0 eq.), HATU (0.10 gm, 1.222 mmol, 1.5 eq.) at 0° C. The resulting reaction mixture was stirred at room temperature for 12 h. After completion of reaction as monitored by TLC, the reaction mixture was diluted with water (10 ml) and extracted with ethyl acetate (3*20 ml). The organic layer was washed with brine (10 ml), dried over sodium sulphate and concentrated under vacuum to get crude material which was purified by combi-flash using 10% Methanol in Dichloromethane as eluent to get 2-(2-ethoxy-4-fluorobenzoyl)-N-(2-isopropylphenyl)-N-methyl-2-azaspiro [3.3] heptane-6-carboxamide (PSY-05-00205) as white solid 0.070 gm (Yield: 20%); LCMS: 439.7 m/z 1H NMR (400 MHz, DMSO-d6) δ 7.51-7.38 (m, 1H), 7.42-7.25 (m, 1H), 7.26 (dd, J=7.9, 4.7 Hz, 1H), 6.95 (ddd, J=19.4, 11.6, 2.4 Hz, 1H), 6.84-6.71 (m, 1H), 4.08 (dq, J=21.4, 6.8 Hz, 2H), 3.82 (t, J=4.8 Hz, 3H), 3.75 (dq, J=14.6, 8.9, 6.8 Hz, 1H), 3.16-3.01 (m, 3H), 2.83 (p, J=6.8 Hz, 1H), 2.68-2.53 (m, 1H), 2.35-2.20 (m, 2H), 2.00 (ddd, J=30.9, 12.2, 8.7 Hz, 2H), 1.31 (dt, J=21.4, 7.0 Hz, 3H), 1.21-1.09 (m, 6H).

Step-1: Synthesis of tert-butyl o-tolyl carbamate (Int-2)

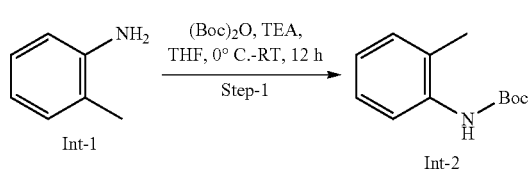

To a stirred solution of o-toluidine (1.0 gm, 9.34 mmol, 1.0 eq.) in N,N-Dimethyl formamide (10 mL) were added TEA (1.88 gm, 18.69 mmol, 2.0 eq.) followed by addition of Boc anhydride (2.24 gm, 10.288 mmol, 1.0 eq.) at 0° C. and allowed to stirred the reaction at room temperature for 12 hr; the progress of the reaction of was monitored by TLC. After completion of reaction, the reaction mixture was diluted with water (10 mL) and extracted with ethyl acetate (3×20 mL), washed with brine. The organic layer was dried over sodium sulphate and concentrated under vacuum to get crude material; which was purified by combi-flash by using 30% Ethyl acetate in n Hexane as mobile phase to give desired product tert-butyl o-tolylcarbamate (Int-2) 1.1 gm (Yield: 56.99%); LCMS: 208.2 m/z [M+1]+

Step-2: Synthesis of tert-butyl ethyl (o-tolyl) carbamate (Int-3)

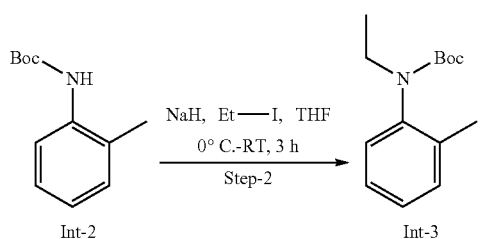

To a stirred solution of tert-butyl o-tolylcarbamate (0.5 gm, 2.415 mmol, 1.0 eq.) in N,N-Dimethyl formamide (8 mL), was added Sodium hydride (0.069 gm, 2.898 mmd, 1.2 eq.) at 0° C. The reaction was stirred at 0° C. for 10 min. Ethyl Iodide (0.741 gm, 2.898 mmd, 1.2 eq.) was added dropwise and stirred the reaction mass at room temperature for 12 hrs. After completion of reaction as monitored by TLC, the reaction mixture was diluted with Ice cold water (10 mL) and extracted with Ethyl acetate (2×30 mL). The combined organic layer was washed with brine solution, dried over sodium sulfate and concentrated to obtain crude product, which was purified by combiflash using 30% Ethyl acetate in Hexane as eluent to afford tert-butyl ethyl(o-tolyl) carbamate (Int-3) 0.45 gm, (Yield—80.35%). LCMS: 180.1 m/z [M−56]+

Step-3: Synthesis of N-ethyl-2-methylaniline (Int-4)

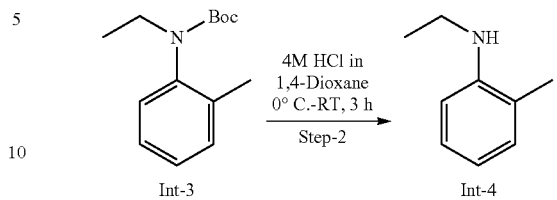

To a stirred solution of tert-butyl ethyl(o-tolyl)carbamate (Int-3) (0.50 gm, 2.127 mmol, 1.0 eq.) in Dichloromethane (10 mL) was added Trifluoroacetic acid (1.0 mL) at 0° C. and allowed to stirred the reaction at Room temperature for 3 hr; the progress of the reaction of the was monitored by TLC. After completion of reaction, the reaction mixture was evaporated under vacuum and basified with bicarbonate solution (5 mL) extracted with Ethyl acetate. Ethyl acetate layer separated dried over sodium sulfate and concentrated to obtain crude product N-ethyl-2-methylaniline (Int-4) 0.350 gm (Yield: quantitative); LCMS: 136.1 m/z [M+1]+

Step-4: Synthesis of 2-(2-ethoxy-4-fluorobenzoyl)-N-ethyl-N-(o-tolyl)-2-azaspiro [3.3] heptane-6-carboxamide (Compound-00203)

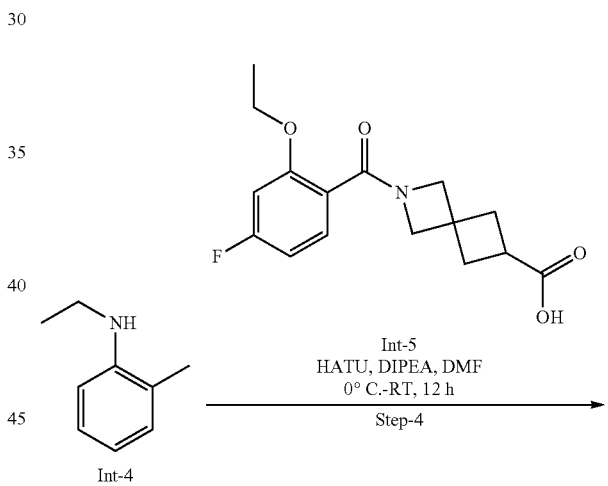

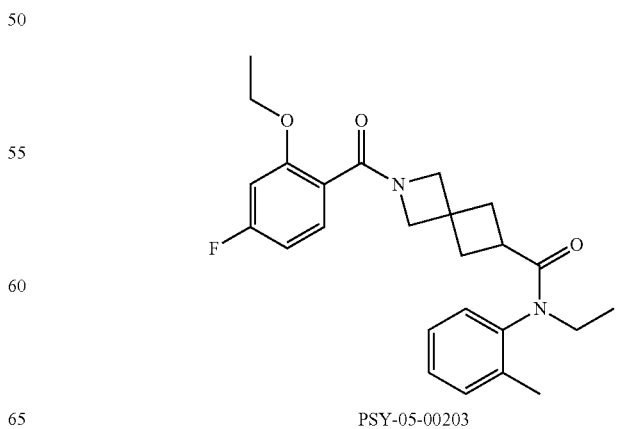

PSY-05-00203

To a stirred solution of 2-(2-ethoxy-4-fluorobenzoyl)-2-azaspiro[3.3]heptane-6-carboxylic acid (Int-5), (0.20 gm, 0.651 mmol 1.eq.) in N,N-Dimethyl formamide (5 ml) were N-ethyl-2-methylaniline (0.096 gm, 0.651 mmol, 1.0 eq.), DIPEA (0.25 gm, 1.954 mmol, 3.0 eq.), HATU (0.371 gm, 0.977 mmol, 1.5 eq.) at 0° C. The resulting reaction mixture was stirred at room temperature for 12 h. After completion of reaction as monitored by TLC, the reaction mixture was diluted with water (10 ml) and extracted with ethyl acetate (3*20 ml). The organic layer was washed with brine (10 ml), dried over sodium sulphate and concentrated under vacuum to get crude material which was purified by combiflash using 10% Methanol in Dichloromethane as eluent to get 2-(2-ethoxy-4-fluorobenzoyl)-N-ethyl-N-(o-tolyl)-2-azaspiro[3.3]heptane-6-carboxamide (PSY-05-00203) as white solid 0.10 gm (Yield: 37.03%); LCMS: 425.7 m/z 1H NMR (400 MHz, DMSO-d6) δ 7.33 (s, 2H), 7.33-7.20 (m, 2H), 7.09 (d, J=7.6 Hz, 1H), 6.94 (ddd, J=17.5, 11.7, 2.4 Hz, 1H), 6.76 (dtd, J=10.8, 8.4, 2.5 Hz, 1H), 4.08 (dt, J=13.8, 6.9 Hz, 3H), 4.06-3.88 (m, 1H), 3.86-3.73 (m, 2H), 3.71 (s, 2H), 3.10 (dt, J=13.6, 6.8 Hz, 1H), 2.33-2.19 (m, 2H), 2.12 (d, J=1.9 Hz, 3H), 1.92 (s, 1H), 1.93-1.82 (m, 1H), 1.30 (dt, J=21.2, 7.0 Hz, 3H), 0.98 (td, J=7.1, 5.2 Hz, 3H).

Example 18: Synthesis of N-(2-chlorophenyl)-2-(2-ethoxy-4-fluorobenzoyl)-N-methyl-2-azaspiro [3.3] heptane-6-carboxamide [Compound 206]

Reaction Scheme:

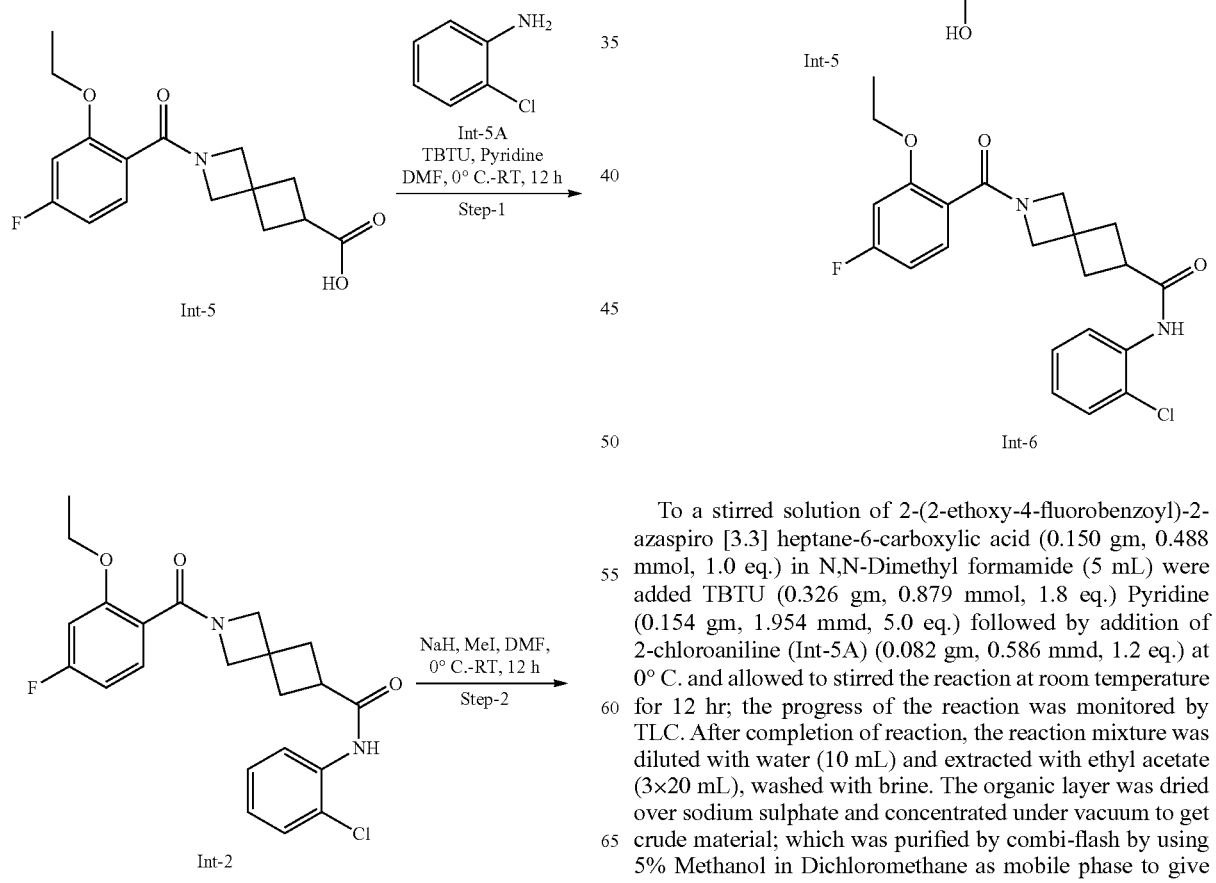

Step-1: Synthesis of N-(2-chlorophenyl)-2-(2-ethoxy-4-fluorobenzoyl)-2-azaspiro [3.3] heptane-6-carboxamide (Int-6)

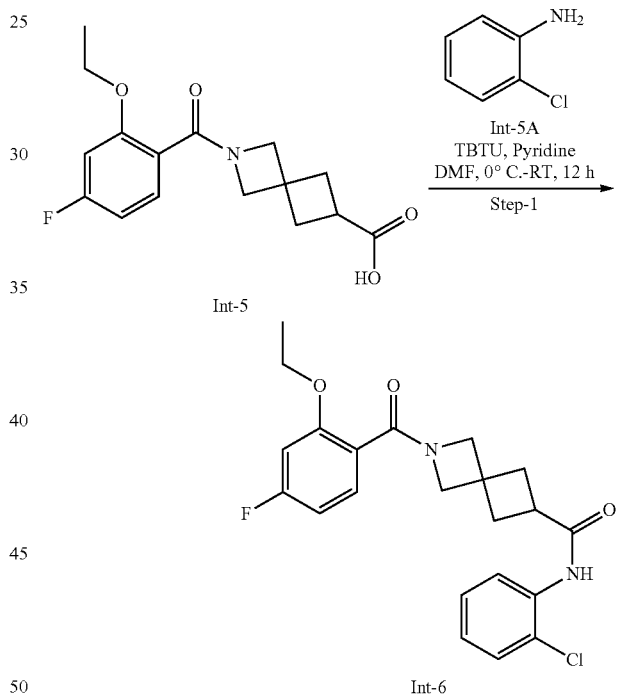

To a stirred solution of 2-(2-ethoxy-4-fluorobenzoyl)-2-azaspiro [3.3] heptane-6-carboxylic acid (0.150 gm, 0.488 mmol, 1.0 eq.) in N,N-Dimethyl formamide (5 mL) were added TBTU (0.326 gm, 0.879 mmol, 1.8 eq.) Pyridine (0.154 gm, 1.954 mmd, 5.0 eq.) followed by addition of 2-chloroaniline (Int-5A) (0.082 gm, 0.586 mmd, 1.2 eq.) at 0° C. and allowed to stirred the reaction at room temperature for 12 hr; the progress of the reaction was monitored by TLC. After completion of reaction, the reaction mixture was diluted with water (10 mL) and extracted with ethyl acetate (3×20 mL), washed with brine. The organic layer was dried over sodium sulphate and concentrated under vacuum to get crude material; which was purified by combi-flash by using 5% Methanol in Dichloromethane as mobile phase to give desired product N-(2-chlorophenyl)-2-(2-ethoxy-4-fluorobenzoyl)-2-azaspiro[3.3]heptane-6-carboxamide (Int-6) 0.150 gm (Yield: 75%); LCMS: 417.7 m/z [M+]

Step-2: Synthesis of N-(2-chlorophenyl)-2-(2-ethoxy-4-fluorobenzoyl)-N-methyl-2-azaspiro [3.3] heptane-6-carboxamide (Compound-00206)

Example 19: Synthesis of (4-fluoro-2-(2,2,2-trifluoroethoxy)phenyl) (6-(3-methyl-1-(o-tolyl)-1H-pyrazol-5-yl)-2-azaspiro[3.3]heptan-2-yl) methanone. [Compound 178]

Reaction Scheme:

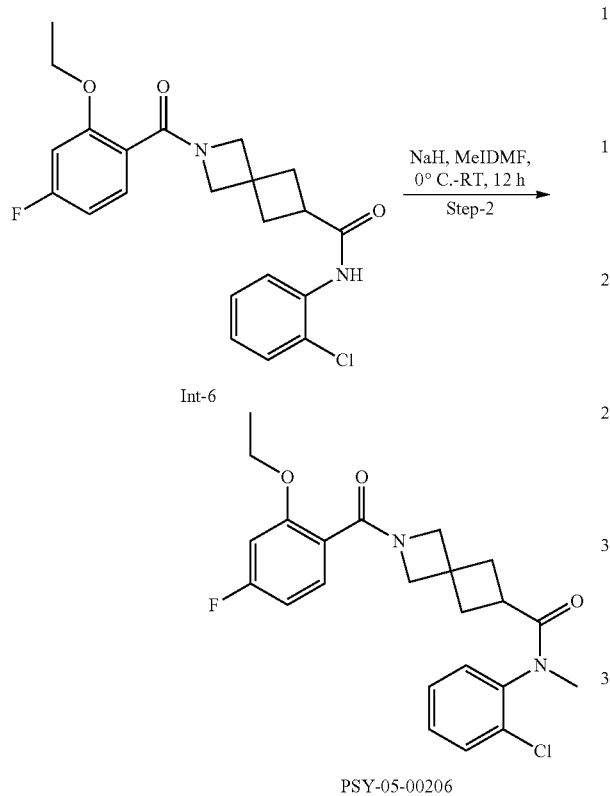

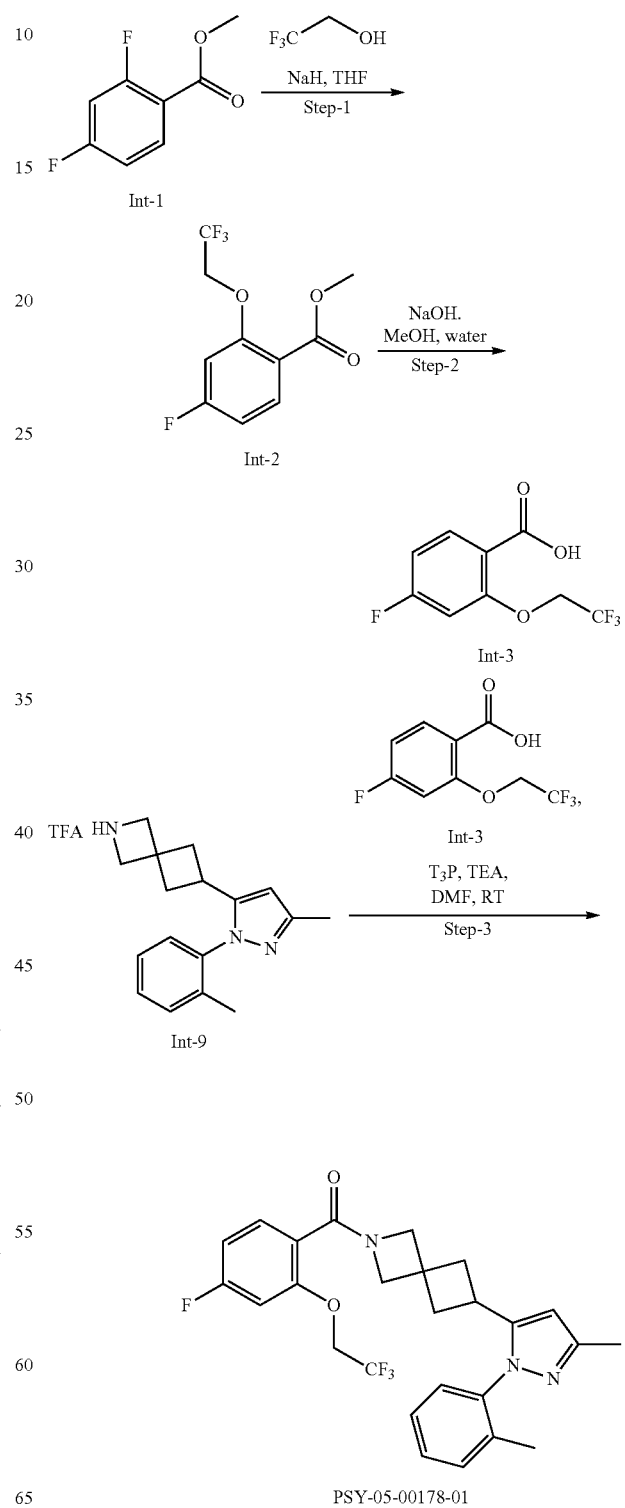

To a stirred solution of N-(2-chlorophenyl)-2-(2-ethoxy-4-fluorobenzoyl)-2-azaspiro [3.3] heptane-6-carboxamide (0.175 gm, 0.420 mmol, 1 eq.) in N,N-Dimethyl formamide (3 mL), was added Sodium hydride (0.012 gm, 0.504 mmol, 1.2 eq.) at 0° C. The reaction was stirred at 0° C. for 10 min. Methyl Iodide (0.071 gm, 0.504 mmol, 1.2 eq.) was added dropwise and stirred the reaction mass at room temperature for 12 hrs. After completion of reaction as monitored by TLC, the reaction mixture was diluted with Ice cold water (10 mL) and extracted with Ethyl acetate (2×20 mL). The combined organic layer was washed with brine solution, dried over sodium sulfate and concentrated to obtain crude product, which was purified by combiflash using 5% Methanol in Dichloromethane as mobile phase to give desired product N-(2-chlorophenyl)-2-(2-ethoxy-4-fluorobenzoyl)-N-methyl-2-azaspiro [3.3] heptane-6-carboxamide (PSY-05-00206) 0.10 gm, (Yield—55.55%). LCMS: 431.4 m/z [M+] 1H NMR (400 MHz, DMSO-d6) δ 7.64 (ddd, J=9.3, 6.6, 3.9 Hz, 1H), 7.46 (ddd, J=13.8, 6.0, 3.3 Hz, 3H), 7.38-7.22 (m, 1H), 6.95 (ddd, J=15.6, 11.6, 2.4 Hz, 1H), 6.77 (dtd, J=10.6, 8.4, 2.4 Hz, 1H), 4.11 (q, J=5.9, 5.1 Hz, 1H), 4.06 (q, J=6.9, 5.9 Hz, 1H), 3.84 (d, J=7.1 Hz, 2H), 3.76 (d, J=14.2 Hz, 2H), 3.07 (d, J=6.4 Hz, 3H), 2.68 (hept, J=8.2 Hz, 1H), 2.34-2.24 (m, 2H), 2.08-1.85 (m, 2H), 1.42-1.22 (m, 3H).

Step-1: Synthesis of methyl 4-fluoro-2-(2, 2, 2-trifluoroethoxy) benzoate (Int-2)

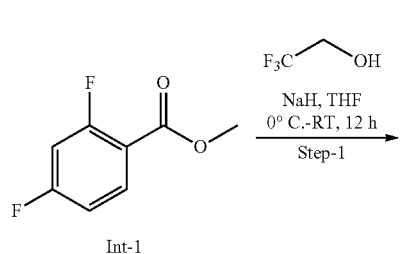

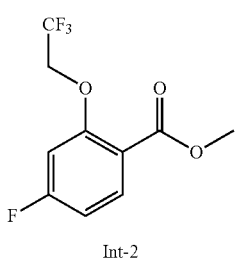

To a stirred solution of methyl 2,4-difluorobenzoate (0.10 gm, 0.58 mmol, 1.0 eq.) in N,N-Dimethyl formamide (2 mL), was added Sodium hydride (0.016 gm, 0.679 mmol, 1.2 eq.) at 0° C. The reaction was stirred at 0° C. for 10 min. 2, 2, 2-trifluoroethan-1-ol (0.081 gm, 0.813 mmol) was added dropwise and stirred the reaction mass at room temperature for 12 hrs. After completion of reaction as monitored by TLC, the reaction mixture was diluted with Ice cold water (5 mL) and extracted with Ethyl acetate (2×20 mL). The combined organic layer was washed with brine solution, dried over sodium sulfate and concentrated to obtain crude product, which was purified by combiflash using 10% Ethyl acetate in Hexane as eluent to afford methyl 4-fluoro-2-(2,2,2-trifluoroethoxy)benzoate (Int-2) 0.10 gm, (Yield—68%). The compound was containing disubstituted product which was non separable by column chromatography was carried forward as a mixture for next step.

Step-2: Synthesis of 4-fluoro-2-(2,2,2-trifluoroethoxy)benzoic acid (Int-3)

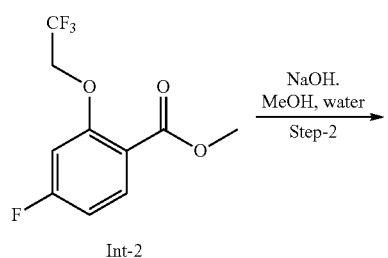

To a stirred solution of methyl 4-fluoro-2-(2,2,2-trifluoroethoxy)benzoate (Int-2) (1.0 gm, 3.96 mmol, 1 eq.) in THF (10 mL), MeOH (5 mL), Water (5 mL) was added Sodium Hydroxide [NaOH] (0.23 gm, 5.95 mmol, 1.5 eq.) at 0° C. The reaction mixture was stirred at room temperature for next 12 hr. The progress of the reaction was monitored by TLC; after completion of reaction, the reaction mixture was evaporated under vacuum. The crude product was acidified with 2N HCL (PH-4) The white solid was precipitated out which was filtered through Buchner funnel and dried under vacuum to give 4-fluoro-2-(2,2,2-trifluoroethoxy)benzoic acid (Int-3) 0.50 gm (Yield: 53%); 1H NMR (400 MHz, DMSO-d6) δ 12.83 (s, 1H), 7.77 (dd, J=8.7, 7.0 Hz, 1H), 7.17 (dd, J=11.1, 2.4 Hz, 1H), 6.96 (td, J=8.4, 2.4 Hz, 1H), 4.84 (q, J=8.8 Hz, 2H).

Step-3: Synthesis of (4-fluoro-2-(2,2,2-trifluoroethoxy)phenyl)(6-(3-methyl-1-(o-tolyl)-1H-pyrazol-5-yl)-2-azaspiro[3.3]heptan-2-yl)methanone (Compound-00178-001)

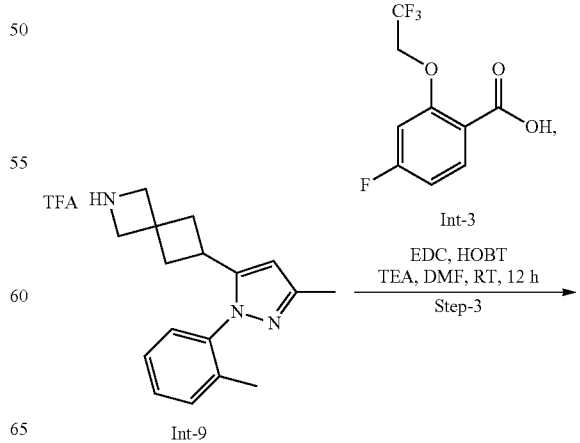

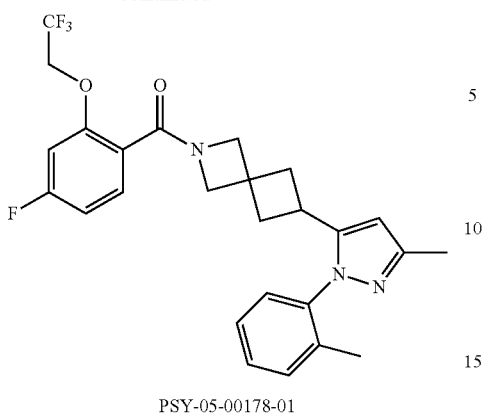

PSY-05-00178-01

To a stirred solution of 6-(3-methyl-1-(o-tolyl)-1H-pyrazol-5-yl)-2-azaspiro [3.3]heptane 2,2,2-trifluoroacetate (0.10 gm, 0.37 mmol 1.eq.) in N,N-Dimethyl formamide (3 ml) were added 4-fluoro-2-(2,2,2-trifluoroethoxy)benzoic acid (0.89 gm, 0.37 mmol, 1.0 eq.), TEA (0.11 gm, 1.12 mmol, 3.0 eq.), EDC-HCl (0.10 gm, 0.56 mmol, 1.5 eq.), and HOBT (0.025 gm, 0.18 mmol, 0.5 eq.) at 0° C. The resulting reaction mixture was stirred at room temperature for 12 h. After completion of reaction as monitored by TLC, the reaction mixture was diluted with water (10 ml) and extracted with ethyl acetate (3*20 ml). The organic layer was washed with brine (10 ml), dried over sodium sulphate and concentrated under vacuum to get crude material which was purified by combiflash using 80% Ethyl acetate in hexane as eluent to get PSY-05-00178 as white solid (0.050. (Yield: 28%); LCMS: 488.5 m/z [M+] 1H NMR (400 MHz, DMSO-d6) δ 7.46-7.36 (m, 2H), 7.40-7.25 (m, 2H), 7.16 (s, 1H), 7.21-7.10 (m, 1H), 6.98-6.87 (m, 1H), 6.17 (s, 1H), 4.93-4.79 (m, 2H), 3.95 (s, 1H), 3.86 (d, J=19.9 Hz, 2H), 3.78 (s, 1H), 3.03-2.92 (m, 1H), 2.33 (t, J=10.4 Hz, 2H), 2.21 (dd, J=23.9, 9.2 Hz, 5H), 1.93 (d, J=2.3 Hz, 3H).

Example 20: Synthesis of (2-cyclopropoxy-4-fluorophenyl)(6-(1-(5-fluoro-2-methylphenyl)-3-methyl-1H-pyrazol-5-yl)-2-azaspiro[3.3]heptan-2-yl)methanone [Compound 418]; and (2-cyclopropoxy-4-fluorophenyl)(6-(1-(5-fluoro-2-methylphenyl)-5-methyl-1H-pyrazol-3-yl)-2-azaspiro[3.3]heptan-2-yl)methanone [Compound 482]

Synthetic Scheme:

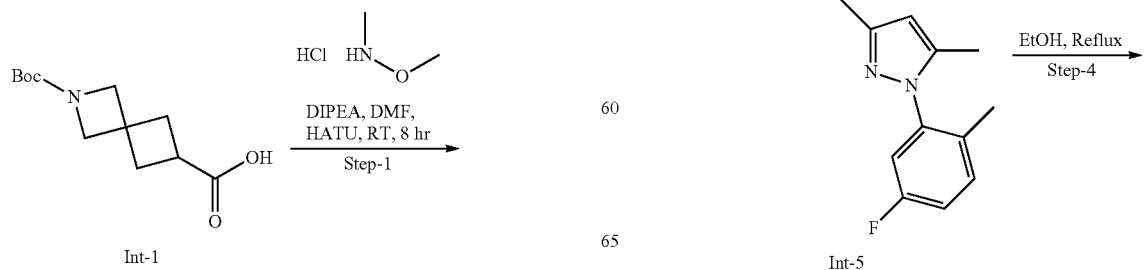

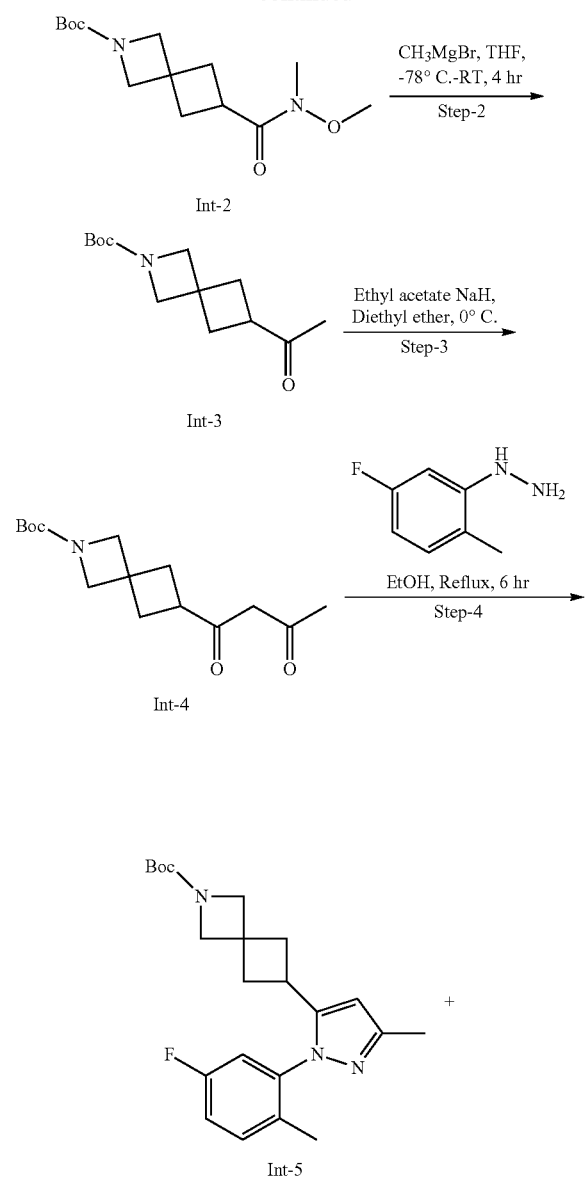

238

Step-1: Tert-butyl 6-(methoxy (methyl)carbamoyl)-2-azaspiro[3.3]heptane-2-carboxylate (Int-2)

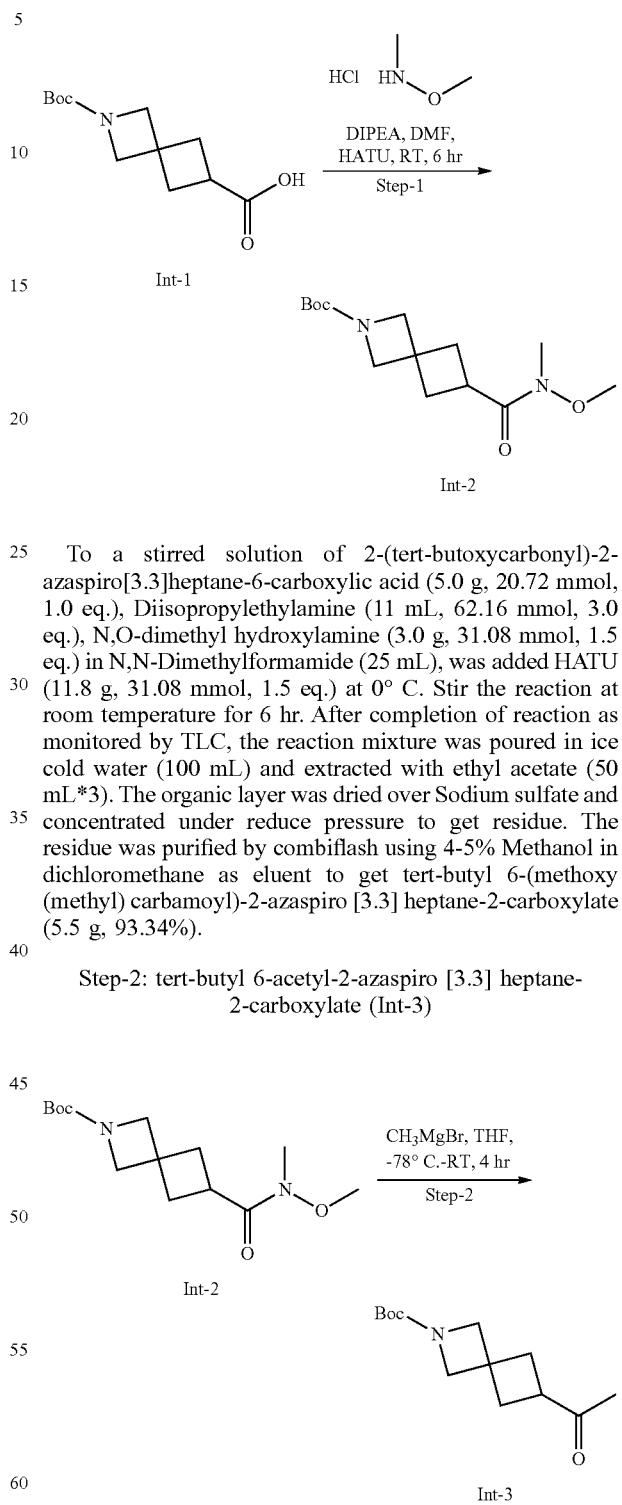

To a stirred solution of 2-(tert-butoxycarbonyl)-2-azaspiro[3.3]heptane-6-carboxylic acid (5.0 g, 20.72 mmol, 1.0 eq.), Diisopropylethylamine (11 mL, 62.16 mmol, 3.0 eq.), N,O-dimethyl hydroxylamine (3.0 g, 31.08 mmol, 1.5 eq.) in N,N-Dimethylformamide (25 mL), was added HATU (11.8 g, 31.08 mmol, 1.5 eq.) at 0° C. Stir the reaction at room temperature for 6 hr. After completion of reaction as monitored by TLC, the reaction mixture was poured in ice cold water (100 mL) and extracted with ethyl acetate (50 mL*3). The organic layer was dried over Sodium sulfate and concentrated under reduce pressure to get residue. The residue was purified by combiflash using 4-5% Methanol in dichloromethane as eluent to get tert-butyl 6-(methoxy (methyl) carbamoyl)-2-azaspiro [3.3] heptane-2-carboxylate (5.5 g, 93.34%).

Step-2: tert-butyl 6-acetyl-2-azaspiro [3.3] heptane-2-carboxylate (Int-3)

To a stirred solution of tert-butyl 6-(methoxy (methyl) carbamoyl)-2-azaspiro [3.3]heptane-2-carboxylate (Int-2) (5.5 g, 19.34 mmol, 1.0 eq.) in tetrahydrofuran (30 mL), was slowly added Methyl Magnesium Bromide 3M (11.6 mL, 34.81 mmol, 1.5 eq.) at −78° C. Stir the reaction at RT for

237

-continued

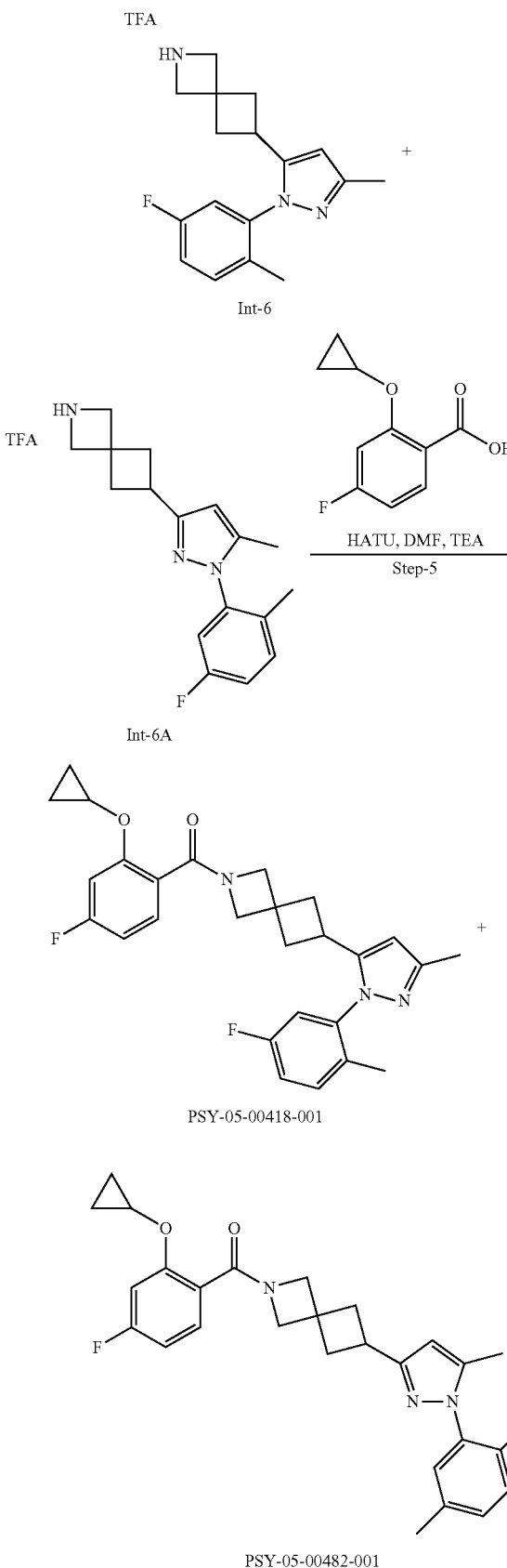

4 hr. After completion of reaction as monitored by TLC, the reaction mixture was poured in ice cold water (100 mL) and extracted with ethyl acetate (50 mL*3). The organic layer was dried over Sodium sulfate and concentrated under reduce pressure to get residue. The residue was purified by combiflash using 12-15% Ethyl acetate in n-hexane as eluent to get tert-butyl 6-acetyl-2-azaspiro [3.3] heptane-2-carboxylate (Int-3) (3.2 g, 69.13%).

Step-3: Tert-butyl 6-(3-oxobutanoyl)-2-azaspiro [3.3] heptane-2-carboxylate (Int-4)

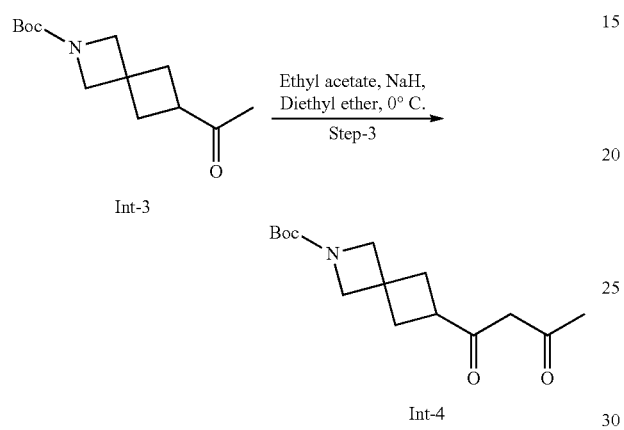

To a stirred solution of tert-butyl 6-acetyl-2-azaspiro[3.3] heptane-2-carboxylate (Int-3) (2.0 g, 8.36 mmol, 1.0 eq.) in diethyl ether (10 mL) was added Sodium hydride 60% (1.67 g, 41.48 mmol, 5.0 eq.) at 0° C., followed by the dropwise addition of ethyl acetate (4.9 g, 56.06 mmol, 6.7 eq.). The reaction mass was stirred at room temperature for 4-5 hr. After completion of reaction as monitored by TLC. The reaction mixture was poured in water (100 mL), acidified with 10% dilute HCl and extracted with ethyl acetate (50 mL*3). The organic layer was washed with brine (100 mL), dried over Sodium sulfate and concentrated under reduce pressure to get residue. The residue was purified by combiflash using 10-15% ethyl acetate in n-hexane as eluent to get tert-butyl 6-(3-oxobutanoyl)-2-azaspiro[3.3]heptane-2-carboxylate (Int-4) (2.1 g, 89.3%).

Step-4: Tert-butyl 6-(1-(5-fluoro-2-methylphenyl)-3-methyl-1H-pyrazol-5-yl)-2-azaspiro [3.3]heptane-2-carboxylate (Int-5) and Tert-butyl 6-(1-(5-fluoro-2-methylphenyl)-5-methyl-1H-pyrazol-3-yl)-2-azaspiro [3.3] heptane-2-carboxylate (Int-5A)

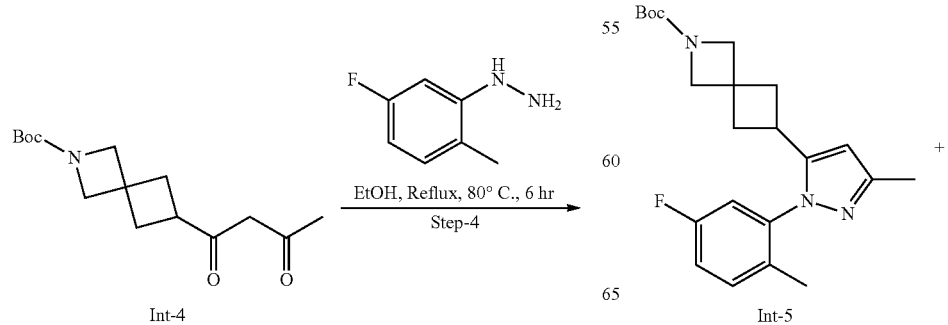

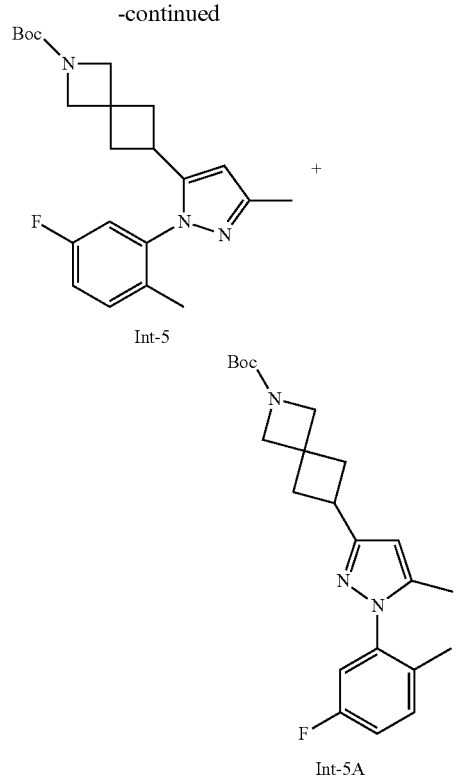

To a stirred solution of tert-butyl 6-(3-oxobutanoyl)-2-azaspiro[3.3]heptane-2-carboxylate (1.6 g, 5.69 mmol, 1.0 eq.) in Ethanol (15 mL) was added (5-fluoro-2-methylphenyl)hydrazine (1.5 g, 8.54 mmol, 1.5 eq.) the reaction mass was heated at 80° C. for 16 hr. After completion of reaction as monitored by TLC, the reaction mixture was concentrated to get residue. The residue was purified by combiflash using 80% ethyl acetate in n-hexane as eluent to get mixture of tert-butyl 6-(1-(5-fluoro-2-methylphenyl)-3-methyl-1H-pyrazol-5-yl)-2-azaspiro[3.3]heptane-2-carboxylate (Int-5) and tert-butyl 6-(1-(5-fluoro-2-methylphenyl)-5-methyl-1H-pyrazol-3-yl)-2-azaspiro[3.3]heptane-2-carboxylate (Int-5A) (2.0 g, 91.3%).

Step-5: 6-(1-(5-fluoro-2-methylphenyl-3-methyl-1H-pyrazol-5-yl)-2-azaspiro [3.3] heptane (Int-6) and 6-(1-(5-fluoro-2-methylphenyl)-5-methyl-1H-pyrazol-3-yl)-2-azaspiro [3.3] heptane) (Int-6A)

241
-continued

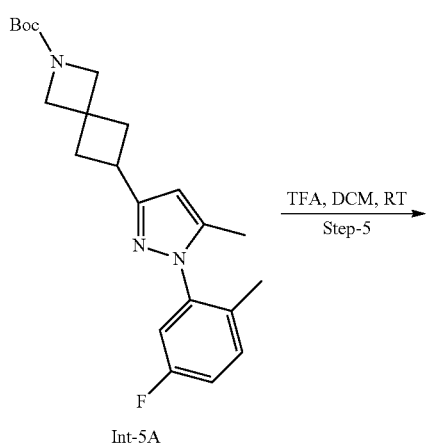

Int-5A

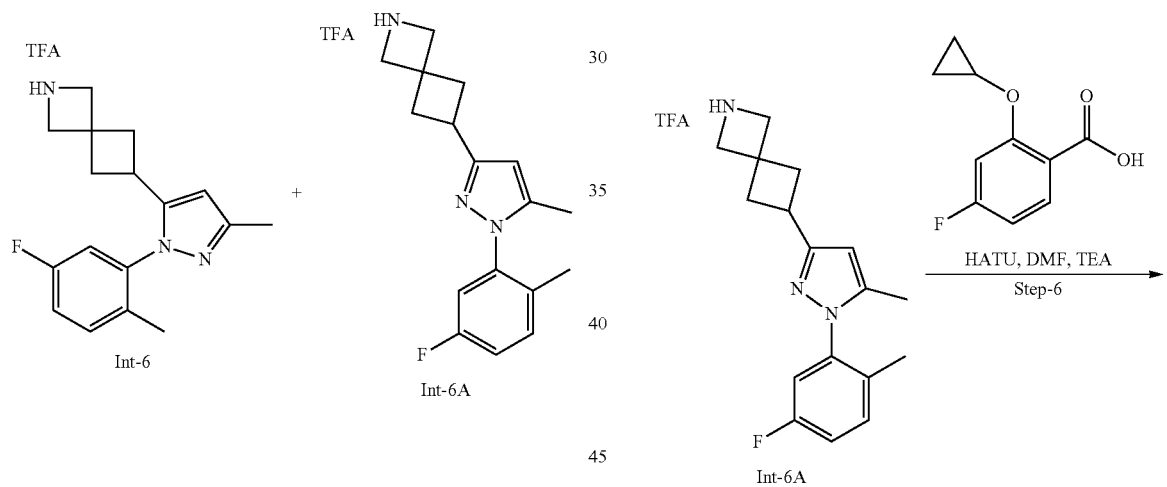

Int-6

Int-6A

To a well stirred reaction mixture of tert-butyl 6-(1-(5-fluoro-2-methylphenyl)-3-methyl-1H-pyrazol-5-yl)-2-azaspiro[3.3]heptane-2-carboxylate (Int-5) and tert-butyl 6-(1-(5-fluoro-2-methylphenyl)-5-methyl-1H-pyrazol-3-yl)-2-azaspiro[3.3]heptane-2-carboxylate (Int-5A) (2.0 g, 6.99 mmol, 1.0 eq.) in Dichloromethane (10 mL) was added Trifluoroacetic acid (3.0 mL) dropwise at 0° C. After completion of reaction as monitored by TLC, the reaction mixture was concentrated to get mixture of 6-(1-(5-fluoro-2-methylphenyl)-3-methyl-1H-pyrazol-5-yl)-2-azaspiro [3.3]heptane (Int-6) and 6-(1-(5-fluoro-2-methylphenyl)-5-methyl-1H-pyrazol-3-yl)-2-azaspiro[3.3]heptane (Int-6A) (0.420 g, 82.58%).

242

Step-6; (2-cyclopropoxy-4-fluorophenyl)(6-(1-(5-fluoro-2-methylphenyl)-3-methyl-1H-pyrazol-5-yl)-2-azaspiro [3.3] heptan-2-yl)methanone (PSY-05-00418-001) and (2-cyclopropoxy-4-fluorophenyl)(6-(1-(5-fluoro-2-methylphenyl)-5-methyl-1H-pyrazol-3-yl)-2-azaspiro [3.3] heptan-2-yl) methanone (PSY-05-00482-001)

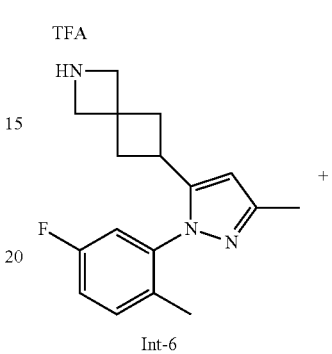

Int-6

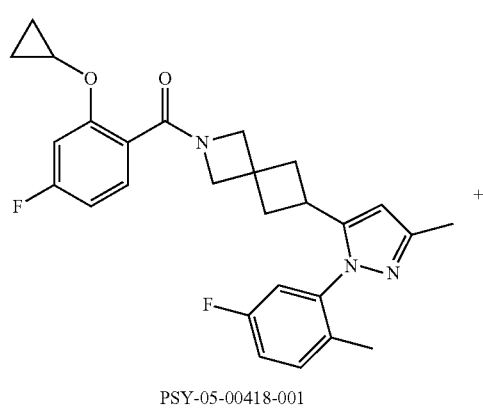

PSY-05-00418-001

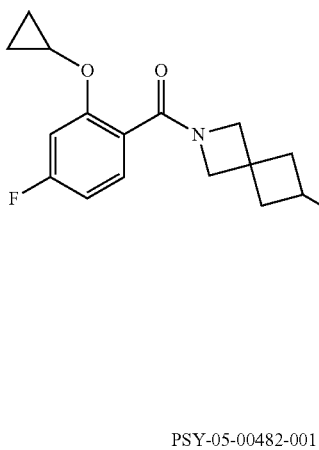

PSY-05-00482-001

Example 21: Synthesis of (2-cyclopropoxy-4-fluorophenyl)(6-(3-(trifluoromethyl)-5-(2-(trifluoromethyl) phenyl)-1H-pyrazol-1-yl)-2-azaspiro[3.3]heptan-2-yl)methanone (Compound 424); and (2-cyclopropoxy-4-fluorophenyl)(6-(5-(trifluoromethyl)-3-(2-(trifluoromethyl) phenyl)-1H-pyrazol-1-yl)-2-azaspiro[3.3]heptan-2-yl)methanone (Compound 451)

Synthetic Scheme:

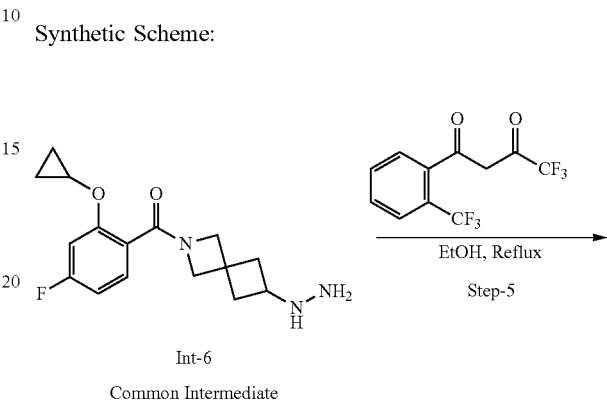

Int-6
Common Intermediate

To a well stirred reaction mixture of 6-(1-(5-fluoro-2-methylphenyl)-3-methyl-1H-pyrazol-5-yl)-2-azaspiro[3.3]heptane (Int-6) and 6-(1-(5-fluoro-2-methylphenyl)-5-methyl-1H-pyrazol-3-yl)-2-azaspiro[3.3]heptane (Int-6A) (0.42 g, 1.56 mmol, 1.2 eq.), N,N-Diisopropylethylamine (0.45 g, 6.50 mmol, 5.0 eq.), Int-D (0.255 g, 1.30 mmol, 1.0 eq.) in N,N-Dimethylformamide (5 mL) was added TBTU (0.63 g, 1.95 mmol, 1.5 eq.) at 0° C. The reaction mass was stirred at room temperature for 3-4 hr. After completion of reaction as monitored by TLC, the reaction mixture was poured in water (100 mL) and extracted with ethyl acetate (50 mL*3). The organic layer was washed with saturated solution of sodium carbonate (50 mL) and brine (100 mL), dried over Sodium sulfate and concentrated under reduce pressure to get residue. The residue was purified by combiflash using 80-90% ethyl acetate in n-hexane as eluent. The crude was submitted to prep HPLC for purification. Two Fraction was collected.

Fraction-1: (2-cyclopropoxy-4-fluorophenyl)(6-(1-(5-fluoro-2-methylphenyl)-3-methyl-1H-pyrazol-5-yl)-2-azaspiro [3.3] heptan-2-yl)methanone (PSY-05-00418-001) (0.027 g, 3.96%). LCMS: m/z 464.44 [M+1]$^+$. NMR: $^1$H NMR (400 MHz, DMSO-d6) δ 7.42 (q, J=7.8 Hz, 1H), 7.30 (t, J=7.6 Hz, 2H), 7.28-7.11 (m, 2H), 6.87-6.81 (m, 1H), 3.98-3.85 (m, 3H), 3.79 (s, 1H), 3.70 (s, 1H), 3.13-2.99 (m, 1H), 2.35 (t, J=10.1 Hz, 1H), 2.22 (dd, J=23.5, 9.3 Hz, 6H), 1.91 (s, 3H), 0.89-0.81 (m, 2H), 0.67 (s, 2H).

Fraction-2: (2-cyclopropoxy-4-fluorophenyl)(6-(1-(5-fluoro-2-methylphenyl)-5-methyl-1H-pyrazol-3-yl)-2-azaspiro [3.3] heptan-2-yl) methanone (PSY-05-00482-001) (0.050 g, 7.33%). LCMS: m/z 464.44 [M+1]+. NMR: $^1$H NMR (400 MHz, DMSO-d$_6$) δ 7.43 (d, J=7.5 Hz, 1H), 7.26 (dq, J=27.9, 10.5, 9.1 Hz, 4H), 6.82 (d, J=13.5 Hz, 1H), 6.12 (d, J=13.5 Hz, 1H), 4.06 (s, 1H), 3.91 (s, 3H), 3.73 (s, 1H), 3.41 (s, 1H), 2.58-2.41 (d, J=18.7 Hz, 2H), 2.04 (d, J=7.3 Hz, 3H), 1.91 (d, J=16.1 Hz, 3H), 0.89-0.80 (m, 2H), 0.72 (s, 2H).

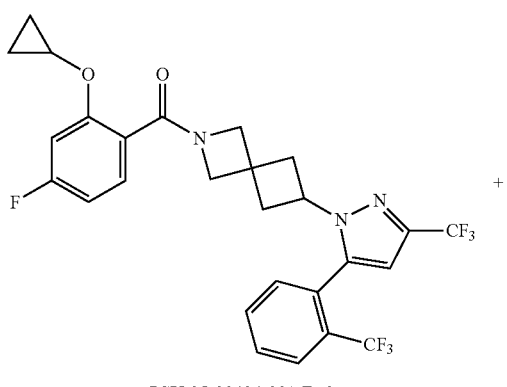

PSY-05-00424-001-Fr-2

+

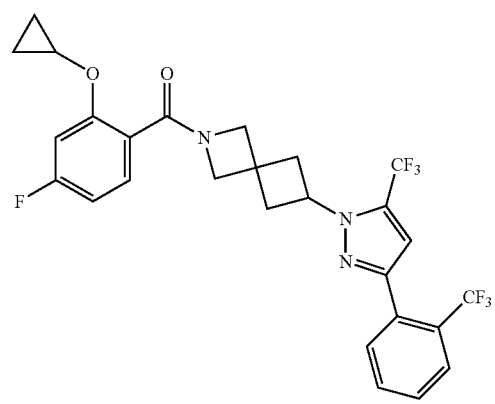

PSY-05-00451-001-Fr-1

245

-continued

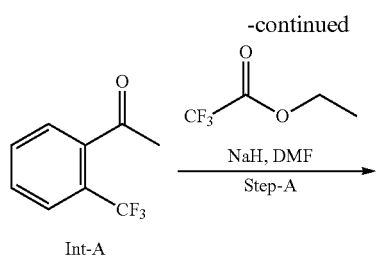

Int-A

Step-A: 4,4,4-trifluoro-1-(2-(trifluoromethyl)phenyl)
butane-1,3-dione (Int-B)

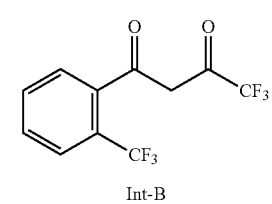

Int-A

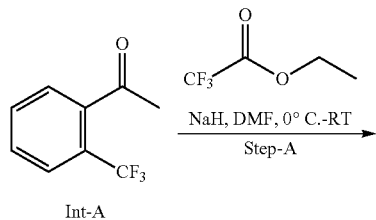

Int-B

To a stirred solution of 1-(2-(trifluoromethyl)phenyl) ethan-1-one (3.0 g, 1.59 mmol, 1.0 eq.) in N,N-Dimethylformamide at 0° C. under $N_2$ atmosphere, NaH 60% (0.500 g, 2.393 mmol, 1.5 eq.) was added and allowed to stir for 30 mins at 0° C. Then added Trifluoroethylacetate (3.50 g, 2.388 mmol, 1.5 eq.) to the reaction mass and stirred the reaction at room temperature for 16 hr. After completion of reaction as monitored by TLC, the reaction mixture was poured in ice cold water (100 mL). Acidified with dil. HCl up to $P^H$ 4.0 and extracted with ethyl acetate (50 mL*3). The organic layer was dried over Sodium sulfate and concentrated under reduce pressure to get residue. The residue was purified by combiflash using 50% ethyl acetate in n-hexane as eluent to get tert-butyl 6-(methoxy (methyl) carbamoyl)-2-azaspiro [3.3] heptane-2-carboxylate (Int-B) (2.0 g, 44.15%).

246

Step-5: (2-cyclopropoxy-4-fluorophenyl)(6-(3-(trifluoromethyl)-5-(2-(trifluoromethyl) phenyl)-1H-pyrazol-1-yl)-2-azaspiro [3.3] heptan-2-yl)methanone (PSY-05-00424-001') and (2-cyclopropoxy-4-fluorophenyl)(6-(5-(trifluoromethyl)-3-(2-(trifluoromethyl) phenyl)-1H-pyrazol-1-yl)-2-azaspiro [3.3] heptan-2-yl) methanone (PSY-05-00451-001)

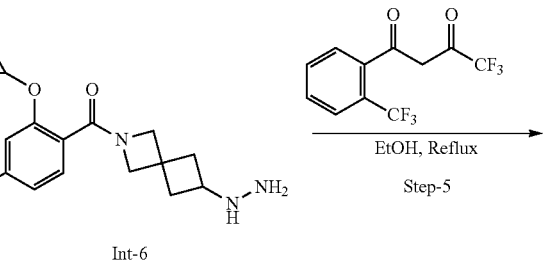

Int-6

Common Intermediate

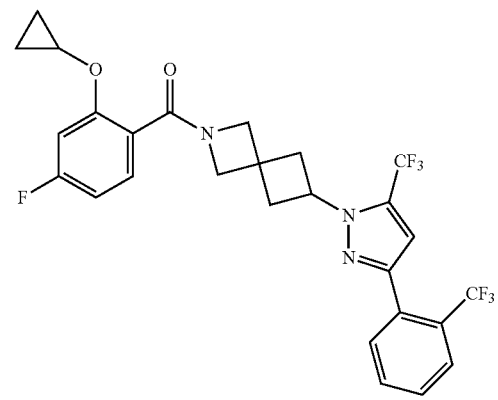

PSY-05-00424-001-Fr-2

PSY-05-00451-001-Fr-1

To a stirred solution of tert-butyl 6-(methoxy (methyl) carbamoyl)-2-azaspiro [3.3] heptane-2-carboxylate (Int-B) (0.3 g, 1.05 mmol, 1.0 eq.) in Ethanol (5 mL) was added (2-cyclopropoxy-4-fluorophenyl)(6-hydrazineyl-2-azaspiro [3.3]heptan-2-yl)methanone (Int-6) (0.62 g, 2.10 mmol, 2.0 eq.) the reaction mass was heated at 80° C. for 16 hr. After completion of reaction as monitored by TLC, the reaction mixture was concentrated to get residue. The residue was purified by combiflash using 80% ethyl acetate in n-hexane as eluent to get mixture of two region isomers. The crude was submitted to prep HPLC for purification. Two Fraction was collected.

Fraction-1: (2-cyclopropoxy-4-fluorophenyl)(6-(5-(trifluoromethyl)-3-(2-(trifluoromethyl) phenyl)-1H-pyrazol-1-yl)-2-azaspiro[3.3]heptan-2-yl)methanone (PSY-05-00451-001) (0.027 g, 4.97%). LCMS: m/z 553.91 [M+1]$^+$. NMR: $^1$H NMR (400 MHz, DMSO-d$_6$) δ 8.68 (s, 1H), 8.05-7.83 (m, 3H), 7.63 (d, J=7.5 Hz, 1H), 7.30 (dq, J=27.9, 10.5, 9.1 Hz, 1H), 7.21-7.28 (dq, J=27.9, 10.5, 9.1 Hz, 1H), 6.92 (d, J=13.5 Hz, 2H), 4.46 (s, 1H), 4.00-3.95 (s, 3H), 3.80 (s, 2H), 2.78-2.70 (d, J=18.7 Hz, 4H), 0.87 (d, J=16.1 Hz, 2H), 0.79-0.70 (m, 2H).

Fraction-2: (2-cyclopropoxy-4-fluorophenyl)(6-(3-(trifluoromethyl)-5-(2-(trifluoromethyl) phenyl)-1H-pyrazol-1-yl)-2-azaspiro[3.3]heptan-2-yl)methanone (PSY-05-00424-001) (0.050 g, 9.20%). LCMS: m/z 553.91 [M+1]. NMR: $^1$H NMR (400 MHz, DMSO-d$_6$) δ 8.68 (s, 1H), 8.15-8.37 (m, 5H), 7.63 (d, J=7.5 Hz, 1H), 7.40 (dq, J=27.9, 10.5, 9.1 Hz, 1H), 6.92 (d, J=13.5 Hz, 1H), 5.52 (d, J=13.5 Hz, 1H), 4.56 (s, 1H), 4.00 (s, 3H), 3.63 (s, 2H), 2.78-2.70 (d, J=18.7 Hz, 2H), 2.24 (d, J=7.3 Hz, 2H), 0.87 (d, J=16.1 Hz, 2H), 0.79-0.70 (m, 2H), 0.72 (s, 2H).

Example 22: Measuring MAGL Inhibition Potency (IC$_{50}$)

The potency of certain compounds for inhibiting MAGL were obtained using the following assays.

The monoacylglycerol lipase inhibitor screening assay kit from Cayman Chemical was used to measure the MAGL potency for the compounds in Table 6 and Table 7.

Cayman's Monoacylglycerol Lipase Inhibitor Screening Assay provides a method for screening human MAGL inhibitors. MAGL hydrolyzes 4-nitrophenylacetate resulting in a yellow product, 4-nitrophenol, with an absorbance of 405-412 nm.

MAGL Inhibition was measured by the following assay. Monoacylglycerol Lipase (MAGL) inhibition was measured using recombinant MAGL enzyme (aa 2-303 RBC, internal preparation) and the substrate 4-Nitrophenyl acetate (4NPA) (Sigma-Aldrich, N8130). Hydrolysis of the substrate in the presence of the enzyme was measured by absorbance at 405 nm. 10 μL of assay buffer (10 mM Tris pH 7.5, 1 mM EDTA, 0.9% DMSO) was added to a black 384-well non-binding plate with clear bottom (Greiner, 781906) for each reaction. Compounds were dispensed using an acoustic liquid handler (Echo, Beckman) at 45 nL (0.1% DMSO). Test compounds and control for MAGL inhibitor JZL-184 (Caymen Chemical, 13158) were tested in 10-concentration IC$_{50}$ mode with 3-fold serial dilution at a starting concentration of 10 μM. DMSO control wells were included for reference. A 10.8 nM (1.8×) MAGL mix in assay buffer was prepared, with 25 μL added to each reaction well, for a final assay concentration of 6 nM. No enzyme wells received 25 μL of buffer. Plate was incubated at room temperature for 30 minutes. 35 mM solution of 4NPA in methanol was prepared daily. A 4.5× 4NPA substrate solution was prepared in assay buffer and 10 μL was added to each reaction well, for a final assay concentration of 0.25 mM. Plate was spun for 1 minute at 1000 rpm before measuring absorbance using a CLARIOstar plate reader (BMG Labtech). A kinetic reading at 405 nm was done every minute for 30 minutes. Data was analyzed using the linear slope of the reaction progress curve and the average of the no-enzyme wells (background) was subtracted from the data. The background-subtracted slope data was converted to % activity using the average of wells with enzyme and DMSO vehicle. IC$_{50}$s were calculated using GraphPad software (Sigmoidal dose response, variable slope equation).

Table 6 and Table 7 provide exemplary compounds of Formula (I) and their potency for MAGL inhibition measured using the Potency Assay of Example 22 above, with the following modifications described in Table C below. Table 8 provides potency measurements of MAGL inhibition measured using the Potency Assay of Example 22 above, with the following modifications described in Table C.

TABLE C

Methods Used to Measure MAGL Inhibition with 4NPA Substrate

| Method No. | Name | Modification to Assay of Example 16 |
|---|---|---|
| 1 | MAGL (6 nM) Reaction Biology Enzyme | Reaction Biology's internal MAGL enzyme prep was used. Concentration of MAGL enzyme in the assay was 6 nM. |
| 2 | MAGL (10 nM) Cayman Chemical Enzyme | Cayman Chemical's MAGL enzyme prep was used. Concentration of MAGL enzyme in the assay was 10 nM. |
| 3 | MAGL (10 nM) Reaction Biology Enzyme | Reaction Biology's internal MAGL enzyme prep was used. Concentration of MAGL enzyme in the assay was 10 nM. |
| 4 | MAGL (15 nM) Cayman Chemical Enzyme | Cayman Chemical's MAGL enzyme prep was used. Concentration of MAGL enzyme in the assay was 15 nM. |
| 5 | MAGL (25 nM) Cayman Chemical Enzyme | Cayman Chemical's MAGL enzyme prep was used. Concentration of MAGL enzyme in the assay was 25 nM. |
| 6 | MAGL IC50 Enzyme Conc 6, Reaction Biology | Reaction Biology's internal MAGL enzyme prep was used. Concentration of MAGL enzyme in the assay was 6 nM. |
| 7 | MAGL IC50 Enzyme Conc 10, Reaction Biology | Reaction Biology's internal MAGL enzyme prep was used. Concentration of MAGL enzyme in the assay was 10 nM. |
| 8 | MAGL IC50 Enzyme Conc 10, Cayman Chemical | Cayman Chemical's MAGL enzyme prep was used. Concentration of MAGL enzyme in the assay was 10 nM. |
| 9 | MAGL IC50 Enzyme Conc 15, Cayman Chemical | Cayman Chemical's MAGL enzyme prep was used. Concentration of MAGL enzyme in the assay was 15 nM. |
| 10 | MAGL IC50 Enzyme Conc 25, Cayman Chemical | Cayman Chemical's MAGL enzyme prep was used. Concentration of MAGL enzyme in the assay was 25 nM. |
| 11 | MAGL IC50 Enzyme Conc 20, Reaction Biology | Reaction Biology's internal MAGL enzyme prep was used. Concentration of MAGL enzyme in the assay was 25 nM. |

TABLE C-continued

Methods Used to Measure MAGL Inhibition with 4NPA Substrate

| Method No. | Name | Modification to Assay of Example 16 |
|---|---|---|
| 12 | MAGL IC50 Enzyme Conc 15, Reaction Biology | Reaction Biology's internal MAGL enzyme prep was used. Concentration of MAGL enzyme in the assay was 15 nM. |
| 13 | MAGL IC50 Enzyme Conc 12, Reaction Biology | Reaction Biology's internal MAGL enzyme prep was used. Concentration of MAGL enzyme in the assay was 12 nM. |
| 14 | MAGL IC50 Enzyme Conc "0", Source "0" | Reaction Biology's internal MAGL enzyme prep was used. Concentration of MAGL enzyme in the assay was 6 nM. |

Results of potency measurements in Table 6, Table 7 and Table 8 are expressed as the following ranges: "A" refers to an $IC_{50}$ measurement of <50 nM, "B" refers to an $IC_{50}$ measurement of between 50 nM and 150 nM, "C" refers to an $IC_{50}$ measurement of greater than 150 nM and less than 500 nM, "D" refers to an $IC_{50}$ measurement of 500 nM to 1 micromolar, and "E" refers to an $IC_{50}$ measurement of greater than 1 micromolar up to 5.1 micromolar. The number after each letter for potency measurement value indicates the Method from Table C that was used to obtain that measurement value (e.g., "A(1)" indicates an $IC_{50}$ measurement of <50 nM obtained from the Method 1 of Example 22 in Table C).

Example 23: Measuring FAAH Inhibition Potency ($IC_{50}$)

Comparative compound potency at FAAH can be obtained with the following assay. A "Selective MAGL Inhibitor Compound" refers to a compound that selectively inhibits MAGL with an $IC_{50}$ that is at least 10× the $IC_{50}$ for its inhibition of fatty acid amide hydrolase (FAAH), and that has an $IC_{50}$ of 150 nM or less for MAGL inhibition (according to the MAGL Potency assay of Example 22).

MAGL inhibitor compounds were also counter-screened for FAAH inhibition potency using the following assay. Assessment of FAAH inhibition was performed using Fatty Acid Amide Hydrolase Inhibitor Screening Assay Kit (Cayman Item No. 10005196) following manufacture's instruction with some modifications. The kit utilizes human recombinant FAAH and the fluorescent substrate, AMC Arachidonoyl amide (AAMCA). 5 μL of assay buffer (125 mM Tris, pH 9.0, 1 mM EDTA, i.e. ethylenediaminetetraacetic acid) was added to a 384-well black plate (Corning, 3573). Test compounds and control inhibitor JZL-195 (Cayman Chemical, 13668) were tested in 10-concentration $IC_{50}$ mode with 3-fold serial dilution at a starting concentration of 100 μM and 10 μM, respectively. 300 nL or 30 nL of test compounds were delivered into a 384-well black plate (Corning, 3573) using a Labcyte Echo, followed by addition of 15 μL of FAAH enzyme (Cayman, 700302) in assay buffer. After a 5-minute pre-incubation at room temperature, 10 μL of AAMCA was added in assay buffer to start the reaction. Final concentration of FAAH enzyme is not specified and AAMCA substrate was used at the 20 uM. After these dilutions, the final concentration of the test compounds ranged from 100 μM to 5.08 nM or 10 μM down to 0.508 nM. The reaction was allowed to progress for 60 minutes, while the plate was read on an Envision plate reader at an Ex/Em of 350/460 nm with readings every minute. The data was analyzed in Microsoft Excel, using the slope between 30 and 59 minutes. The average of the no-enzyme wells (background) was subtracted from the data. The background-subtracted slope data was converted to % activity using the average of wells with enzyme and DMSO vehicle. $IC_{50}$ values were calculated using GraphPad software (Sigmoidal dose response, variable slope equation).

Compounds listed in Table D2 were tested in the FAAH Counterscreen of Example 23

TABLE D1

Methods Used to Measure FAAH Inhibition

| Method | Modification to Assay of Example 23 |
|---|---|
| A | Starting concentration of 100 μM |
| B | Starting concentration of 10 μM |

TABLE D2

FAAH Counter Screen

| Method | Compound | Structure | FAAH $IC_{50}$ (nM) |
|---|---|---|---|
| A | Comparator | 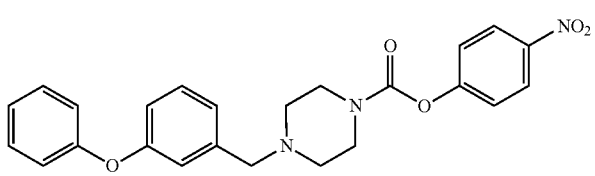 [SMILES: O=C(Oc1ccc([N+](=O)[O-])cc1)N1CCN(Cc2cccc(Oc3ccccc3)c2)CC1] | 459 |

TABLE D2-continued

| | | FAAH Counter Screen | |
|---|---|---|---|
| Method | Compound | Structure | FAAH IC$_{50}$ (nM) |
| A | Comparator | | 14 |
| A | 117 | | >10,000 |
| A | 120 | | >10,000 |
| A | 122 | | >10,000 |
| A | 123 | | >10,000 |

TABLE D2-continued

FAAH Counter Screen

| Method | Compound | Structure | FAAH IC$_{50}$ (nM) |
|---|---|---|---|
| A | 125 | | >10,000 |
| A | 127 | | >10,000 |
| B | 473 | | >10,000 |
| B | 493 | | >10,000 |

Example 24: Measuring Reversible MAGL Inhibition (IC$_{50}$)

The reversible mechanism of MAGL inhibition of a test compound of Formula (I) can be determined. Flag-tagged MAGL enzyme will be immobilized on anti-Flag beads. Immobilized enzyme will be incubated +/− inhibitor at a dose that produces complete inhibition. Colorimetric substrate (4-NPA) will be added and the reaction monitored on a plate reader for 30 minutes to verify complete inhibition. Immobilized enzyme will then be washed thoroughly to remove the inhibitor, and fresh substrate will be added. The reaction will be monitored for an additional 30 minutes; returning enzymatic activity will indicate reversibility of inhibition.

To confirm the hypothesized reversible mechanism of inhibition, the effects of dilution and preincubation on the MAGL inhibitory activity of a compound can be evaluated using methods disclosed in *J. Med. Chem.* 2019, 62, 1932-1958, 1942. In the presence of an irreversible mechanism of inhibition, the potency should not decrease after dilution, whereas for a reversible inhibition, the potency level should be strongly reduced after dilution. Therefore, the inhibition produced by incubation with a 4000 nM concentration of a test compound can be measured after a 40× dilution and compared to the potency observed by a 4000 and a 100 nM of the test compound. A reversible mechanism of inhibition can be identified when the inhibition produced by 100 nM of the test compound is similar to that obtained after a 40× dilution and was considerably lower than that produced by the same compound at a concentration of 4000 nM.

As a second assay to identify or confirm a reversible MAGL inhibitory activity of a test compound, the inhibition activity of a test compound can be measured at different preincubation times with MAGL. The test compound can be preincubated with the enzyme for 0, 30, and 60 min before adding the substrate to start the enzymatic reaction. An irreversible inhibition should produce a higher potency after longer incubation times, whereas a reversible inhibitor should produce a constant inhibition potency overall the different incubation times.

Determining MAGL Reversible Inhibition:

MAGL enzyme was incubated for 30 minutes in the presence of 40× the $IC_{50}$ concentration of inhibitor. Enzyme+inhibitor mix was then diluted 40-fold so that the final concentration of the inhibitor equaled the $IC_{50}$ concentration. Substrate was added and the reaction was monitored for 30 minutes. For a reversible inhibitor, percent inhibition after dilution to the $IC_{50}$ concentration should be 50+15%.

The MAGL reversible inhibition assay of Example 24 above was performed to test reversibility of inhibition by compounds depicted in Table E. Column A shows the degree to which MAGL enzymatic activity returned following washout of test compounds (pre-washout compound concentration: 1 µM), reflecting reversibility of inhibition, as compared to the complete lack of return of MAGL enzymatic activity after washout of the irreversible inhibitor comparator compound JZL-184 (pre-washout compound concentration: 1 µM). Column B shows % MAGL activity returning after washout. % Activity returning after washout represents the amount of MAGL enzymatic activity, relative to control (no inhibitor before washout) reaction amounts, that occurred immediately following a 30 minute washout of the test compound. For some test compounds, % activity returning after washout may be less than 100% if complete compound unbinding takes longer than 30 minutes.

TABLE E

| Compound | Structure | A | B |
|---|---|---|---|
| JZL-184 (comparator) | 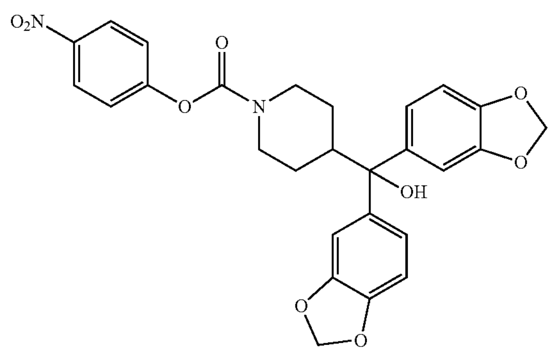 [SMILES: O=C(Oc1ccc([N+](=O)[O-])cc1)N1CCC(C(O)(c2ccc3c(c2)OCO3)c2ccc3c(c2)OCO3)CC1] | | <1% |
| 473 | 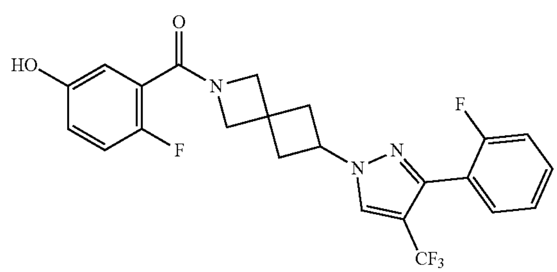 [SMILES: O=C(c1cc(O)ccc1F)N1CC2(CC(n3cc(C(F)(F)F)c(-c4ccccc4F)n3)C2)C1] | 41 | <50% |
| 493 | 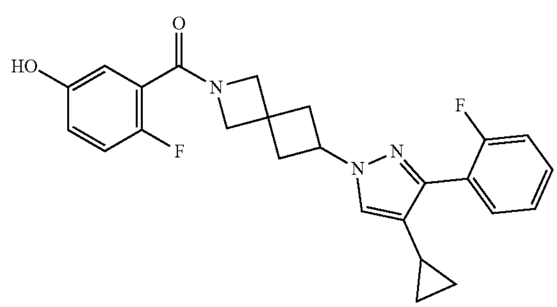 [SMILES: O=C(c1cc(O)ccc1F)N1CC2(CC(n3cc(C4CC4)c(-c4ccccc4F)n3)C2)C1] | 47 | <50% |

TABLE E-continued

Reversible MAGL inhibition

| Compound | Structure | A | B |
|---|---|---|---|
| 519 | 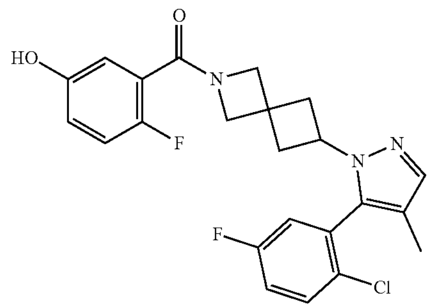 [SMILES: Cc1cnn(C2CC3(C2)CN(C(=O)c2cc(O)ccc2F)C3)c1-c1cc(F)ccc1Cl] | 155 | >50% |
| 520 | 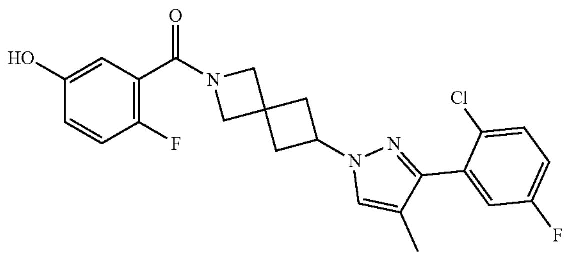 [SMILES: Cc1cn(C2CC3(C2)CN(C(=O)c2cc(O)ccc2F)C3)nc1-c1cc(F)ccc1Cl] | 100 | >50% |

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims.

Example 25: Pharmacokinetic Study of Compounds in Mice

Healthy male C57BL/6 mice (8-12 weeks old) weighing between 17 to 35 g were procured from Global, India. Temperature and humidity were maintained at 22±3° C. and 30-70%, respectively and illumination was controlled to give a sequence of 12 hr light and 12 hr dark cycle. Temperature and humidity were recorded by auto-controlled data logger system. All the animals were provided laboratory rodent diet. Reverse osmosis water treated with ultraviolet light was provided ad libitum.

Protocol A: Twenty-four male mice were divided into two groups as; Group 1: 30 mg/kg/IP; Plasma and brain; Number of animals=12: Animal #1-12. Group 2: 30 mg/kg/PO; Plasma and brain; Number of animals=12; Animal #13-24. Animals in Group 1 were administered intraperitoneally with solution formulation of PSY-05-00074-001 in 5% NMP, 5% Solutol HS-15 and 90% normal saline at 30 mg/kg dose. Animals in Group 2 were administered orally with solution formulation of PSY-05-00074-001 in 5% NMP, 5% Solutol HS-15 and 90% normal saline at 30 mg/kg dose. Blood samples (approximately 60 µL) were collected under light isoflurane anesthesia from retro orbital plexus at 0.25, 0.5, 1, 2, 4 and 8 hr (IP and PO). Plasma samples were separated by centrifugation of whole blood and stored below −70° C. until bioanalysis. Immediately after collection of blood from intraperitoneal and oral group animals, animals were euthanized with excess CO2 and brain samples were collected from set of two mice at each time point. Brain samples were divided into two parts. Half brain samples were homogenized using ice-cold phosphate buffer saline (pH—7.4) and homogenates were stored below −70±10° C. until analysis. Total homogenate volume was three times the brain weight. Other part of brain was stored below −70±10° C. for further analysis. All samples were processed for analysis by protein precipitation using acetonitrile and analyzed with fit-for-purpose LC/MS/MS method (LLOQ—2.02 ng/mL for plasma and 6.06 ng/g for brain). Pharmacokinetic parameters were calculated using the non-compartmental analysis tool of Phoenix WinNonlin®.

Protocol B: Thirty six mice were included into the study and divided in to three groups as Group 1 (n=12), Group 2 (n=12) and Group 3 (n=12) with n=2 mice per time-point design. Animals in Group 1 were administered intravenously with solution formulation of PSY-05-00414-001 at 5 mg/kg dose. Animals in Group 2 were administered orally with solution formulation of PSY-05-00414-001 at a dose of 5 mg/kg. Animals in Group 3 were administered intraperitoneally with solution formulation of PSY-05-00414-001 at 5 mg/kg dose. The formulation vehicle for all the three groups was 5% NMP, 5% Solutol HS-15 and 90% normal saline. Blood samples (approximately 60 µL) were collected under light isoflurane anesthesia from two mice at 0.25, 0.5, 1, 2, 4 and 8 h. Plasma was harvested by centrifugation of blood and stored at −70±10° C. until analysis. After blood collection, brain was perfused and isolated at 0.25, 0.5, 1, 2, 4 and 8 h. Brain samples were dipped thrice in ice-cold phosphate buffer saline, blotted dry and cut in to two equal portion. Half-brain samples from each time-point were weighed and homogenized using ice-cold phosphate buffer saline with twice volume of brain weight making the total homogenate three volumes and stored below −70±10° C. until analysis. Remaining half-portions of brain samples was snap freeze and kept in −70±10° C. until further confirmation from client. Plasma and brain samples were quantified by fit-for-purpose LC-MS/MS method (LLOQ: 1.01 ng/mL for plasma and 2.02 ng/mL for brain).

Protocol C: Fifty four male mice were included in study and divided in to three groups as Group 1 (n=18), Group 2 (n=18) and Group 3 (n=18) with 3 mice/time point design. Animals from Group 1, Group 2 and Group 3 were administered by intravenous, oral and intraperitoneal route with solution formulation of PSY-05-00451-001 at 5 mg/kg dose, respectively. The formulation vehicle used was 5% v/v NMP, 5% v/v Solutol HS-15 and 90% v/v Normal saline. Blood samples (approximately 60 μL) were collected under light isoflurane anesthesia (Surgivet®) from retro orbital plexus from a set of three mice at 0.25, 0.5, 1, 2, 4 and 8 h. Immediately after blood collection, plasma was harvested by centrifugation at 4000 rpm, 10 min at 4° C. and samples were stored at −70±10° C. until bioanalysis. Following blood collection, animals were sacrificed followed by venacava was cut open and whole body was perfused from heart using 10 mL of normal saline. Brain samples were collected from set of three mice at 0.25, 0.5, 1, 2, 4 and 8 h. After isolation, brain samples were rinsed three times in ice cold normal saline (for 5-10 seconds/rinsed using −5-10 mL normal saline in disposable petri dish for each rinse), dried on blotting paper and cut in to two equal portion. Half-brain was used for PK estimation and half brain was snap freezed and stored below −70±10° C. Half brain (for PK estimation) was weighed and homogenized using ice-cold phosphate buffer saline with twice volume of brain weight making the total homogenate three volumes and stored below −70±10° C. until analysis. All samples were processed for analysis by protein precipitation method and analyzed with fit-for-purpose LC-MS/MS method (LLOQ=2.03 ng/mL for plasma and 1.02 ng/mL for brain). The pharmacokinetic parameters were estimated using non-compartmental analysis tool of Phoenix® WinNonlin software.

Protocol D: Thirty six male mice were included in study and divided into two groups as Group 1 (n=18) and Group 2 (n=18) with 3 mice/time point as sparse design. Animals from Group 1 and Group 2 were administered by intravenous and oral route with solution formulation of PSY-05-00473-001 at 5 mg/kg dose, respectively. The formulation vehicle used was 5% v/v NMP, 5% v/v Solutol HS-15 and 90% v/v Normal saline. Blood samples (approximately 60 μL) were collected under light isoflurane anesthesia (Surgivet®) from retro orbital plexus from a set of three mice at 0.25, 0.5, 1, 2, 4 and 8 h. Immediately after blood collection, plasma was harvested by centrifugation at 4000 rpm, 10 min at 4° C. and samples were stored at −70±10° C. until bioanalysis. Following blood collection, whole body was perfused using 10 mL of normal saline. Brain samples were collected from set of three mice at 0.25, 0.5, 1, 2, 4 and 8 h. After isolation, brain samples were rinsed three times in ice cold normal saline (for 5-10 seconds/rinsed using ~5-10 mL normal saline in disposable petri dish for each rinse), dried on blotting paper and cut in to two equal portion. Half-brain was used for PK estimation and half brain was snap freezed and stored below −70±10° C. Half brain (for PK estimation) was weighed and homogenized using ice-cold phosphate buffer saline with twice volume of brain weight making the total homogenate to three volumes and stored below −70±10° C. until analysis. All samples were processed for analysis by protein precipitation method and analyzed with fit-for-purpose LC-MS/MS method (LLOQ=1.01 ng/mL for plasma and 2.01 for brain). The pharmacokinetic parameters were estimated using non-compartmental analysis tool of Phoenix® WinNonlin software.

Protocol E: Total fifty four male mice were included in study and divided in to three groups as Group 1 (n=18), Group 2 (n=18) and Group 3 (n=18) with 3 mice/time point design. Animals from Group 1, Group 2 and Group 3 were administered by intravenous, oral and intraperitoneal route with solution formulation of PSY-05-00476-001 at 5 mg/kg dose, respectively. The formulation vehicle used was 5% v/v NMP, 5% v/v Solutol HS-15 and 90% v/v Normal saline. Blood samples (approximately 60 μL) were collected under light isoflurane anesthesia (Surgivet®) from retro orbital plexus from a set of three mice at 0.25, 0.5, 1, 2, 4 and 8 h. Immediately after blood collection, plasma was harvested by centrifugation at 4000 rpm, 10 min at 4° C. and samples were stored at −70+10° C. until bioanalysis. Following blood collection, animals were sacrificed followed by venacava was cut open and whole body was perfused from heart using 10 mL of normal saline. Brain samples were collected from set of three mice at 0.25, 0.5, 1, 2, 4 and 8 h. After isolation, brain samples were rinsed three times in ice cold normal saline (for 5-10 seconds/rinsed using ~5-10 mL normal saline in disposable petri dish for each rinse), dried on blotting paper and cut in to two equal portion. Half-brain was used for PK estimation and half brain was snap freezed and stored below −70±10° C. Half brain (for PK estimation) was weighed and homogenized using ice-cold phosphate buffer saline with twice volume of brain weight making the total homogenate three volumes and stored below −70±10° C. until analysis. All samples were processed for analysis by protein precipitation method and analyzed with fit-for-purpose LC-MS/MS method (LLOQ=1.01 ng/mL for plasma and brain). The pharmacokinetic parameters were estimated using non-compartmental analysis tool of Phoenix® WinNonlin software.

TABLE F

Data obtained from Pharmacokinetic study of Example 25

| Protocol | Compound | Matrix | Route | Dose (mg/kg) | $C_{max}$ (ng/g) | $AUC_{last}$ (hr*ng/ml) | Brain KP ($C_{max}$) |
|---|---|---|---|---|---|---|---|
| A | Compound 74 | Brain | Oral | 30 | 101.76 | 116.52 | .42 |
| B | Compound 414 | Brain | Oral | 5 | 135.83 | 774.91 | 1.19 |
| C | Compound 451 | Brain | Oral | 5 | 271.39 | 1204.22 | .32 |
| D | Compound 473 | Brain | Oral | 5 | 171.59 | 464.42 | 1.74 |
| E | Compound 476 | Brain | Oral | 5 | 72 | 223.64 | .72 |

Referring to the data in Table F, the $C_{max}$ is the peak concentration of a drug observed over time after a dose of the drug has been administered. Data presented in the table above demonstrate the ability of PSY compounds to enter the brain. $AUC_{last}$ is the area under the brain concentration-time curve to the last measured brain concentration. This reflects the total drug exposure over time after a dose has been administered. Brain $K_p$ ($C_{max}$) is the ratio of the maximum observed concentrations of drug in the brain and plasma. Higher $K_p$ ($C_{max}$) values indicate more delivery of the drug to the brain.

TABLE 6

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 120 | 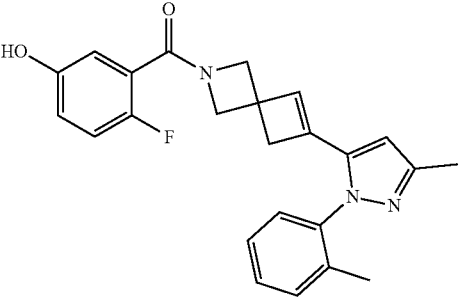<br>(2-fluoro-5-hydroxyphenyl){6-[3-methyl-1-(o-tolyl)-5-pyrazolyl]-2-aza-5-spiro[3.3]hepten-2-yl}methanone | LCMS: 473.7 m/z [M + H]+; ¹H NMR (400 MHz, Methanol-d₄) δ 7.51-7.33 (m, 3H), 7.28 (d, J = 7.9 Hz, 1H), 7.00 (t, J = 9.2 Hz, 1H), 6.92-6.78 (m, 2H), 6.35 (s, 1H), 5.39 (s, 1H), 4.29-4.09 (m, 4H), 2.78 (d, J = 5.6 Hz, 2H), 2.30 (s, 3H), 2.00 (s, 3H). | C (2) |
| 122 | 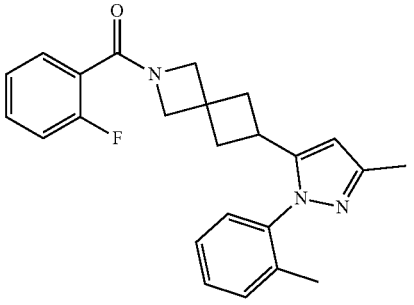 [SMILES: Cc1cc(C2CC3(C2)CN(C(=O)c2ccccc2F)C3)n(-c2ccccc2C)n1]<br>(o-fluorophenyl){6-[3-methyl-1-(o-tolyl)-5-pyrazolyl]-2-aza-2-spiro[3.3]heptyl}methanone | LCMS: 390.4 m/z [M + H]⁺; ¹H NMR (400 MHz, DMSO-d₆) δ 7.58-7.32 (m, 4H), 7.36-7.21 (m, 3H), 7.16 (t, J = 7.0 Hz, 1H), 6.14 (d. J = 22.8 Hz, 1H), 3.96 (dd, J = 23.5, 17.7 Hz, 4H), 3.00 (m, 1H), 2.39-2.21 (m, 4H), 2.18 (d. J = 10.8 Hz. 3H), 1.93 (s, 3H). | E (2) |
| 125 | 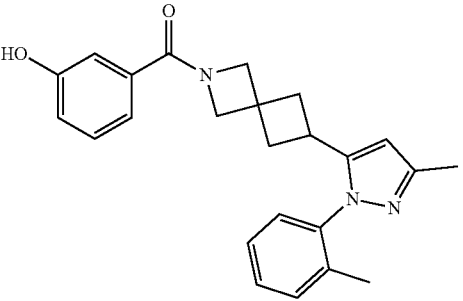 [SMILES: Cc1cc(C2CC3(C2)CN(C(=O)c2cccc(O)c2)C3)n(-c2ccccc2C)n1]<br>(m-hydroxyphenyl){6-[3-methyl-1-(o-tolyl)-5-pyrazolyl]-2-aza-2-spiro[3.3]heptyl}methanone | LCMS: 388.4 m/z [M + H]⁺; ¹H NMR (400 MHz, DMSO-d₆) δ 9.63 (d, J = 13.1 Hz, 1H), 7.44-7.26 (m, 3H), 7.17 (dd, J = 19.2, 8.3 Hz, 2H), 6.96 (d, J = 7.6 Hz, 2H), 6.86 (s, 1H), 6.14 (d, J = 12.2 Hz, 1H), 4.19 (d, J = 25.2 Hz, 2H), 3.94 (d. J = 23.0 Hz. 2H), 3.03-2.94 (m, 1H), 2.33 (s, 3H), 2.27-2.12 (m, 5H), 1.93 (s, 3H). | B (1, 2) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 126 | 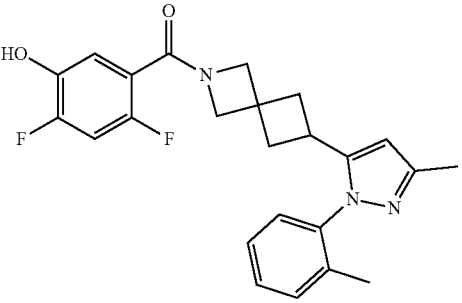 [SMILES: Cc1cc(C2CC3(C2)CN(C(=O)c2cc(O)c(F)cc2F)C3)n(-c2ccccc2C)n1]<br>(2,4-difluoro-5-hydroxyphenyl){6-[3-methyl-1-(o-tolyl)-5-pyrazolyl]-2-aza-2-spiro[3.3]heptyl}methanone | LCMS: 424.4 m/z [M + H]+. $^1$H NMR (400 MHz, Methanol-$d_4$) δ 7.34 (dt, J = 25.4, 8.9 Hz, 3H), 7.18 (t, J = 6.3 Hz, 1H), 7.07-6.91 (m, 2H), 6.18 (d, J = 18.4 Hz, 1H), 4.05 (dd, J = 22.8, 7.5 Hz, 4H). 3.13-3.02 (m, 1H), 2.36 (td, J = 16.6, 14.9, 9.8 Hz, 4H), 2.26 (d, J = 8.4 Hz, 3H), 1.98 (d, J = 2.3 Hz, 3H). | A (1, 2, 3) |
| 127 | 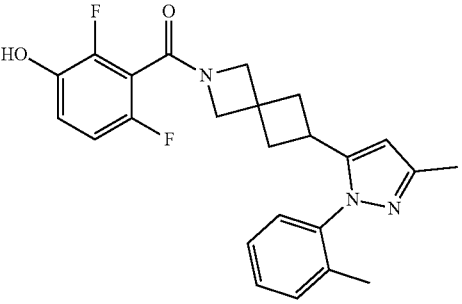<br>(2,6-difluoro-3-hydroxyphenyl){6-[3-methyl-1-(o-tolyl)-5-pyrazolyl]-2-aza-2-spiro[3.3]heptyl}methanone | LCMS: 424.7 m/z [M + H]+; $^1$H NMR (400 MHz, Methanol-$d_4$) δ 7.50-7.25 (m, 3H), 7.18 (dd, J = 7.6, 5.5 Hz, 1H), 6.91-6.81 (m, 1H), 6.18 (d, J = 21.0 Hz, 1H), 4.10 (d, J = 22.2 Hz, 2H), 3.96 (d. J = 23.3 Hz, 2H), 3.15-3.02 (m, 1H), 2.49-2.29 (m, 4H), 2.26 (d, J = 10.5 Hz, 3H), 1.98 (d, J = 2.8 Hz, 3H). | E (2) |
| 128 | 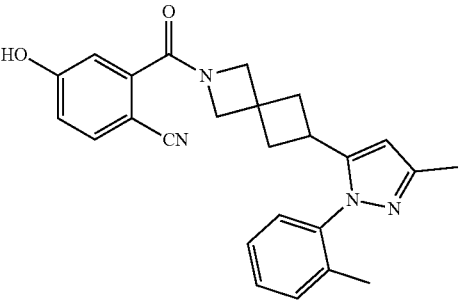 [SMILES: Cc1cc(C2CC3(C2)CN(C(=O)c2cc(O)ccc2C#N)C3)n(-c2ccccc2C)n1]<br>4-hydroxy-2-({6-[3-methyl-1-(o-tolyl)-5-pyrazolyl]-2-aza-2-spiro[3.3]heptyl} carbonyl)benzonitrile | LCMS: 413.4 m/z [M + H]+; $^1$H NMR (400 MHz, DMSO-$d_6$) δ 7.68 (t, J = 7.8 Hz, 1H), 7.43-7.26 (m, 3H), 7.15 (dd, J = 7.8, 3.9 Hz, 1H), 6.98-6.85 (m, 2H), 6.13 (d, J = 19.6 Hz, 1H), 3.99 (dd, J = 24.0, 13.9 Hz, 4H), 2.99 (dt, J = 22.2, 8.4 Hz, 1H), 2.39-2.28 (m, 2H), 2.23 (dd, J = 12.7, 9.0 Hz, 2H), 2.17 (d, J = 8.5 Hz, 3H), 1.92 (s, 3H). | A (1, 2) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 140 | 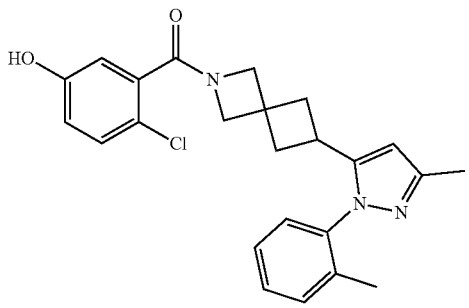<br>(2-chloro-5-hydroxyphenyl){6-[3-methyl-1-(o-tolyl)-5-pyrazolyl]-2-aza-2-spiro[3.3]heptyl}methanone | LCMS: m/z 422.6 [M + 1]⁺; NMR: ¹H NMR (400 MHz, DMSO-d₆) δ 9.95 (s, 1H), 7.40-7.11 (m, 4H), 7.15 (t, J = 7.7 Hz, 1H), 6.80 (t, 1H), 6.67 (d, J = 2.8 Hz, 1H). 6.16-6.10 (s, 1H), 3.97-3.58 (m, 4H), 3.00-2.93 (m, 1H), 2.33-2.15 (m, 7H), 1.91 (s, 3H). | B (2) |
| 141 | 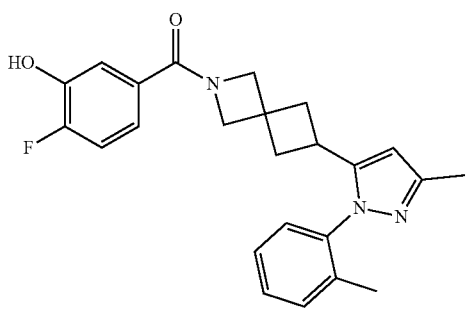 [SMILES: Cc1cc(C2CC3(C2)CN(C(=O)c2ccc(F)c(O)c2)C3)n(-c2ccccc2C)n1]<br>(4-fluoro-3-hydroxyphenyl){6-[3-methyl-1-(o-tolyl)-5-pyrazolyl]-2-aza-2-spiro[3.3]heptyl}methanone | LCMS: 406.3 m/z [M + H]⁺; ¹H NMR (400 MHz, DMSO-d₆) δ 10.16 (s, 1H), 7.38 (s, 2H), 7.30 (d, J = 5.9 Hz, 1H), 7.18 (dd, J = 13.5, 8.4 Hz, 3H), 7.02 (s, 1H), 6.15 (d, J = 10.7 Hz, 1H), 4.25 (s, 1H), 4.19 (s, 1H), 3.97 (s, 1H), 3.92 (s, 1H), 3.04-2.94 (m, 1H), 2.23 (d, J = 9.5 Hz, 2H), 2.19 (s, 5H), 1.93 (s, 3H). | B (1) C (2) |
| 185 | 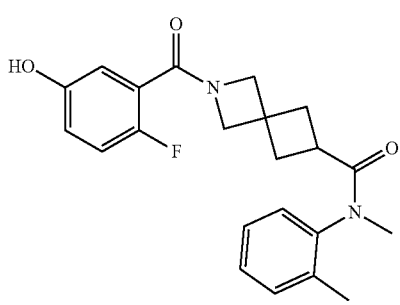 [SMILES: Cc1ccccc1N(C)C(=O)C1CC2(C1)CN(C(=O)c1cc(O)ccc1F)C2]<br>N-methyl-N-o-tolyl-2-(2-fluoro-5-hydroxybenzoyl)-2-aza-6-spiro[3.3]hepta necarboxamide | LCMS: m/z 383.35 [M + 1]⁺ NMR: ¹H NMR (400 MHz, DMSO-d₆) δ 9.62 (d. J = 13.5 Hz, 1H), 7.40 7.23 (m, 3H), 7.16 (s, 1H), 7.17-6.98 (m, 2H), 6.85-6.81 (m, 1H), 6.78-6.69 (m, 1H), 3.97-3.80 (m. 4H), 3.05 (d. J = 6.1 Hz, 3H), 2.62 (td, J = 15.6, 7.7 Hz. 1H). 2.39-2.23 (m, 2H), 2.22-2.05 (m, 3H), 2.00-1.90 (m. 2H). | B (2, 3) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 186 | 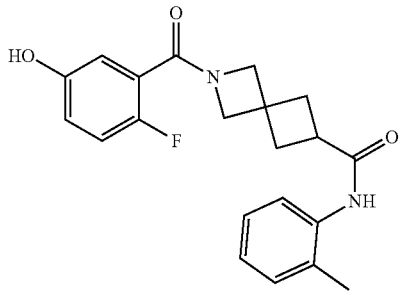 [SMILES: Cc1ccccc1NC(=O)C1CC2(C1)CN(C(=O)c1cc(O)ccc1F)C2]<br>N-o-tolyl-2-(2-fluoro-5-hydroxybenzoyl)-2-aza-6-spiro[3.3]heptanecarboxamide | LCMS: m/z 369.20 [M + 1]+. 1H NMR (400 MHz, DMSO-$d_6$) δ 9.62 (d, J = 4.8 Hz, 1H), 9.17 (s, 1H), 7.36 (d, J = 8.0 Hz, 1H), 7.23-7.12 (m, 3H), 7.08 (s, 1H), 6.90-6.82 (m, 1H), 6.79 (s, 1H), 4.07 (d. J = 6.6 Hz, 2H), 3.97 (d, J = 6.0 Hz, 2H), 3.16 (dd, J = 17.8, 8.9 Hz, 1H), 2.57 (s, 4H), 2.17 (d, J = 4.0 Hz, 3H). | E (2) |
| 365 | 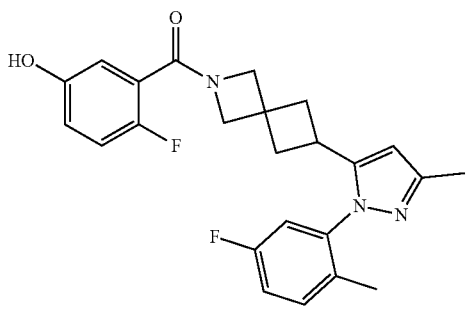 [SMILES: Cc1cc(C2CC3(C2)CN(C(=O)c2cc(O)ccc2F)C3)n(-c2cc(F)ccc2C)n1]<br>(2-fluoro-5-hydroxyphenyl){6-[1-(5-fluoro-2-tolyl)-3-methyl-5-pyrazolyl]-2-aza-2-spiro[3.3]heptyl}methanone | LCMS:424.1 m/z [M + H]+ $^1$H NMR (400 MHz. DMSO-$d_6$) δ 9.64 (s, 1H), 7.66 (s, 1H), 7.20 (s, 2H), 7.06 (s, 1H) 6.83 (t, 1H), 6.75 (s, 1H), 6.28 (s, 1H), 3.99 (d, 2H), 3.82 (d, J = 11.5 Hz, 2H), 3.11 (m, 1H), 2.45 (d, 2H), 2.35 (d, 3H), 2.19 (s, 2H), 1.87 (s, 3H). | A (14) |
| 366 | 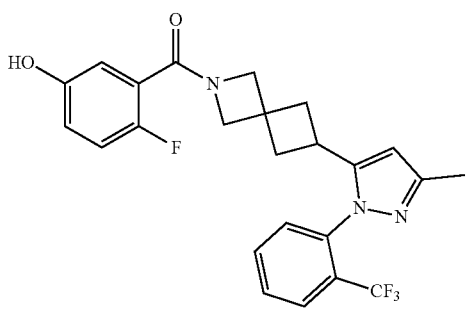 [SMILES: Cc1cc(C2CC3(C2)CN(C(=O)c2cc(O)ccc2F)C3)n(-c2ccccc2C(F)(F)F)n1]<br>(2-fluoro-5-hydroxyphenyl)(6-{3-methyl-1-[o-(trifluoromethyl)phenyl]-5-pyrazolyl}-2-aza-2-spiro[3.3]heptyl)methanone | LCMS: 460.0 [M + H]+ NMR: $^1$H NMR (400 MHz, DMSO-$d_6$) δ 9.63 (s, 1H), 7.80 (s, 1H), 7.77-7.67 (m, 3H), 7.08 (t, 1H), 7.82 (d, 1H), 6.76 (s, 1H), 6.28 (d, J = 15.4 Hz, 1H), 3.98 (d, 2H), 3.87 (d, J = 9.0 Hz, 2H), 2.96 (m, J = 8.7 Hz, 1H), 2.25 (d, J = 15.6 Hz, 6H) | A (14) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 367 | 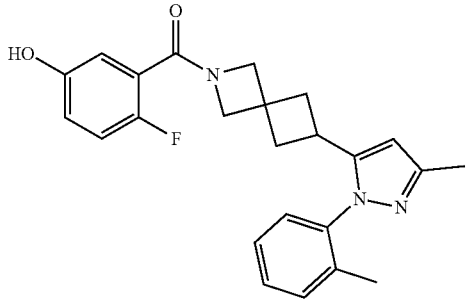 [SMILES: Cc1cc(C2CC3(C2)CN(C(=O)c2cc(O)ccc2F)C3)n(-c2ccccc2C)n1]<br>(2-fluoro-5-hydroxyphenyl){6-[1-(o-tolyl)-5-pyrazolyl]-2-aza-2-spiro[3.3]heptyl}methanone | m/z 422.6 [M + 1]$^+$; $^1$H NMR (400 MHz, DMSO-d$_6$) δ 9.95 (s, 1H), 7.43-7.1 (m, 4H), 7.15 (t, J = 7.7 Hz, 1H), 6.80 (t, 1H), 6.67 (d, J = 2.8 Hz. 1H), 6.16-6.10 (s, 1H), 3.98 (s, 1H), 3.92 (s, 1H), 3.82 (s, 1H), 3.76 (s, 1H), 2.99 (dt, J = 20.8, 8.4 Hz, 1H), 2.32-2.19 (m, 2H), 2.17 (d, J = 10.7 Hz, 2H), 2.09 (s, 3H), 1.93 (d, J = 2.2 Hz, 3H). | B (14) |
| 370 | 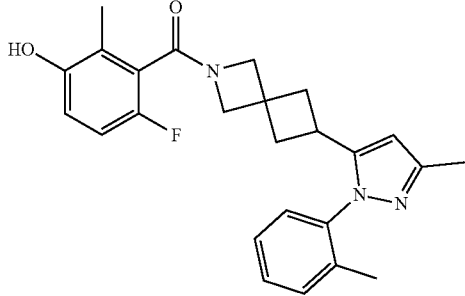 [SMILES: Cc1cc(C2CC3(C2)CN(C(=O)c2c(F)ccc(O)c2C)C3)n(-c2ccccc2C)n1]<br>(6-fluoro-3-hydroxy-2-tolyl) {6-[3-methyl-1-(o-tolyl])-5-pyrazolyl]-2-aza-2-spiro[3.3]heptyl}methanone | LCMS: 420.6 m/z [M + H]$^+$ NMR: $^1$H NMR (400 MHz, DMSO-d$_6$) δ 9.54 (d, J = 10.5 Hz, 1H), 7.44-7.35 (m, 2H), 7.37-7.27 (m, 1H), 7.16 (t, J = 8.1 Hz, 1H), 6.84-6.71 (ddd, J = 36.2, 15.5, 8.7 Hz, 2H), 6.12 (d, 1H), 4.01 (s, 2H), 3.95 (s, 2H), 3.05-2.94 (m, 1H), 2.37 (d, J = 12.5 Hz, 4H), 2.33-2.14 (s, 3H), 2.02-1.91 (s, 6H). | D (14) |
| 371 | 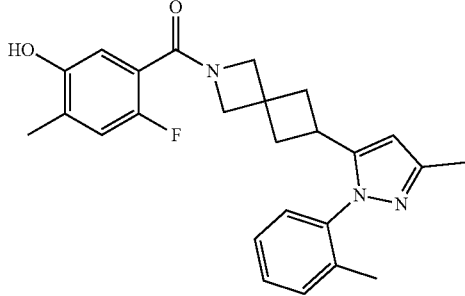<br>(2-fluoro-5-hydroxy-4-tolyl){6-[3-methyl-1-(o-tolyl)-5-pyrazolyl]-2-aza-2-spiro[3.3]heptyl}methanone | LCMS: 420.23 m/z [M + H]$^{+1}$ $^1$H NMR (400 MHz, DMSO-d$_6$) δ 9.56 (d, J = 9.0 Hz, 1H), 7.39 (d, J = 7.9 Hz, 2H), 7.31 (d, J = 7.9 Hz, 1H), 7.16 (s, J = 7.9 Hz, 1H),6.99 (t, J = 10.2 Hz, 1H), 6.78 (d, 1H), 6.15 (d. J = 19.5 Hz, 1H), 3.97 (s, 2H), 3.92 (s, 2H), 3.04-2.95 (m, 1H), 2.35 (s, 2H), 2.26-2.15 (m, 4H), 2.13 (d, J = 4.9 Hz, 3H), 2.20 (d, 3H) , 1.94 (s, 3H). | B (14) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 373 | 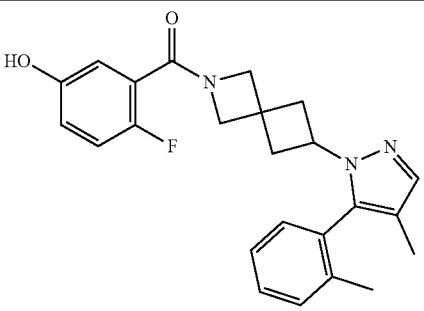<br>(2-fluoro-5-hydroxyphenyl){6-[4-methyl-5-(o-tolyl)-1-pyrazolyl]-2-aza-2-spiro[3.3]heptyl}methanone | LCMS: m/z 406.2 [M + 1]⁺.<br>NMR: ¹H NMR (400 MHz, DMSO-d₆) δ 9.71 (s, 1H), 7.67 (s, 1H), 7.22-7.37 (m, 4H), 7.10 (m, 1H), 6.90-6.75 (m, 2H), 4.71 (m, 1H), 4.14 (d, J = 5.8 Hz. 2H), 4.04 (m, 2H), 2.64 (m, 4H), 2.20 (m, 3H), 1.9 (s, 3H). | C (14) |
| 376 | 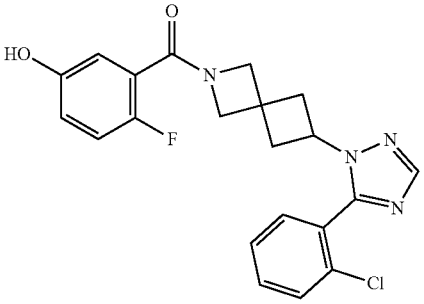<br>{6-[5-(o-chlorophenyl)-1H-1,2,4-triazol-1-yl]-2-aza-2-spiro[3.3]heptyl}(2-fluoro-5-hydroxyphenyl)methanone | LCMS: m/z 413.27 [M + 1]⁺.<br>¹H NMR (400 MHz, DMSO-d₆) δ 9.76 (s,1H), 8.16-8.14 (d, J = 10.0 Hz, IH), 7.80-7.70 (m, 2H), 7.52 (m, 1H), 7.08-7.02 (m, 1H), 6.93 (m, 1H), 6.84 (s, 1H), 4.58-4.51 (m, 1H), 4.09 (s,4H), 2.71 (m, 4H). | B (14) |
| 377 | 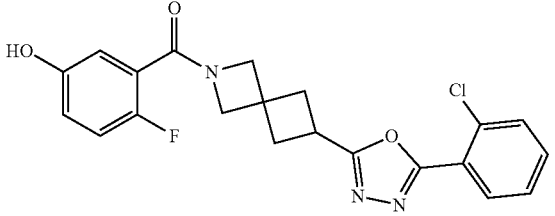 [SMILES: O=C(c1cc(O)ccc1F)N1CC2(CC(c3nnc(-c4ccccc4Cl)o3)C2)C1]<br>{6-[5-(o-chlorophenyl)-1,3,4-oxadiazol-2-yl]-2-aza-2-spiro[3.3]heptyl}(2-fluoro-5-hydroxyphenyl)methanone | LCMS: 414.3 m/z [M + H]⁺¹<br>NMR: ¹H NMR (400 MHz, DMSO-d₆) δ 9.69 (s, 1H), 7.98-7.93 (m, 1H), 7.62 (m, 3H), 7.02 (td, J = 9.2, 2.9 Hz, IH), 6.92-6.79 (m, 2H), 4.31 (d, J = 5.9 Hz, 2H), 4.07 (d, J = 11.5 Hz, 2H), 3.97 (m, J = 10.4 Hz, 1H), 3.41-3.71 (q, J = 6.6 Hz, 4H). | D (14) |
| 378 | 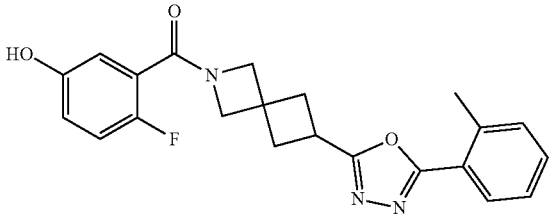<br>(2-fluoro-5-hydroxyphenyl){6-[5-(o-tolyl)-1,3,4-oxadiazol-2-yl]-2-aza-2-spiro[3.3]heptyl}methanone | LCMS: 394.91 m/z [M + H]⁺¹<br>NMR: ¹H NMR (400 MHz, DMSO-d₆) δ 9.69 (s, 1H), 7.85 (dd, J = 18.0, 6.8 Hz, 1H), 7.52-7.39 (m, 3H), 7.10 (d, 1H) 6.88 (s, IH), 6.81 (s, 1H), 4.15 (d, J = 5.1 Hz, 2H), 4.08 (s, 2H), 3.76 (m, 1H) 2.74 (d, J = 9.1 Hz, 1H), 2.62 (d, J = | D (14) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| | | 10.9 Hz, 3H), 2.44 (s, 3H). | |
| 380 | 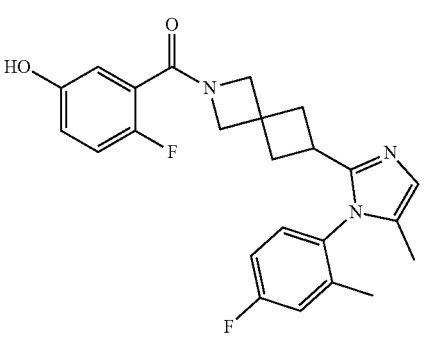 [SMILES: Cc1cc(F)ccc1-n1c(C)cnc1C1CC2(C1)CN(C(=O)c1cc(O)ccc1F)C2]<br>(2-fluoro-5-hydroxyphenyl){6-[1-(4-fluoro-2-tolyl)-5-methyl-2-imidazolyl]-2-aza-2-spiro[3.3]heptyl}methanone | LCMS: m/z 424.31 [M + 1]⁺ ¹H NMR (400 MHz, DMSO-d₆) δ 9.72 (s, 1H), 7.36-7.29 (m. 3H), 7.07 (q, J = 10.2. 9.8 Hz, 1H), 6.85 (d, J = 6.1 Hz, 1H), 6.79-6.69 (m, 2H), 4.00-3.90 (m, 4H), 2.91-2.85 (m, 1H), 2.38 (d. J = 7.8 Hz, 2H), 2.34-2.24 (m, 2H), 1.89-1.80 (m, 6H). | E (14) |
| 381 | 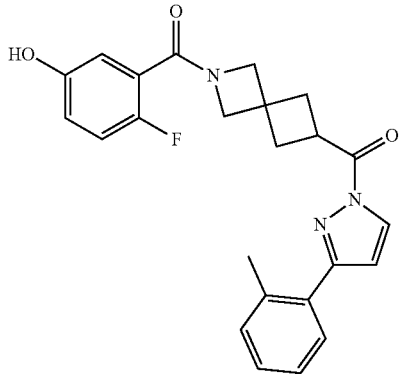 [SMILES: Cc1ccccc1-c1ccn(C(=O)C2CC3(C2)CN(C(=O)c2cc(O)ccc2F)C3)n1]<br>{2-(2-fluoro-5-hydroxybenzoyl)-2-aza-6-spiro[3,3]heptyl}[3-(o-tolyl)-1-pyrazolyl]methanone | LCMS: m/z 419.89 [M + 1]⁺ 1H NMR (400 MHz, DMSO-d6) δ 9.67 (s, 1H), 8.47 (dd, J = 10.0, 2.8 Hz, 1H), 7.64 (d, J = 7.3 Hz, 1H), 7.33 (dd, J = 11.7, 6.1 Hz, 3H), 7.04-7.01 (m, 1H), 7.01-6.94 (m, 1H), 6.90-6.77 (m, 2H), 4.14 (d, J = 6.2 Hz, 3H), 3.99 (d, J = 8.0 Hz, 2H). 2.64-2.2.54 (m, 7H). | C (14) |
| 401 | 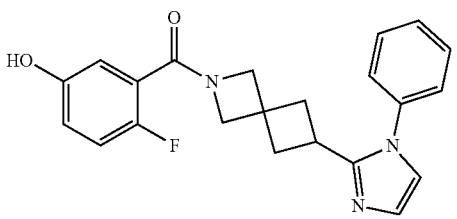 [SMILES: O=C(c1cc(O)ccc1F)N1CC2(CC(c3nccn3-c3ccccc3)C2)C1]<br>(2-fluoro-5-hydroxyphenyl){6-(1-phenyl-2-imidazolyl)-2-aza-2-spiro[3.3]heptyl}methanone | LCMS: m/z 419.89 [M + 1]⁺ ¹H NMR (400 MHz, DMSO-d₆) δ 9.62 (s, 1H), 7.55-7.44 (m, 3H), 7.33 (s, 2H), 7.27 (s, 1H), 7.09-7.03 (m, 1H), 6.96 (d, J = 10.4 Hz, 1H), 6.84 (s, 1H), 6.76 (s, 1H), 4.02 (s, 2H), 3.95 (s, 2H), 2.45 (s. 4H). | D (14) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 407 | 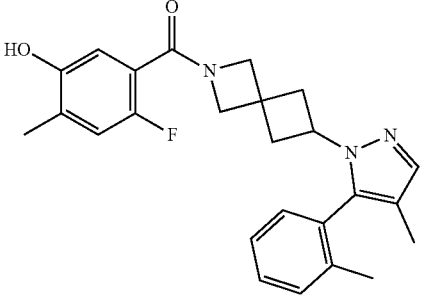 [SMILES: Cc1cc(F)c(C(=O)N2CC3(CC(n4ncc(C)c4-c4ccccc4C)C3)C2)cc1O]<br>(2-fluoro-5-hydroxy-4-tolyl){6-[4-methyl-5-(o-tolyl)-1-pyrazolyl]-2-aza-2-spiro[3.3]heptyl}methanone | LCMS: m/z 420.30 [M + 1]$^+$. NMR: $^1$H NMR (400 MHz, DMSO-d$_6$) δ 9.56 (s, 1H), 7.63 (d, J = 4.5 Hz, 1H), 7.38-7.20 (d, J = 7.6 Hz, 4H), 6.93-6.78 (m, 2H), 4.72 (dt, J = 29.9, 7.9 Hz, 1H), 4.18 (s, 1H), 4.07 (s, 1H), 3.92 (s, 1H), 3.81 (s, 1H), 2.69 (q, J = 12.3, 9.5 Hz, 4H), 2.20 (d, J = 14.3 Hz, 3H), 2.06-1.97 (m, 3H), 1.90 (d, ) = 3.2 Hz, 3H). | B (6) |
| 408 | 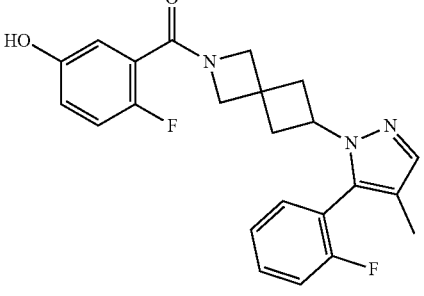<br>(2-fluoro-5-hydroxyphenyl){6-[5-(o-fluorophenyl)-4-methyl-1-pyrazolyl]-2-aza-2-spiro[3.3]heptyl}methanone | LCMS: m/z 410.21 [M + 1]$^+$ NMR: $^1$H NMR (400 MHz, DMSO-d$_6$) δ 9.67 (s, lH), 7.69 (s, 1H), 7.48-7.41 (m, 2H), 7.32-7.23 (m, 2H), 7.13-7.06 (m, 1H), 6.87 (s, 1H), 6.81 (s, 1H), 4.75 (dd, J = 15.0, 7.8 Hz, 1H), 4.15 (d, J = 11.0 Hz, 2H), 4.05 (d, J = 8.7 Hz, 2H), 2.67 (dd, J = 25.9, 9.9 Hz, 4H), 1.97 (s, 3H). | B (6) |
| 410 | 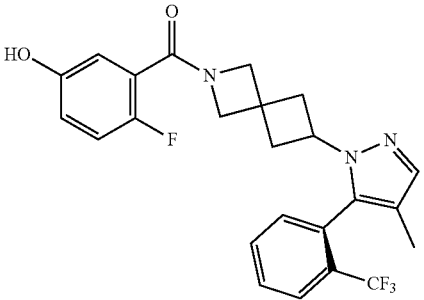<br>4-fluoro-3-{6-[(4M)-4-methyl-5-[2-(trifluoromethyl)phenyl]-1H-pyrazol-1-yl]-2-azaspiro[3.3]heptane-2-carbonyl}phenol | LCMS: m/z 460.44 [M + 1]$^+$. NMR: $^1$H NMR (400 MHz, DMSO-d6) δ 9.68 (s, 1H), 7.94 (d, J = 7.2 Hz, 1H), 7.81 (s, 1H), 7.75 (s, 1H), 7.64 (s, 1H), 7.38 (s, 1H), 7.08 (s, 1H), 6.86 (s, 1H), 6.76 (s, 1H), 3.84 (d, J = 12.8 Hz, 1H), 3.55 (d. J = 9.2 Hz, 2H), 3.47 (d, J = 12.0 Hz, 2H), 2.5 (s, 2H), 1.87-1.74 (m, 5H). | B (6) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 411 | 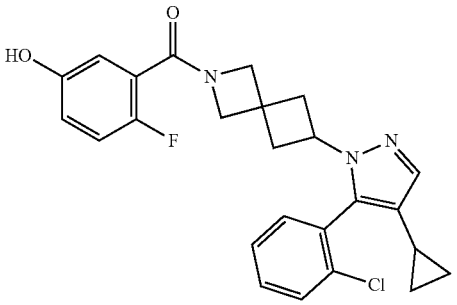 [SMILES: O=C(c1cc(O)ccc1F)N1CC2(CC(n3ncc(C4CC4)c3-c3ccccc3Cl)C2)C1]<br>{6-[5-(o-chlorophenyl)-4-cyclopropyl-1-pyrazolyl]-2-aza-2-spiro[3.3]heptyl}(2-fluoro-5-hydroxyphenyl)methanone | LCMS: m/z 452.26 [M + 1]$^+$. $^1$H NMR (400 MHz, DMSO-d$_6$) δ 8.52-8.42 (m,3 H), 7.80-7.66 (m, 3H), 7.08-7.02 (m, 1H), 6.93 (m, 1H), 6.84 (s, 1H), 5.13 (s, 1H), 4.43 (s, 1H), 4.29 (s, 1H), 3.44 (s, 2H), 2.67-2.61 (m, 2H), 2.1 (d, J = 9.2 Hz, 1H), 1.93 (s, 1H), 1.50 (s, 1H), 0.86 (dd, J = 11.8, 5.9 Hz, 2H), 0.70 (s, 2H). | C (6) |
| 414 | 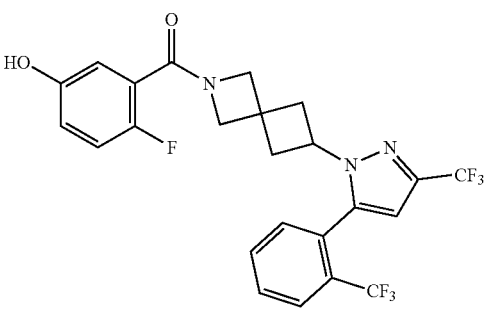 [SMILES: O=C(c1cc(O)ccc1F)N1CC2(CC(n3nc(C(F)(F)F)cc3-c3ccccc3C(F)(F)F)C2)C1]<br>(2-fluoro-5-hydroxyphenyl)(6-{5-(trifluoromethyl)-3-[o-(trifluoromethyl)phenyl]-1-pyrazolyl}-2-aza-2-spiro[3.3]heptyl)methanone | LCMS: m/z 514.20 [M + 1]$^+$. NMR: $^1$NMR (400 MHz, DMSO-d$_6$) δ 9,67 (d, 1H), 7.95 (t, 1H), 7.85-7.77 (m, 3H), 7.06 (s, 2H), 6.84 (s, 1H), 6.75 (s, 1H), 4.92 (m, 1H), 4.22 (m, 2H), 4.03 (s, 2H), 2.68 (s, 4H). | A (14) |
| 415 | 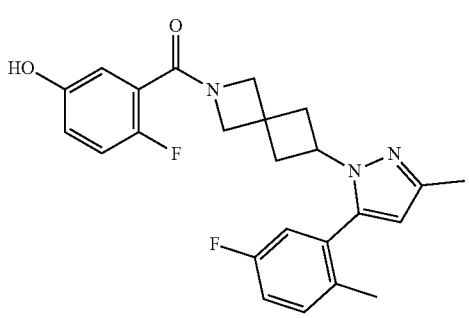 [SMILES: Cc1cc(-c2cc(F)ccc2C)n(C2CC3(C2)CN(C(=O)c2cc(O)ccc2F)C3)n1]<br>(2-fluoro-5-hydroxyphenyl){6-[5-(5-fluoro-2-tolyl)-3-methyl-1-pyrazolyl]-2-aza-2-spiro[3.3]heptyl}methanone | LCMS: m/z 424.3 [M + 1]$^+$. NMR: $^1$NMR (400 MHz, DMSO-d$_6$) δ 9.67 (d, 1H), 7.35-7.23 (m, J = 10.8, 2H), 7.12-7.00 (m, J = 9.6, 2H) 6.85-6.79 (d, 2H), 6.35 (s, 1H), 4.81-4.72 (m, 1H), 4.14 (d, 2H), 4.06 (d, 2H), 2.73-2.71 (m, 4H), 2.39-2.33 (m, 3H), 2.25 (d, 3H). | B (6) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 417 | 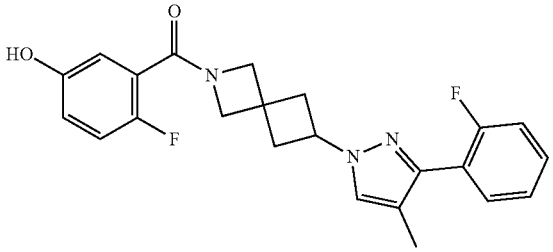 [SMILES: Cc1cn(C2CC3(C2)CN(C(=O)c2cc(O)ccc2F)C3)nc1-c1ccccc1F]<br>(2-fluoro-5-hydroxyphenyl){ 6-[3-(o-fluorophenyl)-4-methyl-1-pyrazolyl]-2-aza-2-spiro[3.3]heptyl}methanone | LCMS: m/z 410.35 [M + 1]⁺. NMR: ¹H NMR (400 MHz, DMSO-d₆) δ 9.67 (s, 1H), 7.56 (s. 1H), 7.46 (d, J = 10.6 Hz, 1H). 7.39 (dd, J = 24.5, 10.1 Hz, 3H), 7.07 (q, J = 9.6, 9.1 Hz, 1H), 6.84 (s, 1H), 6.76 (s, IH), 4.46-4.37 (m, 1H), 4.01 (s, 4H), 2.62 (d, J = 18.8 Hz, 4H), 1.87 (s, 3H). | A (6) |
| 440 | 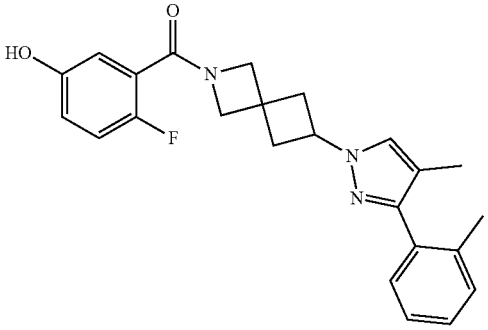 [SMILES: Cc1ccccc1-c1nn(C2CC3(C2)CN(C(=O)c2cc(O)ccc2F)C3)cc1C]<br>(2-fluoro-5-hydroxyphenyl){6-[4-methyl-3-(o-tolyl)-1-pyrazolyl]-2-aza-2-spiro[3.3]heptyl} methanone | LCMS: m/z 406.20 [M + 1]⁺. NMR: ¹H NMR (400 MHz, DMSO-d₆) δ 10.03 (s, 1H), 7.53-7.21 (m, 4H), 7.15-6.96 (m, 2H), 6.86-6.74 (m, 2H), 4.21 (s, 1H), 4.09-3.91 (d, J = 12.2 Hz, 4H), 2.67 (dd, J = 26.0, 10.3 Hz, 4H), 2.00 (s, 3H), 1.78 (s, 3H). | A (14) |
| 443 | 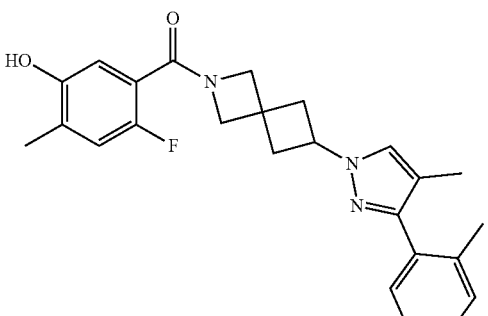<br>(2-fluoro-5-hydroxy-4-tolyl) {6-[4-methyl-3-(o-tolyl)-1-pyrazoly]]-2-aza-2-spiro[3.3]heptyl}methanone | LCMS: m/z 420.30 [M + 1]⁺. NMR ¹H NMR (400 MHz, DMSO-d₆) δ 9.55 (s, 1H), 7.42-7.23 (dt, J = 23,2, 7.2 Hz. 4H), 7.15--7.06 (m, 1H), 6.85 (ddt, J = 26.1, 11.4, 6.6 Hz, 2H), 4.20 (dt, J = 22.6, 7.8 Hz, 1H), 4.04 (s, 2H), 3.74 (d, J = 7.0 Hz, 2H), 2.69 (ddd, J = 34.8, 17.8, 9.6 Hz, 4H), 1.99 (d, J = 6.3 Hz, 6H), 1.77 (s, 3H). | E (6) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 444 | 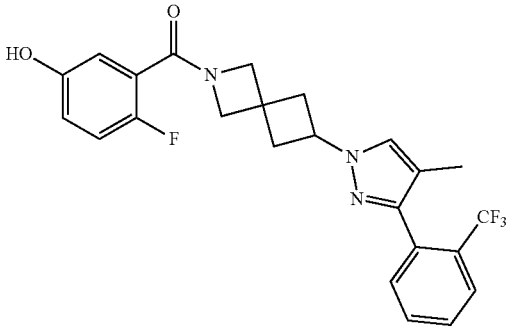 [SMILES: Cc1cn(C2CC3(C2)CN(C(=O)c2cc(O)ccc2F)C3)nc1-c1ccccc1C(F)(F)F]<br>(2-fluoro-5-hydroxyphenyl)(6-{4-methyl-3-[o-(trifluoromethyl)phenyl]-1-pyrazolyl}-2-aza-2-spiro[3.3]heptyl)methanone | LCMS: m/z 459.64 [M + 1]$^+$.<br>NMR: $^1$H NMR (400 MHz, DMSO-d6) δ 9.64 (d, J = 12.1 Hz, 1H), 7.98-7.88 (m, 1H), 7.80 (s, 2H), 7.47-7.36 (m, 2H), 7.09-7.04 (m, 1H), 6.84 (s, 1H), 6.76 (s, 1H), 4.04-3.94 (m, 5H), 2.68-2.35 (s, 4H), 1.74 (s, 3H). | A (6) |
| 446 | 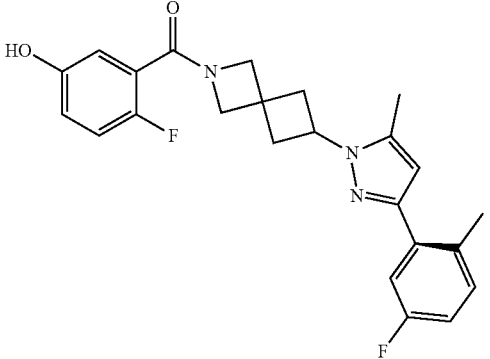<br>(2-fluoro-5-hydroxyphenyl){6-[3-(5-fluoro-2-tolyl)-5-methyl-1-pyrazolyl]-2-aza-2-spiro[3.3]heptyl}methanone | Fraction-1: Compound 446-01<br>LCMS: m/z 424.3 [M + 1]$^+$.<br>NMR: $^1$NMR (400 MHz, DMSO-ds) δ 9.65 (d, 1H), 7.38-7.33 (dd, J= 6.4, 8.6, 1H), 7.21 (t, 1H), 7.10-6.97 (m, J = 9.2, 11.2, 2H), 6.85-6.76 (m, 1H), 6.74 (d, 1H), 6.03 (s, 1H), 4.27-4.21 (m, 1H), 4.02 (s, 2H), 4.00 (s, 2H), 2.71 (s, 2H), 2.65 (s, 2H), 2.23 (d, 3H), 2.03 (d, 3H).<br>Fraction-2: Compound 446-02<br>LCMS: m/z 424.32 [M + 1]$^+$.<br>NMR: $^1$NMR (400 MH$_z$, DMSO-d$_6$) δ 9.65 (d, 1H), 7.38-7.33 (m, J = 6.4, 6.8, 7.2, 1H), 7.22-7.20 (dd, 1H), 7.07-6.97 (m, J = 9.2, 10.8, 9.6, 2H), 6.83 (s, 1H), 6.75 (s, 1H), 6.03 (s, 1H), 4.27-4.21 (m. 1H), 4.00 (d, 4H), 2.69 (d, 4H), 2.19 (d, 3H), 2.03 (d, 3H). | A (6) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 472 | 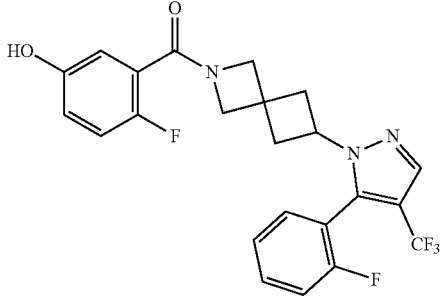 [SMILES: O=C(c1cc(O)ccc1F)N1CC2(CC(n3ncc(C(F)(F)F)c3-c3ccccc3F)C2)C1]<br>(2-fluoro-5-hydroxyphenyl){6-[5-(o-fluorophenyl)-4-(trifluoromethyl)-1-pyrazolyl]-2-aza-2-spiro[3.3]heptyl}methanone | LCMS: m/z 464.41 [M + H]$^+$. $^1$H NMR (400 MHz, DMSO-d$_6$) δ 9.69 (d, J = 5.5 Hz, 1H), 8.62 (d, J = 9.6 Hz, 1H), 7.53 (s, 1H), 7.51-7.42 (m, 1H), 7.39-7.25 (m, 2H), 7.10 (q, J = 9.0 Hz, 1H), 6.89-6.84 (m, 1H), 6.81 (s, 1H), 4.90 (dt, J = 23.7, 7.9 Hz, 1H), 4.16 (d, J = 10.3 Hz, 2H), 4.06 (d, J = 8.1 Hz, 2H), 2.74 (dd, J = 24.9, 10.1 Hz, 4H). | B (12) |
| 473 | 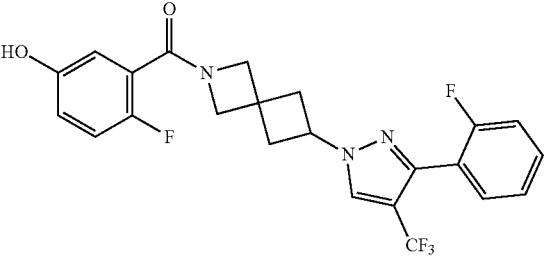 [SMILES: O=C(c1cc(O)ccc1F)N1CC2(CC(n3cc(C(F)(F)F)c(-c4ccccc4F)n3)C2)C1]<br>(2-fluoro-5-hydroxyphenyl){6-[3-(o-fluorophenyl)-4-(trifluoromethyl)-1-pyrazolyl]-2-aza-2-spiro[3.3]heptyl}methanone | LCMS: m/z 464.01 [M + H]$^+$. $^1$H NMR (400 MHz, DMSO-d$_6$) δ 9.68 (s, 1H), 8.12 (d. J = 9.7 Hz. 1H), 7.63-7.43 (dq, J = 19.3, 9.9, 7.4 Hz, 4H), 7.08 (q, J = 9.5 Hz, 1H), 6.85 (s, 1H), 6.77 (s, 1H), 4.50 (dt, J = 14.3, 7.5 Hz, 1H), 4.03 (d, J = 9.0 Hz, 4H), 2.79-2.63 (m, 4H). | A (12) |
| 474 | 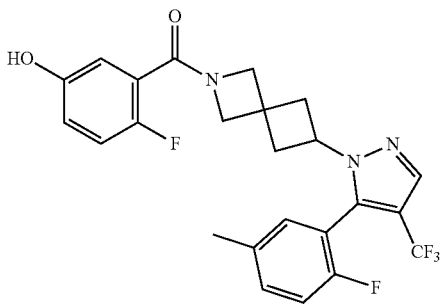 [SMILES: Cc1ccc(F)c(-c2c(C(F)(F)F)cnn2C2CC3(C2)CN(C(=O)c2cc(O)ccc2F)C3)c1]<br>(2-fluoro-5-hydroxyphenyl){6-[5-(2-fluoro-5-tolyl)-4-(trifluoromethyl)-1-pyrazolyl]-2-aza-2-spiro[3.3]heptyl}methanone | LCMS: m/z 478.40 [M + 1]$^+$ $^1$H NMR (400 MHz, DMSO-d$_6$) δ 9.67 (s, 1H), 8.1 (d, J = 9.9 Hz, 1H), 7.29-7.20 (m, 3H), 7.09 (q, J = 9.6 Hz, 1H), 6.84 (s, 1H), 6.79 (s, 1H), 4.88 (dt, J = 14.5, 7.7 Hz, IH), 4.03 (d, J = 8.7 Hz, 4H), 2.74 (ddt, J = 51.2, 19.7, 8.6 Hz, 4H), 2.35 (d, J = 9.5 Hz, 3H). | C (12) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 475 | 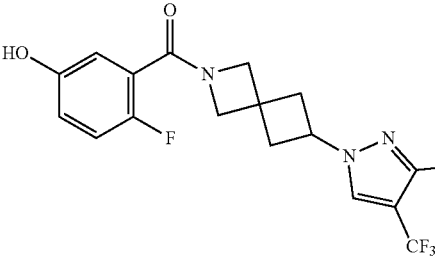<br>(2-fluoro-5-hydroxyphenyl){6-[3-(2-fluoro-5-tolyl)-4-(trifluoromethyl)-1-pyrazolyl]-2-aza-2-spiro[3.3]heptyl}methanone | LCMS: m/z 478.4 [M + 1]$^+$.<br>NMR: $^1$H NMR (400 MHz, DMSO-d$_6$) δ 9.67 (s, 1H), 8.11 (d, J = 9.9 Hz, 1H), 7.45 (s, 1H), 7.39-7.18 (m, 2H), 7.08 (q, J = 9.6 Hz, 1H), 6.85 (s, 1H), 6.77 (s, 1H), 4.49 (dt, J = 14.5, 7.7 Hz, 1H), 4.03 (d, J = 18.8 Hz, 4H), 2.68-2.51 (m, 2H), 2.47 (m, 2H), 2.35 (d, J = 9.5 Hz, 3H). | A (12) |
| 476 | 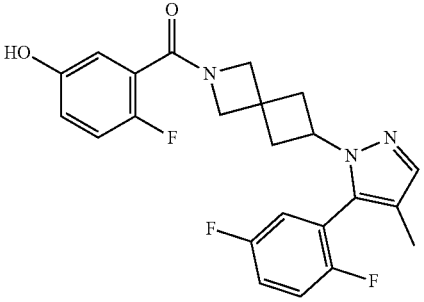 [SMILES: Cc1cnn(C2CC3(C2)CN(C(=O)c2cc(O)ccc2F)C3)c1-c1cc(F)ccc1F]<br>{6-[5-(2,5-difluorophenyl)-4-methyl-1-pyrazolyl]-2-aza-2-spiro[3.3]heptyl}(2-fluoro-5-hydroxyphenyl)methanone | LCMS: m/z 428.3 [M + 1]$^+$.<br>$^1$H NMR (400 MHz, DMSO-d$_6$) δ 9.69 (s, 1H), 7.72 (d, J = 5.9 Hz, 1H), 7.39-7.26 (m, 3H), 7.10 (q, J = 9.1 Hz, 1H), 6.82-6.87 (q, J = 9.1 Hz, 1H), 6.74-6.79 (q, J = 9.1 Hz, 1H), 4.76 (dt, J = 23.3, 7.9 Hz, 1H), 4.15 (d, J = 11.2 Hz, 2H), 4.05 (d. J = 8.7 Hz, 2H), 2.76-2.60 (m, 4H), 1.99 (s, 3H). | B (13) |
| 477 | 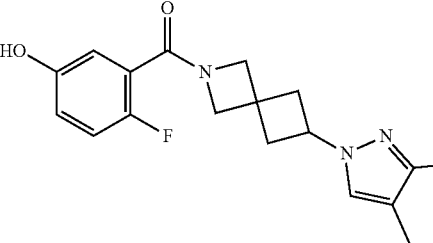<br>{6-[3-(2,5-difluorophenyl)-4-methyl-1-pyrazolyl]-2-aza-2-spiro[3.3]heptyl}(2-fluoro-5-hydroxyphenyl)methanone | LCMS: m/z 428.03 [M + 1]$^+$.<br>$^1$H NMR (400 MHz, DMSO-d$_6$) δ 7.52-7.40 (m, 3H), 7.30 (dd, J = 5.4, 2.8 Hz, 1H), 7.08 (q, J = 8.9 Hz, 1H), 6.85 (d, J = 3.9 Hz, 1H), 6.81-6.75 (m, 1H), 4.47 (dt, J = 15.6, 7.8 Hz, 1H), 4.07 (dd, J = 24.5, 5.0 Hz, 4H), 2.60 (dd, J = 20.2, 8.3 Hz, 4H), 1.90 (s, 3H). | A (13) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 487 | 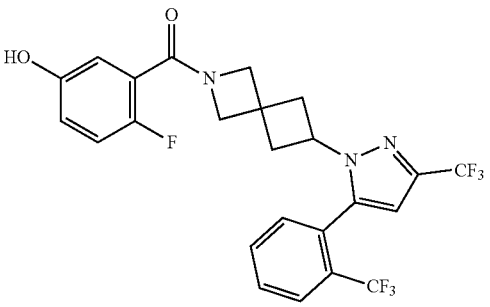 [SMILES: O=C(c1cc(O)ccc1F)N1CC2(CC(n3nc(C(F)(F)F)cc3-c3ccccc3C(F)(F)F)C2)C1]<br>(2-fluoro-5-hydroxyphenyl)(6-{3-(trifluoromethyl)-5-[o-(trifluoromethyl)phenyl]-1-pyrazolyl}-2-aza-2-spiro[3.3]heptyl)methanone | LCMS: m/z 514.20 [M + 1]⁺. NMR: ¹NMR (400 MH$_z$, DMSO-d$_6$) δ 9.67 (d, 1H), 7.96 (m, 1H), 7.78-7.67 (m, 2H), 7.63 (m, 1H), 7.08 (s, 2H), 6.84-6.78 (dd, J = 3.6 Hz, 8.4 Hz, 2H), 6.72 (s, 1H), 4.16 (m, 2H), 4.08-4.02 (m, 2H), 2.79 (s, 4H). | C (13) |
| 488 | 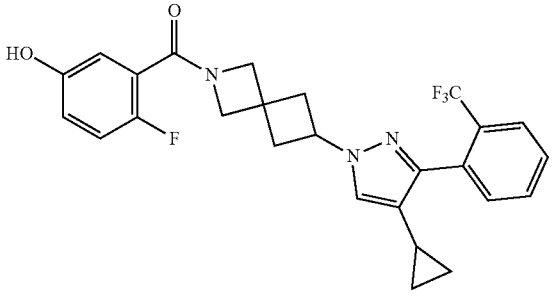<br>(6-{4-cyclopropyl-3-[o-(trifluoromethyl)phenyl]~1-pyrazolyl}-2-aza-2-spiro[3.3]heptyl)(2-fluoro-5-hydroxyphenyl)methanone | LCMS: m/z 486.33 [M + H]⁺. NMR: ¹H NMR (400 MHz, DMSO-d$_6$) δ 9.73 (s, 1H), 7.91 (dd, J = 12.6, 8.1 Hz, 1H), 7.83-7.69 (m, 2H), 7.40 (t, J = 8.0 Hz, 1H), 7.26 (d, J = 10.1 Hz, 1H), 7.04 (dt, J = 17.3, 9.2 Hz, 1H), 6.74 (s, 2H), 4.09 (dd, J = 14.2, 6.8 Hz, 1H), 4.01-3.91 (m, 4H), 2.63 (s, 2H), 2.54 (s, 2H), 1.18 (m, 1H), 0.59 (s, 2H), 0.39 (d, J = 15.1 Hz, 2H). | A (12) |
| 489 | 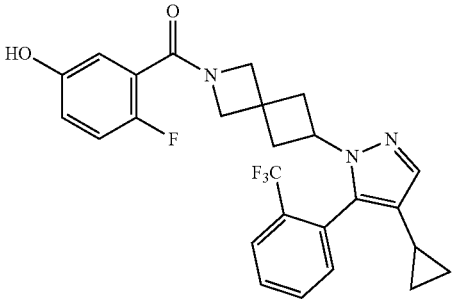 [SMILES: O=C(c1cc(O)ccc1F)N1CC2(CC(n3ncc(C4CC4)c3-c3ccccc3C(F)(F)F)C2)C1]<br>(6-{4-cyclopropyl-5-[o-(trifluoromethyl)phenyl]-1-pyrazolyl}-2-aza-2-spiro[3.3]heptyl)(2~fluoro-5-hydroxyphenyl)methanone | LCMS: m/z 486.33 [M + H]⁺. ¹H NMR (400 MHz, DMSO-d$_6$) δ 9.67 (s, 1H), 7.83 (s, 1H), 7.72 (d, J = 5.2 Hz, 1H), 7.63 (s, 1H), 7.53 (s, 2H), 7.09 (d, J = 8,9 Hz, 1H), 6.85 (s, 2H), 4.70 (d, J = 7.4 Hz, 1H), 4.12 (d, J = 10.2 Hz, 2H), 4.00 (d, J = 8.5 Hz, 2H), 2.65 (dd, J = 19.9, 11.1 Hz, 4H), 1.29 (m, 1H), 0.67 (d, J = 6.9 Hz, 2H), 0.41 (s, 2H). | B (12) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 490 | 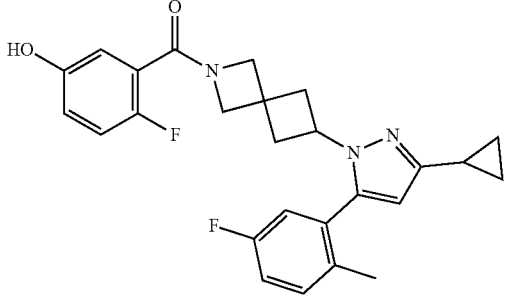 [SMILES: Cc1ccc(F)cc1-c1cc(C2CC2)nn1C1CC2(C1)CN(C(=O)c1cc(O)ccc1F)C2]<br>{6-[3-cyclopropyl-5-(5-fluoro-2-tolyl)-1-pyrazolyl]-2-aza-2-spiro[3.3]heptyl}(2-fluoro-5-hydroxyphenyl)methanone | LCMS: m/z 449.5 [M + 1]$^+$, NMR: $^1$H NMR (400 MHz, DMSO-d6) δ 9.67 (d, J = 8.4 Hz, 1H), 7.37-7.26 (m. 2H), 7.13-6.98 (m, 2H), 6.85 (s, 1H), 6.80 (s, 1H), 6.24 (s, 1H), 4.16 (d, J = 9.1 Hz, 2H), 4.07 (s, 2H), 2.75 (s, 4H), 2.41 (d, J = 17.2 Hz, 3H), 1.85 (s, 1H), 0.94 (s, 2H), 0.65 (s, 2H). | B (13) |
| 491 | 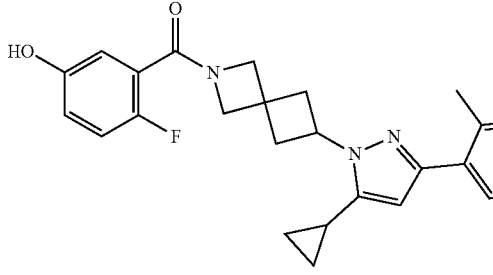<br>{6-[5-cyclopropyl-3-(5-fluoro-2-tolyl)-1-pyrazolyl]-2-aza-2-spiro[3.3]heptyl}(2-fluoro-5-hydroxyphenyl)methanone | LCMS: m/z 449.5 [M + 1]$^+$. NMR: $^1$H NMR (400 MHz, DMSO-d6) δ 9.65 (d, J = 7.5 Hz, 1H), 7.36 (d, J = 5.7 Hz, 1H), 7.21 (d, J = 9.3 Hz, 0H), 7.10-7.00 (m, 1H), 6.99 (d, J = 9.0 Hz, 1H), 6.84 (s, 1H), 6.76 (s, 1H), 5.93 (s, 1H), 4.28-4.19 (m, 1H), 4.01 (d, J = 9.4 Hz, 4H), 2.67 (s, 4H), 2.01 (s, 3H), 1.90 ( s, 1H), 0.87 (s, 2H), 0.66 (d, J = 14.9 Hz, 2H). | A (13) |
| 492 | 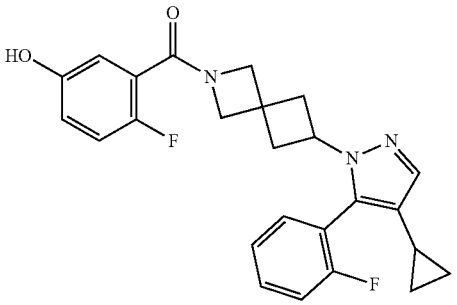 [SMILES: O=C(c1cc(O)ccc1F)N1CC2(CC(n3ncc(C4CC4)c3-c3ccccc3F)C2)C1]<br>{6-[4-cyclopropyl-5-(o-fluorophenyl)-1-pyrazolyl]-2-aza-2-spiro[3.3]heptyl}(2-fluoro-5-hydroxyphenyl)methanone | LCMS: m/z 436.20 [M + H]$^+$. $^1$H NMR (400 MHz, DMSO-d$_6$) δ 9.69 (s, 1H), 7.56 (dd, J = 20.5, 7.4 Hz, 3H), 7.33-7.24 (m, 2H), 6.81 (s, 2H), 4.76-4.66 (m, 1H), 4.15 (d, J = 10.4 Hz, 2H), 4.04 (d, J = 8.4 Hz, 2H), 2.72-2.62 (m, 4H), 1.56 (s, 1H), 0.76 (s, 2H), 0.44 (s, 2H). | B (12) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 493 | 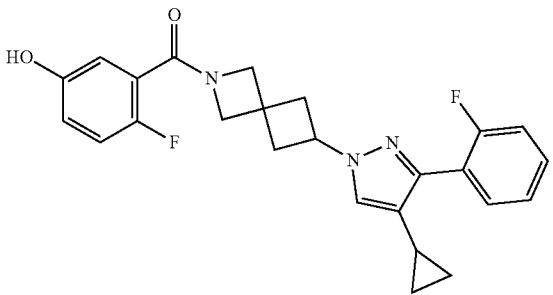 [SMILES: O=C(c1cc(O)ccc1F)N1CC2(CC(n3cc(C4CC4)c(-c4ccccc4F)n3)C2)C1]<br>{6-[4-cyclopropyl-3-(o-fluorophenyl)-1-pyrazolyl]-2-aza-2-spiro[3.3]heptyl}(2-fluoro-5-hydroxyphenyl)methanone | LCMS: m/z 436.22 [M + H]$^+$. $^1$H NMR (400 MHz, DMSO-d$_6$) δ 9.64 (s, 1H), 7.36 (dd, J = 26.7, 8.4 Hz, 4H), 7.08 (d, J = 9.0 Hz, 1H), 6.77 (s, 2H), 4.41 (s, 1H), 4.02 (s, 4H), 2.70 (s, 4H), 1.40 (s, 1H), 0.69 (s, 2H), 0.46 (s, 2H). | A (12) |
| 519 | 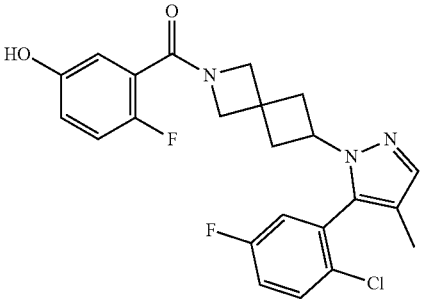<br>{6-[5-(2-chloro-5-fluorophenyl)-4-methyl-1-pyrazolyl]-2-aza-2-spiro[3.3]heptyl}(2-fluoro-5-hydroxyphenyl)methanone | LCMS: m/z 444.40 [M + 1]$^+$. NMR: $^1$H NMR (400 MHz, DMSO-d$_6$) δ 9.80 (s, 1H), 7.68 (d, J = 5.0 Hz, 1H), 7.58 (dt, J = 8.8, 5.6 Hz. 1H), 7.35-7.17 (m, 2H), 7.08 (q, J = 9.1 Hz, 1H), 6.87-6.74 (m, 2H), 4.72 (dq, J = 24.0, 7.9 Hz, 1H), 4.13 (d, J = 10.7 Hz, 2H), 4.02 (d, J = 9.4 Hz, 2H), 2.68 (q, J = 15.2, 13.3 Hz, 4H), 1,91 (d, J = 2.6 Hz. 3H). | B (12) |
| 520 | 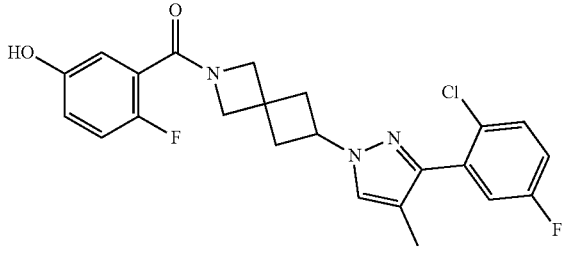 [SMILES: Cc1cn(C2CC3(C2)CN(C(=O)c2cc(O)ccc2F)C3)nc1-c1cc(F)ccc1Cl]<br>{6-[3-(2-chloro-5-fluorophenyl)-4-methyl-1-pyrazolyl]-2-aza-2-spiro[3.3]heptyl}(2-fluoro-5-hydroxyphenyl)methanone | LCMS: m/z 444.40 [M + 1]$^+$. NMR: $^1$H NMR (400 MHz, DMSO-d$_6$) δ 9.70 (s, 1H), 7.68 (d, J = 5.0 Hz, 1H), 7.58 (dt, J = 8.8, 5.6 Hz, 2H), 7.35-7.17 (m, 1H), 7.08 (q, J = 9.1 Hz, 1H), 6.85-6.71 (m, 2H), 4.32 (dq, J = 24.0. 7.9 Hz, 1H), 4.03 (d, J = 10.7 Hz, 4H), 2.68 (q, J = 15.2, 13.3 Hz, 4H), 1.81 (d, J = 2.6 Hz, 3H). | A (12) |

TABLE 6-continued

Compounds of Formula (I), including the value of MAGL inhibition potency measured with a method described in Table C of Example 22.

| Compound | Structure (IUPAC name) | LCMS/NMR | MAGL Potency (Detection Method) |
|---|---|---|---|
| 525 | (2-fluoro-5-hydroxyphenyl)(6-{3-[o-(trifluoromethyl)phenyl]-1-pyrazolyl}-2-aza-2-spiro[3.3]heptyl)methanone | LCMS: m/z 446.30 [M + H]$^+$. $^1$H NMR (400 MHz, DMSO-d$_6$) δ 9.64 (s, 1H), 7.89 (s, 1H), 7.78-7.71 (m, 2H), 7.58 (d, J = 9.1 Hz, 1H), 7.42 (s, 1H), 7.03 (s, 1H), 6.82 (s, 1H), 6.75 (s, 1H), 6.28 (s, 1H), 4.26 (s, 1H), 3.99 (d, J = 19.2 Hz, 4H), 2.78 (s, 4H). | A (12) |
| 526 | (2-fluoro-5-hydroxyphenyl)(6-{5-[o-(trifluoromethyl)phenyl]-1-pyrazolyl}-2-aza-2-spiro[3.3]heptyl)methanone | LCMS: m/z 446.20 [M + H]$^+$. $^1$H NMR (400 MHz, DMSO-d$_6$) δ 9.66 (d, J = 7.4 Hz, 1H), 7.82 (dd, J = 16.3, 9.0 Hz, 2H), 7.73-7.54 (m, 3H), 7.08 (q, J = 8.8 Hz, 1H), 6.88-6.82 (m, 1H), 6.79 (s, 1H), 6.42 (s, 1H), 4.82 (dt, J = 23.6, 7.9 Hz, 1H), 4.14 (d, J = 10.1 Hz, 2H), 4.04 (d, J = 7.9 Hz, 2H), 2.71 (dt, J = 17.5, 10.4 Hz, 4H). | B (12) |

TABLE 7

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 142 | (4-fluoro-2-methoxyphenyl){6-[3-methyl-1-(o-tolyl)-5-pyrazolyl]-2-aza-2-spiro[3.3]heptyl}methanone | LCMS: 420.41 m/z [M + H]+; 1H NMR (400 MHz, DMSO-d6) δ 7.44-7.25 (m, 4H), 7.16 (t, J = 6.5 Hz, 1H), 6.98 (s, 1H), 6.85-6.74 (m, 1H), 6.17 (s, 1H), 3.95 (s, 1H), 3.89 (s, 1H), 3.86-3.75 (m, 5H), 2.99 (dt, J = 25.9, 8.5 Hz, 1H), 2.26-2.43 (m, 3H), 2.26-2.14 (m, 4H), 1.94 (d, J = 2.2 Hz, 3H). | D (2) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 143 | (o-methoxyphenyl){6-[3-methyl-1-(o-tolyl)-5-pyrazolyl]-2-aza-2-spiro[3.3]heptyl}methanone | LCMS: 401.8 m/z [M]+. 1H NMR (400 MHz, Methanol-d4) δ 7.50-7.17 (m, 5H), 7.17-6.96 (m, 3H), 6.23-6.17 (s, 1H), 4.11 (s, 1H), 4.05 (s, 1H), 3.97 (s, 1H), 3.93-3.84 (m, 4H), 3.08 (dq, J = 29.0, 8.5 Hz, 1H), 2.48-2.35 (m, 3H), 2.32 (dd, J = 27.0, 12.1 Hz, 4H), 2.01 (d, J = 3.1 Hz, 3H). | E (2) |
| 145 | (o-ethoxyphenyl){6-[3-methyl-1-(o-tolyl)-5-pyrazolyl]-2-aza-2-spiro[3.3]heptyl}methanone | LCMS: 416.74 m/z [M + H]+; 1H NMR (400 MHz, DMSO-d6) δ 7.45-7.24 (m, 3H), 7.20 (d, J = 7.5 Hz, 1H), 7.14 (q, J = 8.1, 7.2 Hz, 1H), 7.08-6.89 (m, 2H), 6.17-6.07 (s, 1H), 4.06 (dq, J = 9.9, 6.9 Hz, 2H), 3.94 (s, 1H), 3.88 (s, 1H), 3.83 (s, 1H), 3.77 (s, 1H), 2.98 (dq, J = 25.0, 8.4 Hz, 1H), 2.39-2.14 (m, 7H), 1.93 (d, J = 1.9 Hz, 3H), 1.30 (dt, J = 9.8, 6.9 Hz, 3H). | E (2) |
| 146 | (2-ethoxy-4-fluorophenyl){6-[3-methyl-1-(o-tolyl)-5-pyrazolyl]-2-aza-2-spiro[3.3]heptyl}methanone | LCMS: m/z 433.8 [M + 1]+ NMR: 1H NMR (400 MHz, DMSO-d6) δ 7.43-7.22 (m, 4H), 7.15 (dd, J = 7.6, 4.7 Hz, 1H), 6.95 (s, 1H), 6.79-6.74 (m, 1H), 6.11 (d, 1H), 4.10-4.07 (m, 2H), 3.94 (s, 1H), 3.86 (d, J = 14.0 Hz, 2H), 3.78 (s, 1H), 3.04-2.96 (m, 1H), 2.33 (s, 1H), 2.32-2.25 (m, 2H), 2.22 (dd, J = 35.1, 9.2 Hz, 4H), 1.93 (d, J = 1.8 Hz, 3H), 1.30 (dt, J = 9.8, 6.9 Hz, 3H). | C(2) A (3) |

TABLE 7-continued

Compounds of Formula (I), including the value of MAGL inhibition potency
measured with a method described in Table C of Example 22.

| Compound | Structure (IUPAC name) | LCMS / NMR | MAGL Potency (Detection Method) |
|---|---|---|---|
| 177 | 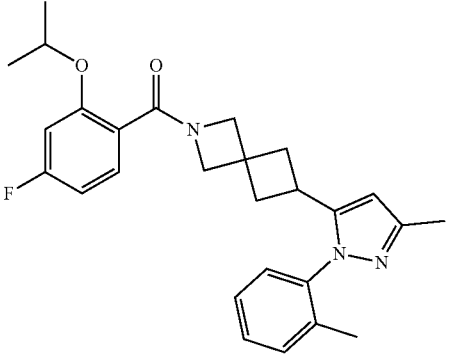 [SMILES: Cc1cc(C2CC3(C2)CN(C(=O)c2ccc(F)cc2OC(C)C)C3)n(-c2ccccc2C)n1]<br>(4-fluoro-2-isopropoxyphenyl){6-[3-methyl-1-(o-tolyl)-5-pyrazolyl]-2-aza-2-spiro[3.3]heptyl}methanone | LCMS: 448.5 m/z [M + H]+.<br>$^1$H NMR (400 MHz, DMSO-d$_6$) δ 7.38 (t, J = 8.3 Hz, 2H), 7.33-7.22 (m, 2H), 7.15 (dd, J = 7.9, 4.2 Hz, 1H), 6.97 (dd, J = 11.6, 8.5 Hz, 1H), 6.75 (q, J = 7.6 Hz, 1H), 6.13 (d, J = 17.6 Hz, 1H), 4.70-4.60 (m, 1H), 3.93 (s, 1H), 3.85 (d. J = 15.1 Hz, 2H), 3.78 (s, 1H), 3.00 (dt, J = 18.8, 8.5 Hz, 1H), 2.34-2.16 (m, 4H), 2.16 (s, 3H), 1.93 (s, 3H), 1.24 (dd, J = 11.5, 6.1 Hz, 6H). | B (2) |
| 178 | 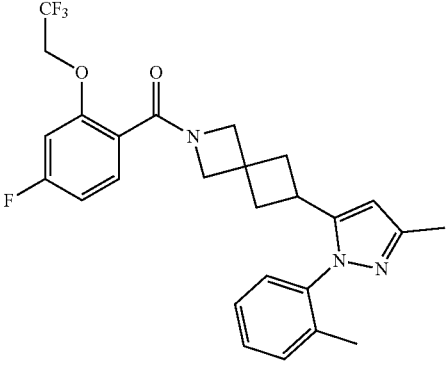 [SMILES: Cc1cc(C2CC3(C2)CN(C(=O)c2ccc(F)cc2OCC(F)(F)F)C3)n(-c2ccccc2C)n1]<br>[4-fluoro-2-(2,2,2-trifluoroethoxy)phenyl]{6-[3-methyl-1-(o-tolyl)-5-pyrazolyl]-2-aza-2-spiro[3.3]heptyl}methanone | LCMS: 488.5 m/z [M+]<br>1H NMR (400 MHz, DMSO-d6) δ 7.46-7.36 (m, 2H), 7.40-7.25 (m, 2H), 7.16 (s, 1H), 7.21-7.10 (m, 1H), 6.98-6.87 (m, 1H), 6.17 (s, 1H), 4,93-4.79 (m, 2H), 3.95 (s, 1H), 3.86 (d, J = 19.9 Hz, 2H), 3.78 (s, IH), 3.03-2.92 (m, 1H), 2.33 (t, J = 10.4 Hz, 2H), 2.21 (dd, J = 23.9, 9.2 Hz, 5H), 1,93 (d, J = 2.3 Hz, 3H). | A (2, 3, 5) |
| 187 | 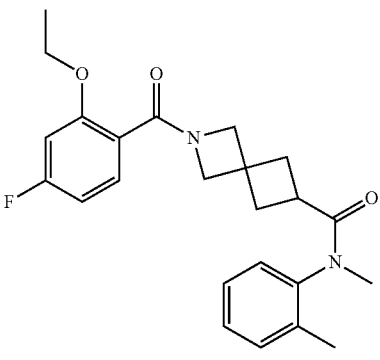 [SMILES: CCOc1cc(F)ccc1C(=O)N1CC2(CC(C(=O)N(C)c3ccccc3C)C2)C1]<br>fluorobenzoyl)-2-aza-6-spiro[3.3]heptanccarboxamide | m/z 411.4 [M + 1]+<br>1H NMR (400 MHz, Methanol-d4) δ 7.42-7.22 (dq, J = 27.9, 7.8 Hz, 4H), 7.14 (d, J = 7.5 Hz, 1H), 6.91-6.66 (m, 2H), 4.18-3.89 (m, 5H), 3.87 (s, 1H), 3.17 (d. J = 5.4 Hz, 3H), 2.79 (dp, J = 24.3, 8.0 Hz, 1H), 2.43 (ddt, J = 27.5, 19.5, 9.9 Hz, 2H), 2.20 (s, 3H), 2.17-1.98 (m, 2H), 1.41 (dt, J = 18.6, 7.0 Hz, 3H). | C (2)<br>E (2, 3) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 203 | 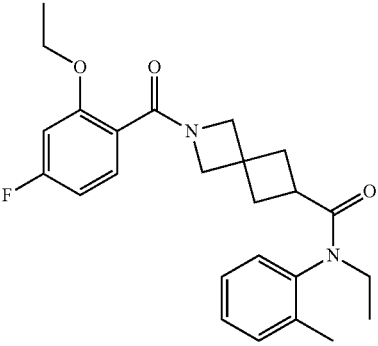 [SMILES: CCOc1cc(F)ccc1C(=O)N1CC2(CC(C(=O)N(CC)c3ccccc3C)C2)C1]<br>N-ethyl-N-o-tolyl-2-(2-ethoxy-4-fluorobenzoyl)-2-aza-6-spiro[3.3]heptanecarboxamide | LCMS: 425.7 m/z<br>1H NMR (400 MHz, DMSO-d6) δ 7.33 (s, 2H), 7.33-7.20 (m, 2H), 7.09 (d, J = 7.6 Hz, 1H), 6.94 (ddd, J = 17.5, 11.7, 2.4 Hz, 1H), 6.76 (dtd, J = 10.8, 8.4, 2.5 Hz, 1H), 4.08 (dt, J = 13.8, 6.9 Hz, 3H), 4.06-3.88 (m, 1H), 3.86-3.73 (m, 2H), 3.71 (s, 2H), 3.10 (dt, J = 13.6, 6.8 Hz, 1H), 2.33-2.19 (m, 2H), 2.12 (d, J = 1.9 Hz, 3H), 1.92 (s, 1H), 1.93-1.82 (m, 1H), 1.30 (dt, J = 21.2, 7.0 Hz, 3H), 0.98 (td, J = 7.1, 5.2 Hz, 3H). | C (4) |
| 205 | 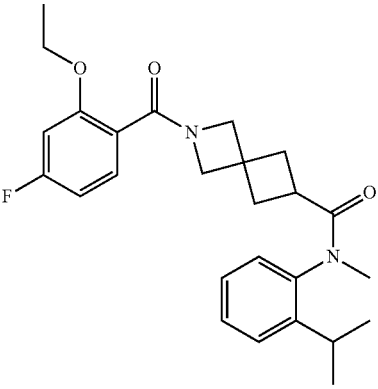 [SMILES: CCOc1cc(F)ccc1C(=O)N1CC2(CC(C(=O)N(C)c3ccccc3C(C)C)C2)C1]<br>N-o-cumenyl-N-methyl-2-(2-ethoxy-4-fluorobenzoyl)-2-aza-6-spiro[3.3]heptanccarboxamide | LCMS: 439.7 m/z<br>1H NMR (400 MHz, DMSO-d6) δ 7.51-7.38 (m, 1H), 7.42-7.25 (m, 1H), 7.26 (dd, J = 7.9, 4.7 Hz, 1H), 6.95 (ddd, J = 19.4, 11.6, 2.4 Hz, 1H), 6.84-6.71 (m, 1H), 4.08 (dq, J = 21.4, 6,8 Hz, 2H), 3.82 (t, J = 4.8 Hz, 3H), 3.75 (dq, J = 14.6, 8.9, 6.8 Hz, 1H), 3.16-3.01 (m, 3H), 2.83 (p, J = 6.8 Hz, 1H), 2.68-2.53 (m, 1H), 2.35-2.20 (m, 2H), 2.00 (ddd, J = 30.9, 12.2, 8.7 Hz, 2H), 1.31 (dt, J = 21.4, 7.0 Hz, 3H), 1.21-1.09 (m, 6H). | D (4) |
| 206 | 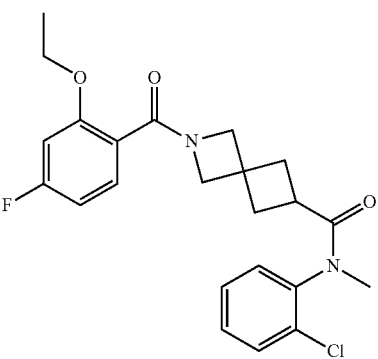 [SMILES: CCOc1cc(F)ccc1C(=O)N1CC2(CC(C(=O)N(C)c3ccccc3Cl)C2)C1]<br>N-o-chlorophenyl-N-methyl-2-(2-ethoxy-4-fluorobenzoyl)-2-aza-6-spiro[3.3]heptanecarboxamide | LCMS: 431.4 m/z [M+]<br>1H NMR (400 MHz, DMSO-d6) δ 7.64 (ddd, J = 9.3, 6.6, 3.9 Hz, 1H), 7.46 (ddd, J = 13.8, 6.0, 3.3 Hz, 3H), 7.38-7.22 (m, 1H), 6.95 (ddd, J = 15.6, 11.6, 2.4 Hz, 1H), 6.77 (dtd, J = 10.6, 8.4, 2.4 Hz, 1H), 4.11 (q, J = 5.9, 5.1 Hz, 1H), 4.06 (g, J = 6.9, 5.9 Hz, 1H), 3.84 (d, J = 7.1 Hz, 2H), 3.76 (d, J = 14.2 Hz, 2H), 3.07 (d, J = 6.4 Hz, 3H), 2.68 (hept, J = 8.2 Hz, 1H), 2.34-2.24 (m, 2H), 2.08-1.85 (m, 2H), 1.42-1.22 (m, 3H). | E (4) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 374 | 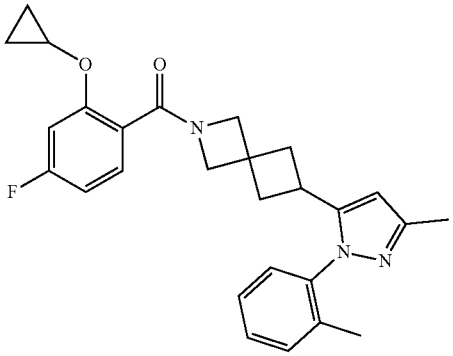 [SMILES: Cc1cc(C2CC3(C2)CN(C(=O)c2ccc(F)cc2OC2CC2)C3)n(-c2ccccc2C)n1]<br>(2-cyclopropoxy-4-fluorophenyl){6-[3-methyl-1-(o-tolyl)-5-pyrazolyl]-2-aza-2-spiro[3.3]heptyl}methanone | LCMS: m/z 446.3 [M + 1]⁺, NMR: 1H NMR (400 MHz, Chloroform-d) δ 7.36 (m, 4H), 7.18 (dd, 1H), 7.07-6.97 (t, 1H), 6.72 (d, J = 7.7 Hz, 1H), 6.07-6.00 (s, 1H), 4.10 (dt, J = 18.6 Hz, 2H), 3.91 (s, 1H), 3.84 (s, 1H), 3.76 (m, 1H), 3.11-2.96 (m, J = 8.5 Hz, 1H), 2.44 (d, 1H), 2.34 (d, J = 6.2 Hz, 5H), 2.25 (d, J = 11.0 Hz, 1H), 2.06 (s, J = 3.1 Hz, 3H), 0.85 (d, J = 13.3 Hz, 4H). | C (14) |
| 418 | 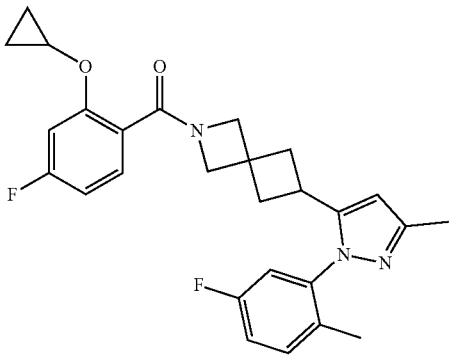 [SMILES: Cc1cc(C2CC3(C2)CN(C(=O)c2ccc(F)cc2OC2CC2)C3)n(-c2cc(F)ccc2C)n1]<br>(2-cyclopropoxy-4-fluorophenyl){6-[1-(5-fluoro-2-tolyl)-3-methyl-5-pyrazolyl]-2-aza-2-spiro[3.3]heptyl}methanone | LCMS: m/z 464.44 [M + 1]⁺.<br>NMR: ¹H NMR (400 MHz, DMSO-d6) δ 7.42 (q, J = 7.8 Hz, 1H), 7.30 (t, J = 7.6 Hz, 2H), 7.28-7.11 (m, 2H), 6.87-6.81 (m, 1H), 3.98-3.85 (m, 3H), 3.79 (s, 1H), 3.70 (s, 1H), 3.13-2.99 (m, 1H), 2.35 (t, J = 10.1 Hz, 1H), 2.22 (dd, J = 23.5, 9.3 Hz, 6H), 1.91 (s, 3H), 0.89 0.81 (m, 2H), 0.67 (s, 2H). | B (12) |
| 419 | 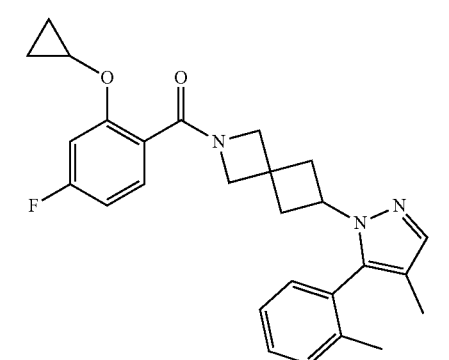<br>(2-cyclopropoxy-4-fluorophenyl){6-[4-methyl-5-(o-tolyl)-1-pyrazolyl]-2-aza-2-spiro[3.3]heptyl}methanone | LCMS: m/z 446.39 [M + 1]⁺.<br>¹H NMR (400 MHz, DMSO-d₆) δ 7.64 (s, 1H), 7.38-7.28 (m, 3H), 7.22-7.16 (m, 3H), 6.81 (m, 1H), 4.77 (m, 1H), 4.11 (s, 1H), 4.05 (s, 1H), 3.97 (s, 2H), 3.85 (s, 1H), 2.74-2.68 (m, 4H), 2.20 (d, J = 8.0 Hz, 3H), 1.92 (s, 3H), 0.89-0.84 (m, 2H), 0.70 (s, 2H). | E (6) |

TABLE 7-continued

Compounds of Formula (I), including the value of MAGL inhibition potency
measured with a method described in Table C of Example 22.

| Compound | Structure (IUPAC name) | LCMS / NMR | MAGL Potency (Detection Method) |
|---|---|---|---|
| 420 | 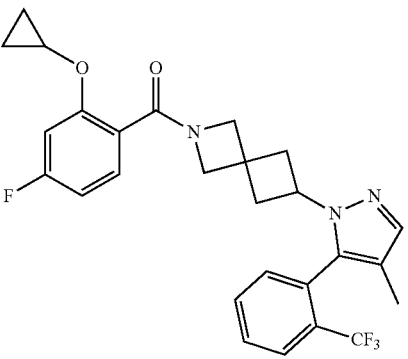 [SMILES: Cc1cnn(C2CC3(C2)CN(C(=O)c2ccc(F)cc2OC2CC2)C3)c1-c1ccccc1C(F)(F)F]<br>(2-cyclopropoxy-4-fluorophenyl)(6-{4-methyl-5-[o-(trifluoromethyl)phenyl]-1-pyrazolyl}-2-aza-2-spiro[3.3]heptyl)methanone | LCMS: m/z 500.2 [M + 1]$^+$.<br>NMR: 1H NMR (400 MHz, DMSO-d6) δ 7.83 (t, J = 7.6 Hz, 1H), 7.71 (d, J = 6.6 Hz, 1H), 7.62 (s, 2H), 7.45-7.37 (m, 1H), 7.36-7.27 (m, 1H), 7.21 (t, J = 11.7 Hz, 1H), 6.86 (d, J = 7.5 Hz, 1H), 4.70 (dd, J = 20.2, 7.8 Hz, 1H), 4.09 (s, 1H), 3.95 (d, J = 17.4 Hz, 3H), 3.80 (s, 1H), 2.71 (s, 2H), 2.64 (d, J = 7.7 Hz, 2H), 1.84 (s, 3H), 0.89-0.83 (m, 2H), 0.72 (s, 1H), 0.66 (s, 1H). | E (6) |
| 422 | 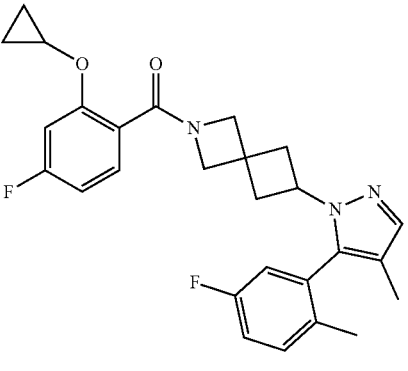 [SMILES: Cc1ccc(F)cc1-c1c(C)cnn1C1CC2(C1)CN(C(=O)c1ccc(F)cc1OC1CC1)C2]<br>(2-cyclopropoxy-4-fluorophenyl){6-[5-(5-fluoro-2-tolyl)-4-methyl-1-pyrazolyl]-2-aza-2-spiro[3.3]heptyl}methanone | LCMS: m/z 464.30 [M + 1]$^+$.<br>$^1$H NMR (400 MHz, DMSO-d$_6$) δ 7.67-7.67 (d, J = 2.4 Hz, 1H), 7.38-7.20 (m, 3H), 7.12 (s, 1H), 7.03 (s, 1H), 6.86 (d, J = 6.4 Hz 1H), 4.78 (m, 1H), 4.11 (s, 1H), 4.05 (s, 1H), 3.94 (s, 2H), 3.84 (s, 1H), 2.68 (m, 4H), 2.20 (d, J = 6.0 Hz, 3H), 1.92 (s, 3H), 0.86 (dd, J = 11.8, 5.9 Hz, 2H), 0.70 (s, 2H). | E (6) |
| 423 | 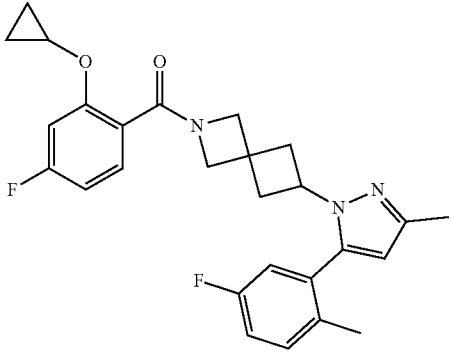 [SMILES: Cc1cc(-c2cc(F)ccc2C)n(C2CC3(C2)CN(C(=O)c2ccc(F)cc2OC2CC2)C3)n1]<br>(2-cyclopropoxy-4-fluorophenyl){6-[5-(5-fluoro-2-tolyl)-3-methyl-1-pyrazolyl]-2-aza-2-spiro[3.3]heptyl}methanone | LCMS: m/z 464.34 [M + 1]$^+$<br>$^1$H NMR (400 MHz, DMSO-d$_6$) δ 7.43-7.33 (m, 2H), 7.28 (dd, J = 24.8, 11.2 Hz, 2H), 7.08 (d, J = 8.6 Hz, 1H), 6.90 (d, J = 8.1 Hz, 1H), 6.40 (s, 1H), 4.81 (dt, J = 22.3, 7.4 Hz, 1H), 4.16 (s, 1H), 4.06 (s, 1H), 4.00 (s, 2H), 3.92 (s, 1H), 2.67 (d, J = 17.7 Hz, 4H), 2.59-2.44 (m, 3H), 2.30 (d, J = 9.7 Hz, 3H), 0.94-0.86 (m, 2H), 0.76 (d, J = 18.2 Hz, 2H). | E (6) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 425 | 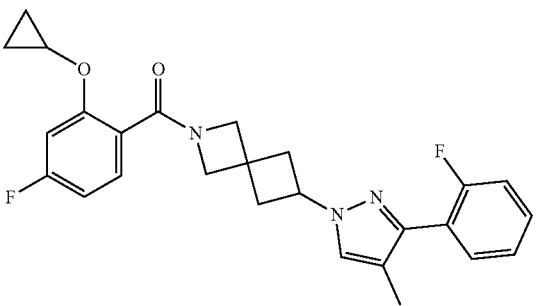 [SMILES: Cc1cn(C2CC3(C2)CN(C(=O)c2ccc(F)cc2OC2CC2)C3)nc1-c1ccccc1F]<br>(2-cyclopropoxy-4-fluorophenyl){6-[3-(o-fluorophenyl)-4-methyl-1-pyrazolyl]-2-aza-2-spiro[3.3]heptyl}methanone | LCMS: m/z 449.9 [M + 1]$^+$<br>$^1$H NMR (400 MHz, DMSO-d$_6$) δ 7.56 (s, 1H), 7.44 (dd, J = 17.5, 10.9 Hz, 1H), 7.34 (dq, J = 15.5, 8.3, 7.9 Hz, 4H), 7.25-7.15 (m, 1H), 6.85 (s, 1H), 4.41 (dt, J = 16.5, 7.8 Hz, 1H), 4.01-3.95 (m, 4H), 3.82 (s, 2H), 2.74-2.55 (m, 3H), 1.87 (s, 3H), 0.84 (s, 2H), 0.69 (s, 2H). | C (6) |
| 428 | 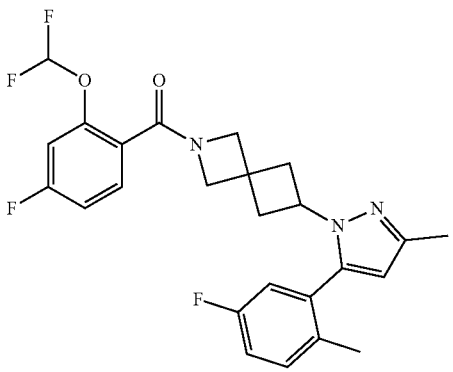 [SMILES: Cc1cc(-c2cc(F)ccc2C)n(C2CC3(C2)CN(C(=O)c2ccc(F)cc2OC(F)F)C3)n1]<br>(2-difluoromethoxy-4-fluorophenyl){6-15-(5-fluoro-2-tolyl)-3-methyl-1-pyrazolyl]-2-aza-2-spiro[3.3]heptyl}methanone | LCMS: m/z 474.23 [M]$^+$.<br>NMR: $^1$H NMR (400 MHz, DMSO-d$_6$) δ 7.58-7.49 (m, 1H), 7.35-7.02 (m 6H), 6.36 (s, 1H), 4.82-4.72 (m, 1H), 4.17 (s, 1H), 4.07 (d, J = 4.4 Hz, 2H), 3.99 (s, 1H), 2.77-2.66 (m, 4H), 2.42 (d, J = 19.1 Hz, 3H), 2.26 (d, J = 11.6 Hz, 3H). | C (6) |
| 437 | 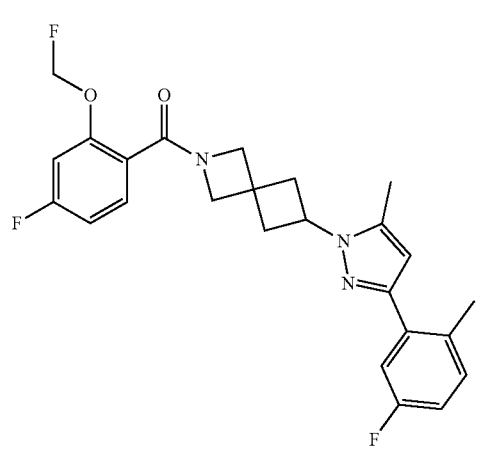 [SMILES: Cc1ccc(F)cc1-c1cc(C)n(C2CC3(C2)CN(C(=O)c2ccc(F)cc2OCF)C3)n1]<br>(4-fluoro-2-fluoromethoxyphenyl){6-[3-(5-fluoro-2-tolyl)-5-methyl-1-pyrazolyl]-2-aza-2-spiro[3.3]heptyl}methanone | LCMS: m/z 456.34 [M + 1]$^+$<br>$^1$H NMR (400 MHz, DMSO-d$_6$) δ 7.43-7.32 (m, 2H), 7.29-7.11 (m, 2H), 7.01 (t, J = 9.1 Hz, 2H), 6.08-5.98 (m, 3H), 4.26 (dt, J = 25.0, 7.9 Hz, 1H), 4.03 (s, 2H), 3.92 (d, J = 6.8 Hz, 2H), 2.70 (dd, J = 20.4, 10.5 Hz, 4H), 2.23 (d, J = 15.1 Hz, 3H), 2.04 (d. J = 8.0 Hz, 3H). | E (11) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 439 | 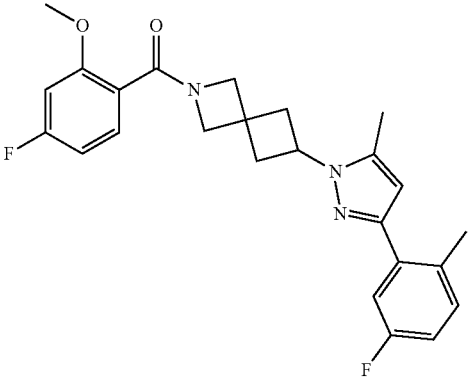 [SMILES: COc1cc(F)ccc1C(=O)N1CC2(CC(n3nc(-c4cc(F)ccc4C)cc3C)C2)C1]<br>(4-fluoro-2-methoxyphenyl){6-[3-(5-fluoro-2-tolyl)-5-methyl-1-pyrazolyl]-2-aza-2-spiro[3.3]heptyl}methanone | LCMS; m/z 438.20 [M + 1]$^+$<br>1H NMR (400 MHz, DMSO-d6) δ 7.43-7.16 (m, 3H), 7.04-6.94 (m, 2H), 6.79 (g, J = 6.5 Hz, 1H), 6.05 (s, 1H), 4.24 (dt, J = 24.2, 7.9 Hz, 1H), 3.99 (s, 2H), 3.88 (d, J = 4.0 Hz, 2H), 3.82 (d, J = 10.0 Hz, 3H), 2.70 (dt, J = 21.5, 11.0 Hz, 2H), 2.55 (s, 2H), 2.21 (d, J = 14.1 Hz, 3H), 2.02 (d, J = 7.5 Hz, 3H) | E (6) |
| 447 | 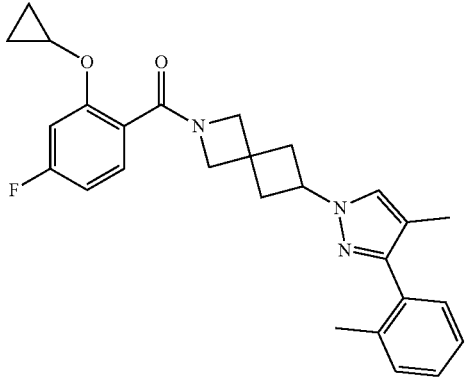 [SMILES: Cc1ccccc1-c1nn(C2CC3(C2)CN(C(=O)c2ccc(F)cc2OC2CC2)C3)cc1C]<br>(2-cyclopropoxy-4-fluorophenyl){6-[4-methyl-3-(o-tolyl)-1-pyrazolyl]-2-aza-2-spiro[3.3]heptyl}methanone | LCMS: m/z 446.40 [M + 1]$^+$<br>$^1$H NMR (400 MHz, DMSO-d$_6$) δ 7.48-7.28 (m, 5H), 7.26-7.08 (m, 2H), 6.81 (m, 1H), 4.21 (dt, J = 16.1, 7.9 Hz, 1H), 3.97 (s, 2H), 3.91 (s, 1H), 3.82 (d, J = 6.0 Hz, 2H), 2.68 (ddt, J = 26.0, 18.1, 9.5 Hz, 4H), 2.00 (d, J = 6.0 Hz, 3H), 1.79 (s, 3H), 0.86 (dd, J = 11.8, 5.9 Hz, 2H), 0.70 (s, 2H). | C (6) |
| 448 | 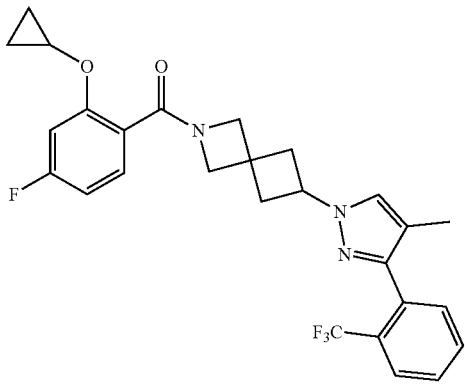 [SMILES: Cc1cn(C2CC3(C2)CN(C(=O)c2ccc(F)cc2OC2CC2)C3)nc1-c1ccccc1C(F)(F)F]<br>(2-cyclopropoxy-4-fluorophenyl)(6-{4-methyl-3-[o-(trifluoromethyl)phenyl]-1-pyrazolyl}-2-aza-2-spiro[3.3]heptyl)methanone | LCMS: m/z 500.2 [M + 1]$^+$.<br>NMR: $^1$H NMR (400 MHz, DMSO-d$_6$) δ 7.97-7.87 (m, 1H), 7.83 (d, J = 7.1 Hz, 2H), 7.76-7.70 (m, 2H), 7.47-7.35 (m, 1H), 7.38-7.24 (m, 1H), 6.87-6.81 (m, 1H), 4.16-4.08 (m, 1H), 3.92 (t, J = 17.8 Hz, 3H), 3.84-3.73 (m, 2H), 2.77-2.57 (m, 2H), 2.45-2.40 (m, 2H), 1.73 (s, 3H), 0.87-0.82 (m, 2H), 0.69-0.66 (m, 2H). | B (6) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 449 | 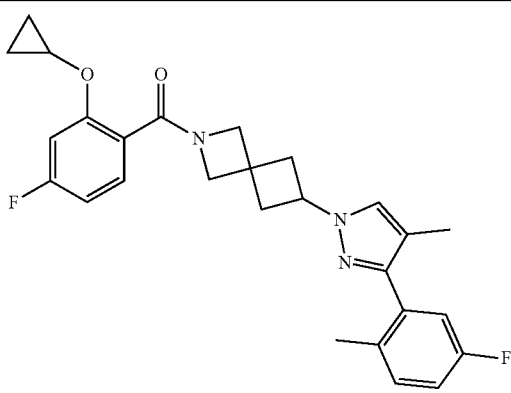<br>(2-cyclopropoxy-4-fluorophenyl){6-[3-(5-fluoro-2-tolyl)-4-methyl-1-pyrazolyl]-2-aza-2-spiro[3.3]beptyl}methanone | LCMS: m/z 464.35 [M + 1]+<br>1H NMR (400 MHz, DMSO-d6) δ 7.46-7.43 (m, 2H), 7.28-7.18 (m, 3H), 7.02 (s. 1H), 6.84 (m, 1H), 4.26 (m, 1H), 3.97 (s, 3H), 3.82 (s, 2H), 2.78-2.68 (m, 3H), 1.97 (d, J = 6.0 Hz, 3H), 1.79 (s, 3H), 0.86 (dd, J = 11.8, 5.9 Hz, 2H), 0.70 (s, 2H). | C (6) |
| 450 | 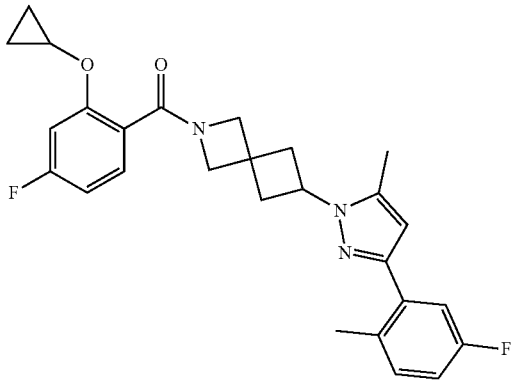 [SMILES: Cc1ccc(F)cc1-c1cc(C)n(C2CC3(C2)CN(C(=O)c2ccc(F)cc2OC2CC2)C3)n1]<br>(2-cyclopropoxy-4-fluorophenyl){6-[3-(5-fluoro-2-tolyl)-5-methyl-1-pyrazolyl]-2-aza-2-spiro[3.3]heptyl}methanone | LCMS: m/z 463.7 [M + 1]$^+$<br>$^1$H NMR (400 MHz, DMSO-d$_6$) δ 7.56-7.35 (m, 2H), 7.24 (t, J = 9,7 Hz, 2H), 7.04 (t, J = 9.7 Hz, 1H), 6.88 (d, J = 7.4 Hz, 1H), 6.09 (s, 1H), 4.30 (dt, J = 15.9, 8.0 Hz, 1H), 4.02 (s, 3H), 3.86 (s, 2H), 2.79-2.69 (m, 4H), 2.26 (d, J = 12.5 Hz, 3H), 2.07 (d, J = 6.0 Hz, 3H), 0.93-0.84 (m, 2H), 0.73 (s, 2H). | C (6) |
| 451 | 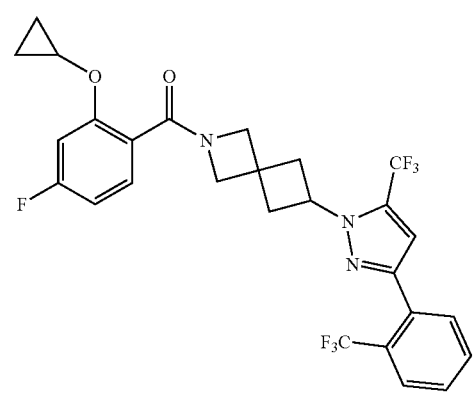 [SMILES: O=C(c1ccc(F)cc1OC1CC1)N1CC2(CC(n3nc(-c4ccccc4C(F)(F)F)cc3C(F)(F)F)C2)C1]<br>(2-cyclopropoxy-4-fluorophenyl)(6-{5-(trifluoromethyl)-3-[o-(trifluoromethyl)phenyl]-1-pyrazolyl}-2-aza-2-spiro[3.3]heptyl)methanone | LCMS: m/z 553.91 [M + 1]$^+$<br>NMR: $^1$H NMR (400 MHz, DMSO-d$_6$) δ 8.68 (s, 1H), 8.05-7.83 (m, 3H), 7.63 (d, J = 7.5 Hz, 1H), 7.30 (dq, J = 27.9, 10.5, 9.1 Hz, 1H), 7.21-7.28 (dq, J = 27.9, 10.5, 9.1 Hz, 1H), 6.92 (d, J = 13.5 Hz, 2H), 4.46 (s, 1H), 4.00-3.95 (s, 3H), 3.80 (s, 2H), 2.78-2.70 (d, J = 18.7 Hz, 4H), 0.87 (d, J = 16.1 Hz, 2H), 0.79-0.70 (m, 2H). | B (6) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 452 | 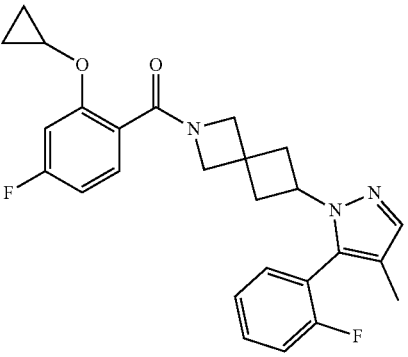<br>(2-cyclopropoxy-4-fluorophenyl){6-[5-(o-fluorophenyl)-4-methyl-1-pyrazolyl]-2-aza-2-spiro[3.3]heptyl}methanone | LCMS: m/z 450.41 [M + 1]$^+$<br>$^1$H NMR (400 MHz, DMSO-d$_6$) δ 7.69 (s, 1H), 7.48-7.41 (m, 2H), 7.31-7.13 (m, 4H), 6.85 (s, 1H), 4.73 (m, 1H), 4.11 (s, 1H), 4.01 (s, 1H), 3.95 (s, 2H), 3.85 (s, 1H), 2.64 (dd, J = 21.4, 9.3 Hz, 4H), 1.97 (s, 3H), 0.90-0.84 (m, 2H), 0.73 (d, J= 14.9 Hz, 2H). | E (6) |
| 454 | 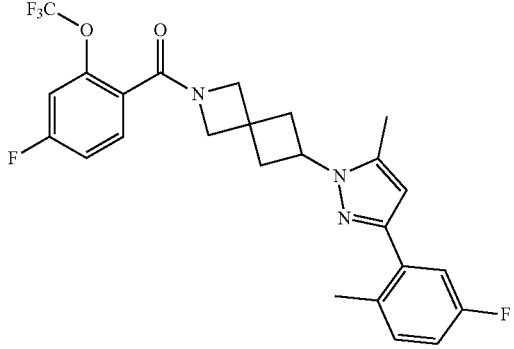 [SMILES: Cc1ccc(F)cc1-c1cc(C)n(C2CC3(C2)CN(C(=O)c2ccc(F)cc2OC(F)(F)F)C3)n1]<br>{6-[3-(5-fluoro-2-tolyl)-5-methyl-1-pyrazolyl]-2-aza-2-spiro[3.3]heptyl}(4-fluoro-2-trifluoromethoxyphenyl)methanone | LCMS: m/z 492.31 [M + 1]$^+$<br>NMR: $^1$H NMR (400 MHz, DMSO-d$_6$) δ 7.65 (d, J = 6.0 Hz, 1H), 7.49 (d, J = 8.3 Hz, 1H), 7.38 (dd, J = 12.8, 6.5 Hz, 2H), 7.23 (dt, J = 14.3. 7.5 Hz, 1H), 7.01 (t, J = 9.1 Hz, 1H), 6.06 (s, 1H), 4.28 (dt, J = 22.1, 7.9 Hz, 1H), 4.06 (s, 2H), 3.96 (d, J = 3.9 Hz, 2H), 2.70 (dd, J = 25.2, 10.0 Hz, 4H), 2.23 (d, J = 15.5 Hz, 3H), 2.04 (d, J = 7.4 Hz, 3H). | E (11) |
| 455 | 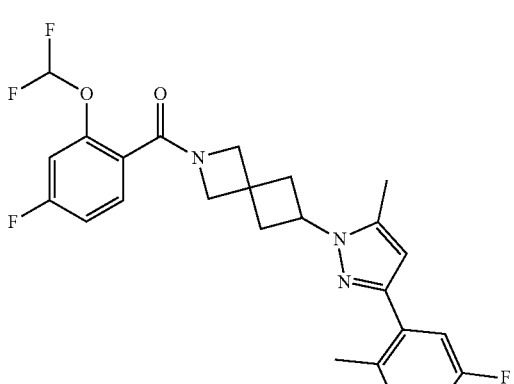<br>(2-difluoromethoxy-4-fluorophenyl){6-[3-(5-fluoro-2-tolyl)-5-methyl-1-pyrazolyl]-2-aza-2-spiro[3.3]heptyl}methanone | LCMS: m/z 474.23 [M + 1]$^+$.<br>$^1$H NMR (400 MHz, DMSO-d$_6$) δ 7.50 (d, J = 18.0 Hz, 1H), 7.38 (dd, J = 14.4, 6.2 Hz, 1H), 7.28 (dd, J = 20.8, 10.0 Hz, 2H), 7.24-7.09 (m, 2H), 7.02 (t, J = 8.7 Hz, 1H), 6.06 (s, 1H), 4.27 (dt, J = 24.5, 7.8 Hz, 1H), 4.05 (s, 2H), 3,95 (d, J = 5.6 Hz, 2H), 2.77-2.66 (m, 4H), 2.23 (d, J = 14.9 Hz, 3H), 2.04 (d, J = 7.1 Hz, 3H). | B (6) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 456 | 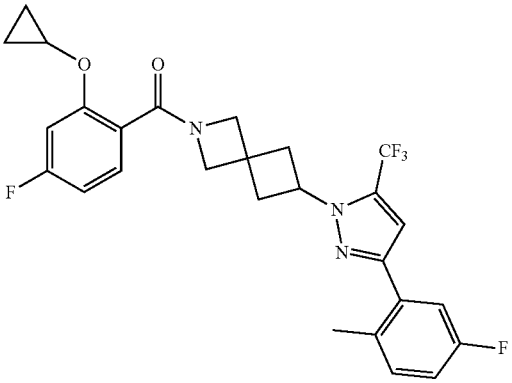 [SMILES: Cc1ccc(F)cc1-c1cc(C(F)(F)F)n(C2CC3(C2)CN(C(=O)c2ccc(F)cc2OC2CC2)C3)n1]<br>(2-cyclopropoxy-4-fluorophenyl){6-[3-(5-fluoro-2-tolyl)-5-(trifluoromethyl)-1-pyrazolyl]-2-aza-2-spiro[3.3]heptyl}methanone | LCMS: m/z 518.45 [M + 1]$^{+1}$<br>NMR: $^1$H NMR (400 MHz, DMSO-d$_6$) δ 7.44 (dd, J = 15.7, 9.9 Hz, 1H), 7.32 (t, J = 8.3 Hz, 2H), 7.30-7.14 (m, 2H), 6.85 (m, 2H), 4.51 (dt, J = 16.6, 7.9 Hz, 1H), 4.00 (dd, 2H), 3.98-3.84 (dd, J = 6.6 Hz,3H), 2.77-2.67 (m, 2H), 2.62 (d, J = 6.4 Hz, 2H), 2.06 (d, J = 5.1 Hz, 3H), 0.90 - 0.82 (m, 2H), 0.68 74 (d, J = 6.5 Hz, 2H). | D (11) |
| 457 | 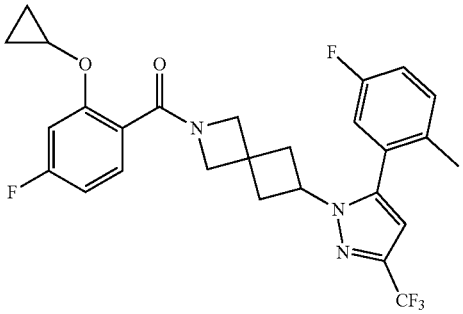 [SMILES: Cc1ccc(F)cc1-c1cc(C(F)(F)F)nn1C1CC2(C1)CN(C(=O)c1ccc(F)cc1OC1CC1)C2]<br>(2-cyclopropoxy-4-fluorophenyl){6-[5-(5-fluoro-2-tolyl)-3-(trifluoromethyl)-1-pyrazolyl]-2-aza-2-spiro[3.3]heptyl}methanone | LCMS: 518.45 m/z [M]$^{+1}$<br>NMR: $^1$H NMR (400 MHz, DMSO-d$_6$) δ 7.44 (dd, J = 19.6, 10.1 Hz, 1H), 7.38-7.29 (m, 2H), 7.31-7.11 (m, 3H), 6.86 (d, J = 7.5 Hz, 1H), 4.93 (dt, J = 16.0, 7.7 Hz, 1H), 4.12 (s, 1H), 4.04 (s, 1H), 3.96 (s, 2H), 3.89 (s, 1H), 2.78 (dd, J = 21,8, 8.8 Hz, 4H), 2.47 (s, 3H), 0.86 (dd, J = 11.9, 6.0 Hz, 2H), 0.74 (m, 1H), 0.69 (d, 1H). | E (11) |
| 458 | 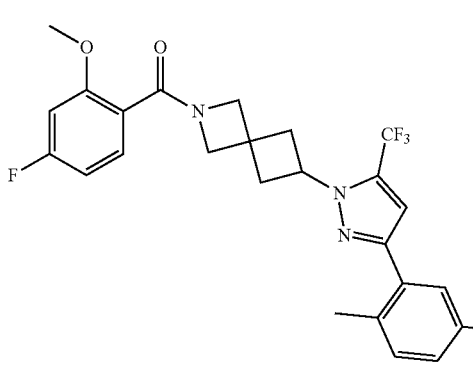<br>(4-fluoro-2-methoxyphenyl){6-[3-(5-fluoro-2-tolyl)-5-(trifluoromethyl)-1-pyrazolyl]-2-aza-2-spiro[3.3]heptyl}methanone | LCMS: m/z 492.4 [M + 1]$^{+1}$<br>NMR: $^1$H NMR (400 MHz, DMSO-d$_6$) δ 7.43 (dt, J = 13.7, 8.2 Hz, 1H), 7.31 (dd, J = 10.5, 5.0 Hz, 2H), 7.18 (t, J = 10.3 Hz, 1H), 6.99 (t, J = 10.1 Hz, 1H), 6.86-6.77 (m, 2H), 4.49 (dt, J = 26.5, 7.9 Hz, 1H), 4.01 (s, 2H), 3.90 (d, J = 6.2 Hz, 2H), 3,82 (d, J = 7.2 Hz, 3H), 2.77-2.66 (m, 1H), 2.68-2.58 (m, 1H), 2.55 (s, 2H), 2.04 (d, J = 6.9 Hz, 3H). | E (11) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 460 | 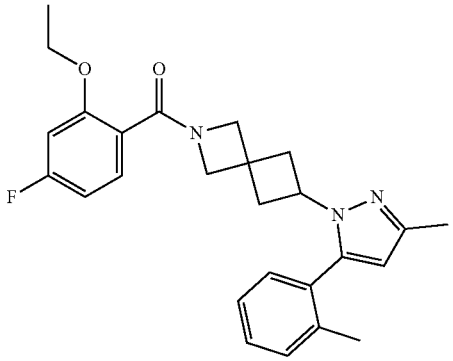 [SMILES: CCOc1cc(F)ccc1C(=O)N1CC2(CC(n3nc(C)cc3-c3ccccc3C)C2)C1]<br>(2-ethoxy-4-fluorophenyl){6-[3-methyl-5-(o-tolyl)-1-pyrazolyl]-2-aza-2-spiro[3.3]heptyl}methanone | LCMS:m/z 434.44 [M + 1]$^{+1}$<br>$^1$H NMR (400 MHz, DMSO-d$_6$) δ 7.54-7.50 (m, 1H), 7.16-7.40 (m, 4H), 7.03-6.98 (m, 1H), 6.76-6.88 (m, 1H), 6.29 (s, 1H), 4.75 (m, 1H), 4.13 (q, J = 7.5, 6.2 Hz, 2H), 4.05 (d, J = 3.4 Hz, 2H), 3.97 (s, 1H), 2.74-2.67 (m, 4H), 2.27 (d, J= 10.4 Hz, 3H), 2.44 (d, J = 17.6 Hz,3H), 1.40-1.33 (m, 3H). | E (11) |
| 461 | 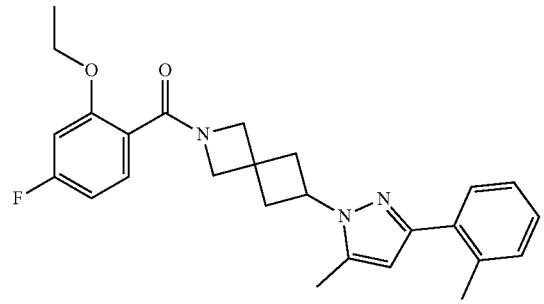 [SMILES: CCOc1cc(F)ccc1C(=O)N1CC2(CC(n3nc(-c4ccccc4C)cc3C)C2)C1]<br>(2-ethoxy-4-fluorophenyl){6-[5-methyl-3-(o-tolyl)-1-pyrazolyl]-2-aza-2-spiro[3.3]heptyl}methanone | LCMS:434.44 m/z,<br>$^1$H NMR (400 MHz, DMSO-d$_6$) δ 7.39-7.26 (m, 4H), 7.15 (m, 1H), 7.00-6.78 (m, 2H), 6.02 (s, 1H), 4.11-4.31 (m, 1H), 4.03-4.14 (m, 2H), 4.00 (d, J = 4.9 Hz, 2H), 3.91 (d, J = 9.8 Hz, 2H), 2.75 (t, J = 10.5 Hz, 4H), 2.23 (d, J = 13.6 Hz, 3H), 2.08 (d, J = 7.3 Hz, 3H), 1.33 (q, J = 7.5 Hz, 3H). | D (11) |
| 462 | 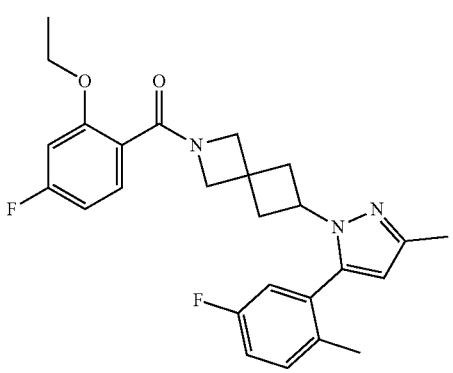 [SMILES: CCOc1cc(F)ccc1C(=O)N1CC2(CC(n3nc(C)cc3-c3cc(F)ccc3C)C2)C1]<br>(2-ethoxy-4-fluorophenyl){6-[5-(5-fluoro-2-tolyl)-3-methyl-1-pyrazolyl]-2-aza-2-spiro[3.3]heptyl}methanone | LCMS: m/z 452.4 [M + 1]$^+$<br>$^1$H NMR (400 MHz, DMSO-d$_6$) δ 7.35-7.23 (m, 3H), 7.06-6.96 (m, 2H), 6.81 (q, J = 8.2 Hz, 1H), 6.35 (s, 1H), 4.8 (dt, J = 25.1, 7.7 Hz, 1H), 4.13 (m, 3H), 4.03 (s, 2H), 3.91 (s, 1H), 2.70 (dd, J = 18.6, 8.1 Hz, 4H), 2.42 (d, J = 17.3 Hz, 3H), 2.26 (d, J = 10.4 Hz, 3H), 1.36 (dt, J = 13.9, 6.9 Hz, 3H). | E (11) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 463 | 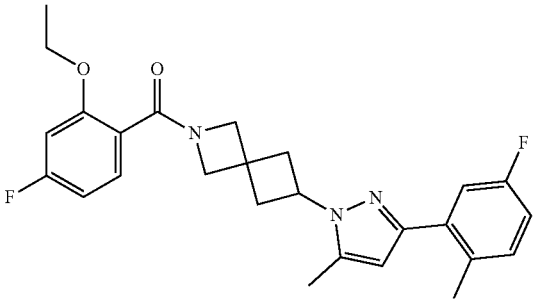 [SMILES: CCOc1cc(F)ccc1C(=O)N1CC2(CC(n3nc(-c4cc(F)ccc4C)cc3C)C2)C1]<br>(2-ethoxy-4-fluorophenyl){6-[3-(5-fluoro-2-tolyl)-5-methyl-1-pyrazolyl]-2-aza-2-spiro[3.3]heptyl}methanone | LCMS: m/z 452.4 [M + 1]$^{+1}$<br>$^1$H NMR (400 MHz, DMSO-d$_6$) δ 7.41-7.3 (m, 2H), 7.05 (m, 1H), 6.98 (q, J = 11.6, 10.7 Hz, 2H), 6.74 (m, 1H), 6.0 (s, 1H), 4.26 (dt, J = 19.9, 7.9 Hz, 1H), 4.08 (dt, J = 13.6, 6.8 Hz, 2H), 3.99 (s, 2H), 3.90 (d. J = 4.1 Hz, 2H), 2.70 (dt, J = 20.7, 10.5 Hz, 4H), 2.21 (d ) = 13.5 Hz, 3H), 2.03 (d. J = 6.5 Hz, 3H), 1.32 (q, J = 6.7 Hz, 3H). | D (11) |
| 464 | 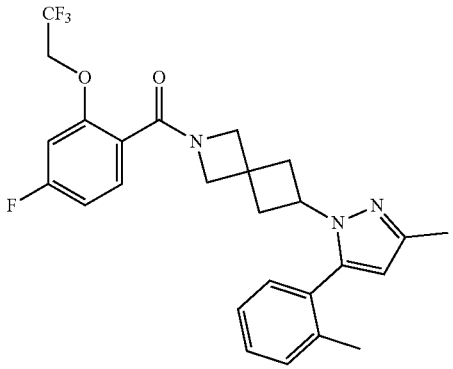 [SMILES: Cc1cc(-c2ccccc2C)n(C2CC3(C2)CN(C(=O)c2ccc(F)cc2OCC(F)(F)F)C3)n1]<br>[4-fluoro-2-(2,2,2-trifluoroethoxy)phenyl]{6-[3-methyl-5-(o-tolyl)-1-pyrazolyl]-2-aza-2-spiro[3.3]heptyl}methanone | LCMS: m/z 488.4 [M + 1]$^{+1}$<br>NMR: $^1$H NMR (400 MHz, DMSO-d$_6$) δ 7.53-7.37 (m, 2H), 7.22-7.18 (m, 4H), 6.99-6.96 (m, 1H), 6.26 (s 1H), 4.92 (d, J = 8.9 Hz, 2H), 4.66-4.91 (m, 1H), 4.15 (s, 1H), 4.04 (d, J = 8.1 Hz, 2H), 3.94 (s, 1H), 2.70 (ddd, J = 20.2, 12.6, 8.6 Hz, 4H), 2.44 (d, J = 19.3 Hz, 3H), 2.27 (d, J = 12.5 Hz, 3H), | D (11) |
| 465 | 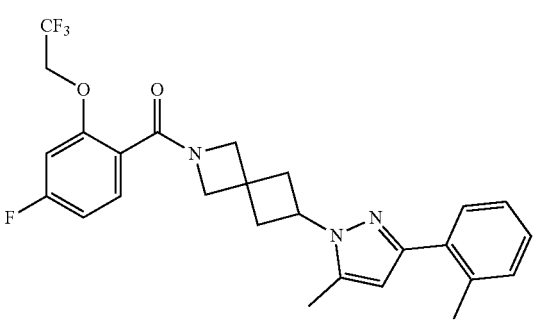 [SMILES: Cc1ccccc1-c1cc(C)n(C2CC3(C2)CN(C(=O)c2ccc(F)cc2OCC(F)(F)F)C3)n1]<br>[4-fluoro-2-(2,2,2-trifluoroethoxy )phenyl]{6-[5-methyl-3-(o-tolyl)-1-pyrazolyl]-2-aza-2-spiro[3.3]heptyl}methanone | LCMS: m/z 488.4 [M + 1]$^{+1}$<br>$^1$H NMR (400 MHz, DMSO-d$_6$) δ 8.50 (s, 1H), 7.33 (ddt, J = 23.2, 15.4, 7.3 Hz, 4H), 7.09-7.22 (m, 2H), 6.88-7.00 (m, 1H), 6.01 (d, J = 2.6 Hz, 1H), 4.88 (dq, J = 17.3, 8.8 Hz, 2H), 4.22 (dt, J = 35.6, 8.0 Hz, 1H), 4.00 (d, J = 5.5 Hz, 2H), 3.89 (d, J = 10.3 Hz, 2H), 2.76 (d, J = 11.0 Hz, 1H), 2.67 (d, J = 12.5 Hz, 1H), 2.45 (t, J = 10.4 Hz, 2H), 2.23 (d. J = 14.5 Hz, 3H), 2.08 (d, J = 8.4 Hz, 3H), | C (11) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 466 | 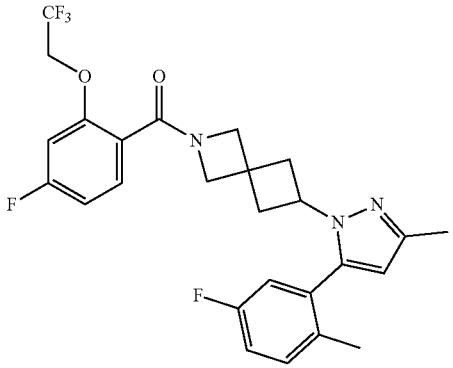 [SMILES: Cc1cc(-c2cc(F)ccc2C)n(C2CC3(C2)CN(C(=O)c2ccc(F)cc2OCC(F)(F)F)C3)n1] {6-[5-(5-fluoro-2-tolyl)-3-methyl-1-pyrazolyl]-2-aza-2-spiro[3.3]beptyl} [4-fluoro-2-(2,2,2-trifluoroethoxy )phenyl]methanone | LCMS: m/z 506.41 [M]$^+$ NMR: $^1$H NMR (400 MHz, DMSO-d$_6$) δ 7.43-7.01 (m, 4H), 7.05-6.95 (m. 2H), 6.37 (s, 1H), 4.92 (q, J = 8.9 Hz, 2H), 4.83-4.69 (m, 1H), 4.15 (s, 1H), 4.05 (d, J = 10.2 Hz, 2H), 3.95 (s, 1H), 2.75-2.63 (m, 4H), 2.43 (d, J = 19.1 Hz, 3H), 2.27 (d, J = 12.2 Hz, 3H). | D (11) |
| 467 | 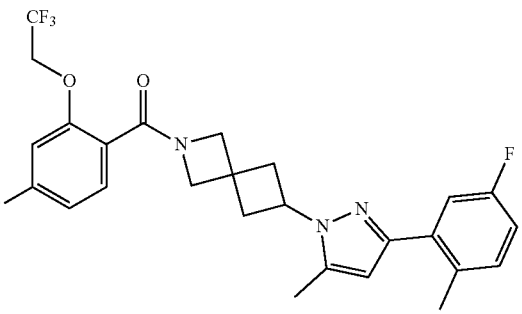 {6-[3-(5-fluoro-2-tolyl)-5-methyl-1-pyrazolyl]-2-aza-2-spiro[3.3]heptyl} [4-fluoro-2-(2,2,2-trifluoroethoxy)phenyl]methanone | LCMS: m/z 506.4 [M]$^+$ $^1$H NMR (400 MHz, DMSO-d$_6$) δ 7.41-7.32 (m, 2H), 7.29-7.13 (m, 2H), 7.06-6.91 (m, 2H), 6.03 (s, 1H), 4.88 (dq, J = 17.9, 8.9 Hz, 2H), 4.26 (dt, J = 34.0, 7.9 Hz, 1H), 4.02 (d, J = 10.2 Hz, 2H), 3.89 (d, J = 5.1 Hz, 2H), 2.76-2.54 (m, 2H), 2.46 (s, 2H), 2.24 (t, J = 12.5 Hz, 3H), 2.04 (d, J = 6.4 Hz, 3H). | C (11) |
| 482 | 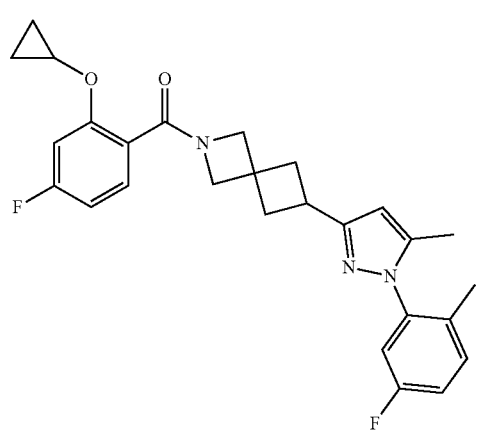 [SMILES: Cc1ccc(F)cc1-n1nc(C2CC3(C2)CN(C(=O)c2ccc(F)cc2OC2CC2)C3)cc1C] (2-cyclopropoxy-4-fluorophenyl) {6-[1-(5-fluoro-2-tolyl)-5-methyl-3-pyrazolyl]-2-aza-2-spiro[3.3]heptyl}methanone | LCMS: m/z 464.44 [M + 1]$^+$. NMR: $^1$H NMR (400 MHz, DMSO-d$_6$) δ 7.43 (d, J = 7.5 Hz, 1H), 7.26 (dq, J = 27.9, 10.5, 9.1 Hz, 4H), 6.82 (d, J = 13.5 Hz, 1H), 6.12 (d, J = 13.5 Hz, 1H), 4.06 (s, 1H), 3.91 (s, 3H), 3.73 (s, 1H), 2.58-2.41 (d, J = 18.7 Hz, 5H), 2.04 (d, J = 7.3 Hz, 3H), 1.91 (d, J = 16.1 Hz, 3H), 0.89-0.80 (m, 2H), 0.72 (s, 2H). | D (12) |

TABLE 7-continued

Compounds of Formula (I), including the value of MAGL inhibition potency measured with a method described in Table C of Example 22.

| Compound | Structure (IUPAC name) | LCMS / NMR | MAGL Potency (Detection Method) |
|---|---|---|---|
| 522 | 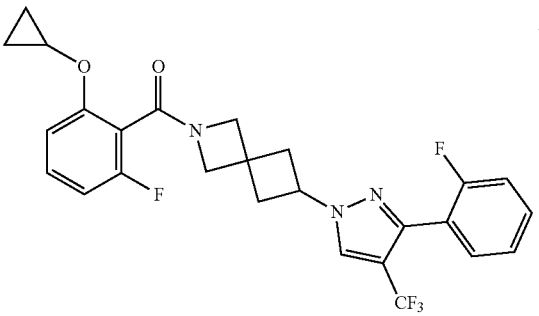 [SMILES: O=C(c1c(F)cccc1OC1CC1)N1CC2(CC(n3cc(C(F)(F)F)c(-c4ccccc4F)n3)C2)C1]<br>(2-cyclopropoxy-6-fluorophenyl){6-[3-(o-fluorophenyl)-4-(trifluoromethyl)-1-pyrazolyl]-2-aza-2-spiro[3.3]heptyl}methanone | LCMS: m/z 504.60 [M + 1]$^+$.<br>NMR: $^1$H NMR (400 MHz, DMSO-d$_6$) δ 8.10 (d, J = 12.9 Hz, 1H), 7.60-7.35 (dt, J = 14.0, 7.7 Hz, 5H), 7.18 (t, J = 8.1 Hz, 1H), 6.92-6.83 (m, 1H), 4.53-4.43 (m, 1H), 4.03 (d, J = 19.0 Hz, 2H), 3.95-3.73 (m, 3H), 2.62-2.55 (s, 4H), 0.80 (s, 2H), 0.63 (s, 2H). | E (12) |
| 523 | 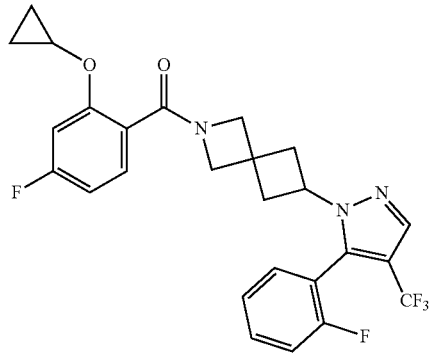 [SMILES: O=C(c1ccc(F)cc1OC1CC1)N1CC2(CC(n3ncc(C(F)(F)F)c3-c3ccccc3F)C2)C1]<br>(2-cyclopropoxy-4-fluorophenyl){6-[5-(o-fluorophenyl)-4-(trifluoromethyl)~1-pyrazolyl]-2-aza-2-spiro[3.3]heptyl}methanone | LCMS: m/z 504.50 [M + 1]$^+$.<br>NMR: $^1$H NMR (400 MHz, DMSO-d$_6$) δ 8.58 (d, J = 6.5 Hz, 1H), 7.44 (d, J = 19.5 Hz, 2H), 7.31 (dd, J = 19.0, 7.7 Hz, 3H), 7.19 (d, J = 10.9 Hz, 1H), 6.85 (d. J = 7.7 Hz, 1H), 4.90 (s, 1H), 4.10 (s, 1H), 4.02-3.99 (s, 1H), 3.94 (s, 2H), 3.81 (d, J = 19.8 Hz, 1H), 2.72 (dt, J = 19.7, 9.9 Hz, 4H), 0.85 (s, 2H), 0.70 (d, J = 17.1 Hz, 2H). | E (12) |
| 524 | 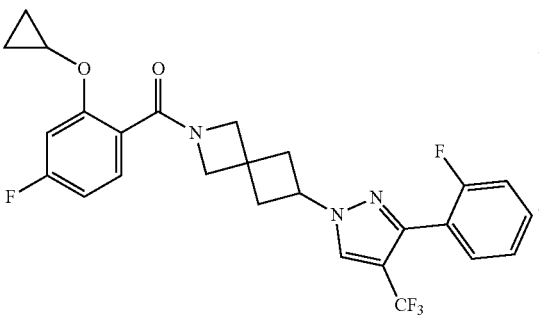 [SMILES: O=C(c1ccc(F)cc1OC1CC1)N1CC2(CC(n3cc(C(F)(F)F)c(-c4ccccc4F)n3)C2)C1]<br>(2-cyclopropoxy-4-fluorophenyl){6-[3-(o-fluorophenyl)-4-(trifluoromethyl)-1-pyrazolyl]-2-aza-2-spiro[3.3]heptyl}methanone | LCMS: m/z 504.50 [M + 1]$^+$.<br>NMR: $^1$H NMR (400 MHz, DMSO-d$_6$) δ 8.07 (dd, J = 20.1, 11.5 Hz, 1H), 7.62 (dt, J = 19.5, 10.9 Hz, 1H), 7.48-7.26 (m, 4H), 7.21 (dt, J = 17.6, 8.0 Hz, 1H), 6.86-6.79 (m, 1H), 4.48 (dt, J = 16.3, 7.4 Hz, 1H), 4.05-3.73 (m, 5H), 2.58 (d, J = 18.8 Hz, 4H), 0.88 - 0.80 (m, 2H), 0.71 (d, J = 19.9 Hz, 2H). | C (12) |

TABLE 8

Compounds

| Comparator | Structure | Potency |
|---|---|---|
| 123 | 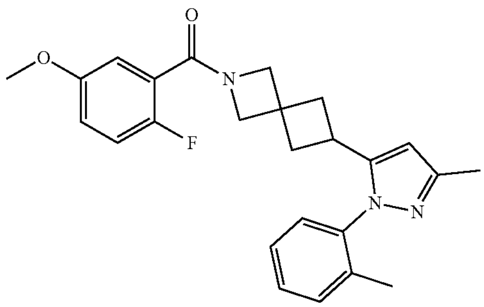 | >10,000 nM (2) |
| 144 | 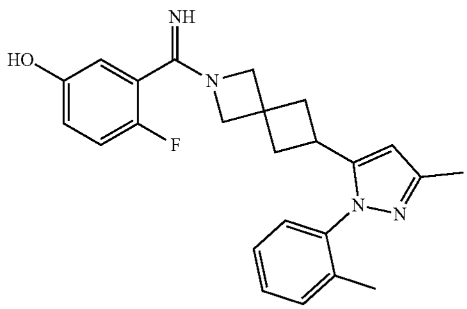 [SMILES: Cc1cc(C2CC3(C2)CN(C(=N)c2cc(O)ccc2F)C3)n(-c2ccccc2C)n1] | >10,000 nM (2) |
| 149 | 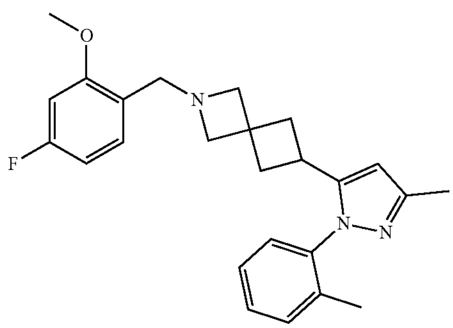 [SMILES: COc1cc(F)ccc1CN1CC2(CC(c3cc(C)nn3-c3ccccc3C)C2)C1] | >10,000 nM (2) |
| 150 | 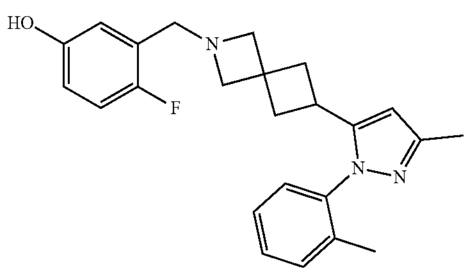 [SMILES: Cc1cc(C2CC3(C2)CN(Cc2cc(O)ccc2F)C3)n(-c2ccccc2C)n1] | >10,000 nM |
| 152, 153 | 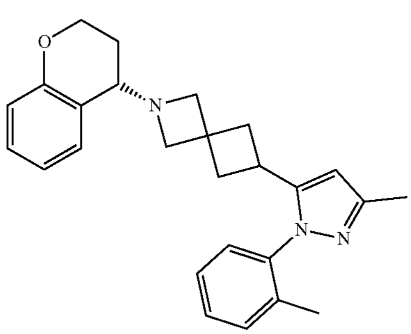 | >10,000 nM (2) |

TABLE 8-continued

Compounds

| Comparator | Structure | Potency |
|---|---|---|
| | (chroman-4-yl R-azetidine spiro compound with pyrazole-o-tolyl) | |
| 154, 155 | (2,3-dihydrobenzofuran-3-yl R-azetidine spiro compound with pyrazole-o-tolyl) | >10,000 nM (2) |
| | (2,3-dihydrobenzofuran-3-yl S-azetidine spiro compound with pyrazole-o-tolyl) | |
| 179 | (furan-3-yl carbonyl azetidine spiro compound with pyrazole-o-tolyl) | >10,000 nM (2) |
| 181 | (1-methylpyrrole-2-yl carbonyl azetidine spiro compound with pyrazole-o-tolyl) | >10,000 nM (2) |

TABLE 8-continued

| Compounds | | |
|---|---|---|
| Comparator | Structure | Potency |
| 182 | | >10,000 nM (2) |
| 183 | | >10,000 nM (2) |
| 184 | | >10,000 nM (2) |
| 188 | | >10,000 nM (2) |

TABLE 8-continued

| Compounds | | |
|---|---|---|
| Comparator | Structure | Potency |
| 198 | | >10,000 nM (4) |
| 368 | | >10,000 nM (14) |
| 384 | | >10,000 nM (14) |
| 388 | | >10,000 nM (14) |

TABLE 8-continued

| Compounds | | |
|---|---|---|
| Comparator | Structure | Potency |
| 391 | | >10,000 nM (14) |
| 395 | | >10,000 nM (14) |
| 400 | | >10,000 nM (14) |
| 402 | | >10,000 nM (14) |
| 403 | | >10,000 nM (14) |

TABLE 8-continued

Compounds

| Comparator | Structure | Potency |
|---|---|---|
| 404 | 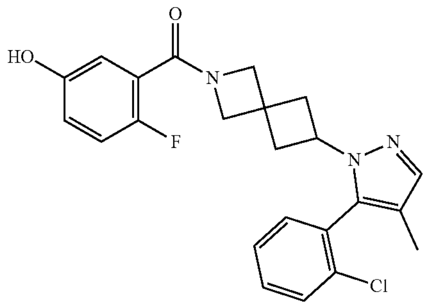 [SMILES: Cc1cnn(C2CC3(C2)CN(C(=O)c2cc(O)ccc2F)C3)c1-c1ccccc1Cl] | >10,000 nM (6) |
| 405 | 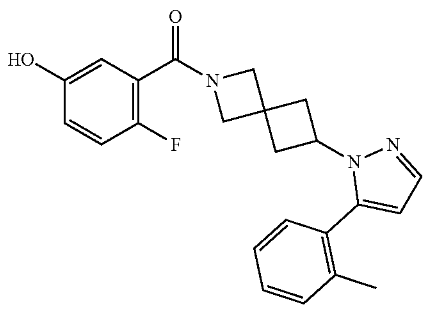 [SMILES: Cc1ccccc1-c1ccnn1C1CC2(C1)CN(C(=O)c1cc(O)ccc1F)C2] | >10,000 nM (6) |
| 406 | 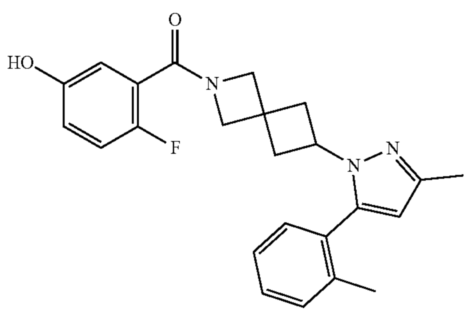 [SMILES: Cc1cc(-c2ccccc2C)n(C2CC3(C2)CN(C(=O)c2cc(O)ccc2F)C3)n1] | >10,000 nM (6) |
| 416 | 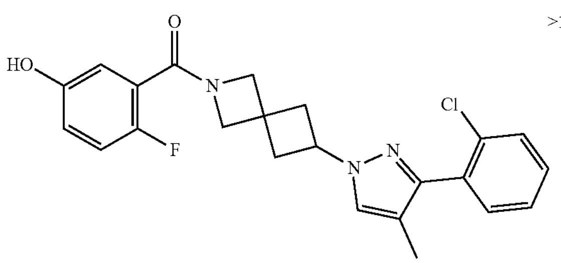 | >10,000 nM (6) |
| 424 | 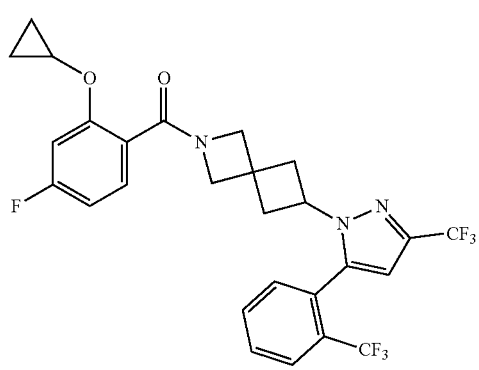 [SMILES: O=C(c1ccc(F)cc1OC1CC1)N1CC2(CC(n3nc(C(F)(F)F)cc3-c3ccccc3C(F)(F)F)C2)C1] | >10,000 nM (6) |

TABLE 8-continued

| Compounds | | |
|---|---|---|
| Comparator | Structure | Potency |
| 427 | [structure] | >10,000 nM (11) |
| 441 | [structure] | >10,000 nM (6) |
| 442 | [structure] | >10,000 nM (6) |
| 445 | [structure] | >10,000 nM (6) |

TABLE 8-continued

Compounds

| Comparator | Structure | Potency |
|---|---|---|
| 494 | 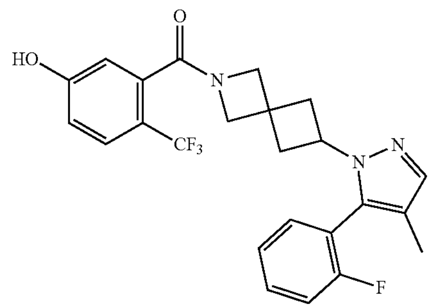 [SMILES: Cc1cnn(C2CC3(C2)CN(C(=O)c2cc(O)ccc2C(F)(F)F)C3)c1-c1ccccc1F] | >10,000 nM (12) |
| 495 | 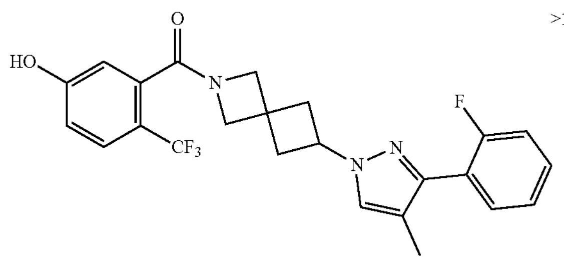 | >10,000 nM (12) |
| 521 | 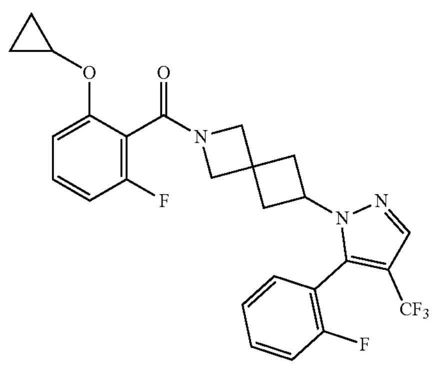 [SMILES: O=C(c1c(F)cccc1OC1CC1)N1CC2(CC(n3ncc(C(F)(F)F)c3-c3ccccc3F)C2)C1] | >10,000 nM (12) |

Further, although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:
1. A compound selected from the group consisting of:
(2-fluoro-5-hydroxyphenyl)(6-{5-(trifluoromethyl)-3-[o-(trifluoromethyl)phenyl]-1-pyrazolyl}-2-aza-2-spiro[3.3]heptyl)methanone;
(2-fluoro-5-hydroxyphenyl){6-[3-(o-fluorophenyl)-4-methyl-1-pyrazolyl]-2-aza-2-spiro[3.3]heptyl}methanone;
(2-fluoro-5-hydroxyphenyl){6-[4-methyl-3-(o-tolyl)-1-pyrazolyl]-2-aza-2-spiro[3.3]heptyl}methanone;
(2-fluoro-5-hydroxyphenyl)(6-{4-methyl-3-[o-(trifluoromethyl)phenyl]-1-pyrazolyl}-2-aza-2-spiro[3.3]heptyl)methanone;
(2-fluoro-5-hydroxyphenyl){6-[3-(5-fluoro-2-tolyl)-5-methyl-1-pyrazolyl]-2-aza-2-spiro[3.3]heptyl}methanone;
(2-fluoro-5-hydroxyphenyl){6-[3-(o-fluorophenyl)-4-(trifluoromethyl)-1-pyrazolyl]-2-aza-2-spiro[3.3]heptyl}methanone;
(2-fluoro-5-hydroxyphenyl){6-[3-(2-fluoro-5-tolyl)-4-(trifluoromethyl)-1-pyrazolyl]-2-aza-2-spiro[3.3]heptyl}methanone;
{6-[3-(2,5-difluorophenyl)-4-methyl-1-pyrazolyl]-2-aza-2-spiro[3.3]heptyl}(2-fluoro-5-hydroxyphenyl)methanone;
(6-{4-cyclopropyl-3-[o-(trifluoromethyl)phenyl]-1-pyrazolyl}-2-aza-2-spiro[3.3]heptyl)(2-fluoro-5-hydroxyphenyl)methanone;
{6-[5-cyclopropyl-3-(5-fluoro-2-tolyl)-1-pyrazolyl]-2-aza-2-spiro[3.3]heptyl}(2-fluoro-5-hydroxyphenyl)methanone;
{6-[4-cyclopropyl-3-(o-fluorophenyl)-1-pyrazolyl]-2-aza-2-spiro[3.3]heptyl}(2-fluoro-5-hydroxyphenyl)methanone;

{6-[3-(2-chloro-5-fluorophenyl)-4-methyl-1-pyrazolyl]-2-aza-2-spiro[3.3]heptyl}(2-fluoro-5-hydroxyphenyl)methanone; and (2-fluoro-5-hydroxyphenyl)(6-{3-[o-(trifluoromethyl)phenyl]-1-pyrazolyl}-2-aza-2-spiro[3.3]heptyl)methanone, or a pharmaceutically acceptable salt thereof.

2. The compound of claim 1, wherein the compound is (2-fluoro-5-hydroxyphenyl)(6-{5-(trifluoromethyl)-3-[o-(trifluoromethyl)phenyl]-1-pyrazolyl}-2-aza-2-spiro[3.3]heptyl)methanone, or a pharmaceutically acceptable salt thereof.

3. The compound of claim 1, wherein the compound is (2-fluoro-5-hydroxyphenyl){6-[3-(o-fluorophenyl)-4-methyl-1-pyrazolyl]-2-aza-2-spiro[3.3]heptyl}methanone, or a pharmaceutically acceptable salt thereof.

4. The compound of claim 1, wherein the compound is (2-fluoro-5-hydroxyphenyl){6-[4-methyl-3-(o-tolyl)-1-pyrazolyl]-2-aza-2-spiro[3.3]heptyl}methanone, or a pharmaceutically acceptable salt thereof.

5. The compound of claim 1, wherein the compound is (2-fluoro-5-hydroxyphenyl)(6-{4-methyl-3-[o-(trifluoromethyl)phenyl]-1-pyrazolyl}-2-aza-2-spiro[3.3]heptyl)methanone, or a pharmaceutically acceptable salt thereof.

6. The compound of claim 1, wherein the compound is (2-fluoro-5-hydroxyphenyl){6-[3-(5-fluoro-2-tolyl)-5-methyl-1-pyrazolyl]-2-aza-2-spiro[3.3]heptyl}methanone, or a pharmaceutically acceptable salt thereof.

7. The compound of claim 1, wherein the compound is (2-fluoro-5-hydroxyphenyl){6-[3-(o-fluorophenyl)-4-(trifluoromethyl)-1-pyrazolyl]-2-aza-2-spiro[3.3]heptyl}methanone, or a pharmaceutically acceptable salt thereof.

8. The compound of claim 1, wherein the compound is (2-fluoro-5-hydroxyphenyl){6-[3-(2-fluoro-5-tolyl)-4-(trifluoromethyl)-1-pyrazolyl]-2-aza-2-spiro[3.3]heptyl}methanone, or a pharmaceutically acceptable salt thereof.

9. The compound of claim 1, wherein the compound is {6-[3-(2,5-difluorophenyl)-4-methyl-1-pyrazolyl]-2-aza-2-spiro[3.3]heptyl}(2-fluoro-5-hydroxyphenyl)methanone, or a pharmaceutically acceptable salt thereof.

10. The compound of claim 1, wherein the compound is (6-{4-cyclopropyl-3-[o-(trifluoromethyl)phenyl]-1-pyrazolyl}-2-aza-2-spiro[3.3]heptyl)(2-fluoro-5-hydroxyphenyl)methanone, or a pharmaceutically acceptable salt thereof.

11. The compound of claim 1, wherein the compound is {6-[5-cyclopropyl-3-(5-fluoro-2-tolyl)-1-pyrazolyl]-2-aza-2-spiro[3.3]heptyl}(2-fluoro-5-hydroxyphenyl)methanone, or a pharmaceutically acceptable salt thereof.

12. The compound of claim 1, wherein the compound is {6-[4-cyclopropyl-3-(o-fluorophenyl)-1-pyrazolyl]-2-aza-2-spiro[3.3]heptyl}(2-fluoro-5-hydroxyphenyl)methanone, or a pharmaceutically acceptable salt thereof.

13. The compound of claim 1, wherein the compound is {6-[3-(2-chloro-5-fluorophenyl)-4-methyl-1-pyrazolyl]-2-aza-2-spiro[3.3]heptyl}(2-fluoro-5-hydroxyphenyl)methanone, or a pharmaceutically acceptable salt thereof.

14. The compound of claim 1, wherein the compound is (2-fluoro-5-hydroxyphenyl)(6-{3-[o-(trifluoromethyl)phenyl]-1-pyrazolyl}-2-aza-2-spiro[3.3]heptyl)methanone, or a pharmaceutically acceptable salt thereof.

* * * * *